US012577244B2

(12) United States Patent
Shimamura et al.

(10) Patent No.: US 12,577,244 B2
(45) Date of Patent: Mar. 17, 2026

(54) HETEROCYCLIC COMPOUND AND HARMFUL ARTHROPOD-CONTROLLING COMPOSITION CONTAINING SAME

(71) Applicant: SUMITOMO CHEMICAL COMPANY, LIMITED, Chuo-ku (JP)

(72) Inventors: Ayano Shimamura, Chuo-ku (JP); Takayuki Shioda, Takarazuka (JP); Takeshi Tsuruda, Takarazuka (JP); Risa Kono, Chuo-ku (JP); Saki Sato, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 384 days.

(21) Appl. No.: 18/247,369

(22) PCT Filed: Sep. 29, 2021

(86) PCT No.: PCT/JP2021/035965

§ 371 (c)(1),
(2) Date: Mar. 30, 2023

(87) PCT Pub. No.: WO2022/071434

PCT Pub. Date: Apr. 7, 2022

(65) Prior Publication Data

US 2024/0010648 A1 Jan. 11, 2024

(30) Foreign Application Priority Data

Sep. 30, 2020 (JP) ................................ 2020-165684
Jun. 21, 2021 (JP) ................................ 2021-102389

(51) Int. Cl.
*C07D 471/04* (2006.01)
*A01N 43/50* (2006.01)
(Continued)

(52) U.S. Cl.
CPC ........... *C07D 471/04* (2013.01); *A01N 43/50* (2013.01); *A01N 43/54* (2013.01); *A01P 7/04* (2021.08)

(58) Field of Classification Search
CPC ......... C07D 471/04; A01P 7/04; A01N 43/50; A01N 43/54
See application file for complete search history.

(56) References Cited

U.S. PATENT DOCUMENTS

2010/0029619 A1 2/2010 Uchikawa et al.
2018/0022760 A1 1/2018 Kudo et al.
(Continued)

FOREIGN PATENT DOCUMENTS

JP 2018-24660 A 2/2018
JP 2020189891 A * 11/2020
(Continued)

OTHER PUBLICATIONS

English machine translation of JP 2020-189891 A provided by applicant dated Dec. 5, 2023. (Year: 2023).*
(Continued)

*Primary Examiner* — Michael B. Pallay
(74) *Attorney, Agent, or Firm* — Oblon, McClelland, Maier & Neustadt, L.L.P.

(57) ABSTRACT

A compound of formula (I) or its N-oxide, (I)

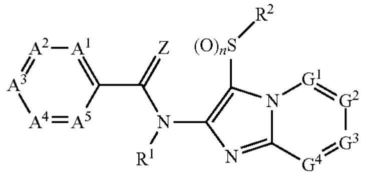

where Z represents an oxygen atom or the like; $G^1$ represents $CR^{3a}$ or the like; $G^2$ represents $CR^{3b}$ or the like; $G^3$ represents $CR^{3c}$ or the like; $G^4$ represents $CR^{3d}$ or the like; $A^1$ represents $CR^{4a}$ or the like; $A^2$ represents $CR^{4b}$ or the like; $A^3$ represents $CR^{4c}$ or the like; $A^4$ represents $CR^{4d}$ or the like; $A^5$ represents $CR^{4e}$ or the like; $R^1$ represents a C1-C6 chain hydrocarbon group or the like; $R^2$ represents a C1-C6 alkyl group or the like; $R^{3a}$, $R^{3b}$, $R^{3c}$, and $R^{3d}$ are identical to or different from each other, and each represent a C1-C6 chain hydrocarbon group or the like; $R^{4a}$, $R^{4b}$, $R^{4c}$, $R^{4d}$, and $R^{4e}$ are identical to or different from each other, and each represent a C1-C6 chain hydrocarbon group or the like; and n represents 0, 1, or 2.

16 Claims, No Drawings

(51) Int. Cl.
*A01N 43/54* (2006.01)
*A01P 7/04* (2006.01)

(56) References Cited

U.S. PATENT DOCUMENTS

| | | | | |
|---|---|---|---|---|
| 2021/0059255 | A1 | 3/2021 | Tanaka et al. | |
| 2021/0115015 | A1 | 4/2021 | Yoneda et al. | |
| 2022/0095620 | A1 | 3/2022 | Tashiro et al. | |
| 2022/0217979 | A1* | 7/2022 | Tsuruda | A01N 43/90 |

FOREIGN PATENT DOCUMENTS

| | | | | |
|---|---|---|---|---|
| WO | WO 2007/002481 | A2 | 1/2007 | |
| WO | WO 2007/095588 | A1 | 8/2007 | |
| WO | WO 2008/016131 | A1 | 2/2008 | |
| WO | WO 2008/016192 | A2 | 2/2008 | |
| WO | WO 2008/150015 | A1 | 12/2008 | |
| WO | WO 2016/129684 | A1 | 8/2016 | |
| WO | WO 2017/222037 | A1 | 12/2017 | |
| WO | WO 2018/199175 | A1 | 11/2018 | |
| WO | WO 2019/131575 | A1 | 7/2019 | |
| WO | WO 2020/158889 | A1 | 8/2020 | |
| WO | WO-2020203763 | A1 * | 10/2020 | A61K 45/00 |
| WO | WO 2021/033141 | A1 | 2/2021 | |
| WO | WO 2021/140122 | A1 | 7/2021 | |
| WO | WO 2022/049144 | A1 | 3/2022 | |
| WO | WO 2023/017094 | A1 | 2/2023 | |

OTHER PUBLICATIONS

International Search Report issued Nov. 22, 2021 in PCT/JP2021/035965 filed Sep. 29, 2021, 3 pages.

English translation of International Preliminary Report on Patentability and Written Opinion issued Mar. 28, 2023 in PCT/JP2021/035965, 5 pages.

Ann-Maree Duncan, et al., "Assessment of novel inhibitors of Helicoverpa aminopeptidases as anti-insect agents," Pest Management Science, vol. 62, 2006, pp. 1098-1108.

* cited by examiner

HETEROCYCLIC COMPOUND AND HARMFUL ARTHROPOD-CONTROLLING COMPOSITION CONTAINING SAME

CROSS-REFERENCE TO RELATED APPLICATIONS

The present application is a 35 U.S.C. § 371 national stage patent application of International patent application PCT/JP2021/035965, filed on Sep. 29, 2021, which is based on and claims the benefits of priority to Japanese Application No. 2020-165684, filed on Sep. 30, 2020 and Japanese Application No. 2021-102389, filed on Jun. 21, 2021. The entire contents of all of the above applications are incorporated herein by reference.

TECHNICAL FIELD

This patent application claims the priorities to and the benefits under the Paris convention of Japanese Patent Application No. 2020-165684 filed on Sep. 30, 2020 and Japanese Patent Application No. 2021-102389 filed on Jun. 21, 2021, the entire contents of which are incorporated herein by reference.

The present invention relates to heterocyclic compounds and compositions for controlling harmful arthropods comprising the same.

BACKGROUND ART

To date, various compounds have been studied in order to control harmful arthropods. For example, Patent Document 1 discloses that certain kinds of compounds have control effects on pests.

CITATION LIST

Patent Document

Patent Document 1: WO 2016/129684 pamphlet

SUMMARY OF THE INVENTION

Problems to be Solved by Invention

An object of the present invention is to provide compounds having excellent control efficacy against harmful arthropods.

Means to Solve Problems

The present invention provides the followings.

[1] A compound represented by formula (I)

(I)

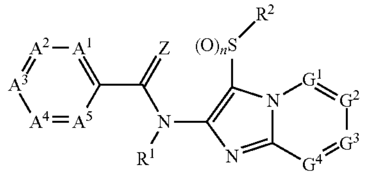

[wherein:

Z represents an oxygen atom or a sulfur atom;

$R^1$ represents a C1-C6 chain hydrocarbon group optionally substituted with one or more substituent (s) selected from Group W, a C3-C7 cycloalkyl group optionally substituted with one or more substituent(s) selected from Group U, a phenyl group optionally substituted with one or more substituent(s) selected from Group V, a 5 or 6 membered aromatic heterocyclic group optionally substituted with one or more substituent(s) selected from Group V, $C(O)R^{51}$, $C(O)OR^{51}$, or $C(O)NR^{51}R^{52}$;

$R^{51}$ and $R^{52}$ are identical to or different from each other, and each represent a C1-C6 chain hydrocarbon group optionally substituted with one or more halogen atom(s), a phenyl group optionally substituted with one or more substituent(s) selected from Group V, a 5 or 6 membered heterocyclic group optionally substituted with one or more substituent(s) selected from Group V, or a hydrogen atom;

$R^2$ represents a C1-C6 alkyl group optionally substituted with one or more halogen atom(s), a cyclopropyl group, or a cyclopropylmethyl group;

n represents 0, 1, or 2;

$G^1$ represents a nitrogen atom or $CR^{3a}$;

$G^2$ represents a nitrogen atom or $CR^{3b}$;

$G^3$ represents a nitrogen atom or $CR^{3c}$;

$G^4$ represents a nitrogen atom or $CR^{3d}$;

$R^{3a}$, $R^{3b}$, $R^{3c}$, and $R^{3d}$ are identical to or different from each other, and each represent a C1-C6 chain hydrocarbon group optionally substituted with one or more substituent(s) selected from Group B, a C3-C7 cycloalkyl group optionally substituted with one or more substituent(s) selected from Group E, a phenyl group optionally substituted with one or more substituent(s) selected from Group H, a 5 or 6 membered aromatic heterocyclic group optionally substituted with one or more substituent(s) selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N{=}CHNR^{31}R^{32}$, $N{=}S(O)_pR^{15}R^{16}$, $C(O)R^{13}$, $C(O)OR^{17}$, $C(O)NR^{31}R^{32}$, $C(O)NR^{11}S(O)_2R^{23}$, $CR^{30}{=}NOR^{17}$, $NR^{11}CR^{24}{=}NOR^{17}$, $S(O)_mR^{23}$, a cyano group, a nitro group, a hydrogen atom, or a halogen atom;

p represents 0 or 1;

m represents 0, 1, or 2;

$R^{30}$ represents a C1-C6 chain hydrocarbon group optionally substituted with one or more halogen atom(s), a halogen atom, $OR^{35}$, $NR^{36}R^{37}$, or a hydrogen atom;

$R^{35}$ represents a C1-C6 chain hydrocarbon group optionally substituted with one or more halogen atom(s);

$R^{17}$ represents a C1-C6 chain hydrocarbon group optionally substituted with one or more halogen atom(s), a phenyl group optionally substituted with one or more substituent(s) selected from Group D, or a hydrogen atom;

$R^{11}$, $R^{24}$, $R^{36}$, and $R^{37}$ are identical to or different from each other, and each represent a C1-C6 chain hydrocarbon group optionally substituted with one or more halogen atom(s), or a hydrogen atom;

$R^{12}$ represents a C1-C6 chain hydrocarbon group optionally substituted with one or more substituent(s) selected from Group F, a C3-C7 cycloalkyl group optionally substituted with one or more substituent(s) selected from Group J, a C3-C7 cycloalkenyl group optionally substituted with one or more substituent(s) selected from Group J, a phenyl group optionally substituted with one or more substituent(s) selected from Group D, a 6 membered aromatic heterocyclic group optionally substituted with one or more substituent(s) selected from Group D, a hydrogen atom, or $S(O)_2R^{23}$;

$R^{23}$ represents a C1-C6 chain hydrocarbon group optionally substituted with one or more halogen atom(s) or a phenyl group optionally substituted with one or more substituent(s) selected from Group D;

$R^{11a}$ and $R^{12a}$ are combined with the nitrogen atom to which they are attached to form a 3-7 membered nonaromatic heterocyclic group optionally substituted with one or more substituent(s) selected from Group E;

$R^{13}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, or a hydrogen atom;

$R^{14}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), or a phenyl C1-C3 alkyl group {wherein the phenyl moiety in said phenyl C1-C3 alkyl group is optionally substituted with one or more substituent(s) selected from Group D};

$R^{15}$ and $R^{16}$ are identical to or different from each other, and each represent a C1-C6 alkyl group optionally substituted with one or more halogen atom(s);

$R^{31}$ represents a C1-C6 alkyl group optionally substituted with one or more halogen atom(s), or a hydrogen atom;

$R^{32}$ represents a C1-C6 chain hydrocarbon group optionally substituted with one or more substituent(s) selected from Group F, a C3-C7 cycloalkyl group optionally substituted with one or more substituent(s) selected from Group J, $S(O)_2R^{23}$, or a hydrogen atom;

$A^1$ represents a nitrogen atom or $CR^{4a}$;

$A^2$ represents a nitrogen atom or $CR^{4b}$;

$A^3$ represents a nitrogen atom or $CR^{4c}$;

$A^4$ represents a nitrogen atom or $CR^{4d}$;

$A^5$ represents a nitrogen atom or $CR^{4e}$;

provided that not all of $A^2$, $A^3$, and $A^4$ represent nitrogen atoms;

$R^{4a}$ and $R^{4e}$ are identical to or different from each other, and each represent a C1-C6 chain hydrocarbon group optionally substituted with one or more substituent(s) selected from Group X, a C3-C6 cycloalkyl group optionally substituted with one or more substituent(s) selected from Group Y, a phenyl group optionally substituted with one or more substituent(s) selected from Group Z, a 5 or 6 membered heterocyclic group optionally substituted with one or more substituent(s) selected from Group Z, $OR^{44}$, $S(O)_kR^{41}$, $S(O)_2NR^{41}R^{42}$, $NR^{41}R^{43}$, $NR^{41}C(O)R^{42}$, $NR^{41}C(O)OR^{42}$, $NR^{41}S(O)_2R^{43}$, $C(O)R^{41}$, $C(O)OR^{41}$, $C(O)NR^{41}R^{42}$, $CR^{42}{=}NOR^{41}$, a hydroxy group, a cyano group, a nitro group, a halogen atom, or a hydrogen atom;

when $A^5$ represents $CR^{4e}$, $R^{4e}$ and $R^1$ are optionally combined with each other to form $—NR^{45}—CR^{41}R^{42}$-# {wherein # represents the binding position to the nitrogen atom to which $R^1$ is bound};

$R^{4b}$, $R^{4c}$, and $R^{4d}$ are identical to or different from each other, and each represent a C1-C6 chain hydrocarbon group optionally substituted with one or more substituent(s) selected from Group X, a C3-C6 cycloalkyl group optionally substituted with one or more substituent(s) selected from Group Y, a phenyl group optionally substituted with one or more substituent(s) selected from Group Z, a 5 or 6 membered heterocyclic group optionally substituted with one or more substituent(s) selected from Group Z, $OR^{44}$, $S(O)_qR^{41}$, $S(O)_2NR^{41}R^{42}$, $NR^{41}R^{42}$, $NR^{41}C(O)R^{42}$, $NR^{41}C(O)OR^{42}$, $NR^{41}S(O)_2R^{43}$, $C(O)R^{41}$, $C(O)OR^{41}$, $C(O)NR^{41}R^{42}$, $CR^{42}{=}NOR^{41}$, a hydroxy group, a cyano group, a nitro group, a halogen atom, or a hydrogen atom;

provided that not all of present $R^{4a}$, $R^{4b}$, $R^{4c}$, $R^{4d}$, and $R^{4e}$ represent hydrogen atoms;

k represents 0, 1, or 2;

q represents 0, 1, or 2;

$R^{41}$ and $R^{42}$ are identical to or different from each other, and each represent a C1-C6 chain hydrocarbon group optionally substituted with one or more halogen atom(s), a phenyl group optionally substituted with one or more substituent(s) selected from Group Z, a 5 or 6 membered heterocyclic group optionally substituted with one or more substituent(s) selected from Group Z, or a hydrogen atom;

$R^{43}$ represents a C1-C6 chain hydrocarbon group optionally substituted with one or more halogen atom(s), a phenyl group optionally substituted with one or more substituent(s) selected from Group Z, or a 5 or 6 membered heterocyclic group optionally substituted with one or more substituent(s) selected from Group Z;

$R^{44}$ represents a C1-C6 chain hydrocarbon group optionally substituted with one or more halogen atom(s);

$R^{45}$ represents a C1-C6 chain hydrocarbon group optionally substituted with one or more substituent(s) selected from Group $W^2$, a C3-C7 cycloalkyl group optionally substituted with one or more substituent(s) selected from Group Y, a phenyl group optionally substituted with one or more substituent(s) selected from Group Z, a 5 or 6 membered aromatic heterocyclic group optionally substituted with one or more substituent(s) selected from Group Z, $C(O)R^{46}$, $C(O)OR^{46}$, $C(O)NR^{46}R^{47}$, or a hydrogen atom; and $R^{46}$ and $R^{47}$ are identical to or different from each other, and each represent a C1-C6 chain hydrocarbon group optionally substituted with one or more halogen atom(s), a phenyl group optionally substituted with one or more substituent(s) selected from Group Z, a 5 or 6 membered heterocyclic group optionally substituted with one or more substituent(s) selected from Group Z, or a hydrogen atom;

Group B: a group consisting of a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a cyano group, a hydroxy group, and a halogen atom;

Group C: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), and a halogen atom;

Group D: a group consisting of a C1-C6 chain hydrocarbon group optionally substituted with one or more halogen atom(s), a hydroxy group, a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a sulfanyl group, a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), an amino group, $NHR^{21}$, $NR^{21}R^{22}$, $C(O)R^{21}$, $OC(O)R^{21}$, $C(O)OR^{21}$, a cyano group, a nitro group, and a halogen atom;

$R^{21}$ and $R^{22}$ are identical to or different from each other, and each represent a C1-C6 alkyl group optionally substituted with one or more halogen atom(s);

Group E: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a halogen atom, an oxo group, a hydroxy group, a cyano group, and a nitro group;

Group F: a group consisting of a C1-C6 alkoxy group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, a C3-C7 cycloalkyl group optionally substituted with one or more halogen atom(s), a 3-7 membered nonaromatic heterocyclic group optionally substituted with one or more substituent(s) selected from Group C, an amino group, $NHR^{21}$, $NR^{21}R^{22}$, a halogen atom, and a cyano group;

Group H: a group consisting of a C1-C6 alkyl group optionally substituted with one or more halogen atom(s), a 5 or 6 membered aromatic heterocyclic group optionally substituted with one or more substituent(s) selected from Group D, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, and an amino group;

$R^9$ represents a C1-C6 alkyl group optionally substituted with one or more halogen atom(s) or a C3-C6 cycloalkyl group optionally substituted with one or more halogen atom(s);

$R^{10}$ represents a C1-C6 alkyl group optionally substituted with one or more halogen atom(s), a C3-C6 cycloalkyl group optionally substituted with one or more halogen atom(s), or a hydrogen atom;

Group J: a group consisting of a C1-C6 alkyl group optionally substituted with one or more halogen atom(s), a halogen atom, and a cyano group;

Group U: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), and a halogen atom;

Group V: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C1-C6 alkylamino group optionally substituted with one or more halogen atom(s), a di(C1-C6 alkyl optionally substituted with one or more halogen atom(s))amino group, a C2-C6 alkylcarbonyl group optionally substituted with one or more halogen atom(s), a C2-C6 alkoxycarbonyl group optionally substituted with one or more halogen atom(s), a hydroxy group, a sulfanyl group, an amino group, a cyano group, a nitro group, and a halogen atom;

Group W: a group consisting of a C3-C6 cycloalkyl group optionally substituted with one or more substituent(s) selected from the group consisting of a halogen atom and a C1-C3 alkyl group, a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a phenyl group optionally substituted with one or more substituent(s) selected from Group Z, a 5 or 6 membered aromatic heterocyclic group optionally substituted with one or more substituent(s) selected from Group Z, a hydroxy group, a cyano group, and a halogen atom;

Group X: a group consisting of a C3-C6 cycloalkyl group optionally substituted with one or more substituent(s) selected from the group consisting of a halogen atom and a C1-C3 alkyl group, a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a hydroxy group, a sulfanyl group, a cyano group, and a halogen atom;

Group Y: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), and a halogen atom;

Group Z: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C1-C6 alkylamino group optionally substituted with one or more halogen atom(s), a di(C1-C6 alkyl optionally substituted with one or more halogen atom(s))amino group, a C2-C6 alkylcarbonyl group optionally substituted with one or more halogen atom(s), a C2-C6 alkoxycarbonyl group optionally substituted with one or more halogen atom(s), a hydroxy group, a sulfanyl group, an amino group, a cyano group, a nitro group, and a halogen atom;

Group $W^2$: a group consisting of a C3-C6 cycloalkyl group optionally substituted with one or more substituent(s) selected from the group consisting of a halogen atom and a C1-C3 alkyl group, a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a phenyl group optionally substituted with one or more substituent(s) selected from Group Z, a 5 or 6 membered aromatic heterocyclic group optionally substituted with one or more substituent(s) selected from Group Z, a hydroxy group, a sulfanyl group, a cyano group, and a halogen atom]

(hereinafter referred to as "Present compound P" or "Compound P of the present invention") or an N-oxide thereof (hereinafter the compound represented by formula (I) or an N-oxide thereof is referred to as "Present compound X" or "Compound X of the resent invention").

[2] The compound according to [1], wherein $R^{45}$ represents a C1-C6 chain hydrocarbon group optionally substituted with one or more substituent(s) selected from Group X, a C3-C7 cycloalkyl group optionally substituted with one or more substituent(s) selected from Group Y, a phenyl group optionally substituted with one or more substituent(s) selected from Group Z, a 5 or 6 membered aromatic heterocyclic group optionally substituted with one or more substituent(s) selected from Group Z, $C(O)R^{46}$, $C(O)OR^{46}$, $C(O)NR^{46}R^{47}$, or a hydrogen atom (hereinafter referred to as "Present compound N" or "Compound N of the present invention") or an N-oxide thereof (hereinafter the Present compound N or an N-oxide thereof is referred to as "Present compound" or "Compound of the present invention").

[3] The compound or an N-oxide thereof according to [1] or [2], wherein $G^1$ represents $CR^{3a}$, $G^2$ represents $CR^{3b}$, $G^3$ represents $CR^{3c}$, and $G^4$ represents a nitrogen atom or $CR^{3d}$.

[4] The compound or an N-oxide thereof according to any one of [1] to [3], wherein $A^1$ represents $CR^{4a}$, $A^2$ represents $CR^{4b}$, $A^3$ represents a nitrogen atom or $CR^{4c}$, $A^4$ represents a nitrogen atom or $CR^{4d}$, and $A^5$ represents a nitrogen atom or $CR^{4e}$.

[5] The compound or an N-oxide thereof according to any one of [1] to [3], wherein the combination of $A^1$, $A^2$, $A^3$, $A^4$, and $A^5$ represents:

a combination wherein $A^1$ represents $CR^{4a}$, $A^2$ represents $CR^{4b}$, $A^3$ represents $CR^{4c}$, $A^4$ represents $CR^{4d}$, and $A^5$ represents $CR^{4e}$;

a combination wherein $A^1$ represents $CR^{4a}$, $A^2$ represents $CR^{4b}$, $A^3$ represents a nitrogen atom, $A^4$ represents $CR^{4d}$, and $A^5$ represents $CR^{4e}$;

a combination wherein $A^1$ represents $CR^{4a}$, $A^2$ represents $CR^{4b}$, $A^3$ represents $CR^{4c}$, $A^4$ represents a nitrogen atom, and $A^5$ represents $CR^{4e}$; or a combination wherein $A^1$ represents $CR^{4a}$, $A^2$ represents $CR^{4b}$, $A^3$ represents $CR^{4c}$, $A^4$ represents $CR^{4d}$, and $A^5$ represents a nitrogen atom.

[6] The compound or an N-oxide thereof according to any one of [1] to [3], wherein $A^1$ represents $CR^{4a}$, $A^2$ represents $CR^{4b}$, $A^3$ represents $CR^{4c}$, $A^4$ represents $CR^{4d}$, and $A^5$ represents $CR^{4e}$.

[7] The compound or an N-oxide thereof according to [1] or [2], wherein $G^1$ represents $CR^{3a}$, $G^2$ represents $CR^{3b}$, $G^3$ represents $CR^{3}$c, and $G^4$ represents $CR^{3d}$; and $A^1$ represents $CR^{4a}$, $A^2$ represents $CR^{4b}$, $A^3$ represents $CR^{4c}$, $A^4$ represents $CR^{4d}$, and $A^5$ represents $CR^{4e}$.

[8] The compound or an N-oxide thereof according to any one of [1] to [7], wherein $R^2$ represents an ethyl group.

[9] The compound or an N-oxide thereof according to any one of [1] to [8], wherein Z represents an oxygen atom.

[10] A composition for controlling a harmful arthropod comprising the compound or an N-oxide thereof according to any one of [1] to [9].

[11] A composition comprising one or more ingredient(s) selected from the group consisting of Group (a), Group (b), Group (c), and Group (d), and the compound or an N-oxide thereof according to any one of [1] to [9]:

Group (a): a group consisting of insecticidal active ingredients, miticidal active ingredients, and nematicidal active ingredients;

Group (b): fungicidal active ingredients;

Group (c): plant growth regulatory ingredients;

Group (d): repellent ingredients.

[12] A method for controlling a harmful arthropod which comprises applying an effective amount of the compound or an N-oxide thereof according to any one of [1] to [9] or an effective amount of the composition according to [11] to a harmful arthropod or a habitat where a harmful arthropod lives.

[13] A seed or a vegetative reproductive organ holding an effective amount of the compound or an N-oxide thereof according to any one of [1] to [9] or an effective amount of the composition according to [11].

[14] A compound represented by formula (II)

(II)

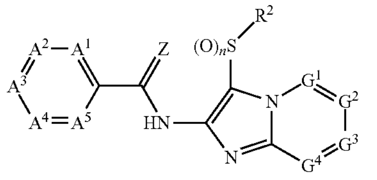

[wherein the symbols are the same as defined above,]

or a salt thereof (hereinafter the compound represented by formula (II) or a salt thereof is referred to as "Intermediate compound A").

Effect of Invention

According to the present invention, harmful arthropods can be controlled.

MODE FOR CARRYING OUT THE INVENTION

The substituents in the present invention are explained as follows.

The term of "halogen atom" represents a fluorine atom, a chlorine atom, a bromine atom, or an iodine atom.

When a substituent is substituted with two or more halogen atoms or substituents, these halogen atoms or substituents may be identical to or different from each other.

The expression of "CX-CY" as described herein means that the number of carbon atom is X to Y. For example, the expression of "C1-C6" means that the number of carbon atom is 1 to 6.

The term of "chain hydrocarbon group" represents an alkyl group, an alkenyl group, or an alkynyl group.

Examples of the term of "alkyl group" include a methyl group, an ethyl group, a propyl group, an isopropyl group, a 1,1-dimethylpropyl group, a 1,2-dimethylpropyl group, a 1-ethylpropyl group, a butyl group, a sec-butyl group, a tert-butyl group, a pentyl group, and a hexyl group.

Examples of the term of "alkenyl group" include a vinyl group, a 1-propenyl group, a 2-propenyl group, a 1-methyl-1-propenyl group, a 1-methyl-2-propenyl group, a 1,2-dimethyl-1-propenyl group, a 1-ethyl-2-propenyl group, a 3-butenyl group, a 4-pentenyl group, and a 5-hexenyl group.

Examples of the term of "alkynyl group" include an ethynyl group, a 1-propynyl group, a 2-propynyl group, a 1-methyl-2-propynyl group, a 1,1-dimethyl-2-propynyl group, a 1-ethyl-2-propynyl group, a 2-butynyl group, a 4-pentynyl group, and a 5-hexynyl group.

Examples of the term of "alkoxy group" include a methoxy group, an ethoxy group, a propoxy group, an isopropoxy group, a butoxy group, a tert-butoxy group, a pentyloxy group, and a hexyloxy group.

Examples of the term of "alkenyloxy group" include a 2-propenyloxy group, a 2-butenyloxy group, and a 5-hexenyloxy group.

Examples of the term of "alkynyloxy group" include a 2-propynyloxy group, a 2-butynyloxy group, and a 5-hexynyloxy group.

Examples of the term of "cycloalkyl group" include a cyclopropyl group, a cyclobutyl group, a cyclopentyl group, a cyclohexyl group, and a cycloheptyl group.

Examples of the term of "cycloalkenyl group" include a cyclopropenyl group, a cyclobutenyl group, a cyclopentenyl group, a cyclohexenyl group, and a cycloheptenyl group.

The term of "3-7 membered nonaromatic heterocyclic group" represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring.

Examples of the term of "3-7 membered nonaromatic heterocyclic group optionally substituted with one or more substituent(s) selected from Group E" include the following groups,

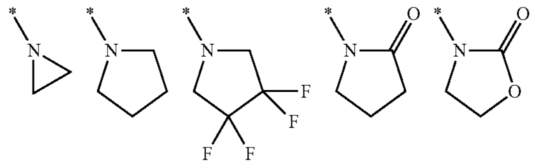

-continued

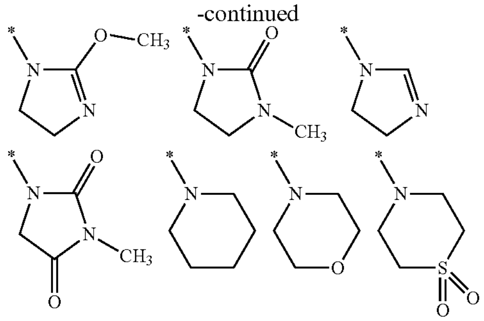

The term of "5 or 6 membered aromatic heterocyclic group" represents a 5 membered aromatic heterocyclic group or a 6 membered aromatic heterocyclic group. The term of "5 membered aromatic heterocyclic group" represents a pyrrolyl group, a furyl group, a thienyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, or a thiadiazolyl group. The term of "6 membered aromatic heterocyclic group" represents a pyridyl group, a pyridazinyl group, a pyrimidinyl group, a pyrazinyl group, a triazinyl group, or a tetrazinyl group.

The term of "5 or 6 membered heterocyclic group" represents a 5 or 6 membered aromatic heterocyclic group or a 5 or 6 membered nonaromatic heterocyclic group, and examples thereof include a pyrrolyl group, a furyl group, a thienyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a pyridyl group, a pyridazinyl group, a pyrimidinyl group, a pyrazinyl group, a triazinyl group, a tetrazinyl group, a pyrrolidinyl group, an imidazolinyl group, an imidazolidinyl group, a piperidinyl group, a tetrahydropyrimidinyl group, a hexahydropyrimidinyl group, a piperazinyl group, an oxazolidinyl group, an isoxazolidinyl group, a 1,3-oxazinanyl group, a morpholinyl group, a thiazolidinyl group, an isothiazolidinyl group, a 1,3-thiazinanyl group, and a thiomorpholinyl group.

Examples of the term of "(C3-C6 cycloalkyl) C1-C3 alkyl group optionally substituted with one or more halogen atom(s)" include a cyclopropylmethyl group, a (2-fluorocyclopropyl)methyl group, a cyclopropyl(fluoro)methyl group, and a (2-fluorocyclopropyl) (fluoro)methyl group.

Examples of the term of "phenyl C1-C3 alkyl group {wherein the phenyl moiety in said phenyl C1-C3 alkyl group is optionally substituted with one or more substituent(s) selected from Group D}" include a benzyl group, a 2-fluorobenzyl group, a 4-chlorobenzyl group, a 4-(trifluoromethyl)benzyl group, and a 2-[4-(trifluoromethyl)phenyl]ethyl group.

Examples of the term of "alkylsulfanyl group" include a methylsulfanyl group, an ethylsulfanyl group, a propylsulfanyl group, and an isopropylsulfanyl group.

Examples of the term of "alkylsulfinyl group" include a methylsulfinyl group, an ethylsulfinyl group, a propylsulfinyl group, and an isopropylsulfinyl group.

Examples of the term of "alkylsulfonyl group" include a methylsulfonyl group, an ethylsulfonyl group, a propylsulfonyl group, and an isopropylsulfonyl group.

Examples of the term of "alkylamino group" include a methylamino group, an ethylamino group, an isopropylamino group, and a hexylamino group.

Examples of the term of "dialkylamino group" include a dimethylamino group, an ethylmethylamino group, an isopropylmethylamino group, and a dihexylamino group.

Examples of the term of "alkylcarbonyl group" include an acetyl group, a propanoyl group, a 2-methylpropanoyl group, and a hexanoyl group.

Examples of the term of "alkoxycarbonyl group" include a methoxycarbonyl group, an ethoxycarbonyl group, an isopropoxycarbonyl group, and a pentyloxycarbonyl group.

In $R^{4a}$, $R^{4b}$, $R^{4c}$, $R^{4d}$, and $R^{4e}$, the expression of "provided that not all of present $R^{4a}$, $R^{4b}$, $R^{4c}$, $R^{4d}$, and $R^{4e}$ represent hydrogen atoms" means that the 6 membered ring containing $A^1$, $A^2$, $A^3$, $A^4$, and $A^5$ (namely, a phenyl group or a 6 membered aromatic heterocyclic group) has one or more substituent (s), and that at least one of present $R^{4a}$, $R^{4b}$, $R^{4c}$, $R^{4d}$, and $R^{4e}$ is not a hydrogen atom. For example, in the compounds wherein $A^1$ represents $CR^{4a}$, $A^2$ represents $CR^{4b}$, $A^3$ represents $CR^{4c}$, $A^4$ represents $CR^{4a}$, and $A^5$ represents $CR^{4a}$, the compounds wherein all of $R^{4a}$, $R^{4b}$, $R^{4c}$, $R^{4d}$, and $R^{4a}$ are hydrogen atoms are excluded, and in the compounds wherein $A^1$ represents $CR^{4a}$, $A^2$ represents $CR^{4b}$, $A^3$ represents $CR^{4c}$, $A^4$ represents a nitrogen atom, and $A^5$ represents $CR^{4b}$, the compounds wherein all of $R^{4a}$, $R^{4b}$, $R^{4c}$, and $R^{4e}$ are hydrogen atoms are excluded.

In other words, in formula (I) or formula (II), a phenyl group or a 6 membered aromatic heterocyclic group represented by formula (I-P)

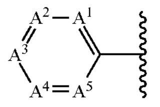

(I-P)

[wherein the wavy line represents the binding position to C(Z); and the other symbols are the same as defined above.] is not unsubstituted.

Examples of the N-oxide of the compound represented by formula (I) include a compound represented by the following formula.

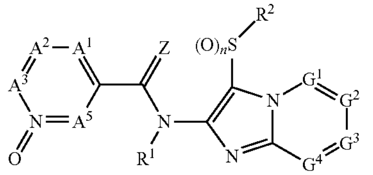

[wherein the symbols are the same as defined above.]

The Present compound X and the Intermediate compound A may optionally have one or more stereoisomer (s). Examples of the stereoisomer(s) include enantiomers, diastereomers, and geometric isomers. The Present compound X and the Intermediate compound A encompass each stereoisomer and mixtures of stereoisomers at any ratio.

The Present compound X and the compound represented by formula (II) may optionally form an acid addition salt. Examples of the acid to form the acid addition salt include inorganic acids such as hydrogen chloride, phosphoric acid, and sulfuric acid; and organic acids such as acetic acid, trifluoroacetic acid, benzoic acid, and p-toluenesulfonic acid. Such acid addition salt may be prepared by mixing the Present compound X or the compound represented by formula (II) with an acid.

Aspects of the Present compound N include the following compounds.

[Aspect 1] The Present compound N, wherein $R^1$ represents a C1-C6 chain hydrocarbon group optionally substituted with one or more substituent(s) selected from Group W;

when $A^5$ represents $CR^{4e}$, $R^{4e}$ and $R^1$ are optionally combined with each other to form $—NR^{45}—CR^{41}R^{42}$-#;

$R^{41}$ and $R^{42}$ are identical to or different from each other, and each represent a C1-C6 chain hydrocarbon group optionally substituted with one or more halogen atom (s), or a hydrogen atom; and $R^{45}$ represents a C1-C6 chain hydrocarbon group optionally substituted with one or more substituent(s) selected from Group X, or a hydrogen atom.

[Aspect 2] The Present compound N, wherein $R^1$ represents a C1-C6 alkyl group;

when $A^5$ represents $CR^{4e}$, $R^{4e}$ and $R^1$ are optionally combined with each other to form $—NR^{45}—CR^{41}R^{42}$-#; and $R^{41}$, $R^{42}$, and $R^{45}$ are identical to or different from each other, and each represent a C1-C6 alkyl group or a hydrogen atom.

[Aspect 3] The Present compound N, wherein the combination of $G^1$, $G^2$, $G^3$, and $G^4$ represents:

a combination wherein $G^1$ represents $CR^{3a}$, $G^2$ represents $CR^{3b}$, $G^3$ represents $CR^{3c}$, and $G^4$ represents a nitrogen atom or $CR^{3d}$;

a combination wherein $G^1$ represents a nitrogen atom, $G^2$ represents $CR^{3b}$, $G^3$ represents $CR^{3c}$, and $G^4$ represents $CR^{3d}$;

a combination wherein $G^1$ represents $CR^{3a}$, $G^2$ represents a nitrogen atom, $G^3$ represents $CR^{3c}$, and $G^4$ represents $CR^{3d}$; or a combination wherein $G^1$ represents $CR^{3a}$, $G^2$ represents $CR^{3b}$, $G^3$ represents a nitrogen atom, and $G^4$ represents $CR^{3a}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect 4] The Present compound N, wherein $G^1$ represents $CR^{3a}$;

$G^2$ represents $CR^{3b}$;

$G^3$ represents $CR^{3c}$;

$G^4$ represents a nitrogen atom or $CR^{3d}$;

$R^{3a}$, $R^{3c}$, and $R^{3d}$ each represent a hydrogen atom; and $R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect 5] The Present compound N, wherein $G^1$ represents $CR^{3a}$;

$G^2$ represents $CR^{3b}$;

$G^3$ represents $CR^{3c}$;

$G^4$ represents a nitrogen atom or $CR^{3d}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect 6] The Present compound N, wherein $G^1$ represents $CR^{3a}$;

$G^2$ represents $CR^{3b}$;

$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect 7] The Present compound N, wherein
$G^1$ represents $CR^{3a}$;
$G^2$ represents $CR^{3b}$;
$G^3$ represents $CR^{3c}$;
$G^4$ represents $CR^{3a}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect 8] The compound according to the Aspect 1, wherein
the combination of $G^1$, $G^2$, $G^3$, and $G^4$ represents:
a combination wherein $G^1$ represents $CR^{3a}$, $G^2$ represents $CR^{3b}$, $G^3$ represents $CR^{3c}$, and $G^4$ represents a nitrogen atom or $CR^{3d}$;
a combination wherein $G^1$ represents a nitrogen atom, $G^2$ represents $CR^{3b}$, $G^3$ represents $CR^{3c}$, and $G^4$ represents $CR^{3d}$;
a combination wherein $G^1$ represents $CR^{3a}$, $G^2$ represents a nitrogen atom, $G^3$ represents $CR^{3c}$, and $G^4$ represents $CR^{3d}$; or
a combination wherein $G^1$ represents $CR^{3a}$, $G^2$ represents $CR^{3b}$, $G^3$ represents a nitrogen atom, and $G^4$ represents $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect 9] The compound according to the Aspect 2, wherein
the combination of $G^1$, $G^2$, $G^3$, and $G^4$ represents:
a combination wherein $G^1$ represents $CR^{3a}$, $G^2$ represents $CR^{3b}$, $G^3$ represents $CR^3$c, and $G^4$ represents a nitrogen atom or $CR^{3a}$;
a combination wherein $G^1$ represents a nitrogen atom, $G^2$ represents $CR^{3b}$, $G^3$ represents $CR^{3c}$, and $G^4$ represents $CR^{3d}$;
a combination wherein $G^1$ represents $CR^{3a}$, $G^2$ represents a nitrogen atom, $G^3$ represents $CR^3$c, and $G^4$ represents $CR^{3d}$; or
a combination wherein $G^1$ represents $CR^{3a}$, $G^2$ represents $CR^{3b}$, $G^3$ represents a nitrogen atom, and $G^4$ represents $CR^{3a}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect 10] The compound according to the Aspect 1, wherein
$G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect 11] The compound according to the Aspect 2, wherein
$G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect 12] The compound according to the Aspect 1, wherein
$G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect 13] The compound according to the Aspect 2, wherein
$G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect 14] The compound according to the Aspect 1, wherein
$G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect 15] The compound according to the Aspect 2, wherein
$G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect 16] The compound according to the Aspect 1, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect 17] The compound according to the Aspect 2, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect 18] The Present compound N, wherein

Z represents an oxygen atom; and
$R^2$ represents a C1-C6 alkyl group.

[Aspect 19] The Present compound N, wherein

Z represents an oxygen atom; and
$R^2$ represents an ethyl group.

[Aspect 20] The compound according to the Aspect 1, wherein

Z represents an oxygen atom; and
$R^2$ represents a C1-C6 alkyl group.

[Aspect 21] The compound according to the Aspect 2, wherein

Z represents an oxygen atom; and
$R^2$ represents a C1-C6 alkyl group.

[Aspect 22] The compound according to the Aspect 3, wherein

Z represents an oxygen atom; and
$R^2$ represents a C1-C6 alkyl group.

[Aspect 23] The compound according to the Aspect 4, wherein

Z represents an oxygen atom; and
$R^2$ represents a C1-C6 alkyl group.

[Aspect 24] The compound according to the Aspect 5, wherein

Z represents an oxygen atom; and
$R^2$ represents a C1-C6 alkyl group.

[Aspect 25] The compound according to the Aspect 6, wherein

Z represents an oxygen atom; and
$R^2$ represents a C1-C6 alkyl group.

[Aspect 26] The compound according to the Aspect 7, wherein

Z represents an oxygen atom; and
$R^2$ represents a C1-C6 alkyl group.

[Aspect 27] The compound according to the Aspect 8, wherein

Z represents an oxygen atom; and
$R^2$ represents a C1-C6 alkyl group.

[Aspect 28] The compound according to the Aspect 9, wherein

Z represents an oxygen atom; and
$R^2$ represents a C1-C6 alkyl group.

[Aspect 29] The compound according to the Aspect 10, wherein

Z represents an oxygen atom; and
$R^2$ represents a C1-C6 alkyl group.

[Aspect 30] The compound according to the Aspect 11, wherein

Z represents an oxygen atom; and
$R^2$ represents a C1-C6 alkyl group.

[Aspect 31] The compound according to the Aspect 12, wherein

Z represents an oxygen atom; and
$R^2$ represents a C1-C6 alkyl group.

[Aspect 32] The compound according to the Aspect 13, wherein

Z represents an oxygen atom; and
$R^2$ represents a C1-C6 alkyl group.

[Aspect 33] The compound according to the Aspect 14, wherein

Z represents an oxygen atom; and
$R^2$ represents a C1-C6 alkyl group.

[Aspect 34] The compound according to the Aspect 15, wherein

Z represents an oxygen atom; and
$R^2$ represents a C1-C6 alkyl group.

[Aspect 35] The compound according to the Aspect 16, wherein

Z represents an oxygen atom; and
$R^2$ represents a C1-C6 alkyl group.

[Aspect 36] The compound according to the Aspect 17, wherein

Z represents an oxygen atom; and
$R^2$ represents a C1-C6 alkyl group.

[Aspect 37] The compound according to the Aspect 1, wherein

Z represents an oxygen atom; and
$R^2$ represents an ethyl group.

[Aspect 38] The compound according to the Aspect 2, wherein

Z represents an oxygen atom; and
$R^2$ represents an ethyl group.

[Aspect 39] The compound according to the Aspect 3, wherein

Z represents an oxygen atom; and
$R^2$ represents an ethyl group.

[Aspect 40] The compound according to the Aspect 4, wherein

Z represents an oxygen atom; and
$R^2$ represents an ethyl group.

[Aspect 41] The compound according to the Aspect 5, wherein

Z represents an oxygen atom; and
$R^2$ represents an ethyl group.

[Aspect 42] The compound according to the Aspect 6, wherein

Z represents an oxygen atom; and
$R^2$ represents an ethyl group.

[Aspect 43] The compound according to the Aspect 7, wherein

Z represents an oxygen atom; and
$R^2$ represents an ethyl group.

[Aspect 44] The compound according to the Aspect 8, wherein

Z represents an oxygen atom; and
$R^2$ represents an ethyl group.

[Aspect 45] The compound according to the Aspect 9, wherein

Z represents an oxygen atom; and $R^2$ represents an ethyl group.

[Aspect 46] The compound according to the Aspect 10, wherein

Z represents an oxygen atom; and $R^2$ represents an ethyl group.

[Aspect 47] The compound according to the Aspect 11, wherein

Z represents an oxygen atom; and $R^2$ represents an ethyl group.

[Aspect 48] The compound according to the Aspect 12, wherein

Z represents an oxygen atom; and $R^2$ represents an ethyl group.

[Aspect 49] The compound according to the Aspect 13, wherein

Z represents an oxygen atom; and $R^2$ represents an ethyl group.

[Aspect 50] The compound according to the Aspect 14, wherein

Z represents an oxygen atom; and $R^2$ represents an ethyl group.

[Aspect 51] The compound according to the Aspect 15, wherein

Z represents an oxygen atom; and $R^2$ represents an ethyl group.

[Aspect 52] The compound according to the Aspect 16, wherein

Z represents an oxygen atom; and $R^2$ represents an ethyl group.

[Aspect 53] The compound according to the Aspect 17, wherein

Z represents an oxygen atom; and $R^2$ represents an ethyl group.

[Aspect 54] The compound according to any one of the Aspects 1 to 53 or the Present compound N, wherein the combination of $A^1$, $A^2$, $A^3$, $A^4$, and $A^5$ represents:

a combination wherein $A^1$ represents $CR^{4a}$, $A^2$ represents $CR^{4b}$, $A^3$ represents $CR^{4c}$, $A^4$ represents a nitrogen atom or $CR^{4d}$, and $A^5$ represents $CR^{4e}$;

a combination wherein $A^1$ represents $CR^{4a}$, $A^2$ represents $CR^{4b}$, $A^3$ represents a nitrogen atom, $A^4$ represents $CR^{4d}$, and $A^5$ represents $CR^{4e}$; or a combination wherein $A^1$ represents $CR^{4a}$, $A^2$ represents $CR^{4b}$, $A^3$ represents $CR^{4c}$, $A^4$ represents $CR^{4d}$, and $A^5$ represents a nitrogen atom;

$R^{4a}$ represents a hydrogen atom;

$R^{4b}$, $R^{4c}$, and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom, or a hydrogen atom; and $R^{4e}$ represents a C1-C6 alkyl group, a halogen atom, or a hydrogen atom;

provided that in the combinations of $A^1$, $A^2$, $A^3$, $A^4$, and $A^5$:

a combination wherein $A^1$, $A^2$, $A^3$, $A^4$, and $A^5$ each represent CH;

a combination wherein $A^1$, $A^2$, $A^3$, and $A^4$ each represent CH, and $A^5$ represents a nitrogen atom;

a combination wherein $A^1$, $A^2$, $A^3$, and $A^5$ each represent CH, and $A^4$ represents a nitrogen atom; and a combination wherein $A^1$, $A^2$, $A^4$, and $A^5$ each represent CH, and $A^3$ represents a nitrogen atom are excluded.

[Aspect 55] The compound according to any one of the Aspects 1 to 53 or the Present compound N, wherein the combination of $A^1$, $A^2$, $A^3$, $A^4$, and $A^5$ represents:

a combination wherein $A^1$ represents $CR^{4a}$, $A^2$ represents $CR^{4b}$, $A^3$ represents $CR^{4c}$, $A^4$ represents a nitrogen atom or $CR^{4d}$, and $A^5$ represents $CR^{4e}$;

a combination wherein $A^1$ represents $CR^{4a}$, $A^2$ represents $CR^{4b}$, $A^3$ represents a nitrogen atom, $A^4$ represents $CR^{4d}$, and $A^5$ represents $CR^{4e}$; or a combination wherein $A^1$ represents $CR^{4a}$, $A^2$ represents $CR^{4b}$, $A^3$ represents $CR^{4c}$, $A^4$ represents $CR^{4d}$, and $A^5$ represents a nitrogen atom;

$R^{4a}$ represents a hydrogen atom; and $R^{4b}$, $R^{4c}$, and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; and $R^{4e}$ represents a halogen atom or a hydrogen atom;

provided that in the combinations of $A^1$, $A^2$, $A^3$, $A^4$, and $A^5$:

a combination wherein $A^1$, $A^2$, $A^3$, $A^4$, and $A^5$ each represent CH;

a combination wherein $A^1$, $A^2$, $A^3$, and $A^4$ each represent CH, and $A^5$ represents a nitrogen atom;

a combination wherein $A^1$, $A^2$, $A^3$, and $A^5$ each represent CH, and $A^4$ represents a nitrogen atom; and a combination wherein $A^1$, $A^2$, $A^4$, and $A^5$ each represent CH, and $A^3$ represents a nitrogen atom are excluded.

[Aspect 56] The compound according to any one of the Aspects 1 to 53 or the Present compound N, wherein $A^1$ represents $CR^{4a}$;

$A^2$ represents $CR^{4b}$;

$A^3$ represents $CR^{4c}$;

$A^4$ represents a nitrogen atom or $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom, or a hydrogen atom; and $R^{4e}$ represents a C1-C6 alkyl group, a halogen atom, or a hydrogen atom; provided that in the combinations of $A^1$, $A^2$, $A^3$, $A^4$, and $A^5$:

a combination wherein $A^1$, $A^2$, $A^3$, $A^4$, and $A^5$ each represent CH; and a combination wherein $A^1$, $A^2$, $A^3$, and $A^5$ each represent CH, and $A^4$ represents a nitrogen atom are excluded.

[Aspect 57] The compound according to any one of the Aspects 1 to 53 or the Present compound N, wherein $A^1$ represents $CR^{4a}$;

$A^2$ represents $CR^{4b}$;

$A^3$ represents $CR^{4c}$;

$A^4$ represents a nitrogen atom or $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; and $R^{4e}$ represents a halogen atom or a hydrogen atom;

provided that in the combinations of $A^1$, $A^2$, $A^3$, $A^4$, and $A^5$:

a combination wherein $A^1$, $A^2$, $A^3$, $A^4$, and $A^5$ each represent CH; and a combination wherein $A^1$, $A^2$, $A^3$, and $A^5$ each represent CH, and $A^4$ represents a nitrogen atom are excluded.

[Aspect 58] The compound according to any one of the Aspects 1 to 53 or the Present compound N, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom, or a hydrogen atom; and $R^{4e}$ represents a C1-C6 alkyl group, a halogen atom, or a hydrogen atom; provided that not all of $R^{4b}$, $R^{4c}$, $R^{4d}$, and $R^{4e}$ represent hydrogen atoms.

[Aspect 59] The compound according to any one of the Aspects 1 to 53 or the Present compound N, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4e}$ represents a C1-C6 alkyl group, a halogen atom, or a hydrogen atom; and the combination of $R^{4b}$, $R^{4c}$, and $R^{4d}$ represents:

a combination wherein $R^{4b}$ represents a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, or a halogen atom; and $R^{4c}$ and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom or a hydrogen atom; or a combination wherein $R^{4b}$ represents a hydrogen atom;

$R^{4c}$ represents a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, or a halogen atom; and $R^{4d}$ represents a hydrogen atom.

[Aspect 60] The compound according to any one of the Aspects 1 to 53 or the Present compound N, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; and $R^{4e}$ represents a halogen atom or a hydrogen atom; provided that not all of $R^{4b}$, $R^{4c}$, $R^{4d}$, and $R^{4e}$ represent hydrogen atoms.

[Aspect 61] The compound according to any one of the Aspects 1 to 53 or the Present compound N, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4e}$ represents a halogen atom or a hydrogen atom; and the combination of $R^{4b}$, $R^{4c}$, and $R^{4d}$ represents:

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4c}$ and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; or a combination wherein $R^{4b}$ represents a hydrogen atom;

$R^{4c}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4d}$ represents a hydrogen atom.

[Aspect 62] The compound according to any one of the Aspects 1 to 53 or the Present compound N, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4e}$ represents a halogen atom or a hydrogen atom; and the combination of $R^{4b}$, $R^{4c}$, and $R^{4d}$ represents:

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom;

$R^{4c}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4d}$ represents a hydrogen atom;

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom;

$R^{4c}$ represents a hydrogen atom; and $R^{4d}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom;

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4c}$ and $R^{4d}$ each represent a hydrogen atom; or a combination wherein $R^{4b}$ represents a hydrogen atom;

$R^{4c}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4d}$ represents a hydrogen atom.

[Aspect 63] The compound according to any one of the Aspects 1 to 53 or the Present compound N, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkoxy group optionally substituted with one or more halogen atom(s), a C1-C6 alkylsulfanyl group optionally substituted with one or more halogen atom(s), or a hydrogen atom; and $R^{4e}$ represents a halogen atom or a hydrogen atom;

provided that not all of $R^{4b}$, $R^{4c}$, $R^{4d}$, and $R^{4e}$ represent hydrogen atoms.

[Aspect 64] The compound according to any one of the Aspects 1 to 53 or the Present compound N, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkoxy group optionally substituted with one or more halogen atom(s), a C1-C6 alkylsulfanyl group optionally substituted with one or more halogen atom(s), or a hydrogen atom; and $R^{4e}$ represents a hydrogen atom;

provided that not all of $R^{4b}$, $R^{4c}$, $R^{4d}$, and $R^{4e}$ represent hydrogen atoms.

[Aspect A1] A compound represented by formula (IA)

(IA)

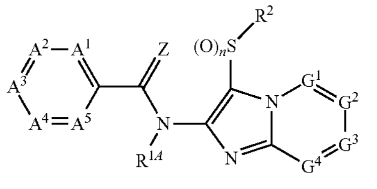

[wherein $R^{1A}$ represents a C1-C6 chain hydrocarbon group optionally substituted with one or more substituent (s) selected from Group W, a C3-C7 cycloalkyl group optionally substituted with one or more substituent (s) selected from Group U, a phenyl group optionally substituted with one or more substituent (s) selected from Group V, a 5 or 6 membered aromatic heterocyclic group optionally substituted with one or more substituent(s) selected from Group V, C(O) $R^{51}$, C(O) $OR^{51}$, or C(O) $NR^{51}R^{52}$ and the other symbols are the same as defined in [1]].

[Aspect A2] The compound according to the Aspect A1, wherein $R^{1A}$ represents a C1-C6 chain hydrocarbon group optionally substituted with one or more substituent(s) selected from Group W.

[Aspect A3] The compound according to the Aspect A1, wherein $R^{1A}$ represents a C1-C6 alkyl group.

[Aspect A4] The compound according to the Aspect A1, wherein the combination of $G^1$, $G^2$, $G^3$, and $G^4$ represents:

a combination wherein $G^1$ represents $CR^{3a}$, $G^2$ represents $CR^{3b}$, $G^3$ represents $CR^{3c}$, and $G^4$ represents a nitrogen atom or $CR^{3a}$;

a combination wherein $G^1$ represents a nitrogen atom, $G^2$ represents $CR^{3b}$, $G^3$ represents $CR^{3c}$, and $G^4$ represents $CR^{3d}$;

a combination wherein $G^1$ represents $CR^{3a}$, $G^2$ represents a nitrogen atom, $G^3$ represents $CR^{3c}$, and $G^4$ represents $CR^{3d}$; or a combination wherein $G^1$ represents $CR^{3a}$, $G^2$ represents $CR^{3b}$, $G^3$ represents a nitrogen atom, and $G^4$ represents $CR^{3a}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect A5] The compound according to the Aspect A1, wherein $G^1$ represents $CR^{3a}$;

$G^2$ represents $CR^{3b}$;

$G^3$ represents $CR^{3c}$;

$G^4$ represents a nitrogen atom or $CR^{3d}$;

$R^{3a}$, $R^{3c}$, and $R^{3d}$ each represent a hydrogen atom; and $R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect A6] The compound according to the Aspect A1, wherein $G^1$ represents $CR^{3a}$;

$G^2$ represents $CR^{3b}$;

$G^3$ represents $CR^{3c}$;

$G^4$ represents a nitrogen atom or $CR^{3d}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect A7] The compound according to the Aspect A1, wherein $G^1$ represents $CR^{3a}$;

$G^2$ represents $CR^{3b}$;

$G^3$ represents $CR^{3c}$;

$G^4$ represents $CR^{3d}$;

$R^{3a}$, $R^{3c}$, and $R^{3d}$ each represent a hydrogen atom; and $R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect A8] The compound according to the Aspect A1, wherein $G^1$ represents $CR^{3a}$;

$G^2$ represents $CR^{3b}$;

$G^3$ represents $CR^{3c}$;

$G^4$ represents $CR^{3d}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect A9] The compound according to the Aspect A2, wherein the combination of $G^1$, $G^2$, $G^3$, and $G^4$ represents:

a combination wherein $G^1$ represents $CR^{3a}$, $G^2$ represents $CR^{3b}$, $G^3$ represents $CR^{3c}$, and $G^4$ represents a nitrogen atom or $CR^{3a}$;

a combination wherein $G^1$ represents a nitrogen atom, $G^2$ represents $CR^{3b}$, $G^3$ represents $CR^{3c}$, and $G^4$ represents $CR^{3d}$;

a combination wherein $G^1$ represents $CR^{3a}$, $G^2$ represents a nitrogen atom, $G^3$ represents $CR^{3c}$, and $G^4$ represents $CR^{3d}$; or a combination wherein $G^1$ represents $CR^{3a}$, $G^2$ represents $CR^{3b}$, $G^3$ represents a nitrogen atom, and $G^4$ represents $CR^{3a}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect A10] The compound according to the Aspect A3, wherein the combination of $G^1$, $G^2$, $G^3$, and $G^4$ represents:

a combination wherein $G^1$ represents $CR^{3a}$, $G^2$ represents $CR^{3b}$, $G^3$ represents $CR^{3c}$, and $G^4$ represents a nitrogen atom or $CR^{3a}$;

a combination wherein $G^1$ represents a nitrogen atom, $G^2$ represents $CR^{3b}$, $G^3$ represents $CR^{3c}$, and $G^4$ represents $CR^{3d}$;

a combination wherein $G^1$ represents $CR^{3a}$, $G^2$ represents a nitrogen atom, $G^3$ represents $CR^{3c}$, and $G^4$ represents $CR^{3d}$; or a combination wherein $G^1$ represents $CR^{3a}$, $G^2$ represents $CR^{3b}$, $G^3$ represents a nitrogen atom, and $G^4$ represents $CR^{3d}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect A11] The compound according to the Aspect A2, wherein $G^1$ represents $CR^{3a}$;

$G^2$ represents $CR^{3b}$;

$G^3$ represents $CR^{3c}$;

$G^4$ represents a nitrogen atom or $CR^{3d}$;

$R^{3a}$, $R^{3c}$, and $R^{3d}$ each represent a hydrogen atom; and $R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect A12] The compound according to the Aspect A3, wherein $G^1$ represents $CR^{3a}$;

$G^2$ represents $CR^{3b}$;

$G^3$ represents $CR^{3c}$;

$G^4$ represents a nitrogen atom or $CR^{3d}$;

$R^{3a}$, $R^{3c}$, and $R^{3d}$ each represent a hydrogen atom; and $R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect A13] The compound according to the Aspect A2, wherein $G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect A14] The compound according to the Aspect A3, wherein $G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect A15] The compound according to the Aspect A2, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect A16] The compound according to the Aspect A3, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect A17] The compound according to the Aspect A2, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect A18] The compound according to the Aspect A3, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), or a halogen atom.

[Aspect A19] The compound according to the Aspect A1, wherein

Z represents an oxygen atom; and
$R^2$ represents a C1-C6 alkyl group.

[Aspect A20] The compound according to the Aspect A1, wherein

Z represents an oxygen atom; and
$R^2$ represents an ethyl group.

[Aspect A21] The compound according to the Aspect A2, wherein

Z represents an oxygen atom; and
$R^2$ represents a C1-C6 alkyl group.

[Aspect A22] The compound according to the Aspect A3, wherein

Z represents an oxygen atom; and
$R^2$ represents a C1-C6 alkyl group.

[Aspect A23] The compound according to the Aspect A4, wherein

Z represents an oxygen atom; and
$R^2$ represents a C1-C6 alkyl group.

[Aspect A24] The compound according to the Aspect A5, wherein

Z represents an oxygen atom; and
$R^2$ represents a C1-C6 alkyl group.

[Aspect A25] The compound according to the Aspect A6, wherein

Z represents an oxygen atom; and
$R^2$ represents a C1-C6 alkyl group.

[Aspect A26] The compound according to the Aspect A7, wherein

Z represents an oxygen atom; and
$R^2$ represents a C1-C6 alkyl group.

[Aspect A27] The compound according to the Aspect A8, wherein

Z represents an oxygen atom; and
$R^2$ represents a C1-C6 alkyl group.

[Aspect A28] The compound according to the Aspect A9, wherein

Z represents an oxygen atom; and
$R^2$ represents a C1-C6 alkyl group.

[Aspect A29] The compound according to the Aspect A10, wherein

Z represents an oxygen atom; and
$R^2$ represents a C1-C6 alkyl group.

[Aspect A30] The compound according to the Aspect A11, wherein

Z represents an oxygen atom; and
$R^2$ represents a C1-C6 alkyl group.

[Aspect A31] The compound according to the Aspect A12, wherein

Z represents an oxygen atom; and
$R^2$ represents a C1-C6 alkyl group.

[Aspect A32] The compound according to the Aspect A13, wherein

Z represents an oxygen atom; and
$R^2$ represents a C1-C6 alkyl group.

[Aspect A33] The compound according to the Aspect A14, wherein

Z represents an oxygen atom; and $R^2$ represents a C1-C6 alkyl group.

[Aspect A34] The compound according to the Aspect A15, wherein

Z represents an oxygen atom; and $R^2$ represents a C1-C6 alkyl group.

[Aspect A35] The compound according to the Aspect A16, wherein

Z represents an oxygen atom; and $R^2$ represents a C1-C6 alkyl group.

[Aspect A36] The compound according to the Aspect A17, wherein

Z represents an oxygen atom; and $R^2$ represents a C1-C6 alkyl group.

[Aspect A37] The compound according to the Aspect A18, wherein

Z represents an oxygen atom; and $R^2$ represents a C1-C6 alkyl group.

[Aspect A38] The compound according to the Aspect A2, wherein

Z represents an oxygen atom; and $R^2$ represents an ethyl group.

[Aspect A39] The compound according to the Aspect A3, wherein

Z represents an oxygen atom; and $R^2$ represents an ethyl group.

[Aspect A40] The compound according to the Aspect A4, wherein

Z represents an oxygen atom; and $R^2$ represents an ethyl group.

[Aspect A41] The compound according to the Aspect A5, wherein

Z represents an oxygen atom; and $R^2$ represents an ethyl group.

[Aspect A42] The compound according to the Aspect A6, wherein

Z represents an oxygen atom; and $R^2$ represents an ethyl group.

[Aspect A43] The compound according to the Aspect A7, wherein

Z represents an oxygen atom; and $R^2$ represents an ethyl group.

[Aspect A44] The compound according to the Aspect A8, wherein

Z represents an oxygen atom; and $R^2$ represents an ethyl group.

[Aspect A45] The compound according to the Aspect A9, wherein

Z represents an oxygen atom; and $R^2$ represents an ethyl group.

[Aspect A46] The compound according to the Aspect A10, wherein

Z represents an oxygen atom; and $R^2$ represents an ethyl group.

[Aspect A47] The compound according to the Aspect A11, wherein

Z represents an oxygen atom; and $R^2$ represents an ethyl group.

[Aspect A48] The compound according to the Aspect A12, wherein

Z represents an oxygen atom; and $R^2$ represents an ethyl group.

[Aspect A49] The compound according to the Aspect A13, wherein

Z represents an oxygen atom; and $R^2$ represents an ethyl group.

[Aspect A50] The compound according to the Aspect A14, wherein

Z represents an oxygen atom; and $R^2$ represents an ethyl group.

[Aspect A51] The compound according to the Aspect A15, wherein

Z represents an oxygen atom; and $R^2$ represents an ethyl group.

[Aspect A52] The compound according to the Aspect A16, wherein

Z represents an oxygen atom; and $R^2$ represents an ethyl group.

[Aspect A53] The compound according to the Aspect A17, wherein

Z represents an oxygen atom; and $R^2$ represents an ethyl group.

[Aspect A54] The compound according to the Aspect A18, wherein

Z represents an oxygen atom; and $R^2$ represents an ethyl group.

[Aspect A55] The compound according to any one of the Aspects A1 to A54, wherein the combination of $A^1$, $A^2$, $A^3$, $A^4$, and $A^5$ represents:

a combination wherein $A^1$ represents $CR^{4a}$, $A^2$ represents $CR^{4b}$, $A^3$ represents $CR^{4a}$, $A^4$ represents a nitrogen atom or $CR^{4d}$, and $A^5$ represents $CR^{4e}$;

a combination wherein $A^1$ represents $CR^{4a}$, $A^2$ represents $CR^{4b}$, $A^3$ represents a nitrogen atom, $A^4$ represents $CR^{4d}$, and $A^5$ represents $CR^{4e}$; or a combination wherein $A^1$ represents $CR^{4a}$, $A^2$ represents $CR^{4b}$, $A^3$ represents $CR^{4c}$, $A^4$ represents $CR^{4d}$, and $A^5$ represents a nitrogen atom;

$R^{4a}$ represents a hydrogen atom;

$R^{4b}$, $R^{4c}$, and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom, or a hydrogen atom; and $R^{4e}$ represents a C1-C6 alkyl group, a halogen atom, or a hydrogen atom;

provided that in the combinations of $A^1$, $A^2$, $A^3$, $A^4$, and $A^5$:

a combination wherein $A^1$, $A^2$, $A^3$, $A^4$, and $A^5$ each represent CH;

a combination wherein $A^1$, $A^2$, $A^3$, and $A^4$ each represent CH, and $A^5$ represents a nitrogen atom;

a combination wherein $A^1$, $A^2$, $A^3$, and $A^5$ each represent CH, and $A^4$ represents a nitrogen atom; and a combination wherein $A^1$, $A^2$, $A^4$, and $A^5$ each represent CH, and $A^3$ represents a nitrogen atom are excluded.

[Aspect A56] The compound according to any one of the Aspects A1 to A54, wherein the combination of $A^1$, $A^2$, $A^3$, $A^4$, and $A^5$ represents:

a combination wherein $A^1$ represents $CR^{4a}$, $A^2$ represents $CR^{4b}$, $A^3$ represents $CR^{4c}$, $A^4$ represents a nitrogen atom or $CR^{4d}$, and $A^5$ represents $CR^{4e}$;

a combination wherein $A^1$ represents $CR^{4a}$, $A^2$ represents $CR^{4b}$, $A^3$ represents a nitrogen atom, $A^4$ represents $CR^{4d}$, and $A^5$ represents $CR^{4e}$; or a combination wherein $A^1$ represents $CR^{4a}$, $A^2$ represents $CR^{4b}$, $A^3$ represents $CR^{4c}$, $A^4$ represents $CR^{4d}$, and $A^5$ represents a nitrogen atom;

$R^{4a}$ represents a hydrogen atom;

$R^{4b}$, $R^{4c}$, and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; and $R^{4e}$ represents a halogen atom or a hydrogen atom;

provided that in the combinations of $A^1$, $A^2$, $A^3$, $A^4$, and $A^5$:

a combination wherein $A^1$, $A^2$, $A^3$, $A^4$, and $A^5$ each represent CH;

a combination wherein $A^1$, $A^2$, $A^3$, and $A^4$ each represent CH, and $A^5$ represents a nitrogen atom;

a combination wherein $A^1$, $A^2$, $A^3$, and $A^5$ each represent CH, and $A^4$ represents a nitrogen atom; and a combination wherein $A^1$, $A^2$, $A^4$, and $A^5$ each represent CH, and $A^3$ represents a nitrogen atom are excluded.

[Aspect $A^{57}$] The compound according to any one of the Aspects $A^1$ to $A^{54}$, wherein $A^1$ represents $CR^{4a}$;

$A^2$ represents $CR^{4b}$;

$A^3$ represents $CR^{4c}$;

$A^4$ represents a nitrogen atom or $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom, or a hydrogen atom; and $R^{4e}$ represents a C1-C6 alkyl group, a halogen atom, or a hydrogen atom; provided that in the combinations of $A^1$, $A^2$, $A^3$, $A^4$, and $A^5$:

a combination wherein $A^1$, $A^2$, $A^3$, $A^4$, and $A^5$ each represent CH; and a combination wherein $A^1$, $A^2$, $A^3$, and $A^5$ each represent CH, and $A^4$ represents a nitrogen atom are excluded.

[Aspect $A^{58}$] The compound according to any one of the Aspects $A^1$ to $A^{54}$, wherein $A^1$ represents $CR^{4a}$;

$A^2$ represents $CR^{4b}$;

$A^3$ represents $CR^{4c}$;

$A^4$ represents a nitrogen atom or $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; and $R^{4e}$ represents a halogen atom or a hydrogen atom; provided that in the combinations of $A^1$, $A^2$, $A^3$, $A^4$, and $A^5$:

a combination wherein $A^1$, $A^2$, $A^3$, $A^4$, and $A^5$ each represent CH; and a combination wherein $A^1$, $A^2$, $A^3$, and $A^5$ each represent CH, and $A^4$ represents a nitrogen atom are excluded.

[Aspect A59] The compound according to any one of the Aspects A1 to A54, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom, or a hydrogen atom; and $R^{4e}$ represents a C1-C6 alkyl group, a halogen atom, or a hydrogen atom; provided that not all of $R^{4b}$, $R^{4c}$, $R^{4d}$, and $R^{4e}$ represent hydrogen atoms.

[Aspect A60] The compound according to any one of the Aspects A1 to A54, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4e}$ represents a C1-C6 alkyl group, a halogen atom, or a hydrogen atom; and the combination of $R^{4b}$, $R^{4c}$, and $R^{4d}$ represents:

a combination wherein $R^{4b}$ represents a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, or a halogen atom; and $R^{4c}$ and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom or a hydrogen atom; or a combination wherein $R^{4b}$ represents a hydrogen atom;

$R^{4c}$ represents a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, or a halogen atom; and $R^{4d}$ represents a hydrogen atom.

[Aspect A61] The compound according to any one of the Aspects A1 to A54, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; and $R^{4e}$ represents a halogen atom or a hydrogen atom;

provided that not all of $R^{4b}$, $R^{4c}$, $R^{4d}$, and $R^{4e}$ represent hydrogen atoms.

[Aspect A62] The compound according to any one of the Aspects A1 to A54, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4e}$ represents a halogen atom or a hydrogen atom; and the combination of $R^{4b}$, $R^{4c}$, and $R^{4d}$ represents:

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4c}$ and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; or a combination wherein $R^{4b}$ represents a hydrogen atom;

$R^{4c}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4d}$ represents a hydrogen atom.

[Aspect A63] The compound according to any one of the Aspects A1 to A54, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4e}$ represents a halogen atom or a hydrogen atom; and the combination of $R^{4b}$, $R^{4c}$, and $R^{4d}$ represents:

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom;

$R^{4c}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4d}$ represents a hydrogen atom;

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom;

$R^{4c}$ represents a hydrogen atom; and $R^{4d}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom;

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4c}$ and $R^{4d}$ each represent a hydrogen atom; or a combination wherein $R^{4b}$ represents a hydrogen atom;

$R^{4c}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4d}$ represents a hydrogen atom.

[Aspect $A^{64}$] The compound according to any one of the Aspects $A^1$ to $A^{54}$, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkoxy group optionally substituted with one or more halogen atom(s), a C1-C6 alkylsulfanyl group optionally substituted with one or more halogen atom(s), or a hydrogen atom; and $R^{4e}$ represents a halogen atom or a hydrogen atom;

provided that not all of $R^{4b}$, $R^{4c}$, $R^{4d}$, and $R^{4e}$ represent hydrogen atoms.

[Aspect A65] The compound according to any one of the Aspects A1 to A54, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkoxy group optionally substituted with one or more halogen atom(s), a C1-C6 alkylsulfanyl group optionally substituted with one or more halogen atom(s), or a hydrogen atom; and $R^{4e}$ represents a hydrogen atom;

provided that not all of $R^{4b}$, $R^{4c}$, $R^{4d}$, and $R^{4e}$ represent hydrogen atoms.

[Aspect B1] A compound represented by formula (IB)

(IB)

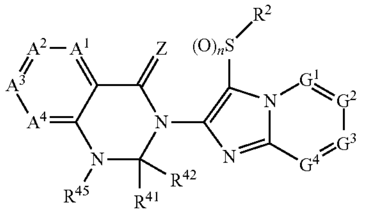

[wherein the symbols are the same as defined in [2]],

[Aspect B2] The compound according to the Aspect B1, wherein $R^{41}$ and $R^{42}$ are identical to or different from each other, and each represent a C1-C6 chain hydrocarbon group optionally substituted with one or more halogen atom (s), or a hydrogen atom; and $R^{45}$ represents a C1-C6 chain hydrocarbon group optionally substituted with one or more substituent(s) selected from Group X, or a hydrogen atom.

[Aspect B3] The compound according to the Aspect B1, wherein $R^{41}$, $R^{42}$, and $R^{45}$ are identical to or different from each other, and each represent a C1-C6 alkyl group or a hydrogen atom.

[Aspect B4] The compound according to the Aspect B1, wherein $G^1$ represents $CR^{3a}$;

$G^2$ represents $CR^{3b}$;

$G^3$ represents $CR^{3c}$;

$G^4$ represents a nitrogen atom or $CR^{3a}$;

$R^{3a}$, $R^{3c}$, and $R^{3d}$ each represent a hydrogen atom; and $R^{3b}$ represents a C1-C6 alkyl group optionally substituted with one or more halogen atom(s), a halogen atom, or a hydrogen atom.

[Aspect B5] The compound according to the Aspect B1, wherein $G^1$ represents $CR^{3a}$;

$G^2$ represents $CR^{3b}$;

$G^3$ represents $CR^{3c}$;

$G^4$ represents a nitrogen atom or $CR^{3d}$;

$R^{3a}$, $R^{3c}$, and $R^{3d}$ each represent a hydrogen atom; and $R^{3b}$ represents a halogen atom.

[Aspect B6] The compound according to the Aspect B1, wherein $G^1$ represents $CR^{3a}$;

$G^2$ represents $CR^{3b}$;

$G^3$ represents $CR^{3c}$;

$G^4$ represents $CR^{3a}$;

$R^{3a}$, $R^{3c}$, and $R^{3d}$ each represent a hydrogen atom; and $R^{3b}$ represents a C1-C6 alkyl group optionally substituted with one or more halogen atom(s), a halogen atom, or a hydrogen atom.

[Aspect B7] The compound according to the Aspect B1, wherein $G^1$ represents $CR^{3a}$;

$G^2$ represents $CR^{3b}$;

$G^3$ represents $CR^{3c}$;

$G^4$ represents $CR^{3d}$;

$R^{3a}$, $R^{3c}$, and $R^{3d}$ each represent a hydrogen atom; and $R^{3b}$ represents a halogen atom.

[Aspect B8] The compound according to the Aspect B2, wherein $G^1$ represents $CR^{3a}$;

$G^2$ represents $CR^{3b}$;

$G^3$ represents $CR^{3c}$;

$G^4$ represents a nitrogen atom or $CR^{3a}$;

$R^{3a}$, $R^{3c}$, and $R^{3d}$ each represent a hydrogen atom; and $R^{3b}$ represents a C1-C6 alkyl group optionally substituted with one or more halogen atom(s), a halogen atom, or a hydrogen atom.

[Aspect B9] The compound according to the Aspect B3, wherein $G^1$ represents $CR^{3a}$;

$G^2$ represents $CR^{3b}$;

$G^3$ represents $CR^{3c}$;

$G^4$ represents a nitrogen atom or $CR^{3a}$;

$R^{3a}$, $R^{3c}$, and $R^{3d}$ each represent a hydrogen atom; and $R^{3b}$ represents a C1-C6 alkyl group optionally substituted with one or more halogen atom(s), a halogen atom, or a hydrogen atom.

[Aspect B10] The compound according to the Aspect B2, wherein $G^1$ represents $CR^{3a}$;

$G^2$ represents $CR^{3b}$;

$G^3$ represents $CR^{3c}$;

$G^4$ represents a nitrogen atom or $CR^{3a}$;

$R^{3a}$, $R^{3c}$, and $R^{3d}$ each represent a hydrogen atom; and $R^{3b}$ represents a halogen atom.

[Aspect B11] The compound according to the Aspect B3, wherein $G^1$ represents $CR^{3a}$;

$G^2$ represents $CR^{3b}$;

$G^3$ represents $CR^{3c}$;

$G^4$ represents a nitrogen atom or $CR^{3a}$;

$R^{3a}$, $R^{3c}$, and $R^{3d}$ each represent a hydrogen atom; and $R^{3b}$ represents a halogen atom.

[Aspect B12] The compound according to the Aspect B2, wherein $G^1$ represents $CR^{3a}$;

$G^2$ represents $CR^{3b}$;

$G^3$ represents $CR^{3c}$;

$G^4$ represents $CR^{3d}$;

$R^{3a}$, $R^{3c}$, and $R^{3d}$ each represent a hydrogen atom; and $R^{3b}$ represents a C1-C6 alkyl group optionally substituted with one or more halogen atom(s), a halogen atom, or a hydrogen atom.

[Aspect B13] The compound according to the Aspect B3, wherein $G^1$ represents $CR^{3a}$;

$G^2$ represents $CR^{3b}$;

$G^3$ represents $CR^{3c}$;

$G^4$ represents $CR^{3d}$;

$R^{3a}$, $R^{3c}$, and $R^{3d}$ each represent a hydrogen atom; and $R^{3b}$ represents a C1-C6 alkyl group optionally substituted with one or more halogen atom(s), a halogen atom, or a hydrogen atom.

[Aspect B14] The compound according to the Aspect B2, wherein $G^1$ represents $CR^{3a}$;

$G^2$ represents $CR^{3b}$;

$G^3$ represents $CR^{3c}$;

$G^4$ represents $CR^{3a}$;

$R^{3a}$, $R^{3c}$, and $R^{3d}$ each represent a hydrogen atom; and $R^{3b}$ represents a halogen atom.

[Aspect B15] The compound according to the Aspect B3, wherein $G^1$ represents $CR^{3a}$;

$G^2$ represents $CR^{3b}$;

$G^3$ represents $CR^{3c}$;

$G^4$ represents $CR^{3d}$;

$R^{3a}$, $R^{3c}$, and $R^{3d}$ each represent a hydrogen atom; and $R^{3b}$ represents a halogen atom.

[Aspect B16] The compound according to the Aspect B1, wherein

Z represents an oxygen atom; and $R^2$ represents a C1-C6 alkyl group.

[Aspect B17] The compound according to the Aspect B1, wherein

Z represents an oxygen atom; and $R^2$ represents an ethyl group.

[Aspect B18] The compound according to the Aspect B2, wherein

Z represents an oxygen atom; and $R^2$ represents a C1-C6 alkyl group.

[Aspect B19] The compound according to the Aspect B3, wherein

Z represents an oxygen atom; and $R^2$ represents a C1-C6 alkyl group.

[Aspect B20] The compound according to the Aspect B4, wherein

Z represents an oxygen atom; and $R^2$ represents a C1-C6 alkyl group.

[Aspect B21] The compound according to the Aspect B5, wherein

Z represents an oxygen atom; and $R^2$ represents a C1-C6 alkyl group.

[Aspect B22] The compound according to the Aspect B6, wherein

Z represents an oxygen atom; and $R^2$ represents a C1-C6 alkyl group.

[Aspect B23] The compound according to the Aspect B7, wherein

Z represents an oxygen atom; and $R^2$ represents a C1-C6 alkyl group.

[Aspect B24] The compound according to the Aspect B8, wherein

Z represents an oxygen atom; and $R^2$ represents a C1-C6 alkyl group.

[Aspect B25] The compound according to the Aspect B9, wherein

Z represents an oxygen atom; and $R^2$ represents a C1-C6 alkyl group.

[Aspect B26] The compound according to the Aspect B10, wherein

Z represents an oxygen atom; and $R^2$ represents a C1-C6 alkyl group.

[Aspect B27] The compound according to the Aspect B11, wherein

Z represents an oxygen atom; and $R^2$ represents a C1-C6 alkyl group.

[Aspect B28] The compound according to the Aspect B12, wherein

Z represents an oxygen atom; and $R^2$ represents a C1-C6 alkyl group.

[Aspect B29] The compound according to the Aspect B13, wherein

Z represents an oxygen atom; and $R^2$ represents a C1-C6 alkyl group.

[Aspect B30] The compound according to the Aspect B14, wherein

Z represents an oxygen atom; and $R^2$ represents a C1-C6 alkyl group.

[Aspect B31] The compound according to the Aspect B15, wherein

Z represents an oxygen atom; and $R^2$ represents a C1-C6 alkyl group.

[Aspect B32] The compound according to the Aspect B2, wherein

Z represents an oxygen atom; and $R^2$ represents an ethyl group.

[Aspect B33] The compound according to the Aspect B3, wherein

Z represents an oxygen atom; and $R^2$ represents an ethyl group.

[Aspect B34] The compound according to the Aspect B4, wherein

Z represents an oxygen atom; and $R^2$ represents an ethyl group.

[Aspect B35] The compound according to the Aspect B5, wherein

Z represents an oxygen atom; and $R^2$ represents an ethyl group.

[Aspect B36] The compound according to the Aspect B6, wherein

Z represents an oxygen atom; and $R^2$ represents an ethyl group.

[Aspect B37] The compound according to the Aspect B7, wherein

Z represents an oxygen atom; and $R^2$ represents an ethyl group.

[Aspect B38] The compound according to the Aspect B8, wherein

Z represents an oxygen atom; and $R^2$ represents an ethyl group.

[Aspect B39] The compound according to the Aspect B9, wherein

Z represents an oxygen atom; and $R^2$ represents an ethyl group.

[Aspect B40] The compound according to the Aspect B10, wherein

Z represents an oxygen atom; and $R^2$ represents an ethyl group.

[Aspect B41] The compound according to the Aspect B11, wherein

Z represents an oxygen atom; and $R^2$ represents an ethyl group.

[Aspect B42] The compound according to the Aspect B12, wherein

Z represents an oxygen atom; and $R^2$ represents an ethyl group.

[Aspect B43] The compound according to the Aspect B13, wherein

Z represents an oxygen atom; and $R^2$ represents an ethyl group.

[Aspect B44] The compound according to the Aspect B14, wherein

Z represents an oxygen atom; and $R^2$ represents an ethyl group.

[Aspect B45] The compound according to the Aspect B15, wherein

Z represents an oxygen atom; and $R^2$ represents an ethyl group.

[Aspect B46] The compound according to any one of the Aspects B1 to B45, wherein the combination of $A^1$, $A^2$, $A^3$, and $A^4$ represents:

a combination wherein $A^1$ represents $CR^{4a}$, $A^2$ represents $CR^{4b}$, $A^3$ represents $CR^{4a}$, and $A^4$ represents a nitrogen atom or $CR^{4d}$;

a combination wherein $A^1$ represents $CR^{4a}$, $A^2$ represents a nitrogen atom, $A^3$ represents $CR^{4a}$, and $A^4$ represents $CR^{4d}$; or a combination wherein $A^1$ represents $CR^{4a}$, $A^2$ represents $CR^{4b}$, $A^3$ represents a nitrogen atom, and $A^4$ represents $CR^{4d}$;

$R^{4a}$ and $R^{4d}$ each represent a hydrogen atom; and $R^{4b}$ and $R^{4c}$ are identical to or different from each other, and each represent a C1-C6 chain hydrocarbon group optionally substituted with one or more substituent(s) selected from Group X, $OR^{44}$, a halogen atom, or a hydrogen atom;

provided that in the combinations of $A^1$, $A^2$, $A^3$, and $A^4$:

a combination wherein $A^1$, $A^2$, $A^3$, and $A^4$ each represent CH;

a combination wherein $A^1$, $A^2$, and $A^3$ each represent CH, and $A^4$ represents a nitrogen atom;

a combination wherein $A^1$, $A^2$, and $A^4$ each represent CH, and $A^3$ represents a nitrogen atom; and a combination wherein $A^1$, $A^3$, and $A^4$ each represent CH, and $A^2$ represents a nitrogen atom are excluded.

[Aspect B47] The compound according to any one of the Aspects B1 to B45, wherein the combination of $A^1$, $A^2$, $A^3$, and $A^4$ represents:

a combination wherein $A^1$ represents $CR^{4a}$, $A^2$ represents $CR^{4b}$, $A^3$ represents $CR^{4c}$, and $A^4$ represents a nitrogen atom or $CR^{4d}$;

a combination wherein $A^1$ represents $CR^{4a}$, $A^2$ represents a nitrogen atom, $A^3$ represents $CR^{4c}$, and $A^4$ represents $CR^{4d}$; or a combination wherein $A^1$ represents $CR^{4a}$, $A^2$ represents $CR^{4b}$, $A^3$ represents a nitrogen atom, and $A^4$ represents $CR^{4d}$;

$R^{4a}$ and $R^{4d}$ each represent a hydrogen atom; and $R^{4b}$ and $R^{4c}$ are identical to or different from each other, and each represent a C1-C6 alkyl group optionally substituted with one or more halogen atom(s), a C1-C6 alkoxy group optionally substituted with one or more halogen atom(s), or a hydrogen atom; provided that in the combinations of $A^1$, $A^2$, $A^3$, and $A^4$:

a combination wherein $A^1$, $A^2$, $A^3$, and $A^4$ each represent CH;

a combination wherein $A^1$, $A^2$, and $A^3$ each represent CH, and $A^4$ represents a nitrogen atom;

a combination wherein $A^1$, $A^2$, and $A^4$ each represent CH, and $A^3$ represents a nitrogen atom; and a combination wherein $A^1$, $A^3$, and $A^4$ each represent CH, and $A^2$ represents a nitrogen atom are excluded.

[Aspect B48] The compound according to any one of the Aspects B1 to B45, wherein $A^1$ represents $CR^{4a}$;

$A^2$ represents $CR^{4b}$;

$A^3$ represents $CR^{4c}$;

$A^4$ represents $CR^{4d}$;

$R^{4a}$ and $R^{4d}$ each represent a hydrogen atom; and $R^{4b}$ and $R^{4c}$ are identical to or different from each other, and each represent a C1-C6 chain hydrocarbon group optionally substituted with one or more substituent(s) selected from Group X, $OR^{44}$, a halogen atom, or a hydrogen atom;

provided that a combination wherein $R^{4b}$ and $R^{4c}$ each represent a hydrogen atom is excluded.

[Aspect B49] The compound according to any one of the Aspects B1 to B45, wherein $A^1$ represents $CR^{4a}$;

$A^2$ represents $CR^{4b}$;

$A^3$ represents $CR^{4c}$;

$A^4$ represents $CR^{4d}$;

$R^{4a}$ and $R^{4d}$ each represent a hydrogen atom; and $R^{4b}$ and $R^{4c}$ are identical to or different from each other, and each represent a C1-C6 alkyl group optionally substituted with one or more halogen atom(s), a C1-C6 alkoxy group optionally substituted with one or more halogen atom(s), or a hydrogen atom;

provided that a combination wherein $R^{4b}$ and $R^{4c}$ each represent a hydrogen atom is excluded.

[Aspect B50] A compound represented by formula (IB)

(IB)

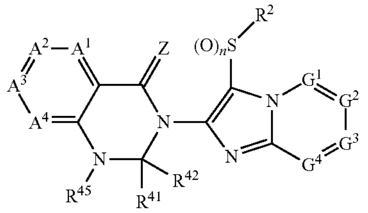

[wherein the symbols are the same as defined in [1]].

[Aspect B51] The compound according to the Aspect B50, wherein $R^{41}$ and $R^{42}$ are identical to or different from each other, and each represent a C1-C6 chain hydrocarbon group optionally substituted with one or more halogen atom(s), or a hydrogen atom; and $R^{45}$ represents a C1-C6 chain hydrocarbon group optionally substituted with one or more substituent (s) selected from Group X, or a hydrogen atom.

[Aspect B52] The compound according to the Aspect B50, wherein $R^{41}$,$R^{42}$ and $R^{45}$ are identical to or different from each other, and each represent a C1-C6 alkyl group or a hydrogen atom.

[Aspect B53] The compound according to the Aspect B50, wherein $G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), a halogen atom, or a hydrogen atom.

[Aspect B54] The compound according to the Aspect B50, wherein $G^1$ represents $CR^{3a}$;
$G^2$ represents $CR^{3b}$;
$G^3$ represents $CR^{3c}$;
$G^4$ represents a nitrogen atom or $CR^{3a}$;
$R^{3a}$, $R^{3c}$, and $R^{3d}$ each represent a hydrogen atom; and
$R^{3b}$ represents a halogen atom.

[Aspect B55] The compound according to the Aspect B50, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), a halogen atom, or a hydrogen atom.

[Aspect B56] The compound according to the Aspect B50, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a halogen atom.

[Aspect B57] The compound according to the Aspect B51, wherein $G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), a halogen atom, or a hydrogen atom.

[Aspect B58] The compound according to the Aspect B52, wherein $G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), a halogen atom, or a hydrogen atom.

[Aspect B59] The compound according to the Aspect B51, wherein $G^1$ represents $CR^{3a}$;
$G^2$ represents $CR^{3b}$;
$G^3$ represents $CR^{3c}$;
$G^4$ represents a nitrogen atom or $CR^{3a}$;
$R^{3a}$, $R^{3c}$, and $R^{3d}$ each represent a hydrogen atom; and
$R^{3b}$ represents a halogen atom.

[Aspect B60] The compound according to the Aspect B52, wherein $G^1$ represents $CR^{3a}$;
$G^2$ represents $CR^{3b}$;
$G^3$ represents $CR^{3c}$;
$G^4$ represents a nitrogen atom or $CR^{3d}$;
$R^{3a}$, $R^{3c}$, and $R^{3d}$ each represent a hydrogen atom; and
$R^{3b}$ represents a halogen atom.

[Aspect B61] The compound according to the Aspect B51, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a C1-C6 alkyl group optionally substituted with one or more halogen atom(s), a halogen atom, or a hydrogen atom.

[Aspect B62] The compound according to the Aspect B52, wherein $G^1$ represents $CR^{3a}$;
$G^2$ represents $CR^{3b}$;
$G^3$ represents $CR^{3c}$;
$G^4$ represents $CR^{3a}$;
$R^{3a}$, $R^{3c}$, and $R^{3d}$ each represent a hydrogen atom; and
$R^{3b}$ represents a C1-C6 alkyl group optionally substituted with one or more halogen atom(s), a halogen atom, or a hydrogen atom.

[Aspect B63] The compound according to the Aspect B51, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a halogen atom.

[Aspect B64] The compound according to the Aspect B52, wherein $G^1$ represents $CR^{3a}$;
$G^2$ represents $CR^{3b}$;
$G^3$ represents $CR^{3c}$;
$G^4$ represents $CR^{3d}$;
$R^{3a}$, $R^{3c}$, and $R^{3d}$ each represent a hydrogen atom; and
$R^{3b}$ represents a halogen atom.

[Aspect B65] The compound according to the Aspect B50, wherein

Z represents an oxygen atom; and
$R^2$ represents a C1-C6 alkyl group.

[Aspect B66] The compound according to the Aspect B50, wherein

Z represents an oxygen atom; and
$R^2$ represents an ethyl group.

[Aspect B67] The compound according to the Aspect B51, wherein

Z represents an oxygen atom; and
$R^2$ represents a C1-C6 alkyl group.

[Aspect B68] The compound according to the Aspect B52, wherein

Z represents an oxygen atom; and
$R^2$ represents a C1-C6 alkyl group.

[Aspect B69] The compound according to the Aspect B53, wherein

Z represents an oxygen atom; and
$R^2$ represents a C1-C6 alkyl group.

[Aspect B70] The compound according to the Aspect B54, wherein

Z represents an oxygen atom; and $R^2$ represents a C1-C6 alkyl group.

[Aspect B71] The compound according to the Aspect B55, wherein

Z represents an oxygen atom; and $R^2$ represents a C1-C6 alkyl group.

[Aspect B72] The compound according to the Aspect B56, wherein

Z represents an oxygen atom; and $R^2$ represents a C1-C6 alkyl group.

[Aspect B73] The compound according to the Aspect B57, wherein

Z represents an oxygen atom; and $R^2$ represents a C1-C6 alkyl group.

[Aspect B74] The compound according to the Aspect B58, wherein

Z represents an oxygen atom; and $R^2$ represents a C1-C6 alkyl group.

[Aspect B75] The compound according to the Aspect B59, wherein

Z represents an oxygen atom; and $R^2$ represents a C1-C6 alkyl group.

[Aspect B76] The compound according to the Aspect B60, wherein

Z represents an oxygen atom; and $R^2$ represents a C1-C6 alkyl group.

[Aspect B77] The compound according to the Aspect B61, wherein

Z represents an oxygen atom; and $R^2$ represents a C1-C6 alkyl group.

[Aspect B78] The compound according to the Aspect B62, wherein

Z represents an oxygen atom; and $R^2$ represents a C1-C6 alkyl group.

[Aspect B79] The compound according to the Aspect B63, wherein

Z represents an oxygen atom; and $R^2$ represents a C1-C6 alkyl group.

[Aspect B80] The compound according to the Aspect B64, wherein

Z represents an oxygen atom; and $R^2$ represents a C1-C6 alkyl group.

[Aspect B81] The compound according to the Aspect B51, wherein

Z represents an oxygen atom; and $R^2$ represents an ethyl group.

[Aspect B82] The compound according to the Aspect B52, wherein

Z represents an oxygen atom; and $R^2$ represents an ethyl group.

[Aspect B83] The compound according to the Aspect B53, wherein

Z represents an oxygen atom; and $R^2$ represents an ethyl group.

[Aspect B84] The compound according to the Aspect B54, wherein

Z represents an oxygen atom; and $R^2$ represents an ethyl group.

[Aspect B85] The compound according to the Aspect B55, wherein

Z represents an oxygen atom; and $R^2$ represents an ethyl group.

[Aspect B86] The compound according to the Aspect B56, wherein

Z represents an oxygen atom; and $R^2$ represents an ethyl group.

[Aspect B87] The compound according to the Aspect B57, wherein

Z represents an oxygen atom; and $R^2$ represents an ethyl group.

[Aspect B88] The compound according to the Aspect B58, wherein

Z represents an oxygen atom; and $R^2$ represents an ethyl group.

[Aspect B89] The compound according to the Aspect B59, wherein

Z represents an oxygen atom; and $R^2$ represents an ethyl group.

[Aspect B90] The compound according to the Aspect B60, wherein

Z represents an oxygen atom; and $R^2$ represents an ethyl group.

[Aspect B91] The compound according to the Aspect B61, wherein

Z represents an oxygen atom; and $R^2$ represents an ethyl group.

[Aspect B92] The compound according to the Aspect B62, wherein

Z represents an oxygen atom; and $R^2$ represents an ethyl group.

[Aspect B93] The compound according to the Aspect B63, wherein

Z represents an oxygen atom; and $R^2$ represents an ethyl group.

[Aspect B94] The compound according to the Aspect B64, wherein

Z represents an oxygen atom; and $R^2$ represents an ethyl group.

[Aspect B95] The compound according to any one of the Aspects B50 to B94, wherein the combination of $A^1$, $A^2$, $A^3$, and $A^4$ represents:

a combination wherein $A^1$ represents $CR^{4a}$, $A^2$ represents $CR^{4b}$, $A^3$ represents $CR^{4a}$, and $A^4$ represents a nitrogen atom or $CR^{4d}$;

a combination wherein $A^1$ represents $CR^{4a}$, $A^2$ represents a nitrogen atom, $A^3$ represents $CR^{4c}$, and $A^4$ represents $CR^{4d}$; or a combination wherein $A^1$ represents $CR^{4a}$, $A^2$ represents $CR^{4b}$, $A^3$ represents a nitrogen atom, and $A^4$ represents $CR^{4d}$;

$R^{4a}$ and $R^{4d}$ each represent a hydrogen atom; and $R^{4b}$ and $R^{4c}$ are identical to or different from each other, and each represent a C1-C6 chain hydrocarbon group optionally substituted with one or more substituent(s) selected from Group X, $OR^{44}$, a halogen atom, or a hydrogen atom;

provided that in the combinations of $A^1$, $A^2$, $A^3$, and $A^4$:

a combination wherein $A^1$, $A^2$, $A^3$, and $A^4$ each represent CH;

a combination wherein $A^1$, $A^2$, and $A^3$ each represent CH, and $A^4$ represents a nitrogen atom;

a combination wherein $A^1$, $A^2$, and $A^4$ each represent CH, and $A^3$ represents a nitrogen atom; and a combination wherein $A^1$, $A^3$, and $A^4$ each represent CH, and $A^2$ represents a nitrogen atom are excluded.

[Aspect B96] The compound according to any one of the Aspects B50 to B94, wherein the combination of $A^1$, $A^2$, $A^3$, and $A^4$ represents:

a combination wherein $A^1$ represents $CR^{4a}$, $A^2$ represents $CR^{4b}$, $A^3$ represents $CR^{4c}$, and $A^4$ represents a nitrogen atom or $CR^{4d}$;

a combination wherein $A^1$ represents $CR^{4a}$, $A^2$ represents a nitrogen atom, $A^3$ represents $CR^{4c}$, and $A^4$ represents $CR^{4d}$; or a combination wherein $A^1$ represents $CR^{4a}$, $A^2$ represents $CR^{4b}$, $A^3$ represents a nitrogen atom, and $A^4$ represents $CR^{4d}$;

$R^{4a}$ and $R^{4d}$ each represent a hydrogen atom; and $R^{4b}$ and $R^{4c}$ are identical to or different from each other, and each represent a C1-C6 alkyl group optionally substituted with one or more halogen atom(s), a C1-C6 alkoxy group optionally substituted with one or more halogen atom(s), or a hydrogen atom; provided that in the combinations of $A^1$, $A^2$, $A^3$, and $A^4$:

a combination wherein $A^1$, $A^2$, $A^3$, and $A^4$ each represent CH;

a combination wherein $A^1$, $A^2$, and $A^3$ each represent CH, and $A^4$ represents a nitrogen atom;

a combination wherein $A^1$, $A^2$, and $A^4$ each represent CH, and $A^3$ represents a nitrogen atom; and a combination wherein $A^1$, $A^3$, and $A^4$ each represent CH, and $A^2$ represents a nitrogen atom are excluded.

[Aspect B97] The compound according to any one of the Aspects B50 to B94, wherein $A^1$ represents $CR^{4a}$;

$A^2$ represents $CR^{4b}$;

$A^3$ represents $CR^{4c}$;

$A^4$ represents $CR^{4d}$;

$R^{4a}$ and $R^{4d}$ each represent a hydrogen atom; and $R^{4b}$ and $R^{4c}$ are identical to or different from each other, and each represent a C1-C6 chain hydrocarbon group optionally substituted with one or more substituent(s) selected from Group X, $OR^{44}$, a halogen atom, or a hydrogen atom;

provided that a combination wherein $R^{4b}$ and $R^{4c}$ each represent a hydrogen atom is excluded.

[Aspect B98] The compound according to any one of the Aspects B50 to B94, wherein $A^1$ represents $CR^{4a}$;

$A^2$ represents $CR^{4b}$;

$A^3$ represents $CR^{4c}$;

$A^4$ represents $CR^{4d}$;

$R^{4a}$ and $R^{4d}$ each represent a hydrogen atom; and $R^{4b}$ and $R^{4c}$ are identical to or different from each other, and each represent a C1-C6 alkyl group optionally substituted with one or more halogen atom(s), a C1-C6 alkoxy group optionally substituted with one or more halogen atom(s), or a hydrogen atom;

provided that a combination wherein $R^{4b}$ and $R^{4c}$ each represent a hydrogen atom is excluded.

Aspects of the compound represented by formula (II) (hereinafter also referred to as "Intermediate compound C") include the following compounds.

[Aspect C1] The compound according to the Intermediate compound C, wherein the combination of $G^1$, $G^2$, $G^3$, and $G^4$ represents:

a combination wherein $G^1$ represents $CR^{3a}$, $G^2$ represents $CR^{3b}$, $G^3$ represents $CR^{3c}$, and $G^4$ represents a nitrogen atom or $CR^{3a}$;

a combination wherein $G^1$ represents a nitrogen atom, $G^2$ represents $CR^{3b}$, $G^3$ represents $CR^{3c}$, and $G^4$ represents $CR^{3d}$;

a combination wherein $G^1$ represents $CR^{3a}$, $G^2$ represents a nitrogen atom, $G^3$ represents $CR^{3c}$, and $G^4$ represents $CR^{3d}$; or a combination wherein $G^1$ represents $CR^{3a}$, $G^2$ represents $CR^{3b}$, $G^3$ represents a nitrogen atom, and $G^4$ represents $CR^{3d}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect C2] The compound according to the Intermediate compound C, wherein $G^1$ represents $CR^{3a}$;

$G^2$ represents $CR^{3b}$;

$G^3$ represents $CR^{3c}$;

$G^4$ represents a nitrogen atom or $CR^{3a}$;

$R^{3a}$, $R^{3c}$, and $R^{3d}$ each represent a hydrogen atom; and $R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect C3] The compound according to the Intermediate compound C, wherein $G^1$ represents $CR^{3a}$;

$G^2$ represents $CR^{3b}$;

$G^3$ represents $CR^{3c}$;

$G^4$ represents a nitrogen atom or $CR^{3d}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect C4] The compound according to the Intermediate compound C, wherein $G^1$ represents $CR^{3a}$;

$G^2$ represents $CR^{3b}$;

$G^3$ represents $CR^{3c}$;

$G^4$ represents $CR^{3d}$;

$R^{3a}$, $R^{3c}$, and $R^{3d}$ each represent a hydrogen atom; and $R^{3b}$ represents a C1-C6 alkyl group, a C3-C7 cycloalkyl group {wherein said C1-C6 alkyl group and said C3-C7 cycloalkyl group are optionally substituted with one or more substituent(s) selected from the group consisting of a halogen atom and a cyano group}, a phenyl group, a pyridyl group {wherein said phenyl group and said pyridyl group are optionally substituted with one or more halogen atom(s)}, a halogen atom, or a hydrogen atom.

[Aspect C5] The compound according to the Intermediate compound C, wherein $G^1$ represents $CR^{3a}$;

$G^2$ represents $CR^{3b}$;

$G^3$ represents $CR^{3c}$;

$G^4$ represents $CR^{3d}$;

$R^{3a}$, $R^{3c}$, and $R^{3d}$ each represent a hydrogen atom; and $R^{3b}$ represents a C1-C6 alkyl group optionally substituted with one or more halogen atom(s), or a halogen atom.

[Aspect C6] The compound according to the Intermediate compound C, wherein

Z represents an oxygen atom; and $R^2$ represents a C1-C6 alkyl group.

[Aspect C7] The compound according to the Intermediate compound C, wherein

Z represents an oxygen atom; and $R^2$ represents an ethyl group.

[Aspect C8] The compound according to the Aspect C1, wherein

Z represents an oxygen atom; and $R^2$ represents a C1-C6 alkyl group.

[Aspect C9] The compound according to the Aspect C2, wherein

Z represents an oxygen atom; and $R^2$ represents a C1-C6 alkyl group.

[Aspect C10] The compound according to the Aspect C3, wherein

Z represents an oxygen atom; and $R^2$ represents a C1-C6 alkyl group.

[Aspect C11] The compound according to the Aspect C4, wherein

Z represents an oxygen atom; and $R^2$ represents a C1-C6 alkyl group.

[Aspect C12] The compound according to the Aspect C5, wherein

Z represents an oxygen atom; and $R^2$ represents a C1-C6 alkyl group.

[Aspect C13] The compound according to the Aspect C1, wherein

Z represents an oxygen atom; and $R^2$ represents an ethyl group.

[Aspect C14] The compound according to the Aspect C2, wherein

Z represents an oxygen atom; and $R^2$ represents an ethyl group.

[Aspect C15] The compound according to the Aspect C3, wherein

Z represents an oxygen atom; and $R^2$ represents an ethyl group.

[Aspect C16] The compound according to the Aspect C4, wherein

Z represents an oxygen atom; and $R^2$ represents an ethyl group.

[Aspect C17] The compound according to the Aspect C5, wherein

Z represents an oxygen atom; and $R^2$ represents an ethyl group.

[Aspect C18] The compound according to any one of the Aspects C1 to C17 or the Intermediate compound C, wherein the combination of $A^1$, $A^2$, $A^3$, $A^4$, and $A^5$ represents:

a combination wherein $A^1$ represents $CR^{4a}$, $A^2$ represents $CR^{4b}$, $A^3$ represents $CR^{4a}$, $A^4$ represents a nitrogen atom or $CR^{4d}$, and $A^5$ represents $CR^{4e}$;

a combination wherein $A^1$ represents $CR^{4a}$, $A^2$ represents $CR^{4b}$, $A^3$ represents a nitrogen atom, $A^4$ represents $CR^{4d}$, and $A^5$ represents $CR^{4e}$; or a combination wherein $A^1$ represents $CR^{4a}$, $A^2$ represents $CR^{4b}$, $A^3$ represents $CR^{4c}$, $A^4$ represents $CR^{4d}$, and $A^5$ represents a nitrogen atom;

$R^{4a}$ represents a hydrogen atom;

$R^{4b}$, $R^{4c}$, and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom, or a hydrogen atom; and $R^{4e}$ represents a C1-C6 alkyl group, a halogen atom, or a hydrogen atom; provided that in the combinations of $A^1$, $A^2$, $A^3$, $A^4$, and $A^5$:

a combination wherein $A^1$, $A^2$, $A^3$, $A^4$, and $A^5$ each represent CH;

a combination wherein $A^1$, $A^2$, $A^3$, and $A^4$ each represent CH, and $A^5$ represents a nitrogen atom;

a combination wherein $A^1$, $A^2$, $A^3$, and $A^5$ each represent CH, and $A^4$ represents a nitrogen atom; and a combination wherein $A^1$, $A^2$, $A^4$, and $A^5$ each represent CH, and $A^3$ represents a nitrogen atom are excluded.

[Aspect C19] The compound according to any one of the Aspects C1 to C17 or the Intermediate compound C, wherein the combination of $A^1$, $A^2$, $A^3$, $A^4$, and $A^5$ represents:

a combination wherein $A^1$ represents $CR^{4a}$, $A^2$ represents $CR^{4b}$, $A^3$ represents $CR^{4c}$, $A^4$ represents a nitrogen atom or $CR^{4d}$, and $A^5$ represents $CR^{4e}$;

a combination wherein $A^1$ represents $CR^{4a}$, $A^2$ represents $CR^{4b}$, $A^3$ represents a nitrogen atom, $A^4$ represents $CR^{4d}$, and $A^5$ represents $CR^{4e}$; or a combination wherein $A^1$ represents $CR^{4a}$, $A^2$ represents $CR^{4b}$, $A^3$ represents $CR^{4c}$, $A^4$ represents $CR^{4d}$, and $A^5$ represents a nitrogen atom;

$R^{4a}$ represents a hydrogen atom;

$R^{4b}$, $R^{4c}$, and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; and $R^{4e}$ represents a halogen atom or a hydrogen atom;

provided that in the combinations of $A^1$, $A^2$, $A^3$, $A^4$, and $A^5$:

a combination wherein $A^1$, $A^2$, $A^3$, $A^4$, and $A^5$ each represent CH;

a combination wherein $A^1$, $A^2$, $A^3$, and $A^4$ each represent CH, and $A^5$ represents a nitrogen atom;

a combination wherein $A^1$, $A^2$, $A^3$, and $A^5$ each represent CH, and $A^4$ represents a nitrogen atom; and a combination wherein $A^1$, $A^2$, $A^4$, and $A^5$ each represent CH, and $A^3$ represents a nitrogen atom are excluded.

[Aspect C20] The compound according to any one of the Aspects C1 to C17 or the Intermediate compound C, wherein $A^1$ represents $CR^{4a}$;

$A^2$ represents $CR^{4b}$;

$A^3$ represents $CR^{4c}$;

$A^4$ represents a nitrogen atom or $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom, or a hydrogen atom; and $R^{4e}$ represents a C1-C6 alkyl group, a halogen atom, or a hydrogen atom; provided that in the combinations of $A^1$, $A^2$, $A^3$, $A^4$, and $A^5$:

a combination wherein $A^1$, $A^2$, $A^3$, $A^4$, and $A^5$ each represent CH; and a combination wherein $A^1$, $A^2$, $A^3$, and $A^5$ each represent CH, and $A^4$ represents a nitrogen atom are excluded.

[Aspect C21] The compound according to any one of the Aspects C1 to C17 or the Intermediate compound C, wherein $A^1$ represents $CR^{4a}$;

$A^2$ represents $CR^{4b}$;

$A^3$ represents $CR^{4c}$;

$A^4$ represents a nitrogen atom or $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; and $R^{4e}$ represents a halogen atom or a hydrogen atom;

provided that in the combinations of $A^1$, $A^2$, $A^3$, $A^4$, and $A^5$:

a combination wherein $A^1$, $A^2$, $A^3$, $A^4$, and $A^5$ each represent CH; and a combination wherein $A^1$, $A^2$, $A^3$, and $A^5$ each represent CH, and $A^4$ represents a nitrogen atom are excluded.

[Aspect C22] The compound according to any one of the Aspects C1 to C17 or the Intermediate compound C, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom, or a hydrogen atom; and $R^{4e}$ represents a C1-C6 alkyl group, a halogen atom, or a hydrogen atom; provided that not all of $R^{4b}$, $R^{4c}$, $R^{4d}$, and $R^{4e}$ represent hydrogen atoms.

[Aspect C23] The compound according to any one of the Aspects C1 to C17 or the Intermediate compound C, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4e}$ represents a C1-C6 alkyl group, a halogen atom, or a hydrogen atom; and the combination of $R^{4b}$, $R^{4c}$, and $R^{4d}$ represents:

a combination wherein $R^{4b}$ represents a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, or a halogen atom; and $R^{4c}$ and $R^{4d}$ are identical to or different from each other, and each represent a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, a halogen atom or a hydrogen atom; or a combination wherein $R^{4b}$ represents a hydrogen atom;

$R^{4c}$ represents a C1-C6 alkyl group, a C1-C6 alkenyl group, a C3-C7 cycloalkyl group {wherein said C1-C6 alkyl group, said C1-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group, a pyrazolyl group, a triazolyl group {wherein said phenyl group, said pyridyl group, said pyrimidinyl group, said pyrazolyl group, and said triazolyl group are optionally substituted with one or more substituent(s) selected from Group J}, $OR^{44}$, $S(O)_qR^{41}$, a cyano group, or a halogen atom; and $R^{4d}$ represents a hydrogen atom.

[Aspect C24] The compound according to any one of the Aspects C1 to C17 or the Intermediate compound C, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; and $R^{4e}$ represents a halogen atom or a hydrogen atom;

provided that not all of $R^{4b}$, $R^{4c}$, $R^{4d}$, and $R^{4e}$ represent hydrogen atoms.

[Aspect C25] The compound according to any one of the Aspects C1 to C17 or the Intermediate compound C, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4e}$ represents a halogen atom or a hydrogen atom; and the combination of $R^{4b}$, $R^{4c}$, and $R^{4d}$ represents:

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4c}$ and $R^{4d}$ are identical to or different from each other, and each represent a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, a halogen atom, or a hydrogen atom; or a combination wherein $R^{4b}$ represents a hydrogen atom;

$R^{4c}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4d}$ represents a hydrogen atom.

[Aspect C26] The compound according to any one of the Aspects C1 to C17 or the Intermediate compound C, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4e}$ represents a halogen atom or a hydrogen atom; and the combination of $R^{4b}$, $R^{4c}$, and $R^{4d}$ represents: a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom;

$R^{4c}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4d}$ represents a hydrogen atom;

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom;

$R^{4c}$ represents a hydrogen atom; and $R^{4d}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom;

a combination wherein $R^{4b}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4c}$ and $R^{4d}$ each represent a hydrogen atom; or a combination wherein $R^{4b}$ represents a hydrogen atom;

$R^{4c}$ represents a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a cyano group, or a halogen atom; and $R^{4d}$ represents a hydrogen atom.

[Aspect C27] The compound according to any one of the Aspects C1 to C17 or the Intermediate compound C, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkoxy group optionally substituted with one or more halogen atom(s), a C1-C6 alkylsulfanyl group optionally substituted with one or more halogen atom(s), or a hydrogen atom; and $R^{4e}$ represents a halogen atom or a hydrogen atom;

provided that not all of $R^{4b}$, $R^{4c}$, $R^{4d}$, and $R^{4e}$ represent hydrogen atoms.

[Aspect C28] The compound according to any one of the Aspects C1 to C17 or the Intermediate compound C, wherein $A^1$ represents $CR^{4a}$;

$A^2$ represents $CR^{4b}$;

$A^3$ represents $CR^{4c}$;

$A^4$ represents $CR^{4d}$;

$A^5$ represents $CR^{4e}$;

$R^{4a}$ represents a hydrogen atom;

$R^{4b}$, $R^{4c}$, and $R^{4d}$ are identical to or different from each other, and each represent a C1-C6 alkoxy group optionally substituted with one or more halogen atom(s), a C1-C6 alkylsulfanyl group optionally substituted with one or more halogen atom(s), or a hydrogen atom; and $R^{4e}$ represents a hydrogen atom;

provided that not all of $R^{4b}$, $R^{4c}$, $R^{4d}$, and $R^{4e}$ represent hydrogen atoms.

Next, production methods for the Present compounds X are described.

Production Method 1

A compound represented by formula (I-b) (hereinafter referred to as "Compound (I-b)") or a compound represented by formula (I-c) (hereinafter referred to as "Compound (I-c)") may be prepared by reacting a compound represented by formula (I-a) (hereinafter referred to as "Compound (I-a)") with an oxidizing agent.

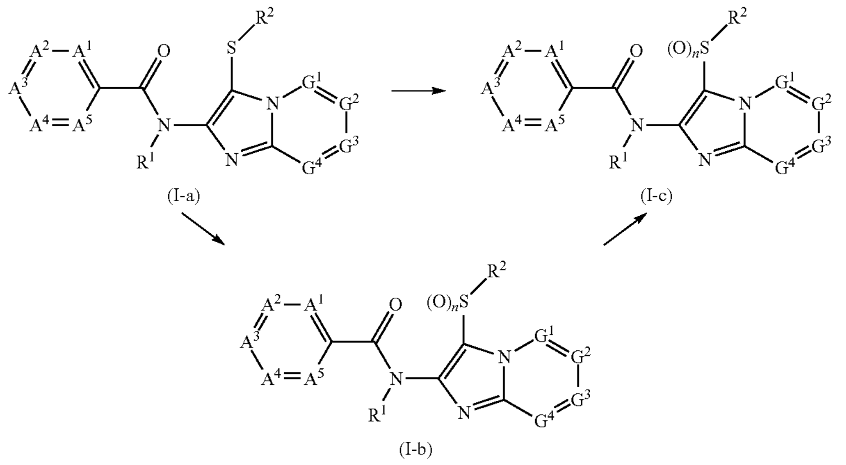

[wherein the symbols are the same as defined above.]

First, a method for producing the Compound (I-b) from the Compound (I-a) is described.

The reaction is usually carried out in a solvent. Examples of the solvent to be used in the reaction include halogenated hydrocarbons such as dichloromethane and chloroform (hereinafter collectively referred to as "halogenated hydrocarbons"); nitriles such as acetonitrile (hereinafter collectively referred to as "nitriles"); alcohols such as methanol and ethanol (hereinafter collectively re erred to as "alcohols"); acetic acid; water; and mixtures of two or more of them.

Examples of the oxidizing agent to be used in the reaction include sodium periodate, m-chloroperbenzoic acid (hereinafter referred to as "mCPBA"), and hydrogen peroxide.

When hydrogen peroxide is used as the oxidizing agent, a base or a catalyst may be used as needed.

Examples of the base to be used in the reaction include sodium carbonate. When a base is used in the reaction, the base is usually used at a ratio of 0.01 to 1 mol relative to 1 mol of the Compound (I-a).

Examples of the catalyst to be used in the reaction include tungstic acid and sodium tungstate. When a catalyst is used in the reaction, the catalyst is usually used at a ratio of 0.01 to 0.5 mol relative to 1 mol of the Compound (I-a).

In the reaction, the oxidizing agent is usually used at a ratio of 1 to 1.2 mol relative to 1 mol of the Compound (I-a).

The reaction temperature is usually within the range of −20 to 80° C. The reaction time is usually within the range of 0.1 to 12 hours(s).

When the reaction is completed, to the reaction mixture is added water, the resulting mixture is subjected to extraction with organic solvent(s), and the resulting organic layer is washed with an aqueous solution of a reducing agent (for example, sodium sulfite or sodium thiosulfate) and an aqueous solution of a base (for example, sodium hydrogen carbonate) as needed. The resulting organic layer is dried and/or concentrated to give the Compound (I-b).

Next, a method for producing the Compound (I-c) from the Compound (I-b) is described.

The reaction is usually carried out in a solvent. Examples of the solvent to be used in the reaction include halogenated hydrocarbons, nitriles, alcohols, acetic acid, water, and mixtures of two or more of them.

Examples of the oxidizing agent to be used in the reaction include mCPBA and hydrogen peroxide.

When hydrogen peroxide is used as the oxidizing agent, a base or a catalyst may be used as needed.

Examples of the base to be used in the reaction include sodium carbonate. When a base is used in the reaction, the base is usually used at a ratio of 0.01 to 1 mol relative to 1 mol of the Compound (I-b).

Examples of the catalyst to be used in the reaction include sodium tungstate. When a catalyst is used in the reaction, the catalyst is usually used at a ratio of 0.01 to 0.5 mol relative to 1 mol of the Compound (I-b).

In the reaction, the oxidizing agent is usually used at a ratio of 1 to 2 mol relative to 1 mol of the Compound (I-b).

The reaction temperature is usually within the range of −20 to 120° C. The reaction time is usually within the range of 0.1 to 12 hours(s).

When the reaction is completed, to the reaction mixture is added water, the resulting mixture is subjected to extraction with organic solvent(s), and the resulting organic layer is washed with an aqueous solution of a reducing agent (for example, sodium sulfite or sodium thiosulfate) and an aqueous solution of a base (for example, sodium hydrogen carbonate) as needed. The resulting organic layer is dried and/or concentrated to give the Compound (I-c).

Also, the Compound (I-c) may be prepared in one step reaction (one-pot) by reacting the Compound (I-a) with an oxidizing agent.

The reaction may be carried out according to the method for producing the Compound (I-c) from the Compound (I-b) by usually using the oxidizing agent at a ratio of 2 to 5 mol relative to 1 mol of the Compound (I-a).

Production Method 2

A compound represented by formula (I-1-A) (hereinafter referred to as "Compound (I-1-A)") may be prepared by reacting a compound represented by formula (M1-1-A) (hereinafter referred to as "Compound (M1-1-A)") with a compound represented by formula (M2-1) (hereinafter referred to as "Compound (M2-1)") in the presence of a condensing agent.

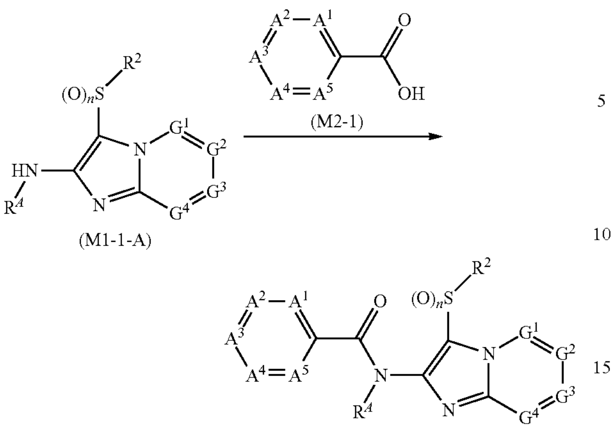

(M2-1)

(M1-1-A)

(I-1-A)

[wherein $R^A$ represents a C1-C6 chain hydrocarbon group optionally substituted with one or more substituent(s) selected from Group W, a C3-C7 cycloalkyl group optionally substituted with one or more substituent (s) selected from Group U, a phenyl group optionally substituted with one or more substituent(s) selected from Group V, a 5 or 6 membered aromatic heterocyclic group optionally substituted with one or more substituent (s) selected from Group V; and the other symbols are the same as defined above.]

The reaction is usually carried out in a solvent. Examples of the solvent to be used in the reaction include ethers such as tetrahydrofuran (hereinafter referred to as "THF") and methyl tert-butyl ether (hereinafter referred to as "MTBE") (hereinafter collectively referred to as "ethers"); halogenated hydrocarbons; aromatic hydrocarbons such as toluene and xylene (hereinafter collectively referred to as "aromatic hydrocarbons"); esters such as ethyl acetate and butyl acetate (hereinafter collectively referred to as "esters"); nitriles; aprotic polar solvents such as N-methylpyrrolidone (hereinafter referred to as "NMP"), N,N-dimethylformamide (hereinafter referred to as "DMF"), and dimethyl sulfoxide (hereinafter referred to as "DMSO") (hereinafter collectively referred to as "aprotic polar solvents"); nitrogen-containing aromatic compounds such as pyridine, picoline, lutidine, and quinoline (hereinafter collectively referred to as "nitrogen-containing aromatic compounds"); and mixtures of two or more of them.

Examples of the condensing agent to be used in the reaction include carbodiimides such as 1-ethyl-3-[3-(dimethylamino)propyl]carbodiimide hydrochloride and 1,3-dicyclohexylcarbodiimide.

In the reaction, a catalyst may be used as needed. Examples of the catalyst to be used in the reaction include 1-hydroxybenzotriazole. When a catalyst is used in the reaction, the catalyst is usually used at a ratio of 0.01 to 0.5 mol relative to 1 mol of the Compound (M1-1-A).

In the reaction, a base may be used as needed. Examples of the base to be used in the reaction include organic bases such as triethylamine, N,N-diisopropylethylamine, pyridine, and 4-(dimethylamino)pyridine (hereinafter collectively referred to as "organic bases"). When a base is used in the reaction, the base is usually used at a ratio of 1 to 2 mol relative to 1 mol of the Compound (M1-1-A).

In the reaction, the Compound (M2-1) is usually used at a ratio of 1 to 2 mol, and the condensing agent is usually used at a ratio of 1 to 2 mol, relative to 1 mol of the Compound (M1-1-A).

The reaction temperature is usually within the range of 0 to 200° C. The reaction time is usually within the range of 0.1 to 12 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-1-A).

The Compound (M2-1) is a commercially available compound or may be prepared by using known method(s).

Production Method 3

The Compound (I-1-A) may also be prepared by reacting the Compound (M1-1-A) with a compound represented by formula (M2-2) (hereinafter referred to as "Compound (M2-2)").

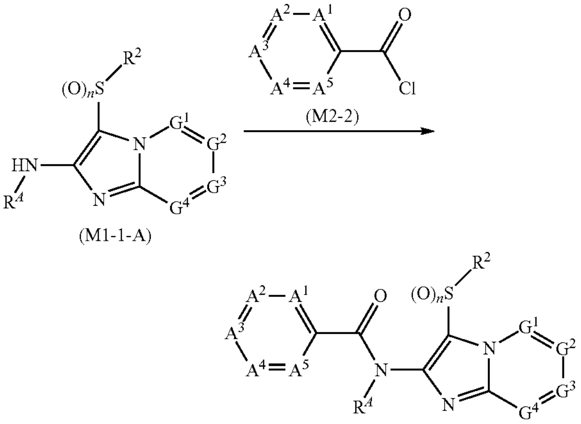

(M2-2)

(M1-1-A)

(I-1-A)

[wherein the symbols are the same as defined above.]

The reaction is usually carried out in a solvent. Examples of the solvent to be used in the reaction include ethers; aliphatic hydrocarbons such as hexane, heptane, and octane (hereinafter collectively referred to as "aliphatic hydrocarbons"); aromatic hydrocarbons; halogenated hydrocarbons; esters; nitriles; aprotic polar solvents; and mixtures of two or more of them.

In the reaction, a base may be used as needed. Examples of the base to be used in the reaction include alkali metal carbonates such as sodium carbonate and potassium carbonate (hereinafter collectively referred to as "alkali metal carbonates"); alkali metal hydroxides such as sodium hydroxide and potassium hydroxide (hereinafter collectively referred to as "alkali metal hydroxides"); and organic bases. When a base is used in the reaction, the base is usually used at a ratio of 1 to 2 mol relative to 1 mol of the Compound (M1-1-A).

In the reaction, the Compound (M2-2) is usually used at a ratio of 0.8 to 1.2 mol relative to 1 mol of the Compound (M1-1-A).

The reaction temperature is usually within the range of −20 to 200° C. The reaction time is usually within the range of 0.1 to 24 hours (s).

When the reaction is completed, the reaction mixture may be subjected to a work-up such as adding water to the reaction mixture, subjecting the resulting mixture to extraction with organic solvent (s), and drying and/or concentrating the resulting organic layer to give the Compound (I-1-A).

The Compound (M2-2) is a commercially available compound or may be prepared by using known method(s).

Production Method 4

A compound represented by formula (I-2-B) (hereinafter referred to as "Compound (I-2-B)") may be prepared by reacting the compound represented by formula (II) (hereinafter referred to as "Compound (II)") with a compound represented by formula (R-1) (hereinafter referred to as "Compound (R-1)") in the presence of a base.

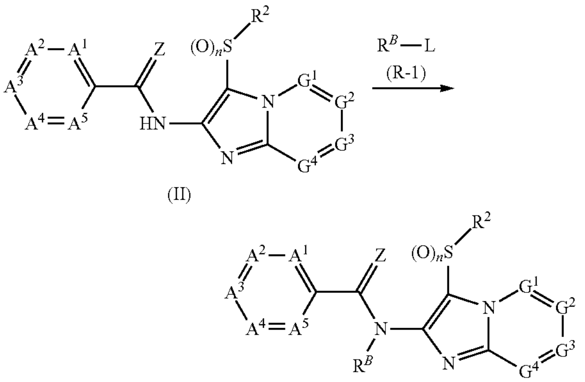

(II)

(I-2-B)

[wherein $R^B$ represents a C1-C6 chain hydrocarbon group optionally substituted with one or more substituent(s) selected from Group W, a C3-C7 cycloalkyl group optionally substituted with one or more substituent(s) selected from Group U, $C(O)R^{51}$, $C(O)OR^{51}$, or $C(O)NR^{51}R^{52}$; L represents a leaving group such as a chlorine atom and a bromine atom; and the other symbols are the same as defined above.]

The reaction is usually carried out in a solvent. Examples of the solvent to be used in the reaction include ethers, aromatic hydrocarbons, nitriles, aprotic polar solvents, and mixtures of two or more of them.

Examples of the base to be used in the reaction include alkali metal hydrides such as sodium hydride (hereinafter collectively referred to as "alkali metal hydrides"), alkali metal carbonates, and organic bases.

In the reaction, the Compound (R-1) is usually used at a ratio of 1 to 5 mol, and the base is usually used at a ratio of 1 to 2 mol, relative to 1 mol of the Compound (II).

The reaction temperature is usually within the range of 0 to 100° C. The reaction time is usually within the range of 0.1 to 24 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-2-B).

The Compound (R-1) is a commercially available compound or may be prepared by using known method(s).

Production Method 5

A compound represented by formula (I-1) (hereinafter referred to as "Compound (I-1)") may be prepared by reacting a compound represented by formula (M1-2) (hereinafter referred to as "Compound (M1-2)") with a compound represented by formula (M2-3) (hereinafter referred to as "Compound (M2-3)").

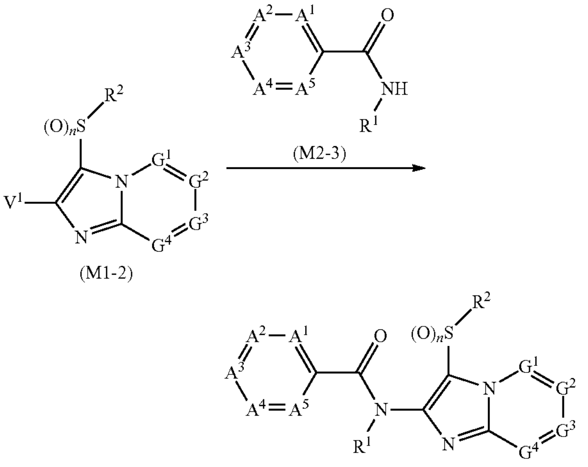

(M1-2)

(I-1)

[wherein $V^1$ represents a halogen atom; and the other symbols are the same as defined above.]

When $V^1$ represents a fluorine atom, the Compound (I-1 may be prepared by reacting the Compound (M1-2) with the Compound (M2-3) in the presence of a base.

The reaction is usually carried out in a solvent. Examples of the solvent to be used in the reaction include ethers, aromatic hydrocarbons, nitriles, aprotic polar solvents, water, and mixtures of two or more of them.

Examples of the base to be used in the reaction include alkali metal carbonates and alkali metal hydrides.

In the reaction, the Compound (M2-3) is usually used at a ratio of 0.8 to 1.2 mol, and the base is usually used at a ratio of 1 to 2 mol, relative to 1 mol of the Compound (M1-2).

The reaction temperature is usually within the range of 0 to 200° C. The reaction time is usually within the range of 0.5 to 24 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-1).

When $V^1$ represents a chlorine atom, a bromine atom, or an iodine atom, the Compound (I-1) may be prepared by reacting the Compound (M1-2) with the Compound (M2-3) in the presence of a base and a copper catalyst or a palladium catalyst.

The reaction is usually carried out in a solvent. Examples of the solvent to be used in the reaction include ethers, aromatic hydrocarbons, nitriles, aprotic polar solvents, water, and mixtures of two or more of them.

Examples of the base to be used in the reaction include alkali metal carbonates; phosphates such as trisodium phosphate and tripotassium phosphate; alkali metal hydrides; organic bases; and cyclic amines such as 1,4-diazabicyclo [2,2,2]octane and diazabicycloundecene.

Examples of the copper catalyst to be used in the reaction include copper(I) iodide, copper(I) bromide, copper(I) chloride, and copper(I) oxide. When a copper catalyst is used in the reaction, the copper catalyst is usually used at a ratio of 0.01 to 0.5 mol relative to 1 mol of the Compound (M1-2).

Examples of the palladium catalyst to be used in the reaction include palladium(II) acetate and tris(dibenzylideneacetone)dipalladium(0). When a palladium catalyst is used in the reaction, the palladium catalyst is usually used at a ratio of 0.01 to 0.2 mol relative to 1 mol of the Compound (M1-2).

In the reaction, a ligand may be used as needed. Examples of the ligand to be used in the reaction include acetylacetone, salen, phenanthroline, triphenylphosphine, and 4,5'-bis(diphenylphosphino)-9,9'-dimethylxanthene. When a ligand is used in the reaction, the ligand is usually used at a ratio of 0.01 to 0.5 mol relative to 1 mol of the Compound (M1-2).

In the reaction, the Compound (M2-3) is usually used at a ratio of 0.8 to 1.2 mol, and the base is usually used at a ratio of 1 to 2 mol, relative to 1 mol of the Compound (M1-2).

The reaction temperature is usually within the range of 0 to 200° C. The reaction time is usually within the range of 0.5 to 24 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-1).

A compound according to the Compound (M2-3) wherein $R^1$ represents $R^A$ or $R^B$ is a commercially available compound or may be prepared by using known method(s).

Production Method 6

The Compound (I-a) may be prepared according to the following scheme.

The reaction temperature is usually within the range of −20 to 200° C. The reaction time is usually within the range of 0.1 to 72 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M3-1).

Next, a step to produce the Compound (I-a) from the Compound (M3-1) is described.

The Compound (I-a) may be prepared by reacting the Compound (M3-1) with a compound represented by formula (R-2) (hereinafter referred to as "Compound (R-2)") in the presence of a metal catalyst and a base.

The reaction is usually carried out in a solvent. Examples of the solvent to be used in the reaction include alcohols, nitriles, ethers, aromatic hydrocarbons, aprotic polar solvents, water, and mixtures of two or more of them.

Examples of the metal catalyst to be used in the reaction include palladium catalysts such as tetrakis(triphenylphosphine)palladium(0), [1,1'-bis(diphenylphosphino)ferrocene] palladium(II) dichloride, tris(dibenzylideneacetone)dipalladium(0), and palladium(II) acetate; nickel catalysts such as bis(cyclooctadiene)nickel(0) and nickel(II) chloride; and copper catalysts such as copper(I) iodide and copper(I) chloride.

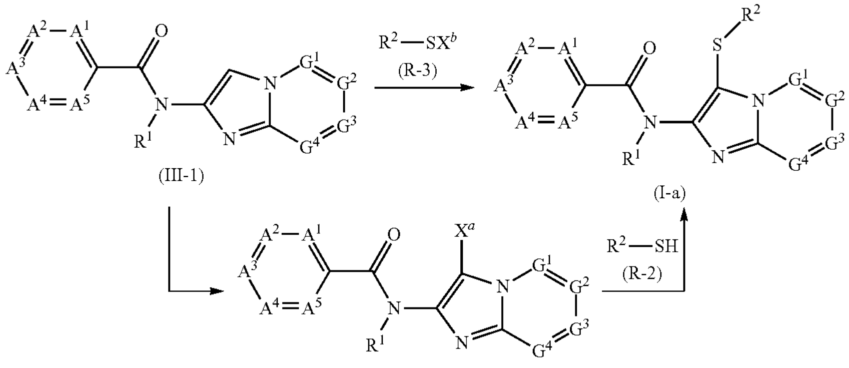

(III-1)

(I-a)

(M3-1)

[wherein $X^a$ represents a chlorine atom, a bromine atom, or an iodine atom; $X^b$ represents $SR^2$ or a hydrogen atom; and the other symbols are the same as defined above.]

First, a step to produce a compound represented by formula (M3-1) (hereinafter referred to as "Compound (M3-1)") from a compound represented by formula (III-1) (hereinafter referred to as "Compound (III-1)") (hereinafter referred to as "Step 6-A") is described.

The Compound (M3-1) may be prepared by reacting the Compound (III-1) with a halogenating agent.

The reaction is usually carried out in a solvent. Examples of the solvent to be used in the reaction include alcohols, nitriles, ethers, aromatic hydrocarbons, aprotic polar solvents, halogenated hydrocarbons, water, and mixtures of two or more of them.

Examples of the halogenating agent include chlorine, bromine, iodine, N-chlorosuccinimide, N-bromosuccinimide, and N-iodosuccinimide.

In the reaction, the halogenating agent is usually used at a ratio of 1 to 20 mol relative to 1 mol of the Compound (III-1).

Examples of the base to be used in the reaction include alkali metal hydrides, alkali metal carbonates, and organic bases.

In the reaction, a ligand may be used. Examples of the ligand include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline. When a ligand is used in the reaction, the ligand is usually used at a ratio of 0.01 to 1 mol relative to 1 mol of the Compound (M3-1).

In the reaction, the Compound (R-2) is usually used at a ratio of 1 to 20 mol, the metal catalyst is usually used at a ratio of 0.01 to 0.5 mol, and the base is usually used at a ratio of 0.1 to 5 mol, relative to 1 mol of the Compound (M3-1).

The reaction temperature is usually within the range of −20 to 200° C. The reaction time is usually within the range of 0.1 to 72 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-a).

The Compound (R-2) is known or may be prepared according to known method(s).

Next, a step to produce the Compound (I-a) from the Compound (III-1) is described.

The Compound (I-a) may also be prepared by reacting the Compound (III-1) with a compound represented by formula (R-3) (hereinafter referred to as "Compound (R-3)") in the presence of a halogenating agent.

The reaction is usually carried out in a solvent. Examples of the solvent to be used in the reaction include alcohols, nitriles, ethers, aromatic hydrocarbons, aprotic polar solvents, water, and mixtures of two or more of them.

Examples of the halogenating agent include bromine, iodine, sodium bromide, potassium bromide, sodium iodide, and potassium iodide.

In the reaction, an oxidizing agent may be used as needed. Examples of the oxidizing agent to be used in the reaction include hydrogen peroxide, tert-butyl hydroperoxide, and DMSO. When an oxidizing agent is used in the reaction, the oxidizing agent is usually used at a ratio of 1 to 20 mol relative to 1 mol of the Compound (III-1).

In the reaction, the Compound (R-3) is usually used at a ratio of 0.5 to 10 mol, and the halogenating agent is usually used at a ratio of 0.05 to 10 mol, relative to 1 mol of the Compound (III-1).

The reaction temperature is usually within the range of 0 to 200° C. The reaction time is usually within the range of 0.1 to 72 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-a).

The Compound (R-3) is known or may be prepared according to known method(s).

Production Method 7

A compound represented by formula (I-S) (hereinafter referred to as "Compound (I-S)") may be prepared by reacting the Compound (I-1) with a sulfating agent.

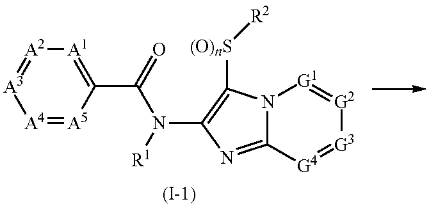

(I-1)

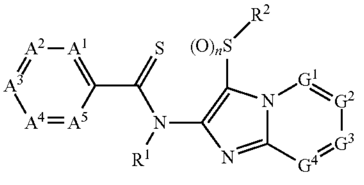

(I-S)

[wherein the symbols are the same as defined above.]

The reaction is carried out in a solvent or in the absence of a solvent. Examples of the solvent include ethers, halogenated hydrocarbons, aromatic hydrocarbons, nitriles, nitrogen-containing aromatic compounds, and mixtures of two or more of them.

Examples of the sulfating agent include phosphorus pentasulfide and Lawesson's reagent (2,4-bis(4-methoxyphenyl)-1,3-dithia-2,4-diphosphetane-2,4-disulfide).

In the reaction, the sulfating agent is usually used at a ratio of 1 to 3 mol relative to 1 mol of the Compound (I-1).

The reaction temperature is usually within the range of 0 to 200° C. The reaction time is usually within the range of 1 to 24 hours(s).

When the reaction is completed, the reaction mixture may be subjected to a work-up such as adding water to the reaction mixture, subjecting the resulting mixture to extraction with organic solvent (s), and drying and/or concentrating the resulting organic layer to give the Compound (I-S).

Production Method 8

A compound represented by formula (II-S) (hereinafter referred to as "Compound (II-S)") may be prepared by reacting the Compound (II-O) with a sulfating agent.

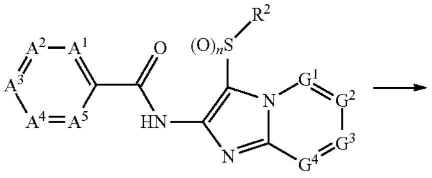

(II-O)

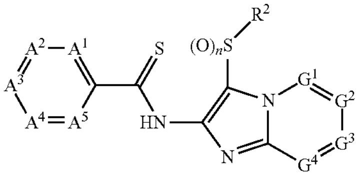

(II-S)

[wherein the symbols are the same as defined above.]

The reaction may be carried out according to the Production method 7 by using the Compound (II-O) instead of the Compound (I-1).

Production Method 9

A compound represented by formula (I-3-H) (hereinafter referred to as "Compound (I-3-H)") may be prepared by reacting a compound represented by formula (M4-1) (hereinafter referred to as "Compound (M4-1)") with a reducing agent.

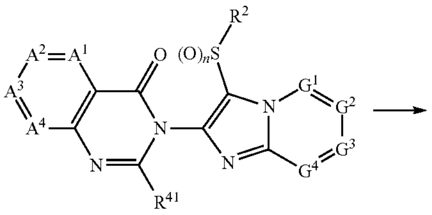

(M4-1)

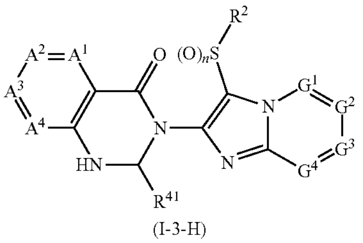

(I-3-H)

[wherein the symbols are the same as defined above.]

The reaction is usually carried out in a solvent. Examples of the solvent to be used in the reaction include ethers, alcohols, and mixtures of two or more of them.

Examples of the reducing agent to be used in the reaction include sodium borohydride, sodium cyanoborohydride, and lithium aluminum hydride.

In the reaction, the reducing agent is usually used at a ratio of 1 to 2 mol relative to 1 mol of the Compound (M4-1).

The reaction temperature is usually within the range of 0 to 100° C. The reaction time is usually within the range of 0.1 to 24 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (I-3-H).

Production Method 10

A compound represented by formula (I-3-C) may be prepared by reacting the Compound (I-3-H) with a compound represented by formula (R-4) (hereinafter referred to as "Compound (R-4)") in the presence of a base.

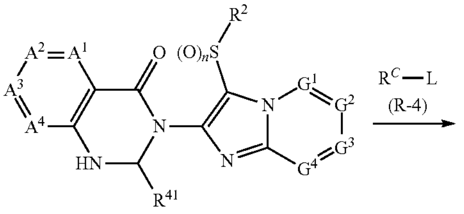

(I-3-H)

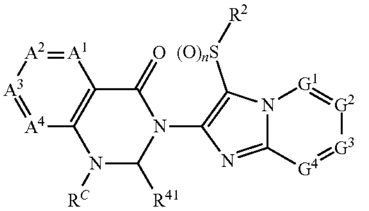

(I-3-C)

[wherein $R^c$ represents a C1-C6 chain hydrocarbon group optionally substituted with one or more substituent (s) selected from Group X, a C3-C7 cycloalkyl group optionally substituted with one or more substituent (s) selected from Group Y, $C(O)R^{46}$, $C(O)OR^{46}$, or $C(O)NR^{46}R^{47}$; and the other symbols are the same as defined above.]

The reaction may be carried out according to the Production method 4 by using the Compound (I-3-H) instead of the Compound (II).

The Compound (R-4) is a commercially available compound or may be prepared by using known method(s).

Production Method 11

An N-oxide of the compound represented by formula (I) may be prepared by reacting the compound represented by formula (I) with an oxidizing agent. The reaction may be carried out according to the method described in, for example, the Production method 1, US Patent Application Publication No. 2018/0009778, or WO 2016/121970 pamphlet.

Hereinafter, production methods for the production intermediate compounds are described.

Reference Production Method 1

A compound represented by formula (M1-1-D) (hereinafter referred to as "Compound (M1-1-D)") may be prepared by reacting a compound represented by formula (M1-3) (hereinafter referred to as "Compound (M1-3)") with a compound represented by formula (R-5) (hereinafter referred to as "Compound (R-5)") in the presence of a base.

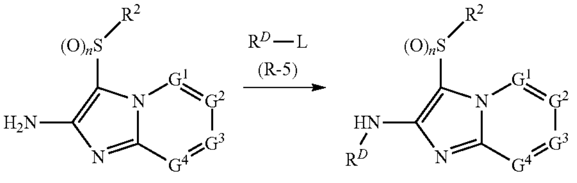

(M1-3) (M1-1-D)

[wherein $R^D$ represents a C1-C6 chain hydrocarbon group optionally substituted with one or more substituent(s) selected from Group W, or a C3-C7 cycloalkyl group optionally substituted with one or more substituent (s) selected from Group U; and the other symbols are the same as defined above.]

The reaction is usually carried out in a solvent. Examples of the solvent to be used in the reaction include ethers, aromatic hydrocarbons, nitriles, aprotic polar solvents, and mixtures of two or more of them.

Examples of the base to be used in the reaction include alkali metal hydrides, alkali metal carbonates, and organic bases.

In the reaction, the Compound (R-5) is usually used at a ratio of 1 to 5 mol, and the base is usually used at a ratio of 1 to 2 mol, relative to 1 mol of the Compound (M1-3).

The reaction temperature is usually within the range of 0 to 100° C. The reaction time is usually within the range of 0.1 to 24 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M1-1-D).

Reference Production Method 2

The Compound (M1-1-A) may be prepared by reacting a compound represented by formula (M1-2-2) (hereinafter referred to as "Compound (M1-2-2)") with a compound represented by formula (R-6) (hereinafter referred to as "Compound (R-6)")

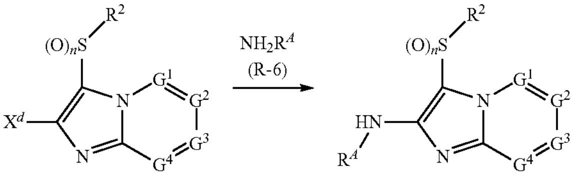

(M1-2-2) (M1-1-A)

[wherein $X^d$ represents a fluorine atom or a chlorine atom; and the other symbols are the same as defined above.]

The reaction is usually carried out in a solvent. Examples of the solvent to be used in the reaction include aprotic polar solvents, alcohols, and mixtures of two or more of them.

In the reaction, a base may be used as needed. Examples of the base to be used in the reaction include organic bases and alkali metal carbonates. When a base is used in the reaction, the base is usually used at a ratio of 0.1 to 5 mol relative to 1 mol of the Compound (M1-2-2).

In the reaction, the Compound (R-6) is usually used at a ratio of 1 to 100 mol relative to 1 mol of the Compound (M11-2-2).

The reaction temperature is usually within the range of 25 to 200° C. The reaction time is usually within the range of 01 to 48 hours(s).

When the reaction is completed, the reaction mixture may be subjected to a work-up such as adding water to the reaction mixture, subjecting the resulting mixture to extraction with organic solvent (s), and drying and/or concentrating the resulting organic layer to give the Compound (M1-1-A).

The Compound (R-6) is a commercially available compound or may be prepared by using known method(s).

Reference Production Method 3

The Compound (M1-3) may be prepared by reacting the Compound (M1-2-2) with ammonia.

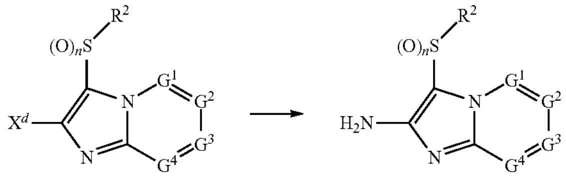

(M1-2-2) (M1-3)

[wherein the symbols are the same as defined above,]

The reaction is usually carried out in a solvent. Examples of the solvent to be used in the reaction include ethers, nitriles, aprotic polar solvents, alcohols, water, and mixtures of two or more of them.

In the reaction, a base may be used as needed, Examples of the base to be used in the reaction include organic bases and alkali metal carbonates. When a base is used in the reaction, the base is usually used at a ratio of 0.1 to 5 mol relative to 1 mol of the Compound (M1-2-2).

The ammonia may also be used as a solution such as an ammonia solution in water and an ammonia solution in methanol.

In the reaction, the ammonia is usually used at a ratio of 1 to 100 mol relative to 1 mol of the Compound (M1-2-2).

The reaction temperature is usually within the range of −20 to 100° C. The reaction time is usually within the range of 0.1 to 48 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M1-3).

Reference Production Method 4

A compound represented by formula (M1-2b) and a compound represented by formula (M1-2c) may be prepared by reacting a compound represented by formula (M1-2a) (hereinafter referred to as "Compound (M1-2a)") with an oxidizing agent. The compound represented by formula (M1-2c) may also be prepared by reacting the compound represented by formula (M1-2b) with an oxidizing agent.

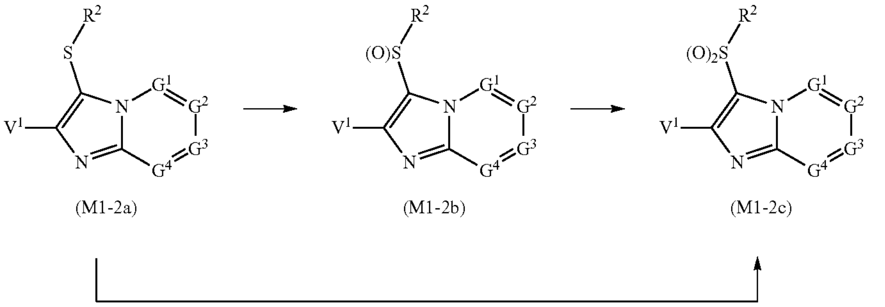

(M1-2a) (M1-2b) (M1-2c)

[wherein the symbols are the same as defined above.]

These reactions may be carried out according to the Production method 1.

Reference Production Method 5

The Compound (M1-2a) may be prepared according to the following scheme.

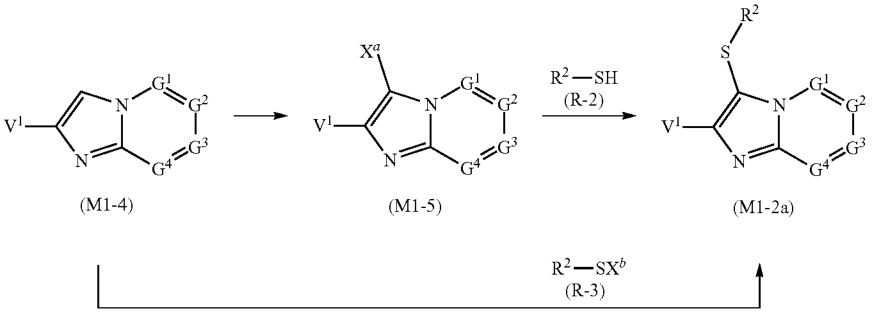

(M1-4) (M1-5) (M1-2a)

[wherein the symbols are the same as defined above.]

These reactions may be carried out according to the Production method 6.

A compound represented by formula (M1-4) (hereinafter referred to as "Compound (M1-4)") is known or may be prepared according to the method(s) described in, for example, WO 2015/157093 pamphlet, WO 2016/109706 pamphlet, Organic & Biomolecular Chemistry, 2017, 15, 4199, or European Journal of Medicinal Chemistry, 2016, 123, 916.

Reference Production Method 6

The Compound (II-~) may be prepared by reacting the Compound (M1-3) with the Compound (M2-1) or the Compound (M2-2).

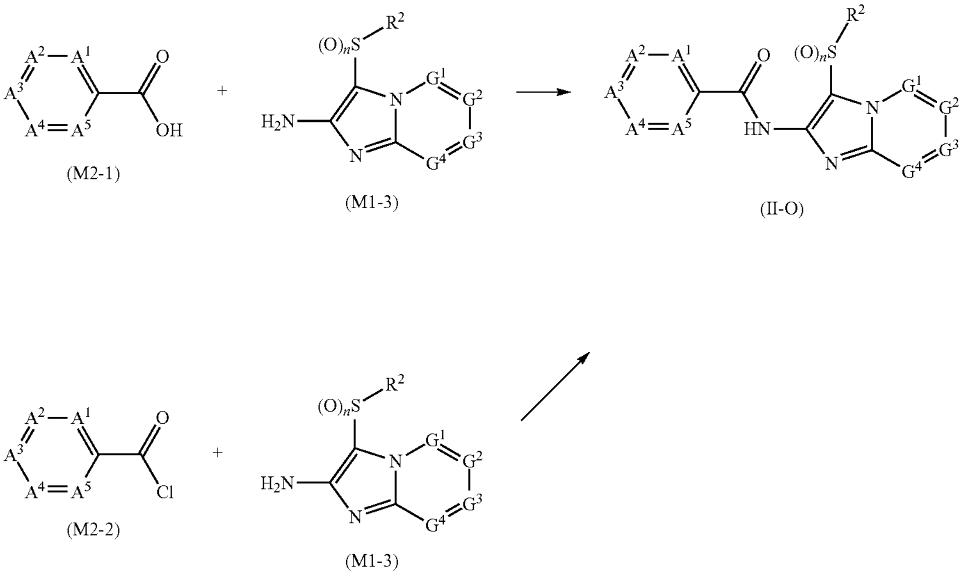

(M2-1) (M1-3) (II-O)

(M2-2) (M1-3)

[wherein the symbols are the same as defined above.]

These reactions may be carried out according to the Production method 2 or the Production method 3 by using the Compound (M1-3) instead of the Compound (M1-1-A).

Reference Production Method 7

A compound represented by formula (M3-1-A) may be prepared by reacting a compound represented by formula (M1-6-A) (hereinafter referred to as "Compound (M1-6-A)") with the Compound (M2-1) or the Compound (M2-2),

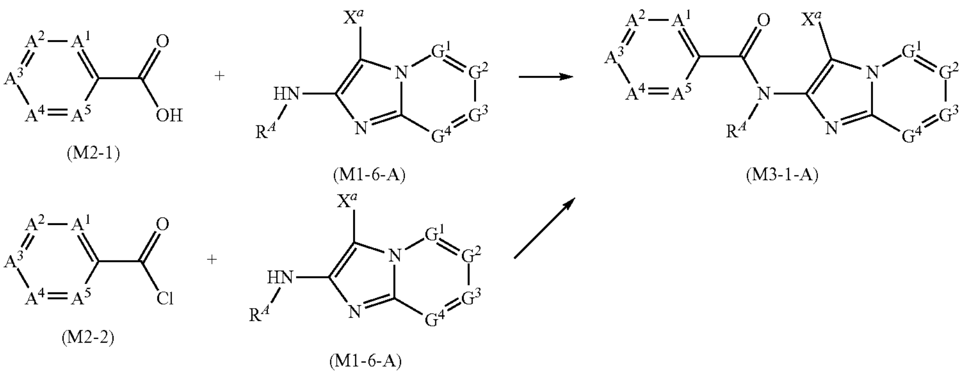

(M2-1) (M1-6-A) (M3-1-A)

(M2-2) (M1-6-A)

[wherein the symbols are the same as defined above.]

These reactions may be carried out according to the Production method 2 or the Production method 3 by using the Compound (M1-6-A) instead of the Compound (M1-1-A).

Reference Production Method 8

A compound represented by formula (M1-6-D) (hereinafter referred to as "Compound (M1~6-D)") may be prepared according to the following scheme.

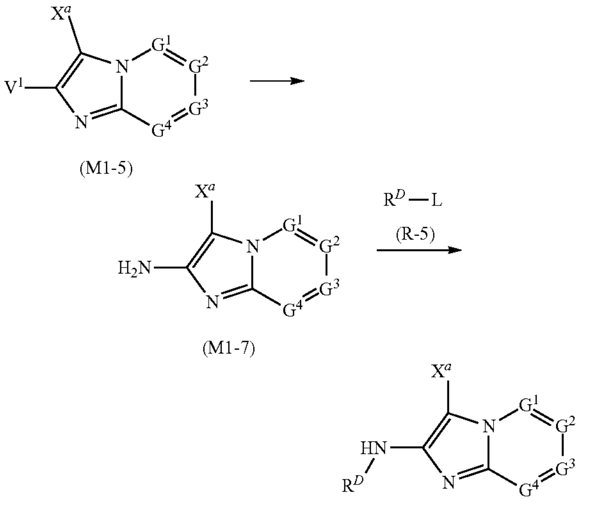

(M1-5)

(M1-7)

(M1-6-D)

[wherein the symbols are the same as defined above.]

First, a method for producing a compound represented by formula (M1-7) (hereinafter referred to as "Compound (M1-7)") is described.

The Compound (M1-7) may be prepared by reacting a compound represented by formula (M1-5) (hereinafter referred to as "Compound (M1-5)") with ammonia. The reaction may be carried out according to the Reference Production method 3 by using the Compound (M1-5) instead of the Compound (M1-2-2).

Next, a method for producing the Compound (M1-6-D) is described.

The Compound (M1-6-D) may be prepared by reacting the Compound (M1-7) with the Compound (R-5) in the presence of a base. The reaction may be carried out according to the Reference Production method 1 by using the Compound (M1-7) instead of the Compound (M1-3).

Reference Production Method 9

The Compound (M1-6-A) may be prepared according to the following scheme.

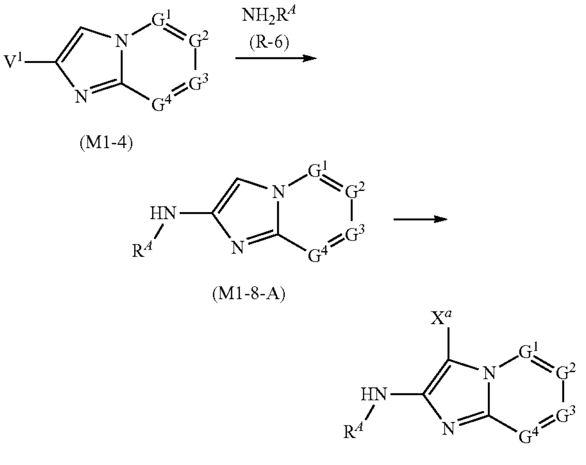

(M1-4)

(M1-8-A)

(M1-6-A)

[wherein the symbols are the same as defined above.]

First, a method for producing a compound represented by formula (M1-8-A) (hereinafter referred to as "Compound (M1-8-A)") is described.

The Compound (M1-8-A) may be prepared by reacting the Compound (M1-4) with the Compound (R-6). The reaction may be carried out according to the Reference Production method 2 by using the Compound (M1-4) instead of the Compound (M1-2-2).

Next, a method for producing the Compound (M1-6-A) is described.

The Compound (M1-6-A) may be prepared by reacting the Compound (M1-8-A) with a halogenating agent. The reaction may be carried out according to the Step 6-A in the Production method 6 by using the Compound (M1-8-A) instead of the Compound (III-1).

Reference Production Method 10

A compound represented by formula (M3-1-B) (hereinafter referred to as "Compound (M3-1-B)") may be prepared according to the following scheme.

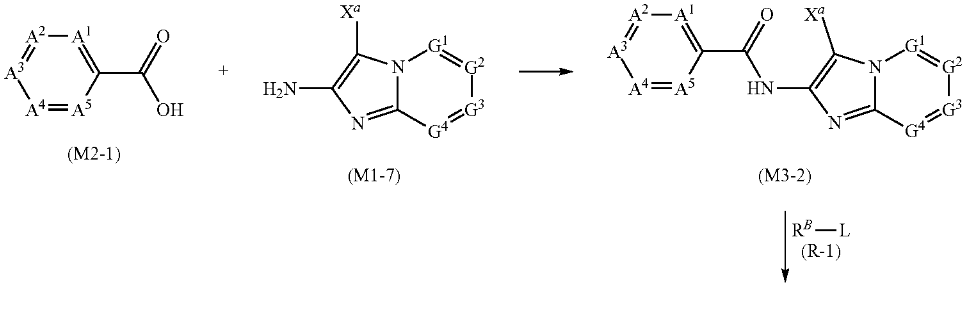

(M2-1)

(M1-7)

(M3-2)

-continued

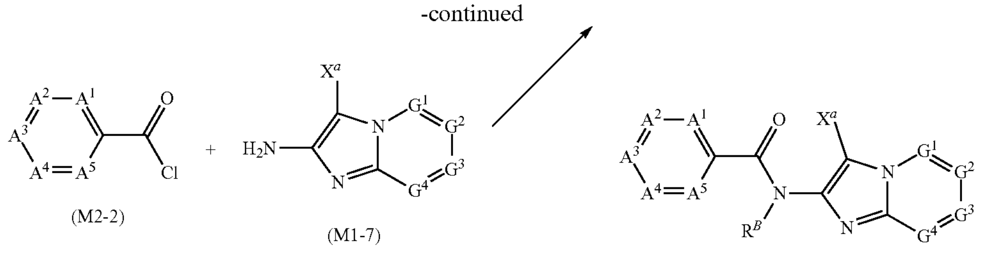

(M2-2) (M1-7) (M3-1-B)

[wherein the symbols are the same as defined above.]

First, a method for producing a compound represented by formula (M3-2) (hereinafter referred to as "Compound (M3-2)") is described.

The Compound (M3-2) may be prepared by reacting the Compound (M1-7) with the Compound (M2-1) or the Compound (M2-2). These reactions may be carried out according to the Production method 2 or the Production method 3 by using the Compound (M1-7) instead of the Compound (M1-1-A).

Next, a method for producing the Compound (M3-1-B) is described.

The Compound (M3-1-B) may be prepared by reacting the Compound (M3-2) with the Compound (R-1) in the presence of a base. The reaction may be carried out according to the Production method 4 by using the Compound (M3-2) instead of the Compound (II)

Reference Production Method 11

A compound represented by formula (III-1-A) (hereinafter referred to as "Compound (III-1-A)") may be prepared according to the following scheme,

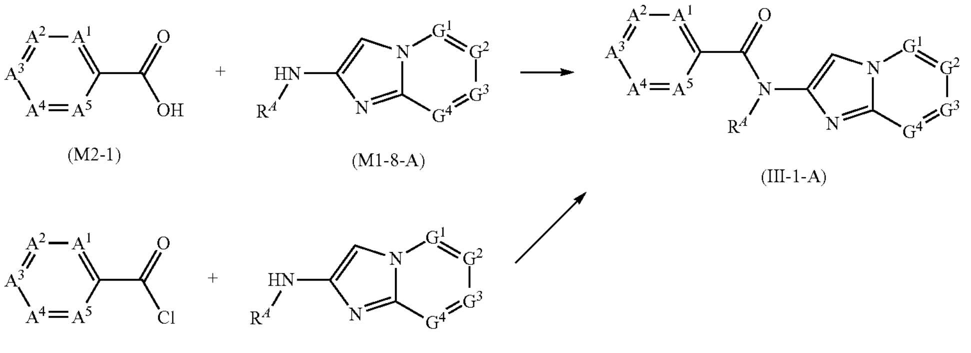

(M2-1) (M1-8-A) (III-1-A)

(M2-2) (M1-8-A)

[wherein the symbols are the same as defined above,]

The Compound (III-1-A) may be prepared by reacting the Compound (M1-8-A) with the Compound (M2-1) or the Compound (M2-2). These reactions may be carried out according to the Production method 2 or the Production method 3 by using the Compound (M1-M-A) instead of the Compound Reference Production Method 12

A compound represented by formula (III-1-B) (hereinafter referred to as "Compound (III-1-B)") may be prepared according to the following scheme,

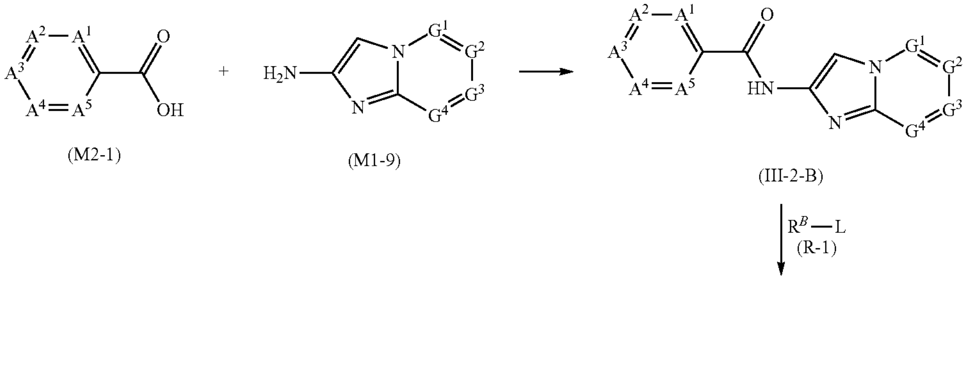

(M2-1) (M1-9) (III-2-B)

(R-1)

-continued

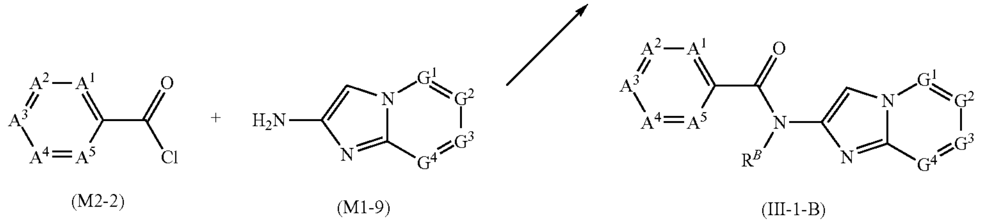

(M2-2) (M1-9) (III-1-B)

[wherein the symbols are the same as defined above.]

First, a method for producing a compound represented by formula (III-2-B) (hereinafter referred to as "Compound (III-2-B)") is described.

The Compound (III-2-B) may be prepared by reacting a compound represented by formula (M1-9) (hereinafter referred to as "Compound (M1-9)") with the Compound (M2-1) or the Compound (M2-2). These reactions may be carried out according to the Production method 2 or the Production method 3 by using the Compound (M1-9) instead of the Compound (M1-1-A).

Next, a method for producing the Compound (III-1-B) is described.

The Compound (III-1-B) may be prepared by reacting the Compound (III-2-B) with the Compound (R-1) in the presence of a base. The reaction may be carried out according to the Production method 4 by using the Compound (III-2-B) instead of the Compound (II).

Reference Production Method 13

The Compound (M1-9) may be prepared by reacting the Compound (M1-4) with ammonia.

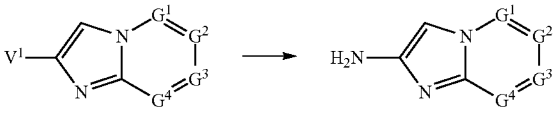

(M1-4) (M1-9)

[wherein the symbols are the same as defined above.]

The reaction may be carried out according to the Reference Production method 3 by using the Compound (M1-4) instead of the Compound (M1-2-2.

Reference Production Method 14

A compound represented by formula (III-1-P) (hereinafter referred to as "Compound (III-1-P)") may be prepared by reacting a compound represented by formula (M2-3-P) (hereinafter referred to as "Compound (M2-3-P)) with the Compound (M1-4).

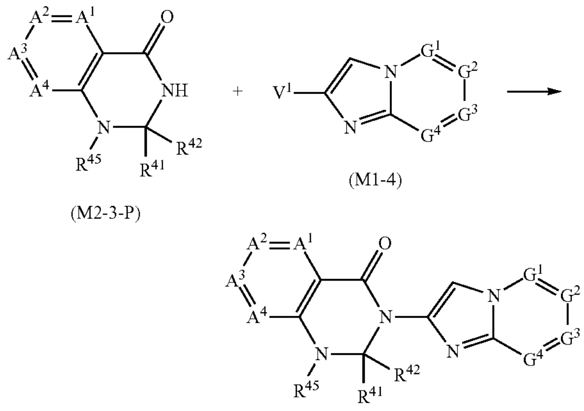

(M2-3-P) (M1-4) (III-1-P)

[wherein the symbols are the same as defined above.]

The reaction may be carried out according to the Production method 5 by using the Compound (M1-4) instead of the Compound (M1-2), and using the Compound (M2-3-P) instead of the Compound (M2-3), Reference Production Method 15

The Compound (M4-1) may be prepared according to the following scheme.

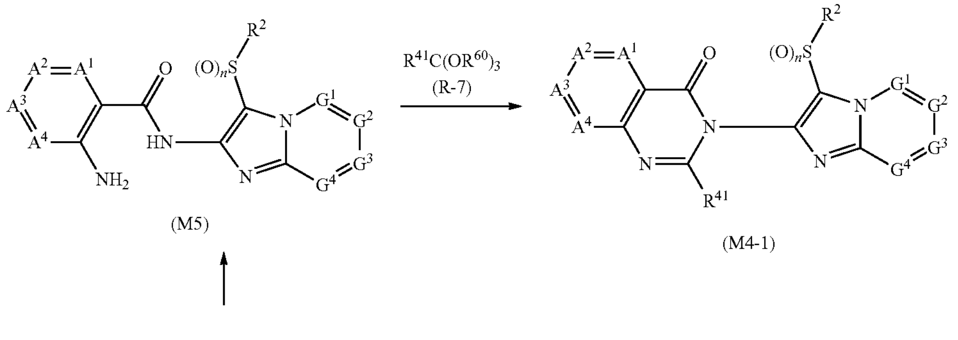

(M5) (M4-1)

-continued

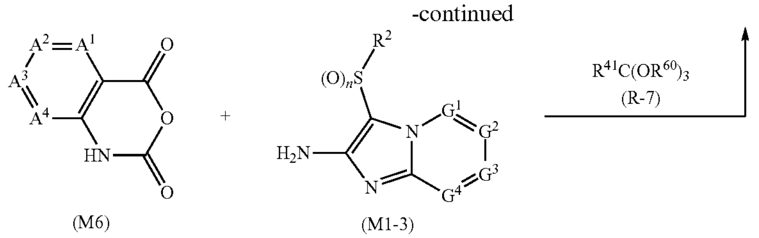

(M6) (M1-3)

[wherein $R^{60}$ represents a methyl group or an ethyl group; and the other symbols are the same as defined above.]

First, a method for producing a compound represented by formula (M5) (hereinafter referred to as "Compound (M5)") is described.

The Compound (M5) may be prepared by reacting a compound represented by formula (M6) (hereinafter referred to as "Compound (M6)") with the Compound (M1-3).

The reaction is usually carried out in a solvent. Examples of the solvent include alcohols, ethers, aromatic hydrocarbons, nitriles, aprotic polar solvents, and mixtures of two or more of them.

In the reaction, a base may be used as needed. Examples of the base include organic bases. When a base is used in the reaction, the base is usually used at a ratio of 1 to 5 mol relative to 1 mol of the Compound (M6).

In the reaction, the Compound (M1-3) is usually used at a ratio of 1 to 5 mol relative to 1 mol of the Compound (M6).

The reaction temperature is usually within the range of 0 to 150° C. The reaction time is usually within the range of 0.5 to 12 hours(s).

When the reaction is completed, the reaction mixture may be subjected to a work-up such as adding water to the reaction mixture, then subjecting the resulting mixture to extraction with organic solvent(s), and drying and/or concentrating the resulting organic layer to give the Compound (M5).

The Compound (M6) may be prepared according to the method(s) described in, for example, Journal of Biological Chemistry, 2016, 291, 14146.

Next, a method for producing the Compound (M4-1) from the Compound (M5) is described.

The Compound (M4-1) may be prepared by reacting the Compound (M5) with a compound represented by formula (R-7) (hereinafter referred to as "Compound (R-7)").

The reaction is usually carried out in a solvent or in the absence of a solvent. Examples of the solvent include ethers, aromatic hydrocarbons, halogenated hydrocarbons, nitriles, aprotic polar solvents, and mixtures of two or more of them.

In the reaction, the Compound (R-7) is usually used at a ratio of 1 to 50 mol relative to 1 mol of the Compound (M5).

In the reaction, an acid or a base may be used as needed. Examples of the acid to be used in the reaction include sulfonic acids such as p-toluenesulfonic acid, carboxylic acids such as acetic acid, and polyphosphoric acid. When an acid is used in the reaction, the acid is usually used at a ratio of 0.01 to 5 mol relative to 1 mol of the Compound (M5).

Examples of the base to be used in the reaction include organic bases. When a base is used in the reaction, the base is usually used at a ratio of 1 to 5 mol relative to 1 mol of the Compound (M5).

The reaction temperature is usually within the range of 0 to 150° C. The reaction time is usually within the range of 0.5 to 24 hours(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M4-1).

The Compound (R-7) is a commercially available compound or may be prepared by using known method(s).

Also, the Compound (M4-1) may be prepared in one step reaction (one-pot) by reacting the Compound (M6), the Compound (M1-3), and the Compound (R-7).

The reaction may be carried out according to the method for producing the Compound (M4-1) from the Compound (M5) by usually using the Compound (M1-3) at a ratio of 1 to 5 mol, and usually using the Compound (R-7) at a ratio of 1 to 50 mol, relative to 1 mol of the Compound (M6).

Reference Production Method 16

The Compound (M2-3-P) may be prepared by reacting a compound represented by formula (M7) (hereinafter referred to as "Compound (M7)") with a compound represented by formula (R-8) (hereinafter referred to as "Compound (R-8)").

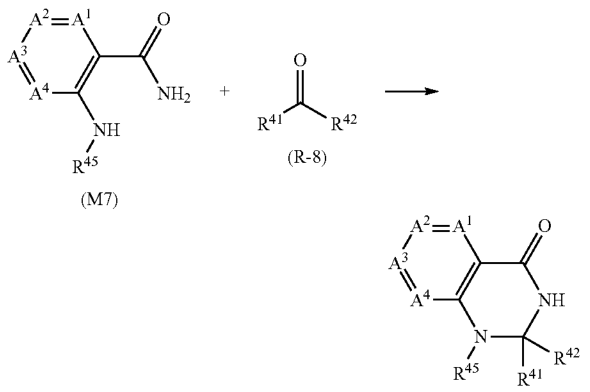

(M7) (R-8) (M2-3-P)

[wherein the symbols are the same as defined above.]

The reaction may be carried out according to the method(s) described in, for example, Organic Letters, 2020, 22, 3825.

The Compound (M7) and the Compound (R-8) are commercially available compounds or may be prepared by using known methods.

The Present compound or the Present compound X may be mixed with or used in combination with one or more ingredient (s) selected from the group consisting of the following Group (a), Group (b), Group (c), and Group (d) (hereinafter referred to as "Present ingredient").

When the Present compound or the Present compound X is mixed with or used in combination with the Present ingredient, they are used simultaneously, separately, or at time intervals with each other.

When the Present compound or the Present compound X is used simultaneously with the Present ingredient, the Present compound or the Present compound X and the Present ingredient may be contained in separate formulations or contained in one formulation.

One aspect of the present invention provides a composition comprising one or more ingredient (s) selected from the group consisting of Group (a), Group (b), Group (c), and Group (d), and the Present compound.

One aspect of the present invention provides a composition comprising one or more ingredient (s) selected from the group consisting of Group (a), Group (b), Group (c), and Group (d), and the Present compound X (hereinafter referred to as "Composition A").

Group (a) is a group consisting of acetylcholinesterase inhibitors (for example, carbamate insecticides and organophosphate insecticides), GABA-gated chloride channel blockers (for example, phenylpyrazole insecticides), sodium channel modulators (for example, pyrethroid insecticides), nicotinic acetylcholine receptor competitive modulators (for example, neonicotinoid insecticides), nicotinic acetylcholine receptor allosteric modulators, glutamate-gated chloride channel allosteric modulators (for example, macrolide insecticides), juvenile hormone mimics, multisite inhibitors, chordotonal organ TRPV channel modulators, mite growth inhibitors, microbial disruptors of insect midgut membranes, inhibitors of mitochondrial ATP synthase, uncouplers of oxidative phosphorylation, nicotinic acetylcholine receptor channel blockers (for example, nereistoxin insecticides), inhibitors of chitin biosynthesis, moulting disruptors, ecdysone receptor agonists, octopamine receptor agonists, mitochondrial complexes I, II, III, and IV electron transport inhibitors, voltage-dependent sodium channel blockers, inhibitors of acetyl CoA carboxylase, ryanodine receptor modulators (for example, diamide insecticides), chordotonal organ modulators, and microbial insecticides, and other insecticidal active ingredients, miticidal active ingredients, and nematicidal active ingredients. These ingredients are described in the classification on the basis of action mechanism by IRAC.

Group (b) is a group consisting of nucleic acids synthesis inhibitors (for example, phenylamide fungicides and acylamino acid fungicides), cell division and cytoskeleton inhibitors (for example, MBC fungicides), respiration inhibitors (for example, QoI fungicides and QiI fungicides), amino acids synthesis and protein synthesis inhibitors (for example, anilino-pyrimidine fungicides), signal transduction inhibitors, lipid synthesis and membrane synthesis inhibitors, sterol biosynthesis inhibitors (for example, DMI fungicides such as triazole fungicides), cell wall biosynthesis inhibitors, melanin synthesis inhibitors, plant defense inducers, fungicides with multi-site contact activity, microbial fungicides, and other fungicidal active ingredients. These ingredients are described in the classification on the basis of action mechanism by FRAC.

Group (c) is a group of plant growth regulatory ingredients (including mycorrhizal fungi and root nodule bacteria).

Group (d) is a group of repellent ingredients.

Hereinafter, examples of the combination of the Present ingredient and the Present compound X are described. For example, "alanycarb+SX" indicates a combination of alanycarb and SX.

The abbreviation of "SX" indicates any one of the Present compound X selected from the Compound groups SX1 to SX2299 described in Examples. Also, all of the following Present ingredient are known ingredients, and may be obtained from commercially available formulations, or may be prepared by known methods. When the Present ingredient is a microorganism, it may also be available from a bacterial authority depository. Further, the number in parentheses represents the CAS RN (registered trademark).

Combinations of the Present ingredient in the above Group (a) and the Present compound X:

abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cyclaniliprole+SX, cyclobutrifluram+SX, cycloprothrin+SX, cycloxaprid+SX, cyenopyrafen+SX, cyetpyrafen+SX, cyflumetofen+SX, cyfluthrin+SX, cyhalodiamide+SX, cyhalothrin+SX, cyhexatin+SX, cypermethrin+SX, cyphenothrin+SX, cyproflanilide+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dimpropyridaz+SX, dinotefuran+SX, disodium octaborate+SX, disulfoton+SX, DNOC(2-methyl-4,6-dinitrophenol)+SX, doramectin+SX, dried leaves of Dryopteris filix-mas+SX, emamectin-benzoate+SX, empenthrin+SX, endosulfan+SX, EPN(O-ethyl O-(4-nitrophenyl)phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of Azadirachta indica+SX, extract of *Cassia nigricans*+SX, extract of clitoria ternatea+SX, extract of Symphytum *officinale*+SX, extract or simulated blend of *Chenopodium ambrosioides*+SX, extract of *Tanacetum vulgare*+SX, extract of *Urtica dioica*+SX, extract of Viscum album+SX, famphur+SX, fenamiphos+SX, fenazaquin+SX, fenbutatin oxide+SX, fenitrothion+SX, fenmezoditiaz+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, fluchlordiniliprole+SX, flucycloxuron+SX, flucythrinate+SX, fluensulfone+SX, flufenoprox+SX, flufenoxuron+SX, flufiprole+SX, flumethrin+SX, flupentiofenox+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX- Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imidaclothiz+SX, imiprothrin+SX, indazapyroxamet+SX, indoxacarb+SX, isocycloseram+SX, isofenphos+SX, isoprocarb+SX, isopropyl-O-(methoxyaminothiophosphoryl) salicylate+SX, isoxathion+SX, ivermectin+SX, kadethrin+SX, kappa-tefluthrin+SX, kappa-bifenthrin+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, nicofluprole+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spidoxamat+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *chenopodium ambrosioides* near *ambrosioides*+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, 2-({2-fluoro-4-methyl-5-[(2,2,2-trifluoroethyl)sulfinyl] phenyl}imino)-3-(2,2,2-trifluoroethyl)-1,3-thiazolidin-4-one (1445683-71-5)+SX, (2Z)-2-({2-fluoro-4-methyl-5-[(R)-(2,2,2-trifluoroethyl)sulfinyl]phenyl}imino)-3-(2,2,2-trifluoroethyl)-1,3-thiazolidin-4-one (2377084-09-6)+SX, N-{4-chloro-3-[(1-cyanocyclopropyl)carbamoyl]phenyl}-1-methyl-4-(methanesulfonyl)-3-(1,1,2,2,2-pentafluoroethyl)-1H-pyrazole-3-carboxamide (1400768-21-9)+SX, N-[3-chloro-1-(pyridin-3-yl)-1H-pyrazol-4-yl]-2-(methanesulfonyl)propanamide (2396747-83-2)+SX, 1,4-dimethyl-2-[2-(pyridin-3-yl)-2H-indazol-5-yl]-1,2,4-triazolidine-3,5-dione (2171099-09-3)+SX, 2-isopropyl-5-[(3,4,4-trifluoro-3-buten-1-yl)sulfonyl]-1,3,4-thiadiazole (2058052-95-0)+SX, N-({2-fluoro-4-[(2S,3S)-2-hydroxy-3-(3,4,5-trichlorophenyl)-3-(trifluoromethyl)pyrrolidin-1-yl] phenyl}methyl)cyclopropanecarboxamide+SX, 7-fluoro-N-[1-(methylsulfanyl)-2-methylpropan-2-yl]-2-(pyridin-3-yl)-2H-indazole-4-carboxamide+SX, 7-fluoro-N-[1-(methanesulfinyl)-2-methylpropan-2-yl]-2-(pyridin-3-yl)-2H-indazole-4-carboxamide+SX, 7-fluoro-N-[1-(methanesulfonyl)-2-methylpropan-2-yl]-2-(pyridin-3-yl)-2H-indazole-4-carboxamide+SX, N-[1-(difluoromethyl) cyclopropyl]-2-(pyridin-3-yl)-2H-indazole-4-carboxamide+SX, 2,9-dihydro-9-(methoxymethyl)-2-(pyridin-3-yl)-10H-pyrazolo[3,4-f]pyrido[2,3-b] [1,4]oxazepin-10-one (2607927-97-7)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein mCry3A+SX, BT crop protein Cry3Ab+SX, BT crop protein Cry3Bb+SX, BT crop protein Cry34Ab1/Cry35Ab1+SX, *Adoxophyes orana* granulosis virus strain BV-0001+SX, *Anticarsia gemmatalis* mNPV+SX, *Autographa californica* mNPV+SX, *Cydia pomonella* GV strain V15+SX, *Cydia pomonella* GV strain V22+SX, *Cryptophlebia leucotreta* GV+SX, *Dendrolimus* punctatus cypovirus+SX, *Helicoverpa armigera* NPV strain BV-0003+SX, *Helicoverpa zea* NPV+SX, *Lymantria dispar* NPV+SX, *Mamestra brassicae* NPV+SX, *Mamestra* configurata NPV+SX, Neodiprion *abietis* NPV+SX, Neodiprion *lecontei* NPV+SX, Neodiprion sertifer NPV+SX, *Nosema* locustae+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, Arthrobotrys *dactyloides*+SX, *Bacillus firmus* strain GB-126+SX, *Bacillus firmus* strain I-1582+SX, *Bacillus firmus* strain NCIM2637+SX, *Bacillus megaterium*+SX, *Bacillus* sp. strain AQ175+SX, *Bacillus* sp. strain AQ177+SX, *Bacillus* sp. strain AQ178+SX, *Bacillus sphaericus* strain 2362 serotype H5a5b+SX, *Bacillus sphaericus* strain ABTS1743+SX, *Bacillus sphaericus* Serotype strain H5a5b+SX, *Bacillus thuringiensis* strain AQ52+SX, *Bacillus thuringiensis* strain BD #32+SX, *Bacillus thuringiensis* strain CR-371+SX, *Bacillus thuringiensis* subsp. Aizawai strain ABTS-1857+SX, *Bacillus thuringiensis* subsp. Aizawai strain AM65-52+SX, *Bacillus thuringiensis* subsp. Aizawai strain GC-91+SX, *Bacillus thuringiensis* subsp. Aizawai strain NB200+SX, *Bacillus thuringiensis* subsp. Aizawai Serotype strain H-7+SX, *Bacillus thuringiensis* subsp. Kurstaki strain ABTS351+SX, *Bacillus thuringiensis* subsp. Kurstaki strain BMP123+SX, *Bacillus thuringiensis* subsp. Kurstaki strain CCT1306)+SX, *Bacillus thuringiensis* subsp. Kurstaki strain EG2348+SX, *Bacillus thuringiensis* subsp. Kurstaki strain EG7841+SX, *Bacillus thuringiensis* subsp. Kurstaki strain EVB113-19+SX, *Bacillus thuringiensis* subsp. Kurstaki strain F810+SX, *Bacillus thuringiensis* subsp. Kurstaki strain HD-1+SX, *Bacillus thuringiensis* subsp. Kurstaki strain PB54+SX, *Bacillus thuringiensis* subsp. Kurstaki strain SA-11+SX, *Bacillus thuringiensis* subsp. Kurstaki strain SA-12+SX, *Bacillus thuringiensis* subsp. Tenebriosis strain NB176+SX, *Bacillus thuringiensis* subsp. *Thuringiensis* strain MPPL002+SX, *Bacillus thuringiensis* subsp. morrisoni+SX, *Bacillus thu-*

*ringiensis* var. colmeri+SX, *Bacillus thuringiensis* var. darmstadiensis strain 24-91+SX, *Bacillus thuringiensis* var. *dendrolimus*+SX, *Bacillus thuringiensis* var. *galleriae*+SX, *Bacillus thuringiensis* var. *israelensis* strain BMP144+SX, *Bacillus thuringiensis* var. *israelensis* serotype strain H-14+SX, *Bacillus thuringiensis* var. japonensis strain buibui+SX, *Bacillus thuringiensis* var. san diego strain M-7+SX, *Bacillus thuringiensis* var. 7216+SX, *Bacillus thuringiensis* var. *aegypti*+SX, *Bacillus thuringiensis* var. T36+SX, *Beauveria bassiana* strain ANT-03+SX, *Beauveria bassiana* strain ATCC74040+SX, *Beauveria bassiana* strain GHA+SX, *Beauveria brongniartii*+SX, *Burkholderia* rinojensis strain A396+SX, Chromobacterium subtsugae strain PRAA4-1T+SX, Dactyllela ellipsospora+SX, Dectylaria thaumasia+SX, *Hirsutella minnesotensis*+SX, *Hirsutella rhossiliensis*+SX, *Hirsutella thompsonii*+SX, *Lagenidium giganteum*+SX, *Lecanicillium lecanii* strain KV01+SX, *Lecanicillium lecanii* conidia of strain DAOM198499+SX, *Lecanicillium lecanii* conidia of strain DAOM216596+SX, *Lecanicillium muscarium* strain Ve6+SX, *Metarhizium anisopliae* strain F52+SX, *Metarhizium anisopliae* var. *acridum*+SX, *Metarhizium anisopliae* var. anisopliae BIPESCO 5/F52+SX, *Metarhizium flavoviride*+SX, *Monacrosporium phymatopagum*+SX, *Paecilomyces fumosoroseus* Apopka strain 97+SX, *Paecilomyces lilacinus* strain 251+SX, *Paecilomyces tenuipes* strain T1+SX, *Paenibacillus popilliae*+SX, Pasteuria nishizawae strain Pn1+SX, Pasteuria *penetrans*+SX, Pasteuria usgae+SX, Pasteuria thornei+SX, *Serratia entomophila*+SX, *Verticillium chlamydosporium*+SX, *Verticillium* lecani strain NCIM1312+SX, *Wolbachia pipientis*+SX.

Combination of the Present ingredient in the above Group (b) and the Present compound X:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthiavalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroinconazide+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract of *Melaleuca* alternifolia+SX, extract of *Reynoutria sachalinensis*+SX, extract of the cotyledons of lupine plantlets ("BLAD")+SX, extract of *Allium sativum*+SX, extract of Equisetum *arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, flubeneteram+SX, fludioxonil+SX, flufenoxadiazam+SX, flufenoxystrobin+SX, fluindapyr+SX, flumetylsulforim+SX, flumorph+SX, fluopicolide+SX, fluopyram+SX, fluopimomide+SX, fluoroimide+SX, fluoxapiprolin+SX, fluoxastrobin+SX, fluoxytioconazole+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metarylpicoxamid+SX, metconazole+SX, methasulfocarb+SX, metiram+SX, metominostrobin+SX, metrafenone+SX, metyltetraprole+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, Quillaja extract+SX, quinconazole+SX, quinofumelin+SX, quinoxyfen+SX, quintozene+SX, Saponins of *Chenopodium quinoa*+SX, seboctylamine+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, N'-{4-[(4,5-dichlorothiazol-2-yl)oxy]-2,5-dimethylphenyl}-N-ethyl-N-methylmethanimidamide (929908-57-6)+SX, N'-(2,5-dimethyl-4-phenoxyphenyl)-N-ethyl-N-methylmethanimidamide (1052688-31-9)+SX, N'-[5-chloro-4-(2-fluorophenoxy)-2-methylphenyl]-N-ethyl-N-methylmethanimidamide (2055589-28-9)+SX, N'-[2- chloro-4-(2-fluorophenoxy)-5-methylphenyl]-N-ethyl-N-methylmethanimidamide (2055756-21-1)+SX, N'-(2-chloro-4-phenoxy-5-methylphenyl)-N-ethyl-N-methylmethanimidamide (2062599-39-5)+SX, N'-[4-(1-hydroxy-1-phenyl-2,2,2-trifluoroethyl)-2-methyl-5-methoxyphenyl]-N-isopropyl-N-methylmethanimidamide (2101814-55-3)+SX, N'-[5-bromo-6-(1-methyl-2-propoxyethoxy)-2-methylpyridin-3-yl]-N-ethyl-N-methylmethanimidamide (1817828-69-5)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1-ylmethyl)cyclopentan-1-ol (1394057-11-4)+SX, (1R, 2S, 5S)-5-(4-chlorobenzyl)-2-(chloromethyl)-2-methyl-1-(1H-1,2,4-triazol-1-ylmethyl)cyclopentan-1-ol (1801930-06-2)+SX, (1S, 2R, 5R)-5-(4-chlorobenzyl)-2-(chloromethyl)-2-methyl-1-(1H-1,2,4-triazol-1-ylmethyl)cyclopentan-1-ol (1801930-07-3)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R, 2S, 5S)-2-(chloromethyl)-5-(4-fluorobenzyl)-2-methyl-1-(1H-1,2,4-triazol-1-ylmethyl)cyclopentan-1-ol (1801930-08-4)+SX, (1S, 2R, 5R)-2-(chloromethyl)-5-(4-fluorobenzyl)-2-methyl-1-(1H-1,2,4-triazol-1-ylmethyl)cyclopentan-1-ol (1801930-09-5)+SX, methyl 3-[(4-chlorophenyl)methyl]-2-hydroxy-1-methyl-2-(1H-1,2,4-triazol-1-ylmethyl)cyclopentan-1-carboxylate (1791398-02-1)+SX, 1-(2,4-difluorophenyl)-2-(1H-1,2,4-triazol-1-yl)-1-[1-(4-bromo-2,6-difluorophenoxy)cyclopropyl]ethanol (2019215-86-0)+SX, 1-(2,4-difluorophenyl)-2-(1H-1,2,4-triazol-1-yl)-1-[l-(4-chloro-2,6-difluorophenoxy)cyclopropyl]ethanol (2019215-84-8)+SX, 1-[2-(1-chlorocyclopropyl)-3-(2-fluorophenyl)-2-hydroxypropyl]-1H-imidazole-5-carbonitrile (2018316-13-5)+SX, 1-[2-(1-chlorocyclopropyl)-3-(2,3-difluorophenyl)-2-hydroxypropyl]-1H-imidazole-5-carbonitrile (2018317-25-2)+SX, 2-[6-(4-bromophenoxy)-2-(trifluoromethyl)pyridin-3-yl]-1-(1H-1,2,4-triazol-1-yl)propan-2-ol (2082661-43-4)+SX, 2-[6-(4-chlorophenoxy)-2-(trifluoromethyl)pyridin-3-yl]-1-(1H-1,2,4-triazol-1-yl)propan-2-ol (2082660-27-1)+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, (2E,3Z)-5-{[1-(2,4-dichlorophenyl)-1H-pyrazol-3-yl]oxy}-2-(methoxyimino)-N,3-dimethylpent-3-enamide (1445331-54-3)+SX, 5-chloro-4-({2-[6-(4-chlorophenoxy)pyridin-3-yl]ethyl}amino)-6-methylpyrimidine (1605340-92-8)+SX, N-(1-benzyl-1,3-dimethylbutyl)-8-fluoroquinoline-3-carboxamide (2132414-04-9)+SX, N-(1-benzyl-3,3,3-trifluoro-1-methylpropyl)-8-fluoroquinoline-3-carboxamide (2132414-00-5)+SX, 4,4-dimethyl-2-({4-[5-(trifluoromethyl)-1,2,4-oxadiazol-3-yl]phenyl}methyl)isoxazolidin-3-one (2098918-25-1)+SX, 5,5-dimethyl-2-({4-[5-(trifluoromethyl)-1,2,4-oxadiazol-3-yl]phenyl}methyl)isoxazolidin-3-one (2098918-26-2)+SX, N-ethyl-2-methyl-N-({4-[5-(trifluoromethyl)-1,2,4-oxadiazol-3-yl]phenyl}methyl)propanamide+SX, N,2-dimethoxy-N-({4-[5-(trifluoromethyl)-1,2,4-oxadiazol-3-yl]phenyl}methyl)propanamide+SX, N-methoxy-N-({4-[5-(trifluoromethyl)-1,2,4-oxadiazol-3-yl]phenyl}methyl)cyclopropanecarboxamide+SX, N-methoxy-N'-methyl-N-({4-[5-(trifluoromethyl)-1,2,4-oxadiazol-3-yl]phenyl}methyl)urea+SX, N'-ethyl-N-methoxy-N-({4-[5-(trifluoromethyl)-1,2,4-oxadiazol-3-yl]phenyl}methyl)urea+SX, N,N'-dimethoxy-N-({4-[5-(trifluoromethyl)-1,2,4-oxadiazol-3-yl]phenyl}methyl)urea+SX, N-acetyl-2-(ethanesulfonyl)-N-[2-(methoxycarbonyl)-4-(trifluoromethoxy)phenyl]-4-(trifluoromethyl)benzamide (2043675-28-9)+SX, 3-(4-bromo-7-fluoroindol-1-yl)butan-2-yl N-[(3-hydroxy-4-methoxypyridin-2-yl)carbonyl]-L-alaninate+SX, 3-(7-bromoindol-1-yl)butan-2-yl N-[(3-hydroxy-4-methoxypyridin-2-yl)carbonyl]-L-alaninate+SX, 3-(7-bromo-4-fluoroindol-1-yl)butan-2-yl N-[(3-hydroxy-4-methoxypyridin-2-yl)carbonyl]-L-alaninate+SX, 3-(3,5-dichloropyridin-2-yl)butan-2-yl N-[(3-hydroxy-4-methoxypyridin-2-yl)carbonyl]-L-alaninate+SX, 3-(3,5-dichloropyridin-2-yl)butan-2-yl N-{[3-(acetoxymethoxy)-4-methoxypyridin-2-yl]carbonyl}-L-alaninate+SX, (1S)-1-[1-(naphthalen-1-yl)cyclopropyl]ethyl N-[(3-hydroxy-4-methoxypyridin-2-yl)carbonyl]-L-alaninate+SX, (1S)-1-[1-(naphthalen-1-yl)cyclopropyl]ethyl N-[(3-acetoxy-4-methoxypyridin-2-yl)carbonyl]-L-alaninate+SX, (1S)-1-[1-(naphthalen-1-yl)cyclopropyl]ethyl N-{[3-(acetoxymethoxy)-4-methoxypyridin-2-yl]carbonyl}-L-alaninate+SX, *Agrobacterium* radiobactor strain K1026+SX, *Agrobacterium* radiobactor strain K84+SX, *Bacillus amyloliquefaciens* strain PTA-4838 (Aveo (registered trademark) EZ Nematicide)+SX, *Bacillus amyloliquefaciens* strain AT332+SX, *Bacillus amyloliquefaciens* strain B3+SX, *Bacillus amyloliquefaciens* strain D747+SX, *Bacillus amyloliquefaciens* strain DB101+SX, *Bacillus amyloliquefaciens* strain DB102+SX, *Bacillus amyloliquefaciens* strain GB03+SX, *Bacillus amyloliquefaciens* strain FZB24+SX, *Bacillus amyloliquefaciens* strain FZB42+SX, *Bacillus amyloliquefaciens* strain IN937a+SX, *Bacillus amyloliquefaciens* strain MBI600+SX, *Bacillus amyloliquefaciens* strain QST713+SX, *Bacillus amyloliquefaciens* isolate strain B246+SX, *Bacillus amyloliquefaciens* strain F727+SX, *Bacillus amyloliquefaciens* subsp. *plantarum* strain D747+SX, *Bacillus licheniformis* strain HB-2+SX, *Bacillus licheniformis* strain SB3086+SX, *Bacillus pumilus* strain AQ717+SX, *Bacillus pumilus* strain BUF-33+SX, *Bacillus pumilus* strain GB34+SX, *Bacillus pumilus* strain QST2808+SX, *Bacillus simplex* strain CGF2856+SX, *Bacillus subtilis* strain AQ153+SX, *Bacillus subtilis* strain AQ743+SX, *Bacillus subtilis* strain BU1814+SX, *Bacillus subtilis* strain D747+SX, *Bacillus subtilis* strain DB101+SX, *Bacillus subtilis* strain FZB24+SX, *Bacillus subtilis* strain GB03+SX, *Bacillus subtilis* strain HAI0404+SX, *Bacillus subtilis* strain IAB/BS03+SX, *Bacillus subtilis* strain MBI600+SX, *Bacillus subtilis* strain QST30002/AQ30002+SX, *Bacillus subtilis* strain QST30004/AQ30004+SX, *Bacillus subtilis* strain QST713+SX, *Bacillus subtilis* strain QST714+SX, *Bacillus subtilis* var. *Amyloliquefaciens* strain FZB24+SX, *Bacillus subtilis* strain Y1336+SX, *Burkholderia cepacia*+SX, *Burkholderia cepacia* type Wisconsin strain J82+SX, *Burkholderia cepacia* type Wisconsin strain M54+SX, *Candida oleophila* strain O+SX, *Candida saitoana*+SX, *Chaetomium cupreum*+SX, *Clonostachys rosea*+SX, *Coniothyrium minitans* strain CGMCC8325+SX, *Coniothyrium minitans* strain CON/M/91-8+SX, *cryptococcus albidus*+SX, *Erwinia carotovora* subsp. *carotovora* strain CGE234M403+SX, *Fusarium oxysporum* strain Fo47+SX, *Gliocladium catenulatum* strain J1446+SX, *Paenibacillus polymyxa* strain AC-1+SX, *Paenibacillus polymyxa* strain BS-0105+SX, *Pantoea agglomerans* strain E325+SX, *Phlebiopsis gigantea* strain VRA1992+SX, *Pseudomonas aureofaciens* strain TX-1+SX, *Pseudomonas chlororaphis* strain 63-28+SX, *Pseudomonas chlororaphis* strain AFS009+SX, *Pseudomonas chlororaphis* strain MA342+SX, *Pseudomonas fluorescens* strain 1629RS+SX, *Pseudomonas fluorescens* strain A506+SX, *Pseudomonas fluorescens* strain CL145A+SX, *Pseudomonas fluorescens* strain G7090+SX, *Pseudomonas* sp. strain CAB-02+SX, *Pseudomonas syringae* strain 742RS+SX, *Pseudomonas syringae* strain MA-4+SX, *Pseudozyma flocculosa* strain PF-A22UL+SX, *Pseudomonas rhodesiae* strain HAI-0804+SX, *Pythium oligandrum* strain DV74+SX, *Pythium oligandrum* strain M1+SX, *Streptomyces griseoviridis* strain K61+SX, *Streptomyces lydicus* strain WYCD108US+SX, *Streptomyces lydicus* strain WYEC108+SX, *Talaromyces flavus* strain SAY-Y-94-01+SX, *Talaromyces flavus* strain V117b+SX, *Trichoderma* asperellum strain ICC012+SX, *Trichoderma* asperellum SKT-1+SX, *Trichoderma* asperellum strain T25+SX, *Trichoderma* asperellum strain T34+SX, *Trichoderma* asperellum strain TV1+SX, *Trichoderma* atroviride strain CNCM 1-1237+SX, *Trichoderma* atroviride strain LC52+SX, *Trichoderma* atroviride strain IMI 206040+SX, *Trichoderma* atroviride strain SC1+SX, *Trichoderma* atroviride strain SKT-1+SX, *Trichoderma* atroviride strain T11+SX, *Trichoderma gamsii* strain ICC080+SX, *Trichoderma harzianum* strain 21+SX, *Trichoderma harzianum* strain DB104+SX, *Trichoderma harzianum* strain DSM 14944+SX, *Trichoderma harzianum* strain ESALQ-1303+SX, *Trichoderma harzianum* strain ESALQ-1306+SX, *Trichoderma harzianum* strain IIHR-Th-2+SX, *Trichoderma harzianum* strain ITEM908+SX, *Trichoderma harzianum* strain kd+SX, *Trichoderma harzianum* strain MO1+SX, *Trichoderma harzianum* strain SF+SX, *Trichoderma harzianum* strain T22+SX, *Trichoderma harzianum* strain T39+SX, *Trichoderma harzianum* strain T78+SX, *Trichoderma harzianum* strain TH35+SX, *Trichoderma polysporum* strain IMI206039+SX, *trichoderma stromaticum*+SX, *Trichoderma virens* strain G-41+SX, *Trichoderma virens* strain GL-21+SX, *Trichoderma viride*+SX, Variovorax *paradoxus* strain CGF4526+SX, Harpin protein+SX.

Combination of the Present ingredient in the above Group (c) and the Present compound X:

1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, anisiflupurin+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized glutathione+SX, paclobutrazol+SX, pendimethalin+SX, prohexadione-calcium+SX, prohydrojasmon+SX, pyraflufen-ethyl+SX, sintofen+SX, sodium 1-naphthaleneacetate+SX, sodium cyanate+SX, thidiazuron+SX, triapenthenol+SX, tribufos+SX, trinexapac-ethyl+SX, uniconazole-P+SX, 2-(naphthalen-1-yl)acetamide+SX, [4-oxo-4-(2-phenylethyl)amino]butylate+SX, methyl 5-(trifluoromethyl)benzo[b]thiophene-2-carboxylate+SX, 3-[(6-chloro-4-phenylquinazolin-2-yl)amino]propan-1-ol+SX, *Claroideoglomus etunicatum*+SX, *Claroideoglomus claroideum*+SX, *Funneliformis mosseae*+SX, *Gigaspora margarita*+SX, *Gigaspora rosea*+SX, *Glomus aggregatum*+SX, *Glomus deserticola*+SX, *Glomus monosporum*+SX, Paraglomus brasillianum+SX, *Rhizophagus clarus*+SX, *Rhizophagus intraradices* RTI-801+SX, *Rhizophagus irregularis* DAOM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Bradyrhizobium lupini*+SX, *Delftia acidovorans* RAY209+SX, *Mesorhizobium ciceri*+SX, *Mesorhizobium* huakii+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium trifolii*+SX, *Rhizobium tropici*+SX, *Sinorhizobium fredii*+SX, *Sinorhizobium meliloti*+SX, Zucchini Yellow Mosaik Virus weak strain+SX.

Combination of the Present ingredient in the above Group (d) and the Present compound X:

anthraquinone+SX, deet+SX, icaridin+SX.

The ratio of the Present compound X to the Present ingredient includes, but not limited thereto, as a ratio by weight (the Present compound X:the Present ingredient) 1,000:1 to 1:1,000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:50, and the others.

The Present compound X has control effect on harmful arthropods such as harmful insects and harmful mites, harmful nematodes, and harmful mollusks. Examples of the harmful arthropods, harmful nematodes, and harmful mollusks include the followings.

Hemiptera:

from the family Delphacidae, for example, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), and *Tagosodes orizicolus;* from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), rice leafhopper (*Cofana spectra*), and *Amrasca biguttula biguttula;* from the family Aphrophoridae, for example, European spittlebug (*Philaenus spumarius*);

from the family Cercopidae, for example, *Mahanarva posticata* and *Mahanarva fimbriolata;* from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), apple woolly aphid (*Eriosoma lanigerum*), and English grain aphid (*Sitobion avenae*);

from the family Phylloxeridae, for example, grapevine *phylloxera* (*Daktulosphaira vitifoliae*), Pecan *phylloxera* (*Phylloxera devastatrix*), Pecan leaf *phylloxera* (*Phylloxera notabilis*), and Southern pecan leaf *phylloxera* (*Phylloxera* russelae);

from the family Adelgidae, for example, hemlock woolly aphid (*Adelges tsugae*), balsam woolly aphid (*Adelges piceae*), and *Aphrastasia pectinatae;* from the family Pentatomidae, for example, black rice bug (*Scotinophara lurida*), black paddy bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), brown stink bug(*Euschistus heros*), red banded stink bug (*Piezodorus guildinii*), *Oebalus pugnax*, and *Dichelops melacanthus*; from the family Cydnidae, for example, *Scaptocoris castanea;* from the family Alydidae, for example, bean bug (*Riptortus clavatus*), corbett rice bug (*Leptocorisa chinensis*), and rice bug (*Leptocorisa acuta*);

from the family Coreidae, for example, *Cletus punctiger* and Australian leaf-footed bug (*Leptoglossus australis*);

from the family Lygaeidae, for example, oriental chinch bug (*Cavelerius saccharivorus*), seed bug (*Togo hemipterus*), and chinch bug (*Blissus leucopterus*);

from the family Miridae, for example, rice leaf bug (*Trigonotylus caelestialium*), sorghum plant bug (*Stenotus rubrovittatus*), wheat leaf bug (*Stenodema calcarata*), and American tarnished plant bug (*Lygus lineolaris*);

from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), and *Pealius euryae;* from the family Diaspididae, for example, *Abgrallaspis cyanophylli*, red scale (*Aonidiella aurantii*), San José scale (*Diaspidiotus perniciosus*), white peach scale (*Pseudaulacaspis pentagona*), arrowhead scale (*Unaspis yanonensis*), and citrus snow scale (*Unaspis citri*);

from the family Coccidae, for example, pink wax scale (*Ceroplastes rubens*);

from the family Margarodidae, for example, fluted scale (*Icerya purchasi*) and seychelles fluted scale (*Icerya seychellarum*);

from the family Pseudococcidae, for example, *solanum* mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), and tuttle mealybug (*Brevennia rehi*);

from the family Psyllidae, for example, citrus *psylla* (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), and Pear *psylla* (*Cacopsylla pyricola*);

from the family Tingidae, for example, sycamore lace bug (*Corythucha ciliata*), aster tingid (*Corythucha marmorata*), Japanese pear lace bug (*Stephanitis nashi*), and azalea lace bug (*Stephanitis pyrioides*);

from the family Cimicidae, for example, common bed bug (*Cimex lectularius*) and tropical bed bug(*Cimex hemipterus*);

from the family Cicadidae, for example, Quesada *gigas;* from the family Reduviidae, for example, *Triatoma infestans*, large kissing bug (*Triatoma rubrofasciata*), *Triatoma dimidiata*, and *Rhodonius prolixus;* and the others.

Lepidoptera:

from the family Crambidae, for example, rice stem borer (*Chilo suppressalis*), Dark-headed stem borer (*Chilo* polychrysus), white stem borer (*Scirpophaga innotata*), yellow paddy borer (*Scirpophaga incertulas*), *Rupela albina*, rice leaf roller (*Cnaphalocrocis medinalis*), Marasmia patnalis, rice leaf roller (Marasmia *exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma* luctuosale), bluegrass webworm (*Parapediasia teterrellus*), rice caseworm (*Nymphula* depunctalis), Sugarcane borer (*Diatraea saccharalis*), and eggplant fruit borer (*Leucinodes orbonalis*);

from the family Pyralidae, for example, lesser cornstalk borer (*Elasmopalpus lignosellus*), mealworm moth (*Plodia interpunctella*), persimmon bark borer (*Euzophera batangensis*), and fig moth (*Cadra cautella*);

from the family Noctuidae, for example, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), semitropical armyworm (*Spodoptera eridania*), black cutworm (*Agrotis ipsilon*), beet worm (*Autographa nigrisigna*), rice looper (*Plusia festucae*), Soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*), corn earworm (*Helicoverpa zea*)), velvet-bean caterpillar (*Anticarsia gemmatalis*), cotton leafworm (*Alabama argillacea*), and hop vine borer (*Hydraecia immanis*);

from the family Pieridae, for example, common cabbage worm (*Pieris rapae*);

from the family Tortricidae, for example, oriental fruit moth (*Grapholita molesta*), *Grapholita dimorpha*, soybean moth (*Leguminivora glycinivorella*), *Matsumuraeses azukivora*, summer fruit *tortrix* (*Adoxophyes orana fasciata*), smaller tea *tortrix* (*Adoxophyes honmai*), Japanese tea *tortrix* (*Homona magnanima*), apple *tortrix* (*Archips fuscocupreanus*), codling moth (*Cydia pomonella*), sugarcane shoot borer (*Tetramoera schistaceana*), bean shoot borer (*Epinotia aporema*), citrus fruit borer (*Citripestis sagittiferella*), and European grapevine moth (*Lobesia botrana*);

from the family Gracillariidae, for example, tea leaf roller (*Caloptilia theivora*) and Asiatic apple leaf miner (*Phyllonorycter ringoniella*);

from the family Carposinidae, for example, peach fruit moth (*Carposina sasakii*);

from the family Lyonetiidae, for example, coffee leaf miner (*Leucoptera coffeella*), peach leaf miner (*Lyonetia clerkella*), and *Lyonetia prunifoliella;* from the family Lymantriidae, for example, *Lymantria* spp. (such as gypsy moth (*Lymantria dispar*)) and *Euproctis* spp. (such as tea lymantriid (*Euproctis pseudoconspersa*));

from the family Plutellidae, for example, diamondback moth (*Plutella xylostella*);

from the family Gelechiidae, for example, peach worm (*Anarsia lineatella*), sweetpotato leaf folder (*Helcystogramma triannulella*), pink bollworm (*Pectinophora gossypiella*), potato moth (*Phthorimaea operculella*), and *Tuta absoluta;* from the family Arctiidae, for example, American white moth (*Hyphantria cunea*);

from the family Castniidae, for example, giant sugarcane borer (Telchin *licus*);

from the family Cossidae, for example, *Cossus insularis;* from the family Geometridae, for example, *Ascotis selenaria;* from the family Limacodidae, for example, blue-striped nettle grub (*Parasa lepida*);

from the family Stathmopodidae, for example, persimmon fruit moth (*Stathmopoda masinissa*);

from the family Sphingidae, for example, tobacco hornworm (*Acherontia lachesis*);

from the family Sesiidae, for example, *Nokona feralis*, cherry borer (*Synanthedon hector*), and *Synanthedon tenuis;* from the family Hesperiidae, for example, rice skipper (*Parnara guttata*);

from the family Tineidae, for example, casemaking clothes moth (*Tinea translucens*), common clothes moth (*Tineola bisselliella*);

and the others.

Thysanoptera:

from the family Thripidae, for example, western flower *thrips* (*Frankliniella occidentalis*), oriental *thrips* (*Thrips palmi*), yellow tea *thrips* (*Scirtothrips dorsalis*), onion *thrips* (*Thrips tabaci*), eastern flower *thrips* (*Frankliniella intonsa*), rice *thrips* (*Stenchaetothrips biformis*), *Echinothrips americanus*, and avocado *thrips* (*Scirtothrips perseae*);

from the family Phlaeothripidae, for example, aculeated rice *thrips* (*Haplothrips aculeatus*);

and the others.

Diptera:

from the family Anthomyiidae, for example, seedcorn maggot (*Delia platura*), onion maggot (*Delia antiqua*), and beet leaf miner (*Pegomya cunicularia*);

from the family Ulidiidae, for example, sugarbeet root maggot (*Tetanops myopaeformis*);

from the family Agromyzidae, for example, rice leaf miner (*Agromyza oryzae*), tomato leaf miner (*Liriomyza sativae*), *chrysanthemum* leaf miner (*Liriomyza trifolii*), and pea leafminer (*Chromatomyia horticola*);

from the family Chloropidae, for example, rice stem maggot (*Chlorops oryzae*);

from the family Tephritidae, for example, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), Mediterranean fruit fly (*Ceratitis capitata*), apple maggot (*Rhagoletis pomonella*), and Japanese cherry fruit fly (*Rhacochlaena japonica*);

from the family Ephydridae, for example, smaller rice leaf miner (*Hydrellia griseola*), whorl maggot (*Hydrellia philippina*), and paddy stem maggot (*Hydrellia sasakii*);

from the family Drosophilidae, for example, cherry *drosophila* (*Drosophila* suzukii), and common fruit fly (*Drosophila melanogaster*);

from the family Phoridae, for example, *Megaselia spiracularis;* from the family Psychodidae, for example, Clogmia *albipunctata;* from the family Sciaridae, for example, *Bradysia difformis;* from the family Cecidomyiidae, for example, hessian fly (*Mayetiola destructor*) and paddy gall fly (*Orseolia oryzae*);

from the family Diopsidae, for example, *Diopsis macrophthalma;* from the family Glossinidae, for example, *Glossina palpalis* and *Glossina morsitans;* from the family Simuliidae, for example, *Simulium japonicum* and *Simulium damnosum;* from the subfamily Phlebotominae;

from the family Tipulidae, for example, rice crane fly (*Tipula aino*), common cranefly (*Tipula oleracea*), and European cranefly (*Tipula paludosa*);

from the family Culicidae, for example, southern house mosquito (*Culex pipiens pallens*), *Culex tritaeniorhynchus, Culex pipiens* f. *molestus*, brown house mosquito (*Culex quinquefasciatus*), northern house mosquito (*Culex pipiens pipiens*), *Culex vishnui*, Asian tiger mosquito (*Aedes albopictus*), dengue mosquito (*Aedes aegypti*), Chinese malaria mosquito (*Anopheles sinensis*), *Anopheles gambiae, Anopheles stephensi, Anopheles coluzzii, Anopheles albimanus, Anopheles sundaicus, Anopheles arabiensis, Anopheles funestus, Anopheles darlingi, Anopheles farauti*, and *Anopheles minimus;* from the family Simulidae, for example, *Prosimulium yezoensis* and *Simulium ornatum;* from the family Tabanidae, for example, *Tabanus trigonus;* from the family Muscidae, for example, house fly (*Musca domestica*), false stable fly (*Muscina stabulans*), biting house fly (*Stomoxys calcitrans*), and buffalo fly (*Haematobia irritans*);

from the family Calliphoridae;

from the family Sarcophagidae;

from the family Chironomidae, for example, *Chironomus plumosus, Chironomus yoshimatsui*, and *Glyptotendipes tokunagai;* from the family Fannidae;

and the others.

Coleoptera:

from the family Chrysomelidae, for example, *Diabrotica* spp. (such as western corn rootworm (*Diabrotica virgifera virgifera*), southern corn rootworm (*Diabrotica* undecimpunctata howardi), northern corn rootworm (*Diabrotica barberi*), Mexican corn rootworm (*Diabrotica virgifera zeae*), banded cucumber beetle (*Diabrotica balteata*), cucurbit beetle(*Diabrotica speciosa*)), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), cabbage flea beetle (*Phyllotreta cruciferae*), western black flea beetle (*Phyllotreta pusilla*), cabbage stem flea beetle (*Psylliodes chrysocephala*), hop flea beetle (*Psylliodes punctulata*), Colorado potato beetle (*Leptinotarsa decemlineata*), rice leaf beetle (*Oulema oryzae*), grape *colaspis* (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (Dicladispa *armigera*), southern corn leaf beetle (*Myochrous denticollis*), Laccoptera *quadrimaculata*, and tobacco flea beetle (*Epitrix hirtipennis*);

from the family Carabidae, for example, Seedcorn beetle (*Stenolophus lecontei*) and slender seed-corn ground beetle (*Clivina impressifrons*);

from the family Scarabaeidae, for example, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer(*Rhizotrogus majalis*), *Tomarus gibbosus, Holotrichia* spp., *Phyllophaga* spp. (such as June beetle (*Phyllophaga crinita*)), and *Diloboderus* spp. (such as *Diloboderus abderus*);

from the family Anthriibidae, for example, coffee bean weevil(*Araecerus coffeae*);

from the family Aponidae, for example, sweet-potato weevil (*Cylas formicarius*);

from the family Bruchidae, for example, Mexican bean weevil (Zabrotes *subfasciatus*);

from the family Scolytidae, for example, pine beetle (*Tomicus piniperda*) and coffee berry borer (*Hypothenemus hampei*);

from the family Curculionidae, for example, West Indian sweet-potato weevil (*Euscepes postfasciatus*), alfalfa weevil (*Hypera postica*), maize wevil (*Sitophilus zeamais*), rice weevil (*Sitophilus oryzae*), grain weevil (*Sitophilus granarius*), rice plant weevil (*Echinocnemus squameus*), rice water weevil (*Lissorhoptrus oryzophilus*), *Rhabdoscelus lineaticollis*, boll weevil (*Anthonomus grandis*), nunting billbug (*Sphenophorus venatus*), southern corn billbug (*Sphenophorus callosus*), soybean stalk weevil (*Sternechus subsignatus*), sugarcane weevil (*Sphenophorus levis*), rusty gourd-shaped weevil (*Scepticus griseus*), brown gourd-shaped weevil (*Scepticus uniformis*), *Aracanthus* spp. (such as *Aracanthus mourei*), and cotton root borer (*Eutinobothrus brasiliensis*);

from the family Tenebrionidae, for example, red meal beetle (*Tribolium castaneum*), mason beetle (*Tribolium confusum*), and lesser mealworm (Alphitobius diaperinus);

from the family Coccinellidae, for example, twenty-eight-spotted ladybird (*Epilachna* vigintioctopunctata);

from the family Bostrychidae, for example, common powder-post beetle (*Lyctus brunneus*), and lesser grain borer (Rhizopertha dominica);

from the family Ptinidae;

from the family Cerambycidae, for example, citrus long-horned beetle (*Anoplophora malasiaca*), *Migdolus fryanus*, and peach borer (*Aromia bungii*);

from the family Elateridae, for example, *Melanotus okinawensis*, barley wireworm (*Agriotes fuscicollis*), *Melanotus legatus, Anchastus* spp., *Conoderus* spp., *Ctenicera* spp., *Limonius* spp., and *Aeolus* spp.;

from the family Staphylinidae, for example, *Paederus fuscipes;* from the family Dermestidae, for example, varied carpet beetle (*Anthrenus verbasci*), hide beetle (*Dermestes maculates*), and khapra beetle (Trogoderma granarium);

from the family Anobiidae, for example, tobacco beetle (*Lasioderma serricorne*), and biscuit beetle (Stegobium paniceum);

from the family Laemophloeidae, for example, flat grain beetle (Cryptolestes *ferrugineus*);

from the family Silvanidae, for example, saw-toothed grain beetle (Oryzaephilus surinamensis);

from the family Nitidulidae, for example, blossom beetle (Brassicogethes *aeneus*);

and the others.

Orthoptera:

from the family Acrididae, for example, oriental migratory locust (*Locusta migratoria*), Moroccan locust (*Dociostaurus maroccanus*), Australian plague locust (*Chortoicetes terminifera*), red locust (*Nomadacris septemfasciata*), brown locust(*Locustana pardalina*), tree locust (*Anacridium melanorhodon*), Italian locust (*Calliptamus italicus*), differential grasshopper (*Melanoplus differentialis*), two-striped grasshopper (*Melanoplus bivittatus*), migratory grasshopper (*Melanoplus sanguinipes*), red-legged grasshopper (*Melanoplus femurrubrum*), clear-winged grasshopper (*Camnula pellucida*), desert locust (*Schistocerca gregaria*), Yellow-winged locust(*Gastrimargus musicus*), spur-throated locust (*Austracris guttulosa*), Japanese grasshopper (*Oxya yezoensis*), rice grasshopper (*Oxya japonica*), and Bombay locust (*Patanga succincta*);

from the family Gryllotalpidae, for example, oriental mole cricket (*Gryllotalpa orientalis*);

from the family Gryllidae, for example, house cricket (*Acheta domestica*), and emma field cricket (*Teleogryllus emma*);

from the family Tettigoniidae, for example, mormon cricket (*Anabrus simplex*);

and the others.

Hymenoptera:

from the family Tenthredinidae, for example, beet sawfly (*Athalia rosae*) and nippon cabbage sawfly (*Athalia japonica*);

from the family Formicidae, for example, *Solenopsis* spp. (such as red imported fire ant (*Solenopsis invicta*), tropical fire ant (*Solenopsis geminata*)), *Atta* spp. (such as brown leaf-cutting ant (*Atta capiguara*), *Acromyrmex* spp., *Paraponera clavata*, black house ant (*Ochetellus glaber*), little red ant (*Monomorium pharaonis*), Argentine ant (*Linepithema humile*), Formica *japonica, Pristomyrmex punctutus, Pheidole* noda, big-headed ant (*Pheidole megacephala*), *Camponotus* spp. (such as *Camponotus japonicus, Camponotus obscuripes*), *Pogonomyrmex* spp. (such as western harvester ant (*Pogonomyrmex occidentalis*)), *Wasmania* spp. (such as *Wasmania auropunctata*), and long-legged ant (*Anoplolepis gracilipes*);

from the family Vespidae, for example, Asian giant hornet (*Vespa mandarinia, Vespa simillima, Vespa analis*, Asian hornet(*Vespa velutina*), and *Polistes jokahamae;* from the family Siricidae, for example, pine wood wasp (*Urocerus gigas*);

from the family Bethylidae;

and the others.

Blattodea:

from the family Ectobiidae, for example, German cockroach (*Blattella germanica*);

from the family Blattidae, for example, smoky-brown cockroach (*Periplaneta fuliginosa*), American cockroach (*Periplaneta americana*), Australian cockroach (*Periplaneta australasiae*), brown cockroach (*Periplaneta brunnea*), and black cockroach (*Blatta orientalis*);

from the family Termitidae, for example, Japanese termite (*Reticulitermes speratus*), Formosan termite (*Coptotermes formosanus*), western drywood termite (*Incisitermes minor*), *Cryptotermes domesticus, Odontotermes formosanus, Neotermes koshunensis, Glyptotermes satsumensis, Glyptotermes nakajimai, Glyptotermes fuscus, Hodotermopsis*

*sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae*, and *Cornitermes cumulans*; and the others.

Siphonaptera:

from the family Pulicidae, for example, human flea (*Pulex irritans*), cat flea (*Ctenocephalides felis*), dog flea (*Ctenocephalides canis*), oriental rat flea (*Xenopsylla cheopis*), and chicken flea (*Echidnophaga gallinacea*); from the family Pulicidae, for example, chigoe flea (*Tunga penetrans*);

from the family Ceratophyllidae, for example, European rat flea (*Nosopsyllus fasciatus*);

and the others.

Psocodae:

from the family Pediculidae, for example, head louse (*Pediculus humanus* capitis);

from the family Pthiridae, for example, crab louse (*Pthirus pubis*);

from the family Haematopinidae, for example, short-nosed cattle louse (*Haematopinus eurysternus*) and pig louse (*Haematopinus suis*);

from the family Linognathidae, for example, blue cattle louse (*Linognathus vituli*), sheep face louse (*Linognathus ovillus*), and capillate louse (*Solenopotes capillatus*);

from the family Bovicoliidae, for example, cattle biting louse (*Bovicola bovis*), sheep biting louse (*Bovicola ovis*), *Bovicola breviceps, Damalinia forficula*, and *Werneckiella* spp.;

from the family Trichodectidae, for example, dog biting louse (*Trichodectes canis*) and cat louse (*Felicola subrostratus*);

from the family Menoponidae, for example, common chicken louse (*Menopon gallinae*), chicken body louse (*Menacanthus stramineus*), and *Trinoton* spp.;

from the family Trimenoponidae, for example, *Cummingsia* spp.;

from the family Trogiidae, for example, death watch (*Trogium pulsatorium*);

from the family Liposcelidae or Liposcelididae, for example, book louse (*Liposcelis corrodens*), *Liposcelis bostrychophila, Liposcelis pearmani*, and *Liposcelis entomophila;* and the other.

Thysanura:

from the family Lepismatidae, for example, oriental silverfish (Ctenolepisma *villosa*) and moth fish (*Lepisma saccharina*);

and the others.

Acari:

from the family Tetranychidae, for example, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), and *Oligonychus* spp.;

from the family Eriophyidae, for example, Japanese citrus rust mite (Aculops pelekassi), Phyllocoptruta *citri*, tomato mite (Aculops *lycopersici*), purple mite (Calacarus *carinatus*), tea rust mite (Acaphylla theavagrans), *Eriophyes chibaensis*, apple bud mite (*Aculus schlechtendali*), Aceria *diospyri*, Aceria tosichella, and *Shevtchenkella* sp.;

from the family Tarsonemidae, for example, broad mite (*Polyphagotarsonemus latus*);

from the family Tenuipalpidae, for example, *Brevipalpus phoenicis;* from the family Tuckerellidae;

from the family Ixodidae, for example, *Haemaphysalis longicornis, Haemaphysalis flava, Haemaphysalis japonica, Haemaphysalis campanulata*, American dog tick (*Dermacentor variabilis*), *Dermacentor taiwanensis*, Rocky Mountain wood tick (*Dermacentor andersoni*), netted tick (*Dermacentor reticulatus*), *Ixodes ovatus, Ixodes persulcatus*, black-legged tick (*Ixodes scapularis*), *Ixodes pacificus, Ixodes holocyclus, Ixodes ricinus*, lone star tick (*Amblyomma americanum*), gulf coast tick (*Amblyomma maculatum*), *Rhipicephalus microplus*, cattle tick (*Rhipicephalus annulatus*), brown dog tick (*Rhipicephalus sanguineus*), *Rhipicephalus appendiculatus*, and *Rhipicephalus decoloratus;* from the family Argasidae, for example, fowl tick (*Argas persicus*), *Ornithodoros hermsi*, and *Ornithodoros turicata;* from the family Acaridae, for example, cereal mite (Tyrophagus putrescentiae) and grassland mite (Tyrophagus *similis*);

from the family Pyroglyphidae, for example, American house dust mite (*Dermatophagoides farinae*) and European house dust mite (*Dermatophagoides pteronyssinus*);

from the family Cheyletidae, for example, Cheyletus eruditus, Cheyletus *malaccensis, Chelacaropsis moorei*, and *Cheyletiella yasguri;* from the family Psoroptidae, for example, sheep scab mite (*Psoroptes ovis*), horse psoroptic mange mite (*Psoroptes equi*), Knemidocoptes *mutans*, ear mange mite (Otodectes cynotis), and Chorioptes spp.;

from the family Sarcoptidae, for example, Notoedres cati, Notoedres *muris*, and itch mite (*Sarcoptes scabiei*);

from the family Listrophoridae, for example, Listrophorus gibbus;

from the family Dermanyssidae, for example, bird mite (*Dermanyssus gallinae*);

from the family Macronyssidae, for example, feather mite (*Ornithonyssus* sylviarum) and tropical rat mite (*Ornithonyssus bacoti*);

from the family Varroidae, for example, *Varroa jacobsoni;* from the family Demodicidae, for example, dog follicle mite (*Demodex canis*) and cat follicle mite (*Demodex cati*);

from the family Trombiculidae, for example, Leptotrombidium akamushi, Leptotrombidium *pallidum*, and Leptotrombidium scutellare;

and the others.

Araneae:

from the family Eutichuridae, for example, *Cheiracanthium japonicum;* from the family Theridiidae, for example, red-back spider (*Latrodectus hasseltii*);

and the others.

Polydesmida:

from the family Paradoxosomatidae, for example, flat-backed millipede (*Oxidus gracilis*) and *Nedyopus tambanus*;

and the others.

Isopoda:

from the family Armadillidiidae, for example, common pill bug (*Armadillidium vulgare*);

and the others.

Chilopoda:

from the family Scutigeridae, for example, *Thereuonema hilgendorfi;* from the family Scolopendridae, for example, giant tropical centipede (*Scolopendra subspinipes*);

from the family Ethopolyidae, for example, *Bothropolys rugosus;* and the others.

Gastropoda:

from the family Limacidae, for example, tree slug (*Limax marginatus*) and garden tawny slug (*Limax flavus*);

from the family Philomycidae, for example, *Meghimatium bilineatum;* from the family Ampullariidae, for example, golden apple snail (*Pomacea canaliculata*);

from the family Lymnaeidae, for example, *Austropeplea ollula;* and the others.

Nematoda:

from the family Aphelenchoididae, for example, rice white-tip nematode (*Aphelenchoides besseyi*);

from the family Pratylenchidae, for example, root lesion nematode (*Pratylenchus coffeae*), *Pratylenchus brachyurus*, California meadow nematode (*Pratylenchus neglectus*), and *Radopholus similis;* from the family Heteroderidae, for example, javanese root-knot nematode (*Meloidogyne javanica*), southern root-knot nematode (*Meloidogyne incognita*), guava root-knot nematodes (*Meloidogyne enterolobii*), northern root-knot nematode (*Meloidogyne hapla*), soybean cyst nematode (*Heterodera glycines*), potato cyst nematode (*Globodera rostochiensis*), and white potato cyst nematode (*Globodera pallida*);

from the family Hoplolaimidae, for example, *Rotylenchulus reniformis;* from the family Anguinidae, for example, strawberry bud nematode (Nothotylenchus *acris*), and stem nematode (*Ditylenchus dipsaci*);

from the family Tylenchulidae, for example, citrus nematode (*Tylenchulus semipenetrans*);

from the family Longidoridae, for example, dagger nematode (*Xiphinema index*);

from the family Trichodoridae;

from the family Parasitaphelenchidae, for example, pine wilt disease (*Bursaphelenchus xylophilus*);

and the others.

The harmful arthropods such as harmful insects and harmful mites, harmful mollusks, and harmful nematodes may be those having a reduced susceptibility to or a developed resistance to an insecticide, a miticide, a molluscicide, or a nematicide.

The method for controlling harmful arthropods of the present invention is carried out by applying an effective amount of the Present compound, the Present compound X, or the Composition A to a harmful arthropod directly and/or a habitat thereof (for example, plant bodies, soil, an interior of a house, animal bodies). Examples of the method for controlling harmful arthropods of the present invention include foliage treatment, soil treatment, root treatment, shower treatment, smoking treatment, water surface treatment, and seed treatment.

The Present compound, the Present compound X, or the Composition A is usually used by mixing it with inert carrier(s) such as solid carrier(s), liquid carrier(s), and gaseous carrier(s), surfactant(s), and the like, and as needed, adding thereto auxiliary agent(s) for formulation such as binder(s), dispersant(s), and stabilizer(s) to be formulated into an aqueous suspension formulation, an oily suspension formulation, an oil solution, an emulsifiable concentrate, an emulsion formulation, a microemulsion formulation, a microcapsule formulation, a wettable powder, a granular wettable powder, a dust formulation, a granule, a tablet, an aerosol formulation, a resin formulation, or the like. In addition to these formulations, the Present compound, the Present compound X, or the Composition A may be used by formulating it into a dosage form described in Manual on development and use of FAO and WHO Specifications for pesticides, FAO Plant Production and Protection Papers-271-276, prepared by the FAO/WHO Joint Meeting on Pesticide Specifications, 2016, ISSN:0259-2517.

These formulations usually comprise 0.0001 to 99% by weight ratio of the Present compound, the Present compound X, or the Composition A.

Examples of the solid carrier include fine powders and granules of clays (for example, pyrophyllite clay and kaolin clay), talc, calcium carbonate, diatomaceous earth, zeolite, bentonite, acid white clay, attapulgite, white carbon, ammonium sulfate, vermiculite, perlite, pumice, silica sand, chemical fertilizers (for example, ammonium sulfate, ammonium phosphate, ammonium nitrate, urea, and ammonium chloride), and the others; as well as resins (for example, polypropylene, polyester, polyurethane, polyamide, and polyvinyl chloride).

Examples of the liquid carrier include water, alcohols (for example, ethanol, cyclohexanol, benzyl alcohol, propylene glycol, and polyethylene glycol), ketones (for example, acetone and cyclohexanone), aromatic hydrocarbons (for example, xylene, phenyl xylyl ethane, and methylnaphthalene), aliphatic hydrocarbons (for example, hexane and cyclohexane), esters (for example, ethyl acetate, methyl oleate, and propylene carbonate), nitriles (for example, acetonitrile), ethers (for example, ethylene glycol dimethyl ether), amides (for example, N,N-dimethylformamide and N,N-dimethyloctanamide), sulfoxides (for example, dimethyl sulfoxide), lactams (for example, N-methylpyrrolidone and N-octylpyrrolidone), fatty acids (for example, oleic acid), and vegetable oils (for example, soybean oil).

Examples of the gaseous carrier include fluorocarbon, butane gas, LPG (liquefied petroleum gas), dimethyl ether, nitrogen, and carbon dioxide.

Examples of the surfactant include nonionic surfactants (for example, polyoxyethylene alkyl ethers, polyoxyethylene alkyl aryl ethers, and polyethylene glycol fatty acid esters), and anionic surfactants (for example, alkyl sulfonates, alkyl aryl sulfonates, and alkyl sulfates). The specific examples thereof include Nimbus (registered trademark), Assist (registered trademark), Aureo (registered trademark), Iharol (registered trademark), Silwet L-77 (registered trademark), BreakThru (registered trademark), SundanceII (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), and BANOLE (registered trademark).

Examples of the other auxiliary agent for formulation include binders, dispersants, colorants, and stabilizers, and the specific examples thereof include polysaccharides (for example, starch, gum arabic, cellulose derivatives, and alginic acid), lignin derivatives, water-soluble synthetic polymers (for example, polyvinyl alcohol, polyvinyl pyrrolidone, and polyacrylic acids), acidic isopropyl phosphate, and dibutylhydroxytoluene.

As used herein, examples of the plant include whole plant, stem and leaf, flower, ear, fruit, tree stem, branch, crown, seed, vegetative reproductive organ, and seedling.

A vegetative reproductive organ means a part of plant such as root, stem, and leaf which has a growth capability even when said part is separated from the plant body and placed into soil. Examples of the vegetative reproductive organ include tuberous root, creeping root, bulb, corm or solid bulb, tuber, rhizome, stolon, rhizophore, cane cuttings, propagule, and vine cutting. Stolon is also referred to as “runner”, and propagule is also referred to as “propagulum” and categorized into broad bud and bulbil. Vine cutting means a shoot (collective term of leaf and stem) of sweet potato, glutinous yam, or the like. Bulb, corm or solid bulb, tuber, rhizome, cane cuttings, rhizophore, and tuberous root are also collectively referred to as “bulb”. For example, cultivation of potato starts with planting a tuber into soil, and the tuber to be used is generally referred to as “seed potato”.

Examples of a method for controlling harmful arthropods by applying an effective amount of the Present compound, the Present compound X, or the Composition A to soils include a method of applying an effective amount of the Present compound, the Present compound X, or the Composition A to soil before planting plants or after planting plants, a method of applying an effective amount of the Present compound, the Present compound X, or the Composition A to a root part of a crop to be protected from damage such as ingestion by harmful arthropods, and a method of controlling harmful arthropods that ingest a plant by permeating and transferring an effective amount of the Present compound, the Present compound X, or the Composition A from a root into the interior of the plant body. Specifically, examples of the application method include planting hole treatment (for example, spraying into planting holes and soil mixing after planting hole treatment), plant foot treatment (for example, plant foot spraying, soil mixing after plant foot treatment, irrigation at plant foot, and plant foot treatment at a later seeding raising stage), planting furrow treatment (for example, planting furrow spraying and soil mixing after planting furrow treatment), planting row treatment (for example, planting row spraying, soil mixing after planting row treatment, and planting row spraying at a growing stage), planting row treatment at the time of sowing (for example, planting row spraying at the time of sowing and soil mixing after planting row treatment at the time of sowing), broadcast treatment (for example, overall soil surface spraying and soil mixing after broadcast treatment), side-article treatment, treatment of water surface (for example, application to water surface and application to water surface after flooding), other soil spraying treatment (for example, spraying of a granular formulation on leaves at a growing stage, spraying under a canopy or around a tree stem, spraying on the soil surface, mixing with surface soil, spraying into seed holes, spraying on the ground surfaces of furrows, and spraying between plants), other irrigation treatment (for example, soil irrigation, irrigation at a seedling raising stage, chemical solution injection treatment, irrigation of a plant part just above the ground, chemical solution drip irrigation, and chemigation), seedling raising box treatment (for example, spraying into a seedling raising box, irrigation of a seedling raising box, and flooding into a seedling raising box with chemical solution), seedling raising tray treatment (for example, spraying on a seedling raising tray, irrigation of a seedling raising tray, and flooding into a seedling raising tray with chemical solution), seedbed treatment (for example, spraying on a seedbed, irrigation of a seedbed, spraying on a lowland rice nursery, and immersion of seedlings), seedbed soil incorporation treatment (for example, mixing with seedbed soil, mixing with seedbed soil before sowing, spraying at sowing before covering with soils, spraying at sowing after covering with soils, and mixing with covering with soils), and other treatment (for example, mixing with culture soil, plowing under, mixing with surface soil, mixing with soil at the place where raindrops fall from a canopy, treatment at a planting position, spraying of a granule formulation on flower clusters, and mixing with a paste fertilizer).

Examples of the application to seeds (or seed treatments) include an application of the Present compound, the Present compound X, or the Composition A to seeds or vegetative reproductive organs, and specific examples thereof include spraying treatment in which a suspension of the Present compound, the Present compound X, or the Composition A is sprayed onto seed surface or the vegetative reproductive organ surface in the form of mist; smearing treatment in which the Present compound, the Present compound X, or the Composition A is coated on a surface of seeds or the vegetative reproductive organs; a soaking treatment in which the seeds or vegetative reproductive organs are soaked into the solution of the Present compound, the Present compound X, or the Composition A for a certain time; and a method for coating the seeds or the vegetative reproductive organs with a carrier containing the Present compound, the Present compound X, or the Composition A (for example, film coating treatment and pellet coating treatment). Examples of the above-described vegetative reproductive organ include particularly seed potato.

When the Composition A is applied to seeds or vegetative reproductive organs, the Composition A may be also applied to seeds or vegetative reproductive organs as a single formulation, or the Composition A may be applied to seeds or vegetative reproductive organs as multiple different formulations by multiple times. Examples of the method in which the Composition A is applied as multiple different formulations by multiple times include, for example, a method in which the formulations comprising as an active component the Present compound or the Present compound X only are applied, and seeds or vegetative reproductive organs are air dried, followed by applying the formulations comprising the Present ingredient: and a method in which the formulations comprising as an active component the Present compound or the Present compound X and the Present ingredients are applied, and seeds or vegetative reproductive organs are air dried, followed by applying the formulations comprising the Present ingredients other than the already-applied Present ingredients, are included.

As used herein, seeds or vegetative reproductive organs holding the Present compound, the Present compound X, or the Composition A mean seeds or vegetative reproductive organs in the state where the Present compound, the Present compound X, or the Composition A is adhered to a surface of the seeds or the vegetative reproductive organs. The above-described seeds or vegetative reproductive organs holding the Present compound, the Present compound X, or the Composition A may be adhered by any other materials that are different from the Present compound, the Present compound X, or the Composition A before or after being adhered the Present compound, the Present compound X, or the Composition A to the seeds or vegetative reproductive organs.

Also, when the Composition A is adhered in a form of layer(s) to a surface of seeds or vegetative reproductive organs, the layer(s) is/are composed of one layer or a multiple layers. Also, when multiple layers are formed, each of the layer may be composed of a layer comprising one or more active ingredients, or a combination of a layer comprising one or more active ingredients and a layer not comprising an active ingredient.

Seeds or vegetative reproductive organs holding the Present compound, the Present compound X, or the Composition A can be obtained, for example, by applying the formulations comprising the Present compound, the Present compound X, or the Composition A by the above-described application method to seeds or vegetative reproductive organs.

When the Present compound, the Present compound X, or the Composition A is applied for harmful arthropods control in agricultural fields, the application dose thereof is usually within a range of 1 to 10,000 g of the Present compound or the Present compound X per 10,000 $m^2$. In the case of being applied to seeds or vegetative reproductive organs, the application dose thereof is usually within a range of 0.001 to 100 g of the Present compound or the Present compound X per 1 Kg of seeds or vegetative reproductive organs. When the Present compound, the Present compound X, or the Composition A is formulated into an emulsifiable concentrate, a wettable powder, or a flowable, etc., they are usually applied by diluting them with water so as to make an effective concentration of the active ingredients 0.01 to 10,000 ppm, and the granular formulation, the dust formulation, or the like is usually applied as itself without diluting them.

Also, the resin preparation of the Present compound X or the Composition A which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the Present compound, the Present compound X, or the Composition A is used to control harmful arthropods that live inside a house, the application dose as an amount of the Present compound or the Present compound X is usually within a range from 0.01 to 1,000 mg per 1 $m^2$ of an area to be treated, in the case of using it on a planar area. In the case of using it spatially, the application dose as an amount of the Present compound or the Present compound X is usually within a range from 0.01 to 500 mg per 1 $m^3$ of the space to be treated. When the Present compound, the Present compound X, or the Composition A is formulated into emulsifiable concentrates, wettable powders, flowables, or the others, such formulations are usually applied after diluting them with water in such a way that a concentration of the active ingredient is within a range from 0.1 to 10,000 ppm. In the case of being formulated into oil solutions, aerosols, smoking agents, poison baits, and the others, such formulations are used as themselves without diluting them.

When the Present compound, the Present compound X, or the Composition A is used for controlling external parasites of livestock such as cows, horses, pigs, sheep, goats, and chickens and small animals such as dogs, cats, rats, and mice, the composition of the present invention may be applied to the animals by a known method in the veterinary field. Specifically, when systemic control is intended, the composition of the present invention is administered to the animals as a tablet, a mixture with feed or a suppository, or by injection (including intramuscular, subcutaneous, intravenous, and intraperitoneal injections). On the other hand, when non-systemic control is intended, the composition of the present invention is applied to the animals by means of spraying of the oil solution or aqueous solution, pour-on or spot-on treatment, washing of the animals with a shampoo formulation, or by putting a collar or ear tag made of the resin formulations to the animals. In the case of being administered to an animal body, the dose of the Present compound or the Present compound X is usually within a range from 0.1 to 1,000 mg per 1 kg of an animal body weight.

Also, the Present compound, the Present compound X, or the Composition A may be used as an agent for controlling harmful arthropods in agricultural lands such as fields, paddy fields, turfs, and orchards. Examples of the plants include the followings.

corn (dent corn, flint corn, flour corn, popcorn, waxy corn, sweet corn, and field corn), rice (long grain rice, short grain rice, medium grain rice, *japonica* rice, tropical *japonica* rice, indica rice, *javanica* rice, paddy rice, upland rice, floating rice, direct-seeded rice, transplanted rice, and glutinous rice), wheat (bread wheat (hard wheat, soft wheat, medium wheat, red wheat, and white wheat), durum wheat, spelt wheat, and club wheat, winter wheat and spring wheat of them), barley (two-rowed barley (=barley for brewery), six-rowed barley, hull-less barley, and pearl barley, winter barley and spring barley of them), rye (winter rye and spring rye), triticale (winter triticale and spring triticale), oat (winter oat and spring oat), sorghum, cotton (upland cotton and Pima cotton), soybean (ripe seed harvest soybean, green soybeans, and early harvest soybeans, indeterminate type, determinate type, and semi-determinate type of them), peanut, buckwheat, beet (beets for sugar production, beets for feed, beets for root vegetable, beets for leaf vegetable, and beets for fuel), rapeseed (winter rapeseed and spring rapeseed), canola (winter canola and spring canola), sunflower (sunflowers for oil extraction, edible sunflowers, and sunflowers for ornamental purpose), sugar cane, tobacco, tea, mulberry, solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, welsh onion, onion, garlic, and asparagus), ammiaceous vegetables (for example, carrot, parsley, celery, and parsnip), chenopodiaceous vegetables (for example, spinach and Swiss chard), lamiaceous vegetables (for example, *perilla*, mint, and basil), strawberry, sweet potato, glutinous yam, eddoe, pomaceous fruits (for example, apple, pear, Japanese pear, Chinese white pear, Chinese quince, and quince), stone fleshy fruits (for example, peach, plum, nectarine, Japanese apricot (*Prunus mume*), cherry fruit, apricot, and prune), citrus fruits (for example, Citrus unshiu, orange, lemon, lime, and grapefruit), nuts (for example, chestnuts, walnuts, hazelnuts, almond, pistachio, cashew nuts, and macadamia nuts), berry fruits (for example, blueberry, cranberry, blackberry, and raspberry), grapes, Japanese persimmon, fig, olive, Japanese plum, banana, coffee, date palm, coconuts, ornamental plants, forest plants, turfs, grasses, and the others.

The above plants are not specifically limited as long as they are generally cultivated cultivars. The above plants also include plants which may be produced by natural breeding, plants which may be generated by mutation, F1 hybrid plants, and genetically modified crops. Examples of the genetically modified crops include plants which have resistance to HPPD (4-hydroxyphenylpyruvate dioxygenase enzyme) inhibitors such as isoxaflutole, ALS (acetolactate synthase) inhibitors such as imazethapyr and thifensulfuron-methyl, EPSP (5-enolpyruvylshikimate-3-phosphate synthase) inhibitors, glutamine synthetase inhibitors, PPO (protoporphyrinogen oxidase) inhibitors, or herbicide such as bromoxynil and dicamba; plants which can synthesize a selective toxin known in *Bacillus* spp. such as *Bacillus thuringiensis* or the like; and plants which can synthesize a gene fragment or the like which is partially identical to an endogenous gene derived from a harmful insect, and induce a gene silencing (RNAi; RNA interference) in the target harmful insect to achieve a specific insecticidal activity.

EXAMPLES

Hereinafter, the present invention is illustrated more in detail by Preparation Examples, Formulation Examples, Test Examples, and the like, but the present invention is not limited to these Examples only.

In the present description, Me represents a methyl group, Et represents an ethyl group, Pr represents a propyl group, i-Pr represents an isopropyl group, t-Bu represents a tert-butyl group, $C_2F_5$ represents a perfluoroethyl group, c-Pr represents a cyclopropyl group, Bn represents a benzyl group, Ph represents a phenyl group, Py2 represents a 2-pyridyl group, Py3 represents a 3-pyridyl group, and Py4 represents a 4-pyridyl group. When c-Pr, Ph, Py2, Py3, and Py4 have substituent(s), the substituent(s) is/are indicated before the symbols with the substitution position(s). For example, 1-CN-c-Pr represents a 1-cyanocyclopropyl group, 3,4-$F_2$-Ph represents a 3,4-difluorophenyl group, 2-$C_2$F5-Ph represents a 2-(perfluoroethyl)phenyl group, 4-$SO_2CF_3$-Ph represents a 4-(trifluoromethanesulfonyl)phenyl group, 3,4-$(OCF_3)_2$-Ph represents a 3,4-bis(trifluoromethoxy)phenyl group, 3-$SCF_3$-4-$OCF_3$-Ph represents a 3-[(trifluoromethyl)thio]-4-(trifluoromethoxy)phenyl group, and 4-$CF_3$—Py2 represents a 4-(trifluoromethyl)-2-pyridyl group.

First, Preparation Examples of the Present compounds X and the preparation intermediate compounds thereof are shown below.

When a physical property of a compound is measured by liquid chromatography/mass spectrometry (hereinafter referred to as "LCMS"), the measured molecular ion value $[M+H]^+$ or $[M-H]^-$, and retention time (hereinafter referred to as "RT") are described. The conditions of liquid chromatography (hereinafter referred to as "LC") are as follows.

[LC Conditions]

Column: L-column2 ODS, inner diameter: 4.6 mm, length: 30 mm, particle size: 3 μm (Chemicals Evaluation and Research Institute, Japan)

UV measurement wavelength: 254 nm

Mobile phase: Solution A: 0.1% formic acid in water, Solution B: 0.1% formic acid in acetonitrile Flow rate: 2.0 mL/min Gradient conditions: sending a solution with the concentration gradient described in Table LC1.

TABLE LC1

| Time (min) | Solution A (%) | Solution B (%) |
|---|---|---|
| 0.01 | 90 | 10 |
| 2.00 | 0 | 100 |
| 4.00 | 0 | 100 |
| 4.01 | 90 | 10 |

Reference Preparation Example 1

To a mixture of 6-bromo-3-(ethylthio)imidazo[1,2-a]pyridine-2-amine (hereinafter referred to as "Intermediate compound Z") (1.1 g) prepared according to the method described in WO 2018/052136 pamphlet and THF (8 mL) was added 4-(trifluoromethyl)benzoyl chloride (0.83 g), then triethylamine (1.1 mL) was added thereto, and the resulting mixture was stirred at room temperature for 30 minutes. To the resulting mixture was added water, and the resulting mixture was subjected to extraction with chloroform. The resulting organic layer was dried over anhydrous magnesium sulfate, and concentrated under reduced pressure to give the Intermediate compound 1 represented by the following formula (1.4 g).

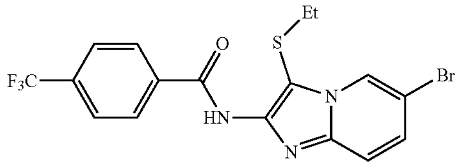 [SMILES: CCSc1c(NC(=O)c2ccc(C(F)(F)F)cc2)nc2ccc(Br)cn12]

Intermediate compound 1: $^1$H-NMR ($CDCl_3$) δ: 9.39 (1H, s), 8.52 (1H, s), 8.07 (2H, d), 7.79 (2H, d), 7.57 (1H, d), 7.47 (1H, d), 2.75 (2H, q), 1.24 (3H, t).

Reference Preparation Example 2

A mixture of the Intermediate compound Z (6.12 g), 3-(trifluoromethylthio)benzoic acid (5.0 g), 4-(dimethylamino)pyridine (0.55 g), pyridine (50 mL), and 1-ethyl-3-[3-(dimethylamino)propyl]carbodiimide hydrochloride (6.47 g) was stirred at 100° C. for 2 hours. To the resulting mixture was added water, and the resulting mixture was subjected to extraction with ethyl acetate. The resulting organic layer was dried over anhydrous magnesium sulfate, and concentrated under reduced pressure to give the Intermediate compound 2 represented by the following formula (6.57 g).

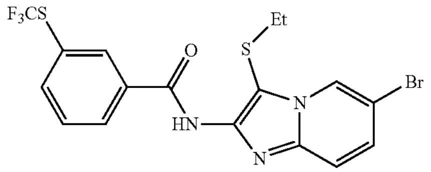

Intermediate compound 2: $^1$H-NMR ($CDCl_3$) δ: 8.56-8.53 (2H, m), 8.24 (1H, s), 8.10 (1H, d), 7.87 (1H, d), 7.60 (1H, t), 7.54 (1H, d), 7.39 (1H, d), 2.77 (2H, q), 1.25 (3H, t).

Reference Preparation Example 2-1

The compounds prepared according to the Reference Preparation Example 2 and physical properties thereof are shown below.

A Compound Represented by Formula (A-1)

(A-1)

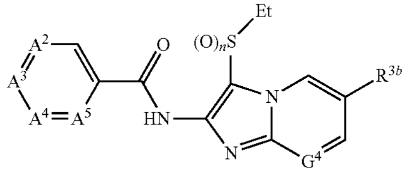

wherein the combination of $A^2$, $A^3$, $A^4$, $A^5$, $G^4$, and $R^{3b}$ represents any one combination indicated in Table A-1.

TABLE A-1

| Intermediate compound | $A^2$ | $A^3$ | $A^4$ | $A^5$ | $G^4$ | $R^{3b}$ |
|---|---|---|---|---|---|---|
| 3 | C-$SCF_3$ | CH | CH | CH | CH | $CF_3$ |
| 4 | C-$SCF_3$ | CH | CH | CH | CH | Cl |
| 5 | C-$SCF_3$ | CH | CH | CH | N | Br |
| 6 | CH | C-$SCF_3$ | CH | CH | CH | Br |
| 7 | CH | C-$SCF_3$ | CH | CH | CH | I |
| 8 | CH | C-$SCF_3$ | CH | CH | N | H |
| 12 | C-I | CH | CH | CH | CH | Br |
| 13 | CH | C-Br | CH | CH | CH | Br |
| 14 | CH | C-$OCF_3$ | CH | CH | CH | Cl |
| 15 | CH | C-$OCH_2CF_3$ | CH | CH | CH | Cl |
| 16 | CH | C-CN | CH | CH | CH | Br |
| 17 | C-$CF_3$ | CH | C-$CF_3$ | CH | CH | I |
| 18 | C-$CF_3$ | CH | C-CN | CH | CH | Br |
| 19 | C-$CF_3$ | CH | C-Br | CH | CH | I |
| 20 | C-Br | CH | C-Br | CH | CH | I |
| 21 | C-Br | CH | N | CH | CH | I |
| 22 | C-Cl | CH | C-Cl | CH | CH | I |
| 23 | C-$OCF_3$ | CH | C-F | CH | CH | Br |
| 24 | C-F | C-CN | CH | CH | CH | Br |
| 25 | C-F | C-F | CH | CH | CH | Br |

Intermediate compound 3: $^1$H-NMR ($CDCl_3$) δ: 8.56 (1H, s), 8.38 (1H, s), 8.23 (1H, s), 8.09 (1H, t), 7.89 (1H, d), 7.85-7.40 (3H, m), 2.78 (2H, q), 1.18 (3H, t).

Intermediate compound 4: $^1$H-NMR ($CDCl_3$) δ: 8.63-8.61 (2H, m), 8.23 (1H, s), 8.08 (1H, d), 7.87 (1H, d), 7.75-7.48 (3H, m), 2.76 (2H, q), 1.19 (3H, t).

Intermediate compound 5: $^1$H-NMR ($CDCl_3$) δ: 8.62 (1H, s), 8.53 (1H, d), 8.34 (1H, d), 7.76-7.46 (3H, m), 7.31-7.29 (1H, m), 2.64 (2H, q), 1.19 (3H, t).

Intermediate compound 6: $^1$H-NMR ($CDCl_3$) δ: 8.53 (1H, s), 8.34 (1H, s), 7.99 (2H, d), 7.80 (2H, d), 7.56 (1H, d), 7.39 (1H, d), 2.75 (2H, q), 1.24 (3H, t).

Intermediate compound 7: $^1$H-NMR ($CDCl_3$) δ: 8.57 (1H, s), 8.44 (1H, s), 7.99 (2H, d), 7.79 (2H, d), 7.70-7.42 (2H, m), 2.73 (2H, q), 1.23 (3H, t).

Intermediate compound 8: $^1$H-NMR ($CDCl_3$) δ: 8.53 (1H, s), 8.36 (1H, s), 8.12-8.09 (1H, m), 7.84 (2H, d), 7.68 (2H, d), 6.92-6.90 (1H, m), 3.22 (2H, q), 1.32 (3H, t). Intermediate compound 12: $^1$H-NMR ($CDCl_3$) δ: 8.52 (1H, s), 8.45 (1H, s), 8.29 (1H, s), 7.91-7.88 (2H, m), 7.52 (1H, d), 7.37 (1H, d), 7.25-7.20 (1H, m), 2.75 (2H, q), 1.23 (3H, t).

Intermediate compound 13: $^1$H-NMR ($CDCl_3$) δ: 8.53 (1H, s), 8.34 (1H, s), 7.84 (2H, d), 7.69 (2H, d), 7.56 (1H, d), 7.35 (1H, d), 2.75 (2H, q), 1.24 (3H, t).

Intermediate compound 14: $^1$H-NMR ($CDCl_3$) δ: 8.56 (1H, s), 8.35 (1H, s), 7.95 (2H, d), 7.65 (1H, d), 7.54 (2H, d), 7.35 (1H, d), 2.76 (2H, q), 1.23 (3H, t).

Intermediate compound 15: $^1$H-NMR ($CDCl_3$) δ: 8.63 (1H, s), 8.44 (1H, s), 7.97 (2H, d), 7.61 (1H, d), 7.51 (2H, d), 7.31 (1H, d), 4.48-4.36 (2H, m), 2.75 (2H, q), 1.19 (3H, t).

Intermediate compound 16: $^1$H-NMR ($CDCl_3$) δ: 8.63 (1H, s), 8.54 (1H, s), 8.07 (2H, d), 7.82 (2H, d), 7.55 (1H, d), 7.40 (1H, d), 2.76 (2H, q), 1.17 (3H, t).

Intermediate compound 17: $^1$H-NMR ($CDCl_3$) δ: 8.65 (1H, s), 8.41-8.37 (2H, m), 8.09 (1H, s), 7.92 (1H, s), 7.51 (1H, d), 7.45 (1H, d), 2.78 (2H, q), 1.25 (3H, t).

Intermediate compound 18: $^1$H-NMR ($CDCl_3$) δ: 8.54 (1H, s), 8.43-8.41 (2H, m), 8.11 (1H, s), 7.93-7.87 (1H, m), 7.53 (1H, d), 7.41 (1H, d), 2.77 (2H, q), 1.26 (3H, t).

Intermediate compound 19: $^1$H-NMR ($CDCl_3$) δ: 8.70-8.46 (1H, m), 8.64 (1H, s), 8.28 (1H, s), 8.12 (1H, s), 7.96 (1H, s), 7.54-7.48 (1H, m), 7.45-7.38 (1H, m), 2.77 (2H, q), 1.24 (3H, t).

Intermediate compound 20: $^1$H-NMR ($CDCl_3$) δ: 8.63 (1H, s), 8.27-8.22 (1H, m), 7.99 (2H, d), 7.87 (1H, t), 7.53-7.48 (1H, m), 7.44 (1H, d), 2.75 (2H, q), 1.24 (3H, t).

Intermediate compound 21: $^1$H-NMR ($CDCl_3$) δ: 9.05-9.04 (1H, m), 8.87 (1H, d), 8.64-8.62 (1H, m), 8.45-8.40 (2H, m), 7.51 (1H, dd), 7.44 (1H, d), 2.75 (2H, q), 1.24 (3H, t).

Intermediate compound 22: $^1$H-NMR ($CDCl_3$) δ: 8.64-8.61 (1H, m), 8.31-8.26 (1H, m), 7.82-7.78 (2H, m), 7.57 (1H, t), 7.50 (1H, dd), 7.44 (1H, d), 2.75 (2H, q), 1.33-1.19 (3H, m).

Intermediate compound 23: $^1$H-NMR ($CDCl_3$) δ: 8.55-8.54 (1H, m), 8.21 (1H, s), 7.63-7.56 (3H, m), 7.41 (1H, d), 7.20 (1H, d), 2.77 (2H, q), 1.26 (3H, t).

Intermediate compound 24: $^1$H-NMR ($CDCl_3$) δ: 8.54 (1H, s), 8.43 (1H, s), 7.85-7.82 (3H, m), 7.56 (1H, d), 7.42 (1H, d), 2.77 (2H, q), 1.25 (3H, t).

Intermediate compound 25: $^1$H-NMR ($CDCl_3$) δ: 8.53-8.53 (1H, m), 8.30 (1H, s), 7.86-7.81 (1H, m), 7.72-7.70 (1H, m), 7.56 (1H, d), 7.40 (1H, d), 7.35-7.28 (1H, m), 2.75 (2H, q), 1.24 (3H, t).

A compound represented by formula (A-1) wherein the combination of $A^2$, $A^3$, $A^4$, $A^5$, $G^4$, and $R^{3b}$ represents any one combination indicated in Table AA-1.

TABLE AA-1

| Intermediate compound | $A^2$ | $A^3$ | $A^4$ | $A^5$ | $G^4$ | $R^{3b}$ |
|---|---|---|---|---|---|---|
| 41 | CH | C-$CF_3$ | CH | CH | CH | I |
| 43 | C-$CF_3$ | CH | CH | N | CH | Br |
| 44 | CH | CH | C-$CF_3$ | N | CH | Br |
| 45 | C-$CF_3$ | CH | CH | N | CH | I |
| 46 | C-Br | C-F | CH | CH | CH | $CF_3$ |
| 47 | C-$CF_3$ | CH | C-I | CH | CH | I |
| 48 | C -$CF_3$ | N | CH | CH | CH | I |
| 50 | CH | C-Cl | CH | CH | CH | I |
| 51 | C-Cl | CH | CH | CH | CH | I |
| 52 | CH | C-$C_2F_5$ | CH | CH | CH | I |
| 53 | C-I | CH | C-I | CH | CH | I |
| 54 | CH | C-$OCF_3$ | CH | CH | CH | Br |
| 55 | C-$OCF_3$ | CH | CH | CH | CH | Br |
| 56 | CH | C-$OCF_2H$ | CH | CH | CH | Br |
| 57 | C-$OCF_2H$ | CH | CH | CH | CH | Br |
| 58 | CH | C-$CF_3$ | CH | CH | CH | $CF_3$ |
| 59 | CH | C-$SCF_3$ | CH | CH | CH | $CF_3$ |
| 60 | CH | C-$CF_3$ | CH | CH | CH | Cl |
| 61 | CH | C-$SCF_3$ | CH | CH | CH | Cl |
| 62 | C-$CF_3$ | CH | C-$CF_3$ | CH | CH | $CF_3$ |
| 63 | C-F | C-F | C-F | CH | CH | I |
| 64 | C-$OCF_2H$ | CH | C-$OCF_2H$ | CH | CH | I |
| 65 | C-Cl | C-$OCF_2H$ | CH | CH | CH | I |
| 66 | CH | C-$SF_5$ | CH | CH | CH | I |

Intermediate compound 41: $^1$H-NMR ($CDCl_3$) δ: 8.63 (1H, s), 8.34 (1H, s), 8.06 (2H, d), 7.79 (2H, d), 7.47 (2H, dd), 2.74 (2H, q), 1.23 (3H, t).

Intermediate compound 43: $^1$H-NMR ($CDCl_3$) δ: 10.48 (1H, s), 8.88 (1H, d), 8.59 (1H, s), 8.53 (1H, d), 7.75 (1H, d), 7.60 (1H, d), 7.37 (1H, dd), 2.74 (2H, q), 1.24 (3H, t).

Intermediate compound 44: $^1$H-NMR ($CDCl_3$) δ: 10.48 (1H, s), 8.58-8.53 (2H, m), 8.15 (1H, t), 7.90 (1H, d), 7.59 (1H, d), 7.39-7.35 (1H, m), 2.73 (2H, q), 1.27 (3H, t).

Intermediate compound 45: $^1$H-NMR ($CDCl_3$) δ: 10.49 (1H, s), 8.88 (1H, d), 8.64-8.60 (2H, m), 7.75 (1H, dd), 7.50-7.49 (2H, m), 2.74 (2H, q), 1.24 (3H, t).

Intermediate compound 46: $^1$H-NMR (DMSO-$D_6$) δ: 10.79 (1H, s), 8.92 (1H, s), 8.36 (1H, dd), 8.10-8.07 (1H, m), 7.86 (1H, d), 7.69 (1H, dd), 7.58 (1H, t), 2.81 (2H, q), 1.08 (3H, t).

Intermediate compound 47: $^1$H-NMR ($CDCl_3$) δ: 8.65-8.64 (1H, m), 8.45-8.43 (2H, m), 8.14 (1H, s), 7.51 (1H, dd), 7.42 (1H, dd), 4.34 (1H, br s), 2.77 (2H, q), 1.24 (3H, t).

Intermediate compound 48: LCMS: 493 $[M+H]^+$, RT=1.897 min Intermediate compound 50: $^1$H-NMR (DMSO-$D_6$) δ: 10.62 (1H, s), 8.76 (1H, s), 8.02 (2H, d), 7.63 (3H, d), 7.56 (1H, dd), 2.77 (2H, q), 1.08 (3H, t).

Intermediate compound 51: $^1$H-NMR (DMSO-$D_6$) δ: 10.66 (1H, s), 8.76-8.76 (1H, m), 8.04-8.04 (1H, m), 7.97 (1H, d), 7.71-7.70 (1H, m), 7.65-7.55 (3H, m), 2.77 (2H, q), 1.08 (3H, t).

Intermediate compound 52: $^1$H-NMR ($CDCl_3$) δ: 8.63-8.62 (1H, m), 8.37 (1H, br s), 8.08 (2H, d), 7.77 (2H, d), 7.52-7.44 (2H, m), 2.74 (2H, q), 1.24 (3H, t)

Intermediate compound 53: $^1$H-NMR ($CDCl_3$) δ: 8.64-8.63 (1H, m), 8.26-8.25 (1H, m), 8.21-8.20 (3H, m), 7.52-7.42 (2H, m), 2.75 (2H, q), 1.24 (3H, t)

Intermediate compound 54: $^1$H-NMR (DMSO-$D_6$) δ: 10.66 (1H, s), 8.76 (1H, d), 8.13 (2H, d), 7.64 (1H, d), 7.58-7.54 (3H, m), 2.77 (2H, q), 1.08 (3H, t).

Intermediate compound 55: $^1$H-NMR (DMSO-$D_6$) δ: 10.75 (1H, s), 8.77 (1H, d), 8.06 (1H, d), 7.94 (1H, s), 7.71 (1H, t), 7.66-7.64 (2H, m), 7.57 (1H, dd), 2.78 (2H, q), 1.08 (3H, t).

Intermediate compound 56: $^1$H-NMR (DMSO-$D_6$) δ: 10.56 (1H, s), 8.76 (1H, d), 8.08 (2H, d), 7.63 (1H, d), 7.56 (1H, dd), 7.40 (1H, t), 7.33 (2H, d), 2.77 (2H, q), 1.08 (3H, t).

Intermediate compound 57: $^1$H-NMR (DMSO-$D_6$) δ: 10.64 (1H, s), 8.77 (1H, s), 7.90 (1H, d), 7.78 (1H, s), 7.65-7.53 (3H, m), 7.44 (1H, d), 7.35 (1H, t), 2.78 (2H, q), 1.10-1.06 (3H, m).

Intermediate compound 58: $^1$H-NMR (DMSO-$D_6$) δ: 10.90 (1H, s), 8.93 (1H, s), 8.20 (2H, d), 7.95 (2H, d), 7.86 (1H, d), 7.70 (1H, dd), 2.81 (2H, q), 1.09 (3H, t).

Intermediate compound 59: $^1$H-NMR (DMSO-$D_6$) δ: 10.91 (1H, s), 8.93 (1H, s), 8.20 (2H, d), 7.95 (2H, d), 7.86 (1H, d), 7.70 (1H, d), 2.81 (2H, q), 1.09 (3H, t).

Intermediate compound 60: $^1$H-NMR (DMSO-$D_6$) δ: 10.79 (1H, s), 8.73 (1H, dd), 8.19 (2H, d), 7.94 (2H, d), 7.70 (1H, dd), 7.50 (1H, dd), 2.78 (2H, q), 1.08 (3H, t).

Intermediate compound 61: $^1$H-NMR (DMSO-$D_6$) δ: 10.75 (1H, s), 8.73 (1H, dd), 8.10 (2H, d), 7.90 (2H, d), 7.70 (1H, dd), 7.50 (1H, dd), 2.77 (2H, q), 1.08 (3H, t).

Intermediate compound 62: $^1$H-NMR ($CDCl_3$) δ: 8.79-8.77 (1H, m), 8.48-8.44 (1H, br m), 8.41-8.39 (2H, m), 8.10 (1H, s), 7.75 (1H, d), 7.51-7.49 (1H, m), 2.81 (2H, q), 1.27 (3H, t).

Intermediate compound 63: $^1$H-NMR ($CDCl_3$) δ: 8.63-8.62 (1H, m), 8.25-8.19 (1H, br s), 7.61 (2H, t), 7.53-7.43 (2H, m), 2.74 (2H, q), 1.23 (3H, t).

Intermediate compound 64: $^1$H-NMR ($CDCl_3$) δ: 8.64-8.63 (1H, m), 8.57-8.54 (1H, br s), 7.56-7.56 (2H, m), 7.51-7.40 (2H, m), 7.12-7.11 (1H, m), 6.79-6.42 (2H, m), 2.75 (2H, q), 1.24 (3H, t).

Intermediate compound 65: $^1$H-NMR ($CDCl_3$) δ: 8.63-8.62 (1H, m), 8.56-8.53 (1H, br s), 8.08-8.08 (1H, m), 7.87-7.84 (1H, m), 7.51-7.39 (2H, m), 7.35 (1H, d), 6.81-6.45 (1H, m), 2.74 (2H, q), 1.23 (3H, t).

Intermediate compound 66: $^1$H-NMR ($CDCl_3$) δ: 8.63-8.63 (1H, m), 8.41-8.38 (1H, br s), 8.05 (2H, d), 7.91 (2H, d), 7.52-7.43 (2H, m), 2.74 (2H, q), 1.23 (3H, t).

Reference Preparation Example 3

To a mixture of the Intermediate compound 1 (500 mg) and chloroform (5 mL) was added mCPBA (purity: 70%, comprising 30% of water) (830 mg) under ice-cooling, and the resulting mixture was stirred at room temperature for 2 hours. To the resulting mixture were sequentially added a saturated aqueous solution of sodium hydrogen carbonate and an aqueous solution of sodium thiosulfate, and the resulting mixture was subjected to extraction with chloroform. The resulting organic layer was dried over anhydrous magnesium sulfate, and concentrated under reduced pressure. The resulting residue was subjected to silica gel chromatography to give the Intermediate compound 26 (260 mg).

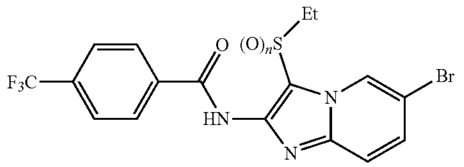

Intermediate compound 26: $^1$H-NMR ($CDCl_3$) δ: 9.83 (1H, s), 8.78 (1H, s), 8.10 (2H, d), 7.82 (2H, d), 7.74 (1H, d), 7.60 (1H, d), 3.32 (2H, q), 1.36 (3H, t).

Reference Preparation Example 3-1

The compounds prepared according to the Reference Preparation Example 3 and physical properties thereof are shown below.

A Compound Represented by Formula (A-2)

(A-2)

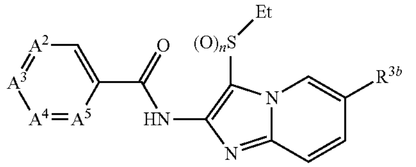

wherein the combination of $A^2$, $A^3$, $A^4$, $A^5$, and $R^{3b}$ represents any one combination indicated in Table A-2.

TABLE A-2

| | Intermediate compound | | | | |
|---|---|---|---|---|---|
| | $A^2$ | $A^3$ | $A^4$ | $A^5$ | $R^{3b}$ |
| 27 | C—$SCF_3$ | CH | CH | CH | Br |
| 28 | CH | C—$SCF_3$ | CH | CH | Br |
| 29 | CH | C—$C_2F_5$ | CH | C—F | Br |
| 42 | CH | C—$CF_3$ | CH | CH | I |

Intermediate compound 27: $^1$H-NMR ($CDCl_3$) δ: 9.78 (1H, s), 8.80-8.76 (1H, m), 8.27 (1H, s), 8.07 (1H, d), 7.89 (1H, d), 7.72 (1H, d), 7.64-7.57 (2H, m), 3.33 (2H, q), 1.36 (3H, t).

Intermediate compound 28: $^1$H-NMR ($CDCl_3$) δ: 9.80 (1H, s), 8.77 (1H, s), 8.02 (2H, d), 7.81 (2H, d), 7.72 (1H, d), 7.59 (1H, d), 3.32 (2H, q), 1.36 (3H, t).

Intermediate compound 29: $^1$H-NMR ($CDCl_3$) δ: 10.09 (1H, s), 8.84-8.82 (1H, m), 8.36 (1H, t), 7.73 (1H, d), 7.61-7.58 (2H, m), 7.49 (1H, d), 3.32 (2H, q), 1.37 (3H, t).

Intermediate compound 42: $^1$H-NMR ($CDCl_3$) δ: 9.83 (1H, s), 8.86 (1H, S), 8.10 (2H, d), 7.80 (2H, d), 7.71 (1H, dd), 7.62 (11H, d), 3.31 (2H, q), 1.36 (3H, t).

Reference Preparation Example 4

To a mixture of 4-(trifluoromethyl)anthranilic acid (3.00 g) and THF (22 mL) was added dropwise a mixture of triphosgene (1.52 g) and THF (15 mL) under ice-cooling. The resulting mixture was stirred at room temperature for 4 hours. To the resulting mixture was added water, and the resulting mixture was subjected to extraction with ethyl acetate. The resulting organic layer was dried over anhydrous sodium sulfate, and concentrated under reduced pressure to give the Intermediate compound 30 represented by the following formula (3.30 g).

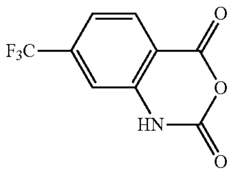 [SMILES: O=c1[nH]c2cc(C(F)(F)F)ccc2c(=O)o1]

Intermediate compound 30: $^1$H-NMR (DMSO-$D_6$) δ: 11.98 (1H, br s), 8.10 (1H, d), 7.54 (1H, d), 7.37 (1H, s).

Reference Preparation Example 4-1

The compound prepared according to the Reference Preparation Example 4 and physical property thereof are shown below.

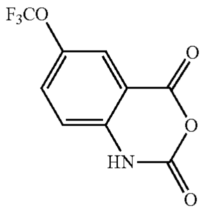 [SMILES: O=c1[nH]c2ccc(OC(F)(F)F)cc2c(=O)o1]

Intermediate compound 31: $^1$H-NMR (DMSO-$D_6$) δ: 9.92 (1H, s), 5.83 (1H, d), 5.80-5.77 (1H, m), 5.26 (1H, d).

Reference Preparation Example 5

To a mixture of the Intermediate compound Z (300 mg) and THF (4 mL) was added dropwise potassium bis(trimethylsilyl)amide (1 mol/L THF solution) (2.2 mL) under nitrogen atmosphere at −78° C., and the resulting mixture was stirred for 30 minutes. To the resulting mixture was added a mixture of the Intermediate compound 30 (254 mg) and THF (4 mL), and the resulting mixture was stirred at room temperature for 30 minutes. To the resulting mixture was added a saturated aqueous solution of ammonium chloride, and the resulting mixture was subjected to extraction with ethyl acetate. The resulting organic layer was dried over anhydrous sodium sulfate, and concentrated under reduced pressure. To the resulting residue was added hexane, and the precipitated solids were filtered. The resulting solids were washed with hexane, and then dried under reduced pressure to give the Intermediate compound 32 represented by the following formula (491 mg).

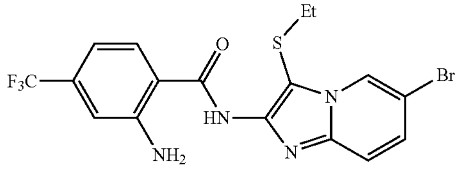 [SMILES: CCSc1c(NC(=O)c2ccc(C(F)(F)F)cc2N)nc2ccc(Br)cn12]

Intermediate compound 32: $^1$H-NMR ($CDCl_3$) δ: 8.54 (1H, dd), 8.35 (1H, s), 7.67 (1H, d), 7.60 (1H, dd), 7.41 (1H, dd), 7.00 (1H, s), 6.98 (1H, d), 5.95 (2H, br s), 2.75 (2H, q), 1.27 (3H, t).

Reference Preparation Example 5-1

The compounds prepared according to the Reference Preparation Example 5 and physical properties thereof are shown below.

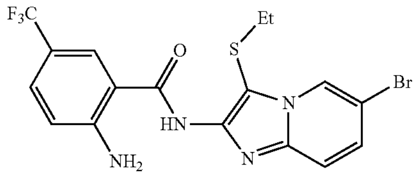 [SMILES: CCSc1c(NC(=O)c2cc(C(F)(F)F)ccc2N)nc2ccc(Br)cn12]

Intermediate compound 33: $^1$H-NMR ($CDCl_3$) δ: 8.53-8.53 (1H, m), 8.33 (1H, s), 7.80 (1H, s), 7.57 (1H, d), 7.50 (1H, dd), 7.39 (1H, dd), 6.78 (1H, d), 6.14 (2H, s), 2.74 (2H, q), 1.26 (3H, t).

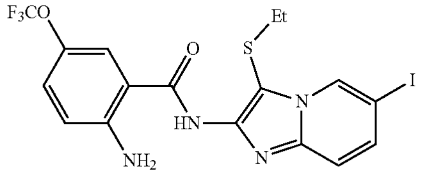 [SMILES: CCSc1c(NC(=O)c2cc(OC(F)(F)F)ccc2N)nc2ccc(I)cn12]

Intermediate compound 34: $^1$H-NMR ($CDCl_3$) δ: 8.61-8.60 (1H, m), 8.28 (1H, s), 7.56 (1H, d), 7.50-7.44 (2H, m), 6.57-6.54 (2H, m), 5.96 (2H, s), 2.71 (2H, q), 1.23 (3H, t).

Reference Preparation Example 6

A mixture of the Intermediate compound 32 (491 mg) and triethyl orthoformate (11 mL) was stirred at 100° C. for 1 hour. The resulting mixture was allowed to cool to room temperature, and concentrated under reduced pressure. The resulting solids were washed with hexane to give the Intermediate compound 35 represented by the following formula (447 mg).

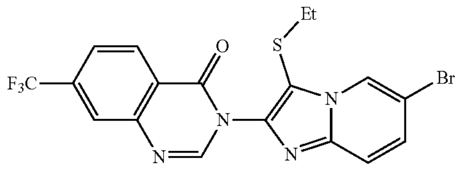 [SMILES: CCSc1c(-n2cnc3cc(C(F)(F)F)ccc3c2=O)nc2ccc(Br)cn12]

Intermediate compound 35: $^1$H-NMR ($CDCl_3$) δ: 8.65 (1H, dd), 8.51 (1H, d), 8.20 (1H, s), 8.08 (1H, d), 7.77 (1H, dd), 7.61 (1H, dd), 7.50 (1H, dd), 2.77 (2H, q), 1.18 (3H, t).

Reference Preparation Example 6-1

The compounds prepared according to the Reference Preparation Example 6 and physical properties thereof are shown below.

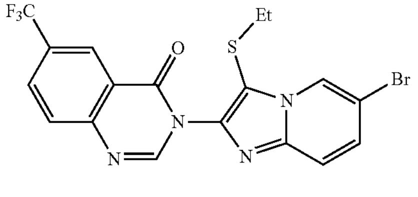 [SMILES: CCSc1c(-n2cnc3ccc(C(F)(F)F)cc3c2=O)nc2ccc(Br)cn12]

Intermediate compound 36: $^1$H-NMR ($CDCl_3$) δ: 8.69-8.67 (1H, m), 8.65-8.64 (1H, m), 8.22 (11H, s), 8.03 (1H, dd), 7.92~7.90 (1H, m), 7.61 (1H, dd), 7.52-7.49 (1H, m), 2.78 (2H, q), 1.19 (3H, t).

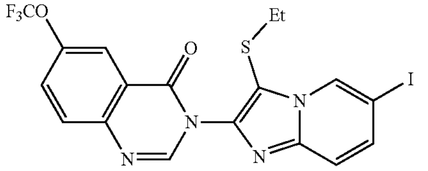 [SMILES: CCSc1c(-n2cnc3ccc(OC(F)(F)F)cc3c2=O)nc2ccc(I)cn12]

Intermediate compound 37: $^1$H-NMR ($CDCl_3$) δ: 8.76-8.74 (1H, m), 8.22-8.20 (11H, m), 8.14 (1H, s), 7.85 (1H, d), 7.66 (1H, dd), 7.61 (1H, dd), 7.49 (1H, d), 2.77 (2H, q), 1.19 (3H, t).

Reference Preparation Example 7

The compounds prepared according to the Reference Preparation Example 3 and physical properties thereof are shown below.

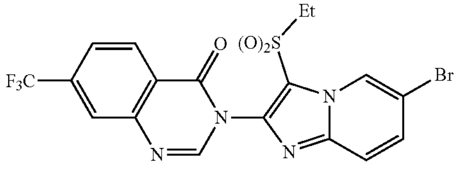

Intermediate compound 38: $^1$H-NMR ($CDCl_3$) δ: 9.06 (1H, dd), 8.47 (1H, d), 8.26 (1H, s), 8.09 (1H, d), 7.78 (1H, dd), 7.73 (1H, dd), 7.68 (1H, dd), 3.56 (2H, q), 1.46 (3H, t).

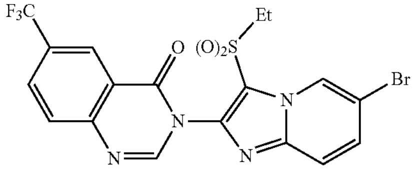

Intermediate compound 39: $^1$H-NMP ($CDCl_3$) δ: 9.06-9.05 (1H, m), 8.64-8.63 (1H, m), 8.28 (1H, s), 8.04 (1H, dd), 7.93-7.91 (1H, m), 7.73 (1H, dd), 7.69 (1H, dd), 3.59 (2H, q), 1.47 (3H, t).

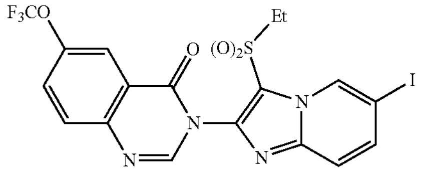

Intermediate compound 40: $^1$H-NMR ($CDCl_3$) δ: 9.14 (1H, dd), 8.20 (1H, s), 8.17-8.15 (1H, m), 7.85 (1H, d), 7.79 (1H, dd), 7.67-7.65 (11H, m), 7.60 (1H, dd), 3.57 (2H, q), 1.46 (3H, t).

Preparation Example 1

To a mixture of the Intermediate compound 1 (1.2 g), cesium carbonate (0.88 g), and DMF (6 mL) was added methyl iodide (0.51 mL) under ice-cooling, and the resulting mixture was stirred at room temperature for 2 hours. To the resulting mixture was added water, and the resulting mixture was subjected to extraction with chloroform. The resulting organic layer was dried over anhydrous magnesium sulfate, and concentrated under reduced pressure. The resulting residue was subjected to silica gel chromatography (hexane: ethyl acetate=1:1) to give the Present compound 1 (810 mg),

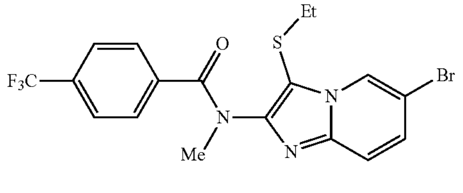 [SMILES: CCSc1c(N(C)C(=O)c2ccc(C(F)(F)F)cc2)nc2ccc(Br)cn12]

Present compound 1: $^1$H-NMR ($CDCl_3$) δ: 8.30 (1H, s), 7.56 (2H, d), 7.50 (1H, d), 7.44-7.38 (3H, m), 3.55 (3H, s), 2.40 (2H, q), 1.10 (3H, t).

Preparation Example 1-1

The compounds prepared according to the Preparation Example 1 and physical properties thereof are shown below. A compound represented by formula (B-1)

(B-1)

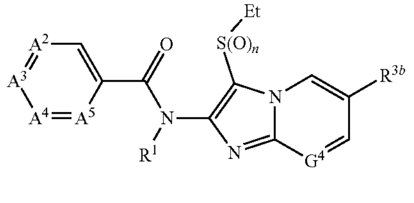

wherein the combination of $A^2$, $A^3$, $A^4$, $A^5$, $G^4$, $R^1$, $R^{3b}$ and n represents any one combination indicated in Table B-1.

TABLE B-1

| Present compound | $A^2$ | $A^3$ | $A^4$ | $A^5$ | $G^4$ | $R^1$ | $R^{3b}$ | n |
|---|---|---|---|---|---|---|---|---|
| 2 | C-$SCF_3$ | CH | CH | CH | CH | Me | Br | 0 |
| 3 | C-$SCF_3$ | CH | CH | CH | CH | Et | Br | 0 |
| 4 | C-$SCF_3$ | CH | CH | CH | CH | Me | $CF_3$ | 0 |
| 5 | C-$SCF_3$ | CH | CH | CH | CH | Me | Cl | 0 |
| 6 | C-$SCF_3$ | CH | CH | CH | N | Me | Br | 0 |
| 7 | CH | C-$SCF_3$ | CH | CH | CH | Me | Br | 0 |
| 8 | CH | C-$SCF_3$ | CH | CH | CH | Et | Br | 0 |
| 9 | CH | C-$SCF_3$ | CH | CH | CH | Me | I | 0 |
| 10 | CH | C-$SCF_3$ | CH | CH | N | Me | H | 0 |
| 15 | C-I | CH | CH | CH | CH | Me | Br | 0 |
| 16 | CH | C-Br | CH | CH | CH | Me | Br | 0 |
| 17 | CH | C-$OCF_3$ | CH | CH | CH | Me | Cl | 0 |
| 18 | CH | C-$OCH_2CF_3$ | CH | CH | CH | Me | Cl | 0 |
| 19 | CH | C-CN | CH | CH | CH | Me | Br | 0 |
| 20 | C-$CF_3$ | CH | C-$CF_3$ | CH | CH | Me | I | 0 |
| 21 | C-$CF_3$ | CH | C-CN | CH | CH | Me | Br | 0 |
| 22 | C-$CF_3$ | CH | C-Br | CH | CH | Me | I | 0 |
| 23 | C-Br | CH | C-Br | CH | CH | Me | I | 0 |
| 24 | C-Br | CH | N | CH | CH | Me | I | 0 |
| 25 | C-Cl | CH | C-Cl | CH | CH | Me | I | 0 |
| 26 | C-$OCF_3$ | CH | C-F | CH | CH | Me | Br | 0 |
| 27 | C-F | C-CN | CH | CH | CH | Me | Br | 0 |
| 28 | C-F | C-F | CH | CH | CH | Me | Br | 0 |
| 32 | C-$SCF_3$ | CH | CH | CH | CH | Me | Br | 2 |
| 33 | C-$SCF_3$ | CH | CH | CH | CH | Et | Br | 2 |
| 38 | CH | C-$SCF_3$ | CH | CH | CH | Me | Br | 2 |
| 44 | CH | C-$C_2F_5$ | CH | C-F | CH | Me | Br | 2 |

Present compound 2: $^1$H-NMR ($CDCl_3$) δ: 8.30 (1H, s), 7.70-7.66 (2H, m), 7.56-7.49 (2H, m), 7.41 (1H, d), 7.29-7.27 (1H, m), 3.58 (3H, s), 2.38 (2H, q), 1.11 (3H, t).

Present compound 3: $^1$H-NMR ($CDCl_3$) δ: 8.30 (1H, d), 7.71-7.66 (2H, m), 7.55-7.50 (2H, m), 7.41 (1H, d), 7.29-7.27 (1H, m), 4.10 (2H, q), 2.31 (2H, q), 1.34 (3H, t), 1.11 (3H, t).

Present compound 4: $^1$H-NMR ($CDCl_3$) δ: 8.51 (1H, s), 7.72-7.69 (2H, m), 7.61 (1H, s), 7.53 (1H, d), 7.48 (1H, d), 7.31-7.30 (1H, m), 3.59 (3H, s), 2.39 (2H, q), 1.11 (3H, t).

Present compound 5: $^1$H-NMR ($CDCl_3$) δ: 8.19 (1H, s), 7.69-7.66 (2H, m), 7.56-7.51 (2H, m), 7.29-7.27 (2H, m), 3.56 (3H, s), 2.37 (2H, q), 1.10 (3H, t).

Present compound 6: $^1$H-NMR ($CDCl_3$) δ: 8.61 (1H, s), 8.52 (1H, s), 7.68-7.66 (2H, m), 7.54 (1H, d), 7.28-7.25 (1H, m), 3.59 (3H, s), 2.38 (2H, q), 1.10 (3H, t).

Present compound 7: $^1$H-NMR ($CDCl_3$) δ: 8.31 (1H, s), 7.53-7.41 (6H, m), 3.56 (3H, s), 2.32 (2H, q), 1.10 (3H, t).

Present compound 8: $^1$H-NMR ($CDCl_3$) δ: 8.31 (1H, s), 7.55-7.40 (6H, m), 4.08 (2H, q), 2.23 (2H, q), 1.32 (3H, t), 1.10 (3H, t).

Present compound 9: $^1$H-NMR ($CDCl_3$) δ: 8.39 (1H, s), 7.53-7.36 (6H, m), 3.53 (3H, s), 2.29 (2H, q), 1.07 (3H, t).

Present compound 10: $^1$H-NMR ($CDCl_3$) δ: 8.51-8.50 (1H, m), 8.07 (1H, d), 7.41-7.36 (4H, m), 6.95-6.93 (1H, m), 3.39 (3H, s), 3.17 (2H, q), 1.27 (3H, t).

Present compound 15: $^1$H-NMR ($CDCl_3$) δ: 8.31 (1H, s), 7.90-7.87 (1H, m), 7.56 (1H, d), 7.51 (1H, d), 7.39 (1H, d), 7.31 (1H, d), 6.84 (1H, t), 3.52 (3H, s), 2.37 (2H, q), 1.12 (3H, t).

Present compound 16: $^1$H-NMR ($CDCl_3$) δ: 8.31 (1H, s), 7.50 (1H, d), 7.40 (1H, d), 7.32-7.28 (4H, m), 3.53 (3H, s), 2.40 (2H, q), 1.11 (3H, t).

Present compound 17: $^1$H-NMR ($CDCl_3$) δ: 8.23 (1H, s), 7.57 (1H, d), 7.51 (2H, d), 7.32 (1H, d), 7.00 (2H, d), 3.55 (3H, s), 2.34 (2H, q), 1.10 (3H, t).

Present compound 18: $^1$H-NMR ($CDCl_3$) δ: 8.22 (1H, s), 7.56 (1H, d), 7.45 (2H, d), 7.30 (1H, d), 6.70 (2H, d), 4.28-4.26 (2H, m), 3.54 (3H, s), 2.37 (2H, q), 1.10 (3H, t).

Present compound 19: $^1$H-NMR ($CDCl_3$) δ: 8.30 (1H, s), 7.53-7.46 (6H, m), 3.56 (3H, s), 2.47 (2H, q), 1.13 (3H, t).

Present compound 20: $^1$H-NMR ($CDCl_3$) δ: 8.38 (1H, s), 7.90-7.87 (2H, m), 7.71 (1H, s), 7.52 (1H, d), 7.38 (1H, d), 3.57 (3H, s), 2.46 (2H, q), 1.11 (3H, t).

Present compound 21: $^1$H-NMR ($CDCl_3$) δ: 8.29 (1H, s), 7.91-7.87 (2H, m), 7.74 (1H, s), 7.50 (1H, d), 7.42 (1H, d), 3.56 (3H, s), 2.51 (2H, q), 1.13 (3H, t).

Present compound 22: $^1$H-NMR ($CDCl_3$) δ: 8.41 (1H, t), 7.80 (1H, s), 7.60 (2H, d), 7.52 (1H, dd), 7.38 (1H, d), 3.54 (3H, s), 2.46 (2H, q), 1.12 (3H, t).

Present compound 23: $^1$H-NMR ($CDCl_3$) δ: 8.45-8.43 (1H, m), 7.54-7.50 (4H, m), 7.39 (1H, d), 3.51 (3H, s), 2.46 (2H, q), 1.13 (3H, t).

Present compound 24: $^1$H-NMR ($CDCl_3$) δ: 8.50 (1H, d), 8.41 (1H, dd), 8.34 (1H, d), 8.06 (1H, t), 7.54-7.51 (1H, m), 7.38 (1H, dd), 3.55 (3H, s), 2.47 (2H, q), 1.13 (3H, t).

Present compound 25: $^1$H-NMR ($CDCl_3$) δ: 8.44-8.43 (1H, m), 7.52 (1H, dd), 7.39 (1H, d), 7.34-7.32 (2H, m), 7.22-7.20 (1H, m), 3.51 (3H, s), 2.46 (2H, q), 1.13 (3H, t).

Present compound 26: $^1$H-NMR ($CDCl_3$) δ: 8.32 (1H, s), 7.50 (1H, d), 7.42 (1H, d), 7.21-7.19 (1H, m), 7.05-7.05 (1H, m), 6.83-6.81 (1H, m), 3.54 (3H, s), 2.46 (2H, q), 1.12 (3H, t).

Present compound 27: $^1$H-NMR ($CDCl_3$) δ: 8.33 (1H, s), 7.51 (1H, d), 7.42-7.36 (3H, m), 7.25 (1H, d), 3.55 (3H, s), 2.52 (2H, q), 1.14 (3H, t).

Present compound 28: $^1$H-NMR ($CDCl_3$) δ: 8.31 (1H, s), 7.49 (1H, d), 7.40 (1H, d), 7.35-7.32 (1H, m), 7.16-7.12 (1H, m), 6.91-6.88 (1H, m), 3.51 (3H, s), 2.43 (2H, q), 1.11 (3H, t).

Present compound 32: $^1$H-NMR ($CDCl_3$) δ: 8.82 (1H, s), 7.88-7.41 (6H, m), 3.53-3.43 (5H, m), 1.38-1.20 (3H, m).

Present compound 33: $^1$H-NMR ($CDCl_3$) δ: 8.97 (1H, s), 7.84-7.39 (6H, m), 4.08-3.86 (2H, m), 3.61-3.36 (2H, m), 1.35-1.17 (6H, m).

Present compound 38: $^1$H-NMR ($CDCl_3$) δ: 8.92-8.84 (1H, s), 7.75-7.55 (6H, m), 3.56-3.31 (5H, m), 1.42-1.26 (3H, m).

Present compound 44: $^1$H-NMR ($CDCl_3$) δ: 9.00 (1H, s), 7.84-7.40 (5H, m), 3.61-3.48 (2H, m), 3.40 (3H, s), 1.49-1.39 (3H, m).

A compound represented by formula (B-1) wherein the combination of $A^2$, $A^3$, $A^4$, $A^5$, $G^4$, $R^1$, $R^{3b}$, and n represents any one combination indicated in Table C-1.

TABLE C-1

| Present compound | $A^2$ | $A^3$ | $A^4$ | $A^5$ | $G^4$ | $R^1$ | $R^{3b}$ | n |
|---|---|---|---|---|---|---|---|---|
| 64 | CH | C-$CF_3$ | CH | CH | CH | Me | I | 0 |
| 65 | CH | C-$CF_3$ | CH | CH | CH | Me | I | 2 |
| 67 | C-$CF_3$ | CH | CH | N | CH | Me | Br | 0 |
| 68 | CH | CH | C-$CF_3$ | N | CH | Me | Br | 0 |
| 73 | C-$CF_3$ | CH | CH | N | CH | Me | I | 0 |
| 75 | C-Br | C-F | CH | CH | CH | Me | $CF_3$ | 0 |
| 76 | C-$CF_3$ | CH | C-I | CH | CH | Me | I | 0 |
| 77 | C-$CF_3$ | N | CH | CH | CH | Me | I | 0 |
| 78 | C-$CF_3$ | CH | C-$CF_3$ | CH | CH | $CH_2CN$ | I | 0 |
| 83 | CH | C-OMe | CH | CH | CH | Me | I | 0 |
| 84 | CH | C-Cl | CH | CH | CH | Me | I | 0 |
| 85 | C-Cl | CH | CH | CH | CH | Me | I | 0 |
| 86 | CH | C-$C_2F_5$ | CH | CH | CH | Me | I | 0 |
| 87 | C-$C_2F_5$ | CH | CH | CH | CH | Me | I | 0 |
| 89 | C-I | CH | C-I | CH | CH | Me | I | 0 |
| 90 | CH | C-$OCF_3$ | CH | CH | CH | Me | Br | 0 |
| 91 | C-$OCF_3$ | CH | CH | CH | CH | Me | Br | 0 |
| 92 | CH | C-$OCF_2H$ | CH | CH | CH | Me | Br | 0 |
| 93 | C-$OCF_2H$ | CH | CH | CH | CH | Me | Br | 0 |

TABLE C-1-continued

| Present compound | $A^2$ | $A^3$ | $A^4$ | $A^5$ | $G^4$ | $R^1$ | $R^{3b}$ | n |
|---|---|---|---|---|---|---|---|---|
| 102 | CH | C-$CF_3$ | CH | CH | CH | Me | $CF_3$ | 0 |
| 103 | CH | C-$SCF_3$ | CH | CH | CH | Me | $CF_3$ | 0 |
| 104 | CH | C-$CF_3$ | CH | CH | CH | Me | Cl | 0 |
| 105 | CH | C-$SCF_3$ | CH | CH | CH | Me | Cl | 0 |
| 106 | CH | C-$CF_3$ | CH | CH | CH | Et | Br | 0 |
| 107 | CH | C-$CF_3$ | CH | CH | CH | $CH_2CPr$ | Br | 0 |
| 108 | CH | C-$CF_3$ | CH | CH | CH | $CH_2CN$ | Br | 0 |
| 113 | C-CN | CH | CH | CH | CH | Me | Br | 0 |
| 114 | C-$CF_3$ | CH | C-$CF_3$ | CH | CH | Me | $CF_3$ | 0 |
| 115 | C-$CF_3$ | CH | C-$CF_3$ | CH | CH | Me | OMe | 0 |
| 116 | CH | C-Cl | CH | CH | CH | Me | Br | 0 |
| 117 | C-Cl | CH | CH | CH | CH | Me | Br | 0 |
| 118 | C-F | C-F | C-F | CH | CH | Me | I | 0 |
| 119 | CH | C-$CF_3$ | CH | CH | CH | Bn | Br | 0 |
| 120 | CH | C-$CF_3$ | CH | CH | CH | $CH_2Py_3$ | Br | 0 |
| 121 | C-$OCF_2H$ | CH | C-$OCF_2H$ | CH | CH | Me | I | 0 |
| 122 | C-Cl | C-$OCF_2H$ | CH | CH | CH | Me | I | 0 |
| 123 | CH | C-$SF_5$ | CH | CH | CH | Me | I | 0 |
| 124 | C-$CF_3$ | CH | C-$CF_3$ | CH | CH | $CH_2OEt$ | $CF_3$ | 0 |

Present compound 64: $^1$H-NMR ($CDCl_3$) δ: 8.40 (1H, s), 7.56 (2H, d), 7.51 (1H, dd), 7.45-7.35 (3H, m), 3.55 (3H, s), 2.39 (2H, q), 1.10 (3H, t).

Present compound 65: $^1$H-NMR ($CDCl_3$) δ: 8.98 (1H, s), 7.88-7.49 (6H, m), 3.50-3.40 (5H, m), 1.35 (3H, t).

Present compound 67: $^1$H-NMR ($CDCl_3$) δ: 8.36 (1H, s), 8.28 (1H, s), 8.14 (1H, s), 7.44-7.31 (3H, m), 3.62 (3H, s), 2.57 (2H, q), 1.15 (3H, t).

Present compound 68: $^1$H-NMR ($CDCl_3$) δ: 8.43 (1H, s), 8.17 (1H, d), 7.90 (1H, t), 7.50 (1H, d), 7.32-7.29 (2H, m), 3.64 (3H, s), 2.65 (2H, q), 1.22 (3H, t).

Present compound 73: $^1$H-NMR ($CDCl_3$) δ: 8.47 (1H, s), 8.32-8.26 (1H, m), 8.14 (1H, s), 7.45 (1H, d), 7.35 (1H, d), 7.31 (1H, d), 3.62 (3H, s), 2.57 (2H, q), 1.15 (3H, t).

Present compound 75: $^1$H-NMR ($CDCl_3$) δ: 8.55 (1H, s), 7.78 (1H, dd), 7.71 (1H, d), 7.49 (1H, dd), 7.30-7.27 (1H, m), 6.84 (1H, t), 3.54 (3H, s), 2.46 (2H, q), 1.13 (3H, t).

Present compound 76: $^1$H-NMR ($CDCl_3$) δ: 8.41 (1H, s), 7.99 (1H, s), 7.78 (1H, s), 7.62 (1H, s), 7.52 (1H, dd), 7.39 (1H, dd), 3.53 (3H, s), 2.46 (2H, q), 1.12 (3H, t).

Present compound 77: LCMS: 507 $[M+H]^+$, RT=1.97 min

Present compound 78: $^1$H-NMR ($CDCl_3$) δ: 8.42-8.41 (1H, m), 7.91-7.89 (2H, m), 7.80-7.78 (1H, m), 7.60-7.57 (1H, m), 7.43-7.40 (1H, m), 4.95 (2H, s), 2.60 (2H, q), 1.18 (3H, t).

Present compound 83: $^1$H-NMR ($CDCl_3$) δ: 8.40-8.40 (1H, m), 7.50-7.47 (1H, m), 7.42-7.38 (3H, m), 6.64 (2H, d), 3.72 (3H, s), 3.53 (3H, s), 2.31 (2H, q), 1.07 (3H, t).

Present compound 84: $^1$H-NMR ($CDCl_3$) δ: 8.41-8.40 (1H, m), 7.53-7.49 (1H, m), 7.39-7.36 (3H, m), 7.13-7.10 (2H, m), 3.52 (3H, s), 2.38 (2H, q), 1.09 (3H, t).

Present compound 85: $^1$H-NMR ($CDCl_3$) δ: 8.41-8.40 (1H, m), 7.54-7.49 (2H, m), 7.40-7.37 (1H, m), 7.23-7.20 (2H, m), 7.06-7.02 (1H, m), 3.52 (3H, s), 2.37 (2H, q), 1.11 (3H, t).

Present compound 86: $^1$H-NMR ($CDCl_3$) δ: 8.41-8.40 (1H, m), 7.59-7.57 (2H, m), 7.53-7.51 (1H, m), 7.41-7.37 (3H, m), 3.55 (3H, s), 2.32 (2H, q), 1.08 (3H, t).

Present compound 87: $^1$H-NMR ($CDCl_3$) δ: 8.38-8.37 (1H, m), 7.71-7.70 (1H, m), 7.64-7.62 (1H, m), 7.52-7.45 (2H, m), 7.39-7.29 (2H, m), 3.56 (3H, s), 2.37 (2H, q), 1.08 (3H, t).

Present compound 89: $^1$H-NMR ($CDCl_3$) δ: 8.45-8.43 (1H, m), 7.89-7.88 (1H, m), 7.73-7.73 (2H, m), 7.54-7.51 (1H, m), 7.41-7.38 (1H, m), 3.50 (3H, s), 2.45 (2H, q), 1.14 (3H, t).

Present compound 90: $^1$H-NMR ($CDCl_3$) δ: 8.31 (1H, dd), 7.51-7.48 (3H, m), 7.40 (1H, dd), 6.99 (2H, d), 3.53 (3H, s), 2.33 (2H, q), 1.08 (3H, t).

Present compound 91: $^1$H-NMR (DMSO-$D_6$) δ: 8.58 (1H, s), 7.67 (1H, d), 7.60 (1H, d), 7.39 (2H, d), 7.31 (1H, s), 7.09 (1H, s), 3.41 (3H, s), 2.43 (2H, q), 0.96 (3H, t).

Present compound 92: $^1$H-NMR (DMSO-$D_6$) δ: 8.59 (1H, s), 7.67 (1H, d), 7.58 (1H, d), 7.35 (2H, d), 7.22 (1H, t), 6.99 (2H, d), 3.38 (3H, s), 2.41 (2H, q), 0.96 (3H, t).

Present compound 93: $^1$H-NMR (DMSO-$D_6$) δ: 8.58 (1H, s), 7.66 (1H, d), 7.58 (1H, d), 7.26 (1H, t), 7.16 (1H, d), 7.11-7.04 (2H, m), 7.07 (1H, t), 3.39 (3H, s), 2.42 (2H, q), 0.96 (3H, t).

Present compound 102: $^1$H-NMR (DMSO-$D_6$) δ: 8.72 (1H, s), 7.89 (1H, d), 7.72 (1H, dd), 7.56 (2H, d), 7.43 (2H, dt), 3.43 (3H, s), 2.42 (2H, q), 0.98 (3H, t).

Present compound 103: $^1$H-NMR ($CDCl_3$) δ: 8.20 (1H, s), 7.56-7.42 (5H, m), 7.31 (1H, m), 3.54 (3H, s), 2.29 (2H, q), 1.08 (3H, t).

Present compound 104: $^1$H-NMR (DMSO-$D_6$) δ: 8.56 (1H, s), 7.73 (1H, t), 7.54 (3H, dt), 7.42 (2H, t), 3.41 (3H, s), 2.37 (2H, q), 0.96 (3H, t).

Present compound 105: $^1$H-NMR (DMSO-$D_6$) δ: 8.56 (1H, s), 7.73 (1H, t), 7.56-7.52 (3H, m), 7.43-7.42 (2H, m), 3.41 (3H, s), 2.37 (2H, q), 0.96 (3H, t).

Present compound 106: $^1$H-NMR ($CDCl_3$) δ: 8.31-8.27 (1H, m), 7.57-7.31 (6H, m), 4.06 (2H, q), 2.33 (2H, q), 1.32 (3H, t), 1.10 (3H, t).

Present compound 107: $^1$H-NMR ($CDCl_3$) δ: 8.31-8.28 (1H, m), 7.59-7.38 (6H, m), 3.92 (2H, d), 2.33 (2H, q), 1.26-1.17 (1H, m), 1.10 (3H, t), 0.45-0.43 (2H, m), 0.24-0.23 (2H, m).

Present compound 108: $^1$H-NMR ($CDCl_3$) δ: 8.33-8.32 (1H, m), 7.60-7.44 (6H, m), 4.93 (2H, s), 2.52 (2H, q), 1.16 (3H, t).

Present compound 113: $^1$H-NMR ($CDCl_3$) δ: 8.40-8.39 (1H, m), 7.80-7.78 (1H, m), 7.62-7.59 (1H, m), 7.54-7.51 (2H, m), 7.40-7.38 (1H, m), 7.25 (1H, t), 3.54 (3H, s), 2.45 (2H, q), 1.12 (3H, t).

Present compound 114: $^1$H-NMR ($CDCl_3$) δ: 8.52-8.51 (1H, m), 7.90-7.88 (2H, m), 7.73-7.70 (2H, m), 7.51-7.49 (1H, m), 3.59 (3H, s), 2.50 (2H, q), 1.13 (3H, t).

Present compound 115: $^1$H-NMR ($CDCl_3$) δ: 7.90 (2H, s), 7.70 (1H, s), 7.66 (1H, d), 7.49 (1H, d), 7.13 (1H, dd), 3.83 (3H, s), 3.57 (3H, s), 2.45 (2H, q), 1.11 (3H, t).

Present compound 116: $^1$H-NMR (DMSO-$D_6$) δ: 8.59-8.58 (1H, m), 7.68-7.57 (2H, m), 7.32-7.26 (4H, m), 3.39 (3H, s), 2.48-2.43 (2H, q), 0.97 (3H, t).

Present compound 117: $^1$H-NMR (DMSO-$D_6$) δ: 8.60-8.60 (1H, m), 7.69-7.58 (2H, m), 7.37-7.35 (2H, m), 7.22-7.14 (2H, m), 3.39 (3H, s), 2.49-2.43 (2H, q), 0.96 (3H, t).

Present compound 118: $^1$H-NMR ($CDCl_3$) δ: 8.45-8.44 (1H, m), 7.55-7.52 (1H, m), 7.41-7.38 (1H, m), 7.12-7.08 (2H, m), 3.51 (3H, s), 2.49 (2H, q), 1.13 (3H, t).

Present compound 119: $^1$H-NMR ($CDCl_3$) δ: 8.18-8.16 (1H, m), 7.58-7.20 (11H, m), 5.27 (2H, s), 1.68-1.66 (2H, m), 0.81 (3H, t).

Present compound 120: $^1$H-NMR ($CDCl_3$) δ: 8.52-8.51 (1H, m), 8.49-8.47 (1H, m), 8.17-8.16 (1H, m), 7.97-7.95 (1H, m), 7.59-7.51 (3H, m), 7.42-7.40 (3H, m), 7.26-7.24 (1H, m), 5.27 (2H, s), 1.76 (2H, q), 0.84 (3H, t).

Present compound 121: $^1$H-NMR ($CDCl_3$) δ: 8.42-8.41 (1H, m), 7.53-7.37 (2H, m), 7.08-7.07 (2H, m), 6.78-6.76 (1H, m), 6.53-6.17 (2H, m), 3.53 (3H, s), 2.42 (2H, q), 1.11 (3H, t).

Present compound 122: $^1$H-NMR ($CDCl_3$) δ: 8.43-8.42 (1H, m), 7.66-7.65 (1H, m), 7.54-7.51 (2H, m), 6.95-6.93 (1H, m), 6.64-6.28 (2H, m), 3.52 (3H, s), 2.41 (2H, q), 1.11 (3H, t).

Present compound 123: $^1$H-NMR ($CDCl_3$) δ: 8.42-8.42 (1H, m), 7.55-7.51 (5H, m), 7.40-7.38 (1H, m), 3.54 (3H, s), 2.40 (2H, q), 1.10 (3H, t).

Present compound 124: LCMS: 618 $[M+H]^+$, RT=2.40 min

Preparation Example 1-2

The compounds prepared according to the Reference Preparation Example 3 and physical properties thereof are shown below.

A Compound Represented by Formula (B-2)

(B-2)

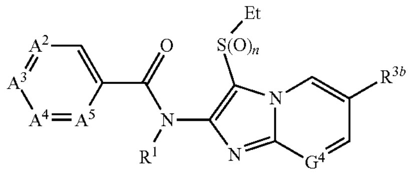

wherein the combination of $A^2$, $A^3$, $A^4$, $A^5$, $G^4$, $R^1$, $R^{3b}$ and n represents any one combination indicated in Table B-2 and Table B-3.

TABLE B-2

| Present compound | $A^2$ | $A^3$ | $A^4$ | $A^5$ | $G^4$ | $R^1$ | $R^{3b}$ | n |
|---|---|---|---|---|---|---|---|---|
| 29 | C-Br | CH | $C-CF_3$ | CH | CH | Me | I | 1 |
| 30 | C-Cl | CH | C-Cl | CH | CH | Me | I | 1 |
| 31 | CH | $C-CF_3$ | CH | CH | CH | Me | Br | 2 |
| 35 | $C-SCF_3$ | CH | CH | CH | CH | Me | CF3 | 2 |
| 36 | $C-SCF_3$ | CH | CH | CH | CH | Me | Cl | 2 |
| 39 | CH | $C-SCF_3$ | CH | CH | CH | Me | I | 2 |
| 40 | CH | $C-SCF_3$ | CH | CH | N | Me | H | 2 |
| 45 | C-I | CH | CH | CH | CH | Me | Br | 2 |
| 47 | CH | $C-OCF_3$ | CH | CH | CH | Me | Cl | 2 |
| 48 | CH | $C-OCH_2CF_3$ | CH | CH | CH | Me | Cl | 2 |
| 49 | CH | C-CN | CH | CH | CH | Me | Br | 2 |
| 50 | $C-CF_3$ | CH | $C-CF_3$ | CH | CH | Me | I | 2 |
| 53 | Br | CH | Br | CH | CH | Me | I | 2 |
| 54 | Br | CH | N | CH | CH | Me | I | 2 |
| 55 | C-Cl | CH | C-Cl | CH | CH | Me | I | 2 |
| 66 | $C-OCF_3$ | CH | CH | CH | CH | Me | Br | 2 |
| 69 | $C-CF_3$ | CH | CH | N | CH | Me | Br | 2 |
| 70 | $C-CF_3$ | CH | $C-CF_3$ | CH | CH | Me | I | 1 |
| 71 | $C-CF_3$ | CH | N | CH | CH | Me | I | 1 |
| 72 | $C-CF_3$ | CH | N | CH | CH | Me | I | 2 |
| 74 | $C-CF_3$ | CH | CH | N | CH | Me | I | 2 |
| 79 | C -CN | CH | CH | CH | CH | Me | I | 2 |
| 80 | $C-CF_3$ | CH | $C-CF_3$ | CH | CH | $CH_2CN$ | I | 2 |
| 81 | CH | $C-SCF_3$ | CH | CH | CH | Me | Br | 1 |
| 82 | CH | $C-CF_3$ | CH | CH | CH | Me | Br | 1 |
| 88 | $C-C_2F_5$ | CH | CH | CH | CH | Me | I | 2 |
| 94 | CH | $C-OCF_3$ | CH | CH | CH | Me | Br | 1 |
| 95 | $C-OCF_3$ | CH | CH | CH | CH | Me | Br | 1 |
| 97 | C-I | CH | C-I | CH | CH | Me | I | 1 |
| 98 | CH | $C-OCF_2H$ | CH | CH | CH | Me | Br | 1 |
| 99 | $C-OCF_2H$ | CH | CH | CH | CH | Me | Br | 1 |
| 100 | CH | $C-OCF_2H$ | CH | CH | CH | Me | Br | 2 |
| 101 | $C-OCF_2H$ | CH | CH | CH | CH | Me | Br | 2 |
| 109 | CH | $C-CF_3$ | CH | CH | CH | Et | Br | 2 |
| 110 | CH | $C-CF_3$ | CH | CH | CH | $CH_2CPr$ | Br | 2 |
| 111 | CH | $C-CF_3$ | CH | CH | CH | $CH_2CN$ | Br | 2 |
| 112 | CH | CH | $C-CF_3$ | N | CH | Me | Br | 2 |
| 125 | $C-CF_3$ | CH | $C-CF_3$ | CH | CH | Me | CF3 | 2 |
| 126 | $C-CF_3$ | CH | $C-CF_3$ | CH | CH | Et | I | 2 |
| 127 | $C-CF_3$ | CH | $C-CF_3$ | CH | CH | $CH_2CPr$ | I | 2 |
| 128 | $C-CF_3$ | CH | $C-CF_3$ | CH | CH | $CH_2OEt$ | I | 2 |
| 129 | CH | $C-CF_3$ | CH | CH | CH | Me | CF3 | 2 |
| 130 | CH | $C-CF_3$ | CH | CH | CH | Me | Cl | 2 |
| 131 | CH | C-Cl | CH | CH | CH | Me | Br | 1 |
| 132 | CH | C-I | CH | CH | CH | Me | Br | 1 |
| 133 | C-I | CH | CH | CH | CH | Me | Br | 1 |
| 134 | CH | $C-SCF_3$ | CH | CH | CH | Me | CF3 | 1 |
| 135 | CH | $C-CF_3$ | CH | CH | CH | Bn | Br | 2 |
| 136 | CH | $C-CF_3$ | CH | CH | CH | $CH_2Py_3$ (N-oxide) | Br | 2 |
| 137 | $C-OCF_2H$ | CH | $C-OCF_2H$ | CH | CH | Me | I | 2 |
| 138 | C-F | $C-OCF_2H$ | CH | CH | CH | Me | I | 2 |
| 139 | CH | $C-SF_5$ | CH | CH | CH | Me | I | 2 |
| 140 | CH | C-Cl | CH | CH | CH | Me | Br | 2 |
| 141 | CH | C-I | CH | CH | CH | Me | Br | 2 |

TABLE B-2-continued

| Present compound | $A^2$ | $A^3$ | $A^4$ | $A^5$ | $G^4$ | $R^1$ | $R^{3b}$ | n |
|---|---|---|---|---|---|---|---|---|
| 142 | C-Cl | CH | CH | CH | CH | Me | Br | 1 |
| 143 | C-Cl | CH | CH | CH | CH | Me | Br | 2 |

Present compound 29: $^1$H-NMR ($CDCl_3$) δ: 8.99 (1H, s), 7.84 (1H, s), 7.77 (1H, s), 7.67-7.60 (2H, m), 7.47 (1H, d), 3.53 (3H, s), 3.48-3.33 (1H, m), 2.90-2.40 (1H, m), 1.41-1.30 (3H, m).

Present compound 30: $^1$H-NMR ($CDCl_3$) δ: 9.00 (1H, s), 7.62 (1H, dq), 7.46 (1H, dd), 7.40-7.30 (3H, m), 3.59-3.33 (4H, m), 2.95-2.43 (1H, m), 1.43-1.32 (3H, m).

Present compound 31: $^1$H-NMR ($CDCl_3$) δ: 8.90 (1H, s), 7.84-7.51 (6H, m), 3.71-3.22 (5H, m), 1.42-1.29 (3H, m).

Present compound 35: $^1$H-NMR ($CDCl_3$) δ: 9.10 (1H, s), 7.98 (1H, d), 7.90-7.67 (5H, m), 3.56-3.34 (5H, m), 1.40-1.36 (3H, m).

Present compound 36: $^1$H-NMR ($CDCl_3$) δ: 8.77 (1H, s), 7.82 (1H, d), 7.73-7.42 (5H, m), 3.60-3.19 (5H, m), 1.30-1.26 (3H, m).

Present compound 39: $^1$H-NMR ($CDCl_3$) δ: 8.95 (1H, s), 7.71-7.65 (5H, m), 7.50 (1H, d), 3.61-3.27 (5H, m), 1.43-1.17 (3H, m).

Present compound 45: $^1$H-NMR ($CDCl_3$) δ: 8.89 (1H, s), 7.99-7.50 (6H, m), 3.58-3.26 (5H, m), 1.44-1.30 (3H, m).

Present compound 47: $^1$H-NMR ($CDCl_3$) δ: 8.81 (1H, s), 7.69-7.68 (4H, m), 7.51 (1H, d), 7.26-7.25 (1H, m), 3.57-3.34 (5H, m), 1.38-1.33 (3H, m).

Present compound 48: $^1$H-NMR ($CDCl_3$) δ: 8.81 (1H, s), 7.64-7.53 (5H, m), 6.98-6.93 (1H, m), 4.39-4.37 (2H, m), 3.47-3.40 (5H, m), 1.31-1.30 (3H, m).

Present compound 49: $^1$H-NMR ($CDCl_3$) δ: 8.89 (1H, s), 7.78-7.67 (6H, m), 3.46-3.31 (5H, m), 1.38-1.35 (3H, m).

Present compound 50: $^1$H-NMR ($CDCl_3$) δ: 8.92 (1H, s), 8.13-7.76 (3H, m), 7.71 (1H, d), 7.50 (1H, d), 3.58-2.91 (5H, m), 1.46-1.28 (3H, m).

Present compound 53: $^1$H-NMR ($CDCl_3$) δ: 9.04-8.92 (1H, m), 7.80-7.59 (4H, m), 7.51 (1H, dd), 3.59-3.16 (5H, m), 1.29-1.23 (3H, m).

Present compound 54: $^1$H-NMR ($CDCl_3$) δ: 9.07-8.43 (3H, m), 8.14-8.11 (1H, m), 7.72 (1H, dd), 7.51 (1H, dd), 3.79-2.63 (5H, m), 1.45-1.24 (3H, m).

Present compound 55: $^1$H-NMR ($CDCl_3$) δ: 9.05-8.87 (1H, m), 7.70 (1H, dd), 7.55-7.36 (4H, m), 3.66-2.79 (5H, m), 1.45-1.32 (3H, m).

Present compound 66: $^1$H-NMR ($CDCl_3$) δ: 8.87 (1H, s), 8.05-7.37 (6H, m), 3.51-3.43 (5H, m), 1.29 (3H, t).

Present compound 69: $^1$H-NMR ($CDCl_3$) δ: 9.17 (1H, s), 8.45-8.21 (2H, m), 7.72-7.43 (3H, m), 3.69 (3H, s), 3.58-3.39 (2H, m), 1.52-1.40 (3H, m).

Present compound 70: $^1$H-NMR ($CDCl_3$) δ: 8.96 (1H, s), 7.97-7.92 (2H, m), 7.87 (1H, s), 7.63 (1H, d), 7.46 (1H, d), 3.60-3.29 (5H, m), 1.30 (3H, t).

Present compound 71: $^1$H-NMR ($CDCl_3$) δ: 8.72 (1H, s), 8.63 (1H, s), 8.53 (1H, s), 7.92 (1H, s), 7.41 (1H, dd), 7.23 (1H, dd), 3.15 (2H, br s), 2.47 (3H, br s), 1.05 (3H, d).

Present compound 72: $^1$H-NMR ($CDCl_3$) δ: 9.10-8.63 (3H, br m), 8.21 (1H, s), 7.72 (1H, dd), 7.51 (1H, dd), 3.58-2.76 (5H, br m), 1.57-1.54 (3H, br m).

Present compound 74: $^1$H-NMR ($CDCl_3$) δ: 9.17 (1H, s), 8.40-7.92 (2H, m), 7.64-7.31 (3H, m), 3.64-3.28 (5H, m), 1.42-1.30 (3H, m).

Present compound 79: LCMS: 495 $[M+H]^+$, RT=1.68 min

Present compound 80: LCMS: 631 $[M+H]^+$, RT=2.07 min

Present compound 81: $^1$H-NMR (DMSO-$D_6$) δ: 8.85 (1H, s), 7.80 (1H, d), 7.73 (1H, dd), 7.68 (2H, d), 7.50 (2H, d), 3.52-3.41 (5H, m), 1.10 (3H, t).

Present compound 82: $^1$H-NMR (DMSO-$D_6$) δ: 8.84 (1H, s), 7.80 (1H, dd), 7.74-7.71 (3H, m), 7.58 (2H, d), 3.52-3.40 (5H, m), 1.10 (3H, t).

Present compound 88: LCMS: 588 $[M+H]^+$, RT=2.03 min

Present compound 94: LCMS: 490 $[M+H]^+$, RT=1.78 min

Present compound 95: LCMS: 490 $[M+H]^+$, RT=1.79 min

Present compound 97: $^1$H-NMR ($CDCl_3$) δ: 9.02-9.00 (1H, m), 8.08-8.06 (1H, m), 7.82-7.77 (2H, m), 7.64-7.61 (1H, m), 7.48-7.45 (1H, m), 3.51 (3H, s), 3.49-3.37 (2H, br m), 1.41 (3H, t).

Present compound 98: LCMS: 472 $[M+H]^+$, RT=1.62 min

Present compound 99: LCMS: 472 $[M+H]^+$, RT=1.62 min

Present compound 100: LCMS: 488 $[M+H]^+$, RT=1.78 min

Present compound 101: LCMS: 488 $[M+H]^+$, RT=1.78 min

Present compound 109: LCMS: 504 $[M+H]^+$, RT=1.98 min

Present compound 110: LCMS: 532 $[M+H]^+$, RT=2.07 min

Present compound 111: LCMS: 517 $[M+H]^+$, RT=1.91 min

Present compound 112: $^1$H-NMR ($CDCl_3$) δ: 9.13 (1H, s), 8.40 (1H, d), 8.07 (1H, t), 7.71-7.58 (2H, m), 7.53-7.45 (1H, m), 3.72 (3H, s), 3.42-3.23 (2H, m), 1.49 (3H, t).

Present compound 125: LCMS: 548 $[M+H]^+$, RT=2.13 min

Present compound 126: LCMS: 620 $[M+H]^+$, RT=2.16 min

Present compound 127: LCMS: 646 $[M+H]^+$, RT=2.24 min

Present compound 128: LCMS: 650 $[M+H]^+$, RT=2.23 min

Present compound 129: $^1$H-NMR (DMSO-$D_6$) δ: 8.94 (1H, br s), 8.07 (1H, d), 7.97 (1H, d), 7.73-7.63 (4H, m), 3.40 (3H, s), 3.36-3.33 (2H, br m), 1.19-1.12 (3H, br m).

Present compound 130: $^1$H-NMR (DMSO-$D_6$) δ: 8.70 (1H, br s), 7.91 (1H, d), 7.79-7.76 (1H, m), 7.71-7.63 (4H, m), 3.42-3.31 (2H, br m), 3.38 (3H, s), 1.19-1.08 (3H, br m).

Present compound 131: $^1$H-NMR (DMSO-$D_6$) δ: 8.83 (1H, br s), 7.81-7.71 (2H, m), 7.42-7.36 (4H, m), 3.50-3.41 (5H, m), 1.10 (3H, t).

Present compound 132: $^1$H-NMR (DMSO-$D_6$) δ: 8.83 (1H, br s), 7.81-7.70 (4H, m), 7.14 (2H, d), 3.51-3.40 (5H, m), 1.10 (3H, t).

Present compound 133: $^1$H-NMR (DMSO-$D_6$) δ: 8.91 (1H, br s), 7.88-7.78 (4H, m), 7.36 (1H, d), 7.16 (1H, t), 3.57-3.47 (5H, m), 1.19 (3H, t).

Present compound 134: $^1$H-NMR (DMSO-$D_6$) δ: 8.94 (1H, s), 8.07 (1H, d), 7.97 (1H, dd), 7.69-7.54 (4H, br m), 3.39 (3H, s), 3.38-3.38 (2H, m), 1.19-1.08 (3H, br m).

Present compound 135: LCMS: 566 $[M+H]^+$, RT=2.15 min

Present compound 136: LCMS: 583 $[M+H]^+$, RT=1.66 min

Present compound 137: LCMS: 602 $[M+H]^+$, RT=1.90 min

Present compound 138: LCMS: 554 $[M+H]^+$, RT=1.81 min

Present compound 139: LCMS: 596 $[M+H]^+$, RT=1.95 min

Present compound 140: LCMS: 456 $[M+H]^+$, RT=1.85 min

Present compound 141: LCMS: 548 $[M+H]^+$, RT=1.87 min

Present compound 142: $^1$H-NMR (DMSO-$D_6$) δ: 8.85 (1H, br s), 7.82-7.72 (2H, m), 7.50-7.47 (2H, m), 7.33 (1H, t), 7.24 (1H, d), 3.52-3.41 (5H, m), 1.12 (3H, t).

Present compound 143: LCMS: 456 $[M+H]^+$, RT=1.79 min

Preparation Example 2

A mixture of the Intermediate compound 2 (370 mg), cesium carbonate (580 mg), 2-iodopropane (200 μL), and DMF (10 mL) was stirred at 50° C. for 8 hours. To the resulting mixture was added water, and the resulting mixture was subjected to extraction with chloroform. The resulting organic layer was dried over anhydrous magnesium sulfate, and concentrated under reduced pressure. To the resulting residue was added chloroform (5 mL), mCPBA (purity: 70%, comprising 30% of water) (400 mg) was added thereto under ice-cooling, and the resulting mixture was stirred at room temperature for 2 hours. To the resulting mixture were sequentially added a saturated aqueous solution of sodium hydrogen carbonate and an aqueous solution of sodium thiosulfate, and the resulting mixture was subjected to extraction with chloroform. The resulting organic layer was dried over anhydrous magnesium sulfate, and concentrated under reduced pressure. The resulting residue was subjected to silica gel chromatography to give the Present compound 34 (110 mg).

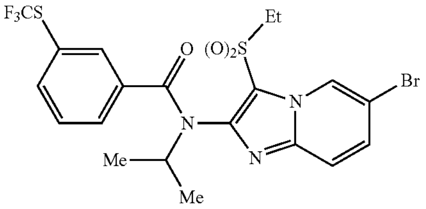

Present compound 34: LCMS: 550 $[M+H]^+$, RT=2.16 min

Preparation Example 3

To a mixture of the Intermediate compound 38 (300 mg) and THF (6 mL) were sequentially added sodium borohydride (45 mg) and methanol (0.5 mL) under ice-cooling, and the resulting mixture was stirred at room temperature for 2 hours. To the resulting mixture was added water under ice-cooling, and the precipitated solids were filtered. The resulting solids were washed with water, and dried under reduced pressure to give the Present compound 59 represented by the following formula (240 mg).

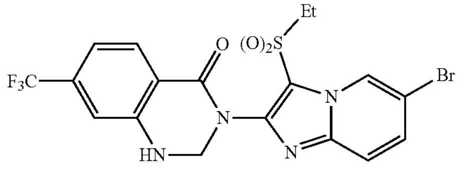

Present compound 59: $^1$H-NMR ($CDCl_3$) δ: 9.02-9.01 (1H, m), 8.13 (1H, d), 7.59-7.56 (2H, m), 7.18 (1H, d), 7.08 (1H, s), 5.19 (2H, d), 4.77 (1H, br s), 3.64 (2H, q), 1.45 (3H, t).

Preparation Example 3-1

The compounds prepared according to the Preparation Example 3 and physical properties thereof are shown below.

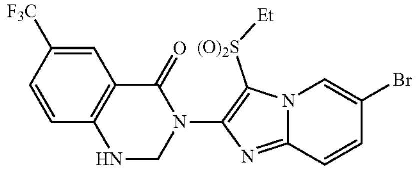

Present compound 60: $^1$H-NMR ($CDCl_3$) δ: 9.01-9.01 (1H, M), 8.28 (1H, s), 7.57-7.54 (3H, m), 6.83 (1H, d), 5.21 (2H, d), 5.01 (1H, br s), 3.67 (2H, q), 1.47 (3H, t).

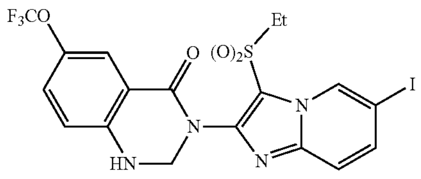

Present compound 61: $^1$H-NMR ($CDCl_3$) δ: 9.09-9.09 (1H, m), 7.87 (1H, d), 7.67 (1H, dd), 7.45 (1H, dd), 7.23-7.20 (1H, m), 6.81 (1H, d), 5.14 (2H, d), 4.80 (1H, br s), 3.65 (2H, q), 1.47-1.43 (3H, m).

Preparation Example 4

To a mixture of the Present compound 60 (150 mg) and DMF (3 mL) were sequentially added methyl iodide (0.2 mL) and potassium carbonate (83 mg) at room temperature, and the resulting mixture was stirred at 80° C. for 16 hours. The resulting mixture was allowed to cool to room temperature, and water was added thereto. The precipitated solids were filtered, the resulting solids were washed with water, and dried under reduced pressure to give the Present compound 62 represented by the following formula (102 mg).

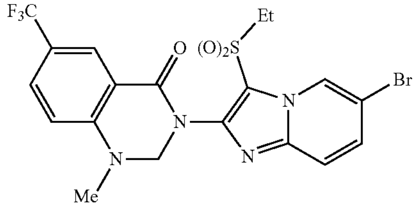

Present compound 62: $^1$H-NMR ($CDCl_3$) δ: 9.01 (1H, S), 8.30 (1H, d), 7.67 (1H, d), 7.59-7.56 (2H, m), 6.84 (1H, d), 5.07 (2H, s), 3.69 (2H, q), 3.07 (3H, s), 1.48 (3H, t).

Preparation Example 4-1

The compound prepared according to the Preparation Example 4 and physical property thereof are shown below.

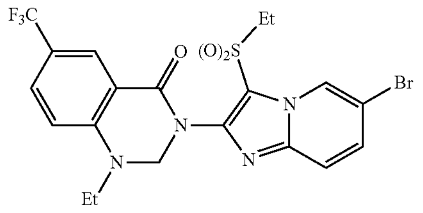

Present compound 63: $^1$H-NMR ($CDCl_3$) δ: 9.01 (1H, s), 8.31 (1H, d), 7.64 (1H, d), 7.58-7.57 (2H, m), 6.89 (1H, d), 5.14 (2H, s), 3.68 (2H, q), 3.57 (2H, q), 1.47 (3H, t), 1.28 (3H, t).

Preparation Example 5

A mixture of the Present compound 7 (0.49 g), cyclopropylboronic acid (260 mg), [1,1'-bis(diphenylphosphino) ferrocene]dichloropalladium (II) (150 mg), tripotassium phosphate (640 mg), toluene (4 mL), and water (0.4 mL) was stirred at 110° C. for 2 hours. The resulting mixture was allowed to cool to room temperature, then water was added thereto, and the resulting mixture was subjected to extraction with ethyl acetate. The resulting organic layer was dried over anhydrous sodium sulfate, and concentrated under reduced pressure. The resulting residue was subjected to silica gel chromatography (ethyl acetate:hexane=1:1) to give the Present compound 11 represented by the following formula (400 mg).

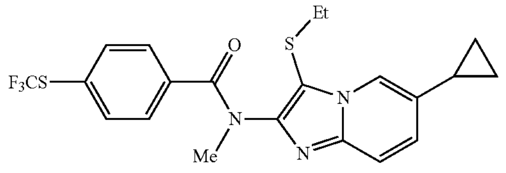

Present compound 11: $^1$H-NMR ($CDCl_3$) δ: 7.95 (1H, s), 7.51-7.50 (3H, m), 7.42 (2H, d), 7.07 (1H, d), 3.54 (3H, s), 2.26 (2H, q), 1.94-1.91 (1H, m), 1.27 (3H, t), 1.02-1.00 (2H, m), 0.73-0.70 (2H, m).

Preparation Example 5-1

The compounds prepared according to the Preparation Example 5 and physical properties thereof are shown below.

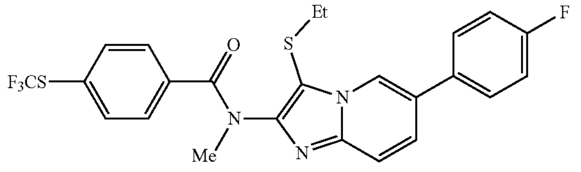

Present compound 12: $^1$H-NMR ($CDCl_3$) δ: 8.28 (1H, s), 7.68 (1H, d), 7.57-7.50 (5H, m), 7.44 (2H, d), 7.20-7.16 (2H, m), 3.58 (3H, s), 2.31 (2H, d), 1.09 (3H, t).

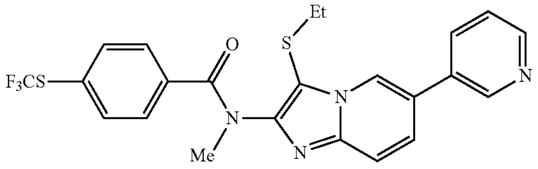

Present compound 13: $^1$H-NMR ($CDCl_3$) δ: 8.84 (1H, S), 8.68 (1H, d), 8.36 (1H, s), 7.89-7.86 (1H, m), 7.73 (1H, d), 7.59-7.53 (3H, m), 7.46-7.42 (3H, m), 3.58 (3H, s), 2.32 (2H, q), 1.10 (3H, t).

Next, examples of the Present compound X prepared according to any one of the Preparation Examples described in the EXAMPLES and the Production methods described in the present description are shown below.

A Compound Represented by Formula (L-1)

(L-1)

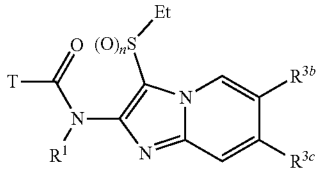

(hereinafter referred to as "Compound (L-1)"), wherein n represents 0, R represents a methyl group, $R^{3b}$ represents a hydrogen atom, $R^{3c}$ represents a hydrogen atom, and T represents any one substituent described in Table L1 to Table L11 (hereinafter referred to as "Compound group SX1").

TABLE L1

| |
|---|
| Ph |
| 2-F—Ph |
| 3-F—Ph |
| 4-F—Ph |
| 2-Cl—Ph |
| 3-Cl—Ph |
| 4-Cl—Ph |
| 2-Br—Ph |
| 3-Br—Ph |
| 4-Br—Ph |
| 2-I—Ph |
| 3-I—Ph |
| 4-I—Ph |
| 2-Me—Ph |
| 3-Me—Ph |
| 4-Me—Ph |
| 2-Et—Ph |
| 3-Et—Ph |
| 4-Et—Ph |
| 2-Pr—Ph |
| 3-Pr—Ph |
| 4-Pr—Ph |
| 2-i-Pr—Ph |
| 3-i-Pr—Ph |
| 4-i-Pr—Ph |
| 2-c-Pr—Ph |
| 3-c-Pr—Ph |
| 4-c-Pr—Ph |
| 2-t-Bu—Ph |
| 3-t-Bu—Ph |
| 4-t-Bu—Ph |
| 2-CN—Ph |

TABLE L1-continued

| |
|---|
| 3-CN—Ph |
| 4-CN—Ph |
| 2-F-5-$CF_3$—Ph |
| 2-F-5-$OCF_3$—Ph |
| 2-F-5-$SCF_3$—Ph |
| 2-$CF_2H$—Ph |
| 2-$OCF_2H$—Ph |
| 3,4-$(CF_2H)_2$—Ph |
| 3,5-$(OCF_2H)_2$—Ph |

TABLE L2

| |
|---|
| 2-$NO_2$—Ph |
| 3-$NO_2$—Ph |
| 4-$NO_2$—Ph |
| 2-OMe—Ph |
| 3-OMe—Ph |
| 4-OMe—Ph |
| 2-$OCF_3$—Ph |
| 3-$OCF_3$—Ph |
| 4-$OCF_3$—Ph |
| 2-$CF_3$—Ph |
| 3-$CF_3$—Ph |
| 4-$CF_3$—Ph |
| 2-$C_2F_5$—Ph |
| 3-$C_2F_5$—Ph |
| 4-$C_2F_5$—Ph |
| 2-$OCH_2CF_3$—Ph |
| 3-$OCH_2CF_3$—Ph |
| 4-$OCH_2CF_3$—Ph |
| 2-SMe—Ph |
| 3-SMe—Ph |
| 4-SMe—Ph |
| 2-S(O)Me—Ph |
| 3-S(O)Me—Ph |
| 4-S(O)Me—Ph |
| 2-$S(O)_2Me$—Ph |
| 3-$S(O)_2Me$—Ph |
| 4-$S(O)_2Me$—Ph |
| 2-$SCF_3$—Ph |
| 3-$SCF_3$—Ph |
| 4-$SCF_3$—Ph |
| 2-$S(O)CF_3$—Ph |
| 3-$S(O)CF_3$—Ph |
| 4-$S(O)CF_3$—Ph |
| 2-F-5-Cl—Ph |
| 2-F-5-Br—Ph |
| 2-F-5-CN—Ph |
| 2-F-5-$OCF_2H$—Ph |
| 3-$CF_2H$—Ph |
| 3-$OCF_2H$—Ph |
| 3,5-$(CF_2H)_2$—Ph |
| 3,4,5-$F_3$—Ph |

TABLE L3

| |
|---|
| 2-$S(O)_2CF_3$—Ph |
| 3-$S(O)_2CF_3$—Ph |
| 4-$S(O)_2CF_3$—Ph |
| 3,4-$F_2$—Ph |
| 3,5-$F_2$—Ph |
| 3,4-$Cl_2$—Ph |
| 3,5-$Cl_2$—Ph |
| 3,4-$Br_2$—Ph |
| 3,5-$Br_2$—Ph |
| 3,4-$I_2$—Ph |
| 3,5-$I_2$—Ph |
| 3,4-$(CN)_2$—Ph |
| 3,5-$(CN)_2$—Ph |
| 3,4-$(OCF_3)_2$—Ph |
| 3,5-$(OCF_3)_2$—Ph |
| 3,4-$(CF_3)_2$—Ph |
| 3,5-$(CF_3)_2$—Ph |
| 3,4-$(SCF_3)_2$—Ph |
| 3,5-$(SCF_3)_2$—Ph |

TABLE L3-continued

| |
|---|
| 3,4-$(NO_2)_2$—Ph |
| 3,5-$(NO_2)_2$—Ph |
| 3,4-$(C_2F_5)_2$—Ph |
| 3,5-$(C_2F_5)_2$—Ph |
| 2-F-4-Cl—Ph |
| 2-F-4-Br—Ph |
| 2-F-4-CN—Ph |
| 2-F-4-$SCF_3$—Ph |
| 2-F-4-$OCF_3$—Ph |
| 2-F-4-$CF_3$—Ph |
| 2-F-4-$C_2F_5$—Ph |
| 2-F-4-$NO_2$—Ph |
| 3-F-4-Cl—Ph |
| 3-F-4-Br—Ph |
| 3-F-4-CN—Ph |
| 2-F-5-$NO_2$—Ph |
| 2-F-5-$C_2F_5$—Ph |
| 2-F-5-$CF_2H$—Ph |
| 4-$CF_2H$—Ph |
| 4-OCFH—Ph |
| 3,4-$(OCF_2H)_2$—Ph |
| 2,4,6-$Cl_3$—Ph |

TABLE L4

| |
|---|
| 3-F-4-$SCF_3$—Ph |
| 3-F-4-$OCF_3$—Ph |
| 3-F-4-$CF_3$—Ph |
| 3-F-4-$C_2F_5$—Ph |
| 3-F-4-$NO_2$—Ph |
| 3-F-5-Cl—Ph |
| 3-F-5-Br—Ph |
| 3-F-5-CN—Ph |
| 3-F-5-$SCF_3$—Ph |
| 3-F-5-$OCF_3$—Ph |
| 3-F-5-$CF_3$—Ph |
| 3-F-5-$C_2F_5$—Ph |
| 3-F-5-$NO_2$—Ph |
| 2-Cl-4-Br—Ph |
| 2-Cl-4-CN—Ph |
| 2-Cl-4-$SCF_3$—Ph |
| 2-Cl-4-$OCF_3$—Ph |
| 2-Cl-4-$CF_3$—Ph |
| 2-Cl-4-$C_2F_5$—Ph |
| 2-Cl-4-$NO_2$—Ph |
| 3-Cl-4-Br—Ph |
| 3-Cl-4-CN—Ph |
| 3-Cl-4-$SCF_3$—Ph |
| 3-Cl-4-$OCF_3$—Ph |
| 3-Cl-4-$CF_3$—Ph |
| 3-Cl-4-$C_2F_5$—Ph |
| 3-Cl-4-$NO_2$—Ph |
| 3-Cl-5-Br—Ph |
| 3-Cl-5-CN—Ph |
| 3-Cl-5-$SCF_3$—Ph |
| 3-Cl-5-$OCF_3$—Ph |
| 3-Cl-5-$CF_3$—Ph |
| 3-Cl-5-$C_2F_5$—Ph |
| 3-Cl-5-$NO_2$—Ph |
| 2-F-4-$OCF_2H$—Ph |
| 3-F-4-$CF_2H$—Ph |
| 3-Cl-4-F—Ph |
| 2-Cl-4-$CF_2H$—Ph |
| 3-Cl-4-$OCF_2H$—Ph |
| 3-Cl-4-$CF_2H$—Ph |
| 2-Br-5-$OCF_2H$—Ph |
| 3-Br-4-$CF_2H$—Ph |
| 3-$OCF_2H$-4-F—Ph |
| 3-$OCF_2H$-4-$NO_2$—Ph |
| 3-$CF_2H$-4-Br—Ph |

TABLE L5

| |
|---|
| 2-Br-4-CN—Ph |
| 2-Br-4-$SCF_3$—Ph |

TABLE L5-continued

| |
|---|
| 2-Br-4-$OCF_3$—Ph |
| 2-Br-4-$CF_3$—Ph |
| 2-Br-4-$C_2F_5$—Ph |
| 2-Br-4-$NO_2$—Ph |
| 3-Br-4-CN—Ph |
| 3-Br-4-$SCF_3$—Ph |
| 3-Br-4-$OCF_3$—Ph |
| 3-Br-4-$CF_3$—Ph |
| 3-Br-4-$C_2F_5$—Ph |
| 3-Br-4-$NO_2$—Ph |
| 3-Br-5-CN—Ph |
| 3-Br-5-$SCF_3$—Ph |
| 3-Br-5-$OCF_3$—Ph |
| 3-Br-5-$CF_3$—Ph |
| 3-Br-5-$C_2F_5$—Ph |
| 3-Br-5-$NO_2$—Ph |
| 2-CN-4-$SCF_3$—Ph |
| 2-CN-4-$OCF_3$—Ph |
| 2-CN-4-$CF_3$—Ph |
| 2-CN-4-$C_2F_5$—Ph |
| 2-CN-4-$NO_2$—Ph |
| 3-CN-4-$SCF_3$—Ph |
| 3-CN-4-$OCF_3$—Ph |
| 3-CN-4-$CF_3$—Ph |
| 3-CN-4-$C_2F_5$—Ph |
| 3-CN-4-$NO_2$—Ph |
| 3-CN-5-$SCF_3$—Ph |
| 3-CN-5-$OCF_3$—Ph |
| 3-CN-5-$CF_3$—Ph |
| 3-CN-5-$C_2F_5$—Ph |
| 3-CN-5-$NO_2$—Ph |
| 2-$SCF_3$-4-$SCF_3$—Ph |
| 2-F-4-$CF_2H$—Ph |
| 3-F-5-$OCF_2H$—Ph |
| 3-Br-4-F—Ph |
| 2-Cl-5-$OCF_2H$—Ph |
| 3-Cl-4-$CF_2H$—Ph |
| 2-Br-4-$OCF_2H$—Ph |
| 2-Br-5-$CF_2H$—Ph |
| 3-Br-5-$OCF_2H$—Ph |
| 3-$OCF_2H$-4-Cl—Ph |
| 3-$CF_2H$-4-F—Ph |
| 3-$CF_2H$-4-$NO_2$—Ph |

TABLE L6

| |
|---|
| 2-$SCF_3$-4-$C_2F_5$—Ph |
| 2-$SCF_3$-4-$NO_2$—Ph |
| 3-$SCF_3$-4-$OCF_3$—Ph |
| 3-$SCF_3$-4-$CF_3$—Ph |
| 3-$SCF_3$-4-$C_2F_5$—Ph |
| 3-$SCF_3$-4-$NO_2$—Ph |
| 3-$SCF_3$-5-$OCF_3$—Ph |
| 3-$SCF_3$-5-$CF_3$—Ph |
| 3-$SCF_3$-5-$C_2F_5$—Ph |
| 3-$SCF_3$-5-$NO_2$—Ph |
| 2-$OCF_3$-4-$SCF_3$—Ph |
| 2-$OCF_3$-4-$OCF_3$—Ph |
| 2-$OCF_3$-4-$CF_3$—Ph |
| 2-$OCF_3$-4-$C_2F_5$—Ph |
| 2-$OCF_3$-4-$NO_2$—Ph |
| 3-$OCF_3$-4-$SCF_3$—Ph |
| 3-$OCF_3$-4-$CF_3$—Ph |
| 3-$OCF_3$-4-$C_2F_5$—Ph |
| 3-$OCF_3$-4-$NO_2$—Ph |
| 3-$OCF_3$-5-$CF_3$—Ph |
| 3-$OCF_3$-5-$C_2F_5$—Ph |
| 3-$OCF_3$-5-$NO_2$—Ph |
| 2-$CF_3$-4-$SCF_3$—Ph |
| 2-$CF_3$-4-$C_2F_5$—Ph |
| 2-$CF_3$-4-$NO_2$—Ph |
| 3-$CF_3$-4-$C_2F_5$—Ph |
| 3-$CF_3$-4-$NO_2$—Ph |
| 3-$CF_3$-5-$C_2F_5$—Ph |
| 3-$CF_3$-5-$NO_2$—Ph |
| 2-$C_2F_5$-4-$NO_2$—Ph |
| 3-$C_2F_5$-4-$NO_2$—Ph |

TABLE L6-continued

| |
|---|
| 3-$C_2F_5$-5-$NO_2$—Ph |
| 2-$SCF_3$-4-$OCF_3$—Ph |
| 2-$SCF_3$-4-$CF_3$—Ph |
| 3-F-4-$OCF_2H$ Ph |
| 3-F-5-$CF_2H$—Ph |
| 2-Cl-4-$OCF_2H$—Ph |
| 2-Cl-5-$CF_2H$—Ph |
| 3-Cl-5-$OCF_2H$—Ph |
| 2-Br-4-$CF_2H$—Ph |
| 3-Br-4-$OCF_2H$—Ph |
| 3-Br-5-$CF_2H$—Ph |
| 3-$OCF_2H$-4-Br—Ph |
| 3-$CF_2H$-4-Cl—Ph |

TABLE L7

| |
|---|
| 3-F—Py2 |
| 3-Cl—Py2 |
| 3-Br—Py2 |
| 3-CN—Py2 |
| 3-$SCF_3$—Py2 |
| 3-$OCF_3$—Py2 |
| 3-$CF_3$—Py2 |
| 3-$C_2F_5$—Py2 |
| 3-$NO_2$—P2 |
| 4-F—Py2 |
| 4-Cl—Py2 |
| 4-Br—Py2 |
| 4-CN—Py2 |
| 4-$SCF_3$—Py2 |
| 4-$OCF_3$—Py2 |
| 4-$CF_3$—Py2 |
| 4-$C_2F_5$—Py2 |
| 4-$NO_2$—Py2 |
| 5-F—Py2 |
| 5-Cl—Py2 |
| 5-Br—Py2 |
| 5-CN—Py2 |
| 5-$SCF_3$—Py2 |
| 5-$OCF_3$—Py2 |
| 5-$CF_3$—Py2 |
| 5-$C_2F_5$—Py2 |
| 5-$NO_2$—Py2 |
| 4-$CF_2H$—Py3 |
| 2-$OCF_2H$—Py4 |
| 3-$CF_2H$—Py4 |

TABLE L8

| |
|---|
| 2-F—Py3 |
| 2-Cl—Py3 |
| 2-Br—Py3 |
| 2-CN—Py3 |
| 2-$SCF_3$—Py3 |
| 2-$OCF_3$—Py3 |
| 2-$CF_3$—Py3 |
| 2-$C_2F_5$—Py3 |
| 2-$NO_2$—Py3 |
| 4-F—Py3 |
| 4-Cl—Py3 |
| 4-Br—Py3 |
| 4-CN—Py3 |
| 4-$SCF_3$—Py3 |
| 4-$OCF_3$—Py3 |
| 4-$CF_3$—Py3 |
| 4-$C_2F_5$—Py3 |
| 4-$NO_2$—Py3 |
| 5-F—Py3 |
| 5-Cl—Py3 |
| 5-Br—Py3 |
| 5-CN—Py3 |
| 5-$SCF_3$—Py3 |
| 5-$OCF_3$—Py3 |
| 5-$CF_3$—Py3 |
| 5-$C_2F_5$—Py3 |

TABLE L8-continued

| |
|---|
| 5-$NO_2$—Py3 |
| 5-$OCF_2H$—Py3 |
| 2-$CF_2H$—Py4 |

TABLE L9

| |
|---|
| 2-F—Py4 |
| 2-Cl—Py4 |
| 2-Br—Py4 |
| 2-CN—Py4 |
| 2-$SCF_3$—Py4 |
| 2-$OCF_3$—Py4 |
| 2-$CF_3$—Py4 |
| 2-$C_2F_5$—Py4 |
| 2-$NO_2$—Py4 |
| 3-F—Py4 |
| 3-Cl—Py4 |
| 3-Br—Py4 |
| 3-CN—Py4 |
| 3-$SCF_3$—Py4 |
| 3-$OCF_3$—Py4 |
| 3-$CF_3$—Py4 |
| 3-$C_2F_5$—Py4 |
| 3-$NO_2$—Py4 |
| 3-$OCF_2H$—Py2 |
| 3-$CF_2H$—Py2 |
| 4-$OCF_2H$—Py2 |
| 4-$CF_2H$—Py2 |
| 5-$OCF_2H$—Py2 |
| 5-$CF_2H$—Py2 |
| 2-$OCF_2H$—Py3 |
| 2-$CF_2H$—Py3 |
| 4-$OCF_2H$—Py3 |
| 5-$CF_2H$—Py3 |
| 3-$OCF_2H$—Py4 |

TABLE L10

| |
|---|
| 5-fluoropyridazin-3-yl |
| 5-chloropyridazin-3-yl |
| 5-bromopyridazin-3-yl |
| 5-cyanopyridazin-3-yl |
| 5-[(trifluoromethyl)thio]pyridazin-3-yl |
| 5-(trifluoromethoxy)pyridazin-3-yl |
| 5-(trifluoromethyl)pyridazin-3-yl |
| 5-(perfluoroethyl)pyridazin-3-yl |
| 5-nitropyridazin-3-yl |
| 6-fluoropyridazin-3-yl |
| 6-chloropyridazin-3-yl |
| 6-bromopyridazin-3-yl |
| 6-cyanopyridazin-3-yl |
| 6-[(trifluoromethyl)thio]pyridazin-3-yl |
| 6-(trifluoromethoxy)pyridazin-3-yl |
| 6-(trifluoromethyl)pyridazin-3-yl |
| 6-(perfluoroethyl)pyridazin-3-yl |
| 6-nitropyridazin-3-yl |
| 4-fluoropyrimidin-2-yl |
| 4-chloropyrimidin-2-yl |
| 4-bromopyrimidin-2-yl |
| 4-cyanopyrimidin-2-yl |
| 4-[(trifluoromethyl)thio]pyrimidin-2-yl |
| 4-(trifluoromethoxy)pyrimidin-2-yl |
| 4-(trifluoromethyl)pyrimidin-2-yl |
| 4-(perfluoroethyl)pyrimidin-2-yl |
| 4-nitropyrimidin-2-yl |
| 5-fluoropyrimidin-2-yl |
| 5-chloropyrimidin-2-yl |

TABLE L11

| |
|---|
| 5-bromopyrimidin-2-yl |
| 5-cyanopyrimidin-2-yl |
| 5-[(trifluoromethyl)thio]pyrimidin-2-yl |

TABLE L11-continued

| |
|---|
| 5-(trifluoromethoxy)pyrimidin-2-yl |
| 5-(trifluoromethyl)pyrimidin-2-yl |
| 5-(perfluoroethyl)pyrimidin2-yl |
| 5-nitropyrimidin-2-yl |
| 4-fluoropyrazin-2-yl |
| 4-chloropyrazin-2-yl |
| 4-bromopyrazin-2-yl |
| 4-cyanopyrazin-2-yl |
| 4-[(trifluoromethyl)thio]pyrazin-2-yl |
| 4-(trifluoromethoxy)pyrazin-2-yl |
| 4-(trifluoromethyl)pyrazin-2-yl |
| 4-(perfluoroethyl)pyrazin-2-yl |
| 4-nitropyrazin-2-yl |
| 5-fluoropyrazin-2-yl |
| 5-chloropyrazin-2-yl |
| 5-bromopyrazin-2-yl |
| 5-cyanopyrazin-2-yl |
| 5-[(trifluoromethyl)thio]pyrazin-2-yl |
| 5-(trifluoromethoxy)pyrazin-2-yl |
| 5-(trifluoromethyl)pyrazin-2-yl |
| 5-(perfluoroethyl)pyrazin-2-yl |
| 5-nitropyrazin-2-yl |

The Compound (L-1), wherein n represents 0, $R^1$ represents a methyl group, $R^{3b}$ represents a chlorine atom, $R^{3c}$ represents a hydrogen atom, and T represents any one substituent described in Table L1 to Table L11 (hereinafter referred to as "Compound group SX2").

The Compound (L-1), wherein n represents 0, $R^1$ represents a methyl group, $R^{3b}$ represents a bromine atom, $R^{3c}$ represents a hydrogen atom, and T represents any one substituent described in Table L1 to Table L11 (hereinafter referred to as "Compound group SX3").

The Compound (L-1), wherein n represents 0, $R^1$ represents a methyl group, $R^{3b}$ represents an iodine atom, $R^{3c}$ represents a hydrogen atom, and T represents any one substituent described in Table L1 to Table L11 (hereinafter referred to as "Compound group SX4").

The Compound (L-1), wherein n represents 0, $R^1$ represents a methyl group, $R^{3b}$ represents $CF_3$, $R^{3c}$ represents a hydrogen atom, and T represents any one substituent described in Table L1 to Table L11 (hereinafter referred to as "Compound group SX5").

The Compound (L-1), wherein n represents 0, $R^1$ represents a methyl group, $R^{3b}$ represents a hydrogen atom, $R^{3c}$ represents a chlorine atom, and T represents any one substituent described in Table L1 to Table L11 (hereinafter referred to as "Compound group SX6").

The Compound (L-1), wherein n represents 0, $R^1$ represents a methyl group, $R^{3b}$ represents a chlorine atom, $R^{3c}$ represents a chlorine atom, and T represents any one substituent described in Table L1 to Table L11 (hereinafter referred to as "Compound group SX7").

The Compound (L-1), wherein n represents 0, $R^1$ represents a methyl group, $R^{3b}$ represents a bromine atom, $R^{3c}$ represents a chlorine atom, and T represents any one substituent described in Table L1 to Table L11 (hereinafter referred to as "Compound group SX8").

The Compound (L-1), wherein n represents 0, $R^1$ represents a methyl group, $R^{3b}$ represents an iodine atom, $R^{3c}$ represents a chlorine atom, and T represents any one substituent described in Table L1 to Table L11 (hereinafter referred to as "Compound group SX9").

The Compound (L-1), wherein n represents 0, $R^1$ represents a methyl group, $R^{3b}$ represents $CF_3$, $R^{3c}$ represents a chlorine atom, and T represents any one substituent described in Table L1 to Table L11 (hereinafter referred to as "Compound group SX10").

The Compound (L-1), wherein n represents 0, $R^1$ represents a methyl group, $R^{3b}$ represents a hydrogen atom, $R^{3c}$ represents a bromine atom, and T represents any one substituent described in Table L1 to Table L11 (hereinafter referred to as "Compound group SX11").

The Compound (L-1), wherein n represents 0, $R^1$ represents a methyl group, $R^{3b}$ represents a chlorine atom, $R^{3c}$ represents a bromine atom, and T represents any one substituent described in Table L1 to Table L11 (hereinafter referred to as "Compound group SX12").

The Compound (L-1), wherein n represents 0, $R^1$ represents a methyl group, $R^{3b}$ represents a bromine atom, $R^{3c}$ represents a bromine atom, and T represents any one substituent described in Table L1 to Table L11 (hereinafter referred to as "Compound group SX13").

The Compound (L-1), wherein n represents 0, $R^1$ represents a methyl group, $R^{3b}$ represents an iodine atom, $R^{3c}$ represents a bromine atom, and T represents any one substituent described in Table L1 to Table L11 (hereinafter referred to as "Compound group SX14").

The Compound (L-1), wherein n represents 0, $R^1$ represents a methyl group, $R^{3b}$ represents $CF_3$, $R^{3c}$ represents a bromine atom, and T represents any one substituent described in Table L1 to Table L11 (hereinafter referred to as "Compound group SX15").

The Compound (L-1), wherein n represents 0, $R^1$ represents a methyl group, $R^{3b}$ represents a hydrogen atom, $R^{3c}$ represents an iodine atom, and T represents any one substituent described in Table L1 to Table L11 (hereinafter referred to as "Compound group SX16").

The Compound (L-1), wherein n represents 0, $R^1$ represents a methyl group, $R^{3b}$ represents a chlorine atom, $R^{3c}$ represents an iodine atom, and T represents any one substituent described in Table L1 to Table L11 (hereinafter referred to as "Compound group SX17").

The Compound (L-1), wherein n represents 0, $R^1$ represents a methyl group, $R^{3b}$ represents a bromine atom, $R^{3c}$ represents an iodine atom, and T represents any one substituent described in Table L1 to Table L11 (hereinafter referred to as "Compound group SX18").

The Compound (L-1), wherein n represents 0, $R^1$ represents a methyl group, $R^{3b}$ represents an iodine atom, $R^{3c}$ represents an iodine atom, and T represents any one substituent described in Table L1 to Table L11 (hereinafter referred to as "Compound group SX19").

The Compound (L-1), wherein n represents 0, $R^1$ represents a methyl group, $R^{3b}$ represents $CF_3$, $R^{3c}$ represents an iodine atom, and T represents any one substituent described in Table L1 to Table L11 (hereinafter referred to as "Compound group SX20").

The Compound (L-1), wherein n represents 0, $R^1$ represents a methyl group, $R^{3b}$ represents a hydrogen atom, $R^{3c}$ represents $CF_3$, and T represents any one substituent described in Table L1 to Table L11 (hereinafter referred to as "Compound group SX21").

The Compound (L-1), wherein n represents 0, $R^1$ represents a methyl group, $R^{3b}$ represents a chlorine atom, $R^{3c}$ represents $CF_3$, and T represents any one substituent described in Table L1 to Table L11 (hereinafter referred to as "Compound group SX22").

The Compound (L-1), wherein n represents 0, $R^1$ represents a methyl group, $R^{3b}$ represents a bromine atom, $R^{3c}$ represents $CF_3$, and T represents any one substituent described in Table L1 to Table L11 (hereinafter referred to as "Compound group SX23").

The Compound (L-1), wherein n represents 0, $R^1$ represents a methyl group, $R^{3b}$ represents an iodine atom, $R^{3c}$ represents $CF_3$, and T represents any one substituent described in Table L1 to Table L11 (hereinafter referred to as "Compound group SX24").

The Compound (L-1), wherein n represents 0, $R^1$ represents a methyl group, $R^{3b}$ represents $CF_3$, $R^{3c}$ represents $CF_3$, and T represents any one substituent described in Table L1 to Table L11 (hereinafter referred to as "Compound group SX25").

The Compound (L-1), wherein n represents 0, $R^1$ represents an ethyl group, $R^{3b}$ represents a hydrogen atom, $R^{3c}$ represents a hydrogen atom, and T represents any one substituent described in Table L1 to Table L11 (hereinafter referred to as "Compound group SX26").

The Compound (L-1), wherein n represents 0, $R^1$ represents an ethyl group, $R^{3b}$ represents a chlorine atom, $R^{3c}$ represents a hydrogen atom, and T represents any one substituent described in Table L1 to Table L11 (hereinafter referred to as "Compound group SX27").

The Compound (L-1), wherein n represents 0, $R^1$ represents an ethyl group, $R^{3b}$ represents a bromine atom, $R^{3c}$ represents a hydrogen atom, and T represents any one substituent described in Table L1 to Table L11 (hereinafter referred to as "Compound group SX28").

The Compound (L-1), wherein n represents 0, $R^1$ represents an ethyl group, $R^{3b}$ represents an iodine atom, $R^{3c}$ represents a hydrogen atom, and T represents any one substituent described in Table L1 to Table L11 (hereinafter referred to as "Compound group SX29").

The Compound (L-1), wherein n represents 0, $R^1$ represents an ethyl group, $R^{3b}$ represents $CF_3$, $R^{3c}$ represents a hydrogen atom, and T represents any one substituent described in Table L1 to Table L11 (hereinafter referred to as "Compound group SX30").

The Compound (L-1), wherein n represents 0, $R^1$ represents an ethyl group, $R^{3b}$ represents a hydrogen atom, $R^{3c}$ represents a chlorine atom, and T represents any one substituent described in Table L1 to Table L11 (hereinafter referred to as "Compound group SX31").

The Compound (L-1), wherein n represents 0, $R^1$ represents an ethyl group, $R^{3b}$ represents a chlorine atom, $R^{3c}$ represents a chlorine atom, and T represents any one substituent described in Table L1 to Table L11 (hereinafter referred to as "Compound group SX32").

The Compound (L-1), wherein n represents 0, $R^1$ represents an ethyl group, $R^{3b}$ represents a bromine atom, $R^{3c}$ represents a chlorine atom, and T represents any one substituent described in Table L1 to Table L11 (hereinafter referred to as "Compound group SX33").

The Compound (L-1), wherein n represents 0, $R^1$ represents an ethyl group, $R^{3b}$ represents an iodine atom, $R^{3c}$ represents a chlorine atom, and T represents any one substituent described in Table L1 to Table L11 (hereinafter referred to as "Compound group SX34").

The Compound (L-1), wherein n represents 0, $R^1$ represents an ethyl group, $R^{3b}$ represents $CF_3$, $R^{3c}$ represents a chlorine atom, and T represents any one substituent described in Table L1 to Table L11 (hereinafter referred to as "Compound group SX35").

The Compound (L-1), wherein n represents 0, $R^1$ represents an ethyl group, $R^{3b}$ represents a hydrogen atom, $R^{3c}$ represents a bromine atom, and T represents any one substituent described in Table L1 to Table L11 (hereinafter referred to as "Compound group SX36").

The Compound (L-1), wherein n represents 0, $R^1$ represents an ethyl group, $R^{3b}$ represents a chlorine atom, $R^{3c}$ represents a bromine atom, and T represents any one substituent described in Table L1 to Table L11 (hereinafter referred to as "Compound group SX37").

The Compound (L-1), wherein n represents 0, $R^1$ represents an ethyl group, $R^{3b}$ represents a bromine atom, $R^{3c}$ represents a bromine atom, and T represents any one substituent described in Table L1 to Table L11 (hereinafter referred to as "Compound group SX38").

The Compound (L-1), wherein n represents 0, $R^1$ represents an ethyl group, $R^{3b}$ represents an iodine atom, $R^{3c}$ represents a bromine atom, and T represents any one substituent described in Table L1 to Table L11 (hereinafter referred to as "Compound group SX39").

The Compound (L-1), wherein n represents 0, $R^1$ represents an ethyl group, $R^{3b}$ represents $CF_3$, $R^{3c}$ represents a bromine atom, and T represents any one substituent described in Table L1 to Table L11 (hereinafter referred to as "Compound group SX40").

The Compound (L-1), wherein n represents 0, $R^1$ represents an ethyl group, $R^{3b}$ represents a hydrogen atom, $R^{3c}$ represents an iodine atom, and T represents any one substituent described in Table L1 to Table L11 (hereinafter referred to as "Compound group SX41").

The Compound (L-1), wherein n represents 0, $R^1$ represents an ethyl group, $R^{3b}$ represents a chlorine atom, $R^{3c}$ represents an iodine atom, and T represents any one substituent described in Table L1 to Table L11 (hereinafter referred to as "Compound group SX42").

The Compound (L-1), wherein n represents 0, $R^1$ represents an ethyl group, $R^{3b}$ represents a bromine atom, $R^{3c}$ represents an iodine atom, and T represents any one substituent described in Table L1 to Table L11 (hereinafter referred to as "Compound group SX43").

The Compound (L-1), wherein n represents 0, $R^1$ represents an ethyl group, $R^{3b}$ represents an iodine atom, $R^{3c}$ represents an iodine atom, and T represents any one substituent described in Table L1 to Table L11 (hereinafter referred to as "Compound group SX44").

The Compound (L-1), wherein n represents 0, $R^1$ represents an ethyl group, $R^{3b}$ represents $CF_3$, $R^{3c}$ represents an iodine atom, and T represents any one substituent described in Table L1 to Table L11 (hereinafter referred to as "Compound group SX45").

The Compound (L-1), wherein n represents 0, $R^1$ represents an ethyl group, $R^{3b}$ represents a hydrogen atom, $R^{3c}$ represents $CF_3$, and T represents any one substituent described in Table L1 to Table L11 (hereinafter referred to as "Compound group SX46").

The Compound (L-1), wherein n represents 0, $R^1$ represents an ethyl group, $R^{3b}$ represents a chlorine atom, $R^{3c}$ represents $CF_3$, and T represents any one substituent described in Table L1 to Table L11 (hereinafter referred to as "Compound group SX47").

The Compound (L-1), wherein n represents 0, $R^1$ represents an ethyl group, $R^{3b}$ represents a bromine atom, $R^{3c}$ represents $CF_3$, and T represents any one substituent described in Table L1 to Table L11 (hereinafter referred to as "Compound group SX48").

The Compound (L-1), wherein n represents 0, $R^1$ represents an ethyl group, $R^{3b}$ represents an iodine atom, $R^{3c}$ represents $CF_3$, and T represents any one substituent described in Table L1 to Table L11 (hereinafter referred to as "Compound group SX49").

The Compound (L-1), wherein n represents 0, $R^1$ represents an ethyl group, $R^{3b}$ represents $CF_3$, $R^{3c}$ represents $CF_3$, and T represents any one substituent described in Table L1 to Table L11 (hereinafter referred to as "Compound group SX50").

The Compound (L-1), wherein n represents 0, $R^1$ represents an isopropyl group, $R^{3b}$ represents a hydrogen atom, $R^{3c}$ represents a hydrogen atom, and T represents any one substituent described in Table L1 to Table L11 (hereinafter referred to as "Compound group SX51").

The Compound (L-1), wherein n represents 0, $R^1$ represents an isopropyl group, $R^{3b}$ represents a chlorine atom, $R^{3c}$ represents a hydrogen atom, and T represents any one substituent described in Table L1 to Table L11 (hereinafter referred to as "Compound group SX52").

The Compound (L-1), wherein n represents 0, $R^1$ represents an isopropyl group, $R^{3b}$ represents a bromine atom, $R^{3c}$ represents a hydrogen atom, and T represents any one substituent described in Table L1 to Table L11 (hereinafter referred to as "Compound group SX53").

The Compound (L-1), wherein n represents 0, $R^1$ represents an isopropyl group, $R^{3b}$ represents an iodine atom, $R^{3c}$ represents a hydrogen atom, and T represents any one substituent described in Table L1 to Table L11 (hereinafter referred to as "Compound group SX54").

The Compound (L-1), wherein n represents 0, $R^1$ represents an isopropyl group, $R^{3b}$ represents $CF_3$, $R^{3c}$ represents a hydrogen atom, and T represents any one substituent described in Table L1 to Table L11 (hereinafter referred to as "Compound group SX55").

The Compound (L-1), wherein n represents 0, $R^1$ represents an isopropyl group, $R^{3b}$ represents a hydrogen atom, $R^{3c}$ represents a chlorine atom, and T represents any one substituent described in Table L1 to Table L11 (hereinafter referred to as "Compound group SX56").

The Compound (L-1), wherein n represents 0, $R^1$ represents an isopropyl group, $R^{3b}$ represents a chlorine atom, $R^{3c}$ represents a chlorine atom, and T represents any one substituent described in Table L1 to Table L11 (hereinafter referred to as "Compound group SX57").

The Compound (L-1), wherein n represents 0, $R^1$ represents an isopropyl group, $R^{3b}$ represents a bromine atom, $R^{3c}$ represents a chlorine atom, and T represents any one substituent described in Table L1 to Table L11 (hereinafter referred to as "Compound group SX58").

The Compound (L-1), wherein n represents 0, $R^1$ represents an isopropyl group, $R^{3b}$ represents an iodine atom, $R^{3c}$ represents a chlorine atom, and T represents any one substituent described in Table L1 to Table L11 (hereinafter referred to as "Compound group SX59").

The Compound (L-1), wherein n represents 0, $R^1$ represents an isopropyl group, $R^{3b}$ represents $CF_3$, $R^{3e}$ represents a chlorine atom, and T represents any one substituent described in Table L1 to Table L11 (hereinafter referred to as "Compound group SX60").

The Compound (L-1), wherein n represents 0, $R^1$ represents an isopropyl group, $R^{3b}$ represents a hydrogen atom, $R^{3c}$ represents a bromine atom, and T represents any one substituent described in Table L1 to Table L11 (hereinafter referred to as "Compound group SX61").

The Compound (L-1), wherein n represents 0, $R^1$ represents an isopropyl group, $R^{3b}$ represents a chlorine atom, $R^{3c}$ represents a bromine atom, and T represents any one substituent described in Table L1 to Table L11 (hereinafter referred to as "Compound group SX62").

The Compound (L-1), wherein n represents 0, $R^1$ represents an isopropyl group, $R^{3b}$ represents a bromine atom, $R^{3c}$ represents a bromine atom, and T represents any one substituent described in Table L1 to Table L11 (hereinafter referred to as "Compound group SX63").

The Compound (L-1), wherein n represents 0, $R^1$ represents an isopropyl group, $R^{3b}$ represents an iodine atom, $R^{3c}$ represents a bromine atom, and T represents any one substituent described in Table L1 to Table L11 (hereinafter referred to as "Compound group SX64").

The Compound (L-1), wherein n represents 0, $R^1$ represents an isopropyl group, $R^{3b}$ represents $CF_3$, $R^{3c}$ represents a bromine atom, and T represents any one substituent described in Table L1 to Table L11 (hereinafter referred to as "Compound group SX65").

The Compound (L-1), wherein n represents 0, $R^1$ represents an isopropyl group, $R^{3b}$ represents a hydrogen atom, $R^{3c}$ represents an iodine atom, and T represents any one substituent described in Table L1 to Table L11 (hereinafter referred to as "Compound group SX66").

The Compound (L-1), wherein n represents 0, $R^1$ represents an isopropyl group, $R^{3b}$ represents a chlorine atom, $R^{3c}$ represents an iodine atom, and T represents any one substituent described in Table L1 to Table L11 (hereinafter referred to as "Compound group SX67").

The Compound (L-1), wherein n represents 0, $R^1$ represents an isopropyl group, $R^{3b}$ represents a bromine atom, $R^{3c}$ represents an iodine atom, and T represents any one substituent described in Table L1 to Table L11 (hereinafter referred to as "Compound group SX68").

The Compound (L-1), wherein n represents 0, $R^1$ represents an isopropyl group, $R^{3b}$ represents an iodine atom, $R^{3c}$ represents an iodine atom, and T represents any one substituent described in Table L1 to Table L11 (hereinafter referred to as "Compound group SX69").

The Compound (L-1), wherein n represents 0, $R^1$ represents an isopropyl group, $R^{3b}$ represents $CF_3$, $R^{3c}$ represents an iodine atom, and T represents any one substituent described in Table L1 to Table L11 (hereinafter referred to as "Compound group SX70").

The Compound (L-1), wherein n represents 0, $R^1$ represents an isopropyl group, $R^{3b}$ represents a hydrogen atom, $R^{3c}$ represents $CF_3$, and T represents any one substituent described in Table L1 to Table L11 (hereinafter referred to as "Compound group SX71").

The Compound (L-1), wherein n represents 0, $R^1$ represents an isopropyl group, $R^{3b}$ represents a chlorine atom, $R^{3c}$ represents $CF_3$, and T represents any one substituent described in Table L1 to Table L11 (hereinafter referred to as "Compound group SX72").

The Compound (L-1), wherein n represents 0, $R^1$ represents an isopropyl group, $R^{3b}$ represents a bromine atom, $R^{3c}$ represents $CF_3$, and T represents any one substituent described in Table L1 to Table L11 (hereinafter referred to as "Compound group SX73").

The Compound (L-1), wherein n represents 0, $R^1$ represents an isopropyl group, $R^{3b}$ represents an iodine atom, $R^{3c}$ represents $CF_3$, and T represents any one substituent described in Table L1 to Table L11 (hereinafter referred to as "Compound group SX74").

The Compound (L-1), wherein n represents 0, $R^1$ represents an isopropyl group, $R^{3b}$ represents $CF_3$, $R^{3c}$ represents $CF_3$, and T represents any one substituent described in Table L1 to Table L11 (hereinafter referred to as "Compound group SX75").

The Compound (L-1), wherein n represents 1, $R^1$ represents a methyl group, $R^{3b}$ represents a hydrogen atom, $R^{3c}$ represents a hydrogen atom, and T represents any one substituent described in Table L1 to Table L11 (hereinafter referred to as "Compound group SX76").

The Compound (L-1), wherein n represents 1, $R^1$ represents a methyl group, $R^{3b}$ represents a chlorine atom, $R^{3c}$ represents a hydrogen atom, and T represents any one substituent described in Table L1 to Table L11 (hereinafter referred to as "Compound group SX77").

The Compound (L-1), wherein n represents 1, $R^1$ represents a methyl group, $R^{3b}$ represents a bromine atom, $R^{3c}$ represents a hydrogen atom, and T represents any one substituent described in Table L1 to Table L11 (hereinafter referred to as "Compound group SX78").

The Compound (L-1), wherein n represents 1, $R^1$ represents a methyl group, $R^{3b}$ represents an iodine atom, $R^{3c}$ represents a hydrogen atom, and T represents any one substituent described in Table L1 to Table L11 (hereinafter referred to as "Compound group SX79").

The Compound (L-1), wherein n represents 1, $R^1$ represents a methyl group, $R^{3b}$ represents $CF_3$, $R^{3c}$ represents a hydrogen atom, and T represents any one substituent described in Table L1 to Table L11 (hereinafter referred to as "Compound group SX80").

The Compound (L-1), wherein n represents 1, $R^1$ represents a methyl group, $R^{3b}$ represents a hydrogen atom, $R^{3c}$ represents a chlorine atom, and T represents any one substituent described in Table L1 to Table L11 (hereinafter referred to as "Compound group SX81").

The Compound (L-1), wherein n represents 1, $R^1$ represents a methyl group, $R^{3b}$ represents a chlorine atom, $R^{3c}$ represents a chlorine atom, and T represents any one substituent described in Table L1 to Table L11 (hereinafter referred to as "Compound group SX82").

The Compound (L-1), wherein n represents 1, $R^1$ represents a methyl group, $R^{3b}$ represents a bromine atom, $R^{3c}$ represents a chlorine atom, and T represents any one substituent described in Table L1 to Table L11 (hereinafter referred to as "Compound group SX83").

The Compound (L-1), wherein n represents 1, $R^1$ represents a methyl group, $R^{3b}$ represents an iodine atom, $R^{3c}$ represents a chlorine atom, and T represents any one substituent described in Table L1 to Table L11 (hereinafter referred to as "Compound group SX84").

The Compound (L-1), wherein n represents 1, $R^1$ represents a methyl group, $R^{3b}$ represents $CF_3$, $R^{3c}$ represents a chlorine atom, and T represents any one substituent described in Table L1 to Table L11 (hereinafter referred to as "Compound group SX85").

The Compound (L-1), wherein n represents 1, $R^1$ represents a methyl group, $R^{3b}$ represents a hydrogen atom, $R^{3c}$ represents a bromine atom, and T represents any one substituent described in Table L1 to Table L11 (hereinafter referred to as "Compound group SX86").

The Compound (L-1), wherein n represents 1, $R^1$ represents a methyl group, $R^{3b}$ represents a chlorine atom, $R^{3c}$ represents a bromine atom, and T represents any one substituent described in Table L1 to Table L11 (hereinafter referred to as "Compound group SX87").

The Compound (L-1), wherein n represents 1, $R^1$ represents a methyl group, $R^{3b}$ represents a bromine atom, $R^{3c}$ represents a bromine atom, and T represents any one substituent described in Table L1 to Table L11 (hereinafter referred to as "Compound group SX88").

The Compound (L-1), wherein n represents 1, $R^1$ represents a methyl group, $R^{3b}$ represents an iodine atom, $R^{3c}$ represents a bromine atom, and T represents any one substituent described in Table L1 to Table L11 (hereinafter referred to as "Compound group SX89").

The Compound (L-1), wherein n represents 1, $R^1$ represents a methyl group, $R^{3b}$ represents $CF_3$, $R^{3c}$ represents a bromine atom, and T represents any one substituent described in Table L1 to Table L11 (hereinafter referred to as "Compound group SX90").

The Compound (L-1), wherein n represents 1, $R^1$ represents a methyl group, $R^{3b}$ represents a hydrogen atom, $R^{3c}$ represents an iodine atom, and T represents any one substituent described in Table L1 to Table L11 (hereinafter referred to as "Compound group SX91").

The Compound (L-1), wherein n represents 1, $R^1$ represents a methyl group, $R^{3b}$ represents a chlorine atom, $R^{3c}$ represents an iodine atom, and T represents any one substituent described in Table L1 to Table L11 (hereinafter referred to as "Compound group SX92").

The Compound (L-1), wherein n represents 1, $R^1$ represents a methyl group, $R^{3b}$ represents a bromine atom, $R^{3c}$ represents an iodine atom, and T represents any one substituent described in Table L1 to Table L11 (hereinafter referred to as "Compound group SX93").

The Compound (L-1), wherein n represents 1, $R^1$ represents a methyl group, $R^{3b}$ represents an iodine atom, $R^{3c}$ represents an iodine atom, and T represents any one substituent described in Table L1 to Table L11 (hereinafter referred to as "Compound group SX94").

The Compound (L-1), wherein n represents 1, $R^1$ represents a methyl group, $R^{3b}$ represents $CF_3$, $R^{3c}$ represents an iodine atom, and T represents any one substituent described in Table L1 to Table L11 (hereinafter referred to as "Compound group SX95").

The Compound (L-1), wherein n represents 1, $R^1$ represents a methyl group, $R^{3b}$ represents a hydrogen atom, $R^{3c}$ represents $CF_3$, and T represents any one substituent described in Table L1 to Table L11 (hereinafter referred to as "Compound group SX96").

The Compound (L-1), wherein n represents 1, $R^1$ represents a methyl group, $R^{3b}$ represents a chlorine atom, $R^{3c}$ represents $CF_3$, and T represents any one substituent described in Table L1 to Table L11 (hereinafter referred to as "Compound group SX97").

The Compound (L-1), wherein n represents 1, $R^1$ represents a methyl group, $R^{3b}$ represents a bromine atom, $R^{3c}$ represents $CF_3$, and T represents any one substituent described in Table L1 to Table L11 (hereinafter referred to as "Compound group SX98").

The Compound (L-1), wherein n represents 1, $R^1$ represents a methyl group, $R^{3b}$ represents an iodine atom, $R^{3c}$ represents $CF_3$, and T represents any one substituent described in Table L1 to Table L11 (hereinafter referred to as "Compound group SX99").

The Compound (L-1), wherein n represents 1, $R^1$ represents a methyl group, $R^{3b}$ represents $CF_3$, $R^{3c}$ represents $CF_3$, and T represents any one substituent described in Table L1 to Table L11 (hereinafter referred to as "Compound group SX100").

The Compound (L-1), wherein n represents 1, $R^1$ represents an ethyl group, $R^{3b}$ represents a hydrogen atom, $R^{3c}$ represents a hydrogen atom, and T represents any one substituent described in Table L1 to Table L11 (hereinafter referred to as "Compound group SX101").

The Compound (L-1), wherein n represents 1, $R^1$ represents an ethyl group, $R^{3b}$ represents a chlorine atom, $R^{3c}$ represents a hydrogen atom, and T represents any one substituent described in Table L1 to Table L11 (hereinafter referred to as "Compound group SX102").

The Compound (L-1), wherein n represents 1, $R^1$ represents an ethyl group, $R^{3b}$ represents a bromine atom, $R^{3c}$ represents a hydrogen atom, and T represents any one substituent described in Table L1 to Table L11 (hereinafter referred to as "Compound group SX103").

The Compound (L-1), wherein n represents 1, $R^1$ represents an ethyl group, $R^{3b}$ represents an iodine atom, $R^{3c}$ represents a hydrogen atom, and T represents any one substituent described in Table L1 to Table L11 (hereinafter referred to as "Compound group SX104").

The Compound (L-1), wherein n represents 1, $R^1$ represents an ethyl group, $R^{3b}$ represents $CF_3$, $R^{3c}$ represents a hydrogen atom, and T represents any one substituent described in Table L1 to Table L11 (hereinafter referred to as "Compound group SX105").

The Compound (L-1), wherein n represents 1, $R^1$ represents an ethyl group, $R^{3b}$ represents a hydrogen atom, $R^{3c}$ represents a chlorine atom, and T represents any one substituent described in Table L1 to Table L11 (hereinafter referred to as "Compound group SX106").

The Compound (L-1), wherein n represents 1, $R^1$ represents an ethyl group, $R^{3b}$ represents a chlorine atom, $R^{3c}$ represents a chlorine atom, and T represents any one substituent described in Table L1 to Table L11 (hereinafter referred to as "Compound group SX107").

The Compound (L-1), wherein n represents 1, $R^1$ represents an ethyl group, $R^{3b}$ represents a bromine atom, $R^{3c}$ represents a chlorine atom, and T represents any one substituent described in Table L1 to Table L11 (hereinafter referred to as "Compound group SX108").

The Compound (L-1), wherein n represents 1, $R^1$ represents an ethyl group, $R^{3b}$ represents an iodine atom, $R^{3c}$ represents a chlorine atom, and T represents any one substituent described in Table L1 to Table L11 (hereinafter referred to as "Compound group SX109").

The Compound (L-1), wherein n represents 1, $R^1$ represents an ethyl group, $R^{3b}$ represents $CF_3$, $R^{3c}$ represents a chlorine atom, and T represents any one substituent described in Table L1 to Table L11 (hereinafter referred to as "Compound group SX110").

The Compound (L-1), wherein n represents 1, $R^1$ represents an ethyl group, $R^{3b}$ represents a hydrogen atom, $R^{3c}$ represents a bromine atom, and T represents any one substituent described in Table L1 to Table L11 (hereinafter referred to as "Compound group SX111").

The Compound (L-1), wherein n represents 1, $R^1$ represents an ethyl group, $R^{3b}$ represents a chlorine atom, $R^{3c}$ represents a bromine atom, and T represents any one substituent described in Table L1 to Table L11 (hereinafter referred to as "Compound group SX112").

The Compound (L-1), wherein n represents 1, $R^1$ represents an ethyl group, $R^{3b}$ represents a bromine atom, $R^{3c}$ represents a bromine atom, and T represents any one substituent described in Table L1 to Table L11 (hereinafter referred to as "Compound group SX113").

The Compound (L-1), wherein n represents 1, $R^1$ represents an ethyl group, $R^{3b}$ represents an iodine atom, $R^{3c}$ represents a bromine atom, and T represents any one substituent described in Table L1 to Table L11 (hereinafter referred to as "Compound group SX114").

The Compound (L-1), wherein n represents 1, $R^1$ represents an ethyl group, $R^{3b}$ represents $CF_3$, $R^{3c}$ represents a bromine atom, and T represents any one substituent described in Table L1 to Table L11 (hereinafter referred to as "Compound group SX115").

The Compound (L-1), wherein n represents 1, $R^1$ represents an ethyl group, $R^{3b}$ represents a hydrogen atom, $R^{3c}$ represents an iodine atom, and T represents any one substituent described in Table L1 to Table L11 (hereinafter referred to as "Compound group SX116").

The Compound (L-1), wherein n represents 1, $R^1$ represents an ethyl group, $R^{3b}$ represents a chlorine atom, $R^{3c}$ represents an iodine atom, and T represents any one substituent described in Table L1 to Table L11 (hereinafter referred to as "Compound group SX117").

The Compound (L-1), wherein n represents 1, $R^1$ represents an ethyl group, $R^{3b}$ represents a bromine atom, $R^{3c}$ represents an iodine atom, and T represents any one substituent described in Table L1 to Table L11 (hereinafter referred to as "Compound group SX118").

The Compound (L-1), wherein n represents 1, $R^1$ represents an ethyl group, $R^{3b}$ represents an iodine atom, $R^{3c}$ represents an iodine atom, and T represents any one substituent described in Table L1 to Table L11 (hereinafter referred to as "Compound group SX119").

The Compound (L-1), wherein n represents 1, $R^1$ represents an ethyl group, $R^{3b}$ represents $CF_3$, $R^{3c}$ represents an iodine atom, and T represents any one substituent described in Table L1 to Table L11 (hereinafter referred to as "Compound group SX120").

The Compound (L-1), wherein n represents 1, $R^1$ represents an ethyl group, $R^{3b}$ represents a hydrogen atom, $R^{3c}$ represents $CF_3$, and T represents any one substituent described in Table L1 to Table L11 (hereinafter referred to as "Compound group SX121").

The Compound (L-1), wherein n represents 1, $R^1$ represents an ethyl group, $R^{3b}$ represents a chlorine atom, $R^{3c}$ represents $CF_3$, and T represents any one substituent described in Table L1 to Table L11 (hereinafter referred to as "Compound group SX122").

The Compound (L-1), wherein n represents 1, $R^1$ represents an ethyl group, $R^{3b}$ represents a bromine atom, $R^{3c}$ represents $CF_3$, and T represents any one substituent described in Table L1 to Table L11 (hereinafter referred to as "Compound group SX123").

The Compound (L-1), wherein n represents 1, $R^1$ represents an ethyl group, $R^{3b}$ represents an iodine atom, $R^{3c}$ represents $CF_3$, and T represents any one substituent described in Table L1 to Table L11 (hereinafter referred to as "Compound group SX124").

The Compound (L-1), wherein n represents 1, $R^1$ represents an ethyl group, $R^{3b}$ represents $CF_3$, $R^{3c}$ represents $CF_3$, and T represents any one substituent described in Table L1 to Table L11 (hereinafter referred to as "Compound group SX125").

The Compound (L-1), wherein n represents 1, $R^1$ represents an isopropyl group, $R^{3b}$ represents a hydrogen atom, $R^{3c}$ represents a hydrogen atom, and T represents any one substituent described in Table L1 to Table L11 (hereinafter referred to as "Compound group SX126").

The Compound (L-1), wherein n represents 1, $R^1$ represents an isopropyl group, $R^{3b}$ represents a chlorine atom, $R^{3c}$ represents a hydrogen atom, and T represents any one substituent described in Table L1 to Table L11 (hereinafter referred to as "Compound group SX127").

The Compound (L-1), wherein n represents 1, $R^1$ represents an isopropyl group, $R^{3b}$ represents a bromine atom, $R^{3c}$ represents a hydrogen atom, and T represents any one substituent described in Table L1 to Table L11 (hereinafter referred to as "Compound group SX128").

The Compound (L-1), wherein n represents 1, $R^1$ represents an isopropyl group, $R^{3b}$ represents an iodine atom, $R^{3c}$ represents a hydrogen atom, and T represents any one substituent described in Table L1 to Table L11 (hereinafter referred to as "Compound group SX129").

The Compound (L-1), wherein n represents 1, $R^1$ represents an isopropyl group, $R^{3b}$ represents $CF_3$, $R^{3c}$ represents a hydrogen atom, and T represents any one substituent described in Table L1 to Table L11 (hereinafter referred to as "Compound group SX130").

The Compound (L-1), wherein n represents 1, $R^1$ represents an isopropyl group, $R^{3b}$ represents a hydrogen atom, $R^{3c}$ represents a chlorine atom, and T represents any one substituent described in Table L1 to Table L11 (hereinafter referred to as "Compound group SX131").

The Compound (L-1), wherein n represents 1, $R^1$ represents an isopropyl group, $R^{3b}$ represents a chlorine atom, $R^{3c}$ represents a chlorine atom, and T represents any one substituent described in Table L1 to Table L11 (hereinafter referred to as "Compound group SX132").

The Compound (L-1), wherein n represents 1, $R^1$ represents an isopropyl group, $R^{3b}$ represents a bromine atom, $R^{3c}$ represents a chlorine atom, and T represents any one substituent described in Table L1 to Table L11 (hereinafter referred to as "Compound group SX133").

The Compound (L-1), wherein n represents 1, $R^1$ represents an isopropyl group, $R^{3b}$ represents an iodine atom, $R^{3c}$ represents a chlorine atom, and T represents any one substituent described in Table L1 to Table L11 (hereinafter referred to as "Compound group SX134").

The Compound (L-1), wherein n represents 1, $R^1$ represents an isopropyl group, $R^{3b}$ represents $CF_3$, $R^{3c}$ represents a chlorine atom, and T represents any one substituent described in Table L1 to Table L11 (hereinafter referred to as "Compound group SX135").

The Compound (L-1), wherein n represents 1, $R^1$ represents an isopropyl group, $R^{3b}$ represents a hydrogen atom, $R^{3c}$ represents a bromine atom, and T represents any one substituent described in Table L1 to Table L11 (hereinafter referred to as "Compound group SX136").

The Compound (L-1), wherein n represents 1, $R^1$ represents an isopropyl group, $R^{3b}$ represents a chlorine atom, $R^{3c}$ represents a bromine atom, and T represents any one substituent described in Table L1 to Table L11 (hereinafter referred to as "Compound group SX137").

The Compound (L-1), wherein n represents 1, $R^1$ represents an isopropyl group, $R^{3b}$ represents a bromine atom, $R^{3c}$ represents a bromine atom, and T represents any one substituent described in Table L1 to Table L11 (hereinafter referred to as "Compound group SX138").

The Compound (L-1), wherein n represents 1, $R^1$ represents an isopropyl group, $R^{3b}$ represents an iodine atom, $R^{3c}$ represents a bromine atom, and T represents any one substituent described in Table L1 to Table L11 (hereinafter referred to as "Compound group SX139").

The Compound (L-1), wherein n represents 1, $R^1$ represents an isopropyl group, $R^{3b}$ represents $CF_3$, $R^{3c}$ represents a bromine atom, and T represents any one substituent described in Table L1 to Table L11 (hereinafter referred to as "Compound group SX140").

The Compound (L-1), wherein n represents 1, $R^1$ represents an isopropyl group, $R^{3b}$ represents a hydrogen atom, $R^{3c}$ represents an iodine atom, and T represents any one substituent described in Table L1 to Table L11 (hereinafter referred to as "Compound group SX141").

The Compound (L-1), wherein n represents 1, $R^1$ represents an isopropyl group, $R^{3b}$ represents a chlorine atom, $R^{3c}$ represents an iodine atom, and T represents any one substituent described in Table L1 to Table L11 (hereinafter referred to as "Compound group SX142").

The Compound (L-1), wherein n represents 1, $R^1$ represents an isopropyl group, $R^{3b}$ represents a bromine atom, $R^{3c}$ represents an iodine atom, and T represents any one substituent described in Table L1 to Table L11 (hereinafter referred to as "Compound group SX143").

The Compound (L-1), wherein n represents 1, $R^1$ represents an isopropyl group, $R^{3b}$ represents an iodine atom, $R^{3c}$ represents an iodine atom, and T represents any one substituent described in Table L1 to Table L11 (hereinafter referred to as "Compound group SX144").

The Compound (L-1), wherein n represents 1, $R^1$ represents an isopropyl group, $R^{3b}$ represents $CF_3$, $R^{3c}$ represents an iodine atom, and T represents any one substituent described in Table L1 to Table L11 (hereinafter referred to as "Compound group SX145").

The Compound (L-1), wherein n represents 1, $R^1$ represents an isopropyl group, $R^{3b}$ represents a hydrogen atom, $R^{3c}$ represents $CF_3$, and T represents any one substituent described in Table L1 to Table L11 (hereinafter referred to as "Compound group SX146").

The Compound (L-1), wherein n represents 1, $R^1$ represents an isopropyl group, $R^{3b}$ represents a chlorine atom, $R^{3c}$ represents $CF_3$, and T represents any one substituent described in Table L1 to Table L11 (hereinafter referred to as "Compound group SX147").

The Compound (L-1), wherein n represents 1, $R^1$ represents an isopropyl group, $R^{3b}$ represents a bromine atom, $R^{3c}$ represents $CF_3$, and T represents any one substituent described in Table L1 to Table L11 (hereinafter referred to as "Compound group SX148").

The Compound (L-1), wherein n represents 1, $R^1$ represents an isopropyl group, $R^{3b}$ represents an iodine atom, $R^{3c}$ represents $CF_3$, and T represents any one substituent described in Table L1 to Table L11 (hereinafter referred to as "Compound group SX149").

The Compound (L-1), wherein n represents 1, $R^1$ represents an isopropyl group, $R^{3b}$ represents $CF_3$, $R^{3c}$ represents $CF_3$, and T represents any one substituent described in Table L1 to Table L11 (hereinafter referred to as "Compound group SX150").

The Compound (L-1), wherein n represents 2, $R^1$ represents a methyl group, $R^{3b}$ represents a hydrogen atom, $R^{3c}$ represents a hydrogen atom, and T represents any one substituent described in Table L1 to Table L11 (hereinafter referred to as "Compound group SX151").

The Compound (L-1), wherein n represents 2, $R^1$ represents a methyl group, $R^{3b}$ represents a chlorine atom, $R^{3c}$ represents a hydrogen atom, and T represents any one substituent described in Table L1 to Table L11 (hereinafter referred to as "Compound group SX152").

The Compound (L-1), wherein n represents 2, $R^1$ represents a methyl group, $R^{3b}$ represents a bromine atom, $R^{3c}$ represents a hydrogen atom, and T represents any one substituent described in Table L1 to Table L11 (hereinafter referred to as "Compound group SX153").

The Compound (L-1), wherein n represents 2, $R^1$ represents a methyl group, $R^{3b}$ represents an iodine atom, $R^{3c}$ represents a hydrogen atom, and T represents any one substituent described in Table L1 to Table L11 (hereinafter referred to as "Compound group SX154").

The Compound (L-1), wherein n represents 2, $R^1$ represents a methyl group, $R^{3b}$ represents $CF_3$, $R^{3c}$ represents a hydrogen atom, and T represents any one substituent described in Table L1 to Table L11 (hereinafter referred to as "Compound group SX155").

The Compound (L-1), wherein n represents 2, $R^1$ represents a methyl group, $R^{3b}$ represents a hydrogen atom, $R^{3c}$ represents a chlorine atom, and T represents any one substituent described in Table L1 to Table L11 (hereinafter referred to as "Compound group SX156").

The Compound (L-1), wherein n represents 2, $R^1$ represents a methyl group, $R^{3b}$ represents a chlorine atom, $R^{3c}$ represents a chlorine atom, and T represents any one substituent described in Table L1 to Table L11 (hereinafter referred to as "Compound group SX157").

The Compound (L-1), wherein n represents 2, $R^1$ represents a methyl group, $R^{3b}$ represents a bromine atom, $R^{3c}$ represents a chlorine atom, and T represents any one substituent described in Table L1 to Table L11 (hereinafter referred to as "Compound group SX158").

The Compound (L-1), wherein n represents 2, $R^1$ represents a methyl group, $R^{3b}$ represents an iodine atom, $R^{3c}$ represents a chlorine atom, and T represents any one substituent described in Table L1 to Table L11 (hereinafter referred to as "Compound group SX159").

The Compound (L-1), wherein n represents 2, $R^1$ represents a methyl group, $R^{3b}$ represents $CF_3$, $R^{3c}$ represents a chlorine atom, and T represents any one substituent described in Table L1 to Table L11 (hereinafter referred to as "Compound group SX160").

The Compound (L-1), wherein n represents 2, $R^1$ represents a methyl group, $R^{3b}$ represents a hydrogen atom, $R^{3c}$ represents a bromine atom, and T represents any one substituent described in Table L1 to Table L11 (hereinafter referred to as "Compound group SX161").

The Compound (L-1), wherein n represents 2, $R^1$ represents a methyl group, $R^{3b}$ represents a chlorine atom, $R^{3c}$ represents a bromine atom, and T represents any one substituent described in Table L1 to Table L11 (hereinafter referred to as "Compound group SX162").

The Compound (L-1), wherein n represents 2, $R^1$ represents a methyl group, $R^{3b}$ represents a bromine atom, $R^{3c}$ represents a bromine atom, and T represents any one substituent described in Table L1 to Table L11 (hereinafter referred to as "Compound group SX163").

The Compound (L-1), wherein n represents 2, $R^1$ represents a methyl group, $R^{3b}$ represents an iodine atom, $R^{3c}$ represents a bromine atom, and T represents any one substituent described in Table L1 to Table L11 (hereinafter referred to as "Compound group SX164").

The Compound (L-1), wherein n represents 2, $R^1$ represents a methyl group, $R^{3b}$ represents $CF_3$, $R^{3c}$ represents a bromine atom, and T represents any one substituent described in Table L1 to Table L11 (hereinafter referred to as "Compound group SX165").

The Compound (L-1), wherein n represents 2, $R^1$ represents a methyl group, $R^{3b}$ represents a hydrogen atom, $R^{3c}$ represents an iodine atom, and T represents any one substituent described in Table L1 to Table L11 (hereinafter referred to as "Compound group SX166").

The Compound (L-1), wherein n represents 2, $R^1$ represents a methyl group, $R^{3b}$ represents a chlorine atom, $R^{3c}$ represents an iodine atom, and T represents any one substituent described in Table L1 to Table L11 (hereinafter referred to as "Compound group SX167").

The Compound (L-1), wherein n represents 2, $R^1$ represents a methyl group, $R^{3b}$ represents a bromine atom, $R^{3c}$ represents an iodine atom, and T represents any one substituent described in Table L1 to Table L11 (hereinafter referred to as "Compound group SX168").

The Compound (L-1), wherein n represents 2, $R^1$ represents a methyl group, $R^{3b}$ represents an iodine atom, $R^{3c}$ represents an iodine atom, and T represents any one substituent described in Table L1 to Table L11 (hereinafter referred to as "Compound group SX169").

The Compound (L-1), wherein n represents 2, $R^1$ represents a methyl group, $R^{3b}$ represents $CF_3$, $R^{3c}$ represents an iodine atom, and T represents any one substituent described in Table L1 to Table L11 (hereinafter referred to as "Compound group SX170").

The Compound (L-1), wherein n represents 2, $R^1$ represents a methyl group, $R^{3b}$ represents a hydrogen atom, $R^{3c}$ represents $CF_3$, and T represents any one substituent described in Table L1 to Table L11 (hereinafter referred to as "Compound group SX171").

The Compound (L-1), wherein n represents 2, $R^1$ represents a methyl group, $R^{3b}$ represents a chlorine atom, $R^{3c}$ represents $CF_3$, and T represents any one substituent described in Table L1 to Table L11 (hereinafter referred to as "Compound group SX172").

The Compound (L-1), wherein n represents 2, $R^1$ represents a methyl group, $R^{3b}$ represents a bromine atom, $R^{3c}$ represents $CF_3$, and T represents any one substituent described in Table L1 to Table L11 (hereinafter referred to as "Compound group SX173").

The Compound (L-1), wherein n represents 2, $R^1$ represents a methyl group, $R^{3b}$ represents an iodine atom, $R^{3c}$ represents $CF_3$, and T represents any one substituent described in Table L1 to Table L11 (hereinafter referred to as "Compound group SX174").

The Compound (L-1), wherein n represents 2, $R^1$ represents a methyl group, $R^{3b}$ represents $CF_3$, $R^{3c}$ represents $CF_3$, and T represents any one substituent described in Table L1 to Table L11 (hereinafter referred to as "Compound group SX175").

The Compound (L-1), wherein n represents 2, $R^1$ represents an ethyl group, $R^{3b}$ represents a hydrogen atom, $R^{3c}$ represents a hydrogen atom, and T represents any one substituent described in Table L1 to Table L11 (hereinafter referred to as "Compound group SX176").

The Compound (L-1), wherein n represents 2, $R^1$ represents an ethyl group, $R^{3b}$ represents a chlorine atom, $R^{3c}$ represents a hydrogen atom, and T represents any one substituent described in Table L1 to Table L11 (hereinafter referred to as "Compound group SX177").

The Compound (L-1), wherein n represents 2, $R^1$ represents an ethyl group, $R^{3b}$ represents a bromine atom, $R^{3c}$ represents a hydrogen atom, and T represents any one substituent described in Table L1 to Table L11 (hereinafter referred to as "Compound group SX178").

The Compound (L-1), wherein n represents 2, $R^1$ represents an ethyl group, $R^{3b}$ represents an iodine atom, $R^{3c}$ represents a hydrogen atom, and T represents any one substituent described in Table L1 to Table L11 (hereinafter referred to as "Compound group SX179").

The Compound (L-1), wherein n represents 2, $R^1$ represents an ethyl group, $R^{3b}$ represents $CF_3$, $R^{3c}$ represents a hydrogen atom, and T represents any one substituent described in Table L1 to Table L11 (hereinafter referred to as "Compound group SX180").

The Compound (L-1), wherein n represents 2, $R^1$ represents an ethyl group, $R^{3b}$ represents a hydrogen atom, $R^{3c}$ represents a chlorine atom, and T represents any one substituent described in Table L1 to Table L11 (hereinafter referred to as "Compound group SX181").

The Compound (L-1), wherein n represents 2, $R^1$ represents an ethyl group, $R^{3b}$ represents a chlorine atom, $R^{3c}$ represents a chlorine atom, and T represents any one substituent described in Table L1 to Table L11 (hereinafter referred to as "Compound group SX182").

The Compound (L-1), wherein n represents 2, $R^1$ represents an ethyl group, $R^{3b}$ represents a bromine atom, $R^{3c}$ represents a chlorine atom, and T represents any one substituent described in Table L1 to Table L11 (hereinafter referred to as "Compound group SX183").

The Compound (L-1), wherein n represents 2, $R^1$ represents an ethyl group, $R^{3b}$ represents an iodine atom, $R^{3c}$ represents a chlorine atom, and T represents any one substituent described in Table L1 to Table L11 (hereinafter referred to as "Compound group SX184").

The Compound (L-1), wherein n represents 2, $R^1$ represents an ethyl group, $R^{3b}$ represents $CF_3$, $R^{3c}$ represents a chlorine atom, and T represents any one substituent described in Table L1 to Table L11 (hereinafter referred to as "Compound group SX185").

The Compound (L-1), wherein n represents 2, $R^1$ represents an ethyl group, $R^{3b}$ represents a hydrogen atom, $R^{3c}$ represents a bromine atom, and T represents any one substituent described in Table L1 to Table L11 (hereinafter referred to as "Compound group SX186").

The Compound (L-1), wherein n represents 2, $R^1$ represents an ethyl group, $R^{3b}$ represents a chlorine atom, $R^{3c}$ represents a bromine atom, and T represents any one substituent described in Table L1 to Table L11 (hereinafter referred to as "Compound group SX187").

The Compound (L-1), wherein n represents 2, $R^1$ represents an ethyl group, $R^{3b}$ represents a bromine atom, $R^{3c}$ represents a bromine atom, and T represents any one substituent described in Table L1 to Table L11 (hereinafter referred to as "Compound group SX188").

The Compound (L-1), wherein n represents 2, $R^1$ represents an ethyl group, $R^{3b}$ represents an iodine atom, $R^{3c}$ represents a bromine atom, and T represents any one substituent described in Table L1 to Table L11 (hereinafter referred to as "Compound group SX189").

The Compound (L-1), wherein n represents 2, $R^1$ represents an ethyl group, $R^{3b}$ represents $CF_3$, $R^{3c}$ represents a bromine atom, and T represents any one substituent described in Table L1 to Table L11 (hereinafter referred to as "Compound group SX190").

The Compound (L-1), wherein n represents 2, $R^1$ represents an ethyl group, $R^{3b}$ represents a hydrogen atom, $R^{3c}$ represents an iodine atom, and T represents any one substituent described in Table L1 to Table L11 (hereinafter referred to as "Compound group SX191").

The Compound (L-1), wherein n represents 2, $R^1$ represents an ethyl group, $R^{3b}$ represents a chlorine atom, $R^{3c}$ represents an iodine atom, and T represents any one substituent described in Table L1 to Table L11 (hereinafter referred to as "Compound group SX192").

The Compound (L-1), wherein n represents 2, $R^1$ represents an ethyl group, $R^{3b}$ represents a bromine atom, $R^{3c}$ represents an iodine atom, and T represents any one substituent described in Table L1 to Table L11 (hereinafter referred to as "Compound group SX193").

The Compound (L-1), wherein n represents 2, $R^1$ represents an ethyl group, $R^{3b}$ represents an iodine atom, $R^{3c}$ represents an iodine atom, and T represents any one substituent described in Table L1 to Table L11 (hereinafter referred to as "Compound group SX194").

The Compound (L-1), wherein n represents 2, $R^1$ represents an ethyl group, $R^{3b}$ represents $CF_3$, $R^{3c}$ represents an iodine atom, and T represents any one substituent described in Table L1 to Table L11 (hereinafter referred to as "Compound group SX195").

The Compound (L-1), wherein n represents 2, $R^1$ represents an ethyl group, $R^{3b}$ represents a hydrogen atom, $R^{3c}$ represents $CF_3$, and T represents any one substituent described in Table L1 to Table L11 (hereinafter referred to as "Compound group SX196").

The Compound (L-1), wherein n represents 2, $R^1$ represents an ethyl group, $R^{3b}$ represents a chlorine atom, $R^{3c}$ represents $CF_3$, and T represents any one substituent described in Table L1 to Table L11 (hereinafter referred to as “Compound group SX197”).

The Compound (L-1), wherein n represents 2, $R^1$ represents an ethyl group, $R^{3b}$ represents a bromine atom, $R^{3c}$ represents $CF_3$, and T represents any one substituent described in Table L1 to Table L11 (hereinafter referred to as “Compound group SX198”).

The Compound (L-1), wherein n represents 2, $R^1$ represents an ethyl group, $R^{3b}$ represents an iodine atom, $R^{3c}$ represents $CF_3$, and T represents any one substituent described in Table L1 to Table L11 (hereinafter referred to as “Compound group SX199”).

The Compound (L-1), wherein n represents 2, $R^1$ represents an ethyl group, $R^{3b}$ represents $CF_3$, $R^{3c}$ represents $CF_3$, and T represents any one substituent described in Table L1 to Table L11 (hereinafter referred to as “Compound group SX200”).

The Compound (L-1), wherein n represents 2, $R^1$ represents an isopropyl group, $R^{3b}$ represents a hydrogen atom, $R^{3c}$ represents a hydrogen atom, and T represents any one substituent described in Table L1 to Table L11 (hereinafter referred to as “Compound group SX201”).

The Compound (L-1), wherein n represents 2, $R^1$ represents an isopropyl group, $R^{3b}$ represents a chlorine atom, $R^{3c}$ represents a hydrogen atom, and T represents any one substituent described in Table L1 to Table L11 (hereinafter referred to as “Compound group SX202”).

The Compound (L-1), wherein n represents 2, $R^1$ represents an isopropyl group, $R^{3b}$ represents a bromine atom, $R^{3c}$ represents a hydrogen atom, and T represents any one substituent described in Table L1 to Table L11 (hereinafter referred to as “Compound group SX203”).

The Compound (L-1), wherein n represents 2, $R^1$ represents an isopropyl group, $R^{3b}$ represents an iodine atom, $R^{3c}$ represents a hydrogen atom, and T represents any one substituent described in Table L1 to Table L11 (hereinafter referred to as “Compound group SX204”).

The Compound (L-1), wherein n represents 2, $R^1$ represents an isopropyl group, $R^{3b}$ represents $CF_3$, $R^{3c}$ represents a hydrogen atom, and T represents any one substituent described in Table L1 to Table L11 (hereinafter referred to as “Compound group SX205”).

The Compound (L-1), wherein n represents 2, $R^1$ represents an isopropyl group, $R^{3b}$ represents a hydrogen atom, $R^{3c}$ represents a chlorine atom, and T represents any one substituent described in Table L1 to Table L11 (hereinafter referred to as “Compound group SX206”).

The Compound (L-1), wherein n represents 2, $R^1$ represents an isopropyl group, $R^{3b}$ represents a chlorine atom, $R^{3c}$ represents a chlorine atom, and T represents any one substituent described in Table L1 to Table L11 (hereinafter referred to as “Compound group SX207”).

The Compound (L-1), wherein n represents 2, $R^1$ represents an isopropyl group, $R^{3b}$ represents a bromine atom, $R^{3c}$ represents a chlorine atom, and T represents any one substituent described in Table L1 to Table L11 (hereinafter referred to as “Compound group SX208”).

The Compound (L-1), wherein n represents 2, $R^1$ represents an isopropyl group, $R^{3b}$ represents an iodine atom, $R^{3c}$ represents a chlorine atom, and T represents any one substituent described in Table L1 to Table L11 (hereinafter referred to as “Compound group SX209”).

The Compound (L-1), wherein n represents 2, $R^1$ represents an isopropyl group, $R^{3b}$ represents $CF_3$, $R^{3c}$ represents a chlorine atom, and T represents any one substituent described in Table L1 to Table L11 (hereinafter referred to as “Compound group SX210”).

The Compound (L-1), wherein n represents 2, $R^1$ represents an isopropyl group, $R^{3b}$ represents a hydrogen atom, $R^{3c}$ represents a bromine atom, and T represents any one substituent described in Table L1 to Table L11 (hereinafter referred to as “Compound group SX211”).

The Compound (L-1), wherein n represents 2, $R^1$ represents an isopropyl group, $R^{3b}$ represents a chlorine atom, $R^{3c}$ represents a bromine atom, and T represents any one substituent described in Table L1 to Table L11 (hereinafter referred to as “Compound group SX212”).

The Compound (L-1), wherein n represents 2, $R^1$ represents an isopropyl group, $R^{3b}$ represents a bromine atom, $R^{3c}$ represents a bromine atom, and T represents any one substituent described in Table L1 to Table L11 (hereinafter referred to as “Compound group SX213”).

The Compound (L-1), wherein n represents 2, $R^1$ represents an isopropyl group, $R^{3b}$ represents an iodine atom, $R^{3c}$ represents a bromine atom, and T represents any one substituent described in Table L1 to Table L11 (hereinafter referred to as “Compound group SX214”).

The Compound (L-1), wherein n represents 2, $R^1$ represents an isopropyl group, $R^{3b}$ represents $CF_3$, $R^{3c}$ represents a bromine atom, and T represents any one substituent described in Table L1 to Table L11 (hereinafter referred to as “Compound group SX215”).

The Compound (L-1), wherein n represents 2, $R^1$ represents an isopropyl group, $R^{3b}$ represents a hydrogen atom, $R^{3c}$ represents an iodine atom, and T represents any one substituent described in Table L1 to Table L11 (hereinafter referred to as “Compound group SX216”).

The Compound (L-1), wherein n represents 2, $R^1$ represents an isopropyl group, $R^{3b}$ represents a chlorine atom, $R^{3c}$ represents an iodine atom, and T represents any one substituent described in Table L1 to Table L11 (hereinafter referred to as “Compound group SX217”).

The Compound (L-1), wherein n represents 2, $R^1$ represents an isopropyl group, $R^{3b}$ represents a bromine atom, $R^{3c}$ represents an iodine atom, and T represents any one substituent described in Table L1 to Table L11 (hereinafter referred to as “Compound group SX218”).

The Compound (L-1), wherein n represents 2, $R^1$ represents an isopropyl group, $R^{3b}$ represents an iodine atom, $R^{3c}$ represents an iodine atom, and T represents any one substituent described in Table L1 to Table L11 (hereinafter referred to as “Compound group SX219”).

The Compound (L-1), wherein n represents 2, $R^1$ represents an isopropyl group, $R^{3b}$ represents $CF_3$, $R^{3c}$ represents an iodine atom, and T represents any one substituent described in Table L1 to Table L11 (hereinafter referred to as “Compound group SX220”).

The Compound (L-1), wherein n represents 2, $R^1$ represents an isopropyl group, $R^{3b}$ represents a hydrogen atom, $R^{3c}$ represents $CF_3$, and T represents any one substituent described in Table L1 to Table L11 (hereinafter referred to as “Compound group SX221”).

The Compound (L-1), wherein n represents 2, $R^1$ represents an isopropyl group, $R^{3b}$ represents a chlorine atom, $R^{3c}$ represents $CF_3$, and T represents any one substituent described in Table L1 to Table L11 (hereinafter referred to as “Compound group SX222”).

The Compound (L-1), wherein n represents 2, $R^1$ represents an isopropyl group, $R^{3b}$ represents a bromine atom, $R^{3c}$ represents $CF_3$, and T represents any one substituent described in Table L1 to Table L11 (hereinafter referred to as “Compound group SX223”).

The Compound (L-1), wherein n represents 2, $R^1$ represents an isopropyl group, $R^{3b}$ represents an iodine atom, $R^{3c}$ represents $CF_3$, and T represents any one substituent described in Table L1 to Table L11 (hereinafter referred to as "Compound group SX224").

The Compound (L-1), wherein n represents 2, $R^1$ represents an isopropyl group, $R^{3b}$ represents $CF_3$, $R^{3c}$ represents $CF_3$, and T represents any one substituent described in Table L1 to Table L11 (hereinafter referred to as "Compound group SX225").

The Compound (L-1), wherein n represents 0, $R^1$ represents a methyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX226").

TABLE L12

| |
|---|
| F |
| Cl |
| Br |
| I |
| Me |
| $CF_3$ |
| $CHF_2$ |
| $CH{=}CH_2$ |
| $CMe{=}CH_2$ |
| c-Pr |
| 1-CN-c-Pr |
| CHO |
| C(O)Me |
| CMe═N—OH |
| CMe═N—OMe |
| CMe═N—OEt |
| $NO_2$ |
| CN |

TABLE L13

| |
|---|
| Ph |
| 4-F—Ph |
| 4-Cl—Ph |
| OPh |
| $NH_2$ |
| NHMe |
| $NMe_2$ |
| NHC(O)Me |
| Py2 |
| Py3 |
| Py4 |
| OPy2 |
| OPy3 |
| OPy4 |
| $CMe_2CN$ |
| OMe |
| OEt |
| $OCF_3$ |
| $OCH_2CF_3$ |

TABLE L14

| |
|---|
| pyrimidin-2-yl |
| pyrimidin-4-yl |
| pyrimidin-5-yl |
| pyrazin-2-yl |
| pyridazin-3-yl |
| pyridazin-4-yl |
| 3-chloro-1H-pyrazol-1-yl |
| 4-chloro-1H-pyrazol-1-yl |
| 3-(trifluoromethyl)-1H-pyrazol-1-yl |
| 4-(trifluoromethyl)-1H-pyrazol-1-yl |
| 1,2,4-triazol-1-yl |

The Compound (L-1), wherein n represents 0, $R^1$ represents a methyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX227").

The Compound (L-1), wherein n represents 0, $R^1$ represents a methyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX228").

The Compound (L-1), wherein n represents 0, $R^1$ represents a methyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX229").

The Compound (L-1), wherein n represents 0, $R^1$ represents a methyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX230").

The Compound (L-1), wherein n represents 0, $R^1$ represents a methyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX231").

The Compound (L-1), wherein n represents 0, $R^1$ represents a methyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX232").

The Compound (L-1), wherein n represents 0, $R^1$ represents a methyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX233").

The Compound (L-1), wherein n represents 0, $R^1$ represents a methyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX234").

The Compound (L-1), wherein n represents 0, $R^1$ represents a methyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX235").

The Compound (L-1), wherein n represents 0, $R^1$ represents an ethyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX236").

The Compound (L-1), wherein n represents 0, $R^1$ represents an ethyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX237").

The Compound (L-1), wherein n represents 0, $R^1$ represents an ethyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX238").

The Compound (L-1), wherein n represents 0, $R^1$ represents an ethyl group, T represents a 3-[(trifluoromethyl)thio] phenyl group, $R^{3c}$ represents an iodine atom, and $R^{3b}$ represents any one substituent described in Table L12 to Table L14 (hereinafter referred to as "Compound group SX239").

The Compound (L-1), wherein n represents 0, $R^1$ represents an ethyl group, T represents a 3-[(trifluoromethyl)thio] phenyl group, $R^{3c}$ represents $CF_3$, and $R^{3b}$ represents any one substituent described in Table L12 to Table L14 (hereinafter referred to as "Compound group SX240").

The Compound (L-1), wherein n represents 0, $R^1$ represents an ethyl group, T represents a 4-[(trifluoromethyl)thio] phenyl group, $R^{3c}$ represents a hydrogen atom, and $R^{3b}$ represents any one substituent described in Table L12 to Table L14 (hereinafter referred to as "Compound group SX241").

The Compound (L-1), wherein n represents 0, $R^1$ represents an ethyl group, T represents a 4-[(trifluoromethyl)thio] phenyl group, $R^{3c}$ represents a chlorine atom, and $R^{3b}$ represents any one substituent described in Table L12 to Table L14 (hereinafter referred to as "Compound group SX242").

The Compound (L-1), wherein n represents 0, $R^1$ represents an ethyl group, T represents a 4-[(trifluoromethyl)thio] phenyl group, $R^{3c}$ represents a bromine atom, and $R^{3b}$ represents any one substituent described in Table L12 to Table L14 (hereinafter referred to as "Compound group SX243").

The Compound (L-1), wherein n represents 0, $R^1$ represents an ethyl group, T represents a 4-[(trifluoromethyl)thio] phenyl group, $R^{3c}$ represents an iodine atom, and $R^{3b}$ represents any one substituent described in Table L12 to Table L14 (hereinafter referred to as "Compound group SX244").

The Compound (L-1), wherein n represents 0, $R^1$ represents an ethyl group, T represents a 4-[(trifluoromethyl)thio] phenyl group, $R^{3c}$ represents $CF_3$, and $R^{3b}$ represents any one substituent described in Table L12 to Table L14 (hereinafter referred to as "Compound group SX245").

The Compound (L-1), wherein n represents 0, $R^1$ represents an isopropyl group, T represents a 3-[(trifluoromethyl) thio]phenyl group, $R^{3c}$ represents a hydrogen atom, and $R^{3b}$ represents any one substituent described in Table L12 to Table L14 (hereinafter referred to as "Compound group SX246").

The Compound (L-1), wherein n represents 0, $R^1$ represents an isopropyl group, T represents a 3-[(trifluoromethyl) thio]phenyl group, $R^{3c}$ represents a chlorine atom, and $R^{3b}$ represents any one substituent described in Table L12 to Table L14 (hereinafter referred to as "Compound group SX247").

The Compound (L-1), wherein n represents 0, $R^1$ represents an isopropyl group, T represents a 3-[(trifluoromethyl) thio]phenyl group, $R^{3c}$ represents a bromine atom, and $R^{3b}$ represents any one substituent described in Table L12 to Table L14 (hereinafter referred to as "Compound group SX248").

The Compound (L-1), wherein n represents 0, $R^1$ represents an isopropyl group, T represents a 3-[(trifluoromethyl) thio]phenyl group, $R^{3c}$ represents an iodine atom, and $R^{3b}$ represents any one substituent described in Table L12 to Table L14 (hereinafter referred to as "Compound group SX249").

The Compound (L-1), wherein n represents 0, $R^1$ represents an isopropyl group, T represents a 3-[(trifluoromethyl) thio]phenyl group, $R^{3c}$ represents $CF_3$, and $R^{3b}$ represents any one substituent described in Table L12 to Table L14 (hereinafter referred to as "Compound group SX250").

The Compound (L-1), wherein n represents 0, $R^1$ represents an isopropyl group, T represents a 4-[(trifluoromethyl) thio]phenyl group, $R^{3c}$ represents a hydrogen atom, and $R^{3b}$ represents any one substituent described in Table L12 to Table L14 (hereinafter referred to as "Compound group SX251").

The Compound (L-1), wherein n represents 0, $R^1$ represents an isopropyl group, T represents a 4-[(trifluoromethyl) thio]phenyl group, $R^{3c}$ represents a chlorine atom, and $R^{3b}$ represents any one substituent described in Table L12 to Table L14 (hereinafter referred to as "Compound group SX252").

The Compound (L-1), wherein n represents 0, $R^1$ represents an isopropyl group, T represents a 4-[(trifluoromethyl) thio]phenyl group, $R^{3c}$ represents a bromine atom, and $R^{3b}$ represents any one substituent described in Table L12 to Table L14 (hereinafter referred to as "Compound group SX253").

The Compound (L-1), wherein n represents 0, $R^1$ represents an isopropyl group, T represents a 4-[(trifluoromethyl) thio]phenyl group, $R^{3c}$ represents an iodine atom, and $R^{3b}$ represents any one substituent described in Table L12 to Table L14 (hereinafter referred to as "Compound group SX254").

The Compound (L-1), wherein n represents 0, $R^1$ represents an isopropyl group, T represents a 4-[(trifluoromethyl) thio]phenyl group, $R^{3c}$ represents $CF_3$, and $R^{3b}$ represents any one substituent described in Table L12 to Table L14 (hereinafter referred to as "Compound group SX255").

The Compound (L-1), wherein n represents 0, $R^1$ represents a methyl group, T represents a 4-(trifluoromethoxy) phenyl group, $R^{3c}$ represents a hydrogen atom, and $R^{3b}$ represents any one substituent described in Table L12 to Table L14 (hereinafter referred to as "Compound group SX256").

The Compound (L-1), wherein n represents 0, $R^1$ represents a methyl group, T represents a 4-(trifluoromethoxy) phenyl group, $R^{3c}$ represents a chlorine atom, and $R^{3b}$ represents any one substituent described in Table L12 to Table L14 (hereinafter referred to as "Compound group SX257").

The Compound (L-1), wherein n represents 0, $R^1$ represents a methyl group, T represents a 4-(trifluoromethoxy) phenyl group, $R^{3c}$ represents a bromine atom, and $R^{3b}$ represents any one substituent described in Table L12 to Table L14 (hereinafter referred to as "Compound group SX258").

The Compound (L-1), wherein n represents 0, $R^1$ represents a methyl group, T represents a 4-(trifluoromethoxy) phenyl group, $R^{3c}$ represents an iodine atom, and $R^{3b}$ represents any one substituent described in Table L12 to Table L14 (hereinafter referred to as "Compound group SX259").

The Compound (L-1), wherein n represents 0, $R^1$ represents a methyl group, T represents a 4-(trifluoromethoxy) phenyl group, $R^{3c}$ represents $CF_3$, and $R^{3b}$ represents any one substituent described in Table L12 to Table L14 (hereinafter referred to as "Compound group SX260").

The Compound (L-1), wherein n represents 0, $R^1$ represents a methyl group, T represents a 4-(trifluoromethyl) phenyl group, $R^{3c}$ represents a hydrogen atom, and $R^{3b}$ represents any one substituent described in Table L12 to Table L14 (hereinafter referred to as "Compound group SX261").

The Compound (L-1), wherein n represents 0, $R^1$ represents a methyl group, T represents a 4-(trifluoromethyl) phenyl group, $R^{3c}$ represents a chlorine atom, and $R^{3b}$ represents any one substituent described in Table L12 to Table L14 (hereinafter referred to as "Compound group SX262").

The Compound (L-1), wherein n represents 0, $R^1$ represents a methyl group, T represents a 4-(trifluoromethyl) phenyl group, $R^{3c}$ represents a bromine atom, and $R^{3b}$ represents any one substituent described in Table L12 to Table L14 (hereinafter referred to as "Compound group SX263").

The Compound (L-1), wherein n represents 0, $R^1$ represents a methyl group, T represents a 4-(trifluoromethyl) phenyl group, $R^{3c}$ represents an iodine atom, and $R^{3b}$ represents any one substituent described in Table L12 to Table L14 (hereinafter referred to as "Compound group SX264").

The Compound (L-1), wherein n represents 0, $R^1$ represents a methyl group, T represents a 4-(trifluoromethyl) phenyl group, $R^{3c}$ represents $CF_3$, and $R^{3b}$ represents any one substituent described in Table L12 to Table L14 (hereinafter referred to as "Compound group SX265").

The Compound (L-1), wherein n represents 0, $R^1$ represents a methyl group, T represents a 3,4-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX266").

The Compound (L-1), wherein n represents 0, $R^1$ represents a methyl group, T represents a 3,4-bis[(trifluoromethyl)thio]phenyl group, $R^{3c}$ represents a chlorine atom, and $R^{3b}$ represents any one substituent described in Table L12 to Table L14 (hereinafter referred to as "Compound group SX267").

The Compound (L-1), wherein n represents 0, $R^1$ represents a methyl group, T represents a 3,4-bis[(trifluoromethyl)thio]phenyl group, $R^{3c}$ represents a bromine atom, and $R^{3b}$ represents any one substituent described in Table L12 to Table L14 (hereinafter referred to as "Compound group SX268").

The Compound (L-1), wherein n represents 0, $R^1$ represents a methyl group, T represents a 3,4-bis[(trifluoromethyl)thio]phenyl group, $R^{3c}$ represents an iodine atom, and $R^{3b}$ represents any one substituent described in Table L12 to Table L14 (hereinafter referred to as "Compound group SX269").

The Compound (L-1), wherein n represents 0, $R^1$ represents a methyl group, T represents a 3,4-bis[(trifluoromethyl)thio]phenyl group, $R^{3c}$ represents $CF_3$, and $R^{3b}$ represents any one substituent described in Table L12 to Table L14 (hereinafter referred to as "Compound group SX270").

The Compound (L-1), wherein n represents 0, $R^1$ represents a methyl group, T represents a 3,4-bis(trifluoromethoxy)phenyl group, $R^{3c}$ represents a hydrogen atom, and $R^{3b}$ represents any one substituent described in Table L12 to Table L14 (hereinafter referred to as "Compound group SX271").

The Compound (L-1), wherein n represents 0, $R^1$ represents a methyl group, T represents a 3,4-bis(trifluoromethoxy)phenyl group, $R^{3c}$ represents a chlorine atom, and $R^{3b}$ represents any one substituent described in Table L12 to Table L14 (hereinafter referred to as "Compound group SX272").

The Compound (L-1), wherein n represents 0, $R^1$ represents a methyl group, T represents a 3,4-bis(trifluoromethoxy)phenyl group, $R^{3c}$ represents a bromine atom, and $R^{3b}$ represents any one substituent described in Table L12 to Table L14 (hereinafter referred to as "Compound group SX273").

The Compound (L-1), wherein n represents 0, $R^1$ represents a methyl group, T represents a 3,4-bis(trifluoromethoxy)phenyl group, $R^{3c}$ represents an iodine atom, and $R^{3b}$ represents any one substituent described in Table L12 to Table L14 (hereinafter referred to as "Compound group SX274").

The Compound (L-1), wherein n represents 0, $R^1$ represents a methyl group, T represents a 3,4-bis(trifluoromethoxy)phenyl group, $R^{3c}$ represents $CF_3$, and $R^{3b}$ represents any one substituent described in Table L12 to Table L14 (hereinafter referred to as "Compound group SX275").

The Compound (L-1), wherein n represents 0, $R^1$ represents a methyl group, T represents a 3,4-bis(trifluoromethyl) phenyl group, $R^{3c}$ represents a hydrogen atom, and $R^{3b}$ represents any one substituent described in Table L12 to Table L14 (hereinafter referred to as "Compound group SX276").

The Compound (L-1), wherein n represents 0, $R^1$ represents a methyl group, T represents a 3,4-bis(trifluoromethyl) phenyl group, $R^{3c}$ represents a chlorine atom, and $R^{3b}$ represents any one substituent described in Table L12 to Table L14 (hereinafter referred to as "Compound group SX277").

The Compound (L-1), wherein n represents 0, $R^1$ represents a methyl group, T represents a 3,4-bis(trifluoromethyl) phenyl group, $R^{3c}$ represents a bromine atom, and $R^{3b}$ represents any one substituent described in Table L12 to Table L14 (hereinafter referred to as "Compound group SX278").

The Compound (L-1), wherein n represents 0, $R^1$ represents a methyl group, T represents a 3,4-bis(trifluoromethyl) phenyl group, $R^{3c}$ represents an iodine atom, and $R^{3b}$ represents any one substituent described in Table L12 to Table L14 (hereinafter referred to as "Compound group SX279").

The Compound (L-1), wherein n represents 0, $R^1$ represents a methyl group, T represents a 3,4-bis(trifluoromethyl) phenyl group, $R^{3c}$ represents $CF_3$, and $R^{3b}$ represents any one substituent described in Table L12 to Table L14 (hereinafter referred to as "Compound group SX280").

The Compound (L-1), wherein n represents 0, $R^1$ represents a methyl group, T represents a 3,5-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX281").

The Compound (L-1), wherein n represents 0, $R^1$ represents a methyl group, T represents a 3,5-bis[(trifluoromethyl)thio]phenyl group, $R^{3c}$ represents a chlorine atom, and $R^{3b}$ represents any one substituent described in Table L12 to Table L14 (hereinafter referred to as "Compound group SX282").

The Compound (L-1), wherein n represents 0, $R^1$ represents a methyl group, T represents a 3,5-bis[(trifluoromethyl)thio]phenyl group, $R^{3c}$ represents a bromine atom, and $R^{3b}$ represents any one substituent described in Table L12 to Table L14 (hereinafter referred to as "Compound group SX283").

The Compound (L-1), wherein n represents 0, $R^1$ represents a methyl group, T represents a 3,5-bis[(trifluoromethyl)thio]phenyl group, $R^{3c}$ represents an iodine atom, and $R^{3b}$ represents any one substituent described in Table L12 to Table L14 (hereinafter referred to as "Compound group SX284").

The Compound (L-1), wherein n represents 0, $R^1$ represents a methyl group, T represents a 3,5-bis[(trifluoromethyl)thio]phenyl group, $R^{3c}$ represents $CF_3$, and $R^{3b}$ represents any one substituent described in Table L12 to Table L14 (hereinafter referred to as "Compound group SX285").

The Compound (L-1), wherein n represents 0, $R^1$ represents a methyl group, T represents a 3,5-bis(trifluoromethoxy)phenyl group, $R^{3c}$ represents a hydrogen atom, and $R^{3b}$ represents any one substituent described in Table L12 to Table L14 (hereinafter referred to as "Compound group SX286").

The Compound (L-1), wherein n represents 0, $R^1$ represents a methyl group, T represents a 3,5-bis(trifluoromethoxy)phenyl group, $R^{3c}$ represents a chlorine atom, and $R^{3b}$ represents any one substituent described in Table L12 to Table L14 (hereinafter referred to as "Compound group SX287").

The Compound (L-1), wherein n represents 0, $R^1$ represents a methyl group, T represents a 3,5-bis(trifluoromethoxy)phenyl group, $R^{3c}$ represents a bromine atom, and $R^{3b}$ represents any one substituent described in Table L12 to Table L14 (hereinafter referred to as "Compound group SX288").

The Compound (L-1), wherein n represents 0, $R^1$ represents a methyl group, T represents a 3,5-bis(trifluoromethoxy)phenyl group, $R^{3c}$ represents an iodine atom, and $R^{3b}$ represents any one substituent described in Table L12 to Table L14 (hereinafter referred to as "Compound group SX289").

The Compound (L-1), wherein n represents 0, $R^1$ represents a methyl group, T represents a 3,5-bis(trifluoromethoxy)phenyl group, $R^{3c}$ represents $CF_3$, and $R^{3b}$ represents any one substituent described in Table L12 to Table L14 (hereinafter referred to as "Compound group SX290").

The Compound (L-1), wherein n represents 0, $R^1$ represents a methyl group, T represents a 3,5-bis(trifluoromethyl)phenyl group, $R^{3c}$ represents a hydrogen atom, and $R^{3b}$ represents any one substituent described in Table L12 to Table L14 (hereinafter referred to as "Compound group SX291").

The Compound (L-1), wherein n represents 0, $R^1$ represents a methyl group, T represents a 3,5-bis(trifluoromethyl)phenyl group, $R^{3c}$ represents a chlorine atom, and $R^{3b}$ represents any one substituent described in Table L12 to Table L14 (hereinafter referred to as "Compound group SX292").

The Compound (L-1), wherein n represents 0, $R^1$ represents a methyl group, T represents a 3,5-bis(trifluoromethyl)phenyl group, $R^{3c}$ represents a bromine atom, and $R^{3b}$ represents any one substituent described in Table L12 to Table L14 (hereinafter referred to as "Compound group SX293").

The Compound (L-1), wherein n represents 0, $R^1$ represents a methyl group, T represents a 3,5-bis(trifluoromethyl)phenyl group, $R^{3c}$ represents an iodine atom, and $R^{3b}$ represents any one substituent described in Table L12 to Table L14 (hereinafter referred to as "Compound group SX294").

The Compound (L-1), wherein n represents 0, $R^1$ represents a methyl group, T represents a 3,5-bis(trifluoromethyl)phenyl group, $R^{3c}$ represents $CF_3$, and $R^{3b}$ represents any one substituent described in Table L12 to Table L14 (hereinafter referred to as "Compound group SX295").

The Compound (L-1), wherein n represents 0, $R^1$ represents a methyl group, T represents a 3-fluoro-5-(trifluoromethoxy)phenyl group, $R^{3c}$ represents a hydrogen atom, and $R^{3b}$ represents any one substituent described in Table L12 to Table L14 (hereinafter referred to as "Compound group SX296").

The Compound (L-1), wherein n represents 0, $R^1$ represents a methyl group, T represents a 3-fluoro-5-(trifluoromethoxy)phenyl group, $R^{3c}$ represents a chlorine atom, and $R^{3b}$ represents any one substituent described in Table L12 to Table L14 (hereinafter referred to as "Compound group SX297").

The Compound (L-1), wherein n represents 0, $R^1$ represents a methyl group, T represents a 3-fluoro-5-(trifluoromethoxy)phenyl group, $R^{3c}$ represents a bromine atom, and $R^{3b}$ represents any one substituent described in Table L12 to Table L14 (hereinafter referred to as "Compound group SX298").

The Compound (L-1), wherein n represents 0, $R^1$ represents a methyl group, T represents a 3-fluoro-5-(trifluoromethoxy)phenyl group, $R^{3c}$ represents an iodine atom, and $R^{3b}$ represents any one substituent described in Table L12 to Table L14 (hereinafter referred to as "Compound group SX299").

The Compound (L-1), wherein n represents 0, $R^1$ represents a methyl group, T represents a 3-fluoro-5-(trifluoromethoxy)phenyl group, $R^{3c}$ represents $CF_3$, and $R^{3b}$ represents any one substituent described in Table L12 to Table L14 (hereinafter referred to as "Compound group SX300").

The Compound (L-1), wherein n represents 1, $R^1$ represents a methyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX301").

The Compound (L-1), wherein n represents 1, $R^1$ represents a methyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX302").

The Compound (L-1), wherein n represents 1, $R^1$ represents a methyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX303").

The Compound (L-1), wherein n represents 1, $R^1$ represents a methyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX304").

The Compound (L-1), wherein n represents 1, $R^1$ represents a methyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX305").

The Compound (L-1), wherein n represents 1, $R^1$ represents a methyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX306").

The Compound (L-1), wherein n represents 1, $R^1$ represents a methyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX307").

The Compound (L-1), wherein n represents 1, $R^1$ represents a methyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX308").

The Compound (L-1), wherein n represents 1, $R^1$ represents a methyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX309").

The Compound (L-1), wherein n represents 1, $R^1$ represents a methyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX310").

The Compound (L-1), wherein n represents 1, $R^1$ represents an ethyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX311").

The Compound (L-1), wherein n represents 1, $R^1$ represents an ethyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX312").

The Compound (L-1), wherein n represents 1, $R^1$ represents an ethyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX313").

The Compound (L-1), wherein n represents 1, $R^1$ represents an ethyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX314").

The Compound (L-1), wherein n represents 1, $R^1$ represents an ethyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX315").

The Compound (L-1), wherein n represents 1, $R^1$ represents an ethyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX316").

The Compound (L-1), wherein n represents 1, $R^1$ represents an ethyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX317").

The Compound (L-1), wherein n represents 1, $R^1$ represents an ethyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX318").

The Compound (L-1), wherein n represents 1, $R^1$ represents an ethyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX319").

The Compound (L-1), wherein n represents 1, $R^1$ represents an ethyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX320").

The Compound (L-1), wherein n represents 1, $R^1$ represents an isopropyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX321").

The Compound (L-1), wherein n represents 1, $R^1$ represents an isopropyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX322").

The Compound (L-1), wherein n represents 1, $R^1$ represents an isopropyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX323").

The Compound (L-1), wherein n represents 1, $R^1$ represents an isopropyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX324").

The Compound (L-1), wherein n represents 1, $R^1$ represents an isopropyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX325").

The Compound (L-1), wherein n represents 1, $R^1$ represents an isopropyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX326").

The Compound (L-1), wherein n represents 1, $R^1$ represents an isopropyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX327").

The Compound (L-1), wherein n represents 1, $R^1$ represents an isopropyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX328").

The Compound (L-1), wherein n represents 1, $R^1$ represents an isopropyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX329").

The Compound (L-1), wherein n represents 1, $R^1$ represents an isopropyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX330").

The Compound (L-1), wherein n represents 1, $R^1$ represents a methyl group, T represents a 4-(trifluoromethoxy)

phenyl group, $R^{3c}$ represents a hydrogen atom, and $R^{3b}$ represents any one substituent described in Table L12 to Table L14 (hereinafter referred to as "Compound group SX331").

The Compound (L-1), wherein n represents 1, $R^1$ represents a methyl group, T represents a 4-(trifluoromethoxy) phenyl group, $R^{3c}$ represents a chlorine atom, and $R^{3b}$ represents any one substituent described in Table L12 to Table L14 (hereinafter referred to as "Compound group SX332").

The Compound (L-1), wherein n represents 1, $R^1$ represents a methyl group, T represents a 4-(trifluoromethoxy) phenyl group, $R^{3c}$ represents a bromine atom, and $R^{3b}$ represents any one substituent described in Table L12 to Table L14 (hereinafter referred to as "Compound group SX333").

The Compound (L-1), wherein n represents 1, $R^1$ represents a methyl group, T represents a 4-(trifluoromethoxy) phenyl group, $R^{3c}$ represents an iodine atom, and $R^{3b}$ represents any one substituent described in Table L12 to Table L14 (hereinafter referred to as "Compound group SX334").

The Compound (L-1), wherein n represents 1, $R^1$ represents a methyl group, T represents a 4-(trifluoromethoxy) phenyl group, $R^{3c}$ represents $CF_3$, and $R^{3b}$ represents any one substituent described in Table L12 to Table L14 (hereinafter referred to as "Compound group SX335").

The Compound (L-1), wherein n represents 1, $R^1$ represents a methyl group, T represents a 4-(trifluoromethyl) phenyl group, $R^{3c}$ represents a hydrogen atom, and $R^{3b}$ represents any one substituent described in Table L12 to Table L14 (hereinafter referred to as "Compound group SX336").

The Compound (L-1), wherein n represents 1, $R^1$ represents a methyl group, T represents a 4-(trifluoromethyl) phenyl group, $R^{3c}$ represents a chlorine atom, and $R^{3b}$ represents any one substituent described in Table L12 to Table L14 (hereinafter referred to as "Compound group SX337").

The Compound (L-1), wherein n represents 1, $R^1$ represents a methyl group, T represents a 4-(trifluoromethyl) phenyl group, $R^{3c}$ represents a bromine atom, and $R^{3b}$ represents any one substituent described in Table L12 to Table L14 (hereinafter referred to as "Compound group SX338").

The Compound (L-1), wherein n represents 1, $R^1$ represents a methyl group, T represents a 4-(trifluoromethyl) phenyl group, $R^{3c}$ represents an iodine atom, and $R^{3b}$ represents any one substituent described in Table L12 to Table L14 (hereinafter referred to as "Compound group SX339").

The Compound (L-1), wherein n represents 1, $R^1$ represents a methyl group, T represents a 4-(trifluoromethyl) phenyl group, $R^{3c}$ represents $CF_3$, and $R^{3b}$ represents any one substituent described in Table L12 to Table L14 (hereinafter referred to as "Compound group SX340").

The Compound (L-1), wherein n represents 1, $R^1$ represents a methyl group, T represents a 3,4-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX341").

The Compound (L-1), wherein n represents 1, $R^1$ represents a methyl group, T represents a 3,4-bis[(trifluoromethyl)thio]phenyl group, $R^{3c}$ represents a chlorine atom, and $R^{3b}$ represents any one substituent described in Table L12 to Table L14 (hereinafter referred to as "Compound group SX342").

The Compound (L-1), wherein n represents 1, $R^1$ represents a methyl group, T represents a 3,4-bis[(trifluoromethyl)thio]phenyl group, $R^{3c}$ represents a bromine atom, and $R^{3b}$ represents any one substituent described in Table L12 to Table L14 (hereinafter referred to as "Compound group SX343").

The Compound (L-1), wherein n represents 1, $R^1$ represents a methyl group, T represents a 3,4-bis[(trifluoromethyl)thio]phenyl group, $R^{3c}$ represents an iodine atom, and $R^{3b}$ represents any one substituent described in Table L12 to Table L14 (hereinafter referred to as "Compound group SX344").

The Compound (L-1), wherein n represents 1, $R^1$ represents a methyl group, T represents a 3,4-bis[(trifluoromethyl)thio]phenyl group, $R^{3c}$ represents $CF_3$, and $R^{3b}$ represents any one substituent described in Table L12 to Table L14 (hereinafter referred to as "Compound group SX345").

The Compound (L-1), wherein n represents 1, $R^1$ represents a methyl group, T represents a 3,4-bis(trifluoromethoxy)phenyl group, $R^{3c}$ represents a hydrogen atom, and $R^{3b}$ represents any one substituent described in Table L12 to Table L14 (hereinafter referred to as "Compound group SX346").

The Compound (L-1), wherein n represents 1, $R^1$ represents a methyl group, T represents a 3,4-bis(trifluoromethoxy)phenyl group, $R^{3c}$ represents a chlorine atom, and $R^{3b}$ represents any one substituent described in Table L12 to Table L14 (hereinafter referred to as "Compound group SX347").

The Compound (L-1), wherein n represents 1, $R^1$ represents a methyl group, T represents a 3,4-bis(trifluoromethoxy)phenyl group, $R^{3c}$ represents a bromine atom, and $R^{3b}$ represents any one substituent described in Table L12 to Table L14 (hereinafter referred to as "Compound group SX348").

The Compound (L-1), wherein n represents 1, $R^1$ represents a methyl group, T represents a 3,4-bis(trifluoromethoxy)phenyl group, $R^{3c}$ represents an iodine atom, and $R^{3b}$ represents any one substituent described in Table L12 to Table L14 (hereinafter referred to as "Compound group SX349").

The Compound (L-1), wherein n represents 1, $R^1$ represents a methyl group, T represents a 3,4-bis(trifluoromethoxy)phenyl group, $R^{3c}$ represents $CF_3$, and $R^{3b}$ represents any one substituent described in Table L12 to Table L14 (hereinafter referred to as "Compound group SX350").

The Compound (L-1), wherein n represents 1, $R^1$ represents a methyl group, T represents a 3,4-bis(trifluoromethyl) phenyl group, $R^{3c}$ represents a hydrogen atom, and $R^{3b}$ represents any one substituent described in Table L12 to Table L14 (hereinafter referred to as "Compound group SX351").

The Compound (L-1), wherein n represents 1, $R^1$ represents a methyl group, T represents a 3,4-bis(trifluoromethyl) phenyl group, $R^{3c}$ represents a chlorine atom, and $R^{3b}$ represents any one substituent described in Table L12 to Table L14 (hereinafter referred to as "Compound group SX352").

The Compound (L-1), wherein n represents 1, $R^1$ represents a methyl group, T represents a 3,4-bis(trifluoromethyl) phenyl group, $R^{3c}$ represents a bromine atom, and $R^{3b}$ represents any one substituent described in Table L12 to Table L14 (hereinafter referred to as "Compound group SX353").

The Compound (L-1), wherein n represents 1, $R^1$ represents a methyl group, T represents a 3,4-bis(trifluoromethyl) phenyl group, $R^{3c}$ represents an iodine atom, and $R^{3b}$ represents any one substituent described in Table L12 to Table L14 (hereinafter referred to as “Compound group SX354”).

The Compound (L-1), wherein n represents 1, $R^1$ represents a methyl group, T represents a 3,4-bis(trifluoromethyl) phenyl group, $R^{3c}$ represents $CF_3$, and $R^{3b}$ represents any one substituent described in Table L12 to Table L14 (hereinafter referred to as “Compound group SX355”).

The Compound (L-1), wherein n represents 1, $R^1$ represents a methyl group, T represents a 3,5-bis[(trifluoromethyl)thio]phenyl group, $R^{3c}$ represents a hydrogen atom, and $R^{3b}$ represents any one substituent described in Table L12 to Table L14 (hereinafter referred to as “Compound group SX356”).

The Compound (L-1), wherein n represents 1, $R^1$ represents a methyl group, T represents a 3,5-bis[(trifluoromethyl)thio]phenyl group, $R^{3c}$ represents a chlorine atom, and $R^{3b}$ represents any one substituent described in Table L12 to Table L14 (hereinafter referred to as “Compound group SX357”).

The Compound (L-1), wherein n represents 1, $R^1$ represents a methyl group, T represents a 3,5-bis[(trifluoromethyl)thio]phenyl group, $R^{3c}$ represents a bromine atom, and $R^{3b}$ represents any one substituent described in Table L12 to Table L14 (hereinafter referred to as “Compound group SX358”).

The Compound (L-1), wherein n represents 1, $R^1$ represents a methyl group, T represents a 3,5-bis[(trifluoromethyl)thio]phenyl group, $R^{3c}$ represents an iodine atom, and $R^{3b}$ represents any one substituent described in Table L12 to Table L14 (hereinafter referred to as “Compound group SX359”).

The Compound (L-1), wherein n represents 1, $R^1$ represents a methyl group, T represents a 3,5-bis[(trifluoromethyl)thio]phenyl group, $R^{3c}$ represents $CF_3$, and $R^{3b}$ represents any one substituent described in Table L12 to Table L14 (hereinafter referred to as “Compound group SX360”).

The Compound (L-1), wherein n represents 1, $R^1$ represents a methyl group, T represents a 3,5-bis(trifluoromethoxy)phenyl group, $R^{3c}$ represents a hydrogen atom, and $R^{3b}$ represents any one substituent described in Table L12 to Table L14 (hereinafter referred to as “Compound group SX361”).

The Compound (L-1), wherein n represents 1, $R^1$ represents a methyl group, T represents a 3,5-bis(trifluoromethoxy)phenyl group, $R^{3c}$ represents a chlorine atom, and $R^{3b}$ represents any one substituent described in Table L12 to Table L14 (hereinafter referred to as “Compound group SX362”).

The Compound (L-1), wherein n represents 1, $R^1$ represents a methyl group, T represents a 3,5-bis(trifluoromethoxy)phenyl group, $R^{3c}$ represents a bromine atom, and $R^{3b}$ represents any one substituent described in Table L12 to Table L14 (hereinafter referred to as “Compound group SX363”).

The Compound (L-1), wherein n represents 1, $R^1$ represents a methyl group, T represents a 3,5-bis(trifluoromethoxy)phenyl group, $R^{3c}$ represents an iodine atom, and $R^{3b}$ represents any one substituent described in Table L12 to Table L14 (hereinafter referred to as “Compound group SX364”).

The Compound (L-1), wherein n represents 1, $R^1$ represents a methyl group, T represents a 3,5-bis(trifluoromethoxy)phenyl group, $R^{3c}$ represents $CF_3$, and $R^{3b}$ represents any one substituent described in Table L12 to Table L14 (hereinafter referred to as “Compound group SX365”).

The Compound (L-1), wherein n represents 1, $R^1$ represents a methyl group, T represents a 3,5-bis(trifluoromethyl) phenyl group, $R^{3c}$ represents a hydrogen atom, and $R^{3b}$ represents any one substituent described in Table L12 to Table L14 (hereinafter referred to as “Compound group SX366”).

The Compound (L-1), wherein n represents 1, $R^1$ represents a methyl group, T represents a 3,5-bis(trifluoromethyl) phenyl group, $R^{3c}$ represents a chlorine atom, and $R^{3b}$ represents any one substituent described in Table L12 to Table L14 (hereinafter referred to as “Compound group SX367”).

The Compound (L-1), wherein n represents 1, $R^1$ represents a methyl group, T represents a 3,5-bis(trifluoromethyl) phenyl group, $R^{3c}$ represents a bromine atom, and $R^{3b}$ represents any one substituent described in Table L12 to Table L14 (hereinafter referred to as “Compound group SX368”).

The Compound (L-1), wherein n represents 1, $R^1$ represents a methyl group, T represents a 3,5-bis(trifluoromethyl) phenyl group, $R^{3c}$ represents an iodine atom, and $R^{3b}$ represents any one substituent described in Table L12 to Table L14 (hereinafter referred to as “Compound group SX369”).

The Compound (L-1), wherein n represents 1, $R^1$ represents a methyl group, T represents a 3,5-bis(trifluoromethyl) phenyl group, $R^{3c}$ represents $CF_3$, and $R^{3b}$ represents any one substituent described in Table L12 to Table L14 (hereinafter referred to as “Compound group SX370”).

The Compound (L-1), wherein n represents 1, $R^1$ represents a methyl group, T represents a 3-fluoro-5-(trifluoromethoxy)phenyl group, $R^{3c}$ represents a hydrogen Table L12 to Table L14 (hereinafter referred to as “Compound group SX371”).

The Compound (L-1), wherein n represents 1, $R^1$ represents a methyl group, T represents a 3-fluoro-5-(trifluoromethoxy)phenyl group, $R^{3c}$ represents a chlorine atom, and $R^{3b}$ represents any one substituent described in Table L12 to Table L14 (hereinafter referred to as “Compound group SX372”).

The Compound (L-1), wherein n represents 1, $R^1$ represents a methyl group, T represents a 3-fluoro-5-(trifluoromethoxy)phenyl group, $R^{3c}$ represents a bromine atom, and $R^{3b}$ represents any one substituent described in Table L12 to Table L14 (hereinafter referred to as “Compound group SX373”).

The Compound (L-1), wherein n represents 1, $R^1$ represents a methyl group, T represents a 3-fluoro-5-(trifluoromethoxy)phenyl group, $R^{3c}$ represents an iodine atom, and $R^{3b}$ represents any one substituent described in Table L12 to Table L14 (hereinafter referred to as “Compound group SX374”).

The Compound (L-1), wherein n represents 1, $R^1$ represents a methyl group, T represents a 3-fluoro-5-(trifluoromethoxy)phenyl group, $R^{3c}$ represents $CF_3$, and $R^{3b}$ represents any one substituent described in Table L12 to Table L14 (hereinafter referred to as “Compound group SX375”).

The Compound (L-1), wherein n represents 2, $R^1$ represents a methyl group, T represents a 3-[(trifluoromethyl) thio]phenyl group, $R^{3c}$ represents a hydrogen atom, and $R^{3b}$ represents any one substituent described in Table L12 to Table L14 (hereinafter referred to as “Compound group SX376”).

The Compound (L-1), wherein n represents 2, $R^1$ represents a methyl group, T represents a 3-[(trifluoromethyl) thio]phenyl group, $R^{3c}$ represents a chlorine atom, and $R^{3b}$ represents any one substituent described in Table L12 to Table L14 (hereinafter referred to as “Compound group SX377”).

The Compound (L-1), wherein n represents 2, $R^1$ represents a methyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX378").

The Compound (L-1), wherein n represents 2, $R^1$ represents a methyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX379").

The Compound (L-1), wherein n represents 2, $R^1$ represents a methyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX380").

The Compound (L-1), wherein n represents 2, $R^1$ represents a methyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX381").

The Compound (L-1), wherein n represents 2, $R^1$ represents a methyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX382").

The Compound (L-1), wherein n represents 2, $R^1$ represents a methyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX383").

The Compound (L-1), wherein n represents 2, $R^1$ represents a methyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX384").

The Compound (L-1), wherein n represents 2, $R^1$ represents a methyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX385").

The Compound (L-1), wherein n represents 2, $R^1$ represents an ethyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX386").

The Compound (L-1), wherein n represents 2, $R^1$ represents an ethyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX387").

The Compound (L-1), wherein n represents 2, $R^1$ represents an ethyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX388").

The Compound (L-1), wherein n represents 2, $R^1$ represents an ethyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX389").

The Compound (L-1), wherein n represents 2, $R^1$ represents an ethyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX390").

The Compound (L-1), wherein n represents 2, $R^1$ represents an ethyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX391").

The Compound (L-1), wherein n represents 2, $R^1$ represents an ethyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX392").

The Compound (L-1), wherein n represents 2, $R^1$ represents an ethyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX393").

The Compound (L-1), wherein n represents 2, $R^1$ represents an ethyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX394").

The Compound (L-1), wherein n represents 2, $R^1$ represents an ethyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX395").

The Compound (L-1), wherein n represents 2, $R^1$ represents an isopropyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX396").

The Compound (L-1), wherein n represents 2, $R^1$ represents an isopropyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX397").

The Compound (L-1), wherein n represents 2, $R^1$ represents an isopropyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX398").

The Compound (L-1), wherein n represents 2, $R^1$ represents an isopropyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX399").

The Compound (L-1), wherein n represents 2, $R^1$ represents an isopropyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX400").

The Compound (L-1), wherein n represents 2, $R^1$ represents an isopropyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX401").

The Compound (L-1), wherein n represents 2, $R^1$ represents an isopropyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX402").

The Compound (L-1), wherein n represents 2, $R^1$ represents an isopropyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX403").

The Compound (L-1), wherein n represents 2, $R^1$ represents an isopropyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX404").

The Compound (L-1), wherein n represents 2, $R^1$ represents an isopropyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX405").

The Compound (L-1), wherein n represents 2, $R^1$ represents a methyl group, T represents a 4-(trifluoromethoxy)phenyl group, $R^{3c}$ represents a hydrogen atom, and $R^{3b}$ represents any one substituent described in Table L12 to Table L14 (hereinafter referred to as "Compound group SX406").

The Compound (L-1), wherein n represents 2, $R^1$ represents a methyl group, T represents a 4-(trifluoromethoxy)phenyl group, $R^{3c}$ represents a chlorine atom, and $R^{3b}$ represents any one substituent described in Table L12 to Table L14 (hereinafter referred to as "Compound group SX407").

The Compound (L-1), wherein n represents 2, $R^1$ represents a methyl group, T represents a 4-(trifluoromethoxy)phenyl group, $R^{3c}$ represents a bromine atom, and $R^{3b}$ represents any one substituent described in Table L12 to Table L14 (hereinafter referred to as "Compound group SX408").

The Compound (L-1), wherein n represents 2, $R^1$ represents a methyl group, T represents a 4-(trifluoromethoxy)phenyl group, $R^{3c}$ represents an iodine atom, and $R^{3b}$ represents any one substituent described in Table L12 to Table L14 (hereinafter referred to as "Compound group SX409").

The Compound (L-1), wherein n represents 2, $R^1$ represents a methyl group, T represents a 4-(trifluoromethoxy)phenyl group, $R^{3c}$ represents $CF_3$, and $R^{3b}$ represents any one substituent described in Table L12 to Table L14 (hereinafter referred to as "Compound group SX410").

The Compound (L-1), wherein n represents 2, $R^1$ represents a methyl group, T represents a 4-(trifluoromethyl)phenyl group, $R^{3c}$ represents a hydrogen atom, and $R^{3b}$ represents any one substituent described in Table L12 to Table L14 (hereinafter referred to as "Compound group SX411").

The Compound (L-1), wherein n represents 2, $R^1$ represents a methyl group, T represents a 4-(trifluoromethyl)phenyl group, $R^{3c}$ represents a chlorine atom, and $R^{3b}$ represents any one substituent described in Table L12 to Table L14 (hereinafter referred to as "Compound group SX412").

The Compound (L-1), wherein n represents 2, $R^1$ represents a methyl group, T represents a 4-(trifluoromethyl)phenyl group, $R^{3c}$ represents a bromine atom, and $R^{3b}$ represents any one substituent described in Table L12 to Table L14 (hereinafter referred to as "Compound group SX413").

The Compound (L-1), wherein n represents 2, $R^1$ represents a methyl group, T represents a 4-(trifluoromethyl)phenyl group, $R^{3c}$ represents an iodine atom, and $R^{3b}$ represents any one substituent described in Table L12 to Table L14 (hereinafter referred to as "Compound group SX414").

The Compound (L-1), wherein n represents 2, $R^1$ represents a methyl group, T represents a 4-(trifluoromethyl)phenyl group, $R^{3c}$ represents $CF_3$, and $R^{3b}$ represents any one substituent described in Table L12 to Table L14 (hereinafter referred to as "Compound group SX415").

The Compound (L-1), wherein n represents 2, $R^1$ represents a methyl group, T represents a 3,4-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX416").

The Compound (L-1), wherein n represents 2, $R^1$ represents a methyl group, T represents a 3,4-bis[(trifluoromethyl)thio]phenyl group, $R^{3c}$ represents a chlorine atom, and $R^{3b}$ represents any one substituent described in Table L12 to Table L14 (hereinafter referred to as "Compound group SX417").

The Compound (L-1), wherein n represents 2, $R^1$ represents a methyl group, T represents a 3,4-bis[(trifluoromethyl)thio]phenyl group, $R^{3c}$ represents a bromine atom, and $R^{3b}$ represents any one substituent described in Table L12 to Table L14 (hereinafter referred to as "Compound group SX418").

The Compound (L-1), wherein n represents 2, $R^1$ represents a methyl group, T represents a 3,4-bis[(trifluoromethyl)thio]phenyl group, $R^{3c}$ represents an iodine atom, and $R^{3b}$ represents any one substituent described in Table L12 to Table L14 (hereinafter referred to as "Compound group SX419").

The Compound (L-1), wherein n represents 2, $R^1$ represents a methyl group, T represents a 3,4-bis[(trifluoromethyl)thio]phenyl group, $R^{3c}$ represents $CF_3$, and $R^{3b}$ represents any one substituent described in Table L12 to Table L14 (hereinafter referred to as "Compound group SX420").

The Compound (L-1), wherein n represents 2, $R^1$ represents a methyl group, T represents a 3,4-bis(trifluoromethoxy)phenyl group, $R^{3c}$ represents a hydrogen atom, and $R^{3b}$ represents any one substituent described in Table L12 to Table L14 (hereinafter referred to as "Compound group SX421").

The Compound (L-1), wherein n represents 2, $R^1$ represents a methyl group, T represents a 3,4-bis(trifluoromethoxy)phenyl group, $R^{3c}$ represents a chlorine atom, and $R^{3b}$ represents any one substituent described in Table L12 to Table L14 (hereinafter referred to as "Compound group SX422").

The Compound (L-1), wherein n represents 2, $R^1$ represents a methyl group, T represents a 3,4-bis(trifluoromethoxy)phenyl group, $R^{3c}$ represents a bromine atom, and $R^{3b}$ represents any one substituent described in Table L12 to Table L14 (hereinafter referred to as "Compound group SX423").

The Compound (L-1), wherein n represents 2, $R^1$ represents a methyl group, T represents a 3,4-bis(trifluoromethoxy)phenyl group, $R^{3c}$ represents an iodine atom, and $R^{3b}$ represents any one substituent described in Table L12 to Table L14 (hereinafter referred to as "Compound group SX424").

The Compound (L-1), wherein n represents 2, $R^1$ represents a methyl group, T represents a 3,4-bis(trifluoromethoxy)phenyl group, $R^{3c}$ represents $CF_3$, and $R^{3b}$ represents any one substituent described in Table L12 to Table L14 (hereinafter referred to as "Compound group SX425").

The Compound (L-1), wherein n represents 2, $R^1$ represents a methyl group, T represents a 3,4-bis(trifluoromethyl) phenyl group, $R^{3c}$ represents a hydrogen atom, and $R^{3b}$ represents any one substituent described in Table L12 to Table L14 (hereinafter referred to as "Compound group SX426").

The Compound (L-1), wherein n represents 2, $R^1$ represents a methyl group, T represents a 3,4-bis(trifluoromethyl) phenyl group, $R^{3c}$ represents a chlorine atom, and $R^{3b}$ represents any one substituent described in Table L12 to Table L14 (hereinafter referred to as "Compound group SX427").

The Compound (L-1), wherein n represents 2, $R^1$ represents a methyl group, T represents a 3,4-bis(trifluoromethyl) phenyl group, $R^{3c}$ represents a bromine atom, and $R^{3b}$ represents any one substituent described in Table L12 to Table L14 (hereinafter referred to as "Compound group SX428").

The Compound (L-1), wherein n represents 2, $R^1$ represents a methyl group, T represents a 3,4-bis(trifluoromethyl) phenyl group, $R^{3c}$ represents an iodine atom, and $R^{3b}$ represents any one substituent described in Table L12 to Table L14 (hereinafter referred to as "Compound group SX429").

The Compound (L-1), wherein n represents 2, $R^1$ represents a methyl group, T represents a 3,4-bis(trifluoromethyl) phenyl group, $R^{3c}$ represents $CF_3$, and $R^{3b}$ represents any one substituent described in Table L12 to Table L14 (hereinafter referred to as "Compound group SX430").

The Compound (L-1), wherein n represents 2, $R^1$ represents a methyl group, T represents a 3,5-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX431").

The Compound (L-1), wherein n represents 2, $R^1$ represents a methyl group, T represents a 3,5-bis[(trifluoromethyl)thio]phenyl group, $R^{3c}$ represents a chlorine atom, and $R^{3b}$ represents any one substituent described in Table L12 to Table L14 (hereinafter referred to as "Compound group SX432").

The Compound (L-1), wherein n represents 2, $R^1$ represents a methyl group, T represents a 3,5-bis[(trifluoromethyl)thio]phenyl group, $R^{3c}$ represents a bromine atom, and $R^{3b}$ represents any one substituent described in Table L12 to Table L14 (hereinafter referred to as "Compound group SX433").

The Compound (L-1), wherein n represents 2, $R^1$ represents a methyl group, T represents a 3,5-bis[(trifluoromethyl)thio]phenyl group, $R^{3c}$ represents an iodine atom, and $R^{3b}$ represents any one substituent described in Table L12 to Table L14 (hereinafter referred to as "Compound group SX434").

The Compound (L-1), wherein n represents 2, $R^1$ represents a methyl group, T represents a 3,5-bis[(trifluoromethyl)thio]phenyl group, $R^{3c}$ represents $CF_3$, and $R^{3b}$ represents any one substituent described in Table L12 to Table L14 (hereinafter referred to as "Compound group SX435").

The Compound (L-1), wherein n represents 2, $R^1$ represents a methyl group, T represents a 3,5-bis(trifluoromethoxy)phenyl group, $R^{3c}$ represents a hydrogen atom, and $R^{3b}$ represents any one substituent described in Table L12 to Table L14 (hereinafter referred to as "Compound group SX436").

The Compound (L-1), wherein n represents 2, $R^1$ represents a methyl group, T represents a 3,5-bis(trifluoromethoxy)phenyl group, $R^{3c}$ represents a chlorine atom, and $R^{3b}$ represents any one substituent described in Table L12 to Table L14 (hereinafter referred to as "Compound group SX437").

The Compound (L-1), wherein n represents 2, $R^1$ represents a methyl group, T represents a 3,5-bis(trifluoromethoxy)phenyl group, $R^{3c}$ represents a bromine atom, and $R^{3b}$ represents any one substituent described in Table L12 to Table L14 (hereinafter referred to as "Compound group SX438").

The Compound (L-1), wherein n represents 2, $R^1$ represents a methyl group, T represents a 3,5-bis(trifluoromethoxy)phenyl group, $R^{3c}$ represents an iodine atom, and $R^{3b}$ represents any one substituent described in Table L12 to Table L14 (hereinafter referred to as "Compound group SX439").

The Compound (L-1), wherein n represents 2, $R^1$ represents a methyl group, T represents a 3,5-bis(trifluoromethoxy)phenyl group, $R^{3c}$ represents $CF_3$, and $R^{3b}$ represents any one substituent described in Table L12 to Table L14 (hereinafter referred to as "Compound group SX440").

The Compound (L-1), wherein n represents 2, $R^1$ represents a methyl group, T represents a 3,5-bis(trifluoromethyl) phenyl group, $R^{3c}$ represents a hydrogen atom, and $R^{3b}$ represents any one substituent described in Table L12 to Table L14 (hereinafter referred to as "Compound group SX441").

The Compound (L-1), wherein n represents 2, $R^1$ represents a methyl group, T represents a 3,5-bis(trifluoromethyl) phenyl group, $R^{3c}$ represents a chlorine atom, and $R^{3b}$ represents any one substituent described in Table L12 to Table L14 (hereinafter referred to as "Compound group SX442").

The Compound (L-1), wherein n represents 2, $R^1$ represents a methyl group, T represents a 3,5-bis(trifluoromethyl) phenyl group, $R^{3c}$ represents a bromine atom, and $R^{3b}$ represents any one substituent described in Table L12 to Table L14 (hereinafter referred to as "Compound group SX443").

The Compound (L-1), wherein n represents 2, $R^1$ represents a methyl group, T represents a 3,5-bis(trifluoromethyl) phenyl group, $R^{3c}$ represents an iodine atom, and $R^{3b}$ represents any one substituent described in Table L12 to Table L14 (hereinafter referred to as "Compound group SX444").

The Compound (L-1), wherein n represents 2, $R^1$ represents a methyl group, T represents a 3,5-bis(trifluoromethyl) phenyl group, $R^{3c}$ represents $CF_3$, and $R^{3b}$ represents any one substituent described in Table L12 to Table L14 (hereinafter referred to as "Compound group SX445").

The Compound (L-1), wherein n represents 2, $R^1$ represents a methyl group, T represents a 3-fluoro-5-(trifluoromethoxy)phenyl group, $R^{3c}$ represents a hydrogen Table L12 to Table L14 (hereinafter referred to as "Compound group SX446").

The Compound (L-1), wherein n represents 2, $R^1$ represents a methyl group, T represents a 3-fluoro-5-(trifluoromethoxy)phenyl group, $R^{3c}$ represents a chlorine atom, and $R^{3b}$ represents any one substituent described in Table L12 to Table L14 (hereinafter referred to as "Compound group SX447").

The Compound (L-1), wherein n represents 2, $R^1$ represents a methyl group, T represents a 3-fluoro-5-(trifluoromethoxy)phenyl group, $R^{3c}$ represents a bromine atom, and $R^{3b}$ represents any one substituent described in Table L12 to Table L14 (hereinafter referred to as "Compound group SX448").

The Compound (L-1), wherein n represents 2, $R^1$ represents a methyl group, T represents a 3-fluoro-5-(trifluoromethoxy)phenyl group, $R^{3c}$ represents an iodine atom, and $R^{3b}$ represents any one substituent described in Table L12 to Table L14 (hereinafter referred to as "Compound group SX449").

The Compound (L-1), wherein n represents 2, $R^1$ represents a methyl group, T represents a 3-fluoro-5-(trifluoromethoxy)phenyl group, $R^{3c}$ represents $CF_3$, and $R^{3b}$ represents any one substituent described in Table L12 to Table L14 (hereinafter referred to as "Compound group SX450").

The Compound (L-1), wherein n represents 0, $R^1$ represents a methyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX451").

The Compound (L-1), wherein n represents 0, $R^1$ represents a methyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX452").

The Compound (L-1), wherein n represents 0, $R^1$ represents a methyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX453").

The Compound (L-1), wherein n represents 0, $R^1$ represents a methyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX454").

The Compound (L-1), wherein n represents 0, $R^1$ represents a methyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX455").

The Compound (L-1), wherein n represents 0, $R^1$ represents a methyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX456").

The Compound (L-1), wherein n represents 0, $R^1$ represents a methyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX457").

The Compound (L-1), wherein n represents 0, $R^1$ represents a methyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX458").

The Compound (L-1), wherein n represents 0, $R^1$ represents a methyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX459").

The Compound (L-1), wherein n represents 0, $R^1$ represents a methyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX460").

The Compound (L-1), wherein n represents 0, $R^1$ represents an ethyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX461").

The Compound (L-1), wherein n represents 0, $R^1$ represents an ethyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX462").

The Compound (L-1), wherein n represents 0, $R^1$ represents an ethyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX463").

The Compound (L-1), wherein n represents 0, $R^1$ represents an ethyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX464").

The Compound (L-1), wherein n represents 0, $R^1$ represents an ethyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX465").

The Compound (L-1), wherein n represents 0, $R^1$ represents an ethyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX466").

The Compound (L-1), wherein n represents 0, $R^1$ represents an ethyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX467").

The Compound (L-1), wherein n represents 0, $R^1$ represents an ethyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX468").

The Compound (L-1), wherein n represents 0, $R^1$ represents an ethyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX469").

The Compound (L-1), wherein n represents 0, $R^1$ represents an ethyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX470").

The Compound (L-1), wherein n represents 0, $R^1$ represents an isopropyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX471").

The Compound (L-1), wherein n represents 0, $R^1$ represents an isopropyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX472").

The Compound (L-1), wherein n represents 0, $R^1$ represents an isopropyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX473").

The Compound (L-1), wherein n represents 0, $R^1$ represents an isopropyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX474").

The Compound (L-1), wherein n represents 0, $R^1$ represents an isopropyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX475").

The Compound (L-1), wherein n represents 0, $R^1$ represents an isopropyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX476").

The Compound (L-1), wherein n represents 0, $R^1$ represents an isopropyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX477").

The Compound (L-1), wherein n represents 0, $R^1$ represents an isopropyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX478").

The Compound (L-1), wherein n represents 0, $R^1$ represents an isopropyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX479").

The Compound (L-1), wherein n represents 0, $R^1$ represents an isopropyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX480").

The Compound (L-1), wherein n represents 0, $R^1$ represents a methyl group, T represents a 4-(trifluoromethoxy)phenyl group, $R^{3b}$ represents a hydrogen atom, and $R^{3c}$ represents any one substituent described in Table L12 to Table L14 (hereinafter referred to as "Compound group SX481").

The Compound (L-1), wherein n represents 0, $R^1$ represents a methyl group, T represents a 4-(trifluoromethoxy)phenyl group, $R^{3b}$ represents a chlorine atom, and $R^{3c}$ represents any one substituent described in Table L12 to Table L14 (hereinafter referred to as "Compound group SX482").

The Compound (L-1), wherein n represents 0, $R^1$ represents a methyl group, T represents a 4-(trifluoromethoxy)phenyl group, $R^{3b}$ represents a bromine atom, and $R^{3c}$ represents any one substituent described in Table L12 to Table L14 (hereinafter referred to as "Compound group SX483").

The Compound (L-1), wherein n represents 0, $R^1$ represents a methyl group, T represents a 4-(trifluoromethoxy)phenyl group, $R^{3b}$ represents an iodine atom, and $R^{3c}$ represents any one substituent described in Table L12 to Table L14 (hereinafter referred to as "Compound group SX484").

The Compound (L-1), wherein n represents 0, $R^1$ represents a methyl group, T represents a 4-(trifluoromethoxy)phenyl group, $R^{3b}$ represents $CF_3$, and $R^{3c}$ represents any one substituent described in Table L12 to Table L14 (hereinafter referred to as "Compound group SX485").

The Compound (L-1), wherein n represents 0, $R^1$ represents a methyl group, T represents a 4-(trifluoromethyl)phenyl group, $R^{3b}$ represents a hydrogen atom, and $R^{3c}$ represents any one substituent described in Table L12 to Table L14 (hereinafter referred to as "Compound group SX486").

The Compound (L-1), wherein n represents 0, $R^1$ represents a methyl group, T represents a 4-(trifluoromethyl)phenyl group, $R^{3b}$ represents a chlorine atom, and $R^{3c}$ represents any one substituent described in Table L12 to Table L14 (hereinafter referred to as "Compound group SX487").

The Compound (L-1), wherein n represents 0, $R^1$ represents a methyl group, T represents a 4-(trifluoromethyl)phenyl group, $R^{3b}$ represents a bromine atom, and $R^{3c}$ represents any one substituent described in Table L12 to Table L14 (hereinafter referred to as "Compound group SX488").

The Compound (L-1), wherein n represents 0, $R^1$ represents a methyl group, T represents a 4-(trifluoromethyl)phenyl group, $R^{3b}$ represents an iodine atom, and $R^{3c}$ represents any one substituent described in Table L12 to Table L14 (hereinafter referred to as "Compound group SX489").

The Compound (L-1), wherein n represents 0, $R^1$ represents a methyl group, T represents a 4-(trifluoromethyl)phenyl group, $R^{3b}$ represents $CF_3$, and $R^{3e}$ represents any one substituent described in Table L12 to Table L14 (hereinafter referred to as "Compound group SX490").

The Compound (L-1), wherein n represents 0, $R^1$ represents a methyl group, T represents a 3,4-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX491").

The Compound (L-1), wherein n represents 0, $R^1$ represents a methyl group, T represents a 3,4-bis[(trifluoromethyl)thio]phenyl group, $R^{3b}$ represents a chlorine atom, and $R^{3c}$ represents any one substituent described in Table L12 to Table L14 (hereinafter referred to as "Compound group SX492").

The Compound (L-1), wherein n represents 0, $R^1$ represents a methyl group, T represents a 3,4-bis[(trifluoromethyl)thio]phenyl group, $R^{3b}$ represents a bromine atom, and $R^{3c}$ represents any one substituent described in Table L12 to Table L14 (hereinafter referred to as "Compound group SX493").

The Compound (L-1), wherein n represents 0, $R^1$ represents a methyl group, T represents a 3,4-bis[(trifluoromethyl)thio]phenyl group, $R^{3b}$ represents an iodine atom, and $R^{3c}$ represents any one substituent described in Table L12 to Table L14 (hereinafter referred to as "Compound group SX494").

The Compound (L-1), wherein n represents 0, $R^1$ represents a methyl group, T represents a 3,4-bis[(trifluoromethyl)thio]phenyl group, $R^{3b}$ represents $CF_3$, and $R^{3c}$ represents any one substituent described in Table L12 to Table L14 (hereinafter referred to as "Compound group SX495").

The Compound (L-1), wherein n represents 0, $R^1$ represents a methyl group, T represents a 3,4-bis(trifluoromethoxy)phenyl group, $R^{3b}$ represents a hydrogen atom, and $R^{3c}$ represents any one substituent described in Table L12 to Table L14 (hereinafter referred to as "Compound group SX496").

The Compound (L-1), wherein n represents 0, $R^1$ represents a methyl group, T represents a 3,4-bis(trifluoromethoxy)phenyl group, $R^{3b}$ represents a chlorine atom, and $R^{3c}$ represents any one substituent described in Table L12 to Table L14 (hereinafter referred to as "Compound group SX497").

The Compound (L-1), wherein n represents 0, $R^1$ represents a methyl group, T represents a 3,4-bis(trifluoromethoxy)phenyl group, $R^{3b}$ represents a bromine atom, and $R^{3c}$ represents any one substituent described in Table L12 to Table L14 (hereinafter referred to as "Compound group SX498").

The Compound (L-1), wherein n represents 0, $R^1$ represents a methyl group, T represents a 3,4-bis(trifluoromethoxy)phenyl group, $R^{3b}$ represents an iodine atom, and $R^{3c}$ represents any one substituent described in Table L12 to Table L14 (hereinafter referred to as "Compound group SX499").

The Compound (L-1), wherein n represents 0, $R^1$ represents a methyl group, T represents a 3,4-bis(trifluoromethoxy)phenyl group, $R^{3b}$ represents $CF_3$, and $R^{3c}$ represents any one substituent described in Table L12 to Table L14 (hereinafter referred to as "Compound group SX500").

The Compound (L-1), wherein n represents 0, $R^1$ represents a methyl group, T represents a 3,4-bis(trifluoromethyl)phenyl group, $R^{3b}$ represents a hydrogen atom, and $R^{3c}$ represents any one substituent described in Table L12 to Table L14 (hereinafter referred to as "Compound group SX501").

The Compound (L-1), wherein n represents 0, $R^1$ represents a methyl group, T represents a 3,4-bis(trifluoromethyl)phenyl group, $R^{3b}$ represents a chlorine atom, and $R^{3c}$ represents any one substituent described in Table L12 to Table L14 (hereinafter referred to as "Compound group SX502").

The Compound (L-1), wherein n represents 0, $R^1$ represents a methyl group, T represents a 3,4-bis(trifluoromethyl)phenyl group, $R^{3b}$ represents a bromine atom, and $R^{3c}$ represents any one substituent described in Table L12 to Table L14 (hereinafter referred to as "Compound group SX503").

The Compound (L-1), wherein n represents 0, $R^1$ represents a methyl group, T represents a 3,4-bis(trifluoromethyl)phenyl group, $R^{3b}$ represents an iodine atom, and $R^{3c}$ represents any one substituent described in Table L12 to Table L14 (hereinafter referred to as "Compound group SX504").

The Compound (L-1), wherein n represents 0, $R^1$ represents a methyl group, T represents a 3,4-bis(trifluoromethyl)phenyl group, $R^{3b}$ represents $CF_3$, and $R^{3c}$ represents any one substituent described in Table L12 to Table L14 (hereinafter referred to as "Compound group SX505").

The Compound (L-1), wherein n represents 0, $R^1$ represents a methyl group, T represents a 3,5-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX506").

The Compound (L-1), wherein n represents 0, $R^1$ represents a methyl group, T represents a 3,5-bis[(trifluoromethyl)thio]phenyl group, $R^{3b}$ represents a chlorine atom, and $R^{3c}$ represents any one substituent described in Table L12 to Table L14 (hereinafter referred to as "Compound group SX507").

The Compound (L-1), wherein n represents 0, $R^1$ represents a methyl group, T represents a 3,5-bis[(trifluoromethyl)thio]phenyl group, $R^{3b}$ represents a bromine atom, and $R^{3c}$ represents any one substituent described in Table L12 to Table L14 (hereinafter referred to as "Compound group SX508").

The Compound (L-1), wherein n represents 0, $R^1$ represents a methyl group, T represents a 3,5-bis[(trifluoromethyl)thio]phenyl group, $R^{3b}$ represents an iodine atom, and $R^{3c}$ represents any one substituent described in Table L12 to Table L14 (hereinafter referred to as "Compound group SX509").

The Compound (L-1), wherein n represents 0, $R^1$ represents a methyl group, T represents a 3,5-bis[(trifluoromethyl)thio]phenyl group, $R^{3b}$ represents $CF_3$, and $R^{3c}$ represents any one substituent described in Table L12 to Table L14 (hereinafter referred to as "Compound group SX510").

The Compound (L-1), wherein n represents 0, $R^1$ represents a methyl group, T represents a 3,5-bis(trifluoromethoxy)phenyl group, $R^{3b}$ represents a hydrogen atom, and $R^{3c}$ represents any one substituent described in Table L12 to Table L14 (hereinafter referred to as "Compound group SX511").

The Compound (L-1), wherein n represents 0, $R^1$ represents a methyl group, T represents a 3,5-bis(trifluoromethoxy)phenyl group, $R^{3b}$ represents a chlorine atom, and $R^{3c}$ represents any one substituent described in Table L12 to Table L14 (hereinafter referred to as "Compound group SX512").

The Compound (L-1), wherein n represents 0, $R^1$ represents a methyl group, T represents a 3,5-bis(trifluoromethoxy)phenyl group, $R^{3b}$ represents a bromine atom, and $R^{3c}$ represents any one substituent described in Table L12 to Table L14 (hereinafter referred to as "Compound group SX513").

The Compound (L-1), wherein n represents 0, $R^1$ represents a methyl group, T represents a 3,5-bis(trifluoromethoxy)phenyl group, $R^{3b}$ represents an iodine atom, and $R^{3c}$ represents any one substituent described in Table L12 to Table L14 (hereinafter referred to as "Compound group SX514").

The Compound (L-1), wherein n represents 0, $R^1$ represents a methyl group, T represents a 3,5-bis(trifluoromethoxy)phenyl group, $R^{3b}$ represents $CF_3$, and $R^{3c}$ represents any one substituent described in Table L12 to Table L14 (hereinafter referred to as "Compound group SX515").

The Compound (L-1), wherein n represents 0, $R^1$ represents a methyl group, T represents a 3,5-bis(trifluoromethyl)phenyl group, $R^{3b}$ represents a hydrogen atom, and $R^{3c}$ represents any one substituent described in Table L12 to Table L14 (hereinafter referred to as "Compound group SX516").

The Compound (L-1), wherein n represents 0, $R^1$ represents a methyl group, T represents a 3,5-bis(trifluoromethyl)phenyl group, $R^{3b}$ represents a chlorine atom, and $R^{3c}$ represents any one substituent described in Table L12 to Table L14 (hereinafter referred to as "Compound group SX517").

The Compound (L-1), wherein n represents 0, $R^1$ represents a methyl group, T represents a 3,5-bis(trifluoromethyl) phenyl group, $R^{3b}$ represents a bromine atom, and $R^{3c}$ represents any one substituent described in Table L12 to Table L14 (hereinafter referred to as "Compound group SX518").

The Compound (L-1), wherein n represents 0, $R^1$ represents a methyl group, T represents a 3,5-bis(trifluoromethyl) phenyl group, $R^{3b}$ represents an iodine atom, and $R^{3c}$ represents any one substituent described in Table L12 to Table L14 (hereinafter referred to as "Compound group SX519").

The Compound (L-1), wherein n represents 0, $R^1$ represents a methyl group, T represents a 3,5-bis(trifluoromethyl) phenyl group, $R^{3b}$ represents $CF_3$, and $R^{3c}$ represents any one substituent described in Table L12 to Table L14 (hereinafter referred to as "Compound group SX520").

The Compound (L-1), wherein n represents 0, $R^1$ represents a methyl group, T represents a 3-fluoro-5-(trifluoromethoxy)phenyl group, $R^{3b}$ represents a hydrogen Table L12 to Table L14 (hereinafter referred to as "Compound group SX521").

The Compound (L-1), wherein n represents 0, $R^1$ represents a methyl group, T represents a 3-fluoro-5-(trifluoromethoxy)phenyl group, $R^{3b}$ represents a chlorine atom, and $R^{3c}$ represents any one substituent described in Table L12 to Table L14 (hereinafter referred to as "Compound group SX522").

The Compound (L-1), wherein n represents 0, $R^1$ represents a methyl group, T represents a 3-fluoro-5-(trifluoromethoxy)phenyl group, $R^{3b}$ represents a bromine atom, and $R^{3c}$ represents any one substituent described in Table L12 to Table L14 (hereinafter referred to as "Compound group SX523").

The Compound (L-1), wherein n represents 0, $R^1$ represents a methyl group, T represents a 3-fluoro-5-(trifluoromethoxy)phenyl group, $R^{3b}$ represents an iodine atom, and $R^{3c}$ represents any one substituent described in Table L12 to Table L14 (hereinafter referred to as "Compound group SX524").

The Compound (L-1), wherein n represents 0, $R^1$ represents a methyl group, T represents a 3-fluoro-5-(trifluoromethoxy)phenyl group, $R^{3b}$ represents $CF_3$, and $R^{3c}$ represents any one substituent described in Table L12 to Table L14 (hereinafter referred to as "Compound group SX525").

The Compound (L-1), wherein n represents 1, $R^1$ represents a methyl group, T represents a 3-[(trifluoromethyl) thio]phenyl group, $R^{3b}$ represents a hydrogen atom, and $R^{3c}$ represents any one substituent described in Table L12 to Table L14 (hereinafter referred to as "Compound group SX526").

The Compound (L-1), wherein n represents 1, $R^1$ represents a methyl group, T represents a 3-[(trifluoromethyl) thio]phenyl group, $R^{3b}$ represents a chlorine atom, and $R^{3c}$ represents any one substituent described in Table L12 to Table L14 (hereinafter referred to as "Compound group SX527").

The Compound (L-1), wherein n represents 1, $R^1$ represents a methyl group, T represents a 3-[(trifluoromethyl) thio]phenyl group, $R^{3b}$ represents a bromine atom, and $R^{3c}$ represents any one substituent described in Table L12 to Table L14 (hereinafter referred to as "Compound group SX528").

The Compound (L-1), wherein n represents 1, $R^1$ represents a methyl group, T represents a 3-[(trifluoromethyl) thio]phenyl group, $R^{3b}$ represents an iodine atom, and $R^{3c}$ represents any one substituent described in Table L12 to Table L14 (hereinafter referred to as "Compound group SX529").

The Compound (L-1), wherein n represents 1, $R^1$ represents a methyl group, T represents a 3-[(trifluoromethyl) thio]phenyl group, $R^{3b}$ represents $CF_3$, and $R^{3c}$ represents any one substituent described in Table L12 to Table L14 (hereinafter referred to as "Compound group SX530").

The Compound (L-1), wherein n represents 1, $R^1$ represents a methyl group, T represents a 4-[(trifluoromethyl) thio]phenyl group, $R^{3b}$ represents a hydrogen atom, and $R^{3c}$ represents any one substituent described in Table L12 to Table L14 (hereinafter referred to as "Compound group SX531").

The Compound (L-1), wherein n represents 1, $R^1$ represents a methyl group, T represents a 4-[(trifluoromethyl) thio]phenyl group, $R^{3b}$ represents a chlorine atom, and $R^{3c}$ represents any one substituent described in Table L12 to Table L14 (hereinafter referred to as "Compound group SX532").

The Compound (L-1), wherein n represents 1, $R^1$ represents a methyl group, T represents a 4-[(trifluoromethyl) thio]phenyl group, $R^{3b}$ represents a bromine atom, and $R^{3c}$ represents any one substituent described in Table L12 to Table L14 (hereinafter referred to as "Compound group SX533").

The Compound (L-1), wherein n represents 1, $R^1$ represents a methyl group, T represents a 4-[(trifluoromethyl) thio]phenyl group, $R^{3b}$ represents an iodine atom, and $R^{3c}$ represents any one substituent described in Table L12 to Table L14 (hereinafter referred to as "Compound group SX534").

The Compound (L-1), wherein n represents 1, $R^1$ represents a methyl group, T represents a 4-[(trifluoromethyl) thio]phenyl group, $R^{3b}$ represents $CF_3$, and $R^{3c}$ represents any one substituent described in Table L12 to Table L14 (hereinafter referred to as "Compound group SX535").

The Compound (L-1), wherein n represents 1, $R^1$ represents an ethyl group, T represents a 3-[(trifluoromethyl)thio] phenyl group, $R^{3b}$ represents a hydrogen atom, and $R^{3c}$ represents any one substituent described in Table L12 to Table L14 (hereinafter referred to as "Compound group SX536").

The Compound (L-1), wherein n represents 1, $R^1$ represents an ethyl group, T represents a 3-[(trifluoromethyl)thio] phenyl group, $R^{3b}$ represents a chlorine atom, and $R^{3c}$ represents any one substituent described in Table L12 to Table L14 (hereinafter referred to as "Compound group SX537").

The Compound (L-1), wherein n represents 1, $R^1$ represents an ethyl group, T represents a 3-[(trifluoromethyl)thio] phenyl group, $R^{3b}$ represents a bromine atom, and $R^{3c}$ represents any one substituent described in Table L12 to Table L14 (hereinafter referred to as "Compound group SX538").

The Compound (L-1), wherein n represents 1, $R^1$ represents an ethyl group, T represents a 3-[(trifluoromethyl)thio] phenyl group, $R^{3b}$ represents an iodine atom, and $R^{3c}$ represents any one substituent described in Table L12 to Table L14 (hereinafter referred to as "Compound group SX539").

The Compound (L-1), wherein n represents 1, $R^1$ represents an ethyl group, T represents a 3-[(trifluoromethyl)thio] phenyl group, $R^{3b}$ represents $CF_3$, and $R^{3c}$ represents any one substituent described in Table L12 to Table L14 (hereinafter referred to as "Compound group SX540").

The Compound (L-1), wherein n represents 1, $R^1$ represents an ethyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX541").

The Compound (L-1), wherein n represents 1, $R^1$ represents an ethyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX542").

The Compound (L-1), wherein n represents 1, $R^1$ represents an ethyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX543").

The Compound (L-1), wherein n represents 1, $R^1$ represents an ethyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX544").

The Compound (L-1), wherein n represents 1, $R^1$ represents an ethyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX545").

The Compound (L-1), wherein n represents 1, $R^1$ represents an isopropyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX546").

The Compound (L-1), wherein n represents 1, $R^1$ represents an isopropyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX547").

The Compound (L-1), wherein n represents 1, $R^1$ represents an isopropyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX548").

The Compound (L-1), wherein n represents 1, $R^1$ represents an isopropyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX549").

The Compound (L-1), wherein n represents 1, $R^1$ represents an isopropyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX550").

The Compound (L-1), wherein n represents 1, $R^1$ represents an isopropyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX551").

The Compound (L-1), wherein n represents 1, $R^1$ represents an isopropyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX552").

The Compound (L-1), wherein n represents 1, $R^1$ represents an isopropyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX553").

The Compound (L-1), wherein n represents 1, $R^1$ represents an isopropyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX554").

The Compound (L-1), wherein n represents 1, $R^1$ represents an isopropyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX555").

The Compound (L-1), wherein n represents 1, $R^1$ represents a methyl group, T represents a 4-(trifluoromethoxy)phenyl group, $R^{3b}$ represents a hydrogen atom, and $R^{3c}$ represents any one substituent described in Table L12 to Table L14 (hereinafter referred to as "Compound group SX556").

The Compound (L-1), wherein n represents 1, $R^1$ represents a methyl group, T represents a 4-(trifluoromethoxy)phenyl group, $R^{3b}$ represents a chlorine atom, and $R^{3c}$ represents any one substituent described in Table L12 to Table L14 (hereinafter referred to as "Compound group SX557").

The Compound (L-1), wherein n represents 1, $R^1$ represents a methyl group, T represents a 4-(trifluoromethoxy)phenyl group, $R^{3b}$ represents a bromine atom, and $R^{3c}$ represents any one substituent described in Table L12 to Table L14 (hereinafter referred to as "Compound group SX558").

The Compound (L-1), wherein n represents 1, $R^1$ represents a methyl group, T represents a 4-(trifluoromethoxy)phenyl group, $R^{3b}$ represents an iodine atom, and $R^{3c}$ represents any one substituent described in Table L12 to Table L14 (hereinafter referred to as "Compound group SX559").

The Compound (L-1), wherein n represents 1, $R^1$ represents a methyl group, T represents a 4-(trifluoromethoxy)phenyl group, $R^{3b}$ represents $CF_3$, and $R^{3c}$ represents any one substituent described in Table L12 to Table L14 (hereinafter referred to as "Compound group SX560").

The Compound (L-1), wherein n represents 1, $R^1$ represents a methyl group, T represents a 4-(trifluoromethyl)phenyl group, $R^{3b}$ represents a hydrogen atom, and $R^{3c}$ represents any one substituent described in Table L12 to Table L14 (hereinafter referred to as "Compound group SX561").

The Compound (L-1), wherein n represents 1, $R^1$ represents a methyl group, T represents a 4-(trifluoromethyl)phenyl group, $R^{3b}$ represents a chlorine atom, and $R^{3c}$ represents any one substituent described in Table L12 to Table L14 (hereinafter referred to as "Compound group SX562").

The Compound (L-1), wherein n represents 1, $R^1$ represents a methyl group, T represents a 4-(trifluoromethyl)phenyl group, $R^{3b}$ represents a bromine atom, and $R^{3c}$ represents any one substituent described in Table L12 to Table L14 (hereinafter referred to as "Compound group SX563").

The Compound (L-1), wherein n represents 1, $R^1$ represents a methyl group, T represents a 4-(trifluoromethyl) phenyl group, $R^{3b}$ represents an iodine atom, and $R^{3c}$ represents any one substituent described in Table L12 to Table L14 (hereinafter referred to as “Compound group SX564”).

The Compound (L-1), wherein n represents 1, $R^1$ represents a methyl group, T represents a 4-(trifluoromethyl) phenyl group, $R^{3b}$ represents $CF_3$, and $R^{3e}$ represents any one substituent described in Table L12 to Table L14 (hereinafter referred to as “Compound group SX565”).

The Compound (L-1), wherein n represents 1, $R^1$ represents a methyl group, T represents a 3,4-bis[(trifluoromethyl)thio]phenyl group, $R^{3b}$ represents a hydrogen atom, and $R^{3c}$ represents any one substituent described in Table L12 to Table L14 (hereinafter referred to as “Compound group SX566”).

The Compound (L-1), wherein n represents 1, $R^1$ represents a methyl group, T represents a 3,4-bis[(trifluoromethyl)thio]phenyl group, $R^{3b}$ represents a chlorine atom, and $R^{3c}$ represents any one substituent described in Table L12 to Table L14 (hereinafter referred to as “Compound group SX567”).

The Compound (L-1), wherein n represents 1, $R^1$ represents a methyl group, T represents a 3,4-bis[(trifluoromethyl)thio]phenyl group, $R^{3b}$ represents a bromine atom, and $R^{3c}$ represents any one substituent described in Table L12 to Table L14 (hereinafter referred to as “Compound group SX568”).

The Compound (L-1), wherein n represents 1, $R^1$ represents a methyl group, T represents a 3,4-bis[(trifluoromethyl)thio]phenyl group, $R^{3b}$ represents an iodine atom, and $R^{3c}$ represents any one substituent described in Table L12 to Table L14 (hereinafter referred to as “Compound group SX569”).

The Compound (L-1), wherein n represents 1, $R^1$ represents a methyl group, T represents a 3,4-bis[(trifluoromethyl)thio]phenyl group, $R^{3b}$ represents $CF_3$, and $R^{3c}$ represents any one substituent described in Table L12 to Table L14 (hereinafter referred to as “Compound group SX570”).

The Compound (L-1), wherein n represents 1, $R^1$ represents a methyl group, T represents a 3,4-bis(trifluoromethoxy)phenyl group, $R^{3b}$ represents a hydrogen atom, and $R^{3c}$ represents any one substituent described in Table L12 to Table L14 (hereinafter referred to as “Compound group SX571”).

The Compound (L-1), wherein n represents 1, $R^1$ represents a methyl group, T represents a 3,4-bis(trifluoromethoxy)phenyl group, $R^{3b}$ represents a chlorine atom, and $R^{3c}$ represents any one substituent described in Table L12 to Table L14 (hereinafter referred to as “Compound group SX572”).

The Compound (L-1), wherein n represents 1, $R^1$ represents a methyl group, T represents a 3,4-bis(trifluoromethoxy)phenyl group, $R^{3b}$ represents a bromine atom, and $R^{3c}$ represents any one substituent described in Table L12 to Table L14 (hereinafter referred to as “Compound group SX573”).

The Compound (L-1), wherein n represents 1, $R^1$ represents a methyl group, T represents a 3,4-bis(trifluoromethoxy)phenyl group, $R^{3b}$ represents an iodine atom, and $R^{3c}$ represents any one substituent described in Table L12 to Table L14 (hereinafter referred to as “Compound group SX574”).

The Compound (L-1), wherein n represents 1, $R^1$ represents a methyl group, T represents a 3,4-bis(trifluoromethoxy)phenyl group, $R^{3b}$ represents $CF_3$, and $R^{3c}$ represents any one substituent described in Table L12 to Table L14 (hereinafter referred to as “Compound group SX575”).

The Compound (L-1), wherein n represents 1, $R^1$ represents a methyl group, T represents a 3,4-bis(trifluoromethyl) phenyl group, $R^{3b}$ represents a hydrogen atom, and $R^{3c}$ represents any one substituent described in Table L12 to Table L14 (hereinafter referred to as “Compound group SX576”).

The Compound (L-1), wherein n represents 1, $R^1$ represents a methyl group, T represents a 3,4-bis(trifluoromethyl) phenyl group, $R^{3b}$ represents a chlorine atom, and $R^{3c}$ represents any one substituent described in Table L12 to Table L14 (hereinafter referred to as “Compound group SX577”).

The Compound (L-1), wherein n represents 1, $R^1$ represents a methyl group, T represents a 3,4-bis(trifluoromethyl) phenyl group, $R^{3b}$ represents a bromine atom, and $R^{3c}$ represents any one substituent described in Table L12 to Table L14 (hereinafter referred to as “Compound group SX578”).

The Compound (L-1), wherein n represents 1, $R^1$ represents a methyl group, T represents a 3,4-bis(trifluoromethyl) phenyl group, $R^{3b}$ represents an iodine atom, and $R^{3c}$ represents any one substituent described in Table L12 to Table L14 (hereinafter referred to as “Compound group SX579”).

The Compound (L-1), wherein n represents 1, $R^1$ represents a methyl group, T represents a 3,4-bis(trifluoromethyl) phenyl group, $R^{3b}$ represents $CF_3$, and $R^{3c}$ represents any one substituent described in Table L12 to Table L14 (hereinafter referred to as “Compound group SX580”).

The Compound (L-1), wherein n represents 1, $R^1$ represents a methyl group, T represents a 3,5-bis[(trifluoromethyl)thio]phenyl group, $R^{3b}$ represents a hydrogen atom, and $R^{3c}$ represents any one substituent described in Table L12 to Table L14 (hereinafter referred to as “Compound group SX581”).

The Compound (L-1), wherein n represents 1, $R^1$ represents a methyl group, T represents a 3,5-bis[(trifluoromethyl)thio]phenyl group, $R^{3b}$ represents a chlorine atom, and $R^{3c}$ represents any one substituent described in Table L12 to Table L14 (hereinafter referred to as “Compound group SX582”).

The Compound (L-1), wherein n represents 1, $R^1$ represents a methyl group, T represents a 3,5-bis[(trifluoromethyl)thio]phenyl group, $R^{3b}$ represents a bromine atom, and $R^{3c}$ represents any one substituent described in Table L12 to Table L14 (hereinafter referred to as “Compound group SX583”).

The Compound (L-1), wherein n represents 1, $R^1$ represents a methyl group, T represents a 3,5-bis[(trifluoromethyl)thio]phenyl group, $R^{3b}$ represents an iodine atom, and $R^{3c}$ represents any one substituent described in Table L12 to Table L14 (hereinafter referred to as “Compound group SX584”).

The Compound (L-1), wherein n represents 1, $R^1$ represents a methyl group, T represents a 3,5-bis[(trifluoromethyl)thio]phenyl group, $R^{3b}$ represents $CF_3$, and $R^{3c}$ represents any one substituent described in Table L12 to Table L14 (hereinafter referred to as “Compound group SX585”).

The Compound (L-1), wherein n represents 1, $R^1$ represents a methyl group, T represents a 3,5-bis(trifluoromethoxy)phenyl group, $R^{3b}$ represents a hydrogen atom, and $R^{3c}$ represents any one substituent described in Table L12 to Table L14 (hereinafter referred to as “Compound group SX586”).

The Compound (L-1), wherein n represents 1, $R^1$ represents a methyl group, T represents a 3,5-bis(trifluoromethoxy)phenyl group, $R^{3b}$ represents a chlorine atom, and $R^{3c}$ represents any one substituent described in Table L12 to Table L14 (hereinafter referred to as "Compound group SX587").

The Compound (L-1), wherein n represents 1, $R^1$ represents a methyl group, T represents a 3,5-bis(trifluoromethoxy)phenyl group, $R^{3b}$ represents a bromine atom, and $R^{3c}$ represents any one substituent described in Table L12 to Table L14 (hereinafter referred to as "Compound group SX588").

The Compound (L-1), wherein n represents 1, $R^1$ represents a methyl group, T represents a 3,5-bis(trifluoromethoxy)phenyl group, $R^{3b}$ represents an iodine atom, and $R^{3c}$ represents any one substituent described in Table L12 to Table L14 (hereinafter referred to as "Compound group SX589").

The Compound (L-1), wherein n represents 1, $R^1$ represents a methyl group, T represents a 3,5-bis(trifluoromethoxy)phenyl group, $R^{3b}$ represents $CF_3$, and $R^{3c}$ represents any one substituent described in Table L12 to Table L14 (hereinafter referred to as "Compound group SX590").

The Compound (L-1), wherein n represents 1, $R^1$ represents a methyl group, T represents a 3,5-bis(trifluoromethyl) phenyl group, $R^{3b}$ represents a hydrogen atom, and $R^{3c}$ represents any one substituent described in Table L12 to Table L14 (hereinafter referred to as "Compound group SX591").

The Compound (L-1), wherein n represents 1, $R^1$ represents a methyl group, T represents a 3,5-bis(trifluoromethyl) phenyl group, $R^{3b}$ represents a chlorine Table L12 to Table L14 (hereinafter referred to as "Compound group SX592").

The Compound (L-1), wherein n represents 1, $R^1$ represents a methyl group, T represents a 3,5-bis(trifluoromethyl) phenyl group, $R^{3b}$ represents a bromine atom, and $R^{3c}$ represents any one substituent described in Table L12 to Table L14 (hereinafter referred to as "Compound group SX593").

The Compound (L-1), wherein n represents 1, $R^1$ represents a methyl group, T represents a 3,5-bis(trifluoromethyl) phenyl group, $R^{3b}$ represents an iodine atom, and $R^{3c}$ represents any one substituent described in Table L12 to Table L14 (hereinafter referred to as "Compound group SX594").

The Compound (L-1), wherein n represents 1, $R^1$ represents a methyl group, T represents a 3,5-bis(trifluoromethyl) phenyl group, $R^{3b}$ represents $CF_3$, and $R^{3c}$ represents any one substituent described in Table L12 to Table L14 (hereinafter referred to as "Compound group SX595").

The Compound (L-1), wherein n represents 1, $R^1$ represents a methyl group, T represents a 3-fluoro-5-(trifluoromethoxy)phenyl group, $R^{3b}$ represents a hydrogen Table L12 to Table L14 (hereinafter referred to as "Compound group SX596").

The Compound (L-1), wherein n represents 1, $R^1$ represents a methyl group, T represents a 3-fluoro-5-(trifluoromethoxy)phenyl group, $R^{3b}$ represents a chlorine atom, and $R^{3c}$ represents any one substituent described in Table L12 to Table L14 (hereinafter referred to as "Compound group SX597").

The Compound (L-1), wherein n represents 1, $R^1$ represents a methyl group, T represents a 3-fluoro-5-(trifluoromethoxy)phenyl group, $R^{3b}$ represents a bromine atom, and $R^{3c}$ represents any one substituent described in Table L12 to Table L14 (hereinafter referred to as "Compound group SX598").

The Compound (L-1), wherein n represents 1, $R^1$ represents a methyl group, T represents a 3-fluoro-5-(trifluoromethoxy)phenyl group, $R^{3b}$ represents an iodine atom, and $R^{3c}$ represents any one substituent described in Table L12 to Table L14 (hereinafter referred to as "Compound group SX599").

The Compound (L-1), wherein n represents 1, $R^1$ represents a methyl group, T represents a 3-fluoro-5-(trifluoromethoxy)phenyl group, $R^{3b}$ represents $CF_3$, and $R^{3c}$ represents any one substituent described in Table L12 to Table L14 (hereinafter referred to as "Compound group SX600").

The Compound (L-1), wherein n represents 2, $R^1$ represents a methyl group, T represents a 3-[(trifluoromethyl) thio]phenyl group, $R^{3b}$ represents a hydrogen atom, and $R^{3c}$ represents any one substituent described in Table L12 to Table L14 (hereinafter referred to as "Compound group SX601").

The Compound (L-1), wherein n represents 2, $R^1$ represents a methyl group, T represents a 3-[(trifluoromethyl) thio]phenyl group, $R^{3b}$ represents a chlorine atom, and $R^{3c}$ represents any one substituent described in Table L12 to Table L14 (hereinafter referred to as "Compound group SX602").

The Compound (L-1), wherein n represents 2, $R^1$ represents a methyl group, T represents a 3-[(trifluoromethyl) thio]phenyl group, $R^{3b}$ represents a bromine atom, and $R^{3c}$ represents any one substituent described in Table L12 to Table L14 (hereinafter referred to as "Compound group SX603").

The Compound (L-1), wherein n represents 2, $R^1$ represents a methyl group, T represents a 3-[(trifluoromethyl) thio]phenyl group, $R^{3b}$ represents an iodine atom, and $R^{3c}$ represents any one substituent described in Table L12 to Table L14 (hereinafter referred to as "Compound group SX604").

The Compound (L-1), wherein n represents 2, $R^1$ represents a methyl group, T represents a 3-[(trifluoromethyl) thio]phenyl group, $R^{3b}$ represents $CF_3$, and $R^{3c}$ represents any one substituent described in Table L12 to Table L14 (hereinafter referred to as "Compound group SX605").

The Compound (L-1), wherein n represents 2, $R^1$ represents a methyl group, T represents a 4-[(trifluoromethyl) thio]phenyl group, $R^{3b}$ represents a hydrogen atom, and $R^{3c}$ represents any one substituent described in Table L12 to Table L14 (hereinafter referred to as "Compound group SX606").

The Compound (L-1), wherein n represents 2, $R^1$ represents a methyl group, T represents a 4-[(trifluoromethyl) thio]phenyl group, $R^{3b}$ represents a chlorine atom, and $R^{3c}$ represents any one substituent described in Table L12 to Table L14 (hereinafter referred to as "Compound group SX607").

The Compound (L-1), wherein n represents 2, $R^1$ represents a methyl group, T represents a 4-[(trifluoromethyl) thio]phenyl group, $R^{3b}$ represents a bromine atom, and $R^{3c}$ represents any one substituent described in Table L12 to Table L14 (hereinafter referred to as "Compound group SX608").

The Compound (L-1), wherein n represents 2, $R^1$ represents a methyl group, T represents a 4-[(trifluoromethyl) thio]phenyl group, $R^{3b}$ represents an iodine atom, and $R^{3c}$ represents any one substituent described in Table L12 to Table L14 (hereinafter referred to as "Compound group SX609").

The Compound (L-1), wherein n represents 2, $R^1$ represents a methyl group, T represents a 4-[(trifluoromethyl) thio]phenyl group, $R^{3b}$ represents $CF_3$, and $R^{3c}$ represents any one substituent described in Table L12 to Table L14 (hereinafter referred to as "Compound group SX610").

The Compound (L-1), wherein n represents 2, $R^1$ represents an ethyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX611").

The Compound (L-1), wherein n represents 2, $R^1$ represents an ethyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX612").

The Compound (L-1), wherein n represents 2, $R^1$ represents an ethyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX613").

The Compound (L-1), wherein n represents 2, $R^1$ represents an ethyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX614").

The Compound (L-1), wherein n represents 2, $R^1$ represents an ethyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX615").

The Compound (L-1), wherein n represents 2, $R^1$ represents an ethyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX616").

The Compound (L-1), wherein n represents 2, $R^1$ represents an ethyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX617").

The Compound (L-1), wherein n represents 2, $R^1$ represents an ethyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX618").

The Compound (L-1), wherein n represents 2, $R^1$ represents an ethyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX619").

The Compound (L-1), wherein n represents 2, $R^1$ represents an ethyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX620").

The Compound (L-1), wherein n represents 2, $R^1$ represents an isopropyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX621").

The Compound (L-1), wherein n represents 2, $R^1$ represents an isopropyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX622").

The Compound (L-1), wherein n represents 2, $R^1$ represents an isopropyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX623").

The Compound (L-1), wherein n represents 2, $R^1$ represents an isopropyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX624").

The Compound (L-1), wherein n represents 2, $R^1$ represents an isopropyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX625").

The Compound (L-1), wherein n represents 2, $R^1$ represents an isopropyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX626").

The Compound (L-1), wherein n represents 2, $R^1$ represents an isopropyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX627").

The Compound (L-1), wherein n represents 2, $R^1$ represents an isopropyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX628").

The Compound (L-1), wherein n represents 2, $R^1$ represents an isopropyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX629").

The Compound (L-1), wherein n represents 2, $R^1$ represents an isopropyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX630").

The Compound (L-1), wherein n represents 2, $R^1$ represents a methyl group, T represents a 4-(trifluoromethoxy)phenyl group, $R^{3b}$ represents a hydrogen atom, and $R^{3c}$ represents any one substituent described in Table L12 to Table L14 (hereinafter referred to as "Compound group SX631").

The Compound (L-1), wherein n represents 2, $R^1$ represents a methyl group, T represents a 4-(trifluoromethoxy)phenyl group, $R^{3b}$ represents a chlorine atom, and $R^{3c}$ represents any one substituent described in Table L12 to Table L14 (hereinafter referred to as "Compound group SX632").

The Compound (L-1), wherein n represents 2, $R^1$ represents a methyl group, T represents a 4-(trifluoromethoxy)phenyl group, $R^{3b}$ represents a bromine atom, and $R^{3c}$ represents any one substituent described in Table L12 to Table L14 (hereinafter referred to as "Compound group SX633").

The Compound (L-1), wherein n represents 2, $R^1$ represents a methyl group, T represents a 4-(trifluoromethoxy) phenyl group, $R^{3b}$ represents an iodine atom, and $R^{3c}$ represents any one substituent described in Table L12 to Table L14 (hereinafter referred to as "Compound group SX634").

The Compound (L-1), wherein n represents 2, $R^1$ represents a methyl group, T represents a 4-(trifluoromethoxy) phenyl group, $R^{3b}$ represents $CF_3$, and $R^{3c}$ represents any one substituent described in Table L12 to Table L14 (hereinafter referred to as "Compound group SX635").

The Compound (L-1), wherein n represents 2, $R^1$ represents a methyl group, T represents a 4-(trifluoromethyl) phenyl group, $R^{3b}$ represents a hydrogen atom, and $R^{3c}$ represents any one substituent described in Table L12 to Table L14 (hereinafter referred to as "Compound group SX636").

The Compound (L-1), wherein n represents 2, $R^1$ represents a methyl group, T represents a 4-(trifluoromethyl) phenyl group, $R^{3b}$ represents a chlorine atom, and $R^{3c}$ represents any one substituent described in Table L12 to Table L14 (hereinafter referred to as "Compound group SX637").

The Compound (L-1), wherein n represents 2, $R^1$ represents a methyl group, T represents a 4-(trifluoromethyl) phenyl group, $R^{3b}$ represents a bromine atom, and $R^{3c}$ represents any one substituent described in Table L12 to Table L14 (hereinafter referred to as "Compound group SX638").

The Compound (L-1), wherein n represents 2, $R^1$ represents a methyl group, T represents a 4-(trifluoromethyl) phenyl group, $R^{3b}$ represents an iodine atom, and $R^{3c}$ represents any one substituent described in Table L12 to Table L14 (hereinafter referred to as "Compound group SX639").

The Compound (L-1), wherein n represents 2, $R^1$ represents a methyl group, T represents a 4-(trifluoromethyl) phenyl group, $R^{3b}$ represents $CF_3$, and $R^{3e}$ represents any one substituent described in Table L12 to Table L14 (hereinafter referred to as "Compound group SX640").

The Compound (L-1), wherein n represents 2, $R^1$ represents a methyl group, T represents a 3,4-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX641").

The Compound (L-1), wherein n represents 2, $R^1$ represents a methyl group, T represents a 3,4-bis[(trifluoromethyl)thio]phenyl group, $R^{3b}$ represents a chlorine atom, and $R^{3c}$ represents any one substituent described in Table L12 to Table L14 (hereinafter referred to as "Compound group SX642").

The Compound (L-1), wherein n represents 2, $R^1$ represents a methyl group, T represents a 3,4-bis[(trifluoromethyl)thio]phenyl group, $R^{3b}$ represents a bromine atom, and $R^{3c}$ represents any one substituent described in Table L12 to Table L14 (hereinafter referred to as "Compound group SX643").

The Compound (L-1), wherein n represents 2, $R^1$ represents a methyl group, T represents a 3,4-bis[(trifluoromethyl)thio]phenyl group, $R^{3b}$ represents an iodine atom, and $R^{3c}$ represents any one substituent described in Table L12 to Table L14 (hereinafter referred to as "Compound group SX644").

The Compound (L-1), wherein n represents 2, $R^1$ represents a methyl group, T represents a 3,4-bis[(trifluoromethyl)thio]phenyl group, $R^{3b}$ represents $CF_3$, and $R^{3c}$ represents any one substituent described in Table L12 to Table L14 (hereinafter referred to as "Compound group SX645").

The Compound (L-1), wherein n represents 2, $R^1$ represents a methyl group, T represents a 3,4-bis(trifluoromethoxy)phenyl group, $R^{3b}$ represents a hydrogen atom, and $R^{3c}$ represents any one substituent described in Table L12 to Table L14 (hereinafter referred to as "Compound group SX646").

The Compound (L-1), wherein n represents 2, $R^1$ represents a methyl group, T represents a 3,4-bis(trifluoromethoxy)phenyl group, $R^{3b}$ represents a chlorine atom, and $R^{3c}$ represents any one substituent described in Table L12 to Table L14 (hereinafter referred to as "Compound group SX647").

The Compound (L-1), wherein n represents 2, $R^1$ represents a methyl group, T represents a 3,4-bis(trifluoromethoxy)phenyl group, $R^{3b}$ represents a bromine atom, and $R^{3c}$ represents any one substituent described in Table L12 to Table L14 (hereinafter referred to as "Compound group SX648").

The Compound (L-1), wherein n represents 2, $R^1$ represents a methyl group, T represents a 3,4-bis(trifluoromethoxy)phenyl group, $R^{3b}$ represents an iodine atom, and $R^{3c}$ represents any one substituent described in Table L12 to Table L14 (hereinafter referred to as "Compound group SX649").

The Compound (L-1), wherein n represents 2, $R^1$ represents a methyl group, T represents a 3,4-bis(trifluoromethoxy)phenyl group, $R^{3b}$ represents $CF_3$, and $R^{3c}$ represents any one substituent described in Table L12 to Table L14 (hereinafter referred to as "Compound group SX650").

The Compound (L-1), wherein n represents 2, $R^1$ represents a methyl group, T represents a 3,4-bis(trifluoromethyl) phenyl group, $R^{3b}$ represents a hydrogen atom, and $R^{3c}$ represents any one substituent described in Table L12 to Table L14 (hereinafter referred to as "Compound group SX651").

The Compound (L-1), wherein n represents 2, $R^1$ represents a methyl group, T represents a 3,4-bis(trifluoromethyl) phenyl group, $R^{3b}$ represents a chlorine atom, and $R^{3c}$ represents any one substituent described in Table L12 to Table L14 (hereinafter referred to as "Compound group SX652").

The Compound (L-1), wherein n represents 2, $R^1$ represents a methyl group, T represents a 3,4-bis(trifluoromethyl) phenyl group, $R^{3b}$ represents a bromine atom, and $R^{3c}$ represents any one substituent described in Table L12 to Table L14 (hereinafter referred to as "Compound group SX653").

The Compound (L-1), wherein n represents 2, $R^1$ represents a methyl group, T represents a 3,4-bis(trifluoromethyl) phenyl group, $R^{3b}$ represents an iodine atom, and $R^{3c}$ represents any one substituent described in Table L12 to Table L14 (hereinafter referred to as "Compound group SX654").

The Compound (L-1), wherein n represents 2, $R^1$ represents a methyl group, T represents a 3,4-bis(trifluoromethyl) phenyl group, $R^{3b}$ represents $CF_3$, and $R^{3c}$ represents any one substituent described in Table L12 to Table L14 (hereinafter referred to as "Compound group SX655").

The Compound (L-1), wherein n represents 2, $R^1$ represents a methyl group, T represents a 3,5-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX656").

The Compound (L-1), wherein n represents 2, $R^1$ represents a methyl group, T represents a 3,5-bis[(trifluoromethyl)thio]phenyl group, $R^{3b}$ represents a chlorine atom, and $R^{3c}$ represents any one substituent described in Table L12 to Table L14 (hereinafter referred to as "Compound group SX657").

The Compound (L-1), wherein n represents 2, $R^1$ represents a methyl group, T represents a 3,5-bis[(trifluoromethyl)thio]phenyl group, $R^{3b}$ represents a bromine atom, and $R^{3c}$ represents any one substituent described in Table L12 to Table L14 (hereinafter referred to as "Compound group SX658").

The Compound (L-1), wherein n represents 2, $R^1$ represents a methyl group, T represents a 3,5-bis[(trifluoromethyl)thio]phenyl group, $R^{3b}$ represents an iodine atom, and $R^{3c}$ represents any one substituent described in Table L12 to Table L14 (hereinafter referred to as "Compound group SX659").

The Compound (L-1), wherein n represents 2, $R^1$ represents a methyl group, T represents a 3,5-bis[(trifluoromethyl)thio]phenyl group, $R^{3b}$ represents $CF_3$, and $R^{3c}$ represents any one substituent described in Table L12 to Table L14 (hereinafter referred to as "Compound group SX660").

The Compound (L-1), wherein n represents 2, $R^1$ represents a methyl group, T represents a 3,5-bis(trifluoromethoxy)phenyl group, $R^{3b}$ represents a hydrogen atom, and $R^{3c}$ represents any one substituent described in Table L12 to Table L14 (hereinafter referred to as "Compound group SX661").

The Compound (L-1), wherein n represents 2, $R^1$ represents a methyl group, T represents a 3,5-bis(trifluoromethoxy)phenyl group, $R^{3b}$ represents a chlorine atom, and $R^{3c}$ represents any one substituent described in Table L12 to Table L14 (hereinafter referred to as "Compound group SX662").

The Compound (L-1), wherein n represents 2, $R^1$ represents a methyl group, T represents a 3,5-bis(trifluoromethoxy)phenyl group, $R^{3b}$ represents a bromine atom, and $R^{3c}$ represents any one substituent described in Table L12 to Table L14 (hereinafter referred to as "Compound group SX663").

The Compound (L-1), wherein n represents 2, $R^1$ represents a methyl group, T represents a 3,5-bis(trifluoromethoxy)phenyl group, $R^{3b}$ represents an iodine atom, and $R^{3c}$ represents any one substituent described in Table L12 to Table L14 (hereinafter referred to as "Compound group SX664").

The Compound (L-1), wherein n represents 2, $R^1$ represents a methyl group, T represents a 3,5-bis(trifluoromethoxy)phenyl group, $R^{3b}$ represents $CF_3$, and $R^{3c}$ represents any one substituent described in Table L12 to Table L14 (hereinafter referred to as "Compound group SX665").

The Compound (L-1), wherein n represents 2, $R^1$ represents a methyl group, T represents a 3,5-bis(trifluoromethyl)phenyl group, $R^{3b}$ represents a hydrogen atom, and $R^{3c}$ represents any one substituent described in Table L12 to Table L14 (hereinafter referred to as "Compound group SX666").

The Compound (L-1), wherein n represents 2, $R^1$ represents a methyl group, T represents a 3,5-bis(trifluoromethyl)phenyl group, $R^{3b}$ represents a chlorine atom, and $R^{3c}$ represents any one substituent described in Table L12 to Table L14 (hereinafter referred to as "Compound group SX667").

The Compound (L-1), wherein n represents 2, $R^1$ represents a methyl group, T represents a 3,5-bis(trifluoromethyl)phenyl group, $R^{3b}$ represents a bromine atom, and $R^{3c}$ represents any one substituent described in Table L12 to Table L14 (hereinafter referred to as "Compound group SX668").

The Compound (L-1), wherein n represents 2, $R^1$ represents a methyl group, T represents a 3,5-bis(trifluoromethyl)phenyl group, $R^{3b}$ represents an iodine atom, and $R^{3c}$ represents any one substituent described in Table L12 to Table L14 (hereinafter referred to as "Compound group SX669").

The Compound (L-1), wherein n represents 2, $R^1$ represents a methyl group, T represents a 3,5-bis(trifluoromethyl)phenyl group, $R^{3b}$ represents $CF_3$, and $R^{3c}$ represents any one substituent described in Table L12 to Table L14 (hereinafter referred to as "Compound group SX670").

The Compound (L-1), wherein n represents 2, $R^1$ represents a methyl group, T represents a 3-fluoro-5-(trifluoromethoxy)phenyl group, $R^{3b}$ represents a hydrogen atom, and $R^{3c}$ represents any one substituent described in Table L12 to Table L14 (hereinafter referred to as "Compound group SX671").

The Compound (L-1), wherein n represents 2, $R^1$ represents a methyl group, T represents a 3-fluoro-5-(trifluoromethoxy)phenyl group, $R^{3b}$ represents a chlorine atom, and $R^{3c}$ represents any one substituent described in Table L12 to Table L14 (hereinafter referred to as "Compound group SX672").

The Compound (L-1), wherein n represents 2, $R^1$ represents a methyl group, T represents a 3-fluoro-5-(trifluoromethoxy)phenyl group, $R^{3b}$ represents a bromine atom, and $R^{3c}$ represents any one substituent described in Table L12 to Table L14 (hereinafter referred to as "Compound group SX673").

The Compound (L-1), wherein n represents 2, $R^1$ represents a methyl group, T represents a 3-fluoro-5-(trifluoromethoxy)phenyl group, $R^{3b}$ represents an iodine atom, and $R^{3c}$ represents any one substituent described in Table L12 to Table L14 (hereinafter referred to as "Compound group SX674").

The Compound (L-1), wherein n represents 2, $R^1$ represents a methyl group, T represents a 3-fluoro-5-(trifluoromethoxy)phenyl group, $R^{3b}$ represents $CF_3$, and $R^{3c}$ represents any one substituent described in Table L12 to Table L14 (hereinafter referred to as "Compound group SX675").

A compound represented by formula (L-2)

(L-2)

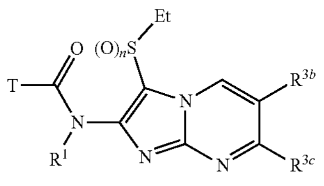

(hereinafter referred to as "Compound (L-2)"), wherein n represents 0, $R^1$ represents a methyl group, $R^{3b}$ represents a hydrogen atom, $R^{3c}$ represents a hydrogen atom, and T represents any one substituent described in Table L1 to Table L11 (hereinafter referred to as "Compound group SX676").

The Compound (L-2), wherein n represents 0, $R^1$ represents a methyl group, $R^{3b}$ represents a chlorine atom, $R^{3c}$ represents a hydrogen atom, and T represents any one substituent described in Table L1 to Table L11 (hereinafter referred to as "Compound group SX677").

The Compound (L-2), wherein n represents 0, $R^1$ represents a methyl group, $R^{21}$ represents a bromine atom, $R^{3c}$ represents a hydrogen atom, and T represents any one substituent described in Table L1 to Table L11 (hereinafter referred to as "Compound group SX678").

The Compound (L-2), wherein n represents 0, $R^1$ represents a methyl group, $R^{21}$ represents an iodine atom, $R^{3c}$ represents a hydrogen atom, and T represents any one substituent described in Table L1 to Table L11 (hereinafter referred to as "Compound group SX679").

The Compound (L-2), wherein n represents 0, $R^1$ represents a methyl group, $R^{3b}$ represents $CF_3$, $R^{3e}$ represents a hydrogen atom, and T represents any one substituent described in Table L1 to Table L11 (hereinafter referred to as "Compound group SX680").

The Compound (L-2), wherein n represents 0, $R^1$ represents a methyl group, $R^{3b}$ represents a hydrogen atom, $R^{3c}$ represents a chlorine atom, and T represents any one substituent described in Table L1 to Table L11 (hereinafter referred to as "Compound group SX681").

The Compound (L-2), wherein n represents 0, $R^1$ represents a methyl group, $R^{3b}$ represents a chlorine atom, $R^{3c}$ represents a chlorine atom, and T represents any one substituent described in Table L1 to Table L11 (hereinafter referred to as "Compound group SX682").

The Compound (L-2), wherein n represents 0, $R^1$ represents a methyl group, $R^{3b}$ represents a bromine atom, $R^{3c}$ represents a chlorine atom, and T represents any one substituent described in Table L1 to Table L11 (hereinafter referred to as "Compound group SX683").

The Compound (L-2), wherein n represents 0, $R^1$ represents a methyl group, $R^{3b}$ represents an iodine atom, $R^{3c}$ represents a chlorine atom, and T represents any one substituent described in Table L1 to Table L11 (hereinafter referred to as "Compound group SX684").

The Compound (L-2), wherein n represents 0, $R^1$ represents a methyl group, $R^{3b}$ represents $CF_3$, $R^{3c}$ represents a chlorine atom, and T represents any one substituent described in Table L1 to Table L11 (hereinafter referred to as "Compound group SX685").

The Compound (L-2), wherein n represents 0, $R^1$ represents a methyl group, $R^{3b}$ represents a hydrogen atom, $R^{3c}$ represents a bromine atom, and T represents any one substituent described in Table L1 to Table L11 (hereinafter referred to as "Compound group SX686").

The Compound (L-2), wherein n represents 0, $R^1$ represents a methyl group, $R^{3b}$ represents a chlorine atom, $R^{3c}$ represents a bromine atom, and T represents any one substituent described in Table L1 to Table L11 (hereinafter referred to as "Compound group SX687").

The Compound (L-2), wherein n represents 0, $R^1$ represents a methyl group, $R^{3b}$ represents a bromine atom, $R^{3c}$ represents a bromine atom, and T represents any one substituent described in Table L1 to Table L11 (hereinafter referred to as "Compound group SX688").

The Compound (L-2), wherein n represents 0, $R^1$ represents a methyl group, $R^{3b}$ represents an iodine atom, $R^{3c}$ represents a bromine atom, and T represents any one substituent described in Table L1 to Table L11 (hereinafter referred to as "Compound group SX689").

The Compound (L-2), wherein n represents 0, $R^1$ represents a methyl group, $R^{3b}$ represents $CF_3$, $R^{3c}$ represents a bromine atom, and T represents any one substituent described in Table L1 to Table L11 (hereinafter referred to as "Compound group SX690").

The Compound (L-2), wherein n represents 0, $R^1$ represents a methyl group, $R^{3b}$ represents a hydrogen atom, $R^{3c}$ represents an iodine atom, and T represents any one substituent described in Table L1 to Table L11 (hereinafter referred to as "Compound group SX691").

The Compound (L-2), wherein n represents 0, $R^1$ represents a methyl group, $R^{3b}$ represents a chlorine atom, $R^{3c}$ represents an iodine atom, and T represents any one substituent described in Table L1 to Table L11 (hereinafter referred to as "Compound group SX692").

The Compound (L-2), wherein n represents 0, $R^1$ represents a methyl group, $R^{3b}$ represents a bromine atom, $R^{3c}$ represents an iodine atom, and T represents any one substituent described in Table L1 to Table L11 (hereinafter referred to as "Compound group SX693").

The Compound (L-2), wherein n represents 0, $R^1$ represents a methyl group, $R^{3b}$ represents an iodine atom, $R^{3c}$ represents an iodine atom, and T represents any one substituent described in Table L1 to Table L11 (hereinafter referred to as "Compound group SX694").

The Compound (L-2), wherein n represents 0, $R^1$ represents a methyl group, $R^{3b}$ represents $CF_3$, $R^{3c}$ represents an iodine atom, and T represents any one substituent described in Table L1 to Table L11 (hereinafter referred to as "Compound group SX695").

The Compound (L-2), wherein n represents 0, $R^1$ represents a methyl group, $R^{3b}$ represents a hydrogen atom, $R^{3c}$ represents $CF_3$, and T represents any one substituent described in Table L1 to Table L11 (hereinafter referred to as "Compound group SX696").

The Compound (L-2), wherein n represents 0, $R^1$ represents a methyl group, $R^{3b}$ represents a chlorine atom, $R^{3c}$ represents $CF_3$, and T represents any one substituent described in Table L1 to Table L11 (hereinafter referred to as "Compound group SX697").

The Compound (L-2), wherein n represents 0, $R^1$ represents a methyl group, $R^{3b}$ represents a bromine atom, $R^{3c}$ represents $CF_3$, and T represents any one substituent described in Table L1 to Table L11 (hereinafter referred to as "Compound group SX698").

The Compound (L-2), wherein n represents 0, $R^1$ represents a methyl group, $R^{3b}$ represents an iodine atom, $R^{3c}$ represents $CF_3$, and T represents any one substituent described in Table L1 to Table L11 (hereinafter referred to as "Compound group SX699").

The Compound (L-2), wherein n represents 0, $R^1$ represents a methyl group, $R^{3b}$ represents $CF_3$, $R^{3c}$ represents $CF_3$, and T represents any one substituent described in Table L1 to Table L11 (hereinafter referred to as "Compound group SX700").

The Compound (L-2), wherein n represents 0, $R^1$ represents an ethyl group, $R^{3b}$ represents a hydrogen atom, $R^{3c}$ represents a hydrogen atom, and T represents any one substituent described in Table L1 to Table L11 (hereinafter referred to as "Compound group SX701").

The Compound (L-2), wherein n represents 0, $R^1$ represents an ethyl group, $R^{3b}$ represents a chlorine atom, $R^{3c}$ represents a hydrogen atom, and T represents any one substituent described in Table L1 to Table L11 (hereinafter referred to as "Compound group SX702").

The Compound (L-2), wherein n represents 0, $R^1$ represents an ethyl group, $R^{3b}$ represents a bromine atom, $R^{3c}$ represents a hydrogen atom, and T represents any one substituent described in Table L1 to Table L11 (hereinafter referred to as "Compound group SX703").

The Compound (L-2), wherein n represents 0, $R^1$ represents an ethyl group, $R^{3b}$ represents an iodine atom, $R^{3c}$ represents a hydrogen atom, and T represents any one substituent described in Table L1 to Table L11 (hereinafter referred to as "Compound group SX704").

The Compound (L-2), wherein n represents 0, $R^1$ represents an ethyl group, $R^{3b}$ represents $CF_3$, $R^{3c}$ represents a hydrogen atom, and T represents any one substituent described in Table L1 to Table L11 (hereinafter referred to as "Compound group SX705").

The Compound (L-2), wherein n represents 0, $R^1$ represents an ethyl group, $R^{3b}$ represents a hydrogen atom, $R^{3c}$ represents a chlorine atom, and T represents any one substituent described in Table L1 to Table L11 (hereinafter referred to as "Compound group SX706").

The Compound (L-2), wherein n represents 0, $R^1$ represents an ethyl group, $R^{3b}$ represents a chlorine atom, $R^{3c}$ represents a chlorine atom, and T represents any one substituent described in Table L1 to Table L11 (hereinafter referred to as "Compound group SX707").

The Compound (L-2), wherein n represents 0, $R^1$ represents an ethyl group, $R^{3b}$ represents a bromine atom, $R^{3c}$ represents a chlorine atom, and T represents any one substituent described in Table L1 to Table L11 (hereinafter referred to as "Compound group SX708").

The Compound (L-2), wherein n represents 0, $R^1$ represents an ethyl group, $R^{3b}$ represents an iodine atom, $R^{3c}$ represents a chlorine atom, and T represents any one substituent described in Table L1 to Table L11 (hereinafter referred to as "Compound group SX709").

The Compound (L-2), wherein n represents 0, $R^1$ represents an ethyl group, $R^{3b}$ represents $CF_3$, $R^{3c}$ represents a chlorine atom, and T represents any one substituent described in Table L1 to Table L11 (hereinafter referred to as "Compound group SX710").

The Compound (L-2), wherein n represents 0, $R^1$ represents an ethyl group, $R^{3b}$ represents a hydrogen atom, $R^{3c}$ represents a bromine atom, and T represents any one substituent described in Table L1 to Table L11 (hereinafter referred to as "Compound group SX711").

The Compound (L-2), wherein n represents 0, $R^1$ represents an ethyl group, $R^{3b}$ represents a chlorine atom, $R^{3c}$ represents a bromine atom, and T represents any one substituent described in Table L1 to Table L11 (hereinafter referred to as "Compound group SX712").

The Compound (L-2), wherein n represents 0, $R^1$ represents an ethyl group, $R^{3b}$ represents a bromine atom, $R^{3c}$ represents a bromine atom, and T represents any one substituent described in Table L1 to Table L11 (hereinafter referred to as "Compound group SX713").

The Compound (L-2), wherein n represents 0, $R^1$ represents an ethyl group, $R^{3b}$ represents an iodine atom, $R^{3c}$ represents a bromine atom, and T represents any one substituent described in Table L1 to Table L11 (hereinafter referred to as "Compound group SX714").

The Compound (L-2), wherein n represents 0, $R^1$ represents an ethyl group, $R^{3b}$ represents $CF_3$, $R^{3c}$ represents a bromine atom, and T represents any one substituent described in Table L1 to Table L11 (hereinafter referred to as "Compound group SX715").

The Compound (L-2), wherein n represents 0, $R^1$ represents an ethyl group, $R^{3b}$ represents a hydrogen atom, $R^{3c}$ represents an iodine atom, and T represents any one substituent described in Table L1 to Table L11 (hereinafter referred to as "Compound group SX716").

The Compound (L-2), wherein n represents 0, $R^1$ represents an ethyl group, $R^{3b}$ represents a chlorine atom, $R^{3c}$ represents an iodine atom, and T represents any one substituent described in Table L1 to Table L11 (hereinafter referred to as "Compound group SX717").

The Compound (L-2), wherein n represents 0, $R^1$ represents an ethyl group, $R^{3b}$ represents a bromine atom, $R^{3c}$ represents an iodine atom, and T represents any one substituent described in Table L1 to Table L11 (hereinafter referred to as "Compound group SX718").

The Compound (L-2), wherein n represents 0, $R^1$ represents an ethyl group, $R^{3b}$ represents an iodine atom, $R^{3c}$ represents an iodine atom, and T represents any one substituent described in Table L1 to Table L11 (hereinafter referred to as "Compound group SX719").

The Compound (L-2), wherein n represents 0, $R^1$ represents an ethyl group, $R^{3b}$ represents $CF_3$, $R^{3c}$ represents an iodine atom, and T represents any one substituent described in Table L1 to Table L11 (hereinafter referred to as "Compound group SX720").

The Compound (L-2), wherein n represents 0, $R^1$ represents an ethyl group, $R^{3b}$ represents a hydrogen atom, $R^{3c}$ represents $CF_3$, and T represents any one substituent described in Table L1 to Table L11 (hereinafter referred to as "Compound group SX721").

The Compound (L-2), wherein n represents 0, $R^1$ represents an ethyl group, $R^{3b}$ represents a chlorine atom, $R^{3c}$ represents $CF_3$, and T represents any one substituent described in Table L1 to Table L11 (hereinafter referred to as "Compound group SX722").

The Compound (L-2), wherein n represents 0, $R^1$ represents an ethyl group, $R^{3b}$ represents a bromine atom, $R^{3c}$ represents $CF_3$, and T represents any one substituent described in Table L1 to Table L11 (hereinafter referred to as "Compound group SX723").

The Compound (L-2), wherein n represents 0, $R^1$ represents an ethyl group, $R^{3b}$ represents an iodine atom, $R^{3c}$ represents $CF_3$, and T represents any one substituent described in Table L1 to Table L11 (hereinafter referred to as "Compound group SX724").

The Compound (L-2), wherein n represents 0, $R^1$ represents an ethyl group, $R^{3b}$ represents $CF_3$, $R^{3c}$ represents $CF_3$, and T represents any one substituent described in Table L1 to Table L11 (hereinafter referred to as "Compound group SX725").

The Compound (L-2), wherein n represents 0, $R^1$ represents an isopropyl group, $R^{3b}$ represents a hydrogen atom, $R^{3c}$ represents a hydrogen atom, and T represents any one substituent described in Table L1 to Table L11 (hereinafter referred to as "Compound group SX726").

The Compound (L-2), wherein n represents 0, $R^1$ represents an isopropyl group, $R^{3b}$ represents a chlorine atom, $R^{3c}$ represents a hydrogen atom, and T represents any one substituent described in Table L1 to Table L11 (hereinafter referred to as "Compound group SX727").

The Compound (L-2), wherein n represents 0, $R^1$ represents an isopropyl group, $R^{3b}$ represents a bromine atom, $R^{3c}$ represents a hydrogen atom, and T represents any one substituent described in Table L1 to Table L11 (hereinafter referred to as "Compound group SX728").

The Compound (L-2), wherein n represents 0, $R^1$ represents an isopropyl group, $R^{3b}$ represents an iodine atom, $R^{3c}$ represents a hydrogen atom, and T represents any one substituent described in Table L1 to Table L11 (hereinafter referred to as "Compound group SX729").

The Compound (L-2), wherein n represents 0, $R^1$ represents an isopropyl group, $R^{3b}$ represents $CF_3$, $R^{3c}$ represents a hydrogen atom, and T represents any one substituent described in Table L1 to Table L11 (hereinafter referred to as "Compound group SX730").

The Compound (L-2), wherein n represents 0, $R^1$ represents an isopropyl group, $R^{3b}$ represents a hydrogen atom, $R^{3c}$ represents a chlorine atom, and T represents any one substituent described in Table L1 to Table L11 (hereinafter referred to as "Compound group SX731").

The Compound (L-2), wherein n represents 0, $R^1$ represents an isopropyl group, $R^{3b}$ represents a chlorine atom, $R^{3c}$ represents a chlorine atom, and T represents any one substituent described in Table L1 to Table L11 (hereinafter referred to as "Compound group SX732").

The Compound (L-2), wherein n represents 0, $R^1$ represents an isopropyl group, $R^{3b}$ represents a bromine atom, $R^{3c}$ represents a chlorine atom, and T represents any one substituent described in Table L1 to Table L11 (hereinafter referred to as "Compound group SX733").

The Compound (L-2), wherein n represents 0, $R^1$ represents an isopropyl group, $R^{3b}$ represents an iodine atom, $R^{3c}$ represents a chlorine atom, and T represents any one substituent described in Table L1 to Table L11 (hereinafter referred to as "Compound group SX734").

The Compound (L-2), wherein n represents 0, $R^1$ represents an isopropyl group, $R^{3b}$ represents $CF_3$, $R^{3c}$ represents a chlorine atom, and T represents any one substituent described in Table L1 to Table L11 (hereinafter referred to as "Compound group SX735").

The Compound (L-2), wherein n represents 0, $R^1$ represents an isopropyl group, $R^{3b}$ represents a hydrogen atom, $R^{3c}$ represents a bromine atom, and T represents any one substituent described in Table L1 to Table L11 (hereinafter referred to as "Compound group SX736").

The Compound (L-2), wherein n represents 0, $R^1$ represents an isopropyl group, $R^{3b}$ represents a chlorine atom, $R^{3c}$ represents a bromine atom, and T represents any one substituent described in Table L1 to Table L11 (hereinafter referred to as "Compound group SX737").

The Compound (L-2), wherein n represents 0, $R^1$ represents an isopropyl group, $R^{3b}$ represents a bromine atom, $R^{3c}$ represents a bromine atom, and T represents any one substituent described in Table L1 to Table L11 (hereinafter referred to as "Compound group SX738").

The Compound (L-2), wherein n represents 0, $R^1$ represents an isopropyl group, $R^{3b}$ represents an iodine atom, $R^{3c}$ represents a bromine atom, and T represents any one substituent described in Table L1 to Table L11 (hereinafter referred to as "Compound group SX739").

The Compound (L-2), wherein n represents 0, $R^1$ represents an isopropyl group, $R^{3b}$ represents $CF_3$, $R^{3c}$ represents a bromine atom, and T represents any one substituent described in Table L1 to Table L11 (hereinafter referred to as "Compound group SX740").

The Compound (L-2), wherein n represents 0, $R^1$ represents an isopropyl group, $R^{3b}$ represents a hydrogen atom, $R^{3c}$ represents an iodine atom, and T represents any one substituent described in Table L1 to Table L11 (hereinafter referred to as "Compound group SX741").

The Compound (L-2), wherein n represents 0, $R^1$ represents an isopropyl group, $R^{3b}$ represents a chlorine atom, $R^{3c}$ represents an iodine atom, and T represents any one substituent described in Table L1 to Table L11 (hereinafter referred to as "Compound group SX742").

The Compound (L-2), wherein n represents 0, $R^1$ represents an isopropyl group, $R^{3b}$ represents a bromine atom, $R^{3c}$ represents an iodine atom, and T represents any one substituent described in Table L1 to Table L11 (hereinafter referred to as "Compound group SX743").

The Compound (L-2), wherein n represents 0, $R^1$ represents an isopropyl group, $R^{3b}$ represents an iodine atom, $R^{3c}$ represents an iodine atom, and T represents any one substituent described in Table L1 to Table L11 (hereinafter referred to as "Compound group SX744").

The Compound (L-2), wherein n represents 0, $R^1$ represents an isopropyl group, $R^{3b}$ represents $CF_3$, $R^{3c}$ represents an iodine atom, and T represents any one substituent described in Table L1 to Table L11 (hereinafter referred to as "Compound group SX745").

The Compound (L-2), wherein n represents 0, $R^1$ represents an isopropyl group, $R^{3b}$ represents a hydrogen atom, $R^{3c}$ represents $CF_3$, and T represents any one substituent described in Table L1 to Table L11 (hereinafter referred to as "Compound group SX746").

The Compound (L-2), wherein n represents 0, $R^1$ represents an isopropyl group, $R^{3b}$ represents a chlorine atom, $R^{3c}$ represents $CF_3$, and T represents any one substituent described in Table L1 to Table L11 (hereinafter referred to as "Compound group SX747").

The Compound (L-2), wherein n represents 0, $R^1$ represents an isopropyl group, $R^{3b}$ represents a bromine atom, $R^{3c}$ represents $CF_3$, and T represents any one substituent described in Table L1 to Table L11 (hereinafter referred to as "Compound group SX748").

The Compound (L-2), wherein n represents 0, $R^1$ represents an isopropyl group, $R^{3b}$ represents an iodine atom, $R^{3c}$ represents $CF_3$, and T represents any one substituent described in Table L1 to Table L11 (hereinafter referred to as "Compound group SX749").

The Compound (L-2), wherein n represents 0, $R^1$ represents an isopropyl group, $R^{3b}$ represents $CF_3$, $R^{3c}$ represents $CF_3$, and T represents any one substituent described in Table L1 to Table L11 (hereinafter referred to as "Compound group SX750").

The Compound (L-2), wherein n represents 1, $R^1$ represents a methyl group, $R^{3b}$ represents a hydrogen atom, $R^{3c}$ represents a hydrogen atom, and T represents any one substituent described in Table L1 to Table L11 (hereinafter referred to as "Compound group SX751").

The Compound (L-2), wherein n represents 1, $R^1$ represents a methyl group, $R^{3b}$ represents a chlorine atom, $R^{3c}$ represents a hydrogen atom, and T represents any one substituent described in Table L1 to Table L11 (hereinafter referred to as "Compound group SX752").

The Compound (L-2), wherein n represents 1, $R^1$ represents a methyl group, $R^{3b}$ represents a bromine atom, $R^{3c}$ represents a hydrogen atom, and T represents any one substituent described in Table L1 to Table L11 (hereinafter referred to as "Compound group SX753").

The Compound (L-2), wherein n represents 1, $R^1$ represents a methyl group, $R^{3b}$ represents an iodine atom, $R^{3c}$ represents a hydrogen atom, and T represents any one substituent described in Table L1 to Table L11 (hereinafter referred to as "Compound group SX754").

The Compound (L-2), wherein n represents 1, $R^1$ represents a methyl group, $R^{3b}$ represents $CF_3$, $R^{3c}$ represents a hydrogen atom, and T represents any one substituent described in Table L1 to Table L11 (hereinafter referred to as "Compound group SX755").

The Compound (L-2), wherein n represents 1, $R^1$ represents a methyl group, $R^{3b}$ represents a hydrogen atom, $R^{3c}$ represents a chlorine atom, and T represents any one substituent described in Table L1 to Table L11 (hereinafter referred to as "Compound group SX756").

The Compound (L-2), wherein n represents 1, $R^1$ represents a methyl group, $R^{3b}$ represents a chlorine atom, $R^{3c}$ represents a chlorine atom, and T represents any one substituent described in Table L1 to Table L11 (hereinafter referred to as "Compound group SX757").

The Compound (L-2), wherein n represents 1, $R^1$ represents a methyl group, $R^{3b}$ represents a bromine atom, $R^{3c}$ represents a chlorine atom, and T represents any one substituent described in Table L1 to Table L11 (hereinafter referred to as "Compound group SX758").

The Compound (L-2), wherein n represents 1, $R^1$ represents a methyl group, $R^{3b}$ represents an iodine atom, $R^{3c}$ represents a chlorine atom, and T represents any one substituent described in Table L1 to Table L11 (hereinafter referred to as "Compound group SX759").

The Compound (L-2), wherein n represents 1, $R^1$ represents a methyl group, $R^{3b}$ represents $CF_3$, $R^{3c}$ represents a chlorine atom, and T represents any one substituent described in Table L1 to Table L11 (hereinafter referred to as "Compound group SX760").

The Compound (L-2), wherein n represents 1, $R^1$ represents a methyl group, $R^{3b}$ represents a hydrogen atom, $R^{3c}$ represents a bromine atom, and T represents any one substituent described in Table L1 to Table L11 (hereinafter referred to as "Compound group SX761").

The Compound (L-2), wherein n represents 1, $R^1$ represents a methyl group, $R^{3b}$ represents a chlorine atom, $R^{3c}$ represents a bromine atom, and T represents any one substituent described in Table L1 to Table L11 (hereinafter referred to as "Compound group SX762").

The Compound (L-2), wherein n represents 1, $R^1$ represents a methyl group, $R^{3b}$ represents a bromine atom, $R^{3c}$ represents a bromine atom, and T represents any one substituent described in Table L1 to Table L11 (hereinafter referred to as "Compound group SX763").

The Compound (L-2), wherein n represents 1, $R^1$ represents a methyl group, $R^{3b}$ represents an iodine atom, $R^{3c}$ represents a bromine atom, and T represents any one substituent described in Table L1 to Table L11 (hereinafter referred to as "Compound group SX764").

The Compound (L-2), wherein n represents 1, $R^1$ represents a methyl group, $R^{3b}$ represents $CF_3$, $R^{3c}$ represents a bromine atom, and T represents any one substituent described in Table L1 to Table L11 (hereinafter referred to as "Compound group SX765").

The Compound (L-2), wherein n represents 1, $R^1$ represents a methyl group, $R^{3b}$ represents a hydrogen atom, $R^{3c}$ represents an iodine atom, and T represents any one substituent described in Table L1 to Table L11 (hereinafter referred to as "Compound group SX766").

The Compound (L-2), wherein n represents 1, $R^1$ represents a methyl group, $R^{3b}$ represents a chlorine atom, $R^{3c}$ represents an iodine atom, and T represents any one substituent described in Table L1 to Table L11 (hereinafter referred to as "Compound group SX767").

The Compound (L-2), wherein n represents 1, $R^1$ represents a methyl group, $R^{3b}$ represents a bromine atom, $R^{3c}$ represents an iodine atom, and T represents any one substituent described in Table L1 to Table L11 (hereinafter referred to as "Compound group SX768").

The Compound (L-2), wherein n represents 1, $R^1$ represents a methyl group, $R^{3b}$ represents an iodine atom, $R^{3c}$ represents an iodine atom, and T represents any one substituent described in Table L1 to Table L11 (hereinafter referred to as "Compound group SX769").

The Compound (L-2), wherein n represents 1, $R^1$ represents a methyl group, $R^{3b}$ represents $CF_3$, $R^{3c}$ represents an iodine atom, and T represents any one substituent described in Table L1 to Table L11 (hereinafter referred to as "Compound group SX770").

The Compound (L-2), wherein n represents 1, $R^1$ represents a methyl group, $R^{3b}$ represents a hydrogen atom, $R^{3c}$ represents $CF_3$, and T represents any one substituent described in Table L1 to Table L11 (hereinafter referred to as "Compound group SX771").

The Compound (L-2), wherein n represents 1, $R^1$ represents a methyl group, $R^{3b}$ represents a chlorine atom, $R^{3c}$ represents $CF_3$, and T represents any one substituent described in Table L1 to Table L11 (hereinafter referred to as "Compound group SX772").

The Compound (L-2), wherein n represents 1, $R^1$ represents a methyl group, $R^{3b}$ represents a bromine atom, $R^{3c}$ represents $CF_3$, and T represents any one substituent described in Table L1 to Table L11 (hereinafter referred to as "Compound group SX773").

The Compound (L-2), wherein n represents 1, $R^1$ represents a methyl group, $R^{3b}$ represents an iodine atom, $R^{3c}$ represents $CF_3$, and T represents any one substituent described in Table L1 to Table L11 (hereinafter referred to as "Compound group SX774").

The Compound (L-2), wherein n represents 1, $R^1$ represents a methyl group, $R^{3b}$ represents $CF_3$, $R^{3c}$ represents $CF_3$, and T represents any one substituent described in Table L1 to Table L11 (hereinafter referred to as "Compound group SX775").

The Compound (L-2), wherein n represents 1, $R^1$ represents an ethyl group, $R^{3b}$ represents a hydrogen atom, $R^{3c}$ represents a hydrogen atom, and T represents any one substituent described in Table L1 to Table L11 (hereinafter referred to as "Compound group SX776").

The Compound (L-2), wherein n represents 1, $R^1$ represents an ethyl group, $R^{3b}$ represents a chlorine atom, $R^{3c}$ represents a hydrogen atom, and T represents any one substituent described in Table L1 to Table L11 (hereinafter referred to as "Compound group SX777").

The Compound (L-2), wherein n represents 1, $R^1$ represents an ethyl group, $R^{3b}$ represents a bromine atom, $R^{3c}$ represents a hydrogen atom, and T represents any one substituent described in Table L1 to Table L11 (hereinafter referred to as "Compound group SX778").

The Compound (L-2), wherein n represents 1, $R^1$ represents an ethyl group, $R^{3b}$ represents an iodine atom, $R^{3c}$ represents a hydrogen atom, and T represents any one substituent described in Table L1 to Table L11 (hereinafter referred to as "Compound group SX779").

The Compound (L-2), wherein n represents 1, $R^1$ represents an ethyl group, $R^{3b}$ represents $CF_3$, $R^{3c}$ represents a hydrogen atom, and T represents any one substituent described in Table L1 to Table L11 (hereinafter referred to as "Compound group SX780").

The Compound (L-2), wherein n represents 1, $R^1$ represents an ethyl group, $R^{3b}$ represents a hydrogen atom, $R^{3c}$ represents a chlorine atom, and T represents any one substituent described in Table L1 to Table L11 (hereinafter referred to as "Compound group SX781").

The Compound (L-2), wherein n represents 1, $R^1$ represents an ethyl group, $R^{3b}$ represents a chlorine atom, $R^{3c}$ represents a chlorine atom, and T represents any one substituent described in Table L1 to Table L11 (hereinafter referred to as "Compound group SX782").

The Compound (L-2), wherein n represents 1, $R^1$ represents an ethyl group, $R^{3b}$ represents a bromine atom, $R^{3c}$ represents a chlorine atom, and T represents any one substituent described in Table L1 to Table L11 (hereinafter referred to as "Compound group SX783").

The Compound (L-2), wherein n represents 1, $R^1$ represents an ethyl group, $R^{3b}$ represents an iodine atom, $R^{3c}$ represents a chlorine atom, and T represents any one substituent described in Table L1 to Table L11 (hereinafter referred to as "Compound group SX784").

The Compound (L-2), wherein n represents 1, $R^1$ represents an ethyl group, $R^{3b}$ represents $CF_3$, $R^{3c}$ represents a chlorine atom, and T represents any one substituent described in Table L1 to Table L11 (hereinafter referred to as "Compound group SX785").

The Compound (L-2), wherein n represents 1, $R^1$ represents an ethyl group, $R^{3b}$ represents a hydrogen atom, $R^{3c}$ represents a bromine atom, and T represents any one substituent described in Table L1 to Table L11 (hereinafter referred to as "Compound group SX786").

The Compound (L-2), wherein n represents 1, $R^1$ represents an ethyl group, $R^{3b}$ represents a chlorine atom, $R^{3c}$ represents a bromine atom, and T represents any one substituent described in Table L1 to Table L11 (hereinafter referred to as "Compound group SX787").

The Compound (L-2), wherein n represents 1, $R^1$ represents an ethyl group, $R^{3b}$ represents a bromine atom, $R^{3c}$ represents a bromine atom, and T represents any one substituent described in Table L1 to Table L11 (hereinafter referred to as "Compound group SX788").

The Compound (L-2), wherein n represents 1, $R^1$ represents an ethyl group, $R^{3b}$ represents an iodine atom, $R^{3c}$ represents a bromine atom, and T represents any one substituent described in Table L1 to Table L11 (hereinafter referred to as "Compound group SX789").

The Compound (L-2), wherein n represents 1, $R^1$ represents an ethyl group, $R^{3b}$ represents $CF_3$, $R^{3c}$ represents a bromine atom, and T represents any one substituent described in Table L1 to Table L11 (hereinafter referred to as "Compound group SX790").

The Compound (L-2), wherein n represents 1, $R^1$ represents an ethyl group, $R^{3b}$ represents a hydrogen atom, $R^{3c}$ represents an iodine atom, and T represents any one substituent described in Table L1 to Table L11 (hereinafter referred to as "Compound group SX791").

The Compound (L-2), wherein n represents 1, $R^1$ represents an ethyl group, $R^{3b}$ represents a chlorine atom, $R^{3c}$ represents an iodine atom, and T represents any one substituent described in Table L1 to Table L11 (hereinafter referred to as "Compound group SX792").

The Compound (L-2), wherein n represents 1, $R^1$ represents an ethyl group, $R^{3b}$ represents a bromine atom, $R^{3c}$ represents an iodine atom, and T represents any one substituent described in Table L1 to Table L11 (hereinafter referred to as "Compound group SX793").

The Compound (L-2), wherein n represents 1, $R^1$ represents an ethyl group, $R^{3b}$ represents an iodine atom, $R^{3c}$ represents an iodine atom, and T represents any one substituent described in Table L1 to Table L11 (hereinafter referred to as "Compound group SX794").

The Compound (L-2), wherein n represents 1, $R^1$ represents an ethyl group, $R^{3b}$ represents $CF_3$, $R^{3c}$ represents an iodine atom, and T represents any one substituent described in Table L1 to Table L11 (hereinafter referred to as "Compound group SX795").

The Compound (L-2), wherein n represents 1, $R^1$ represents an ethyl group, $R^{3b}$ represents a hydrogen atom, $R^{3c}$ represents $CF_3$, and T represents any one substituent described in Table L1 to Table L11 (hereinafter referred to as "Compound group SX796").

The Compound (L-2), wherein n represents 1, $R^1$ represents an ethyl group, $R^{3b}$ represents a chlorine atom, $R^{3c}$ represents $CF_3$, and T represents any one substituent described in Table L1 to Table L11 (hereinafter referred to as "Compound group SX797").

The Compound (L-2), wherein n represents 1, $R^1$ represents an ethyl group, $R^{3b}$ represents a bromine atom, $R^{3c}$ represents $CF_3$, and T represents any one substituent described in Table L1 to Table L11 (hereinafter referred to as "Compound group SX798").

The Compound (L-2), wherein n represents 1, $R^1$ represents an ethyl group, $R^{3b}$ represents an iodine atom, $R^{3c}$ represents $CF_3$, and T represents any one substituent described in Table L1 to Table L11 (hereinafter referred to as "Compound group SX799").

The Compound (L-2), wherein n represents 1, $R^1$ represents an ethyl group, $R^{3b}$ represents $CF_3$, $R^{3c}$ represents $CF_3$, and T represents any one substituent described in Table L1 to Table L11 (hereinafter referred to as "Compound group SX800").

The Compound (L-2), wherein n represents 1, $R^1$ represents an isopropyl group, $R^{3b}$ represents a hydrogen atom, $R^{3c}$ represents a hydrogen atom, and T represents any one substituent described in Table L1 to Table L11 (hereinafter referred to as "Compound group SX801").

The Compound (L-2), wherein n represents 1, $R^1$ represents an isopropyl group, $R^{3b}$ represents a chlorine atom, $R^{3c}$ represents a hydrogen atom, and T represents any one substituent described in Table L1 to Table L11 (hereinafter referred to as "Compound group SX802").

The Compound (L-2), wherein n represents 1, $R^1$ represents an isopropyl group, $R^{3b}$ represents a bromine atom, $R^{3c}$ represents a hydrogen atom, and T represents any one substituent described in Table L1 to Table L11 (hereinafter referred to as "Compound group SX803").

The Compound (L-2), wherein n represents 1, $R^1$ represents an isopropyl group, $R^{3b}$ represents an iodine atom, $R^{3c}$ represents a hydrogen atom, and T represents any one substituent described in Table L1 to Table L11 (hereinafter referred to as "Compound group SX804").

The Compound (L-2), wherein n represents 1, $R^1$ represents an isopropyl group, $R^{3b}$ represents $CF_3$, $R^{3c}$ represents a hydrogen atom, and T represents any one substituent described in Table L1 to Table L11 (hereinafter referred to as "Compound group SX805").

The Compound (L-2), wherein n represents 1, $R^1$ represents an isopropyl group, $R^{3b}$ represents a hydrogen atom, $R^{3c}$ represents a chlorine atom, and T represents any one substituent described in Table L1 to Table L11 (hereinafter referred to as "Compound group SX806").

The Compound (L-2), wherein n represents 1, $R^1$ represents an isopropyl group, $R^{3b}$ represents a chlorine atom, $R^{3c}$ represents a chlorine atom, and T represents any one substituent described in Table L1 to Table L11 (hereinafter referred to as "Compound group SX807").

The Compound (L-2), wherein n represents 1, $R^1$ represents an isopropyl group, $R^{3b}$ represents a bromine atom, $R^{3c}$ represents a chlorine atom, and T represents any one substituent described in Table L1 to Table L11 (hereinafter referred to as "Compound group SX808").

The Compound (L-2), wherein n represents 1, $R^1$ represents an isopropyl group, $R^{3b}$ represents an iodine atom, $R^{3c}$ represents a chlorine atom, and T represents any one substituent described in Table L1 to Table L11 (hereinafter referred to as "Compound group SX809").

The Compound (L-2), wherein n represents 1, $R^1$ represents an isopropyl group, $R^{3b}$ represents $CF_3$, $R^{3c}$ represents a chlorine atom, and T represents any one substituent described in Table L1 to Table L11 (hereinafter referred to as "Compound group SX810").

The Compound (L-2), wherein n represents 1, $R^1$ represents an isopropyl group, $R^{3b}$ represents a hydrogen atom, $R^{3c}$ represents a bromine atom, and T represents any one substituent described in Table L1 to Table L11 (hereinafter referred to as "Compound group SX811").

The Compound (L-2), wherein n represents 1, $R^1$ represents an isopropyl group, $R^{3b}$ represents a chlorine atom, $R^{3c}$ represents a bromine atom, and T represents any one substituent described in Table L1 to Table L11 (hereinafter referred to as "Compound group SX812").

The Compound (L-2), wherein n represents 1, $R^1$ represents an isopropyl group, $R^{3b}$ represents a bromine atom, $R^{3c}$ represents a bromine atom, and T represents any one substituent described in Table L1 to Table L11 (hereinafter referred to as "Compound group SX813").

The Compound (L-2), wherein n represents 1, $R^1$ represents an isopropyl group, $R^{3b}$ represents an iodine atom, $R^{3c}$ represents a bromine atom, and T represents any one substituent described in Table L1 to Table L11 (hereinafter referred to as "Compound group SX814").

The Compound (L-2), wherein n represents 1, $R^1$ represents an isopropyl group, $R^{3b}$ represents $CF_3$, $R^{3c}$ represents a bromine atom, and T represents any one substituent described in Table L1 to Table L11 (hereinafter referred to as "Compound group SX815").

The Compound (L-2), wherein n represents 1, $R^1$ represents an isopropyl group, $R^{3b}$ represents a hydrogen atom, $R^{3c}$ represents an iodine atom, and T represents any one substituent described in Table L1 to Table L11 (hereinafter referred to as "Compound group SX816").

The Compound (L-2), wherein n represents 1, $R^1$ represents an isopropyl group, $R^{3b}$ represents a chlorine atom, $R^{3c}$ represents an iodine atom, and T represents any one substituent described in Table L1 to Table L11 (hereinafter referred to as "Compound group SX817").

The Compound (L-2), wherein n represents 1, $R^1$ represents an isopropyl group, $R^{3b}$ represents a bromine atom, $R^{3c}$ represents an iodine atom, and T represents any one substituent described in Table L1 to Table L11 (hereinafter referred to as "Compound group SX818").

The Compound (L-2), wherein n represents 1, $R^1$ represents an isopropyl group, $R^{3b}$ represents an iodine atom, $R^{3c}$ represents an iodine atom, and T represents any one substituent described in Table L1 to Table L11 (hereinafter referred to as "Compound group SX819").

The Compound (L-2), wherein n represents 1, $R^1$ represents an isopropyl group, $R^{3b}$ represents $CF_3$, $R^{3c}$ represents an iodine atom, and T represents any one substituent described in Table L1 to Table L11 (hereinafter referred to as "Compound group SX820").

The Compound (L-2), wherein n represents 1, $R^1$ represents an isopropyl group, $R^{3b}$ represents a hydrogen atom, $R^{3c}$ represents $CF_3$, and T represents any one substituent described in Table L1 to Table L11 (hereinafter referred to as "Compound group SX821").

The Compound (L-2), wherein n represents 1, $R^1$ represents an isopropyl group, $R^{3b}$ represents a chlorine atom, $R^{3c}$ represents $CF_3$, and T represents any one substituent described in Table L1 to Table L11 (hereinafter referred to as "Compound group SX822").

The Compound (L-2), wherein n represents 1, $R^1$ represents an isopropyl group, $R^{3b}$ represents a bromine atom, $R^{3c}$ represents $CF_3$, and T represents any one substituent described in Table L1 to Table L11 (hereinafter referred to as "Compound group SX823").

The Compound (L-2), wherein n represents 1, $R^1$ represents an isopropyl group, $R^{3b}$ represents an iodine atom, $R^{3c}$ represents $CF_3$, and T represents any one substituent described in Table L1 to Table L11 (hereinafter referred to as "Compound group SX824").

The Compound (L-2), wherein n represents 1, $R^1$ represents an isopropyl group, $R^{3b}$ represents $CF_3$, $R^{3c}$ represents $CF_3$, and T represents any one substituent described in Table L1 to Table L11 (hereinafter referred to as "Compound group SX825").

The Compound (L-2), wherein n represents 2, $R^1$ represents a methyl group, $R^{3b}$ represents a hydrogen atom, $R^{3c}$ represents a hydrogen atom, and T represents any one substituent described in Table L1 to Table L11 (hereinafter referred to as "Compound group SX826").

The Compound (L-2), wherein n represents 2, $R^1$ represents a methyl group, $R^{3b}$ represents a chlorine atom, $R^{3c}$ represents a hydrogen atom, and T represents any one substituent described in Table L1 to Table L11 (hereinafter referred to as "Compound group SX827").

The Compound (L-2), wherein n represents 2, $R^1$ represents a methyl group, $R^{3b}$ represents a bromine atom, $R^{3c}$ represents a hydrogen atom, and T represents any one substituent described in Table L1 to Table L11 (hereinafter referred to as "Compound group SX828").

The Compound (L-2), wherein n represents 2, $R^1$ represents a methyl group, $R^{3b}$ represents an iodine atom, $R^{3c}$ represents a hydrogen atom, and T represents any one substituent described in Table L1 to Table L11 (hereinafter referred to as "Compound group SX829").

The Compound (L-2), wherein n represents 2, $R^1$ represents a methyl group, $R^{3b}$ represents $CF_3$, $R^{3e}$ represents a hydrogen atom, and T represents any one substituent described in Table L1 to Table L11 (hereinafter referred to as "Compound group SX830").

The Compound (L-2), wherein n represents 2, $R^1$ represents a methyl group, $R^{3b}$ represents a hydrogen atom, $R^{3c}$ represents a chlorine atom, and T represents any one substituent described in Table L1 to Table L11 (hereinafter referred to as "Compound group SX831").

The Compound (L-2), wherein n represents 2, $R^1$ represents a methyl group, $R^{3b}$ represents a chlorine atom, $R^{3c}$ represents a chlorine atom, and T represents any one substituent described in Table L1 to Table L11 (hereinafter referred to as "Compound group SX832").

The Compound (L-2), wherein n represents 2, $R^1$ represents a methyl group, $R^{3b}$ represents a bromine atom, $R^{3c}$ represents a chlorine atom, and T represents any one substituent described in Table L1 to Table L11 (hereinafter referred to as "Compound group SX833").

The Compound (L-2), wherein n represents 2, $R^1$ represents a methyl group, $R^{3b}$ represents an iodine atom, $R^{3c}$ represents a chlorine atom, and T represents any one substituent described in Table L1 to Table L11 (hereinafter referred to as "Compound group SX834").

The Compound (L-2), wherein n represents 2, $R^1$ represents a methyl group, $R^{3b}$ represents $CF_3$, $R^{3c}$ represents a chlorine atom, and T represents any one substituent described in Table L1 to Table L11 (hereinafter referred to as "Compound group SX835").

The Compound (L-2), wherein n represents 2, $R^1$ represents a methyl group, $R^{3b}$ represents a hydrogen atom, $R^{3c}$ represents a bromine atom, and T represents any one substituent described in Table L1 to Table L11 (hereinafter referred to as "Compound group SX836").

The Compound (L-2), wherein n represents 2, $R^1$ represents a methyl group, $R^{3b}$ represents a chlorine atom, $R^{3c}$ represents a bromine atom, and T represents any one substituent described in Table L1 to Table L11 (hereinafter referred to as "Compound group SX837").

The Compound (L-2), wherein n represents 2, $R^1$ represents a methyl group, $R^{3b}$ represents a bromine atom, $R^{3c}$ represents a bromine atom, and T represents any one substituent described in Table L1 to Table L11 (hereinafter referred to as "Compound group SX838").

The Compound (L-2), wherein n represents 2, $R^1$ represents a methyl group, $R^{3b}$ represents an iodine atom, $R^{3c}$ represents a bromine atom, and T represents any one substituent described in Table L1 to Table L11 (hereinafter referred to as "Compound group SX839").

The Compound (L-2), wherein n represents 2, $R^1$ represents a methyl group, $R^{3b}$ represents $CF_3$, $R^{3c}$ represents a bromine atom, and T represents any one substituent described in Table L1 to Table L11 (hereinafter referred to as "Compound group SX840").

The Compound (L-2), wherein n represents 2, $R^1$ represents a methyl group, $R^{3b}$ represents a hydrogen atom, $R^{3c}$ represents an iodine atom, and T represents any one substituent described in Table L1 to Table L11 (hereinafter referred to as "Compound group SX841").

The Compound (L-2), wherein n represents 2, $R^1$ represents a methyl group, $R^{3b}$ represents a chlorine atom, $R^{3c}$ represents an iodine atom, and T represents any one substituent described in Table L1 to Table L11 (hereinafter referred to as "Compound group SX842").

The Compound (L-2), wherein n represents 2, $R^1$ represents a methyl group, $R^{3b}$ represents a bromine atom, $R^{3c}$ represents an iodine atom, and T represents any one substituent described in Table L1 to Table L11 (hereinafter referred to as "Compound group SX843").

The Compound (L-2), wherein n represents 2, $R^1$ represents a methyl group, $R^{3b}$ represents an iodine atom, $R^{3c}$ represents an iodine atom, and T represents any one substituent described in Table L1 to Table L11 (hereinafter referred to as "Compound group SX844").

The Compound (L-2), wherein n represents 2, $R^1$ represents a methyl group, $R^{3b}$ represents $CF_3$, $R^{3c}$ represents an iodine atom, and T represents any one substituent described in Table L1 to Table L11 (hereinafter referred to as "Compound group SX845").

The Compound (L-2), wherein n represents 2, $R^1$ represents a methyl group, $R^{3b}$ represents a hydrogen atom, $R^{3c}$ represents $CF_3$, and T represents any one substituent described in Table L1 to Table L11 (hereinafter referred to as "Compound group SX846").

The Compound (L-2), wherein n represents 2, $R^1$ represents a methyl group, $R^{3b}$ represents a chlorine atom, $R^{3c}$ represents $CF_3$, and T represents any one substituent described in Table L1 to Table L11 (hereinafter referred to as "Compound group SX847").

The Compound (L-2), wherein n represents 2, $R^1$ represents a methyl group, $R^{3b}$ represents a bromine atom, $R^{3c}$ represents $CF_3$, and T represents any one substituent described in Table L1 to Table L11 (hereinafter referred to as "Compound group SX848").

The Compound (L-2), wherein n represents 2, $R^1$ represents a methyl group, $R^{3b}$ represents an iodine atom, $R^{3c}$ represents $CF_3$, and T represents any one substituent described in Table L1 to Table L11 (hereinafter referred to as "Compound group SX849").

The Compound (L-2), wherein n represents 2, $R^1$ represents a methyl group, $R^{3b}$ represents $CF_3$, $R^{3c}$ represents $CF_3$, and T represents any one substituent described in Table L1 to Table L11 (hereinafter referred to as "Compound group SX850").

The Compound (L-2), wherein n represents 2, $R^1$ represents an ethyl group, $R^{3b}$ represents a hydrogen atom, $R^{3c}$ represents a hydrogen atom, and T represents any one substituent described in Table L1 to Table L11 (hereinafter referred to as "Compound group SX851").

The Compound (L-2), wherein n represents 2, $R^1$ represents an ethyl group, $R^{3b}$ represents a chlorine atom, $R^{3c}$ represents a hydrogen atom, and T represents any one substituent described in Table L1 to Table L11 (hereinafter referred to as "Compound group SX852").

The Compound (L-2), wherein n represents 2, $R^1$ represents an ethyl group, $R^{3b}$ represents a bromine atom, $R^{3c}$ represents a hydrogen atom, and T represents any one substituent described in Table L1 to Table L11 (hereinafter referred to as "Compound group SX853").

The Compound (L-2), wherein n represents 2, $R^1$ represents an ethyl group, $R^{3b}$ represents an iodine atom, $R^{3c}$ represents a hydrogen atom, and T represents any one substituent described in Table L1 to Table L11 (hereinafter referred to as "Compound group SX854").

The Compound (L-2), wherein n represents 2, $R^1$ represents an ethyl group, $R^{3b}$ represents $CF_3$, $R^{3c}$ represents a hydrogen atom, and T represents any one substituent described in Table L1 to Table L11 (hereinafter referred to as "Compound group SX855").

The Compound (L-2), wherein n represents 2, $R^1$ represents an ethyl group, $R^{3b}$ represents a hydrogen atom, $R^{3c}$ represents a chlorine atom, and T represents any one substituent described in Table L1 to Table L11 (hereinafter referred to as "Compound group SX856").

The Compound (L-2), wherein n represents 2, $R^1$ represents an ethyl group, $R^{3b}$ represents a chlorine atom, $R^{3c}$ represents a chlorine atom, and T represents any one substituent described in Table L1 to Table L11 (hereinafter referred to as "Compound group SX857").

The Compound (L-2), wherein n represents 2, $R^1$ represents an ethyl group, $R^{3b}$ represents a bromine atom, $R^{3c}$ represents a chlorine atom, and T represents any one substituent described in Table L1 to Table L11 (hereinafter referred to as "Compound group SX858").

The Compound (L-2), wherein n represents 2, $R^1$ represents an ethyl group, $R^{3b}$ represents an iodine atom, $R^{3c}$ represents a chlorine atom, and T represents any one substituent described in Table L1 to Table L11 (hereinafter referred to as "Compound group SX859").

The Compound (L-2), wherein n represents 2, $R^1$ represents an ethyl group, $R^{3b}$ represents $CF_3$, $R^{3c}$ represents a chlorine atom, and T represents any one substituent described in Table L1 to Table L11 (hereinafter referred to as "Compound group SX860").

The Compound (L-2), wherein n represents 2, $R^1$ represents an ethyl group, $R^{3b}$ represents a hydrogen atom, $R^{3c}$ represents a bromine atom, and T represents any one substituent described in Table L1 to Table L11 (hereinafter referred to as "Compound group SX861").

The Compound (L-2), wherein n represents 2, $R^1$ represents an ethyl group, $R^{3b}$ represents a chlorine atom, $R^{3c}$ represents a bromine atom, and T represents any one substituent described in Table L1 to Table L11 (hereinafter referred to as "Compound group SX862").

The Compound (L-2), wherein n represents 2, $R^1$ represents an ethyl group, $R^{3b}$ represents a bromine atom, $R^{3c}$ represents a bromine atom, and T represents any one substituent described in Table L1 to Table L11 (hereinafter referred to as "Compound group SX863").

The Compound (L-2), wherein n represents 2, $R^1$ represents an ethyl group, $R^{3b}$ represents an iodine atom, $R^{3c}$ represents a bromine atom, and T represents any one substituent described in Table L1 to Table L11 (hereinafter referred to as "Compound group SX864").

The Compound (L-2), wherein n represents 2, $R^1$ represents an ethyl group, $R^{3b}$ represents $CF_3$, $R^{3c}$ represents a bromine atom, and T represents any one substituent described in Table L1 to Table L11 (hereinafter referred to as "Compound group SX865").

The Compound (L-2), wherein n represents 2, $R^1$ represents an ethyl group, $R^{3b}$ represents a hydrogen atom, $R^{3c}$ represents an iodine atom, and T represents any one substituent described in Table L1 to Table L11 (hereinafter referred to as "Compound group SX866").

The Compound (L-2), wherein n represents 2, $R^1$ represents an ethyl group, $R^{3b}$ represents a chlorine atom, $R^{3c}$ represents an iodine atom, and T represents any one substituent described in Table L1 to Table L11 (hereinafter referred to as "Compound group SX867").

The Compound (L-2), wherein n represents 2, $R^1$ represents an ethyl group, $R^{3b}$ represents a bromine atom, $R^{3c}$ represents an iodine atom, and T represents any one substituent described in Table L1 to Table L11 (hereinafter referred to as "Compound group SX868").

The Compound (L-2), wherein n represents 2, $R^1$ represents an ethyl group, $R^{3b}$ represents an iodine atom, $R^{3c}$ represents an iodine atom, and T represents any one substituent described in Table L1 to Table L11 (hereinafter referred to as "Compound group SX869").

The Compound (L-2), wherein n represents 2, $R^1$ represents an ethyl group, $R^{3b}$ represents $CF_3$, $R^{3c}$ represents an iodine atom, and T represents any one substituent described in Table L1 to Table L11 (hereinafter referred to as "Compound group SX870").

The Compound (L-2), wherein n represents 2, $R^1$ represents an ethyl group, $R^{3b}$ represents a hydrogen atom, $R^{3c}$ represents $CF_3$, and T represents any one substituent described in Table L1 to Table L11 (hereinafter referred to as "Compound group SX871").

The Compound (L-2), wherein n represents 2, $R^1$ represents an ethyl group, $R^{3b}$ represents a chlorine atom, $R^{3c}$ represents $CF_3$, and T represents any one substituent described in Table L1 to Table L11 (hereinafter referred to as "Compound group SX872").

The Compound (L-2), wherein n represents 2, $R^1$ represents an ethyl group, $R^{3b}$ represents a bromine atom, $R^{3c}$ represents $CF_3$, and T represents any one substituent described in Table L1 to Table L11 (hereinafter referred to as "Compound group SX873").

The Compound (L-2), wherein n represents 2, $R^1$ represents an ethyl group, $R^{3b}$ represents an iodine atom, $R^{3c}$ represents $CF_3$, and T represents any one substituent described in Table L1 to Table L11 (hereinafter referred to as "Compound group SX874").

The Compound (L-2), wherein n represents 2, $R^1$ represents an ethyl group, $R^{3b}$ represents $CF_3$, $R^{3c}$ represents $CF_3$, and T represents any one substituent described in Table L1 to Table L11 (hereinafter referred to as "Compound group SX875").

The Compound (L-2), wherein n represents 2, $R^1$ represents an isopropyl group, $R^{3b}$ represents a hydrogen atom, $R^{3c}$ represents a hydrogen atom, and T represents any one substituent described in Table L1 to Table L11 (hereinafter referred to as "Compound group SX876").

The Compound (L-2), wherein n represents 2, $R^1$ represents an isopropyl group, $R^{3b}$ represents a chlorine atom, $R^{3c}$ represents a hydrogen atom, and T represents any one substituent described in Table L1 to Table L11 (hereinafter referred to as "Compound group SX877").

The Compound (L-2), wherein n represents 2, $R^1$ represents an isopropyl group, $R^{3b}$ represents a bromine atom, $R^{3c}$ represents a hydrogen atom, and T represents any one substituent described in Table L1 to Table L11 (hereinafter referred to as "Compound group SX878").

The Compound (L-2), wherein n represents 2, $R^1$ represents an isopropyl group, $R^{3b}$ represents an iodine atom, $R^{3c}$ represents a hydrogen atom, and T represents any one substituent described in Table L1 to Table L11 (hereinafter referred to as "Compound group SX879").

The Compound (L-2), wherein n represents 2, $R^1$ represents an isopropyl group, $R^{3b}$ represents $CF_3$, $R^{3c}$ represents a hydrogen atom, and T represents any one substituent described in Table L1 to Table L11 (hereinafter referred to as "Compound group SX880").

The Compound (L-2), wherein n represents 2, $R^1$ represents an isopropyl group, $R^{3b}$ represents a hydrogen atom, $R^{3c}$ represents a chlorine atom, and T represents any one substituent described in Table L1 to Table L11 (hereinafter referred to as "Compound group SX881").

The Compound (L-2), wherein n represents 2, $R^1$ represents an isopropyl group, $R^{3b}$ represents a chlorine atom, $R^{3c}$ represents a chlorine atom, and T represents any one substituent described in Table L1 to Table L11 (hereinafter referred to as "Compound group SX882").

The Compound (L-2), wherein n represents 2, $R^1$ represents an isopropyl group, $R^{3b}$ represents a bromine atom, $R^{3c}$ represents a chlorine atom, and T represents any one substituent described in Table L1 to Table L11 (hereinafter referred to as "Compound group SX883").

The Compound (L-2), wherein n represents 2, $R^1$ represents an isopropyl group, $R^{3b}$ represents an iodine atom, $R^{3c}$ represents a chlorine atom, and T represents any one substituent described in Table L1 to Table L11 (hereinafter referred to as "Compound group SX884").

The Compound (L-2), wherein n represents 2, $R^1$ represents an isopropyl group, $R^{3b}$ represents $CF_3$, $R^{3c}$ represents a chlorine atom, and T represents any one substituent described in Table L1 to Table L11 (hereinafter referred to as "Compound group SX885").

The Compound (L-2), wherein n represents 2, $R^1$ represents an isopropyl group, $R^{3b}$ represents a hydrogen atom, $R^{3c}$ represents a bromine atom, and T represents any one substituent described in Table L1 to Table L11 (hereinafter referred to as "Compound group SX886").

The Compound (L-2), wherein n represents 2, $R^1$ represents an isopropyl group, $R^{3b}$ represents a chlorine atom, $R^{3c}$ represents a bromine atom, and T represents any one substituent described in Table L1 to Table L11 (hereinafter referred to as "Compound group SX887").

The Compound (L-2), wherein n represents 2, $R^1$ represents an isopropyl group, $R^{3b}$ represents a bromine atom, $R^{3c}$ represents a bromine atom, and T represents any one substituent described in Table L1 to Table L11 (hereinafter referred to as "Compound group SX888").

The Compound (L-2), wherein n represents 2, $R^1$ represents an isopropyl group, $R^{3b}$ represents an iodine atom, $R^{3c}$ represents a bromine atom, and T represents any one substituent described in Table L1 to Table L11 (hereinafter referred to as "Compound group SX889").

The Compound (L-2), wherein n represents 2, $R^1$ represents an isopropyl group, $R^{3b}$ represents $CF_3$, $R^{3c}$ represents a bromine atom, and T represents any one substituent described in Table L1 to Table L11 (hereinafter referred to as "Compound group SX890").

The Compound (L-2), wherein n represents 2, $R^1$ represents an isopropyl group, $R^{3b}$ represents a hydrogen atom, $R^{3c}$ represents an iodine atom, and T represents any one substituent described in Table L1 to Table L11 (hereinafter referred to as "Compound group SX891").

The Compound (L-2), wherein n represents 2, $R^1$ represents an isopropyl group, $R^{3b}$ represents a chlorine atom, $R^{3c}$ represents an iodine atom, and T represents any one substituent described in Table L1 to Table L11 (hereinafter referred to as "Compound group SX892").

The Compound (L-2), wherein n represents 2, $R^1$ represents an isopropyl group, $R^{3b}$ represents a bromine atom, $R^{3c}$ represents an iodine atom, and T represents any one substituent described in Table L1 to Table L11 (hereinafter referred to as "Compound group SX893").

The Compound (L-2), wherein n represents 2, $R^1$ represents an isopropyl group, $R^{3b}$ represents an iodine atom, $R^{3c}$ represents an iodine atom, and T represents any one substituent described in Table L1 to Table L11 (hereinafter referred to as "Compound group SX894").

The Compound (L-2), wherein n represents 2, $R^1$ represents an isopropyl group, $R^{3b}$ represents $CF_3$, $R^{3c}$ represents an iodine atom, and T represents any one substituent described in Table L1 to Table L11 (hereinafter referred to as "Compound group SX895").

The Compound (L-2), wherein n represents 2, $R^1$ represents an isopropyl group, $R^{3b}$ represents a hydrogen atom, $R^{3c}$ represents $CF_3$, and T represents any one substituent described in Table L1 to Table L11 (hereinafter referred to as "Compound group SX896").

The Compound (L-2), wherein n represents 2, $R^1$ represents an isopropyl group, $R^{3b}$ represents a chlorine atom, $R^{3c}$ represents $CF_3$, and T represents any one substituent described in Table L1 to Table L11 (hereinafter referred to as "Compound group SX897").

The Compound (L-2), wherein n represents 2, $R^1$ represents an isopropyl group, $R^{3b}$ represents a bromine atom, $R^{3c}$ represents $CF_3$, and T represents any one substituent described in Table L1 to Table L11 (hereinafter referred to as "Compound group SX898").

The Compound (L-2), wherein n represents 2, $R^1$ represents an isopropyl group, $R^{3b}$ represents an iodine atom, $R^{3c}$ represents $CF_3$, and T represents any one substituent described in Table L1 to Table L11 (hereinafter referred to as "Compound group SX899").

The Compound (L-2), wherein n represents 2, $R^1$ represents an isopropyl group, $R^{3b}$ represents $CF_3$, $R^{3c}$ represents $CF_3$, and T represents any one substituent described in Table L1 to Table L11 (hereinafter referred to as "Compound group SX900").

The Compound (L-2), wherein n represents 0, $R^1$ represents a methyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX901").

The Compound (L-2), wherein n represents 0, $R^1$ represents a methyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX902").

The Compound (L-2), wherein n represents 0, $R^1$ represents a methyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX903").

The Compound (L-2), wherein n represents 0, $R^1$ represents a methyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX904").

The Compound (L-2), wherein n represents 0, $R^1$ represents a methyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX905").

The Compound (L-2), wherein n represents 0, $R^1$ represents a methyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX906").

The Compound (L-2), wherein n represents 0, $R^1$ represents a methyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX907").

The Compound (L-2), wherein n represents 0, $R^1$ represents a methyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX908").

The Compound (L-2), wherein n represents 0, $R^1$ represents a methyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX909").

The Compound (L-2), wherein n represents 0, $R^1$ represents a methyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX910").

The Compound (L-2), wherein n represents 0, $R^1$ represents an ethyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX911").

The Compound (L-2), wherein n represents 0, $R^1$ represents an ethyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX912").

The Compound (L-2), wherein n represents 0, $R^1$ represents an ethyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX913").

The Compound (L-2), wherein n represents 0, $R^1$ represents an ethyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX914").

The Compound (L-2), wherein n represents 0, $R^1$ represents an ethyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX915").

The Compound (L-2), wherein n represents 0, $R^1$ represents an ethyl group, T represents a 4-[(trifluoromethyl)thio]

phenyl group, $R^{3c}$ represents a hydrogen atom, and $R^{3b}$ represents any one substituent described in Table L12 to Table L14 (hereinafter referred to as "Compound group SX916").

The Compound (L-2), wherein n represents 0, $R^1$ represents an ethyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX917").

The Compound (L-2), wherein n represents 0, $R^1$ represents an ethyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX918").

The Compound (L-2), wherein n represents 0, $R^1$ represents an ethyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX919").

The Compound (L-2), wherein n represents 0, $R^1$ represents an ethyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX920").

The Compound (L-2), wherein n represents 0, $R^1$ represents an isopropyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX921").

The Compound (L-2), wherein n represents 0, $R^1$ represents an isopropyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX922").

The Compound (L-2), wherein n represents 0, $R^1$ represents an isopropyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX923").

The Compound (L-2), wherein n represents 0, $R^1$ represents an isopropyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX924").

The Compound (L-2), wherein n represents 0, $R^1$ represents an isopropyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX925").

The Compound (L-2), wherein n represents 0, $R^1$ represents an isopropyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX926").

The Compound (L-2), wherein n represents 0, $R^1$ represents an isopropyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX927").

The Compound (L-2), wherein n represents 0, $R^1$ represents an isopropyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX928").

The Compound (L-2), wherein n represents 0, $R^1$ represents an isopropyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX929").

The Compound (L-2), wherein n represents 0, $R^1$ represents an isopropyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX930").

The Compound (L-2), wherein n represents 0, $R^1$ represents a methyl group, T represents a 4-(trifluoromethoxy)phenyl group, $R^{3c}$ represents a hydrogen atom, and $R^{3b}$ represents any one substituent described in Table L12 to Table L14 (hereinafter referred to as "Compound group SX931").

The Compound (L-2), wherein n represents 0, $R^1$ represents a methyl group, T represents a 4-(trifluoromethoxy)phenyl group, $R^{3c}$ represents a chlorine atom, and $R^{3b}$ represents any one substituent described in Table L12 to Table L14 (hereinafter referred to as "Compound group SX932").

The Compound (L-2), wherein n represents 0, $R^1$ represents a methyl group, T represents a 4-(trifluoromethoxy)phenyl group, $R^{3c}$ represents a bromine atom, and $R^{3b}$ represents any one substituent described in Table L12 to Table L14 (hereinafter referred to as "Compound group SX933").

The Compound (L-2), wherein n represents 0, $R^1$ represents a methyl group, T represents a 4-(trifluoromethoxy)phenyl group, $R^{3c}$ represents an iodine atom, and $R^{3b}$ represents any one substituent described in Table L12 to Table L14 (hereinafter referred to as "Compound group SX934").

The Compound (L-2), wherein n represents 0, $R^1$ represents a methyl group, T represents a 4-(trifluoromethoxy)phenyl group, $R^{3c}$ represents $CF_3$, and $R^{3b}$ represents any one substituent described in Table L12 to Table L14 (hereinafter referred to as "Compound group SX935").

The Compound (L-2), wherein n represents 0, $R^1$ represents a methyl group, T represents a 4-(trifluoromethyl)phenyl group, $R^{3c}$ represents a hydrogen atom, and $R^{3b}$ represents any one substituent described in Table L12 to Table L14 (hereinafter referred to as "Compound group SX936").

The Compound (L-2), wherein n represents 0, $R^1$ represents a methyl group, T represents a 4-(trifluoromethyl)phenyl group, $R^{3c}$ represents a chlorine atom, and $R^{3b}$ represents any one substituent described in Table L12 to Table L14 (hereinafter referred to as "Compound group SX937").

The Compound (L-2), wherein n represents 0, $R^1$ represents a methyl group, T represents a 4-(trifluoromethyl)phenyl group, $R^{3c}$ represents a bromine atom, and $R^{3b}$ represents any one substituent described in Table L12 to Table L14 (hereinafter referred to as "Compound group SX938").

The Compound (L-2), wherein n represents 0, $R^1$ represents a methyl group, T represents a 4-(trifluoromethyl)phenyl group, $R^{3c}$ represents an iodine atom, and $R^{3b}$ represents any one substituent described in Table L12 to Table L14 (hereinafter referred to as "Compound group SX939").

The Compound (L-2), wherein n represents 0, $R^1$ represents a methyl group, T represents a 4-(trifluoromethyl) phenyl group, $R^{3c}$ represents $CF_3$, and $R^{3b}$ represents any one substituent described in Table L12 to Table L14 (hereinafter referred to as "Compound group SX940").

The Compound (L-2), wherein n represents 0, $R^1$ represents a methyl group, T represents a 3,4-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX941").

The Compound (L-2), wherein n represents 0, $R^1$ represents a methyl group, T represents a 3,4-bis[(trifluoromethyl)thio]phenyl group, $R^{3c}$ represents a chlorine atom, and $R^{3b}$ represents any one substituent described in Table L12 to Table L14 (hereinafter referred to as "Compound group SX942").

The Compound (L-2), wherein n represents 0, $R^1$ represents a methyl group, T represents a 3,4-bis[(trifluoromethyl)thio]phenyl group, $R^{3c}$ represents a bromine atom, and $R^{3b}$ represents any one substituent described in Table L12 to Table L14 (hereinafter referred to as "Compound group SX943").

The Compound (L-2), wherein n represents 0, $R^1$ represents a methyl group, T represents a 3,4-bis[(trifluoromethyl)thio]phenyl group, $R^{3c}$ represents an iodine atom, and $R^{3b}$ represents any one substituent described in Table L12 to Table L14 (hereinafter referred to as "Compound group SX944").

The Compound (L-2), wherein n represents 0, $R^1$ represents a methyl group, T represents a 3,4-bis[(trifluoromethyl)thio]phenyl group, $R^{3c}$ represents $CF_3$, and $R^{3b}$ represents any one substituent described in Table L12 to Table L14 (hereinafter referred to as "Compound group SX945").

The Compound (L-2), wherein n represents 0, $R^1$ represents a methyl group, T represents a 3,4-bis(trifluoromethoxy)phenyl group, $R^{3c}$ represents a hydrogen atom, and $R^{3b}$ represents any one substituent described in Table L12 to Table L14 (hereinafter referred to as "Compound group SX946").

The Compound (L-2), wherein n represents 0, $R^1$ represents a methyl group, T represents a 3,4-bis(trifluoromethoxy)phenyl group, $R^{3c}$ represents a chlorine atom, and $R^{3b}$ represents any one substituent described in Table L12 to Table L14 (hereinafter referred to as "Compound group SX947").

The Compound (L-2), wherein n represents 0, $R^1$ represents a methyl group, T represents a 3,4-bis(trifluoromethoxy)phenyl group, $R^{3c}$ represents a bromine atom, and $R^{3b}$ represents any one substituent described in Table L12 to Table L14 (hereinafter referred to as "Compound group SX948").

The Compound (L-2), wherein n represents 0, $R^1$ represents a methyl group, T represents a 3,4-bis(trifluoromethoxy)phenyl group, $R^{3c}$ represents an iodine atom, and $R^{3b}$ represents any one substituent described in Table L12 to Table L14 (hereinafter referred to as "Compound group SX949").

The Compound (L-2), wherein n represents 0, $R^1$ represents a methyl group, T represents a 3,4-bis(trifluoromethoxy)phenyl group, $R^{3c}$ represents $CF_3$, and $R^{3b}$ represents any one substituent described in Table L12 to Table L14 (hereinafter referred to as "Compound group SX950").

The Compound (L-2), wherein n represents 0, $R^1$ represents a methyl group, T represents a 3,4-bis(trifluoromethyl) phenyl group, $R^{3c}$ represents a hydrogen atom, and $R^{3b}$ represents any one substituent described in Table L12 to Table L14 (hereinafter referred to as "Compound group SX951").

The Compound (L-2), wherein n represents 0, $R^1$ represents a methyl group, T represents a 3,4-bis(trifluoromethyl) phenyl group, $R^{3c}$ represents a chlorine atom, and $R^{3b}$ represents any one substituent described in Table L12 to Table L14 (hereinafter referred to as "Compound group SX952").

The Compound (L-2), wherein n represents 0, $R^1$ represents a methyl group, T represents a 3,4-bis(trifluoromethyl) phenyl group, $R^{3c}$ represents a bromine Table L12 to Table L14 (hereinafter referred to as "Compound group SX953").

The Compound (L-2), wherein n represents 0, $R^1$ represents a methyl group, T represents a 3,4-bis(trifluoromethyl) phenyl group, $R^{3c}$ represents an iodine atom, and $R^{3b}$ represents any one substituent described in Table L12 to Table L14 (hereinafter referred to as "Compound group SX954").

The Compound (L-2), wherein n represents 0, $R^1$ represents a methyl group, T represents a 3,4-bis(trifluoromethyl) phenyl group, $R^{3c}$ represents $CF_3$, and $R^{3b}$ represents any one substituent described in Table L12 to Table L14 (hereinafter referred to as "Compound group SX955").

The Compound (L-2), wherein n represents 0, $R^1$ represents a methyl group, T represents a 3,5-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX956").

The Compound (L-2), wherein n represents 0, $R^1$ represents a methyl group, T represents a 3,5-bis[(trifluoromethyl)thio]phenyl group, $R^{3c}$ represents a chlorine atom, and $R^{3b}$ represents any one substituent described in Table L12 to Table L14 (hereinafter referred to as "Compound group SX957").

The Compound (L-2), wherein n represents 0, $R^1$ represents a methyl group, T represents a 3,5-bis[(trifluoromethyl)thio]phenyl group, $R^{3c}$ represents a bromine atom, and $R^{3b}$ represents any one substituent described in Table L12 to Table L14 (hereinafter referred to as "Compound group SX958").

The Compound (L-2), wherein n represents 0, $R^1$ represents a methyl group, T represents a 3,5-bis[(trifluoromethyl)thio]phenyl group, $R^{3c}$ represents an iodine atom, and $R^{3b}$ represents any one substituent described in Table L12 to Table L14 (hereinafter referred to as "Compound group SX959").

The Compound (L-2), wherein n represents 0, $R^1$ represents a methyl group, T represents a 3,5-bis[(trifluoromethyl)thio]phenyl group, $R^{3c}$ represents $CF_3$, and $R^{3b}$ represents any one substituent described in Table L12 to Table L14 (hereinafter referred to as "Compound group SX960").

The Compound (L-2), wherein n represents 0, $R^1$ represents a methyl group, T represents a 3,5-bis(trifluoromethoxy)phenyl group, $R^{3c}$ represents a hydrogen atom, and $R^{3b}$ represents any one substituent described in Table L12 to Table L14 (hereinafter referred to as "Compound group SX961").

The Compound (L-2), wherein n represents 0, $R^1$ represents a methyl group, T represents a 3,5-bis(trifluoromethoxy)phenyl group, $R^{3c}$ represents a chlorine atom, and $R^{3b}$ represents any one substituent described in Table L12 to Table L14 (hereinafter referred to as "Compound group SX962").

The Compound (L-2), wherein n represents 0, $R^1$ represents a methyl group, T represents a 3,5-bis(trifluoromethoxy)phenyl group, $R^{3c}$ represents a bromine atom, and $R^{3b}$ represents any one substituent described in Table L12 to Table L14 (hereinafter referred to as "Compound group SX963").

The Compound (L-2), wherein n represents 0, $R^1$ represents a methyl group, T represents a 3,5-bis(trifluoromethoxy)phenyl group, $R^{3c}$ represents an iodine atom, and $R^{3b}$ represents any one substituent described in Table L12 to Table L14 (hereinafter referred to as "Compound group SX964").

The Compound (L-2), wherein n represents 0, $R^1$ represents a methyl group, T represents a 3,5-bis(trifluoromethoxy)phenyl group, $R^{3c}$ represents $CF_3$, and $R^{3b}$ represents any one substituent described in Table L12 to Table L14 (hereinafter referred to as "Compound group SX965").

The Compound (L-2), wherein n represents 0, $R^1$ represents a methyl group, T represents a 3,5-bis(trifluoromethyl)phenyl group, $R^{3c}$ represents a hydrogen atom, and $R^{3b}$ represents any one substituent described in Table L12 to Table L14 (hereinafter referred to as "Compound group SX966").

The Compound (L-2), wherein n represents 0, $R^1$ represents a methyl group, T represents a 3,5-bis(trifluoromethyl)phenyl group, $R^{3c}$ represents a chlorine atom, and $R^{3b}$ represents any one substituent described in Table L12 to Table L14 (hereinafter referred to as "Compound group SX967").

The Compound (L-2), wherein n represents 0, $R^1$ represents a methyl group, T represents a 3,5-bis(trifluoromethyl)phenyl group, $R^{3c}$ represents a bromine atom, and $R^{3b}$ represents any one substituent described in Table L12 to Table L14 (hereinafter referred to as "Compound group SX968").

The Compound (L-2), wherein n represents 0, $R^1$ represents a methyl group, T represents a 3,5-bis(trifluoromethyl)phenyl group, $R^{3c}$ represents an iodine atom, and $R^{3b}$ represents any one substituent described in Table L12 to Table L14 (hereinafter referred to as "Compound group SX969").

The Compound (L-2), wherein n represents 0, $R^1$ represents a methyl group, T represents a 3,5-bis(trifluoromethyl)phenyl group, $R^{3c}$ represents $CF_3$, and $R^{3b}$ represents any one substituent described in Table L12 to Table L14 (hereinafter referred to as "Compound group SX970").

The Compound (L-2), wherein n represents 0, $R^1$ represents a methyl group, T represents a 3-fluoro-5-(trifluoromethoxy)phenyl group, $R^{3c}$ represents a hydrogen atom, and $R^{3b}$ represents any one substituent described in Table L12 to Table L14 (hereinafter referred to as "Compound group SX971").

The Compound (L-2), wherein n represents 0, $R^1$ represents a methyl group, T represents a 3-fluoro-5-(trifluoromethoxy)phenyl group, $R^{3c}$ represents a chlorine atom, and $R^{3b}$ represents any one substituent described in Table L12 to Table L14 (hereinafter referred to as "Compound group SX972").

The Compound (L-2), wherein n represents 0, $R^1$ represents a methyl group, T represents a 3-fluoro-5-(trifluoromethoxy)phenyl group, $R^{3c}$ represents a bromine atom, and $R^{3b}$ represents any one substituent described in Table L12 to Table L14 (hereinafter referred to as "Compound group SX973").

The Compound (L-2), wherein n represents 0, $R^1$ represents a methyl group, T represents a 3-fluoro-5-(trifluoromethoxy)phenyl group, $R^{3c}$ represents an iodine atom, and $R^{3b}$ represents any one substituent described in Table L12 to Table L14 (hereinafter referred to as "Compound group SX974").

The Compound (L-2), wherein n represents 0, $R^1$ represents a methyl group, T represents a 3-fluoro-5-(trifluoromethoxy)phenyl group, $R^{3c}$ represents $CF_3$, and $R^{3b}$ represents any one substituent described in Table L12 to Table L14 (hereinafter referred to as "Compound group SX975").

The Compound (L-2), wherein n represents 1, $R^1$ represents a methyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX976").

The Compound (L-2), wherein n represents 1, $R^1$ represents a methyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX977").

The Compound (L-2), wherein n represents 1, $R^1$ represents a methyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX978").

The Compound (L-2), wherein n represents 1, $R^1$ represents a methyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX979").

The Compound (L-2), wherein n represents 1, $R^1$ represents a methyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX980").

The Compound (L-2), wherein n represents 1, $R^1$ represents a methyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX981").

The Compound (L-2), wherein n represents 1, $R^1$ represents a methyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX982").

The Compound (L-2), wherein n represents 1, $R^1$ represents a methyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX983").

The Compound (L-2), wherein n represents 1, $R^1$ represents a methyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX984").

The Compound (L-2), wherein n represents 1, $R^1$ represents a methyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX985").

The Compound (L-2), wherein n represents 1, $R^1$ represents an ethyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX986").

The Compound (L-2), wherein n represents 1, $R^1$ represents an ethyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX987").

The Compound (L-2), wherein n represents 1, $R^1$ represents an ethyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX988").

The Compound (L-2), wherein n represents 1, $R^1$ represents an ethyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX989").

The Compound (L-2), wherein n represents 1, $R^1$ represents an ethyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX990").

The Compound (L-2), wherein n represents 1, $R^1$ represents an ethyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX991").

The Compound (L-2), wherein n represents 1, $R^1$ represents an ethyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX992").

The Compound (L-2), wherein n represents 1, $R^1$ represents an ethyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX993").

The Compound (L-2), wherein n represents 1, $R^1$ represents an ethyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX994").

The Compound (L-2), wherein n represents 1, $R^1$ represents an ethyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX995").

The Compound (L-2), wherein n represents 1, $R^1$ represents an isopropyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX996").

The Compound (L-2), wherein n represents 1, $R^1$ represents an isopropyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX997").

The Compound (L-2), wherein n represents 1, $R^1$ represents an isopropyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX998").

The Compound (L-2), wherein n represents 1, $R^1$ represents an isopropyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX999").

The Compound (L-2), wherein n represents 1, $R^1$ represents an isopropyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX1000").

The Compound (L-2), wherein n represents 1, $R^1$ represents an isopropyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX1001").

The Compound (L-2), wherein n represents 1, $R^1$ represents an isopropyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX1002").

The Compound (L-2), wherein n represents 1, $R^1$ represents an isopropyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX1003").

The Compound (L-2), wherein n represents 1, $R^1$ represents an isopropyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX1004").

The Compound (L-2), wherein n represents 1, $R^1$ represents an isopropyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX1005").

The Compound (L-2), wherein n represents 1, $R^1$ represents a methyl group, T represents a 4-(trifluoromethoxy)phenyl group, $R^{3c}$ represents a hydrogen atom, and $R^{3b}$ represents any one substituent described in Table L12 to Table L14 (hereinafter referred to as "Compound group SX1006").

The Compound (L-2), wherein n represents 1, $R^1$ represents a methyl group, T represents a 4-(trifluoromethoxy)phenyl group, $R^{3c}$ represents a chlorine atom, and $R^{3b}$ represents any one substituent described in Table L12 to Table L14 (hereinafter referred to as "Compound group SX1007").

The Compound (L-2), wherein n represents 1, $R^1$ represents a methyl group, T represents a 4-(trifluoromethoxy)phenyl group, $R^{3c}$ represents a bromine atom, and $R^{3b}$ represents any one substituent described in Table L12 to Table L14 (hereinafter referred to as "Compound group SX1008").

The Compound (L-2), wherein n represents 1, $R^1$ represents a methyl group, T represents a 4-(trifluoromethoxy)phenyl group, $R^{3c}$ represents an iodine atom, and $R^{3b}$ represents any one substituent described in Table L12 to Table L14 (hereinafter referred to as "Compound group SX1009").

The Compound (L-2), wherein n represents 1, $R^1$ represents a methyl group, T represents a 4-(trifluoromethoxy) phenyl group, $R^{3c}$ represents $CF_3$, and $R^{3b}$ represents any one substituent described in Table L12 to Table L14 (hereinafter referred to as "Compound group SX1010").

The Compound (L-2), wherein n represents 1, $R^1$ represents a methyl group, T represents a 4-(trifluoromethyl) phenyl group, $R^{3c}$ represents a hydrogen atom, and $R^{3b}$ represents any one substituent described in Table L12 to Table L14 (hereinafter referred to as "Compound group SX1011").

The Compound (L-2), wherein n represents 1, $R^1$ represents a methyl group, T represents a 4-(trifluoromethyl) phenyl group, $R^{3c}$ represents a chlorine atom, and $R^{3b}$ represents any one substituent described in Table L12 to Table L14 (hereinafter referred to as "Compound group SX1012").

The Compound (L-2), wherein n represents 1, $R^1$ represents a methyl group, T represents a 4-(trifluoromethyl) phenyl group, $R^{3c}$ represents a bromine atom, and $R^{3b}$ represents any one substituent described in Table L12 to Table L14 (hereinafter referred to as "Compound group SX1013").

The Compound (L-2), wherein n represents 1, $R^1$ represents a methyl group, T represents a 4-(trifluoromethyl) phenyl group, $R^{3c}$ represents an iodine atom, and $R^{3b}$ represents any one substituent described in Table L12 to Table L14 (hereinafter referred to as "Compound group SX1014").

The Compound (L-2), wherein n represents 1, $R^1$ represents a methyl group, T represents a 4-(trifluoromethyl) phenyl group, $R^{3c}$ represents $CF_3$, and $R^{3b}$ represents any one substituent described in Table L12 to Table L14 (hereinafter referred to as "Compound group SX1015").

The Compound (L-2), wherein n represents 1, $R^1$ represents a methyl group, T represents a 3,4-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX1016").

The Compound (L-2), wherein n represents 1, $R^1$ represents a methyl group, T represents a 3,4-bis[(trifluoromethyl)thio]phenyl group, $R^{3c}$ represents a chlorine atom, and $R^{3b}$ represents any one substituent described in Table L12 to Table L14 (hereinafter referred to as "Compound group SX1017").

The Compound (L-2), wherein n represents 1, $R^1$ represents a methyl group, T represents a 3,4-bis[(trifluoromethyl)thio]phenyl group, $R^{3c}$ represents a bromine atom, and $R^{3b}$ represents any one substituent described in Table L12 to Table L14 (hereinafter referred to as "Compound group SX1018").

The Compound (L-2), wherein n represents 1, $R^1$ represents a methyl group, T represents a 3,4-bis[(trifluoromethyl)thio]phenyl group, $R^{3c}$ represents an iodine atom, and $R^{3b}$ represents any one substituent described in Table L12 to Table L14 (hereinafter referred to as "Compound group SX1019").

The Compound (L-2), wherein n represents 1, $R^1$ represents a methyl group, T represents a 3,4-bis[(trifluoromethyl)thio]phenyl group, $R^{3c}$ represents $CF_3$, and $R^{3b}$ represents any one substituent described in Table L12 to Table L14 (hereinafter referred to as "Compound group SX1020").

The Compound (L-2), wherein n represents 1, $R^1$ represents a methyl group, T represents a 3,4-bis(trifluoromethoxy)phenyl group, $R^{3c}$ represents a hydrogen atom, and $R^{3b}$ represents any one substituent described in Table L12 to Table L14 (hereinafter referred to as "Compound group SX1021").

The Compound (L-2), wherein n represents 1, $R^1$ represents a methyl group, T represents a 3,4-bis(trifluoromethoxy)phenyl group, $R^{3c}$ represents a chlorine atom, and $R^{3b}$ represents any one substituent described in Table L12 to Table L14 (hereinafter referred to as "Compound group SX1022").

The Compound (L-2), wherein n represents 1, $R^1$ represents a methyl group, T represents a 3,4-bis(trifluoromethoxy)phenyl group, $R^{3c}$ represents a bromine atom, and $R^{3b}$ represents any one substituent described in Table L12 to Table L14 (hereinafter referred to as "Compound group SX1023").

The Compound (L-2), wherein n represents 1, $R^1$ represents a methyl group, T represents a 3,4-bis(trifluoromethoxy)phenyl group, $R^{3c}$ represents an iodine atom, and $R^{3b}$ represents any one substituent described in Table L12 to Table L14 (hereinafter referred to as "Compound group SX1024").

The Compound (L-2), wherein n represents 1, $R^1$ represents a methyl group, T represents a 3,4-bis(trifluoromethoxy)phenyl group, $R^{3c}$ represents $CF_3$, and $R^{3b}$ represents any one substituent described in Table L12 to Table L14 (hereinafter referred to as "Compound group SX1025").

The Compound (L-2), wherein n represents 1, $R^1$ represents a methyl group, T represents a 3,4-bis(trifluoromethyl) phenyl group, $R^{3c}$ represents a hydrogen atom, and $R^{3b}$ represents any one substituent described in Table L12 to Table L14 (hereinafter referred to as "Compound group SX1026").

The Compound (L-2), wherein n represents 1, $R^1$ represents a methyl group, T represents a 3,4-bis(trifluoromethyl) phenyl group, $R^{3c}$ represents a chlorine atom, and $R^{3b}$ represents any one substituent described in Table L12 to Table L14 (hereinafter referred to as "Compound group SX1027").

The Compound (L-2), wherein n represents 1, $R^1$ represents a methyl group, T represents a 3,4-bis(trifluoromethyl) phenyl group, $R^{3c}$ represents a bromine Table L12 to Table L14 (hereinafter referred to as "Compound group SX1028").

The Compound (L-2), wherein n represents 1, $R^1$ represents a methyl group, T represents a 3,4-bis(trifluoromethyl) phenyl group, $R^{3c}$ represents an iodine atom, and $R^{3b}$ represents any one substituent described in Table L12 to Table L14 (hereinafter referred to as "Compound group SX1029").

The Compound (L-2), wherein n represents 1, $R^1$ represents a methyl group, T represents a 3,4-bis(trifluoromethyl) phenyl group, $R^{3c}$ represents $CF_3$, and $R^{3b}$ represents any one substituent described in Table L12 to Table L14 (hereinafter referred to as "Compound group SX1030").

The Compound (L-2), wherein n represents 1, $R^1$ represents a methyl group, T represents a 3,5-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX1031").

The Compound (L-2), wherein n represents 1, $R^1$ represents a methyl group, T represents a 3,5-bis[(trifluoromethyl)thio]phenyl group, $R^{3c}$ represents a chlorine atom, and $R^{3b}$ represents any one substituent described in Table L12 to Table L14 (hereinafter referred to as "Compound group SX1032").

The Compound (L-2), wherein n represents 1, $R^1$ represents a methyl group, T represents a 3,5-bis[(trifluoromethyl)thio]phenyl group, $R^{3c}$ represents a bromine atom, and $R^{3b}$ represents any one substituent described in Table L12 to Table L14 (hereinafter referred to as "Compound group SX1033").

The Compound (L-2), wherein n represents 1, $R^1$ represents a methyl group, T represents a 3,5-bis[(trifluoromethyl)thio]phenyl group, $R^{3c}$ represents an iodine atom, and $R^{3b}$ represents any one substituent described in Table L12 to Table L14 (hereinafter referred to as "Compound group SX1034").

The Compound (L-2), wherein n represents 1, $R^1$ represents a methyl group, T represents a 3,5-bis[(trifluoromethyl)thio]phenyl group, $R^{3c}$ represents $CF_3$, and $R^{3b}$ represents any one substituent described in Table L12 to Table L14 (hereinafter referred to as "Compound group SX1035").

The Compound (L-2), wherein n represents 1, $R^1$ represents a methyl group, T represents a 3,5-bis(trifluoromethoxy)phenyl group, $R^{3c}$ represents a hydrogen atom, and $R^{3b}$ represents any one substituent described in Table L12 to Table L14 (hereinafter referred to as "Compound group SX1036").

The Compound (L-2), wherein n represents 1, $R^1$ represents a methyl group, T represents a 3,5-bis(trifluoromethoxy)phenyl group, $R^{3c}$ represents a chlorine atom, and $R^{3b}$ represents any one substituent described in Table L12 to Table L14 (hereinafter referred to as "Compound group SX1037").

The Compound (L-2), wherein n represents 1, $R^1$ represents a methyl group, T represents a 3,5-bis(trifluoromethoxy)phenyl group, $R^{3c}$ represents a bromine atom, and $R^{3b}$ represents any one substituent described in Table L12 to Table L14 (hereinafter referred to as "Compound group SX1038").

The Compound (L-2), wherein n represents 1, $R^1$ represents a methyl group, T represents a 3,5-bis(trifluoromethoxy)phenyl group, $R^{3c}$ represents an iodine atom, and $R^{3b}$ represents any one substituent described in Table L12 to Table L14 (hereinafter referred to as "Compound group SX1039").

The Compound (L-2), wherein n represents 1, $R^1$ represents a methyl group, T represents a 3,5-bis(trifluoromethoxy)phenyl group, $R^{3c}$ represents $CF_3$, and $R^{3b}$ represents any one substituent described in Table L12 to Table L14 (hereinafter referred to as "Compound group SX1040").

The Compound (L-2), wherein n represents 1, $R^1$ represents a methyl group, T represents a 3,5-bis(trifluoromethyl)phenyl group, $R^{3c}$ represents a hydrogen atom, and $R^{3b}$ represents any one substituent described in Table L12 to Table L14 (hereinafter referred to as "Compound group SX1041").

The Compound (L-2), wherein n represents 1, $R^1$ represents a methyl group, T represents a 3,5-bis(trifluoromethyl)phenyl group, $R^{3c}$ represents a chlorine atom, and $R^{3b}$ represents any one substituent described in Table L12 to Table L14 (hereinafter referred to as "Compound group SX1042").

The Compound (L-2), wherein n represents 1, $R^1$ represents a methyl group, T represents a 3,5-bis(trifluoromethyl)phenyl group, $R^{3c}$ represents a bromine atom, and $R^{3b}$ represents any one substituent described in Table L12 to Table L14 (hereinafter referred to as "Compound group SX1043").

The Compound (L-2), wherein n represents 1, $R^1$ represents a methyl group, T represents a 3,5-bis(trifluoromethyl)phenyl group, $R^{3c}$ represents an iodine atom, and $R^{3b}$ represents any one substituent described in Table L12 to Table L14 (hereinafter referred to as "Compound group SX1044").

The Compound (L-2), wherein n represents 1, $R^1$ represents a methyl group, T represents a 3,5-bis(trifluoromethyl)phenyl group, $R^{3c}$ represents $CF_3$, and $R^{3b}$ represents any one substituent described in Table L12 to Table L14 (hereinafter referred to as "Compound group SX1045").

The Compound (L-2), wherein n represents 1, $R^1$ represents a methyl group, T represents a 3-fluoro-5-(trifluoromethoxy)phenyl group, $R^{3c}$ represents a hydrogen atom, and $R^{3b}$ represents any one substituent described in Table L12 to Table L14 (hereinafter referred to as "Compound group SX1046").

The Compound (L-2), wherein n represents 1, $R^1$ represents a methyl group, T represents a 3-fluoro-5-(trifluoromethoxy)phenyl group, $R^{3c}$ represents a chlorine atom, and $R^{3b}$ represents any one substituent described in Table L12 to Table L14 (hereinafter referred to as "Compound group SX1047").

The Compound (L-2), wherein n represents 1, $R^1$ represents a methyl group, T represents a 3-fluoro-5-(trifluoromethoxy)phenyl group, $R^{3c}$ represents a bromine atom, and $R^{3b}$ represents any one substituent described in Table L12 to Table L14 (hereinafter referred to as "Compound group SX1048").

The Compound (L-2), wherein n represents 1, $R^1$ represents a methyl group, T represents a 3-fluoro-5-(trifluoromethoxy)phenyl group, $R^{3c}$ represents an iodine atom, and $R^{3b}$ represents any one substituent described in Table L12 to Table L14 (hereinafter referred to as "Compound group SX1049").

The Compound (L-2), wherein n represents 1, $R^1$ represents a methyl group, T represents a 3-fluoro-5-(trifluoromethoxy)phenyl group, $R^{3c}$ represents $CF_3$, and $R^{3b}$ represents any one substituent described in Table L12 to Table L14 (hereinafter referred to as "Compound group SX1050").

The Compound (L-2), wherein n represents 2, $R^1$ represents a methyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX1051").

The Compound (L-2), wherein n represents 2, $R^1$ represents a methyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX1052").

The Compound (L-2), wherein n represents 2, $R^1$ represents a methyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX1053").

The Compound (L-2), wherein n represents 2, $R^1$ represents a methyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX1054").

The Compound (L-2), wherein n represents 2, $R^1$ represents a methyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX1055").

The Compound (L-2), wherein n represents 2, $R^1$ represents a methyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX1056").

The Compound (L-2), wherein n represents 2, $R^1$ represents a methyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX1057").

The Compound (L-2), wherein n represents 2, $R^1$ represents a methyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX1058").

The Compound (L-2), wherein n represents 2, $R^1$ represents a methyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX1059").

The Compound (L-2), wherein n represents 2, $R^1$ represents a methyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX1060").

The Compound (L-2), wherein n represents 2, $R^1$ represents an ethyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX1061").

The Compound (L-2), wherein n represents 2, $R^1$ represents an ethyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX1062").

The Compound (L-2), wherein n represents 2, $R^1$ represents an ethyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX1063").

The Compound (L-2), wherein n represents 2, $R^1$ represents an ethyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX1064").

The Compound (L-2), wherein n represents 2, $R^1$ represents an ethyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX1065").

The Compound (L-2), wherein n represents 2, $R^1$ represents an ethyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX1066").

The Compound (L-2), wherein n represents 2, $R^1$ represents an ethyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX1067").

The Compound (L-2), wherein n represents 2, $R^1$ represents an ethyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX1068").

The Compound (L-2), wherein n represents 2, $R^1$ represents an ethyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX1069").

The Compound (L-2), wherein n represents 2, $R^1$ represents an ethyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX1070").

The Compound (L-2), wherein n represents 2, $R^1$ represents an isopropyl group, T represents a 3-[(trifluoromethyl)thio]phenyl group, $R^{3c}$ represents a hydrogen atom, and $R^{3b}$ represents any one substituent described in Table L12 to Table L14 (hereinafter referred to as "Compound group SX1071").

The Compound (L-2), wherein n represents 2, $R^1$ represents an isopropyl group, T represents a 3-[(trifluoromethyl)thio]phenyl group, $R^{3c}$ represents a chlorine atom, and $R^{3b}$ represents any one substituent described in Table L12 to Table L14 (hereinafter referred to as "Compound group SX1072").

The Compound (L-2), wherein n represents 2, $R^1$ represents an isopropyl group, T represents a 3-[(trifluoromethyl)thio]phenyl group, $R^{3c}$ represents a bromine atom, and $R^{3b}$ represents any one substituent described in Table L12 to Table L14 (hereinafter referred to as "Compound group SX1073").

The Compound (L-2), wherein n represents 2, $R^1$ represents an isopropyl group, T represents a 3-[(trifluoromethyl)thio]phenyl group, $R^{3c}$ represents an iodine atom, and $R^{3b}$ represents any one substituent described in Table L12 to Table L14 (hereinafter referred to as "Compound group SX1074").

The Compound (L-2), wherein n represents 2, $R^1$ represents an isopropyl group, T represents a 3-[(trifluoromethyl)thio]phenyl group, $R^{3c}$ represents $CF_3$, and $R^{3b}$ represents any one substituent described in Table L12 to Table L14 (hereinafter referred to as "Compound group SX1075").

The Compound (L-2), wherein n represents 2, $R^1$ represents an isopropyl group, T represents a 4-[(trifluoromethyl)thio]phenyl group, $R^{3c}$ represents a hydrogen atom, and $R^{3b}$ represents any one substituent described in Table L12 to Table L14 (hereinafter referred to as "Compound group SX1076").

The Compound (L-2), wherein n represents 2, $R^1$ represents an isopropyl group, T represents a 4-[(trifluoromethyl)thio]phenyl group, $R^{3c}$ represents a chlorine atom, and $R^{3b}$ represents any one substituent described in Table L12 to Table L14 (hereinafter referred to as "Compound group SX1077").

The Compound (L-2), wherein n represents 2, $R^1$ represents an isopropyl group, T represents a 4-[(trifluoromethyl)thio]phenyl group, $R^{3c}$ represents a bromine atom, and $R^{3b}$ represents any one substituent described in Table L12 to Table L14 (hereinafter referred to as "Compound group SX1078").

The Compound (L-2), wherein n represents 2, $R^1$ represents an isopropyl group, T represents a 4-[(trifluoromethyl)thio]phenyl group, $R^{3c}$ represents an iodine atom, and $R^{3b}$ represents any one substituent described in Table L12 to Table L14 (hereinafter referred to as "Compound group SX1079").

The Compound (L-2), wherein n represents 2, $R^1$ represents an isopropyl group, T represents a 4-[(trifluoromethyl)thio]phenyl group, $R^{3c}$ represents $CF_3$, and $R^{3b}$ represents any one substituent described in Table L12 to Table L14 (hereinafter referred to as "Compound group SX1080").

The Compound (L-2), wherein n represents 2, $R^1$ represents a methyl group, T represents a 4-(trifluoromethoxy)phenyl group, $R^{3c}$ represents a hydrogen atom, and $R^{3b}$ represents any one substituent described in Table L12 to Table L14 (hereinafter referred to as "Compound group SX1081").

The Compound (L-2), wherein n represents 2, $R^1$ represents a methyl group, T represents a 4-(trifluoromethoxy)phenyl group, $R^{3c}$ represents a chlorine atom, and $R^{3b}$ represents any one substituent described in Table L12 to Table L14 (hereinafter referred to as "Compound group SX1082").

The Compound (L-2), wherein n represents 2, $R^1$ represents a methyl group, T represents a 4-(trifluoromethoxy)phenyl group, $R^{3c}$ represents a bromine atom, and $R^{3b}$ represents any one substituent described in Table L12 to Table L14 (hereinafter referred to as "Compound group SX1083").

The Compound (L-2), wherein n represents 2, $R^1$ represents a methyl group, T represents a 4-(trifluoromethoxy)phenyl group, $R^{3c}$ represents an iodine atom, and $R^{3b}$ represents any one substituent described in Table L12 to Table L14 (hereinafter referred to as "Compound group SX1084").

The Compound (L-2), wherein n represents 2, $R^1$ represents a methyl group, T represents a 4-(trifluoromethoxy)phenyl group, $R^{3c}$ represents $CF_3$, and $R^{3b}$ represents any one substituent described in Table L12 to Table L14 (hereinafter referred to as "Compound group SX1085").

The Compound (L-2), wherein n represents 2, $R^1$ represents a methyl group, T represents a 4-(trifluoromethyl)phenyl group, $R^{3c}$ represents a hydrogen atom, and $R^{3b}$ represents any one substituent described in Table L12 to Table L14 (hereinafter referred to as "Compound group SX1086").

The Compound (L-2), wherein n represents 2, $R^1$ represents a methyl group, T represents a 4-(trifluoromethyl)phenyl group, $R^{3c}$ represents a chlorine atom, and $R^{3b}$ represents any one substituent described in Table L12 to Table L14 (hereinafter referred to as "Compound group SX1087").

The Compound (L-2), wherein n represents 2, $R^1$ represents a methyl group, T represents a 4-(trifluoromethyl)phenyl group, $R^{3c}$ represents a bromine atom, and $R^{3b}$ represents any one substituent described in Table L12 to Table L14 (hereinafter referred to as "Compound group SX1088").

The Compound (L-2), wherein n represents 2, $R^1$ represents a methyl group, T represents a 4-(trifluoromethyl)phenyl group, $R^{3c}$ represents an iodine atom, and $R^{3b}$ represents any one substituent described in Table L12 to Table L14 (hereinafter referred to as "Compound group SX1089").

The Compound (L-2), wherein n represents 2, $R^1$ represents a methyl group, T represents a 4-(trifluoromethyl)phenyl group, $R^{3c}$ represents $CF_3$, and $R^{3b}$ represents any one substituent described in Table L12 to Table L14 (hereinafter referred to as "Compound group SX1090").

The Compound (L-2), wherein n represents 2, $R^1$ represents a methyl group, T represents a 3,4-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX1091").

The Compound (L-2), wherein n represents 2, $R^1$ represents a methyl group, T represents a 3,4-bis[(trifluoromethyl)thio]phenyl group, $R^{3c}$ represents a chlorine atom, and $R^{3b}$ represents any one substituent described in Table L12 to Table L14 (hereinafter referred to as "Compound group SX1092").

The Compound (L-2), wherein n represents 2, $R^1$ represents a methyl group, T represents a 3,4-bis[(trifluoromethyl)thio]phenyl group, $R^{3c}$ represents a bromine atom, and $R^{3b}$ represents any one substituent described in Table L12 to Table L14 (hereinafter referred to as "Compound group SX1093").

The Compound (L-2), wherein n represents 2, $R^1$ represents a methyl group, T represents a 3,4-bis[(trifluoromethyl)thio]phenyl group, $R^{3c}$ represents an iodine atom, and $R^{3b}$ represents any one substituent described in Table L12 to Table L14 (hereinafter referred to as "Compound group SX1094").

The Compound (L-2), wherein n represents 2, $R^1$ represents a methyl group, T represents a 3,4-bis[(trifluoromethyl)thio]phenyl group, $R^{3c}$ represents $CF_3$, and $R^{3b}$ represents any one substituent described in Table L12 to Table L14 (hereinafter referred to as "Compound group SX1095").

The Compound (L-2), wherein n represents 2, $R^1$ represents a methyl group, T represents a 3,4-bis(trifluoromethoxy)phenyl group, $R^{3c}$ represents a hydrogen atom, and $R^{3b}$ represents any one substituent described in Table L12 to Table L14 (hereinafter referred to as "Compound group SX1096").

The Compound (L-2), wherein n represents 2, $R^1$ represents a methyl group, T represents a 3,4-bis(trifluoromethoxy)phenyl group, $R^{3c}$ represents a chlorine atom, and $R^{3b}$ represents any one substituent described in Table L12 to Table L14 (hereinafter referred to as "Compound group SX1097").

The Compound (L-2), wherein n represents 2, $R^1$ represents a methyl group, T represents a 3,4-bis(trifluoromethoxy)phenyl group, $R^{3c}$ represents a bromine atom, and $R^{3b}$ represents any one substituent described in Table L12 to Table L14 (hereinafter referred to as "Compound group SX1098").

The Compound (L-2), wherein n represents 2, $R^1$ represents a methyl group, T represents a 3,4-bis(trifluoromethoxy)phenyl group, $R^{3c}$ represents an iodine atom, and $R^{3b}$ represents any one substituent described in Table L12 to Table L14 (hereinafter referred to as "Compound group SX1099").

The Compound (L-2), wherein n represents 2, $R^1$ represents a methyl group, T represents a 3,4-bis(trifluoromethoxy)phenyl group, $R^{3c}$ represents $CF_3$, and $R^{3b}$ represents any one substituent described in Table L12 to Table L14 (hereinafter referred to as "Compound group SX1100").

The Compound (L-2), wherein n represents 2, $R^1$ represents a methyl group, T represents a 3,4-bis(trifluoromethyl)phenyl group, $R^{3c}$ represents a hydrogen atom, and $R^{3b}$ represents any one substituent described in Table L12 to Table L14 (hereinafter referred to as "Compound group SX1101").

The Compound (L-2), wherein n represents 2, $R^1$ represents a methyl group, T represents a 3,4-bis(trifluoromethyl)phenyl group, $R^{3c}$ represents a chlorine atom, and $R^{3b}$ represents any one substituent described in Table L12 to Table L14 (hereinafter referred to as "Compound group SX1102").

The Compound (L-2), wherein n represents 2, $R^1$ represents a methyl group, T represents a 3,4-bis(trifluoromethyl) phenyl group, $R^{3c}$ represents a bromine Table L12 to Table L14 (hereinafter referred to as "Compound group SX1103").

The Compound (L-2), wherein n represents 2, $R^1$ represents a methyl group, T represents a 3,4-bis(trifluoromethyl) phenyl group, $R^{3c}$ represents an iodine atom, and $R^{3b}$ represents any one substituent described in Table L12 to Table L14 (hereinafter referred to as "Compound group SX1104").

The Compound (L-2), wherein n represents 2, $R^1$ represents a methyl group, T represents a 3,4-bis(trifluoromethyl) phenyl group, $R^{3c}$ represents $CF_3$, and $R^{3b}$ represents any one substituent described in Table L12 to Table L14 (hereinafter referred to as "Compound group SX1105").

The Compound (L-2), wherein n represents 2, $R^1$ represents a methyl group, T represents a 3,5-bis[(trifluoromethyl)thio]phenyl group, $R^{3c}$ represents a hydrogen atom, and $R^{3b}$ represents any one substituent described in Table L12 to Table L14 (hereinafter referred to as "Compound group SX1106").

The Compound (L-2), wherein n represents 2, $R^1$ represents a methyl group, T represents a 3,5-bis[(trifluoromethyl)thio]phenyl group, $R^{3c}$ represents a chlorine atom, and $R^{3b}$ represents any one substituent described in Table L12 to Table L14 (hereinafter referred to as "Compound group SX1107").

The Compound (L-2), wherein n represents 2, $R^1$ represents a methyl group, T represents a 3,5-bis[(trifluoromethyl)thio]phenyl group, $R^{3c}$ represents a bromine atom, and $R^{3b}$ represents any one substituent described in Table L12 to Table L14 (hereinafter referred to as "Compound group SX1108").

The Compound (L-2), wherein n represents 2, $R^1$ represents a methyl group, T represents a 3,5-bis[(trifluoromethyl)thio]phenyl group, $R^{3c}$ represents an iodine atom, and $R^{3b}$ represents any one substituent described in Table L12 to Table L14 (hereinafter referred to as "Compound group SX1109").

The Compound (L-2), wherein n represents 2, $R^1$ represents a methyl group, T represents a 3,5-bis[(trifluoromethyl)thio]phenyl group, $R^{3c}$ represents $CF_3$, and $R^{3b}$ represents any one substituent described in Table L12 to Table L14 (hereinafter referred to as "Compound group SX1110").

The Compound (L-2), wherein n represents 2, $R^1$ represents a methyl group, T represents a 3,5-bis(trifluoromethoxy)phenyl group, $R^{3c}$ represents a hydrogen atom, and $R^{3b}$ represents any one substituent described in Table L12 to Table L14 (hereinafter referred to as "Compound group SX1111").

The Compound (L-2), wherein n represents 2, $R^1$ represents a methyl group, T represents a 3,5-bis(trifluoromethoxy)phenyl group, $R^{3c}$ represents a chlorine atom, and $R^{3b}$ represents any one substituent described in Table L12 to Table L14 (hereinafter referred to as "Compound group SX1112").

The Compound (L-2), wherein n represents 2, $R^1$ represents a methyl group, T represents a 3,5-bis(trifluoromethoxy)phenyl group, $R^{3c}$ represents a bromine atom, and $R^{3b}$ represents any one substituent described in Table L12 to Table L14 (hereinafter referred to as "Compound group SX1113").

The Compound (L-2), wherein n represents 2, $R^1$ represents a methyl group, T represents a 3,5-bis(trifluoromethoxy)phenyl group, $R^{3c}$ represents an iodine atom, and $R^{3b}$ represents any one substituent described in Table L12 to Table L14 (hereinafter referred to as "Compound group SX1114").

The Compound (L-2), wherein n represents 2, $R^1$ represents a methyl group, T represents a 3,5-bis(trifluoromethoxy)phenyl group, $R^{3c}$ represents $CF_3$, and $R^{3b}$ represents any one substituent described in Table L12 to Table L14 (hereinafter referred to as "Compound group SX1115").

The Compound (L-2), wherein n represents 2, $R^1$ represents a methyl group, T represents a 3,5-bis(trifluoromethyl) phenyl group, $R^{3c}$ represents a hydrogen atom, and $R^{3b}$ represents any one substituent described in Table L12 to Table L14 (hereinafter referred to as "Compound group SX1116").

The Compound (L-2), wherein n represents 2, $R^1$ represents a methyl group, T represents a 3,5-bis(trifluoromethyl) phenyl group, $R^{3c}$ represents a chlorine atom, and $R^{3b}$ represents any one substituent described in Table L12 to Table L14 (hereinafter referred to as "Compound group SX1117").

The Compound (L-2), wherein n represents 2, $R^1$ represents a methyl group, T represents a 3,5-bis(trifluoromethyl) phenyl group, $R^{3c}$ represents a bromine atom, and $R^{3b}$ represents any one substituent described in Table L12 to Table L14 (hereinafter referred to as "Compound group SX1118").

The Compound (L-2), wherein n represents 2, $R^1$ represents a methyl group, T represents a 3,5-bis(trifluoromethyl) phenyl group, $R^{3c}$ represents an iodine atom, and $R^{3b}$ represents any one substituent described in Table L12 to Table L14 (hereinafter referred to as "Compound group SX1119").

The Compound (L-2), wherein n represents 2, $R^1$ represents a methyl group, T represents a 3,5-bis(trifluoromethyl) phenyl group, $R^{3c}$ represents $CF_3$, and $R^{3b}$ represents any one substituent described in Table L12 to Table L14 (hereinafter referred to as "Compound group SX1120").

The Compound (L-2), wherein n represents 2, $R^1$ represents a methyl group, T represents a 3-fluoro-5-(trifluoromethoxy)phenyl group, $R^{3c}$ represents a hydrogen atom, and $R^{3b}$ represents any one substituent described in Table L12 to Table L14 (hereinafter referred to as "Compound group SX1121").

The Compound (L-2), wherein n represents 2, $R^1$ represents a methyl group, T represents a 3-fluoro-5-(trifluoromethoxy)phenyl group, $R^{3c}$ represents a chlorine atom, and $R^{3b}$ represents any one substituent described in Table L12 to Table L14 (hereinafter referred to as "Compound group SX1122").

The Compound (L-2), wherein n represents 2, $R^1$ represents a methyl group, T represents a 3-fluoro-5-(trifluoromethoxy)phenyl group, $R^{3c}$ represents a bromine atom, and $R^{3b}$ represents any one substituent described in Table L12 to Table L14 (hereinafter referred to as "Compound group SX1123").

The Compound (L-2), wherein n represents 2, $R^1$ represents a methyl group, T represents a 3-fluoro-5-(trifluoromethoxy)phenyl group, $R^{3c}$ represents an iodine atom, and $R^{3b}$ represents any one substituent described in Table L12 to Table L14 (hereinafter referred to as "Compound group SX1124").

The Compound (L-2), wherein n represents 2, $R^1$ represents a methyl group, T represents a 3-fluoro-5-(trifluoromethoxy)phenyl group, $R^{3c}$ represents $CF_3$, and $R^{3b}$ represents any one substituent described in Table L12 to Table L14 (hereinafter referred to as "Compound group SX1125").

The Compound (L-2), wherein n represents 0, $R^1$ represents a methyl group, T represents a 3-[(trifluoromethyl) thio]phenyl group, $R^{3b}$ represents a hydrogen atom, and $R^{3c}$ represents any one substituent described in Table L12 to Table L14 (hereinafter referred to as "Compound group SX1126").

The Compound (L-2), wherein n represents 0, $R^1$ represents a methyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX1127").

The Compound (L-2), wherein n represents 0, $R^1$ represents a methyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX1128").

The Compound (L-2), wherein n represents 0, $R^1$ represents a methyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX1129").

The Compound (L-2), wherein n represents 0, $R^1$ represents a methyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX1130").

The Compound (L-2), wherein n represents 0, $R^1$ represents a methyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX1131").

The Compound (L-2), wherein n represents 0, $R^1$ represents a methyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX1132").

The Compound (L-2), wherein n represents 0, $R^1$ represents a methyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX1133").

The Compound (L-2), wherein n represents 0, $R^1$ represents a methyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX1134").

The Compound (L-2), wherein n represents 0, $R^1$ represents a methyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX1135").

The Compound (L-2), wherein n represents 0, $R^1$ represents an ethyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX1136").

The Compound (L-2), wherein n represents 0, $R^1$ represents an ethyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX1137").

The Compound (L-2), wherein n represents 0, $R^1$ represents an ethyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX1138").

The Compound (L-2), wherein n represents 0, $R^1$ represents an ethyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX1139").

The Compound (L-2), wherein n represents 0, $R^1$ represents an ethyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX1140").

The Compound (L-2), wherein n represents 0, $R^1$ represents an ethyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX1141").

The Compound (L-2), wherein n represents 0, $R^1$ represents an ethyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX1142").

The Compound (L-2), wherein n represents 0, $R^1$ represents an ethyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX1143").

The Compound (L-2), wherein n represents 0, $R^1$ represents an ethyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX1144").

The Compound (L-2), wherein n represents 0, $R^1$ represents an ethyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX1145").

The Compound (L-2), wherein n represents 0, $R^1$ represents an isopropyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX1146").

The Compound (L-2), wherein n represents 0, $R^1$ represents an isopropyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX1147").

The Compound (L-2), wherein n represents 0, $R^1$ represents an isopropyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX1148").

The Compound (L-2), wherein n represents 0, $R^1$ represents an isopropyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX1149").

The Compound (L-2), wherein n represents 0, $R^1$ represents an isopropyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX1150").

The Compound (L-2), wherein n represents 0, $R^1$ represents an isopropyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX1151").

The Compound (L-2), wherein n represents 0, $R^1$ represents an isopropyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX1152").

The Compound (L-2), wherein n represents 0, $R^1$ represents an isopropyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX1153").

The Compound (L-2), wherein n represents 0, $R^1$ represents an isopropyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX1154").

The Compound (L-2), wherein n represents 0, $R^1$ represents an isopropyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX1155").

The Compound (L-2), wherein n represents 0, $R^1$ represents a methyl group, T represents a 4-(trifluoromethoxy)phenyl group, $R^{3b}$ represents a hydrogen atom, and $R^{3c}$ represents any one substituent described in Table L12 to Table L14 (hereinafter referred to as "Compound group SX1156").

The Compound (L-2), wherein n represents 0, $R^1$ represents a methyl group, T represents a 4-(trifluoromethoxy)phenyl group, $R^{3b}$ represents a chlorine atom, and $R^{3c}$ represents any one substituent described in Table L12 to Table L14 (hereinafter referred to as "Compound group SX1157").

The Compound (L-2), wherein n represents 0, $R^1$ represents a methyl group, T represents a 4-(trifluoromethoxy)phenyl group, $R^{3b}$ represents a bromine atom, and $R^{3c}$ represents any one substituent described in Table L12 to Table L14 (hereinafter referred to as "Compound group SX1158").

The Compound (L-2), wherein n represents 0, $R^1$ represents a methyl group, T represents a 4-(trifluoromethoxy)phenyl group, $R^{3b}$ represents an iodine atom, and $R^{3c}$ represents any one substituent described in Table L12 to Table L14 (hereinafter referred to as "Compound group SX1159").

The Compound (L-2), wherein n represents 0, $R^1$ represents a methyl group, T represents a 4-(trifluoromethoxy)phenyl group, $R^{3b}$ represents $CF_3$, and $R^{3c}$ represents any one substituent described in Table L12 to Table L14 (hereinafter referred to as "Compound group SX1160").

The Compound (L-2), wherein n represents 0, $R^1$ represents a methyl group, T represents a 4-(trifluoromethyl)phenyl group, $R^{3b}$ represents a hydrogen atom, and $R^{3c}$ represents any one substituent described in Table L12 to Table L14 (hereinafter referred to as "Compound group SX1161").

The Compound (L-2), wherein n represents 0, $R^1$ represents a methyl group, T represents a 4-(trifluoromethyl)phenyl group, $R^{3b}$ represents a chlorine atom, and $R^{3c}$ represents any one substituent described in Table L12 to Table L14 (hereinafter referred to as "Compound group SX1162").

The Compound (L-2), wherein n represents 0, $R^1$ represents a methyl group, T represents a 4-(trifluoromethyl)phenyl group, $R^{3b}$ represents a bromine atom, and $R^{3c}$ represents any one substituent described in Table L12 to Table L14 (hereinafter referred to as "Compound group SX1163").

The Compound (L-2), wherein n represents 0, $R^1$ represents a methyl group, T represents a 4-(trifluoromethyl)phenyl group, $R^{3b}$ represents an iodine atom, and $R^{3c}$ represents any one substituent described in Table L12 to Table L14 (hereinafter referred to as "Compound group SX1164").

The Compound (L-2), wherein n represents 0, $R^1$ represents a methyl group, T represents a 4-(trifluoromethyl)phenyl group, $R^{3b}$ represents $CF_3$, and $R^{3c}$ represents any one substituent described in Table L12 to Table L14 (hereinafter referred to as "Compound group SX1165").

The Compound (L-2), wherein n represents 0, $R^1$ represents a methyl group, T represents a 3,4-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX1166").

The Compound (L-2), wherein n represents 0, $R^1$ represents a methyl group, T represents a 3,4-bis[(trifluoromethyl)thio]phenyl group, $R^{3b}$ represents a chlorine atom, and $R^{3c}$ represents any one substituent described in Table L12 to Table L14 (hereinafter referred to as "Compound group SX1167").

The Compound (L-2), wherein n represents 0, $R^1$ represents a methyl group, T represents a 3,4-bis[(trifluoromethyl)thio]phenyl group, $R^{3b}$ represents a bromine atom, and $R^{3c}$ represents any one substituent described in Table L12 to Table L14 (hereinafter referred to as "Compound group SX1168").

The Compound (L-2), wherein n represents 0, $R^1$ represents a methyl group, T represents a 3,4-bis[(trifluoromethyl)thio]phenyl group, $R^{3b}$ represents an iodine atom, and $R^{3c}$ represents any one substituent described in Table L12 to Table L14 (hereinafter referred to as "Compound group SX1169").

The Compound (L-2), wherein n represents 0, $R^1$ represents a methyl group, T represents a 3,4-bis[(trifluoromethyl)thio]phenyl group, $R^{3b}$ represents $CF_3$, and $R^{3c}$ represents any one substituent described in Table L12 to Table L14 (hereinafter referred to as "Compound group SX1170").

The Compound (L-2), wherein n represents 0, $R^1$ represents a methyl group, T represents a 3,4-bis(trifluoromethoxy)phenyl group, $R^{3b}$ represents a hydrogen atom, and $R^{3c}$ represents any one substituent described in Table L12 to Table L14 (hereinafter referred to as "Compound group SX1171").

The Compound (L-2), wherein n represents 0, $R^1$ represents a methyl group, T represents a 3,4-bis(trifluoromethoxy)phenyl group, $R^{3b}$ represents a chlorine atom, and $R^{3c}$ represents any one substituent described in Table L12 to Table L14 (hereinafter referred to as "Compound group SX1172").

The Compound (L-2), wherein n represents 0, $R^1$ represents a methyl group, T represents a 3,4-bis(trifluoromethoxy)phenyl group, $R^{3b}$ represents a bromine atom, and $R^{3c}$ represents any one substituent described in Table L12 to Table L14 (hereinafter referred to as "Compound group SX1173").

The Compound (L-2), wherein n represents 0, $R^1$ represents a methyl group, T represents a 3,4-bis(trifluoromethoxy)phenyl group, $R^{3b}$ represents an iodine atom, and $R^{3c}$ represents any one substituent described in Table L12 to Table L14 (hereinafter referred to as "Compound group SX1174").

The Compound (L-2), wherein n represents 0, $R^1$ represents a methyl group, T represents a 3,4-bis(trifluoromethoxy)phenyl group, $R^{3b}$ represents $CF_3$, and $R^{3c}$ represents any one substituent described in Table L12 to Table L14 (hereinafter referred to as "Compound group SX1175").

The Compound (L-2), wherein n represents 0, $R^1$ represents a methyl group, T represents a 3,4-bis(trifluoromethyl) phenyl group, $R^{3b}$ represents a hydrogen atom, and $R^{3c}$ represents any one substituent described in Table L12 to Table L14 (hereinafter referred to as "Compound group SX1176").

The Compound (L-2), wherein n represents 0, $R^1$ represents a methyl group, T represents a 3,4-bis(trifluoromethyl) phenyl group, $R^{3b}$ represents a chlorine atom, and $R^{3c}$ represents any one substituent described in Table L12 to Table L14 (hereinafter referred to as "Compound group SX1177").

The Compound (L-2), wherein n represents 0, $R^1$ represents a methyl group, T represents a 3,4-bis(trifluoromethyl) phenyl group, $R^{3b}$ represents a bromine Table L12 to Table L14 (hereinafter referred to as "Compound group SX1178").

The Compound (L-2), wherein n represents 0, $R^1$ represents a methyl group, T represents a 3,4-bis(trifluoromethyl) phenyl group, $R^{3b}$ represents an iodine atom, and $R^{3c}$ represents any one substituent described in Table L12 to Table L14 (hereinafter referred to as "Compound group SX1179").

The Compound (L-2), wherein n represents 0, $R^1$ represents a methyl group, T represents a 3,4-bis(trifluoromethyl) phenyl group, $R^{3b}$ represents $CF_3$, and $R^{3c}$ represents any one substituent described in Table L12 to Table L14 (hereinafter referred to as "Compound group SX1180").

The Compound (L-2), wherein n represents 0, $R^1$ represents a methyl group, T represents a 3,5-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX1181").

The Compound (L-2), wherein n represents 0, $R^1$ represents a methyl group, T represents a 3,5-bis[(trifluoromethyl)thio]phenyl group, $R^{3b}$ represents a chlorine atom, and $R^{3c}$ represents any one substituent described in Table L12 to Table L14 (hereinafter referred to as "Compound group SX1182").

The Compound (L-2), wherein n represents 0, $R^1$ represents a methyl group, T represents a 3,5-bis[(trifluoromethyl)thio]phenyl group, $R^{3b}$ represents a bromine atom, and $R^{3c}$ represents any one substituent described in Table L12 to Table L14 (hereinafter referred to as "Compound group SX1183").

The Compound (L-2), wherein n represents 0, $R^1$ represents a methyl group, T represents a 3,5-bis[(trifluoromethyl)thio]phenyl group, $R^{3b}$ represents an iodine atom, and $R^{3c}$ represents any one substituent described in Table L12 to Table L14 (hereinafter referred to as "Compound group SX1184").

The Compound (L-2), wherein n represents 0, $R^1$ represents a methyl group, T represents a 3,5-bis[(trifluoromethyl)thio]phenyl group, $R^{3b}$ represents $CF_3$, and $R^{3c}$ represents any one substituent described in Table L12 to Table L14 (hereinafter referred to as "Compound group SX1185").

The Compound (L-2), wherein n represents 0, $R^1$ represents a methyl group, T represents a 3,5-bis(trifluoromethoxy)phenyl group, $R^{3b}$ represents a hydrogen atom, and $R^{3c}$ represents any one substituent described in Table L12 to Table L14 (hereinafter referred to as "Compound group SX1186").

The Compound (L-2), wherein n represents 0, $R^1$ represents a methyl group, T represents a 3,5-bis(trifluoromethoxy)phenyl group, $R^{3b}$ represents a chlorine atom, and $R^{3c}$ represents any one substituent described in Table L12 to Table L14 (hereinafter referred to as "Compound group SX1187").

The Compound (L-2), wherein n represents 0, $R^1$ represents a methyl group, T represents a 3,5-bis(trifluoromethoxy)phenyl group, $R^{3b}$ represents a bromine atom, and $R^{3c}$ represents any one substituent described in Table L12 to Table L14 (hereinafter referred to as "Compound group SX1188").

The Compound (L-2), wherein n represents 0, $R^1$ represents a methyl group, T represents a 3,5-bis(trifluoromethoxy)phenyl group, $R^{3b}$ represents an iodine atom, and $R^{3c}$ represents any one substituent described in Table L12 to Table L14 (hereinafter referred to as "Compound group SX1189").

The Compound (L-2), wherein n represents 0, $R^1$ represents a methyl group, T represents a 3,5-bis(trifluoromethoxy)phenyl group, $R^{3b}$ represents $CF_3$, and $R^{3c}$ represents any one substituent described in Table L12 to Table L14 (hereinafter referred to as "Compound group SX1190").

The Compound (L-2), wherein n represents 0, $R^1$ represents a methyl group, T represents a 3,5-bis(trifluoromethyl) phenyl group, $R^{3b}$ represents a hydrogen atom, and $R^{3c}$ represents any one substituent described in Table L12 to Table L14 (hereinafter referred to as "Compound group SX1191").

The Compound (L-2), wherein n represents 0, $R^1$ represents a methyl group, T represents a 3,5-bis(trifluoromethyl) phenyl group, $R^{3b}$ represents a chlorine atom, and $R^{3c}$ represents any one substituent described in Table L12 to Table L14 (hereinafter referred to as "Compound group SX1192").

The Compound (L-2), wherein n represents 0, $R^1$ represents a methyl group, T represents a 3,5-bis(trifluoromethyl) phenyl group, $R^{3b}$ represents a bromine atom, and $R^{3c}$ represents any one substituent described in Table L12 to Table L14 (hereinafter referred to as "Compound group SX1193").

The Compound (L-2), wherein n represents 0, $R^1$ represents a methyl group, T represents a 3,5-bis(trifluoromethyl) phenyl group, $R^{3b}$ represents an iodine atom, and $R^{3c}$ represents any one substituent described in Table L12 to Table L14 (hereinafter referred to as "Compound group SX1194").

The Compound (L-2), wherein n represents 0, $R^1$ represents a methyl group, T represents a 3,5-bis(trifluoromethyl) phenyl group, $R^{3b}$ represents $CF_3$, and $R^{3c}$ represents any one substituent described in Table L12 to Table L14 (hereinafter referred to as "Compound group SX1195").

The Compound (L-2), wherein n represents 0, $R^1$ represents a methyl group, T represents a 3-fluoro-5-(trifluoromethoxy)phenyl group, $R^{3b}$ represents a hydrogen atom, and $R^{3c}$ represents any one substituent described in Table L12 to Table L14 (hereinafter referred to as "Compound group SX1196").

The Compound (L-2), wherein n represents 0, $R^1$ represents a methyl group, T represents a 3-fluoro-5-(trifluoromethoxy)phenyl group, $R^{3b}$ represents a chlorine atom, and $R^{3c}$ represents any one substituent described in Table L12 to Table L14 (hereinafter referred to as "Compound group SX1197").

The Compound (L-2), wherein n represents 0, $R^1$ represents a methyl group, T represents a 3-fluoro-5-(trifluoromethoxy)phenyl group, $R^{3b}$ represents a bromine atom, and $R^{3c}$ represents any one substituent described in Table L12 to Table L14 (hereinafter referred to as "Compound group SX1198").

The Compound (L-2), wherein n represents 0, $R^1$ represents a methyl group, T represents a 3-fluoro-5-(trifluoromethoxy)phenyl group, $R^{3b}$ represents an iodine atom, and $R^{3c}$ represents any one substituent described in Table L12 to Table L14 (hereinafter referred to as "Compound group SX1199").

The Compound (L-2), wherein n represents 0, $R^1$ represents a methyl group, T represents a 3-fluoro-5-(trifluoromethoxy)phenyl group, $R^{3b}$ represents $CF_3$, and $R^{3c}$ represents any one substituent described in Table L12 to Table L14 (hereinafter referred to as "Compound group SX1200").

The Compound (L-2), wherein n represents 1, $R^1$ represents a methyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX1201").

The Compound (L-2), wherein n represents 1, $R^1$ represents a methyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX1202").

The Compound (L-2), wherein n represents 1, $R^1$ represents a methyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX1203").

The Compound (L-2), wherein n represents 1, $R^1$ represents a methyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX1204").

The Compound (L-2), wherein n represents 1, $R^1$ represents a methyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX1205").

The Compound (L-2), wherein n represents 1, $R^1$ represents a methyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX1206").

The Compound (L-2), wherein n represents 1, $R^1$ represents a methyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX1207").

The Compound (L-2), wherein n represents 1, $R^1$ represents a methyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX1208").

The Compound (L-2), wherein n represents 1, $R^1$ represents a methyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX1209").

The Compound (L-2), wherein n represents 1, $R^1$ represents a methyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX1210").

The Compound (L-2), wherein n represents 1, $R^1$ represents an ethyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX1211").

The Compound (L-2), wherein n represents 1, $R^1$ represents an ethyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX1212").

The Compound (L-2), wherein n represents 1, $R^1$ represents an ethyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX1213").

The Compound (L-2), wherein n represents 1, $R^1$ represents an ethyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX1214").

The Compound (L-2), wherein n represents 1, $R^1$ represents an ethyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX1215").

The Compound (L-2), wherein n represents 1, $R^1$ represents an ethyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX1216").

The Compound (L-2), wherein n represents 1, $R^1$ represents an ethyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX1217").

The Compound (L-2), wherein n represents 1, $R^1$ represents an ethyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX1218").

The Compound (L-2), wherein n represents 1, $R^1$ represents an ethyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX1219").

The Compound (L-2), wherein n represents 1, $R^1$ represents an ethyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX1220").

The Compound (L-2), wherein n represents 1, $R^1$ represents an isopropyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX1221").

The Compound (L-2), wherein n represents 1, $R^1$ represents an isopropyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX1222").

The Compound (L-2), wherein n represents 1, $R^1$ represents an isopropyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX1223").

The Compound (L-2), wherein n represents 1, $R^1$ represents an isopropyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX1224").

The Compound (L-2), wherein n represents 1, $R^1$ represents an isopropyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX1225").

The Compound (L-2), wherein n represents 1, $R^1$ represents an isopropyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX1226").

The Compound (L-2), wherein n represents 1, $R^1$ represents an isopropyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX1227").

The Compound (L-2), wherein n represents 1, $R^1$ represents an isopropyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX1228").

The Compound (L-2), wherein n represents 1, $R^1$ represents an isopropyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX1229").

The Compound (L-2), wherein n represents 1, $R^1$ represents an isopropyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX1230").

The Compound (L-2), wherein n represents 1, $R^1$ represents a methyl group, T represents a 4-(trifluoromethoxy)phenyl group, $R^{3b}$ represents a hydrogen atom, and $R^{3c}$ represents any one substituent described in Table L12 to Table L14 (hereinafter referred to as "Compound group SX1231").

The Compound (L-2), wherein n represents 1, $R^1$ represents a methyl group, T represents a 4-(trifluoromethoxy)phenyl group, $R^{3b}$ represents a chlorine atom, and $R^{3c}$ represents any one substituent described in Table L12 to Table L14 (hereinafter referred to as "Compound group SX1232").

The Compound (L-2), wherein n represents 1, $R^1$ represents a methyl group, T represents a 4-(trifluoromethoxy)phenyl group, $R^{3b}$ represents a bromine atom, and $R^{3c}$ represents any one substituent described in Table L12 to Table L14 (hereinafter referred to as "Compound group SX1233").

The Compound (L-2), wherein n represents 1, $R^1$ represents a methyl group, T represents a 4-(trifluoromethoxy)phenyl group, $R^{3b}$ represents an iodine atom, and $R^{3c}$ represents any one substituent described in Table L12 to Table L14 (hereinafter referred to as "Compound group SX1234").

The Compound (L-2), wherein n represents 1, $R^1$ represents a methyl group, T represents a 4-(trifluoromethoxy)phenyl group, $R^{3b}$ represents $CF_3$, and $R^{3c}$ represents any one substituent described in Table L12 to Table L14 (hereinafter referred to as "Compound group SX1235").

The Compound (L-2), wherein n represents 1, $R^1$ represents a methyl group, T represents a 4-(trifluoromethyl)phenyl group, $R^{3b}$ represents a hydrogen atom, and $R^{3c}$ represents any one substituent described in Table L12 to Table L14 (hereinafter referred to as "Compound group SX1236").

The Compound (L-2), wherein n represents 1, $R^1$ represents a methyl group, T represents a 4-(trifluoromethyl)phenyl group, $R^{3b}$ represents a chlorine atom, and $R^{3c}$ represents any one substituent described in Table L12 to Table L14 (hereinafter referred to as "Compound group SX1237").

The Compound (L-2), wherein n represents 1, $R^1$ represents a methyl group, T represents a 4-(trifluoromethyl)phenyl group, $R^{3b}$ represents a bromine atom, and $R^{3c}$ represents any one substituent described in Table L12 to Table L14 (hereinafter referred to as "Compound group SX1238").

The Compound (L-2), wherein n represents 1, $R^1$ represents a methyl group, T represents a 4-(trifluoromethyl)phenyl group, $R^{3b}$ represents an iodine atom, and $R^{3c}$ represents any one substituent described in Table L12 to Table L14 (hereinafter referred to as "Compound group SX1239").

The Compound (L-2), wherein n represents 1, $R^1$ represents a methyl group, T represents a 4-(trifluoromethyl)phenyl group, $R^{3b}$ represents $CF_3$, and $R^{3c}$ represents any one substituent described in Table L12 to Table L14 (hereinafter referred to as "Compound group SX1240").

The Compound (L-2), wherein n represents 1, $R^1$ represents a methyl group, T represents a 3,4-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX1241").

The Compound (L-2), wherein n represents 1, $R^1$ represents a methyl group, T represents a 3,4-bis[(trifluoromethyl)thio]phenyl group, $R^{3b}$ represents a chlorine atom, and $R^{3c}$ represents any one substituent described in Table L12 to Table L14 (hereinafter referred to as "Compound group SX1242").

The Compound (L-2), wherein n represents 1, $R^1$ represents a methyl group, T represents a 3,4-bis[(trifluoromethyl)thio]phenyl group, $R^{3b}$ represents a bromine atom, and $R^{3c}$ represents any one substituent described in Table L12 to Table L14 (hereinafter referred to as "Compound group SX1243").

The Compound (L-2), wherein n represents 1, $R^1$ represents a methyl group, T represents a 3,4-bis[(trifluoromethyl)thio]phenyl group, $R^{3b}$ represents an iodine atom, and $R^{3c}$ represents any one substituent described in Table L12 to Table L14 (hereinafter referred to as "Compound group SX1244").

The Compound (L-2), wherein n represents 1, $R^1$ represents a methyl group, T represents a 3,4-bis[(trifluoromethyl)thio]phenyl group, $R^{3b}$ represents $CF_3$, and $R^{3c}$ represents any one substituent described in Table L12 to Table L14 (hereinafter referred to as "Compound group SX1245").

The Compound (L-2), wherein n represents 1, $R^1$ represents a methyl group, T represents a 3,4-bis(trifluoromethoxy)phenyl group, $R^{3b}$ represents a hydrogen atom, and $R^{3c}$ represents any one substituent described in Table L12 to Table L14 (hereinafter referred to as "Compound group SX1246").

The Compound (L-2), wherein n represents 1, $R^1$ represents a methyl group, T represents a 3,4-bis(trifluoromethoxy)phenyl group, $R^{3b}$ represents a chlorine atom, and $R^{3c}$ represents any one substituent described in Table L12 to Table L14 (hereinafter referred to as "Compound group SX1247").

The Compound (L-2), wherein n represents 1, $R^1$ represents a methyl group, T represents a 3,4-bis(trifluoromethoxy)phenyl group, $R^{3b}$ represents a bromine atom, and $R^{3c}$ represents any one substituent described in Table L12 to Table L14 (hereinafter referred to as "Compound group SX1248").

The Compound (L-2), wherein n represents 1, $R^1$ represents a methyl group, T represents a 3,4-bis(trifluoromethoxy)phenyl group, $R^{3b}$ represents an iodine atom, and $R^{3c}$ represents any one substituent described in Table L12 to Table L14 (hereinafter referred to as "Compound group SX1249").

The Compound (L-2), wherein n represents 1, $R^1$ represents a methyl group, T represents a 3,4-bis(trifluoromethoxy)phenyl group, $R^{3b}$ represents $CF_3$, and $R^{3c}$ represents any one substituent described in Table L12 to Table L14 (hereinafter referred to as "Compound group SX1250").

The Compound (L-2), wherein n represents 1, $R^1$ represents a methyl group, T represents a 3,4-bis(trifluoromethyl) phenyl group, $R^{3b}$ represents a hydrogen atom, and $R^{3c}$ represents any one substituent described in Table L12 to Table L14 (hereinafter referred to as "Compound group SX1251").

The Compound (L-2), wherein n represents 1, $R^1$ represents a methyl group, T represents a 3,4-bis(trifluoromethyl) phenyl group, $R^{3b}$ represents a chlorine atom, and $R^{3c}$ represents any one substituent described in Table L12 to Table L14 (hereinafter referred to as "Compound group SX1252").

The Compound (L-2), wherein n represents 1, $R^1$ represents a methyl group, T represents a 3,4-bis(trifluoromethyl) phenyl group, $R^{3b}$ represents a bromine atom, and $R^{3c}$ represents any one substituent described in Table L12 to Table L14 (hereinafter referred to as "Compound group SX1253").

The Compound (L-2), wherein n represents 1, $R^1$ represents a methyl group, T represents a 3,4-bis(trifluoromethyl) phenyl group, $R^{3b}$ represents an iodine atom, and $R^{3c}$ represents any one substituent described in Table L12 to Table L14 (hereinafter referred to as "Compound group SX1254").

The Compound (L-2), wherein n represents 1, $R^1$ represents a methyl group, T represents a 3,4-bis(trifluoromethyl) phenyl group, $R^{3b}$ represents $CF_3$, and $R^{3c}$ represents any one substituent described in Table L12 to Table L14 (hereinafter referred to as "Compound group SX1255").

The Compound (L-2), wherein n represents 1, $R^1$ represents a methyl group, T represents a 3,5-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX1256").

The Compound (L-2), wherein n represents 1, $R^1$ represents a methyl group, T represents a 3,5-bis[(trifluoromethyl)thio]phenyl group, $R^{3b}$ represents a chlorine atom, and $R^{3c}$ represents any one substituent described in Table L12 to Table L14 (hereinafter referred to as "Compound group SX1257").

The Compound (L-2), wherein n represents 1, $R^1$ represents a methyl group, T represents a 3,5-bis[(trifluoromethyl)thio]phenyl group, $R^{3b}$ represents a bromine atom, and $R^{3c}$ represents any one substituent described in Table L12 to Table L14 (hereinafter referred to as "Compound group SX1258").

The Compound (L-2), wherein n represents 1, $R^1$ represents a methyl group, T represents a 3,5-bis[(trifluoromethyl)thio]phenyl group, $R^{3b}$ represents an iodine atom, and $R^{3c}$ represents any one substituent described in Table L12 to Table L14 (hereinafter referred to as "Compound group SX1259").

The Compound (L-2), wherein n represents 1, $R^1$ represents a methyl group, T represents a 3,5-bis[(trifluoromethyl)thio]phenyl group, $R^{3b}$ represents $CF_3$, and $R^{3c}$ represents any one substituent described in Table L12 to Table L14 (hereinafter referred to as "Compound group SX1260").

The Compound (L-2), wherein n represents 1, $R^1$ represents a methyl group, T represents a 3,5-bis(trifluoromethoxy)phenyl group, $R^{3b}$ represents a hydrogen atom, and $R^{3c}$ represents any one substituent described in Table L12 to Table L14 (hereinafter referred to as "Compound group SX1261").

The Compound (L-2), wherein n represents 1, $R^1$ represents a methyl group, T represents a 3,5-bis(trifluoromethoxy)phenyl group, $R^{3b}$ represents a chlorine atom, and $R^{3c}$ represents any one substituent described in Table L12 to Table L14 (hereinafter referred to as "Compound group SX1262").

The Compound (L-2), wherein n represents 1, $R^1$ represents a methyl group, T represents a 3,5-bis(trifluoromethoxy)phenyl group, $R^{3b}$ represents a bromine atom, and $R^{3c}$ represents any one substituent described in Table L12 to Table L14 (hereinafter referred to as "Compound group SX1263").

The Compound (L-2), wherein n represents 1, $R^1$ represents a methyl group, T represents a 3,5-bis(trifluoromethoxy)phenyl group, $R^{3b}$ represents an iodine atom, and $R^{3c}$ represents any one substituent described in Table L12 to Table L14 (hereinafter referred to as "Compound group SX1264").

The Compound (L-2), wherein n represents 1, $R^1$ represents a methyl group, T represents a 3,5-bis(trifluoromethoxy)phenyl group, $R^{3b}$ represents $CF_3$, and $R^{3c}$ represents any one substituent described in Table L12 to Table L14 (hereinafter referred to as "Compound group SX1265").

The Compound (L-2), wherein n represents 1, $R^1$ represents a methyl group, T represents a 3,5-bis(trifluoromethyl)

phenyl group, $R^{3b}$ represents a hydrogen atom, and $R^{3c}$ represents any one substituent described in Table L12 to Table L14 (hereinafter referred to as "Compound group SX1266").

The Compound (L-2), wherein n represents 1, $R^1$ represents a methyl group, T represents a 3,5-bis(trifluoromethyl) phenyl group, $R^{3b}$ represents a chlorine atom, and $R^{3c}$ represents any one substituent described in Table L12 to Table L14 (hereinafter referred to as "Compound group SX1267").

The Compound (L-2), wherein n represents 1, $R^1$ represents a methyl group, T represents a 3,5-bis(trifluoromethyl) phenyl group, $R^{3b}$ represents a bromine atom, and $R^{3c}$ represents any one substituent described in Table L12 to Table L14 (hereinafter referred to as "Compound group SX1268").

The Compound (L-2), wherein n represents 1, $R^1$ represents a methyl group, T represents a 3,5-bis(trifluoromethyl) phenyl group, $R^{3b}$ represents an iodine atom, and $R^{3c}$ represents any one substituent described in Table L12 to Table L14 (hereinafter referred to as "Compound group SX1269").

The Compound (L-2), wherein n represents 1, $R^1$ represents a methyl group, T represents a 3,5-bis(trifluoromethyl) phenyl group, $R^{3b}$ represents $CF_3$, and $R^{3c}$ represents any one substituent described in Table L12 to Table L14 (hereinafter referred to as "Compound group SX1270").

The Compound (L-2), wherein n represents 1, $R^1$ represents a methyl group, T represents a 3-fluoro-5-(trifluoromethoxy)phenyl group, $R^{3b}$ represents a hydrogen atom, and $R^{3c}$ represents any one substituent described in Table L12 to Table L14 (hereinafter referred to as "Compound group SX1271").

The Compound (L-2), wherein n represents 1, $R^1$ represents a methyl group, T represents a 3-fluoro-5-(trifluoromethoxy)phenyl group, $R^{3b}$ represents a chlorine atom, and $R^{3c}$ represents any one substituent described in Table L12 to Table L14 (hereinafter referred to as "Compound group SX1272").

The Compound (L-2), wherein n represents 1, $R^1$ represents a methyl group, T represents a 3-fluoro-5-(trifluoromethoxy)phenyl group, $R^{3b}$ represents a bromine atom, and $R^{3c}$ represents any one substituent described in Table L12 to Table L14 (hereinafter referred to as "Compound group SX1273").

The Compound (L-2), wherein n represents 1, $R^1$ represents a methyl group, T represents a 3-fluoro-5-(trifluoromethoxy)phenyl group, $R^{3b}$ represents an iodine atom, and $R^{3c}$ represents any one substituent described in Table L12 to Table L14 (hereinafter referred to as "Compound group SX1274").

The Compound (L-2), wherein n represents 1, $R^1$ represents a methyl group, T represents a 3-fluoro-5-(trifluoromethoxy)phenyl group, $R^{3b}$ represents $CF_3$, and $R^{3c}$ represents any one substituent described in Table L12 to Table L14 (hereinafter referred to as "Compound group SX1275").

The Compound (L-2), wherein n represents 2, $R^1$ represents a methyl group, T represents a 3-[(trifluoromethyl) thio]phenyl group, $R^{3b}$ represents a hydrogen atom, and $R^{3c}$ represents any one substituent described in Table L12 to Table L14 (hereinafter referred to as "Compound group SX1276").

The Compound (L-2), wherein n represents 2, $R^1$ represents a methyl group, T represents a 3-[(trifluoromethyl) thio]phenyl group, $R^{3b}$ represents a chlorine atom, and $R^{3c}$ represents any one substituent described in Table L12 to Table L14 (hereinafter referred to as "Compound group SX1277").

The Compound (L-2), wherein n represents 2, $R^1$ represents a methyl group, T represents a 3-[(trifluoromethyl) thio]phenyl group, $R^{3b}$ represents a bromine atom, and $R^{3c}$ represents any one substituent described in Table L12 to Table L14 (hereinafter referred to as "Compound group SX1278").

The Compound (L-2), wherein n represents 2, $R^1$ represents a methyl group, T represents a 3-[(trifluoromethyl) thio]phenyl group, $R^{3b}$ represents an iodine atom, and $R^{3c}$ represents any one substituent described in Table L12 to Table L14 (hereinafter referred to as "Compound group SX1279").

The Compound (L-2), wherein n represents 2, $R^1$ represents a methyl group, T represents a 3-[(trifluoromethyl) thio]phenyl group, $R^{3b}$ represents $CF_3$, and $R^{3c}$ represents any one substituent described in Table L12 to Table L14 (hereinafter referred to as "Compound group SX1280").

The Compound (L-2), wherein n represents 2, $R^1$ represents a methyl group, T represents a 4-[(trifluoromethyl) thio]phenyl group, $R^{3b}$ represents a hydrogen atom, and $R^{3c}$ represents any one substituent described in Table L12 to Table L14 (hereinafter referred to as "Compound group SX1281").

The Compound (L-2), wherein n represents 2, $R^1$ represents a methyl group, T represents a 4-[(trifluoromethyl) thio]phenyl group, $R^{3b}$ represents a chlorine atom, and $R^{3c}$ represents any one substituent described in Table L12 to Table L14 (hereinafter referred to as "Compound group SX1282").

The Compound (L-2), wherein n represents 2, $R^1$ represents a methyl group, T represents a 4-[(trifluoromethyl) thio]phenyl group, $R^{3b}$ represents a bromine atom, and $R^{3c}$ represents any one substituent described in Table L12 to Table L14 (hereinafter referred to as "Compound group SX1283").

The Compound (L-2), wherein n represents 2, $R^1$ represents a methyl group, T represents a 4-[(trifluoromethyl) thio]phenyl group, $R^{3b}$ represents an iodine atom, and $R^{3c}$ represents any one substituent described in Table L12 to Table L14 (hereinafter referred to as "Compound group SX1284").

The Compound (L-2), wherein n represents 2, $R^1$ represents a methyl group, T represents a 4-[(trifluoromethyl) thio]phenyl group, $R^{3b}$ represents $CF_3$, and $R^{3c}$ represents any one substituent described in Table L12 to Table L14 (hereinafter referred to as "Compound group SX1285").

The Compound (L-2), wherein n represents 2, $R^1$ represents an ethyl group, T represents a 3-[(trifluoromethyl)thio] phenyl group, $R^{3b}$ represents a hydrogen atom, and $R^{3c}$ represents any one substituent described in Table L12 to Table L14 (hereinafter referred to as "Compound group SX1286").

The Compound (L-2), wherein n represents 2, $R^1$ represents an ethyl group, T represents a 3-[(trifluoromethyl)thio] phenyl group, $R^{3b}$ represents a chlorine atom, and $R^{3c}$ represents any one substituent described in Table L12 to Table L14 (hereinafter referred to as "Compound group SX1287").

The Compound (L-2), wherein n represents 2, $R^1$ represents an ethyl group, T represents a 3-[(trifluoromethyl)thio] phenyl group, $R^{3b}$ represents a bromine atom, and $R^{3c}$ represents any one substituent described in Table L12 to Table L14 (hereinafter referred to as "Compound group SX1288").

The Compound (L-2), wherein n represents 2, $R^1$ represents an ethyl group, T represents a 3-[(trifluoromethyl)thio] phenyl group, $R^{3b}$ represents an iodine atom, and $R^{3c}$ represents any one substituent described in Table L12 to Table L14 (hereinafter referred to as "Compound group SX1289").

The Compound (L-2), wherein n represents 2, $R^1$ represents an ethyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX1290").

The Compound (L-2), wherein n represents 2, $R^1$ represents an ethyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX1291").

The Compound (L-2), wherein n represents 2, $R^1$ represents an ethyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX1292").

The Compound (L-2), wherein n represents 2, $R^1$ represents an ethyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX1293").

The Compound (L-2), wherein n represents 2, $R^1$ represents an ethyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX1294").

The Compound (L-2), wherein n represents 2, $R^1$ represents an ethyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX1295").

The Compound (L-2), wherein n represents 2, $R^1$ represents an isopropyl group, T represents a 3-[(trifluoromethyl)thio]phenyl group, $R^{3b}$ represents a hydrogen atom, and $R^{3c}$ represents any one substituent described in Table L12 to Table L14 (hereinafter referred to as "Compound group SX1296").

The Compound (L-2), wherein n represents 2, $R^1$ represents an isopropyl group, T represents a 3-[(trifluoromethyl)thio]phenyl group, $R^{3b}$ represents a chlorine atom, and $R^{3c}$ represents any one substituent described in Table L12 to Table L14 (hereinafter referred to as "Compound group SX1297").

The Compound (L-2), wherein n represents 2, $R^1$ represents an isopropyl group, T represents a 3-[(trifluoromethyl)thio]phenyl group, $R^{3b}$ represents a bromine atom, and $R^{3c}$ represents any one substituent described in Table L12 to Table L14 (hereinafter referred to as "Compound group SX1298").

The Compound (L-2), wherein n represents 2, $R^1$ represents an isopropyl group, T represents a 3-[(trifluoromethyl)thio]phenyl group, $R^{3b}$ represents an iodine atom, and $R^{3c}$ represents any one substituent described in Table L12 to Table L14 (hereinafter referred to as "Compound group SX1299").

The Compound (L-2), wherein n represents 2, $R^1$ represents an isopropyl group, T represents a 3-[(trifluoromethyl)thio]phenyl group, $R^{3b}$ represents $CF_3$, and $R^{3c}$ represents any one substituent described in Table L12 to Table L14 (hereinafter referred to as "Compound group SX1300").

The Compound (L-2), wherein n represents 2, $R^1$ represents an isopropyl group, T represents a 4-[(trifluoromethyl)thio]phenyl group, $R^{3b}$ represents a hydrogen atom, and $R^{3c}$ represents any one substituent described in Table L12 to Table L14 (hereinafter referred to as "Compound group SX1301").

The Compound (L-2), wherein n represents 2, $R^1$ represents an isopropyl group, T represents a 4-[(trifluoromethyl)thio]phenyl group, $R^{3b}$ represents a chlorine atom, and $R^{3c}$ represents any one substituent described in Table L12 to Table L14 (hereinafter referred to as "Compound group SX1302").

The Compound (L-2), wherein n represents 2, $R^1$ represents an isopropyl group, T represents a 4-[(trifluoromethyl)thio]phenyl group, $R^{3b}$ represents a bromine atom, and $R^{3c}$ represents any one substituent described in Table L12 to Table L14 (hereinafter referred to as "Compound group SX1303").

The Compound (L-2), wherein n represents 2, $R^1$ represents an isopropyl group, T represents a 4-[(trifluoromethyl)thio]phenyl group, $R^{3b}$ represents an iodine atom, and $R^{3c}$ represents any one substituent described in Table L12 to Table L14 (hereinafter referred to as "Compound group SX1304").

The Compound (L-2), wherein n represents 2, $R^1$ represents an isopropyl group, T represents a 4-[(trifluoromethyl)thio]phenyl group, $R^{3b}$ represents $CF_3$, and $R^{3c}$ represents any one substituent described in Table L12 to Table L14 (hereinafter referred to as "Compound group SX1305").

The Compound (L-2), wherein n represents 2, $R^1$ represents a methyl group, T represents a 4-(trifluoromethoxy)phenyl group, $R^{3b}$ represents a hydrogen atom, and $R^{3c}$ represents any one substituent described in Table L12 to Table L14 (hereinafter referred to as "Compound group SX1306").

The Compound (L-2), wherein n represents 2, $R^1$ represents a methyl group, T represents a 4-(trifluoromethoxy)phenyl group, $R^{3b}$ represents a chlorine atom, and $R^{3c}$ represents any one substituent described in Table L12 to Table L14 (hereinafter referred to as "Compound group SX1307").

The Compound (L-2), wherein n represents 2, $R^1$ represents a methyl group, T represents a 4-(trifluoromethoxy)phenyl group, $R^{3b}$ represents a bromine atom, and $R^{3c}$ represents any one substituent described in Table L12 to Table L14 (hereinafter referred to as "Compound group SX1308").

The Compound (L-2), wherein n represents 2, $R^1$ represents a methyl group, T represents a 4-(trifluoromethoxy)phenyl group, $R^{3b}$ represents an iodine atom, and $R^{3c}$ represents any one substituent described in Table L12 to Table L14 (hereinafter referred to as "Compound group SX1309").

The Compound (L-2), wherein n represents 2, $R^1$ represents a methyl group, T represents a 4-(trifluoromethoxy)phenyl group, $R^{3b}$ represents $CF_3$, and $R^{3c}$ represents any one substituent described in Table L12 to Table L14 (hereinafter referred to as "Compound group SX1310").

The Compound (L-2), wherein n represents 2, $R^1$ represents a methyl group, T represents a 4-(trifluoromethyl)phenyl group, $R^{3b}$ represents a hydrogen atom, and $R^{3c}$ represents any one substituent described in Table L12 to Table L14 (hereinafter referred to as "Compound group SX1311").

The Compound (L-2), wherein n represents 2, $R^1$ represents a methyl group, T represents a 4-(trifluoromethyl)phenyl group, $R^{3b}$ represents a chlorine atom, and $R^{3c}$ represents any one substituent described in Table L12 to Table L14 (hereinafter referred to as "Compound group SX1312").

The Compound (L-2), wherein n represents 2, $R^1$ represents a methyl group, T represents a 4-(trifluoromethyl) phenyl group, $R^{3b}$ represents a bromine atom, and $R^{3c}$ represents any one substituent described in Table L12 to Table L14 (hereinafter referred to as "Compound group SX1313").

The Compound (L-2), wherein n represents 2, $R^1$ represents a methyl group, T represents a 4-(trifluoromethyl) phenyl group, $R^{3b}$ represents an iodine atom, and $R^{3c}$ represents any one substituent described in Table L12 to Table L14 (hereinafter referred to as "Compound group SX1314").

The Compound (L-2), wherein n represents 2, $R^1$ represents a methyl group, T represents a 4-(trifluoromethyl) phenyl group, $R^{3b}$ represents $CF_3$, and $R^{3e}$ represents any one substituent described in Table L12 to Table L14 (hereinafter referred to as "Compound group SX1315").

The Compound (L-2), wherein n represents 2, $R^1$ represents a methyl group, T represents a 3,4-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX1316").

The Compound (L-2), wherein n represents 2, $R^1$ represents a methyl group, T represents a 3,4-bis[(trifluoromethyl)thio]phenyl group, $R^{3b}$ represents a chlorine atom, and $R^{3c}$ represents any one substituent described in Table L12 to Table L14 (hereinafter referred to as "Compound group SX1317").

The Compound (L-2), wherein n represents 2, $R^1$ represents a methyl group, T represents a 3,4-bis[(trifluoromethyl)thio]phenyl group, $R^{3b}$ represents a bromine atom, and $R^{3c}$ represents any one substituent described in Table L12 to Table L14 (hereinafter referred to as "Compound group SX1318").

The Compound (L-2), wherein n represents 2, $R^1$ represents a methyl group, T represents a 3,4-bis[(trifluoromethyl)thio]phenyl group, $R^{3b}$ represents an iodine atom, and $R^{3c}$ represents any one substituent described in Table L12 to Table L14 (hereinafter referred to as "Compound group SX1319").

The Compound (L-2), wherein n represents 2, $R^1$ represents a methyl group, T represents a 3,4-bis[(trifluoromethyl)thio]phenyl group, $R^{3b}$ represents $CF_3$, and $R^{3c}$ represents any one substituent described in Table L12 to Table L14 (hereinafter referred to as "Compound group SX1320").

The Compound (L-2), wherein n represents 2, $R^1$ represents a methyl group, T represents a 3,4-bis(trifluoromethoxy)phenyl group, $R^{3b}$ represents a hydrogen atom, and $R^{3c}$ represents any one substituent described in Table L12 to Table L14 (hereinafter referred to as "Compound group SX1321").

The Compound (L-2), wherein n represents 2, $R^1$ represents a methyl group, T represents a 3,4-bis(trifluoromethoxy)phenyl group, $R^{3b}$ represents a chlorine atom, and $R^{3c}$ represents any one substituent described in Table L12 to Table L14 (hereinafter referred to as "Compound group SX1322").

The Compound (L-2), wherein n represents 2, $R^1$ represents a methyl group, T represents a 3,4-bis(trifluoromethoxy)phenyl group, $R^{3b}$ represents a bromine atom, and $R^{3c}$ represents any one substituent described in Table L12 to Table L14 (hereinafter referred to as "Compound group SX1323").

The Compound (L-2), wherein n represents 2, $R^1$ represents a methyl group, T represents a 3,4-bis(trifluoromethoxy)phenyl group, $R^{3b}$ represents an iodine atom, and $R^{3c}$ represents any one substituent described in Table L12 to Table L14 (hereinafter referred to as "Compound group SX1324").

The Compound (L-2), wherein n represents 2, $R^1$ represents a methyl group, T represents a 3,4-bis(trifluoromethoxy)phenyl group, $R^{3b}$ represents $CF_3$, and $R^{3c}$ represents any one substituent described in Table L12 to Table L14 (hereinafter referred to as "Compound group SX1325").

The Compound (L-2), wherein n represents 2, $R^1$ represents a methyl group, T represents a 3,4-bis(trifluoromethyl) phenyl group, $R^{3b}$ represents a hydrogen atom, and $R^{3c}$ represents any one substituent described in Table L12 to Table L14 (hereinafter referred to as "Compound group SX1326").

The Compound (L-2), wherein n represents 2, $R^1$ represents a methyl group, T represents a 3,4-bis(trifluoromethyl) phenyl group, $R^{3b}$ represents a chlorine atom, and $R^{3c}$ represents any one substituent described in Table L12 to Table L14 (hereinafter referred to as "Compound group SX1327").

The Compound (L-2), wherein n represents 2, $R^1$ represents a methyl group, T represents a 3,4-bis(trifluoromethyl) phenyl group, $R^{3b}$ represents a bromine atom, and $R^{3c}$ represents any one substituent described in Table L12 to Table L14 (hereinafter referred to as "Compound group SX1328").

The Compound (L-2), wherein n represents 2, $R^1$ represents a methyl group, T represents a 3,4-bis(trifluoromethyl) phenyl group, $R^{3b}$ represents an iodine atom, and $R^{3c}$ represents any one substituent described in Table L12 to Table L14 (hereinafter referred to as "Compound group SX1329").

The Compound (L-2), wherein n represents 2, $R^1$ represents a methyl group, T represents a 3,4-bis(trifluoromethyl) phenyl group, $R^{3b}$ represents $CF_3$, and $R^{3c}$ represents any one substituent described in Table L12 to Table L14 (hereinafter referred to as "Compound group SX1330").

The Compound (L-2), wherein n represents 2, $R^1$ represents a methyl group, T represents a 3,5-bis[(trifluoromethyl)thio]phenyl group, $R^{3b}$ represents a hydrogen atom, and $R^{3c}$ represents any one substituent described in Table L12 to Table L14 (hereinafter referred to as "Compound group SX1331").

The Compound (L-2), wherein n represents 2, $R^1$ represents a methyl group, T represents a 3,5-bis[(trifluoromethyl)thio]phenyl group, $R^{3b}$ represents a chlorine atom, and $R^{3c}$ represents any one substituent described in Table L12 to Table L14 (hereinafter referred to as "Compound group SX1332").

The Compound (L-2), wherein n represents 2, $R^1$ represents a methyl group, T represents a 3,5-bis[(trifluoromethyl)thio]phenyl group, $R^{3b}$ represents a bromine atom, and $R^{3c}$ represents any one substituent described in Table L12 to Table L14 (hereinafter referred to as "Compound group SX1333").

The Compound (L-2), wherein n represents 2, $R^1$ represents a methyl group, T represents a 3,5-bis[(trifluoromethyl)thio]phenyl group, $R^{3b}$ represents an iodine atom, and $R^{3c}$ represents any one substituent described in Table L12 to Table L14 (hereinafter referred to as "Compound group SX1334").

The Compound (L-2), wherein n represents 2, $R^1$ represents a methyl group, T represents a 3,5-bis[(trifluoromethyl)thio]phenyl group, $R^{3b}$ represents $CF_3$, and $R^{3c}$ represents any one substituent described in Table L12 to Table L14 (hereinafter referred to as "Compound group SX1335").

The Compound (L-2), wherein n represents 2, $R^1$ represents a methyl group, T represents a 3,5-bis(trifluoromethoxy)phenyl group, $R^{3b}$ represents a hydrogen atom, and $R^{3c}$ represents any one substituent described in Table L12 to Table L14 (hereinafter referred to as "Compound group SX1336").

The Compound (L-2), wherein n represents 2, $R^1$ represents a methyl group, T represents a 3,5-bis(trifluoromethoxy)phenyl group, $R^{3b}$ represents a chlorine atom, and $R^{3c}$ represents any one substituent described in Table L12 to Table L14 (hereinafter referred to as "Compound group SX1337").

The Compound (L-2), wherein n represents 2, $R^1$ represents a methyl group, T represents a 3,5-bis(trifluoromethoxy)phenyl group, $R^{3b}$ represents a bromine atom, and $R^{3c}$ represents any one substituent described in Table L12 to Table L14 (hereinafter referred to as "Compound group SX1338").

The Compound (L-2), wherein n represents 2, $R^1$ represents a methyl group, T represents a 3,5-bis(trifluoromethoxy)phenyl group, $R^{3b}$ represents an iodine atom, and $R^{3c}$ represents any one substituent described in Table L12 to Table L14 (hereinafter referred to as "Compound group SX1339").

The Compound (L-2), wherein n represents 2, $R^1$ represents a methyl group, T represents a 3,5-bis(trifluoromethoxy)phenyl group, $R^{3b}$ represents $CF_3$, and $R^{3c}$ represents any one substituent described in Table L12 to Table L14 (hereinafter referred to as "Compound group SX1340").

The Compound (L-2), wherein n represents 2, $R^1$ represents a methyl group, T represents a 3,5-bis(trifluoromethyl) phenyl group, $R^{3b}$ represents a hydrogen atom, and $R^{3c}$ represents any one substituent described in Table L12 to Table L14 (hereinafter referred to as "Compound group SX1341").

The Compound (L-2), wherein n represents 2, $R^1$ represents a methyl group, T represents a 3,5-bis(trifluoromethyl) phenyl group, $R^{3b}$ represents a chlorine atom, and $R^{3c}$ represents any one substituent described in Table L12 to Table L14 (hereinafter referred to as "Compound group SX1342").

The Compound (L-2), wherein n represents 2, $R^1$ represents a methyl group, T represents a 3,5-bis(trifluoromethyl) phenyl group, $R^{3b}$ represents a bromine atom, and $R^{3c}$ represents any one substituent described in Table L12 to Table L14 (hereinafter referred to as "Compound group SX1343").

The Compound (L-2), wherein n represents 2, $R^1$ represents a methyl group, T represents a 3,5-bis(trifluoromethyl) phenyl group, $R^{3b}$ represents an iodine atom, and $R^{3c}$ represents any one substituent described in Table L12 to Table L14 (hereinafter referred to as "Compound group SX1344").

The Compound (L-2), wherein n represents 2, $R^1$ represents a methyl group, T represents a 3,5-bis(trifluoromethyl) phenyl group, $R^{3b}$ represents $CF_3$, and $R^{3c}$ represents any one substituent described in Table L12 to Table L14 (hereinafter referred to as "Compound group SX1345").

The Compound (L-2), wherein n represents 2, $R^1$ represents a methyl group, T represents a 3-fluoro-5-(trifluoromethoxy)phenyl group, $R^{3b}$ represents a hydrogen atom, and $R^{3c}$ represents any one substituent described in Table L12 to Table L14 (hereinafter referred to as "Compound group SX1346").

The Compound (L-2), wherein n represents 2, $R^1$ represents a methyl group, T represents a 3-fluoro-5-(trifluoromethoxy)phenyl group, $R^{3b}$ represents a chlorine atom, and $R^{3c}$ represents any one substituent described in Table L12 to Table L14 (hereinafter referred to as "Compound group SX1347").

The Compound (L-2), wherein n represents 2, $R^1$ represents a methyl group, T represents a 3-fluoro-5-(trifluoromethoxy)phenyl group, $R^{3b}$ represents a bromine atom, and $R^{3c}$ represents any one substituent described in Table L12 to Table L14 (hereinafter referred to as "Compound group SX1348").

The Compound (L-2), wherein n represents 2, $R^1$ represents a methyl group, T represents a 3-fluoro-5-(trifluoromethoxy)phenyl group, $R^{3b}$ represents an iodine atom, and $R^{3c}$ represents any one substituent described in Table L12 to Table L14 (hereinafter referred to as "Compound group SX1349").

The Compound (L-2), wherein n represents 2, $R^1$ represents a methyl group, T represents a 3-fluoro-5-(trifluoromethoxy)phenyl group, $R^{3b}$ represents $CF_3$, and $R^{3c}$ represents any one substituent described in Table L12 to Table L14 (hereinafter referred to as "Compound group SX1350").

A Compound Represented by Formula (L-3)

(L-3)

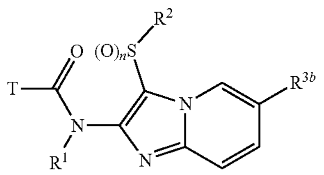

(hereinafter referred to as "Compound (L-3)"), wherein n represents 0, $R^1$ represents a methyl group, $R^2$ represents a methyl group, R a represents a hydrogen atom, and T represents any one substituent described in Table L1 to Table L11 (hereinafter referred to as "Compound group SX1351").

The Compound (L-3), wherein n represents 0, R represents a methyl group, $R^2$ represents a methyl group, $R^{3b}$ represents a chlorine atom, and T represents any one substituent described in Table L1 to Table L11 (hereinafter referred to as "Compound group SX1352").

The Compound (L-3), wherein n represents 0, $R^1$ represents a methyl group, $R^2$ represents a methyl group, $R^{3b}$ represents a bromine atom, and T represents any one substituent described in Table L1 to Table L11 (hereinafter referred to as "Compound group SX1353").

The Compound (L-3), wherein n represents 0, $R^1$ represents a methyl group, $R^2$ represents a methyl group, $R^{3b}$ represents an iodine atom, and T represents any one substituent described in Table L1 to Table L11 (hereinafter referred to as "Compound group SX1354").

The Compound (L-3), wherein n represents 0, $R^1$ represents a methyl group, $R^2$ represents a methyl group, $R^{3b}$ represents $CF_3$, and T represents any one substituent described in Table L1 to Table L11 (hereinafter referred to as "Compound group SX1355").

The Compound (L-3), wherein n represents 0, $R^1$ represents a propargyl group, $R^2$ represents an ethyl group, $R^{3b}$ represents a hydrogen atom, and T represents any one substituent described in Table L1 to Table L11 (hereinafter referred to as "Compound group SX1356").

The Compound (L-3), wherein n represents 0, $R^1$ represents a propargyl group, $R^2$ represents an ethyl group, $R^{3b}$ represents a chlorine atom, and T represents any one substituent described in Table L1 to Table L11 (hereinafter referred to as "Compound group SX1357").

The Compound (L-3), wherein n represents 0, $R^1$ represents a propargyl group, $R^2$ represents an ethyl group, $R^{3b}$ represents a bromine atom, and T represents any one substituent described in Table L1 to Table L11 (hereinafter referred to as "Compound group SX1358").

The Compound (L-3), wherein n represents 0, $R^1$ represents a propargyl group, $R^2$ represents an ethyl group, $R^{3b}$ represents an iodine atom, and T represents any one substituent described in Table L1 to Table L11 (hereinafter referred to as "Compound group SX1359").

The Compound (L-3), wherein n represents 0, $R^1$ represents a propargyl group, $R^2$ represents an ethyl group, $R^{3b}$ represents $CF_3$, and T represents any one substituent described in Table L1 to Table L11 (hereinafter referred to as "Compound group SX1360").

The Compound (L-3), wherein n represents 0, $R^1$ represents a cyclopropylmethyl group, $R^2$ represents an ethyl group, $R^{3b}$ represents a hydrogen atom, and T represents any one substituent described in Table L1 to Table L11 (hereinafter referred to as "Compound group SX1361").

The Compound (L-3), wherein n represents 0, $R^1$ represents a cyclopropylmethyl group, $R^2$ represents an ethyl group, $R^{3b}$ represents a chlorine atom, and T represents any one substituent described in Table L1 to Table L11 (hereinafter referred to as "Compound group SX1362").

The Compound (L-3), wherein n represents 0, $R^1$ represents a cyclopropylmethyl group, $R^2$ represents an ethyl group, $R^{3b}$ represents a bromine atom, and T represents any one substituent described in Table L1 to Table L11 (hereinafter referred to as "Compound group SX1363").

The Compound (L-3), wherein n represents 0, $R^1$ represents a cyclopropylmethyl group, $R^2$ represents an ethyl group, $R^{3b}$ represents an iodine atom, and T represents any one substituent described in Table L1 to Table L11 (hereinafter referred to as "Compound group SX1364").

The Compound (L-3), wherein n represents 0, $R^1$ represents a cyclopropylmethyl group, $R^2$ represents an ethyl group, $R^{3b}$ represents $CF_3$, and T represents any one substituent described in Table L1 to Table L11 (hereinafter referred to as "Compound group SX1365").

The Compound (L-3), wherein n represents 1, $R^1$ represents a methyl group, $R^2$ represents a methyl group, $R^{3b}$ represents a hydrogen atom, and T represents any one substituent described in Table L1 to Table L11 (hereinafter referred to as "Compound group SX1366").

The Compound (L-3), wherein n represents 1, $R^1$ represents a methyl group, $R^2$ represents a methyl group, $R^{3b}$ represents a chlorine atom, and T represents any one substituent described in Table L1 to Table L11 (hereinafter referred to as "Compound group SX1367").

The Compound (L-3), wherein n represents 1, $R^1$ represents a methyl group, $R^2$ represents a methyl group, $R^{3b}$ represents a bromine atom, and T represents any one substituent described in Table L1 to Table L11 (hereinafter referred to as "Compound group SX1368").

The Compound (L-3), wherein n represents 1, $R^1$ represents a methyl group, $R^2$ represents a methyl group, $R^{3b}$ represents an iodine atom, and T represents any one substituent described in Table L1 to Table L11 (hereinafter referred to as "Compound group SX1369").

The Compound (L-3), wherein n represents 1, $R^1$ represents a methyl group, $R^2$ represents a methyl group, $R^{3b}$ represents $CF_3$, and T represents any one substituent described in Table L1 to Table L11 (hereinafter referred to as "Compound group SX1370").

The Compound (L-3), wherein n represents 1, $R^1$ represents a propargyl group, $R^2$ represents an ethyl group, $R^{3b}$ represents a hydrogen atom, and T represents any one substituent described in Table L1 to Table L11 (hereinafter referred to as "Compound group SX1371").

The Compound (L-3), wherein n represents 1, $R^1$ represents a propargyl group, $R^2$ represents an ethyl group, $R^{3b}$ represents a chlorine atom, and T represents any one substituent described in Table L1 to Table L11 (hereinafter referred to as "Compound group SX1372").

The Compound (L-3), wherein n represents 1, $R^1$ represents a propargyl group, $R^2$ represents an ethyl group, $R^{3b}$ represents a bromine atom, and T represents any one substituent described in Table L1 to Table L11 (hereinafter referred to as "Compound group SX1373").

The Compound (L-3), wherein n represents 1, $R^1$ represents a propargyl group, $R^2$ represents an ethyl group, $R^{3b}$ represents an iodine atom, and T represents any one substituent described in Table L1 to Table L11 (hereinafter referred to as "Compound group SX1374").

The Compound (L-3), wherein n represents 1, $R^1$ represents a propargyl group, $R^2$ represents an ethyl group, $R^{3b}$ represents $CF_3$, and T represents any one substituent described in Table L1 to Table L11 (hereinafter referred to as "Compound group SX1375").

The Compound (L-3), wherein n represents 1, $R^1$ represents a cyclopropylmethyl group, $R^2$ represents an ethyl group, $R^{3b}$ represents a hydrogen atom, and T represents any one substituent described in Table L1 to Table L11 (hereinafter referred to as "Compound group SX1376").

The Compound (L-3), wherein n represents 1, $R^1$ represents a cyclopropylmethyl group, $R^2$ represents an ethyl group, $R^{3b}$ represents a chlorine atom, and T represents any one substituent described in Table L1 to Table L11 (hereinafter referred to as "Compound group SX1377").

The Compound (L-3), wherein n represents 1, $R^1$ represents a cyclopropylmethyl group, $R^2$ represents an ethyl group, $R^{3b}$ represents a bromine atom, and T represents any one substituent described in Table L1 to Table L11 (hereinafter referred to as "Compound group SX1378").

The Compound (L-3), wherein n represents 1, $R^1$ represents a cyclopropylmethyl group, $R^2$ represents an ethyl group, $R^{3b}$ represents an iodine atom, and T represents any one substituent described in Table L1 to Table L11 (hereinafter referred to as "Compound group SX1379").

The Compound (L-3), wherein n represents 1, $R^1$ represents a cyclopropylmethyl group, $R^2$ represents an ethyl group, $R^{3b}$ represents $CF_3$, and T represents any one substituent described in Table L1 to Table L11 (hereinafter referred to as "Compound group SX1380").

The Compound (L-3), wherein n represents 2, $R^1$ represents a methyl group, $R^2$ represents a methyl group, $R^{3b}$ represents a hydrogen atom, and T represents any one substituent described in Table L1 to Table L11 (hereinafter referred to as "Compound group SX1381").

The Compound (L-3), wherein n represents 2, $R^1$ represents a methyl group, $R^2$ represents a methyl group, $R^{3b}$ represents a chlorine atom, and T represents any one substituent described in Table L1 to Table L11 (hereinafter referred to as "Compound group SX1382").

The Compound (L-3), wherein n represents 2, $R^1$ represents a methyl group, $R^2$ represents a methyl group, $R^{3b}$ represents a bromine atom, and T represents any one substituent described in Table L1 to Table L11 (hereinafter referred to as "Compound group SX1383").

The Compound (L-3), wherein n represents 2, $R^1$ represents a methyl group, $R^2$ represents a methyl group, $R^{3b}$ represents an iodine atom, and T represents any one substituent described in Table L1 to Table L11 (hereinafter referred to as "Compound group SX1384").

The Compound (L-3), wherein n represents 2, $R^1$ represents a methyl group, $R^2$ represents a methyl group, $R^{3b}$ represents $CF_3$, and T represents any one substituent described in Table L1 to Table L11 (hereinafter referred to as "Compound group SX1385").

The Compound (L-3), wherein n represents 2, $R^1$ represents a propargyl group, $R^2$ represents an ethyl group, $R^{3b}$ represents a hydrogen atom, and T represents any one substituent described in Table L1 to Table L11 (hereinafter referred to as "Compound group SX1386").

The Compound (L-3), wherein n represents 2, $R^1$ represents a propargyl group, $R^2$ represents an ethyl group, $R^{3b}$ represents a chlorine atom, and T represents any one substituent described in Table L1 to Table L11 (hereinafter referred to as "Compound group SX1387").

The Compound (L-3), wherein n represents 2, $R^1$ represents a propargyl group, $R^2$ represents an ethyl group, $R^{3b}$ represents a bromine atom, and T represents any one substituent described in Table L1 to Table L11 (hereinafter referred to as "Compound group SX1388").

The Compound (L-3), wherein n represents 2, $R^1$ represents a propargyl group, $R^2$ represents an ethyl group, $R^{3b}$ represents an iodine atom, and T represents any one substituent described in Table L1 to Table L11 (hereinafter referred to as "Compound group SX1389").

The Compound (L-3), wherein n represents 2, $R^1$ represents a propargyl group, $R^2$ represents an ethyl group, $R^{3b}$ represents $CF_3$, and T represents any one substituent described in Table L1 to Table L11 (hereinafter referred to as "Compound group SX1390").

The Compound (L-3), wherein n represents 2, $R^1$ represents a cyclopropylmethyl group, $R^2$ represents an ethyl group, $R^{3b}$ represents a hydrogen atom, and T represents any one substituent described in Table L1 to Table L11 (hereinafter referred to as "Compound group SX1391").

The Compound (L-3), wherein n represents 2, $R^1$ represents a cyclopropylmethyl group, $R^2$ represents an ethyl group, $R^{3b}$ represents a chlorine atom, and T represents any one substituent described in Table L1 to Table L11 (hereinafter referred to as "Compound group SX1392").

The Compound (L-3), wherein n represents 2, $R^1$ represents a cyclopropylmethyl group, $R^2$ represents an ethyl group, $R^{3b}$ represents a bromine atom, and T represents any one substituent described in Table L1 to Table L11 (hereinafter referred to as "Compound group SX1393").

The Compound (L-3), wherein n represents 2, $R^1$ represents a cyclopropylmethyl group, $R^2$ represents an ethyl group, $R^{3b}$ represents an iodine atom, and T represents any one substituent described in Table L1 to Table L11 (hereinafter referred to as "Compound group SX1394").

The Compound (L-3), wherein n represents 2, $R^1$ represents a cyclopropylmethyl group, $R^2$ represents an ethyl group, $R^{3b}$ represents $CF_3$, and T represents any one Table L12 to Table L14 (hereinafter referred to as referred to as "Compound group SX1395").

The Compound (L-3), wherein n represents 0, $R^1$ represents a hydrogen atom, $R^2$ represents a methyl group, $R^{3b}$ represents a hydrogen atom, and T represents any one substituent described in Table L1 to Table L11 (hereinafter referred to as "Compound group SX1840").

The Compound (L-3), wherein n represents 0, $R^1$ represents a hydrogen atom, $R^2$ represents a methyl group, $R^{3b}$ represents a chlorine atom, and T represents any one substituent described in Table L1 to Table L11 (hereinafter referred to as "Compound group SX1841").

The Compound (L-3), wherein n represents 0, $R^1$ represents a hydrogen atom, $R^2$ represents a methyl group, $R^{3b}$ represents a bromine atom, and T represents any one substituent described in Table L1 to Table L11 (hereinafter referred to as "Compound group SX1842").

The Compound (L-3), wherein n represents 0, $R^1$ represents a hydrogen atom, $R^2$ represents a methyl group, $R^{3b}$ represents an iodine atom, and T represents any one substituent described in Table L1 to Table L11 (hereinafter referred to as "Compound group SX1843").

The Compound (L-3), wherein n represents 0, $R^1$ represents a hydrogen atom, $R^2$ represents a methyl group, $R^{3b}$ represents $CF_3$, and T represents any one substituent described in Table L1 to Table L11 (hereinafter referred to as "Compound group SX1844").

The Compound (L-3), wherein n represents 1, $R^1$ represents a hydrogen atom, $R^2$ represents a methyl group, $R^{3b}$ represents a hydrogen atom, and T represents any one substituent described in Table L1 to Table L11 (hereinafter referred to as "Compound group SX1845").

The Compound (L-3), wherein n represents 1, $R^1$ represents a hydrogen atom, $R^2$ represents a methyl group, $R^{3b}$ represents a chlorine atom, and T represents any one substituent described in Table L1 to Table L11 (hereinafter referred to as "Compound group SX1846").

The Compound (L-3), wherein n represents 1, $R^1$ represents a hydrogen atom, $R^2$ represents a methyl group, $R^{3b}$ represents a bromine atom, and T represents any one substituent described in Table L1 to Table L11 (hereinafter referred to as "Compound group SX1847").

The Compound (L-3), wherein n represents 1, $R^1$ represents a hydrogen atom, $R^2$ represents a methyl group, $R^{3b}$ represents an iodine atom, and T represents any one substituent described in Table L1 to Table L11 (hereinafter referred to as "Compound group SX1848").

The Compound (L-3), wherein n represents 1, $R^1$ represents a hydrogen atom, $R^2$ represents a methyl group, $R^{3b}$ represents $CF_3$, and T represents any one substituent described in Table L1 to Table L11 (hereinafter referred to as "Compound group SX1849").

The Compound (L-3), wherein n represents 2, $R^1$ represents a hydrogen atom, $R^2$ represents a methyl group, $R^{3b}$ represents a hydrogen atom, and T represents any one substituent described in Table L1 to Table L11 (hereinafter referred to as "Compound group SX1850").

The Compound (L-3), wherein n represents 2, $R^1$ represents a hydrogen atom, $R^2$ represents a methyl group, $R^{3b}$ represents a chlorine atom, and T represents any one substituent described in Table L1 to Table L11 (hereinafter referred to as "Compound group SX1851").

The Compound (L-3), wherein n represents 2, $R^1$ represents a hydrogen atom, $R^2$ represents a methyl group, $R^{3b}$ represents a bromine atom, and T represents any one substituent described in Table L1 to Table L11 (hereinafter referred to as "Compound group SX1852").

The Compound (L-3), wherein n represents 2, $R^1$ represents a hydrogen atom, $R^2$ represents a methyl group, $R^{3b}$ represents an iodine atom, and T represents any one substituent described in Table L1 to Table L11 (hereinafter referred to as "Compound group SX1853").

The Compound (L-3), wherein n represents 2, $R^1$ represents a hydrogen atom, $R^2$ represents a methyl group, $R^{3b}$ represents $CF_3$, and T represents any one substituent described in Table L1 to Table L11 (hereinafter referred to as "Compound group SX1854").

The Compound (L-3), wherein n represents 0, $R^1$ represents a benzyl group, $R^2$ represents a methyl group, $R^{3b}$ represents a hydrogen atom, and T represents any one substituent described in Table L1 to Table L11 (hereinafter referred to as "Compound group SX1855").

The Compound (L-3), wherein n represents 0, $R^1$ represents a benzyl group, $R^2$ represents a methyl group, $R^{3b}$ represents a chlorine atom, and T represents any one substituent described in Table L1 to Table L11 (hereinafter referred to as "Compound group SX1856").

The Compound (L-3), wherein n represents 0, $R^1$ represents a benzyl group, $R^2$ represents a methyl group, $R^{3b}$ represents a bromine atom, and T represents any one substituent described in Table L1 to Table L11 (hereinafter referred to as "Compound group SX1857").

The Compound (L-3), wherein n represents 0, $R^1$ represents a benzyl group, $R^2$ represents a methyl group, $R^{3b}$ represents an iodine atom, and T represents any one substituent described in Table L1 to Table L11 (hereinafter referred to as "Compound group SX1858").

The Compound (L-3), wherein n represents 0, $R^1$ represents a benzyl group, $R^2$ represents a methyl group, $R^{3b}$represents $CF_3$, and T represents any one substituent described in Table L1 to Table L11 (hereinafter referred to as "Compound group SX1859").

The Compound (L-3), wherein n represents 1, $R^1$ represents a benzyl group, $R^2$ represents a methyl group, $R^{3b}$ represents a hydrogen atom, and T represents any one substituent described in Table L1 to Table L11 (hereinafter referred to as "Compound group SX1860").

The Compound (L-3), wherein n represents 1, $R^1$ represents a benzyl group, $R^2$ represents a methyl group, $R^{3b}$ represents a chlorine atom, and T represents any one substituent described in Table L1 to Table L11 (hereinafter referred to as "Compound group SX1861").

The Compound (L-3), wherein n represents 1, $R^1$ represents a benzyl group, $R^2$ represents a methyl group, $R^{3b}$ represents a bromine atom, and T represents any one substituent described in Table L1 to Table L11 (hereinafter referred to as "Compound group SX1862").

The Compound (L-3), wherein n represents 1, $R^1$ represents a benzyl group, $R^2$ represents a methyl group, $R^{3b}$ represents an iodine atom, and T represents any one substituent described in Table L1 to Table L11 (hereinafter referred to as "Compound group SX1863").

The Compound (L-3), wherein n represents 1, $R^1$ represents a benzyl group, $R^2$ represents a methyl group, $R^{3b}$represents $CF_3$, and T represents any one substituent described in Table L1 to Table L11 (hereinafter referred to as "Compound group SX1864").

The Compound (L-3), wherein n represents 2, $R^1$ represents a benzyl group, $R^2$ represents a methyl group, $R^{3b}$ represents a hydrogen atom, and T represents any one substituent described in Table L1 to Table L11 (hereinafter referred to as "Compound group SX1865").

The Compound (L-3), wherein n represents 2, $R^1$ represents a benzyl group, $R^2$ represents a methyl group, $R^{3b}$ represents a chlorine atom, and T represents any one substituent described in Table L1 to Table L11 (hereinafter referred to as "Compound group SX1866").

The Compound (L-3), wherein n represents 2, $R^1$ represents a benzyl group, $R^2$ represents a methyl group, $R^{3b}$ represents a bromine atom, and T represents any one substituent described in Table L1 to Table L11 (hereinafter referred to as "Compound group SX1867").

The Compound (L-3), wherein n represents 2, $R^1$ represents a benzyl group, $R^2$ represents a methyl group, $R^{3b}$ represents an iodine atom, and T represents any one substituent described in Table L1 to Table L11 (hereinafter referred to as "Compound group SX1868").

The Compound (L-3), wherein n represents 2, $R^1$ represents a benzyl group, $R^2$ represents a methyl group, $R^{3b}$represents $CF_3$, and T represents any one substituent described in Table L1 to Table L11 (hereinafter referred to as "Compound group SX1869").

The Compound (L-3), wherein n represents 0, $R^1$ represents a cyanomethyl group, $R^2$ represents a methyl group, $R^{3b}$ represents a hydrogen atom, and T represents any one substituent described in Table L1 to Table L11 (hereinafter referred to as "Compound group SX1870").

The Compound (L-3), wherein n represents 0, $R^1$ represents a cyanomethyl group, $R^2$ represents a methyl group, $R^{3b}$ represents a chlorine atom, and T represents any one substituent described in Table L1 to Table L11 (hereinafter referred to as "Compound group SX1871").

The Compound (L-3), wherein n represents 0, $R^1$ represents a cyanomethyl group, $R^2$ represents a methyl group, $R^{3b}$ represents a bromine atom, and T represents any one substituent described in Table L1 to Table L11 (hereinafter referred to as "Compound group SX1872").

The Compound (L-3), wherein n represents 0, $R^1$ represents a cyanomethyl group, $R^2$ represents a methyl group, $R^{3b}$ represents an iodine atom, and T represents any one substituent described in Table L1 to Table L11 (hereinafter referred to as "Compound group SX1873").

The Compound (L-3), wherein n represents 0, $R^1$ represents a cyanomethyl group, $R^2$ represents a methyl group, $R^{3b}$ represents $CF_3$, and T represents any one substituent described in Table L1 to Table L11 (hereinafter referred to as "Compound group SX1874").

The Compound (L-3), wherein n represents 1, $R^1$ represents a cyanomethyl group, $R^2$ represents a methyl group, $R^{3b}$ represents a hydrogen atom, and T represents any one substituent described in Table L1 to Table L11 (hereinafter referred to as "Compound group SX1875").

The Compound (L-3), wherein n represents 1, $R^1$ represents a cyanomethyl group, $R^2$ represents a methyl group, $R^{3b}$ represents a chlorine atom, and T represents any one substituent described in Table L1 to Table L11 (hereinafter referred to as "Compound group SX1876").

The Compound (L-3), wherein n represents 1, $R^1$ represents a cyanomethyl group, $R^2$ represents a methyl group, $R^{3b}$ represents a bromine atom, and T represents any one substituent described in Table L1 to Table L11 (hereinafter referred to as "Compound group SX1877").

The Compound (L-3), wherein n represents 1, $R^1$ represents a cyanomethyl group, $R^2$ represents a methyl group, $R^{3b}$ represents an iodine atom, and T represents any one substituent described in Table L1 to Table L11 (hereinafter referred to as "Compound group SX1878").

The Compound (L-3), wherein n represents 1, $R^1$ represents a cyanomethyl group, $R^2$ represents a methyl group, $R^{3b}$ represents $CF_3$, and T represents any one substituent described in Table L1 to Table L11 (hereinafter referred to as "Compound group SX1879").

The Compound (L-3), wherein n represents 2, $R^1$ represents a cyanomethyl group, $R^2$ represents a methyl group, $R^{3b}$ represents a hydrogen atom, and T represents any one substituent described in Table L1 to Table L11 (hereinafter referred to as "Compound group SX1880").

The Compound (L-3), wherein n represents 2, $R^1$ represents a cyanomethyl group, $R^2$ represents a methyl group, $R^{3b}$ represents a chlorine atom, and T represents any one substituent described in Table L1 to Table L11 (hereinafter referred to as "Compound group SX1881").

The Compound (L-3), wherein n represents 2, $R^1$ represents a cyanomethyl group, $R^2$ represents a methyl group, $R^{3b}$ represents a bromine atom, and T represents any one substituent described in Table L1 to Table L11 (hereinafter referred to as "Compound group SX1882").

The Compound (L-3), wherein n represents 2, $R^1$ represents a cyanomethyl group, $R^2$ represents a methyl group, $R^{3b}$ represents an iodine atom, and T represents any one substituent described in Table L1 to Table L11 (hereinafter referred to as "Compound group SX1883").

The Compound (L-3), wherein n represents 2, $R^1$ represents a cyanomethyl group, $R^2$ represents a methyl group, $R^{3b}$ represents $CF_3$, and T represents any one substituent described in Table L1 to Table L11 (hereinafter referred to as "Compound group SX1884").

The Compound (L-3), wherein n represents 0, $R^1$ represents an ethoxymethyl group, $R^2$ represents a methyl group, $R^{3b}$ represents a hydrogen atom, and T represents any one substituent described in Table L1 to Table L11 (hereinafter referred to as "Compound group SX1885").

The Compound (L-3), wherein n represents 0, $R^1$ represents an ethoxymethyl group, $R^2$ represents a methyl group, $R^{3b}$ represents a chlorine atom, and T represents any one substituent described in Table L1 to Table L11 (hereinafter referred to as "Compound group SX1886").

The Compound (L-3), wherein n represents 0, $R^1$ represents an ethoxymethyl group, $R^2$ represents a methyl group, $R^{3b}$ represents a bromine atom, and T represents any one substituent described in Table L1 to Table L11 (hereinafter referred to as "Compound group SX1887").

The Compound (L-3), wherein n represents 0, $R^1$ represents an ethoxymethyl group, $R^2$ represents a methyl group, $R^{3b}$ represents an iodine atom, and T represents any one substituent described in Table L1 to Table L11 (hereinafter referred to as "Compound group SX1888").

The Compound (L-3), wherein n represents 0, $R^1$ represents an ethoxymethyl group, $R^2$ represents a methyl group, $R^{3b}$ represents $CF_3$, and T represents any one substituent described in Table L1 to Table L11 (hereinafter referred to as "Compound group SX1889").

The Compound (L-3), wherein n represents 1, $R^1$ represents an ethoxymethyl group, $R^2$ represents a methyl group, $R^{3b}$ represents a hydrogen atom, and T represents any one substituent described in Table L1 to Table L11 (hereinafter referred to as "Compound group SX1890").

The Compound (L-3), wherein n represents 1, $R^1$ represents an ethoxymethyl group, $R^2$ represents a methyl group, $R^{3b}$ represents a chlorine atom, and T represents any one substituent described in Table L1 to Table L11 (hereinafter referred to as "Compound group SX1891").

The Compound (L-3), wherein n represents 1, $R^1$ represents an ethoxymethyl group, $R^2$ represents a methyl group, $R^{3b}$ represents a bromine atom, and T represents any one substituent described in Table L1 to Table L11 (hereinafter referred to as "Compound group SX1892").

The Compound (L-3), wherein n represents 1, $R^1$ represents an ethoxymethyl group, $R^2$ represents a methyl group, $R^{3b}$ represents an iodine atom, and T represents any one substituent described in Table L1 to Table L11 (hereinafter referred to as "Compound group SX1893").

The Compound (L-3), wherein n represents 1, $R^1$ represents an ethoxymethyl group, $R^2$ represents a methyl group, $R^{3b}$ represents $CF_3$, and T represents any one substituent described in Table L1 to Table L11 (hereinafter referred to as "Compound group SX1894").

The Compound (L-3), wherein n represents 2, $R^1$ represents an ethoxymethyl group, $R^2$ represents a methyl group, $R^{3b}$ represents a hydrogen atom, and T represents any one substituent described in Table L1 to Table L11 (hereinafter referred to as "Compound group SX1895").

The Compound (L-3), wherein n represents 2, $R^1$ represents an ethoxymethyl group, $R^2$ represents a methyl group, $R^{3b}$ represents a chlorine atom, and T represents any one substituent described in Table L1 to Table L11 (hereinafter referred to as "Compound group SX1896").

The Compound (L-3), wherein n represents 2, $R^1$ represents an ethoxymethyl group, $R^2$ represents a methyl group, $R^{3b}$ represents a bromine atom, and T represents any one substituent described in Table L1 to Table L11 (hereinafter referred to as "Compound group SX1897").

The Compound (L-3), wherein n represents 2, $R^1$ represents an ethoxymethyl group, $R^2$ represents a methyl group, $R^{3b}$ represents an iodine atom, and T represents any one substituent described in Table L1 to Table L11 (hereinafter referred to as "Compound group SX1898").

The Compound (L-3), wherein n represents 2, $R^1$ represents an ethoxymethyl group, $R^2$ represents a methyl group, $R^{3b}$ represents $CF_3$, and T represents any one substituent described in Table L1 to Table L11 (hereinafter referred to as "Compound group SX1899").

The Compound (L-3), wherein n represents 0, $R^1$ represents a 3-pyridylmethyl group, $R^2$ represents a methyl group, $R^{3b}$ represents a hydrogen atom, and T represents any one substituent described in Table L1 to Table L11 (hereinafter referred to as "Compound group SX1900").

The Compound (L-3), wherein n represents 0, $R^1$ represents a 3-pyridylmethyl group, $R^2$ represents a methyl group, $R^{3b}$ represents a chlorine atom, and T represents any one substituent described in Table L1 to Table L11 (hereinafter referred to as "Compound group SX1901").

The Compound (L-3), wherein n represents 0, $R^1$ represents a 3-pyridylmethyl group, $R^2$ represents a methyl group, $R^{3b}$ represents a bromine atom, and T represents any one substituent described in Table L1 to Table L11 (hereinafter referred to as "Compound group SX1902").

The Compound (L-3), wherein n represents 0, $R^1$ represents a 3-pyridylmethyl group, $R^2$ represents a methyl group, $R^{3b}$ represents an iodine atom, and T represents any one substituent described in Table L1 to Table L11 (hereinafter referred to as "Compound group SX1903").

The Compound (L-3), wherein n represents 0, $R^1$ represents a 3-pyridylmethyl group, $R^2$ represents a methyl group, $R^{3b}$ represents $CF_3$, and T represents any one substituent described in Table L1 to Table L11 (hereinafter referred to as "Compound group SX1904").

The Compound (L-3), wherein n represents 1, $R^1$ represents a 3-pyridylmethyl group, $R^2$ represents a methyl group, $R^{3b}$ represents a hydrogen atom, and T represents any one substituent described in Table L1 to Table L11 (hereinafter referred to as "Compound group SX1905").

The Compound (L-3), wherein n represents 1, $R^1$ represents a 3-pyridylmethyl group, $R^2$ represents a methyl group, $R^{3b}$ represents a chlorine atom, and T represents any one substituent described in Table L1 to Table L11 (hereinafter referred to as "Compound group SX1906").

The Compound (L-3), wherein n represents 1, $R^1$ represents a 3-pyridylmethyl group, $R^2$ represents a methyl group, $R^{3b}$ represents a bromine atom, and T represents any one substituent described in Table L1 to Table L11 (hereinafter referred to as "Compound group SX1907").

The Compound (L-3), wherein n represents 1, $R^1$ represents a 3-pyridylmethyl group, $R^2$ represents a methyl group, $R^{3b}$ represents an iodine atom, and T represents any one substituent described in Table L1 to Table L11 (hereinafter referred to as "Compound group SX1908").

The Compound (L-3), wherein n represents 1, $R^1$ represents a 3-pyridylmethyl group, $R^2$ represents a methyl group, $R^{3b}$ represents $CF_3$, and T represents any one substituent described in Table L1 to Table L11 (hereinafter referred to as "Compound group SX1909").

The Compound (L-3), wherein n represents 2, $R^1$ represents a 3-pyridylmethyl group, $R^2$ represents a methyl group, $R^{3b}$ represents a hydrogen atom, and T represents any one substituent described in Table L1 to Table L11 (hereinafter referred to as "Compound group SX1910").

The Compound (L-3), wherein n represents 2, $R^1$ represents a 3-pyridylmethyl group, $R^2$ represents a methyl group, $R^{3b}$ represents a chlorine atom, and T represents any one substituent described in Table L1 to Table L11 (hereinafter referred to as "Compound group SX1911").

The Compound (L-3), wherein n represents 2, $R^1$ represents a 3-pyridylmethyl group, $R^2$ represents a methyl group, $R^{3b}$ represents a bromine atom, and T represents any one substituent described in Table L1 to Table L11 (hereinafter referred to as "Compound group SX1912").

The Compound (L-3), wherein n represents 2, $R^1$ represents a 3-pyridylmethyl group, $R^2$ represents a methyl group, $R^{3b}$ represents an iodine atom, and T represents any one substituent described in Table L1 to Table L11 (hereinafter referred to as "Compound group SX1913").

The Compound (L-3), wherein n represents 2, $R^1$ represents a 3-pyridylmethyl group, $R^2$ represents a methyl group, $R^{3b}$ represents $CF_2$, and T represents any one substituent described in Table L1 to Table L11 (hereinafter referred to as "Compound group SX1914").

A Compound Represented by Formula (L-4)

(L-4)

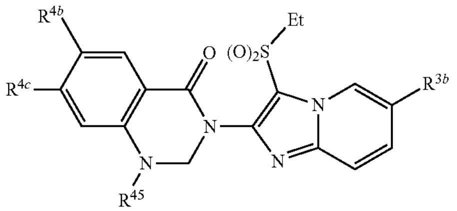

(hereinafter referred to as "Compound (L-4), wherein $R^{45}$ represents a hydrogen atom, R" represents a hydrogen atom, $R^{4c}$ represents a hydrogen atom, and R represents any one substituent described in Table L12 to Table L14 (hereinafter referred to as "Compound group SX1396").

The Compound (L-4), wherein $R^{45}$ represents a hydrogen atom, $R^{4b}$ represents a hydrogen atom, $R^{4c}$ represents a fluorine atom, and $R^{3b}$ represents any one substituent described in Table L12 to Table L14 (hereinafter referred to as "Compound group SX1397").

The Compound (L-4), wherein $R^{45}$ represents a hydrogen atom, $R^{4b}$ represents a hydrogen atom, $R^{4c}$ represents a chlorine atom, and $R^{3b}$ represents any one substituent described in Table L12 to Table L14 (hereinafter referred to as "Compound group SX1398").

The Compound (L-4), wherein $R^{45}$ represents a hydrogen atom, $R^{4b}$ represents a hydrogen atom, $R^{4c}$ represents a bromine atom, and $R^{3b}$ represents any one substituent described in Table L12 to Table L14 (hereinafter referred to as "Compound group SX1399").

The Compound (L-4), wherein $R^{45}$ represents a hydrogen atom, $R^{4b}$ represents a hydrogen atom, $R^{4c}$ represents an iodine atom, and $R^{3b}$ represents any one substituent described in Table L12 to Table L14 (hereinafter referred to as "Compound group SX1400").

The Compound (L-4), wherein $R^{45}$ represents a hydrogen atom, $R^{4b}$ represents a hydrogen atom, $R^{4c}$ represents $CF_3$, and $R^{3b}$ represents any one substituent described in Table L12 to Table L14 (hereinafter referred to as "Compound group SX1401").

The Compound (L-4), wherein $R^{45}$ represents a hydrogen atom, $R^{4b}$ represents a hydrogen atom, $R^{4c}$ represents $OCF_3$, and $R^{3b}$ represents any one substituent described in Table L12 to Table L14 (hereinafter referred to as "Compound group SX1402").

The Compound (L-4), wherein $R^{45}$ represents a hydrogen atom, $R^{4b}$ represents a fluorine atom, $R^{4c}$ represents a hydrogen atom, and $R^{3b}$ represents any one substituent described in Table L12 to Table L14 (hereinafter referred to as "Compound group SX1403").

The Compound (L-4), wherein $R^{45}$ represents a hydrogen atom, $R^{4b}$ represents a fluorine atom, $R^{4c}$ represents a fluorine atom, and $R^{3b}$ represents any one substituent described in Table L12 to Table L14 (hereinafter referred to as "Compound group SX1404").

The Compound (L-4), wherein $R^{45}$ represents a hydrogen atom, $R^{4b}$ represents a fluorine atom, $R^{4c}$ represents a chlorine atom, and $R^{3b}$ represents any one substituent described in Table L12 to Table L14 (hereinafter referred to as "Compound group SX1405").

The Compound (L-4), wherein $R^{45}$ represents a hydrogen atom, $R^{4b}$ represents a fluorine atom, $R^{4c}$ represents a bromine atom, and $R^{3b}$ represents any one substituent described in Table L12 to Table L14 (hereinafter referred to as "Compound group SX1406").

The Compound (L-4), wherein $R^{45}$ represents a hydrogen atom, $R^{4b}$ represents a fluorine atom, $R^{4c}$ represents an iodine atom, and $R^{3b}$ represents any one substituent described in Table L12 to Table L14 (hereinafter referred to as "Compound group SX1407").

The Compound (L-4), wherein $R^{45}$ represents a hydrogen atom, $R^{4b}$ represents a fluorine atom, $R^{4c}$ represents $CF_3$, and $R^{3b}$ represents any one substituent described in Table L12 to Table L14 (hereinafter referred to as "Compound group SX1408").

The Compound (L-4), wherein $R^{45}$ represents a hydrogen atom, $R^{4b}$ represents a fluorine atom, $R^{4c}$ represents $OCF_3$, and $R^{3b}$ represents any one substituent described in Table L12 to Table L14 (hereinafter referred to as "Compound group SX1409").

The Compound (L-4), wherein $R^{45}$ represents a hydrogen atom, $R^{4b}$ represents a chlorine atom, $R^{4c}$ represents a hydrogen atom, and $R^{3b}$ represents any one substituent described in Table L12 to Table L14 (hereinafter referred to as "Compound group SX1410").

The Compound (L-4), wherein $R^{45}$ represents a hydrogen atom, $R^{4b}$ represents a chlorine atom, $R^{4c}$ represents a fluorine atom, and $R^{3b}$ represents any one substituent described in Table L12 to Table L14 (hereinafter referred to as "Compound group SX1411").

The Compound (L-4), wherein $R^{45}$ represents a hydrogen atom, $R^{4b}$ represents a chlorine atom, $R^{4c}$ represents a chlorine atom, and $R^{3b}$ represents any one substituent described in Table L12 to Table L14 (hereinafter referred to as "Compound group SX1412").

The Compound (L-4), wherein $R^{45}$ represents a hydrogen atom, $R^{4b}$ represents a chlorine atom, $R^{4c}$ represents a bromine atom, and $R^{3b}$ represents any one substituent described in Table L12 to Table L14 (hereinafter referred to as "Compound group SX1413").

The Compound (L-4), wherein $R^{45}$ represents a hydrogen atom, $R^{4b}$ represents a chlorine atom, $R^{4c}$ represents an iodine atom, and $R^{3b}$ represents any one substituent described in Table L12 to Table L14 (hereinafter referred to as "Compound group SX1414").

The Compound (L-4), wherein $R^{45}$ represents a hydrogen atom, $R^{4b}$ represents a chlorine atom, $R^{4c}$ represents $CF_3$, and $R^{3b}$ represents any one substituent described in Table L12 to Table L14 (hereinafter referred to as "Compound group SX1415").

The Compound (L-4), wherein $R^{45}$ represents a hydrogen atom, $R^{4b}$ represents a chlorine atom, $R^{4c}$ represents $OCF_3$, and $R^{3b}$ represents any one substituent described in Table L12 to Table L14 (hereinafter referred to as "Compound group SX1416").

The Compound (L-4), wherein $R^{45}$ represents a hydrogen atom, $R^{4b}$ represents an iodine atom, $R^{4c}$ represents a hydrogen atom, and $R^{3b}$ represents any one substituent described in Table L12 to Table L14 (hereinafter referred to as "Compound group SX1417").

The Compound (L-4), wherein $R^{45}$ represents a hydrogen atom, $R^{4b}$ represents an iodine atom, $R^{4c}$ represents a fluorine atom, and $R^{3b}$ represents any one substituent described in Table L12 to Table L14 (hereinafter referred to as "Compound group SX1418").

The Compound (L-4), wherein $R^{45}$ represents a hydrogen atom, $R^{4b}$ represents an iodine atom, $R^{4c}$ represents a chlorine atom, and $R^{3b}$ represents any one substituent described in Table L12 to Table L14 (hereinafter referred to as "Compound group SX1419").

The Compound (L-4), wherein $R^{45}$ represents a hydrogen atom, $R^{4b}$ represents an iodine atom, $R^{4c}$ represents a bromine atom, and $R^{3b}$ represents any one substituent described in Table L12 to Table L14 (hereinafter referred to as "Compound group SX1420").

The Compound (L-4), wherein $R^{45}$ represents a hydrogen atom, $R^{4b}$ represents an iodine atom, $R^{4c}$ represents an iodine atom, and $R^{3b}$ represents any one substituent described in Table L12 to Table L14 (hereinafter referred to as "Compound group SX1421").

The Compound (L-4), wherein $R^{45}$ represents a hydrogen atom, $R^{4b}$ represents an iodine atom, $R^{4c}$ represents $CF_3$, and $R^{3b}$ represents any one substituent described in Table L12 to Table L14 (hereinafter referred to as "Compound group SX1422").

The Compound (L-4), wherein $R^{45}$ represents a hydrogen atom, $R^{4b}$ represents an iodine atom, $R^{4c}$ represents $OCF_3$, and $R^{3b}$ represents any one substituent described in Table L12 to Table L14 (hereinafter referred to as "Compound group SX1423").

The Compound (L-4), wherein $R^{45}$ represents a hydrogen atom, $R^{4b}$ represents $CF_3$, $R^{4c}$ represents a hydrogen atom, and $R^{3b}$ represents any one substituent described in Table L12 to Table L14 (hereinafter referred to as "Compound group SX1424").

The Compound (L-4), wherein $R^{45}$ represents a hydrogen atom, $R^{4b}$ represents $CF_3$, $R^{4c}$ represents a fluorine atom, and $R^{3b}$ represents any one substituent described in Table L12 to Table L14 (hereinafter referred to as "Compound group SX1425").

The Compound (L-4), wherein $R^{45}$ represents a hydrogen atom, $R^{4b}$ represents $CF_3$, $R^{4c}$ represents a chlorine atom, and $R^{3b}$ represents any one substituent described in Table L12 to Table L14 (hereinafter referred to as "Compound group SX1426").

The Compound (L-4), wherein $R^{45}$ represents a hydrogen atom, $R^{4b}$ represents $CF_3$, $R^{4c}$ represents a bromine atom, and $R^{3b}$ represents any one substituent described in Table L12 to Table L14 (hereinafter referred to as "Compound group SX1427").

The Compound (L-4), wherein $R^{45}$ represents a hydrogen atom, $R^{4b}$ represents $CF_3$, $R^{4c}$ represents an iodine atom, and $R^{3b}$ represents any one substituent described in Table L12 to Table L14 (hereinafter referred to as "Compound group SX1428").

The Compound (L-4), wherein $R^{45}$ represents a hydrogen atom, $R^{4b}$ represents $CF_3$, $R^{4c}$ represents $CF_3$, and $R^{3b}$ represents any one substituent described in Table L12 to Table L14 (hereinafter referred to as "Compound group SX1429").

The Compound (L-4), wherein $R^{45}$ represents a hydrogen atom, $R^{4b}$ represents $CF_3$, $R^{4c}$ represents $OCF_3$, and $R^{3b}$ represents any one substituent described in Table L12 to Table L14 (hereinafter referred to as "Compound group SX1430").

The Compound (L-4), wherein $R^{45}$ represents a hydrogen atom, $R^{4b}$ represents $OCF_3$, $R^{4c}$ represents a hydrogen atom, and $R^{3b}$ represents any one substituent described in Table L12 to Table L14 (hereinafter referred to as "Compound group SX1431").

The Compound (L-4), wherein $R^{45}$ represents a hydrogen atom, $R^{4b}$ represents $OCF_3$, $R^{4c}$ represents a fluorine atom, and $R^{3b}$ represents any one substituent described in Table L12 to Table L14 (hereinafter referred to as "Compound group SX1432").

The Compound (L-4), wherein $R^{45}$ represents a hydrogen atom, $R^{4b}$ represents $OCF_3$, $R^{4c}$ represents a chlorine atom, and $R^{3b}$ represents any one substituent described in Table L12 to Table L14 (hereinafter referred to as "Compound group SX1433").

The Compound (L-4), wherein $R^{45}$ represents a hydrogen atom, $R^{4b}$ represents $OCF_3$, $R^{4c}$ represents a bromine atom, and $R^{3b}$ represents any one substituent described in Table L12 to Table L14 (hereinafter referred to as "Compound group SX1434").

The Compound (L-4), wherein $R^{45}$ represents a hydrogen atom, $R^{4b}$ represents $OCF_3$, $R^{4c}$ represents an iodine atom, and $R^{3b}$ represents any one substituent described in Table L12 to Table L14 (hereinafter referred to as "Compound group SX1435").

The Compound (L-4), wherein $R^{45}$ represents a hydrogen atom, $R^{4b}$ represents $OCF_3$, $R^{4c}$ represents $CF_3$, and $R^{3b}$ represents any one substituent described in Table L12 to Table L14 (hereinafter referred to as "Compound group SX1436").

The Compound (L-4), wherein $R^{45}$ represents a hydrogen atom, $R^{4b}$ represents $OCF_3$, $R^{4c}$ represents $OCF_3$, and $R^{3b}$ represents any one substituent described in Table L12 to Table L14 (hereinafter referred to as "Compound group SX1437").

The Compound (L-4), wherein $R^{45}$ represents a methyl group, $R^{4b}$ represents a hydrogen atom, $R^{4c}$ represents a hydrogen atom, and $R^{3b}$ represents any one substituent described in Table L12 to Table L14 (hereinafter referred to as "Compound group SX1438").

The Compound (L-4), wherein $R^{45}$ represents a methyl group, $R^{4b}$ represents a hydrogen atom, $R^{4c}$ represents a fluorine atom, and $R^{3b}$ represents any one substituent described in Table L12 to Table L14 (hereinafter referred to as "Compound group SX1439").

The Compound (L-4), wherein $R^{45}$ represents a methyl group, $R^{4b}$ represents a hydrogen atom, $R^{4c}$ represents a chlorine atom, and $R^{3b}$ represents any one substituent described in Table L12 to Table L14 (hereinafter referred to as "Compound group SX1440").

The Compound (L-4), wherein $R^{45}$ represents a methyl group, $R^{4b}$ represents a hydrogen atom, $R^{4c}$ represents a bromine atom, and $R^{3b}$ represents any one substituent described in Table L12 to Table L14 (hereinafter referred to as "Compound group SX1441").

The Compound (L-4), wherein $R^{45}$ represents a methyl group, $R^{4b}$ represents a hydrogen atom, $R^{4c}$ represents an iodine atom, and $R^{3b}$ represents any one substituent described in Table L12 to Table L14 (hereinafter referred to as "Compound group SX1442").

The Compound (L-4), wherein $R^{45}$ represents a methyl group, $R^{4b}$ represents a hydrogen atom, $R^{4c}$ represents $CF_3$, and $R^{3b}$ represents any one substituent described in Table L12 to Table L14 (hereinafter referred to as "Compound group SX1443").

The Compound (L-4), wherein $R^{45}$ represents a methyl group, $R^{4b}$ represents a hydrogen atom, $R^{4c}$ represents $OCF_3$, and $R^{3b}$ represents any one substituent described in Table L12 to Table L14 (hereinafter referred to as "Compound group SX1444").

The Compound (L-4), wherein $R^{45}$ represents a methyl group, $R^{4b}$ represents a fluorine atom, $R^{4c}$ represents a hydrogen atom, and $R^{3b}$ represents any one substituent described in Table L12 to Table L14 (hereinafter referred to as "Compound group SX1445").

The Compound (L-4), wherein $R^{45}$ represents a methyl group, $R^{4b}$ represents a fluorine atom, $R^{4c}$ represents a fluorine atom, and $R^{3b}$ represents any one substituent described in Table L12 to Table L14 (hereinafter referred to as "Compound group SX1446").

The Compound (L-4), wherein $R^{45}$ represents a methyl group, $R^{4b}$ represents a fluorine atom, $R^{4c}$ represents a chlorine atom, and $R^{3b}$ represents any one substituent described in Table L12 to Table L14 (hereinafter referred to as "Compound group SX1447").

The Compound (L-4), wherein $R^{45}$ represents a methyl group, $R^{4b}$ represents a fluorine atom, $R^{4c}$ represents a bromine atom, and $R^{3b}$ represents any one substituent described in Table L12 to Table L14 (hereinafter referred to as "Compound group SX1448").

The Compound (L-4), wherein $R^{45}$ represents a methyl group, $R^{4b}$ represents a fluorine atom, $R^{4c}$ represents an iodine atom, and $R^{3b}$ represents any one substituent described in Table L12 to Table L14 (hereinafter referred to as "Compound group SX1449").

The Compound (L-4), wherein $R^{45}$ represents a methyl group, $R^{4b}$ represents a fluorine atom, $R^{4c}$ represents $CF_3$, and $R^{3b}$ represents any one substituent described in Table L12 to Table L14 (hereinafter referred to as "Compound group SX1450").

The Compound (L-4), wherein $R^{45}$ represents a methyl group, $R^{4b}$ represents a fluorine atom, $R^{4c}$ represents $OCF_3$, and $R^{3b}$ represents any one substituent described in Table L12 to Table L14 (hereinafter referred to as "Compound group SX1451").

The Compound (L-4), wherein $R^{45}$ represents a methyl group, $R^{4b}$ represents a chlorine atom, $R^{4c}$ represents a hydrogen atom, and $R^{3b}$ represents any one substituent described in Table L12 to Table L14 (hereinafter referred to as "Compound group SX1452").

The Compound (L-4), wherein $R^{45}$ represents a methyl group, $R^{4b}$ represents a chlorine atom, $R^{4c}$ represents a fluorine atom, and $R^{3b}$ represents any one substituent described in Table L12 to Table L14 (hereinafter referred to as "Compound group SX1453").

The Compound (L-4), wherein $R^{45}$ represents a methyl group, $R^{4b}$ represents a chlorine atom, $R^{4c}$ represents a chlorine atom, and $R^{3b}$ represents any one substituent described in Table L12 to Table L14 (hereinafter referred to as "Compound group SX1454").

The Compound (L-4), wherein $R^{45}$ represents a methyl group, $R^{4b}$ represents a chlorine atom, $R^{4c}$ represents a bromine atom, and $R^{3b}$ represents any one substituent described in Table L12 to Table L14 (hereinafter referred to as "Compound group SX1455").

The Compound (L-4), wherein $R^{45}$ represents a methyl group, $R^{4b}$ represents a chlorine atom, $R^{4c}$ represents an iodine atom, and $R^{3b}$ represents any one substituent described in Table L12 to Table L14 (hereinafter referred to as "Compound group SX1456").

The Compound (L-4), wherein $R^{45}$ represents a methyl group, $R^{4b}$ represents a chlorine atom, $R^{4c}$ represents $CF_3$, and $R^{3b}$ represents any one substituent described in Table L12 to Table L14 (hereinafter referred to as "Compound group SX1457").

The Compound (L-4), wherein $R^{45}$ represents a methyl group, $R^{4b}$ represents a chlorine atom, $R^{4c}$ represents $OCF_3$, and $R^{3b}$ represents any one substituent described in Table L12 to Table L14 (hereinafter referred to as "Compound group SX1458").

The Compound (L-4), wherein $R^{45}$ represents a methyl group, $R^{4b}$ represents an iodine atom, $R^{4c}$ represents a hydrogen atom, and $R^{3b}$ represents any one substituent described in Table L12 to Table L14 (hereinafter referred to as "Compound group SX1459").

The Compound (L-4), wherein $R^{45}$ represents a methyl group, $R^{4b}$ represents an iodine atom, $R^{4c}$ represents a fluorine atom, and $R^{3b}$ represents any one substituent described in Table L12 to Table L14 (hereinafter referred to as "Compound group SX1460").

The Compound (L-4), wherein $R^{45}$ represents a methyl group, $R^{4b}$ represents an iodine atom, $R^{4c}$ represents a chlorine atom, and $R^{3b}$ represents any one substituent described in Table L12 to Table L14 (hereinafter referred to as "Compound group SX1461").

The Compound (L-4), wherein $R^{45}$ represents a methyl group, $R^{4b}$ represents an iodine atom, $R^{4c}$ represents a bromine atom, and $R^{3b}$ represents any one substituent described in Table L12 to Table L14 (hereinafter referred to as "Compound group SX1462").

The Compound (L-4), wherein $R^{45}$ represents a methyl group, $R^{4b}$ represents an iodine atom, $R^{4c}$ represents an iodine atom, and $R^{3b}$ represents any one substituent described in Table L12 to Table L14 (hereinafter referred to as "Compound group SX1463").

The Compound (L-4), wherein $R^{45}$ represents a methyl group, $R^{4b}$ represents an iodine atom, $R^{4c}$ represents $CF_3$, and $R^{3b}$ represents any one substituent described in Table L12 to Table L14 (hereinafter referred to as "Compound group SX1464").

The Compound (L-4), wherein $R^{45}$ represents a methyl group, $R^{4b}$ represents an iodine atom, $R^{4c}$ represents $OCF_3$, and $R^{3b}$ represents any one substituent described in Table L12 to Table L14 (hereinafter referred to as "Compound group SX1465").

The Compound (L-4), wherein $R^{45}$ represents a methyl group, $R^{4b}$ represents $CF_3$, $R^{4c}$ represents a hydrogen atom, and $R^{3b}$ represents any one substituent described in Table L12 to Table L14 (hereinafter referred to as "Compound group SX1466").

The Compound (L-4), wherein $R^{45}$ represents a methyl group, $R^{4b}$ represents $CF_3$, $R^{4c}$ represents a fluorine atom, and $R^{3b}$ represents any one substituent described in Table L12 to Table L14 (hereinafter referred to as "Compound group SX1467").

The Compound (L-4), wherein $R^{45}$ represents a methyl group, $R^{4b}$ represents $CF_3$, $R^{4c}$ represents a chlorine atom, and $R^{3b}$ represents any one substituent described in Table L12 to Table L14 (hereinafter referred to as "Compound group SX1468").

The Compound (L-4), wherein $R^{45}$ represents a methyl group, $R^{4b}$ represents $CF_3$, $R^{4c}$ represents a bromine atom, and $R^{3b}$ represents any one substituent described in Table L12 to Table L14 (hereinafter referred to as "Compound group SX1469").

The Compound (L-4), wherein $R^{45}$ represents a methyl group, $R^{4b}$ represents $CF_3$, $R^{4c}$ represents an iodine atom, and $R^{3b}$ represents any one substituent described in Table L12 to Table L14 (hereinafter referred to as "Compound group SX1470").

The Compound (L-4), wherein $R^{45}$ represents a methyl group, $R^{4b}$ represents $CF_3$, $R^{4c}$ represents $CF_3$, and $R^{3b}$ represents any one substituent described in Table L12 to Table L14 (hereinafter referred to as "Compound group SX1471").

The Compound (L-4), wherein $R^{45}$ represents a methyl group, $R^{4b}$ represents $CF_3$, $R^{4c}$ represents $OCF_3$, and $R^{3b}$ represents any one substituent described in Table L12 to Table L14 (hereinafter referred to as "Compound group SX1472").

The Compound (L-4), wherein $R^{45}$ represents a methyl group, $R^{4b}$ represents $OCF_3$, $R^{4c}$ represents a hydrogen atom, and $R^{3b}$ represents any one substituent described in Table L12 to Table L14 (hereinafter referred to as "Compound group SX1473").

The Compound (L-4), wherein $R^{45}$ represents a methyl group, $R^{4b}$ represents $OCF_3$, $R^{4c}$ represents a fluorine atom, and $R^{3b}$ represents any one substituent described in Table L12 to Table L14 (hereinafter referred to as "Compound group SX1474").

The Compound (L-4), wherein $R^{45}$ represents a methyl group, $R^{4b}$ represents $OCF_3$, $R^{4c}$ represents a chlorine atom, and $R^{3b}$ represents any one substituent described in Table L12 to Table L14 (hereinafter referred to as "Compound group SX1475").

The Compound (L-4), wherein $R^{45}$ represents a methyl group, $R^{4b}$ represents $OCF_3$, $R^{4c}$ represents a bromine atom, and $R^{3b}$ represents any one substituent described in Table L12 to Table L14 (hereinafter referred to as "Compound group SX1476").

The Compound (L-4), wherein $R^{45}$ represents a methyl group, $R^{4b}$ represents $OCF_3$, $R^{4c}$ represents an iodine atom, and $R^{3b}$ represents any one substituent described in Table L12 to Table L14 (hereinafter referred to as "Compound group SX1477").

The Compound (L-4), wherein $R^{45}$ represents a methyl group, $R^{4b}$ represents $OCF_3$, $R^{4c}$ represents $CF_3$, and $R^{3b}$ represents any one substituent described in Table L12 to Table L14 (hereinafter referred to as "Compound group SX1478").

The Compound (L-4), wherein $R^{45}$ represents a methyl group, $R^{4b}$ represents $OCF_3$, $R^{4c}$ represents $OCF_3$, and $R^{3b}$ represents any one substituent described in Table L12 to Table L14 (hereinafter referred to as "Compound group SX1479").

The Compound (L-4), wherein $R^{45}$ represents a hydrogen atom, $R^{4b}$ represents a hydrogen atom, $R^{4c}$ represents $OCF_2H$, and $R^{3b}$ represents any one substituent described in Table L12 to Table L14 (hereinafter referred to as "Compound group SX1915").

The Compound (L-4), wherein $R^{45}$ represents a hydrogen atom, $R^{4b}$ represents a hydrogen atom, $R^{4c}$ represents $CF_2H$, and $R^{3b}$ represents any one substituent described in Table L12 to Table L14 (hereinafter referred to as "Compound group SX1916").

The Compound (L-4), wherein $R^{45}$ represents a hydrogen atom, $R^{4b}$ represents a fluorine atom, $R^{4c}$ represents $OCF_2H$, and $R^{3b}$ represents any one substituent described in Table L12 to Table L14 (hereinafter referred to as "Compound group SX1917").

The Compound (L-4), wherein $R^{45}$ represents a hydrogen atom, $R^{4b}$ represents a fluorine atom, $R^{4c}$ represents $CF_2H$, and $R^{3b}$ represents any one substituent described in Table L12 to Table L14 (hereinafter referred to as "Compound group SX1918").

The Compound (L-4), wherein $R^{45}$ represents a hydrogen atom, $R^{4b}$ represents a chlorine atom, $R^{4c}$ represents $OCF_2H$, and $R^{3b}$ represents any one substituent described in Table L12 to Table L14 (hereinafter referred to as "Compound group SX1919").

The Compound (L-4), wherein $R^{45}$ represents a hydrogen atom, $R^{4b}$ represents a chlorine atom, $R^{4c}$ represents $CF_2H$, and $R^{3b}$ represents any one substituent described in Table L12 to Table L14 (hereinafter referred to as "Compound group SX1920").

The Compound (L-4), wherein $R^{45}$ represents a hydrogen atom, $R^{4b}$ represents an iodine atom, $R^{4c}$ represents $OCF_2H$, and $R^{3b}$ represents any one substituent described in Table L12 to Table L14 (hereinafter referred to as "Compound group SX1921").

The Compound (L-4), wherein $R^{45}$ represents a hydrogen atom, $R^{4b}$ represents an iodine atom, $R^{4c}$ represents $CF_2H$, and $R^{3b}$ represents any one substituent described in Table L12 to Table L14 (hereinafter referred to as "Compound group SX1922").

The Compound (L-4), wherein $R^{45}$ represents a hydrogen atom, $R^{4b}$ represents $CF_3$, $R^{4c}$ represents $OCF_2H$, and $R^{3b}$ represents any one substituent described in Table L12 to Table L14 (hereinafter referred to as "Compound group SX1923").

The Compound (L-4), wherein $R^{45}$ represents a hydrogen atom, $R^{4b}$ represents $CF_3$, $R^{4c}$ represents $CF_2H$, and $R^{3b}$ represents any one substituent described in Table L12 to Table L14 (hereinafter referred to as "Compound group SX1924").

The Compound (L-4), wherein $R^{45}$ represents a hydrogen atom, $R^{4b}$ represents $OCF_3$, $R^{4c}$ represents $OCF_2H$, and $R^{3b}$ represents any one substituent described in Table L12 to Table L14 (hereinafter referred to as "Compound group SX1925").

The Compound (L-4), wherein $R^{45}$ represents a hydrogen atom, $R^{4b}$ represents $OCF_3$, $R^{4c}$ represents $CF_2H$, and $R^{3b}$ represents any one substituent described in Table L12 to Table L14 (hereinafter referred to as "Compound group SX1926").

The Compound (L-4), wherein $R^{45}$ represents a hydrogen atom, $R^{4b}$ represents a bromine atom, $R^{4c}$ represents $OCF_2H$, and $R^{3b}$ represents any one substituent described in Table L12 to Table L14 (hereinafter referred to as "Compound group SX1927").

The Compound (L-4), wherein $R^{45}$ represents a hydrogen atom, $R^{4b}$ represents a bromine atom, $R^{4c}$ represents $CF_2H$, and $R^{3b}$ represents any one substituent described in Table L12 to Table L14 (hereinafter referred to as "Compound group SX1928").

The Compound (L-4), wherein $R^{45}$ represents a hydrogen atom, $R^{4b}$ represents $OCF_2H$, $R^{4c}$ represents $OCF_2H$, and $R^{3b}$ represents any one substituent described in Table L12 to Table L14 (hereinafter referred to as "Compound group SX1929").

The Compound (L-4), wherein $R^{45}$ represents a hydrogen atom, $R^{4b}$ represents $OCF_2H$, $R^{4c}$ represents $CF_2H$, and $R^{3b}$ represents any one substituent described in Table L12 to Table L14 (hereinafter referred to as "Compound group SX1930").

The Compound (L-4), wherein $R^{45}$ represents a hydrogen atom, $R^{4b}$ represents $CF_2H$, $R^{4c}$ represents $OCF_2H$, and $R^{3b}$ represents any one substituent described in Table L12 to Table L14 (hereinafter referred to as "Compound group SX1931").

The Compound (L-4), wherein $R^{45}$ represents a hydrogen atom, $R^{4b}$ represents $CF_2H$, $R^{4c}$ represents $CF_2H$, and $R^{3b}$ represents any one substituent described in Table L12 to Table L14 (hereinafter referred to as "Compound group SX1932").

The Compound (L-4), wherein $R^{45}$ represents a hydrogen atom, $R^{4b}$ represents a bromine atom, $R^{4c}$ represents a hydrogen atom, and $R^{3b}$ represents any one substituent described in Table L12 to Table L14 (hereinafter referred to as "Compound group SX1933").

The Compound (L-4), wherein $R^{45}$ represents a hydrogen atom, $R^{4b}$ represents a bromine atom, $R^{4c}$ represents a fluorine atom, and $R^{3b}$ represents any one substituent described in Table L12 to Table L14 (hereinafter referred to as "Compound group SX1934").

The Compound (L-4), wherein $R^{45}$ represents a hydrogen atom, $R^{4b}$ represents a bromine atom, $R^{4c}$ represents a chlorine atom, and $R^{3b}$ represents any one substituent described in Table L12 to Table L14 (hereinafter referred to as "Compound group SX1935").

The Compound (L-4), wherein $R^{45}$ represents a hydrogen atom, $R^{4b}$ represents a bromine atom, $R^{4c}$ represents a bromine atom, and $R^{3b}$ represents any one substituent described in Table L12 to Table L14 (hereinafter referred to as "Compound group SX1936").

The Compound (L-4), wherein $R^{45}$ represents a hydrogen atom, $R^{4b}$ represents a bromine atom, $R^{4c}$ represents an iodine atom, and $R^{3b}$ represents any one substituent described in Table L12 to Table L14 (hereinafter referred to as "Compound group SX1937").

The Compound (L-4), wherein $R^{45}$ represents a hydrogen atom, $R^{4b}$ represents a bromine atom, $R^{4c}$ represents $CF_3$, and $R^{3b}$ represents any one substituent described in Table L12 to Table L14 (hereinafter referred to as "Compound group SX1938").

The Compound (L-4), wherein $R^{45}$ represents a hydrogen atom, $R^{4b}$ represents a bromine atom, $R^{4c}$ represents $OCF_3$, and $R^{3b}$ represents any one substituent described in Table L12 to Table L14 (hereinafter referred to as "Compound group SX1939").

The Compound (L-4), wherein $R^{45}$ represents a methyl group, $R^{4b}$ represents a hydrogen atom, $R^{4c}$ represents $OCF_2H$, and $R^{3b}$ represents any one substituent described in Table L12 to Table L14 (hereinafter referred to as "Compound group SX1940").

The Compound (L-4), wherein $R^{45}$ represents a methyl group, $R^{4b}$ represents a hydrogen atom, $R^{4c}$ represents $CF_2H$, and $R^{3b}$ represents any one substituent described in Table L12 to Table L14 (hereinafter referred to as "Compound group SX1941").

The Compound (L-4), wherein $R^{45}$ represents a methyl group, $R^{4b}$ represents a fluorine atom, $R^{4c}$ represents $OCF_2H$, and $R^{3b}$ represents any one substituent described in Table L12 to Table L14 (hereinafter referred to as "Compound group SX1942").

The Compound (L-4), wherein $R^{45}$ represents a methyl group, $R^{4b}$ represents a fluorine atom, $R^{4c}$ represents $CF_2H$, and $R^{3b}$ represents any one substituent described in Table L12 to Table L14 (hereinafter referred to as "Compound group SX1943").

The Compound (L-4), wherein $R^{45}$ represents a methyl group, $R^{4b}$ represents a chlorine atom, $R^{4c}$ represents $OCF_2H$, and $R^{3b}$ represents any one substituent described in Table L12 to Table L14 (hereinafter referred to as "Compound group SX1944").

The Compound (L-4), wherein $R^{45}$ represents a methyl group, $R^{4b}$ represents a chlorine atom, $R^{4c}$ represents $CF_2H$, and $R^{3b}$ represents any one substituent described in Table L12 to Table L14 (hereinafter referred to as "Compound group SX1945").

The Compound (L-4), wherein $R^{45}$ represents a methyl group, $R^{4b}$ represents an iodine atom, $R^{4c}$ represents $OCF_2H$, and $R^{3b}$ represents any one substituent described in Table L12 to Table L14 (hereinafter referred to as "Compound group SX1946").

The Compound (L-4), wherein $R^{45}$ represents a methyl group, $R^{4b}$ represents an iodine atom, $R^{4c}$ represents $CF_2H$, and $R^{3b}$ represents any one substituent described in Table L12 to Table L14 (hereinafter referred to as "Compound group SX1947").

The Compound (L-4), wherein $R^{45}$ represents a methyl group, $R^{4b}$ represents $CF_3$, $R^{4c}$ represents $OCF_2H$, and $R^{3b}$ represents any one substituent described in Table L12 to Table L14 (hereinafter referred to as "Compound group SX1948").

The Compound (L-4), wherein $R^{45}$ represents a methyl group, $R^{4b}$ represents $CF_3$, $R^{4c}$ represents $CF_2H$, and $R^{3b}$ represents any one substituent described in Table L12 to Table L14 (hereinafter referred to as "Compound group SX1949").

The Compound (L-4), wherein $R^{45}$ represents a methyl group, $R^{4b}$ represents $OCF_3$, $R^{4c}$ represents $OCF_2H$, and $R^{3b}$ represents any one substituent described in Table L12 to Table L14 (hereinafter referred to as "Compound group SX1950").

The Compound (L-4), wherein $R^{45}$ represents a methyl group, $R^{4b}$ represents $OCF_3$, $R^{4c}$ represents $CF_2H$, and $R^{3b}$ represents any one substituent described in Table L12 to Table L14 (hereinafter referred to as "Compound group SX1951").

The Compound (L-4), wherein $R^{45}$ represents a methyl group, $R^{4b}$ represents a bromine atom, $R^{4c}$ represents $OCF_2H$, and $R^{3b}$ represents any one substituent described in Table L12 to Table L14 (hereinafter referred to as "Compound group SX1952").

The Compound (L-4), wherein $R^{45}$ represents a methyl group, $R^{4b}$ represents a bromine atom, $R^{4c}$ represents $CF_2H$, and $R^{3b}$ represents any one substituent described in Table L12 to Table L14 (hereinafter referred to as "Compound group SX1953").

The Compound (L-4), wherein $R^{45}$ represents a methyl group, $R^{4b}$ represents $OCF_2H$, $R^{4c}$ represents $OCF_2H$, and $R^{3b}$ represents any one substituent described in Table L12 to Table L14 (hereinafter referred to as "Compound group SX1954").

The Compound (L-4), wherein $R^{45}$ represents a methyl group, $R^{4b}$ represents $OCF_2H$, $R^{4c}$ represents $CF_2H$, and $R^{3b}$ represents any one substituent described in Table L12 to Table L14 (hereinafter referred to as "Compound group SX1955").

The Compound (L-4), wherein $R^{45}$ represents a methyl group, $R^{4b}$ represents $CF_2H$, $R^{4c}$ represents $OCF_2H$, and $R^{3b}$ represents any one substituent described in Table L12 to Table L14 (hereinafter referred to as "Compound group SX1956").

The Compound (L-4), wherein $R^{45}$ represents a methyl group, $R^{4b}$ represents $CF_2H$, $R^{4c}$ represents $CF_2H$, and $R^{3b}$ represents any one substituent described in Table L12 to Table L14 (hereinafter referred to as "Compound group SX1957").

The Compound (L-4), wherein $R^{45}$ represents a methyl group, $R^{4b}$ represents a bromine atom, $R^{4c}$ represents a hydrogen atom, and $R^{3b}$ represents any one substituent described in Table L12 to Table L14 (hereinafter referred to as "Compound group SX1958").

The Compound (L-4), wherein $R^{45}$ represents a methyl group, $R^{4b}$ represents a bromine atom, $R^{4c}$ represents a fluorine atom, and $R^{3b}$ represents any one substituent described in Table L12 to Table L14 (hereinafter referred to as "Compound group SX1959").

The Compound (L-4), wherein $R^{45}$ represents a methyl group, $R^{4b}$ represents a bromine atom, $R^{4c}$ represents a chlorine atom, and $R^{3b}$ represents any one substituent described in Table L12 to Table L14 (hereinafter referred to as "Compound group SX1960").

The Compound (L-4), wherein $R^{45}$ represents a methyl group, $R^{4b}$ represents a bromine atom, $R^{4c}$ represents a bromine atom, and $R^{3b}$ represents any one substituent described in Table L12 to Table L14 (hereinafter referred to as "Compound group SX1961").

The Compound (L-4), wherein $R^{45}$ represents a methyl group, $R^{4b}$ represents a bromine atom, $R^{4c}$ represents an iodine atom, and $R^{3b}$ represents any one substituent described in Table L12 to Table L14 (hereinafter referred to as "Compound group SX1962").

The Compound (L-4), wherein $R^{45}$ represents a methyl group, $R^{4b}$ represents a bromine atom, $R^{4c}$ represents $CF_3$, and $R^{3b}$ represents any one substituent described in Table L12 to Table L14 (hereinafter referred to as "Compound group SX1963").

The Compound (L-4), wherein $R^{45}$ represents a methyl group, $R^{4b}$ represents a bromine atom, $R^{4c}$ represents $OCF_3$, and $R^{3b}$ represents any one substituent described in Table L12 to Table L14 (hereinafter referred to as "Compound group SX1964").

The Compound (L-4), wherein $R^{45}$ represents an ethyl group, $R^{4b}$ represents a hydrogen atom, $R^{4c}$ represents a hydrogen atom, and $R^{3b}$ represents any one substituent described in Table L12 to Table L14 (hereinafter referred to as "Compound group SX1965").

The Compound (L-4), wherein $R^{45}$ represents an ethyl group, $R^{4b}$ represents a hydrogen atom, $R^{4c}$ represents a fluorine atom, and $R^{3b}$ represents any one substituent described in Table L12 to Table L14 (hereinafter referred to as "Compound group SX1966").

The Compound (L-4), wherein $R^{45}$ represents an ethyl group, $R^{4b}$ represents a hydrogen atom, $R^{4c}$ represents a chlorine atom, and $R^{3b}$ represents any one substituent described in Table L12 to Table L14 (hereinafter referred to as "Compound group SX1967").

The Compound (L-4), wherein $R^{45}$ represents an ethyl group, $R^{4b}$ represents a hydrogen atom, $R^{4c}$ represents a bromine atom, and $R^{3b}$ represents any one substituent described in Table L12 to Table L14 (hereinafter referred to as "Compound group SX1968").

The Compound (L-4), wherein $R^{45}$ represents an ethyl group, $R^{4b}$ represents a hydrogen atom, $R^{4c}$ represents an iodine atom, and $R^{3b}$ represents any one substituent described in Table L12 to Table L14 (hereinafter referred to as "Compound group SX1969").

The Compound (L-4), wherein $R^{45}$ represents an ethyl group, $R^{4b}$ represents a hydrogen atom, $R^{4c}$ represents $CF_3$, and $R^{3b}$ represents any one substituent described in Table L12 to Table L14 (hereinafter referred to as "Compound group SX1970").

The Compound (L-4), wherein $R^{45}$ represents an ethyl group, $R^{4b}$ represents a hydrogen atom, $R^{4c}$ represents $OCF_3$, and $R^{3b}$ represents any one substituent described in Table L12 to Table L14 (hereinafter referred to as "Compound group SX1971").

The Compound (L-4), wherein $R^{45}$ represents an ethyl group, $R^{4b}$ represents a fluorine atom, $R^{4c}$ represents a hydrogen atom, and $R^{3b}$ represents any one substituent described in Table L12 to Table L14 (hereinafter referred to as "Compound group SX1972").

The Compound (L-4), wherein $R^{45}$ represents an ethyl group, $R^{4b}$ represents a fluorine atom, $R^{4c}$ represents a fluorine atom, and $R^{3b}$ represents any one substituent described in Table L12 to Table L14 (hereinafter referred to as "Compound group SX1973").

The Compound (L-4), wherein $R^{45}$ represents an ethyl group, $R^{4b}$ represents a fluorine atom, $R^{4c}$ represents a chlorine atom, and $R^{3b}$ represents any one substituent described in Table L12 to Table L14 (hereinafter referred to as "Compound group SX1974").

The Compound (L-4), wherein $R^{45}$ represents an ethyl group, $R^{4b}$ represents a fluorine atom, $R^{4c}$ represents a bromine atom, and $R^{3b}$ represents any one substituent described in Table L12 to Table L14 (hereinafter referred to as "Compound group SX1975").

The Compound (L-4), wherein $R^{45}$ represents an ethyl group, $R^{4b}$ represents a fluorine atom, $R^{4c}$ represents an iodine atom, and $R^{3b}$ represents any one substituent described in Table L12 to Table L14 (hereinafter referred to as "Compound group SX1976").

The Compound (L-4), wherein $R^{45}$ represents an ethyl group, $R^{4b}$ represents a fluorine atom, $R^{4c}$ represents $CF_3$, and $R^{3b}$ represents any one substituent described in Table L12 to Table L14 (hereinafter referred to as "Compound group SX1977").

The Compound (L-4), wherein $R^{45}$ represents an ethyl group, $R^{4b}$ represents a fluorine atom, $R^{4c}$ represents $OCF_3$, and $R^{3b}$ represents any one substituent described in Table L12 to Table L14 (hereinafter referred to as "Compound group SX1978").

The Compound (L-4), wherein $R^{45}$ represents an ethyl group, $R^{4b}$ represents a chlorine atom, $R^{4c}$ represents a hydrogen atom, and $R^{3b}$ represents any one substituent described in Table L12 to Table L14 (hereinafter referred to as "Compound group SX1979").

The Compound (L-4), wherein $R^{45}$ represents an ethyl group, $R^{4b}$ represents a chlorine atom, $R^{4c}$ represents a fluorine atom, and $R^{3b}$ represents any one substituent described in Table L12 to Table L14 (hereinafter referred to as "Compound group SX1980").

The Compound (L-4), wherein $R^{45}$ represents an ethyl group, $R^{4b}$ represents a chlorine atom, $R^{4c}$ represents a chlorine atom, and $R^{3b}$ represents any one substituent described in Table L12 to Table L14 (hereinafter referred to as "Compound group SX1981").

The Compound (L-4), wherein $R^{45}$ represents an ethyl group, $R^{4b}$ represents a chlorine atom, $R^{4c}$ represents a bromine atom, and $R^{3b}$ represents any one substituent described in Table L12 to Table L14 (hereinafter referred to as "Compound group SX1982").

The Compound (L-4), wherein $R^{45}$ represents an ethyl group, $R^{4b}$ represents a chlorine atom, $R^{4c}$ represents an iodine atom, and $R^{3b}$ represents any one substituent described in Table L12 to Table L14 (hereinafter referred to as "Compound group SX1983").

The Compound (L-4), wherein $R^{45}$ represents an ethyl group, $R^{4b}$ represents a chlorine atom, $R^{4c}$ represents $CF_3$, and $R^{3b}$ represents any one substituent described in Table L12 to Table L14 (hereinafter referred to as "Compound group SX1984").

The Compound (L-4), wherein $R^{45}$ represents an ethyl group, $R^{4b}$ represents a chlorine atom, $R^{4c}$ represents $OCF_3$, and $R^{3b}$ represents any one substituent described in Table L12 to Table L14 (hereinafter referred to as "Compound group SX1985").

The Compound (L-4), wherein $R^{45}$ represents an ethyl group, $R^{4b}$ represents an iodine atom, $R^{4c}$ represents a hydrogen atom, and $R^{3b}$ represents any one substituent described in Table L12 to Table L14 (hereinafter referred to as "Compound group SX1986").

The Compound (L-4), wherein $R^{45}$ represents an ethyl group, $R^{4b}$ represents an iodine atom, $R^{4c}$ represents a fluorine atom, and $R^{3b}$ represents any one substituent described in Table L12 to Table L14 (hereinafter referred to as "Compound group SX1987").

The Compound (L-4), wherein $R^{45}$ represents an ethyl group, $R^{4b}$ represents an iodine atom, $R^{4c}$ represents a chlorine atom, and $R^{3b}$ represents any one substituent described in Table L12 to Table L14 (hereinafter referred to as "Compound group SX1988").

The Compound (L-4), wherein $R^{45}$ represents an ethyl group, $R^{4b}$ represents an iodine atom, $R^{4c}$ represents a bromine atom, and $R^{3b}$ represents any one substituent described in Table L12 to Table L14 (hereinafter referred to as "Compound group SX1989").

The Compound (L-4), wherein $R^{45}$ represents an ethyl group, $R^{4b}$ represents an iodine atom, $R^{4c}$ represents an iodine atom, and $R^{3b}$ represents any one substituent described in Table L12 to Table L14 (hereinafter referred to as "Compound group SX1990").

The Compound (L-4), wherein $R^{45}$ represents an ethyl group, $R^{4b}$ represents an iodine atom, $R^{4c}$ represents $CF_3$, and $R^{3b}$ represents any one substituent described in Table L12 to Table L14 (hereinafter referred to as "Compound group SX1991").

The Compound (L-4), wherein $R^{45}$ represents an ethyl group, $R^{4b}$ represents an iodine atom, $R^{4c}$ represents $OCF_3$, and $R^{3b}$ represents any one substituent described in Table L12 to Table L14 (hereinafter referred to as "Compound group SX1992").

The Compound (L-4), wherein $R^{45}$ represents an ethyl group, $R^{4b}$ represents $CF_3$, $R^{4c}$ represents a hydrogen atom, and $R^{3b}$ represents any one substituent described in Table L12 to Table L14 (hereinafter referred to as "Compound group SX1993").

The Compound (L-4), wherein $R^{45}$ represents an ethyl group, $R^{4b}$ represents $CF_3$, $R^{4c}$ represents a fluorine atom, and $R^{3b}$ represents any one substituent described in Table L12 to Table L14 (hereinafter referred to as "Compound group SX1994").

The Compound (L-4), wherein $R^{45}$ represents an ethyl group, $R^{4b}$ represents $CF_3$, $R^{4c}$ represents a chlorine atom, and $R^{3b}$ represents any one substituent described in Table L12 to Table L14 (hereinafter referred to as "Compound group SX1995").

The Compound (L-4), wherein $R^{45}$ represents an ethyl group, $R^{4b}$ represents $CF_3$, $R^{4c}$ represents a bromine atom, and $R^{3b}$ represents any one substituent described in Table L12 to Table L14 (hereinafter referred to as "Compound group SX1996").

The Compound (L-4), wherein $R^{45}$ represents an ethyl group, $R^{4b}$ represents $CF_3$, $R^{4c}$ represents an iodine atom, and $R^{3b}$ represents any one substituent described in Table L12 to Table L14 (hereinafter referred to as "Compound group SX1997").

The Compound (L-4), wherein $R^{45}$ represents an ethyl group, $R^{4b}$ represents $CF_3$, $R^{4c}$ represents $CF_3$, and $R^{3b}$ represents any one substituent described in Table L12 to Table L14 (hereinafter referred to as "Compound group SX1998").

The Compound (L-4), wherein $R^{45}$ represents an ethyl group, $R^{4b}$ represents $CF_3$, $R^{4c}$ represents $OCF_3$, and $R^{3b}$ represents any one substituent described in Table L12 to Table L14 (hereinafter referred to as "Compound group SX1999").

The Compound (L-4), wherein $R^{45}$ represents an ethyl group, $R^{4b}$ represents $OCF_3$, $R^{4c}$ represents a hydrogen atom, and $R^{3b}$ represents any one substituent described in Table L12 to Table L14 (hereinafter referred to as "Compound group SX2000").

The Compound (L-4), wherein $R^{45}$ represents an ethyl group, $R^{4b}$ represents $OCF_3$, $R^{4c}$ represents a fluorine atom, and $R^{3b}$ represents any one substituent described in Table L12 to Table L14 (hereinafter referred to as "Compound group SX2001").

The Compound (L-4), wherein $R^{45}$ represents an ethyl group, $R^{4b}$ represents $OCF_3$, $R^{4c}$ represents a chlorine atom, and $R^{3b}$ represents any one substituent described in Table L12 to Table L14 (hereinafter referred to as "Compound group SX2002").

The Compound (L-4), wherein $R^{45}$ represents an ethyl group, $R^{4b}$ represents $OCF_3$, $R^{4c}$ represents a bromine atom, and $R^{3b}$ represents any one substituent described in Table L12 to Table L14 (hereinafter referred to as "Compound group SX2003").

The Compound (L-4), wherein $R^{45}$ represents an ethyl group, $R^{4b}$ represents $OCF_3$, $R^{4c}$ represents an iodine atom, and $R^{3b}$ represents any one substituent described in Table L12 to Table L14 (hereinafter referred to as "Compound group SX2004").

The Compound (L-4), wherein $R^{45}$ represents an ethyl group, $R^{4b}$ represents $OCF_3$, $R^{4c}$ represents $CF_3$, and $R^{3b}$ represents any one substituent described in Table L12 to Table L14 (hereinafter referred to as "Compound group SX2005").

The Compound (L-4), wherein $R^{45}$ represents an ethyl group, $R^{4b}$ represents $OCF_3$, $R^{4c}$ represents $OCF_3$, and $R^{3b}$ represents any one substituent described in Table L12 to Table L14 (hereinafter referred to as "Compound group SX2006").

The Compound (L-4), wherein $R^{45}$ represents an ethyl group, $R^{4b}$ represents a hydrogen atom, $R^{4c}$ represents $OCF_2H$, and $R^{3b}$ represents any one substituent described in Table L12 to Table L14 (hereinafter referred to as "Compound group SX2007").

The Compound (L-4), wherein $R^{45}$ represents an ethyl group, $R^{4b}$ represents a hydrogen atom, $R^{4c}$ represents $CF_2H$, and $R^{3b}$ represents any one substituent described in Table L12 to Table L14 (hereinafter referred to as "Compound group SX2008").

The Compound (L-4), wherein $R^{45}$ represents an ethyl group, $R^{4b}$ represents a fluorine atom, $R^{4c}$ represents $OCF_2H$, and $R^{3b}$ represents any one substituent described in Table L12 to Table L14 (hereinafter referred to as "Compound group SX2009").

The Compound (L-4), wherein $R^{45}$ represents an ethyl group, $R^{4b}$ represents a fluorine atom, $R^{4c}$ represents $CF_2H$, and $R^{3b}$ represents any one substituent described in Table L12 to Table L14 (hereinafter referred to as "Compound group SX2010").

The Compound (L-4), wherein $R^{45}$ represents an ethyl group, $R^{4b}$ represents a chlorine atom, $R^{4c}$ represents $OCF_2H$, and $R^{3b}$ represents any one substituent described in Table L12 to Table L14 (hereinafter referred to as "Compound group SX2011").

The Compound (L-4), wherein $R^{45}$ represents an ethyl group, $R^{4b}$ represents a chlorine atom, $R^{4c}$ represents $CF_2H$, and $R^{3b}$ represents any one substituent described in Table L12 to Table L14 (hereinafter referred to as "Compound group SX2012").

The Compound (L-4), wherein $R^{45}$ represents an ethyl group, $R^{4b}$ represents an iodine atom, $R^{4c}$ represents $OCF_2H$, and $R^{3b}$ represents any one substituent described in Table L12 to Table L14 (hereinafter referred to as "Compound group SX2013").

The Compound (L-4), wherein $R^{45}$ represents an ethyl group, $R^{4b}$ represents an iodine atom, $R^{4c}$ represents $CF_2H$, and $R^{3b}$ represents any one substituent described in Table L12 to Table L14 (hereinafter referred to as "Compound group SX2014").

The Compound (L-4), wherein $R^{45}$ represents an ethyl group, $R^{4b}$ represents $CF_3$, $R^{4c}$ represents $OCF_2H$, and $R^{3b}$ represents any one substituent described in Table L12 to Table L14 (hereinafter referred to as "Compound group SX2015").

The Compound (L-4), wherein $R^{45}$ represents an ethyl group, $R^{4b}$ represents $CF_3$, $R^{4c}$ represents $CF_2H$, and $R^{3b}$ represents any one substituent described in Table L12 to Table L14 (hereinafter referred to as "Compound group SX2016").

The Compound (L-4), wherein $R^{45}$ represents an ethyl group, $R^{4b}$ represents $OCF_3$, $R^{4c}$ represents $OCF_2H$, and $R^{3b}$ represents any one substituent described in Table L12 to Table L14 (hereinafter referred to as "Compound group SX2017").

The Compound (L-4), wherein $R^{45}$ represents an ethyl group, $R^{4b}$ represents $OCF_3$, $R^{4c}$ represents $CF_2H$, and $R^{3b}$ represents any one substituent described in Table L12 to Table L14 (hereinafter referred to as "Compound group SX2018").

The Compound (L-4), wherein $R^{45}$ represents an ethyl group, $R^{4b}$ represents a bromine atom, $R^{4c}$ represents $OCF_2H$, and $R^{3b}$ represents any one substituent described in Table L12 to Table L14 (hereinafter referred to as "Compound group SX2019").

The Compound (L-4), wherein $R^{45}$ represents an ethyl group, $R^{4b}$ represents a bromine atom, $R^{4c}$ represents $CF_2H$, and $R^{3b}$ represents any one substituent described in Table L12 to Table L14 (hereinafter referred to as "Compound group SX2020").

The Compound (L-4), wherein $R^{45}$ represents an ethyl group, $R^{4b}$ represents $OCF_2H$, $R^{4c}$ represents $OCF_2H$, and $R^{3b}$ represents any one substituent described in Table L12 to Table L14 (hereinafter referred to as "Compound group SX2021").

The Compound (L-4), wherein $R^{45}$ represents an ethyl group, $R^{4b}$ represents $OCF_2H$, $R^{4c}$ represents $CF_2H$, and $R^{3b}$ represents any one substituent described in Table L12 to Table L14 (hereinafter referred to as "Compound group SX2022").

The Compound (L-4), wherein $R^{45}$ represents an ethyl group, $R^{4b}$ represents $CF_2H$, $R^{4c}$ represents $OCF_2H$, and $R^{3b}$ represents any one substituent described in Table L12 to Table L14 (hereinafter referred to as "Compound group SX2023").

The Compound (L-4), wherein $R^{45}$ represents an ethyl group, $R^{4b}$ represents $CF_2H$, $R^{4c}$ represents $CF_2H$, and $R^{3b}$ represents any one substituent described in Table L12 to Table L14 (hereinafter referred to as "Compound group SX2024").

The Compound (L-4), wherein $R^{45}$ represents an ethyl group, $R^{4b}$ represents a bromine atom, $R^{4c}$ represents a hydrogen atom, and $R^{3b}$ represents any one substituent described in Table L12 to Table L14 (hereinafter referred to as "Compound group SX2025").

The Compound (L-4), wherein $R^{45}$ represents an ethyl group, $R^{4b}$ represents a bromine atom, $R^{4c}$ represents a fluorine atom, and $R^{3b}$ represents any one substituent described in Table L12 to Table L14 (hereinafter referred to as "Compound group SX2026").

The Compound (L-4), wherein $R^{45}$ represents an ethyl group, $R^{4b}$ represents a bromine atom, $R^{4c}$ represents a chlorine atom, and $R^{3b}$ represents any one substituent described in Table L12 to Table L14 (hereinafter referred to as "Compound group SX2027").

The Compound (L-4), wherein $R^{45}$ represents an ethyl group, $R^{4b}$ represents a bromine atom, $R^{4c}$ represents a bromine atom, and $R^{3b}$ represents any one substituent described in Table L12 to Table L14 (hereinafter referred to as "Compound group SX2028").

The Compound (L-4), wherein $R^{45}$ represents an ethyl group, $R^{4b}$ represents a bromine atom, $R^{4c}$ represents an iodine atom, and $R^{3b}$ represents any one substituent described in Table L12 to Table L14 (hereinafter referred to as "Compound group SX2029").

The Compound (L-4), wherein $R^{45}$ represents an ethyl group, $R^{4b}$ represents a bromine atom, $R^{4c}$ represents $CF_3$, and $R^{3b}$ represents any one substituent described in Table L12 to Table L14 (hereinafter referred to as "Compound group SX2030").

The Compound (L-4), wherein $R^{45}$ represents an ethyl group, $R^{4b}$ represents a bromine atom, $R^{4c}$ represents $OCF_3$, and $R^{3b}$ represents any one substituent described in Table L12 to Table L14 (hereinafter referred to as "Compound group SX2031").

The Compound (L-4), wherein $R^{45}$ represents a benzyl group, $R^{4b}$ represents a hydrogen atom, $R^{4c}$ represents a hydrogen atom, and $R^{3b}$ represents any one substituent described in Table L12 to Table L14 (hereinafter referred to as "Compound group SX2032").

The Compound (L-4), wherein $R^{45}$ represents a benzyl group, $R^{4b}$ represents a hydrogen atom, $R^{4c}$ represents a fluorine atom, and $R^{3b}$ represents any one substituent described in Table L12 to Table L14 (hereinafter referred to as “Compound group SX2033”).

The Compound (L-4), wherein $R^{45}$ represents a benzyl group, $R^{4b}$ represents a hydrogen atom, $R^{4c}$ represents a chlorine atom, and $R^{3b}$ represents any one substituent described in Table L12 to Table L14 (hereinafter referred to as “Compound group SX2034”).

The Compound (L-4), wherein $R^{45}$ represents a benzyl group, $R^{4b}$ represents a hydrogen atom, $R^{4c}$ represents a bromine atom, and $R^{3b}$ represents any one substituent described in Table L12 to Table L14 (hereinafter referred to as “Compound group SX2035”).

The Compound (L-4), wherein $R^{45}$ represents a benzyl group, $R^{4b}$ represents a hydrogen atom, $R^{4c}$ represents an iodine atom, and $R^{3b}$ represents any one substituent described in Table L12 to Table L14 (hereinafter referred to as “Compound group SX2036”).

The Compound (L-4), wherein $R^{45}$ represents a benzyl group, $R^{4b}$ represents a hydrogen atom, $R^{4c}$ represents $CF_3$, and $R^{3b}$ represents any one substituent described in Table L12 to Table L14 (hereinafter referred to as “Compound group SX2037”).

The Compound (L-4), wherein $R^{45}$ represents a benzyl group, $R^{4b}$ represents a hydrogen atom, $R^{4c}$ represents $OCF_3$, and $R^{3b}$ represents any one substituent described in Table L12 to Table L14 (hereinafter referred to as “Compound group SX2038”).

The Compound (L-4), wherein $R^{45}$ represents a benzyl group, $R^{4b}$ represents a fluorine atom, $R^{4c}$ represents a hydrogen atom, and $R^{3b}$ represents any one substituent described in Table L12 to Table L14 (hereinafter referred to as “Compound group SX2039”).

The Compound (L-4), wherein $R^{45}$ represents a benzyl group, $R^{4b}$ represents a fluorine atom, $R^{4c}$ represents a fluorine atom, and $R^{3b}$ represents any one substituent described in Table L12 to Table L14 (hereinafter referred to as “Compound group SX2040”).

The Compound (L-4), wherein $R^{45}$ represents a benzyl group, $R^{4b}$ represents a fluorine atom, $R^{4c}$ represents a chlorine atom, and $R^{3b}$ represents any one substituent described in Table L12 to Table L14 (hereinafter referred to as “Compound group SX2041”).

The Compound (L-4), wherein $R^{45}$ represents a benzyl group, $R^{4b}$ represents a fluorine atom, $R^{4c}$ represents a bromine atom, and $R^{3b}$ represents any one substituent described in Table L12 to Table L14 (hereinafter referred to as “Compound group SX2042”).

The Compound (L-4), wherein $R^{45}$ represents a benzyl group, $R^{4b}$ represents a fluorine atom, $R^{4c}$ represents an iodine atom, and $R^{3b}$ represents any one substituent described in Table L12 to Table L14 (hereinafter referred to as “Compound group SX2043”).

The Compound (L-4), wherein $R^{45}$ represents a benzyl group, $R^{4b}$ represents a fluorine atom, $R^{4c}$ represents $CF_3$, and $R^{3b}$ represents any one substituent described in Table L12 to Table L14 (hereinafter referred to as “Compound group SX2044”).

The Compound (L-4), wherein $R^{45}$ represents a benzyl group, $R^{4b}$ represents a fluorine atom, $R^{4c}$ represents $OCF_3$, and $R^{3b}$ represents any one substituent described in Table L12 to Table L14 (hereinafter referred to as “Compound group SX2045”).

The Compound (L-4), wherein $R^{45}$ represents a benzyl group, $R^{4b}$ represents a chlorine atom, $R^{4c}$ represents a hydrogen atom, and $R^{3b}$ represents any one substituent described in Table L12 to Table L14 (hereinafter referred to as “Compound group SX2046”).

The Compound (L-4), wherein $R^{45}$ represents a benzyl group, $R^{4b}$ represents a chlorine atom, $R^{4c}$ represents a fluorine atom, and $R^{3b}$ represents any one substituent described in Table L12 to Table L14 (hereinafter referred to as “Compound group SX2047”).

The Compound (L-4), wherein $R^{45}$ represents a benzyl group, $R^{4b}$ represents a chlorine atom, $R^{4c}$ represents a chlorine atom, and $R^{3b}$ represents any one substituent described in Table L12 to Table L14 (hereinafter referred to as “Compound group SX2048”).

The Compound (L-4), wherein $R^{45}$ represents a benzyl group, $R^{4b}$ represents a chlorine atom, $R^{4c}$ represents a bromine atom, and $R^{3b}$ represents any one substituent described in Table L12 to Table L14 (hereinafter referred to as “Compound group SX2049”).

The Compound (L-4), wherein $R^{45}$ represents a benzyl group, $R^{4b}$ represents a chlorine atom, $R^{4c}$ represents an iodine atom, and $R^{3b}$ represents any one substituent described in Table L12 to Table L14 (hereinafter referred to as “Compound group SX2050”).

The Compound (L-4), wherein $R^{45}$ represents a benzyl group, $R^{4b}$ represents a chlorine atom, $R^{4c}$ represents $CF_3$, and $R^{3b}$ represents any one substituent described in Table L12 to Table L14 (hereinafter referred to as “Compound group SX2051”).

The Compound (L-4), wherein $R^{45}$ represents a benzyl group, $R^{4b}$ represents a chlorine atom, $R^{4c}$ represents $OCF_3$, and $R^{3b}$ represents any one substituent described in Table L12 to Table L14 (hereinafter referred to as “Compound group SX2052”).

The Compound (L-4), wherein $R^{45}$ represents a benzyl group, $R^{4b}$ represents an iodine atom, $R^{4c}$ represents a hydrogen atom, and $R^{3b}$ represents any one substituent described in Table L12 to Table L14 (hereinafter referred to as “Compound group SX2053”).

The Compound (L-4), wherein $R^{45}$ represents a benzyl group, $R^{4b}$ represents an iodine atom, $R^{4c}$ represents a fluorine atom, and $R^{3b}$ represents any one substituent described in Table L12 to Table L14 (hereinafter referred to as “Compound group SX2054”).

The Compound (L-4), wherein $R^{45}$ represents a benzyl group, $R^{4b}$ represents an iodine atom, $R^{4c}$ represents a chlorine atom, and $R^{3b}$ represents any one substituent described in Table L12 to Table L14 (hereinafter referred to as “Compound group SX2055”).

The Compound (L-4), wherein $R^{45}$ represents a benzyl group, $R^{4b}$ represents an iodine atom, $R^{4c}$ represents a bromine atom, and $R^{3b}$ represents any one substituent described in Table L12 to Table L14 (hereinafter referred to as “Compound group SX2056”).

The Compound (L-4), wherein $R^{45}$ represents a benzyl group, $R^{4b}$ represents an iodine atom, $R^{4c}$ represents an iodine atom, and $R^{3b}$ represents any one substituent described in Table L12 to Table L14 (hereinafter referred to as “Compound group SX2057”).

The Compound (L-4), wherein $R^{45}$ represents a benzyl group, $R^{4b}$ represents an iodine atom, $R^{4c}$ represents $CF_3$, and $R^{3b}$ represents any one substituent described in Table L12 to Table L14 (hereinafter referred to as “Compound group SX2058”).

The Compound (L-4), wherein $R^{45}$ represents a benzyl group, $R^{4b}$ represents an iodine atom, $R^{4c}$ represents $OCF_3$, and $R^{3b}$ represents any one substituent described in Table L12 to Table L14 (hereinafter referred to as “Compound group SX2059”).

The Compound (L-4), wherein $R^{45}$ represents a benzyl group, $R^{4b}$ represents $CF_3$, $R^{4c}$ represents a hydrogen atom, and $R^{3b}$ represents any one substituent described in Table L12 to Table L14 (hereinafter referred to as "Compound group SX2060").

The Compound (L-4), wherein $R^{45}$ represents a benzyl group, $R^{4b}$ represents $CF_3$, $R^{4c}$ represents a fluorine atom, and $R^{3b}$ represents any one substituent described in Table L12 to Table L14 (hereinafter referred to as "Compound group SX2061").

The Compound (L-4), wherein $R^{45}$ represents a benzyl group, $R^{4b}$ represents $CF_3$, $R^{4c}$ represents a chlorine atom, and $R^{3b}$ represents any one substituent described in Table L12 to Table L14 (hereinafter referred to as "Compound group SX2062").

The Compound (L-4), wherein $R^{45}$ represents a benzyl group, $R^{4b}$ represents $CF_3$, $R^{4c}$ represents a bromine atom, and $R^{3b}$ represents any one substituent described in Table L12 to Table L14 (hereinafter referred to as "Compound group SX2063").

The Compound (L-4), wherein $R^{45}$ represents a benzyl group, $R^{4b}$ represents $CF_3$, $R^{4c}$ represents an iodine atom, and $R^{3b}$ represents any one substituent described in Table L12 to Table L14 (hereinafter referred to as "Compound group SX2064").

The Compound (L-4), wherein $R^{45}$ represents a benzyl group, $R^{4b}$ represents $CF_3$, $R^{4c}$ represents $CF_3$, and $R^{3b}$ represents any one substituent described in Table L12 to Table L14 (hereinafter referred to as "Compound group SX2065").

The Compound (L-4), wherein $R^{45}$ represents a benzyl group, $R^{4b}$ represents $CF_3$, $R^{4c}$ represents $OCF_3$, and $R^{3b}$ represents any one substituent described in Table L12 to Table L14 (hereinafter referred to as "Compound group SX2066").

The Compound (L-4), wherein $R^{45}$ represents a benzyl group, $R^{4b}$ represents $OCF_3$, $R^{4c}$ represents a hydrogen atom, and $R^{3b}$ represents any one substituent described in Table L12 to Table L14 (hereinafter referred to as "Compound group SX2067").

The Compound (L-4), wherein $R^{45}$ represents a benzyl group, $R^{4b}$ represents $OCF_3$, $R^{4c}$ represents a fluorine atom, and $R^{3b}$ represents any one substituent described in Table L12 to Table L14 (hereinafter referred to as "Compound group SX2068").

The Compound (L-4), wherein $R^{45}$ represents a benzyl group, $R^{4b}$ represents $OCF_3$, $R^{4c}$ represents a chlorine atom, and $R^{3b}$ represents any one substituent described in Table L12 to Table L14 (hereinafter referred to as "Compound group SX2069").

The Compound (L-4), wherein $R^{45}$ represents a benzyl group, $R^{4b}$ represents $OCF_3$, $R^{4c}$ represents a bromine atom, and $R^{3b}$ represents any one substituent described in Table L12 to Table L14 (hereinafter referred to as "Compound group SX2070").

The Compound (L-4), wherein $R^{45}$ represents a benzyl group, $R^{4b}$ represents $OCF_3$, $R^{4c}$ represents an iodine atom, and $R^{3b}$ represents any one substituent described in Table L12 to Table L14 (hereinafter referred to as "Compound group SX2071").

The Compound (L-4), wherein $R^{45}$ represents a benzyl group, $R^{4b}$ represents $OCF_3$, $R^{4c}$ represents $CF_3$, and $R^{3b}$ represents any one substituent described in Table L12 to Table L14 (hereinafter referred to as "Compound group SX2072").

The Compound (L-4), wherein $R^{45}$ represents a benzyl group, $R^{4b}$ represents $OCF_3$, $R^{4c}$ represents $OCF_3$, and $R^{3b}$ represents any one substituent described in Table L12 to Table L14 (hereinafter referred to as "Compound group SX2073").

The Compound (L-4), wherein $R^{45}$ represents a benzyl group, $R^{4b}$ represents a hydrogen atom, $R^{4c}$ represents $OCF_2H$, and $R^{3b}$ represents any one substituent described in Table L12 to Table L14 (hereinafter referred to as "Compound group SX2074").

The Compound (L-4), wherein $R^{45}$ represents a benzyl group, $R^{4b}$ represents a hydrogen atom, $R^{4c}$ represents $CF_2H$, and $R^{3b}$ represents any one substituent described in Table L12 to Table L14 (hereinafter referred to as "Compound group SX2075").

The Compound (L-4), wherein $R^{45}$ represents a benzyl group, $R^{4b}$ represents a fluorine atom, $R^{4c}$ represents $OCF_2H$, and $R^{3b}$ represents any one substituent described in Table L12 to Table L14 (hereinafter referred to as "Compound group SX2076").

The Compound (L-4), wherein $R^{45}$ represents a benzyl group, $R^{4b}$ represents a fluorine atom, $R^{4c}$ represents $CF_2H$, and $R^{3b}$ represents any one substituent described in Table L12 to Table L14 (hereinafter referred to as "Compound group SX2077").

The Compound (L-4), wherein $R^{45}$ represents a benzyl group, $R^{4b}$ represents a chlorine atom, $R^{4c}$ represents $OCF_2H$, and $R^{3b}$ represents any one substituent described in Table L12 to Table L14 (hereinafter referred to as "Compound group SX2078").

The Compound (L-4), wherein $R^{45}$ represents a benzyl group, $R^{4b}$ represents a chlorine atom, $R^{4c}$ represents $CF_2H$, and $R^{3b}$ represents any one substituent described in Table L12 to Table L14 (hereinafter referred to as "Compound group SX2079").

The Compound (L-4), wherein $R^{45}$ represents a benzyl group, $R^{4b}$ represents an iodine atom, $R^{4c}$ represents $OCF_2H$, and $R^{3b}$ represents any one substituent described in Table L12 to Table L14 (hereinafter referred to as "Compound group SX2080").

The Compound (L-4), wherein $R^{45}$ represents a benzyl group, $R^{4b}$ represents an iodine atom, $R^{4c}$ represents $CF_2H$, and $R^{3b}$ represents any one substituent described in Table L12 to Table L14 (hereinafter referred to as "Compound group SX2081").

The Compound (L-4), wherein $R^{45}$ represents a benzyl group, $R^{4b}$ represents $CF_3$, $R^{4c}$ represents $OCF_2H$, and $R^{3b}$ represents any one substituent described in Table L12 to Table L14 (hereinafter referred to as "Compound group SX2082").

The Compound (L-4), wherein $R^{45}$ represents a benzyl group, $R^{4b}$ represents $CF_3$, $R^{4c}$ represents $CF_2H$, and $R^{3b}$ represents any one substituent described in Table L12 to Table L14 (hereinafter referred to as "Compound group SX2083").

The Compound (L-4), wherein $R^{45}$ represents a benzyl group, $R^{4b}$ represents $OCF_3$, $R^{4c}$ represents $OCF_2H$, and $R^{3b}$ represents any one substituent described in Table L12 to Table L14 (hereinafter referred to as "Compound group SX2084").

The Compound (L-4), wherein $R^{45}$ represents a benzyl group, $R^{4b}$ represents $OCF_3$, $R^{4c}$ represents $CF_2H$, and $R^{3b}$ represents any one substituent described in Table L12 to Table L14 (hereinafter referred to as "Compound group SX2085").

The Compound (L-4), wherein $R^{45}$ represents a benzyl group, $R^{4b}$ represents a bromine atom, $R^{4c}$ represents $OCF_2H$, and $R^{3b}$ represents any one substituent described in Table L12 to Table L14 (hereinafter referred to as "Compound group SX2086").

The Compound (L-4), wherein $R^{45}$ represents a benzyl group, $R^{4b}$ represents a bromine atom, $R^{4c}$ represents $CF_2H$, and $R^{3b}$ represents any one substituent described in Table L12 to Table L14 (hereinafter referred to as "Compound group SX2087").

The Compound (L-4), wherein $R^{45}$ represents a benzyl group, $R^{4b}$ represents $OCF_2H$, $R^{4c}$ represents $OCF_2H$, and $R^{3b}$ represents any one substituent described in Table L12 to Table L14 (hereinafter referred to as "Compound group SX2088").

The Compound (L-4), wherein $R^{45}$ represents a benzyl group, $R^{4b}$ represents $OCF_2H$, $R^{4c}$ represents $CF_2H$, and $R^{3b}$ represents any one substituent described in Table L12 to Table L14 (hereinafter referred to as "Compound group SX2089").

The Compound (L-4), wherein $R^{45}$ represents a benzyl group, $R^{4b}$ represents $CF_2H$, $R^{4c}$ represents $OCF_2H$, and $R^{3b}$ represents any one substituent described in Table L12 to Table L14 (hereinafter referred to as "Compound group SX2090").

The Compound (L-4), wherein $R^{45}$ represents a benzyl group, $R^{4b}$ represents $CF_2H$, $R^{4c}$ represents $CF_2H$, and $R^{3b}$ represents any one substituent described in Table L12 to Table L14 (hereinafter referred to as "Compound group SX2091").

The Compound (L-4), wherein $R^{45}$ represents a benzyl group, $R^{4b}$ represents a bromine atom, $R^{4c}$ represents a hydrogen atom, and $R^{3b}$ represents any one substituent described in Table L12 to Table L14 (hereinafter referred to as "Compound group SX2092").

The Compound (L-4), wherein $R^{45}$ represents a benzyl group, $R^{4b}$ represents a bromine atom, $R^{4c}$ represents a fluorine atom, and $R^{3b}$ represents any one substituent described in Table L12 to Table L14 (hereinafter referred to as "Compound group SX2093").

The Compound (L-4), wherein $R^{45}$ represents a benzyl group, $R^{4b}$ represents a bromine atom, $R^{4c}$ represents a chlorine atom, and $R^{3b}$ represents any one substituent described in Table L12 to Table L14 (hereinafter referred to as "Compound group SX2094").

The Compound (L-4), wherein $R^{45}$ represents a benzyl group, $R^{4b}$ represents a bromine atom, $R^{4c}$ represents a bromine atom, and $R^{3b}$ represents any one substituent described in Table L12 to Table L14 (hereinafter referred to as "Compound group SX2095").

The Compound (L-4), wherein $R^{45}$ represents a benzyl group, $R^{4b}$ represents a bromine atom, $R^{4c}$ represents an iodine atom, and $R^{3b}$ represents any one substituent described in Table L12 to Table L14 (hereinafter referred to as "Compound group SX2096").

The Compound (L-4), wherein $R^{45}$ represents a benzyl group, $R^{4b}$ represents a bromine atom, $R^{4c}$ represents $CF_3$, and $R^{3b}$ represents any one substituent described in Table L12 to Table L14 (hereinafter referred to as "Compound group SX2097").

The Compound (L-4), wherein $R^{45}$ represents a benzyl group, $R^{4b}$ represents a bromine atom, $R^{4c}$ represents $OCF_3$, and $R^{3b}$ represents any one substituent described in Table L12 to Table L14 (hereinafter referred to as "Compound group SX2098").

The Compound (L-4), wherein $R^{45}$ represents a 3-pyridylmethyl group, $R^{4b}$ represents a hydrogen atom, $R^{4c}$ represents a hydrogen atom, and $R^{3b}$ represents any one substituent described in Table L12 to Table L14 (hereinafter referred to as "Compound group SX2099").

The Compound (L-4), wherein $R^{45}$ represents a 3-pyridylmethyl group, $R^{4b}$ represents a hydrogen atom, $R^{4c}$ represents a fluorine atom, and $R^{3b}$ represents any one substituent described in Table L12 to Table L14 (hereinafter referred to as "Compound group SX2100").

The Compound (L-4), wherein $R^{45}$ represents a 3-pyridylmethyl group, $R^{4b}$ represents a hydrogen atom, $R^{4c}$ represents a chlorine atom, and $R^{3b}$ represents any one substituent described in Table L12 to Table L14 (hereinafter referred to as "Compound group SX2101").

The Compound (L-4), wherein $R^{45}$ represents a 3-pyridylmethyl group, $R^{4b}$ represents a hydrogen atom, $R^{4c}$ represents a bromine atom, and $R^{3b}$ represents any one substituent described in Table L12 to Table L14 (hereinafter referred to as "Compound group SX2102").

The Compound (L-4), wherein $R^{45}$ represents a 3-pyridylmethyl group, $R^{4b}$ represents a hydrogen atom, $R^{4c}$ represents an iodine atom, and $R^{3b}$ represents any one substituent described in Table L12 to Table L14 (hereinafter referred to as "Compound group SX2103").

The Compound (L-4), wherein $R^{45}$ represents a 3-pyridylmethyl group, $R^{4b}$ represents a hydrogen atom, $R^{4c}$ represents $CF_3$, and $R^{3b}$ represents any one substituent described in Table L12 to Table L14 (hereinafter referred to as "Compound group SX2104").

The Compound (L-4), wherein $R^{45}$ represents a 3-pyridylmethyl group, $R^{4b}$ represents a hydrogen atom, $R^{4c}$ represents $OCF_3$, and $R^{3b}$ represents any one substituent described in Table L12 to Table L14 (hereinafter referred to as "Compound group SX2105").

The Compound (L-4), wherein $R^{45}$ represents a 3-pyridylmethyl group, $R^{4b}$ represents a fluorine atom, $R^{4c}$ represents a hydrogen atom, and $R^{3b}$ represents any one substituent described in Table L12 to Table L14 (hereinafter referred to as "Compound group SX2106").

The Compound (L-4), wherein $R^{45}$ represents a 3-pyridylmethyl group, $R^{4b}$ represents a fluorine atom, $R^{4c}$ represents a fluorine atom, and $R^{3b}$ represents any one substituent described in Table L12 to Table L14 (hereinafter referred to as "Compound group SX2107").

The Compound (L-4), wherein $R^{45}$ represents a 3-pyridylmethyl group, $R^{4b}$ represents a fluorine atom, $R^{4c}$ represents a chlorine atom, and $R^{3b}$ represents any one substituent described in Table L12 to Table L14 (hereinafter referred to as "Compound group SX2108").

The Compound (L-4), wherein $R^{45}$ represents a 3-pyridylmethyl group, $R^{4b}$ represents a fluorine atom, $R^{4c}$ represents a bromine atom, and $R^{3b}$ represents any one substituent described in Table L12 to Table L14 (hereinafter referred to as "Compound group SX2109").

The Compound (L-4), wherein $R^{45}$ represents a 3-pyridylmethyl group, $R^{4b}$ represents a fluorine atom, $R^{4c}$ represents an iodine atom, and $R^{3b}$ represents any one substituent described in Table L12 to Table L14 (hereinafter referred to as "Compound group SX2110").

The Compound (L-4), wherein $R^{45}$ represents a 3-pyridylmethyl group, $R^{4b}$ represents a fluorine atom, $R^{4c}$ represents $CF_3$, and $R^{3b}$ represents any one substituent described in Table L12 to Table L14 (hereinafter referred to as "Compound group SX2111").

The Compound (L-4), wherein $R^{45}$ represents a 3-pyridylmethyl group, $R^{4b}$ represents a fluorine atom, $R^{4c}$ represents $OCF_3$, and $R^{3b}$ represents any one substituent described in Table L12 to Table L14 (hereinafter referred to as "Compound group SX2112").

The Compound (L-4), wherein $R^{45}$ represents a 3-pyridylmethyl group, $R^{4b}$ represents a chlorine atom, $R^{4c}$ represents a hydrogen atom, and $R^{3b}$ represents any one substituent described in Table L12 to Table L14 (hereinafter referred to as "Compound group SX2113").

The Compound (L-4), wherein $R^{45}$ represents a 3-pyridylmethyl group, $R^{4b}$ represents a chlorine atom, $R^{4c}$ represents a fluorine atom, and $R^{3b}$ represents any one substituent described in Table L12 to Table L14 (hereinafter referred to as "Compound group SX2114").

The Compound (L-4), wherein $R^{45}$ represents a 3-pyridylmethyl group, $R^{4b}$ represents a chlorine atom, $R^{4c}$ represents a chlorine atom, and $R^{3b}$ represents any one substituent described in Table L12 to Table L14 (hereinafter referred to as "Compound group SX2115").

The Compound (L-4), wherein $R^{45}$ represents a 3-pyridylmethyl group, $R^{4b}$ represents a chlorine atom, $R^{4c}$ represents a bromine atom, and $R^{3b}$ represents any one substituent described in Table L12 to Table L14 (hereinafter referred to as "Compound group SX2116").

The Compound (L-4), wherein $R^{45}$ represents a 3-pyridylmethyl group, $R^{4b}$ represents a chlorine atom, $R^{4c}$ represents an iodine atom, and $R^{3b}$ represents any one substituent described in Table L12 to Table L14 (hereinafter referred to as "Compound group SX2117").

The Compound (L-4), wherein $R^{45}$ represents a 3-pyridylmethyl group, $R^{4b}$ represents a chlorine atom, $R^{4c}$ represents $CF_3$, and $R^{3b}$ represents any one substituent described in Table L12 to Table L14 (hereinafter referred to as "Compound group SX2118").

The Compound (L-4), wherein $R^{45}$ represents a 3-pyridylmethyl group, $R^{4b}$ represents a chlorine atom, $R^{4c}$ represents $OCF_3$, and $R^{3b}$ represents any one substituent described in Table L12 to Table L14 (hereinafter referred to as "Compound group SX2119").

The Compound (L-4), wherein $R^{45}$ represents a 3-pyridylmethyl group, $R^{4b}$ represents an iodine atom, $R^{4c}$ represents a hydrogen atom, and $R^{3b}$ represents any one substituent described in Table L12 to Table L14 (hereinafter referred to as "Compound group SX2120").

The Compound (L-4), wherein $R^{45}$ represents a 3-pyridylmethyl group, $R^{4b}$ represents an iodine atom, $R^{4c}$ represents a fluorine atom, and $R^{3b}$ represents any one substituent described in Table L12 to Table L14 (hereinafter referred to as "Compound group SX2121").

The Compound (L-4), wherein $R^{45}$ represents a 3-pyridylmethyl group, $R^{4b}$ represents an iodine atom, $R^{4c}$ represents a chlorine atom, and $R^{3b}$ represents any one substituent described in Table L12 to Table L14 (hereinafter referred to as "Compound group SX2122").

The Compound (L-4), wherein $R^{45}$ represents a 3-pyridylmethyl group, $R^{4b}$ represents an iodine atom, $R^{4c}$ represents a bromine atom, and $R^{3b}$ represents any one substituent described in Table L12 to Table L14 (hereinafter referred to as "Compound group SX2123").

The Compound (L-4), wherein $R^{45}$ represents a 3-pyridylmethyl group, $R^{4b}$ represents an iodine atom, $R^{4c}$ represents an iodine atom, and $R^{3b}$ represents any one substituent described in Table L12 to Table L14 (hereinafter referred to as "Compound group SX2124").

The Compound (L-4), wherein $R^{45}$ represents a 3-pyridylmethyl group, $R^{4b}$ represents an iodine atom, $R^{4c}$ represents $CF_3$, and $R^{3b}$ represents any one substituent described in Table L12 to Table L14 (hereinafter referred to as "Compound group SX2125").

The Compound (L-4), wherein $R^{45}$ represents a 3-pyridylmethyl group, $R^{4b}$ represents an iodine atom, $R^{4c}$ represents $OCF_3$, and $R^{3b}$ represents any one substituent described in Table L12 to Table L14 (hereinafter referred to as "Compound group SX2126").

The Compound (L-4), wherein $R^{45}$ represents a 3-pyridylmethyl group, $R^{4b}$ represents $CF_3$, $R^{4c}$ represents a hydrogen atom, and $R^{3b}$ represents any one substituent described in Table L12 to Table L14 (hereinafter referred to as "Compound group SX2127").

The Compound (L-4), wherein $R^{45}$ represents a 3-pyridylmethyl group, $R^{4b}$ represents $CF_3$, $R^{4c}$ represents a fluorine atom, and $R^{3b}$ represents any one substituent described in Table L12 to Table L14 (hereinafter referred to as "Compound group SX2128").

The Compound (L-4), wherein $R^{45}$ represents a 3-pyridylmethyl group, $R^{4b}$ represents $CF_3$, $R^{4c}$ represents a chlorine atom, and $R^{3b}$ represents any one substituent described in Table L12 to Table L14 (hereinafter referred to as "Compound group SX2129").

The Compound (L-4), wherein $R^{45}$ represents a 3-pyridylmethyl group, $R^{4b}$ represents $CF_3$, $R^{4c}$ represents a bromine atom, and $R^{3b}$ represents any one substituent described in Table L12 to Table L14 (hereinafter referred to as "Compound group SX2130").

The Compound (L-4), wherein $R^{45}$ represents a 3-pyridylmethyl group, $R^{4b}$ represents $CF_3$, $R^{4c}$ represents an iodine atom, and $R^{3b}$ represents any one substituent described in Table L12 to Table L14 (hereinafter referred to as "Compound group SX2131").

The Compound (L-4), wherein $R^{45}$ represents a 3-pyridylmethyl group, $R^{4b}$ represents $CF_3$, $R^{4c}$ represents $CF_3$, and $R^{3b}$ represents any one substituent described in Table L12 to Table L14 (hereinafter referred to as "Compound group SX2132").

The Compound (L-4), wherein $R^{45}$ represents a 3-pyridylmethyl group, $R^{4b}$ represents $CF_3$, $R^{4c}$ represents $OCF_3$, and $R^{3b}$ represents any one substituent described in Table L12 to Table L14 (hereinafter referred to as "Compound group SX2133").

The Compound (L-4), wherein $R^{45}$ represents a 3-pyridylmethyl group, $R^{4b}$ represents $OCF_3$, $R^{4c}$ represents a hydrogen atom, and $R^{3b}$ represents any one substituent described in Table L12 to Table L14 (hereinafter referred to as "Compound group SX2134").

The Compound (L-4), wherein $R^{45}$ represents a 3-pyridylmethyl group, $R^{4b}$ represents $OCF_3$, $R^{4c}$ represents a fluorine atom, and $R^{3b}$ represents any one substituent described in Table L12 to Table L14 (hereinafter referred to as "Compound group SX2135").

The Compound (L-4), wherein $R^{45}$ represents a 3-pyridylmethyl group, $R^{4b}$ represents $OCF_3$, $R^{4c}$ represents a chlorine atom, and $R^{3b}$ represents any one substituent described in Table L12 to Table L14 (hereinafter referred to as "Compound group SX2136").

The Compound (L-4), wherein $R^{45}$ represents a 3-pyridylmethyl group, $R^{4b}$ represents $OCF_3$, $R^{4c}$ represents a bromine atom, and $R^{3b}$ represents any one substituent described in Table L12 to Table L14 (hereinafter referred to as "Compound group SX2137").

The Compound (L-4), wherein $R^{45}$ represents a 3-pyridylmethyl group, $R^{4b}$ represents $OCF_3$, $R^{4c}$ represents an iodine atom, and $R^{3b}$ represents any one substituent described in Table L12 to Table L14 (hereinafter referred to as "Compound group SX2138").

The Compound (L-4), wherein $R^{45}$ represents a 3-pyridylmethyl group, $R^{4b}$ represents $OCF_3$, $R^{4c}$ represents $CF_3$, and $R^{3b}$ represents any one substituent described in Table L12 to Table L14 (hereinafter referred to as "Compound group SX2139").

The Compound (L-4), wherein $R^{45}$ represents a 3-pyridylmethyl group, $R^{4b}$ represents $OCF_3$, $R^{4c}$ represents $OCF_3$, and $R^{3b}$ represents any one substituent described in Table L12 to Table L14 (hereinafter referred to as "Compound group SX2140").

The Compound (L-4), wherein $R^{45}$ represents a 3-pyridylmethyl group, $R^{4b}$ represents a hydrogen atom, $R^{4c}$ represents $OCF_2H$, and $R^{3b}$ represents any one substituent described in Table L12 to Table L14 (hereinafter referred to as "Compound group SX2141").

The Compound (L-4), wherein $R^{45}$ represents a 3-pyridylmethyl group, $R^{4b}$ represents a hydrogen atom, $R^{4c}$ represents $CF_2H$, and $R^{3b}$ represents any one substituent described in Table L12 to Table L14 (hereinafter referred to as "Compound group SX2142").

The Compound (L-4), wherein $R^{45}$ represents a 3-pyridylmethyl group, $R^{4b}$ represents a fluorine atom, $R^{4c}$ represents $OCF_2H$, and $R^{3b}$ represents any one substituent described in Table L12 to Table L14 (hereinafter referred to as "Compound group SX2143").

The Compound (L-4), wherein $R^{45}$ represents a 3-pyridylmethyl group, $R^{4b}$ represents a fluorine atom, $R^{4c}$ represents $CF_2H$, and $R^{3b}$ represents any one substituent described in Table L12 to Table L14 (hereinafter referred to as "Compound group SX2144").

The Compound (L-4), wherein $R^{45}$ represents a 3-pyridylmethyl group, $R^{4b}$ represents a chlorine atom, $R^{4c}$ represents $OCF_2H$, and $R^{3b}$ represents any one substituent described in Table L12 to Table L14 (hereinafter referred to as "Compound group SX2145").

The Compound (L-4), wherein $R^{45}$ represents a 3-pyridylmethyl group, $R^{4b}$ represents a chlorine atom, $R^{4c}$ represents $CF_2H$, and $R^{3b}$ represents any one substituent described in Table L12 to Table L14 (hereinafter referred to as "Compound group SX2146").

The Compound (L-4), wherein $R^{45}$ represents a 3-pyridylmethyl group, $R^{4b}$ represents an iodine atom, $R^{4c}$ represents $OCF_2H$, and $R^{3b}$ represents any one substituent described in Table L12 to Table L14 (hereinafter referred to as "Compound group SX2147").

The Compound (L-4), wherein $R^{45}$ represents a 3-pyridylmethyl group, $R^{4b}$ represents an iodine atom, $R^{4c}$ represents $CF_2H$, and $R^{3b}$ represents any one substituent described in Table L12 to Table L14 (hereinafter referred to as "Compound group SX2148").

The Compound (L-4), wherein $R^{45}$ represents a 3-pyridylmethyl group, $R^{4b}$ represents $CF_3$, $R^{4c}$ represents $OCF_2H$, and $R^{3b}$ represents any one substituent described in Table L12 to Table L14 (hereinafter referred to as "Compound group SX2149").

The Compound (L-4), wherein $R^{45}$ represents a 3-pyridylmethyl group, $R^{4b}$ represents $CF_3$, $R^{4c}$ represents $CF_2H$, and $R^{3b}$ represents any one substituent described in Table L12 to Table L14 (hereinafter referred to as "Compound group SX2150").

The Compound (L-4), wherein $R^{45}$ represents a 3-pyridylmethyl group, $R^{4b}$ represents $OCF_3$, $R^{4c}$ represents $OCF_2H$, and $R^{3b}$ represents any one substituent described in Table L12 to Table L14 (hereinafter referred to as "Compound group SX2151").

The Compound (L-4), wherein $R^{45}$ represents a 3-pyridylmethyl group, $R^{4b}$ represents $OCF_3$, $R^{4c}$ represents $CF_2H$, and $R^{3b}$ represents any one substituent described in Table L12 to Table L14 (hereinafter referred to as "Compound group SX2152").

The Compound (L-4), wherein $R^{45}$ represents a 3-pyridylmethyl group, $R^{4b}$ represents a bromine atom, $R^{4c}$ represents $OCF_2H$, and $R^{3b}$ represents any one substituent described in Table L12 to Table L14 (hereinafter referred to as "Compound group SX2153").

The Compound (L-4), wherein $R^{45}$ represents a 3-pyridylmethyl group, $R^{4b}$ represents a bromine atom, $R^{4c}$ represents $CF_2H$, and $R^{3b}$ represents any one substituent described in Table L12 to Table L14 (hereinafter referred to as "Compound group SX2154").

The Compound (L-4), wherein $R^{45}$ represents a 3-pyridylmethyl group, $R^{4b}$ represents $OCF_2H$, $R^{4c}$ represents $OCF_2H$, and $R^{3b}$ represents any one substituent described in Table L12 to Table L14 (hereinafter referred to as "Compound group SX2155").

The Compound (L-4), wherein $R^{45}$ represents a 3-pyridylmethyl group, $R^{4b}$ represents $OCF_2H$, $R^{4c}$ represents $CF_2H$, and $R^{3b}$ represents any one substituent described in Table L12 to Table L14 (hereinafter referred to as "Compound group SX2156").

The Compound (L-4), wherein $R^{45}$ represents a 3-pyridylmethyl group, $R^{4b}$ represents $CF_2H$, $R^{4c}$ represents $OCF_2H$, and $R^{3b}$ represents any one substituent described in Table L12 to Table L14 (hereinafter referred to as "Compound group SX2157").

The Compound (L-4), wherein $R^{45}$ represents a 3-pyridylmethyl group, $R^{4b}$ represents $CF_2H$, $R^{4c}$ represents $CF_2H$, and $R^{3b}$ represents any one substituent described in Table L12 to Table L14 (hereinafter referred to as "Compound group SX2158").

The Compound (L-4), wherein $R^{45}$ represents a 3-pyridylmethyl group, $R^{4b}$ represents a bromine atom, $R^{4c}$ represents a hydrogen atom, and $R^{3b}$ represents any one substituent described in Table L12 to Table L14 (hereinafter referred to as "Compound group SX2159").

The Compound (L-4), wherein $R^{45}$ represents a 3-pyridylmethyl group, $R^{4b}$ represents a bromine atom, $R^{4c}$ represents a fluorine atom, and $R^{3b}$ represents any one substituent described in Table L12 to Table L14 (hereinafter referred to as "Compound group SX2160").

The Compound (L-4), wherein $R^{45}$ represents a 3-pyridylmethyl group, $R^{4b}$ represents a bromine atom, $R^{4c}$ represents a chlorine atom, and $R^{3b}$ represents any one substituent described in Table L12 to Table L14 (hereinafter referred to as "Compound group SX2161").

The Compound (L-4), wherein $R^{45}$ represents a 3-pyridylmethyl group, $R^{4b}$ represents a bromine atom, $R^{4c}$ represents a bromine atom, and $R^{3b}$ represents any one substituent described in Table L12 to Table L14 (hereinafter referred to as "Compound group SX2162").

The Compound (L-4), wherein $R^{45}$ represents a 3-pyridylmethyl group, $R^{4b}$ represents a bromine atom, $R^{4c}$ represents an iodine atom, and $R^{3b}$ represents any one substituent described in Table L12 to Table L14 (hereinafter referred to as "Compound group SX2163").

The Compound (L-4), wherein $R^{45}$ represents a 3-pyridylmethyl group, $R^{4b}$ represents a bromine atom, $R^{4c}$ represents $CF_3$, and $R^{3b}$ represents any one substituent described in Table L12 to Table L14 (hereinafter referred to as "Compound group SX2164").

The Compound (L-4), wherein $R^{45}$ represents a 3-pyridylmethyl group, $R^{4b}$ represents a bromine atom, $R^{4c}$ represents $OCF_3$, and $R^{3b}$ represents any one substituent described in Table L12 to Table L14 (hereinafter referred to as "Compound group SX2165").

The Compound (L-4), wherein $R^{45}$ represents an ethoxymethyl group, $R^{4b}$ represents a hydrogen atom, $R^{4c}$ represents a hydrogen atom, and $R^{3b}$ represents any one substituent described in Table L12 to Table L14 (hereinafter referred to as "Compound group SX2166").

The Compound (L-4), wherein $R^{45}$ represents an ethoxymethyl group, $R^{4b}$ represents a hydrogen atom, $R^{4c}$ represents a fluorine atom, and $R^{3b}$ represents any one substituent described in Table L12 to Table L14 (hereinafter referred to as "Compound group SX2167").

The Compound (L-4), wherein $R^{45}$ represents an ethoxymethyl group, $R^{4b}$ represents a hydrogen atom, $R^{4c}$ represents a chlorine atom, and $R^{3b}$ represents any one substituent described in Table L12 to Table L14 (hereinafter referred to as "Compound group SX2168").

The Compound (L-4), wherein $R^{45}$ represents an ethoxymethyl group, $R^{4b}$ represents a hydrogen atom, $R^{4c}$ represents a bromine atom, and $R^{3b}$ represents any one substituent described in Table L12 to Table L14 (hereinafter referred to as "Compound group SX2169").

The Compound (L-4), wherein $R^{45}$ represents an ethoxymethyl group, $R^{4b}$ represents a hydrogen atom, $R^{4c}$ represents an iodine atom, and $R^{3b}$ represents any one substituent described in Table L12 to Table L14 (hereinafter referred to as "Compound group SX2170").

The Compound (L-4), wherein $R^{45}$ represents an ethoxymethyl group, $R^{4b}$ represents a hydrogen atom, $R^{4c}$ represents $CF_3$, and $R^{3b}$ represents any one substituent described in Table L12 to Table L14 (hereinafter referred to as "Compound group SX2171").

The Compound (L-4), wherein $R^{45}$ represents an ethoxymethyl group, $R^{4b}$ represents a hydrogen atom, $R^{4c}$ represents $OCF_3$, and $R^{3b}$ represents any one substituent described in Table L12 to Table L14 (hereinafter referred to as "Compound group SX2172").

The Compound (L-4), wherein $R^{45}$ represents an ethoxymethyl group, $R^{4b}$ represents a fluorine atom, $R^{4c}$ represents a hydrogen atom, and $R^{3b}$ represents any one substituent described in Table L12 to Table L14 (hereinafter referred to as "Compound group SX2173").

The Compound (L-4), wherein $R^{45}$ represents an ethoxymethyl group, $R^{4b}$ represents a fluorine atom, $R^{4c}$ represents a fluorine atom, and $R^{3b}$ represents any one substituent described in Table L12 to Table L14 (hereinafter referred to as "Compound group SX2174").

The Compound (L-4), wherein $R^{45}$ represents an ethoxymethyl group, $R^{4b}$ represents a fluorine atom, $R^{4c}$ represents a chlorine atom, and $R^{3b}$ represents any one substituent described in Table L12 to Table L14 (hereinafter referred to as "Compound group SX2175").

The Compound (L-4), wherein $R^{45}$ represents an ethoxymethyl group, $R^{4b}$ represents a fluorine atom, $R^{4c}$ represents a bromine atom, and $R^{3b}$ represents any one substituent described in Table L12 to Table L14 (hereinafter referred to as "Compound group SX2176").

The Compound (L-4), wherein $R^{45}$ represents an ethoxymethyl group, $R^{4b}$ represents a fluorine atom, $R^{4c}$ represents an iodine atom, and $R^{3b}$ represents any one substituent described in Table L12 to Table L14 (hereinafter referred to as "Compound group SX2177").

The Compound (L-4), wherein $R^{45}$ represents an ethoxymethyl group, $R^{4b}$ represents a fluorine atom, $R^{4c}$ represents $CF_3$, and $R^{3b}$ represents any one substituent described in Table L12 to Table L14 (hereinafter referred to as "Compound group SX2178").

The Compound (L-4), wherein $R^{45}$ represents an ethoxymethyl group, $R^{4b}$ represents a fluorine atom, $R^{4c}$ represents $OCF_3$, and $R^{3b}$ represents any one substituent described in Table L12 to Table L14 (hereinafter referred to as "Compound group SX2179").

The Compound (L-4), wherein $R^{45}$ represents an ethoxymethyl group, $R^{4b}$ represents a chlorine atom, $R^{4c}$ represents a hydrogen atom, and $R^{3b}$ represents any one substituent described in Table L12 to Table L14 (hereinafter referred to as "Compound group SX2180").

The Compound (L-4), wherein $R^{45}$ represents an ethoxymethyl group, $R^{4b}$ represents a chlorine atom, $R^{4c}$ represents a fluorine atom, and $R^{3b}$ represents any one substituent described in Table L12 to Table L14 (hereinafter referred to as "Compound group SX2181").

The Compound (L-4), wherein $R^{45}$ represents an ethoxymethyl group, $R^{4b}$ represents a chlorine atom, $R^{4c}$ represents a chlorine atom, and $R^{3b}$ represents any one substituent described in Table L12 to Table L14 (hereinafter referred to as "Compound group SX2182").

The Compound (L-4), wherein $R^{45}$ represents an ethoxymethyl group, $R^{4b}$ represents a chlorine atom, $R^{4c}$ represents a bromine atom, and $R^{3b}$ represents any one substituent described in Table L12 to Table L14 (hereinafter referred to as "Compound group SX2183").

The Compound (L-4), wherein $R^{45}$ represents an ethoxymethyl group, $R^{4b}$ represents a chlorine atom, $R^{4c}$ represents an iodine atom, and $R^{3b}$ represents any one substituent described in Table L12 to Table L14 (hereinafter referred to as "Compound group SX2184").

The Compound (L-4), wherein $R^{45}$ represents an ethoxymethyl group, $R^{4b}$ represents a chlorine atom, $R^{4c}$ represents $CF_3$, and $R^{3b}$ represents any one substituent described in Table L12 to Table L14 (hereinafter referred to as "Compound group SX2185").

The Compound (L-4), wherein $R^{45}$ represents an ethoxymethyl group, $R^{4b}$ represents a chlorine atom, $R^{4c}$ represents $OCF_3$, and $R^{3b}$ represents any one substituent described in Table L12 to Table L14 (hereinafter referred to as "Compound group SX2186").

The Compound (L-4), wherein $R^{45}$ represents an ethoxymethyl group, $R^{4b}$ represents an iodine atom, $R^{4c}$ represents a hydrogen atom, and $R^{3b}$ represents any one substituent described in Table L12 to Table L14 (hereinafter referred to as "Compound group SX2187").

The Compound (L-4), wherein $R^{45}$ represents an ethoxymethyl group, $R^{4b}$ represents an iodine atom, $R^{4c}$ represents a fluorine atom, and $R^{3b}$ represents any one substituent described in Table L12 to Table L14 (hereinafter referred to as "Compound group SX2188").

The Compound (L-4), wherein $R^{45}$ represents an ethoxymethyl group, $R^{4b}$ represents an iodine atom, $R^{4c}$ represents a chlorine atom, and $R^{3b}$ represents any one substituent described in Table L12 to Table L14 (hereinafter referred to as "Compound group SX2189").

The Compound (L-4), wherein $R^{45}$ represents an ethoxymethyl group, $R^{4b}$ represents an iodine atom, $R^{4c}$ represents a bromine atom, and $R^{3b}$ represents any one substituent described in Table L12 to Table L14 (hereinafter referred to as "Compound group SX2190").

The Compound (L-4), wherein $R^{45}$ represents an ethoxymethyl group, $R^{4b}$ represents an iodine atom, $R^{4c}$ represents an iodine atom, and $R^{3b}$ represents any one substituent described in Table L12 to Table L14 (hereinafter referred to as "Compound group SX2191").

The Compound (L-4), wherein $R^{45}$ represents an ethoxymethyl group, $R^{4b}$ represents an iodine atom, $R^{4c}$ represents $CF_3$, and $R^{3b}$ represents any one substituent described in Table L12 to Table L14 (hereinafter referred to as "Compound group SX2192").

The Compound (L-4), wherein $R^{45}$ represents an ethoxymethyl group, $R^{4b}$ represents an iodine atom, $R^{4c}$ represents $OCF_3$, and $R^{3b}$ represents any one substituent described in Table L12 to Table L14 (hereinafter referred to as "Compound group SX2193").

The Compound (L-4), wherein $R^{45}$ represents an ethoxymethyl group, $R^{4b}$ represents $CF_3$, $R^{4c}$ represents a hydrogen atom, and $R^{3b}$ represents any one substituent described in Table L12 to Table L14 (hereinafter referred to as "Compound group SX2194").

The Compound (L-4), wherein $R^{45}$ represents an ethoxymethyl group, $R^{4b}$ represents $CF_3$, $R^{4c}$ represents a fluorine atom, and $R^{3b}$ represents any one substituent described in Table L12 to Table L14 (hereinafter referred to as "Compound group SX2195").

The Compound (L-4), wherein $R^{45}$ represents an ethoxymethyl group, $R^{4b}$ represents $CF_3$, $R^{4c}$ represents a chlorine atom, and $R^{3b}$ represents any one substituent described in Table L12 to Table L14 (hereinafter referred to as "Compound group SX2196").

The Compound (L-4), wherein $R^{45}$ represents an ethoxymethyl group, $R^{4b}$ represents $CF_3$, $R^{4c}$ represents a bromine atom, and $R^{3b}$ represents any one substituent described in Table L12 to Table L14 (hereinafter referred to as "Compound group SX2197").

The Compound (L-4), wherein $R^{45}$ represents an ethoxymethyl group, $R^{4b}$ represents $CF_3$, $R^{4c}$ represents an iodine atom, and $R^{3b}$ represents any one substituent described in Table L12 to Table L14 (hereinafter referred to as "Compound group SX2198").

The Compound (L-4), wherein $R^{45}$ represents an ethoxymethyl group, $R^{4b}$ represents $CF_3$, $R^{4c}$ represents $CF_3$, and $R^{3b}$ represents any one substituent described in Table L12 to Table L14 (hereinafter referred to as "Compound group SX2199").

The Compound (L-4), wherein $R^{45}$ represents an ethoxymethyl group, $R^{4b}$ represents $CF_3$, $R^{4c}$ represents $OCF_3$, and $R^{3b}$ represents any one substituent described in Table L12 to Table L14 (hereinafter referred to as "Compound group SX2200").

The Compound (L-4), wherein $R^{45}$ represents an ethoxymethyl group, $R^{4b}$ represents $OCF_3$, $R^{4c}$ represents a hydrogen atom, and $R^{3b}$ represents any one substituent described in Table L12 to Table L14 (hereinafter referred to as "Compound group SX2201").

The Compound (L-4), wherein $R^{45}$ represents an ethoxymethyl group, $R^{4b}$ represents $OCF_3$, $R^{4c}$ represents a fluorine atom, and $R^{3b}$ represents any one substituent described in Table L12 to Table L14 (hereinafter referred to as "Compound group SX2202").

The Compound (L-4), wherein $R^{45}$ represents an ethoxymethyl group, $R^{4b}$ represents $OCF_3$, $R^{4c}$ represents a chlorine atom, and $R^{3b}$ represents any one substituent described in Table L12 to Table L14 (hereinafter referred to as "Compound group SX2203").

The Compound (L-4), wherein $R^{45}$ represents an ethoxymethyl group, $R^{4b}$ represents $OCF_3$, $R^{4c}$ represents a bromine atom, and $R^{3b}$ represents any one substituent described in Table L12 to Table L14 (hereinafter referred to as "Compound group SX2204").

The Compound (L-4), wherein $R^{45}$ represents an ethoxymethyl group, $R^{4b}$ represents $OCF_3$, $R^{4c}$ represents an iodine atom, and $R^{3b}$ represents any one substituent described in Table L12 to Table L14 (hereinafter referred to as "Compound group SX2205").

The Compound (L-4), wherein $R^{45}$ represents an ethoxymethyl group, $R^{4b}$ represents $OCF_3$, $R^{4c}$ represents $CF_3$, and $R^{3b}$ represents any one substituent described in Table L12 to Table L14 (hereinafter referred to as "Compound group SX2206").

The Compound (L-4), wherein $R^{45}$ represents an ethoxymethyl group, $R^{4b}$ represents $OCF_3$, $R^{4c}$ represents $OCF_3$, and $R^{3b}$ represents any one substituent described in Table L12 to Table L14 (hereinafter referred to as "Compound group SX2207").

The Compound (L-4), wherein $R^{45}$ represents an ethoxymethyl group, $R^{4b}$ represents a hydrogen atom, $R^{4c}$ represents $OCF_2H$, and $R^{3b}$ represents any one substituent described in Table L12 to Table L14 (hereinafter referred to as "Compound group SX2208").

The Compound (L-4), wherein $R^{45}$ represents an ethoxymethyl group, $R^{4b}$ represents a hydrogen atom, $R^{4c}$ represents $CF_2H$, and $R^{3b}$ represents any one substituent described in Table L12 to Table L14 (hereinafter referred to as "Compound group SX2209").

The Compound (L-4), wherein $R^{45}$ represents an ethoxymethyl group, $R^{4b}$ represents a fluorine atom, $R^{4c}$ represents $OCF_2H$, and $R^{3b}$ represents any one substituent described in Table L12 to Table L14 (hereinafter referred to as "Compound group SX2210").

The Compound (L-4), wherein $R^{45}$ represents an ethoxymethyl group, $R^{4b}$ represents a fluorine atom, $R^{4c}$ represents $CF_2H$, and $R^{3b}$ represents any one substituent described in Table L12 to Table L14 (hereinafter referred to as "Compound group SX2211").

The Compound (L-4), wherein $R^{45}$ represents an ethoxymethyl group, $R^{4b}$ represents a chlorine atom, $R^{4c}$ represents $OCF_2H$, and $R^{3b}$ represents any one substituent described in Table L12 to Table L14 (hereinafter referred to as "Compound group SX2212").

The Compound (L-4), wherein $R^{45}$ represents an ethoxymethyl group, $R^{4b}$ represents a chlorine atom, $R^{4c}$ represents $CF_2H$, and $R^{3b}$ represents any one substituent described in Table L12 to Table L14 (hereinafter referred to as "Compound group SX2213").

The Compound (L-4), wherein $R^{45}$ represents an ethoxymethyl group, $R^{4b}$ represents an iodine atom, $R^{4c}$ represents $OCF_2H$, and $R^{3b}$ represents any one substituent described in Table L12 to Table L14 (hereinafter referred to as "Compound group SX2214").

The Compound (L-4), wherein $R^{45}$ represents an ethoxymethyl group, $R^{4b}$ represents an iodine atom, $R^{4c}$ represents $CF_2H$, and $R^{3b}$ represents any one substituent described in Table L12 to Table L14 (hereinafter referred to as "Compound group SX2215").

The Compound (L-4), wherein $R^{45}$ represents an ethoxymethyl group, $R^{4b}$ represents $CF_3$, $R^{4c}$ represents $OCF_2H$, and $R^{3b}$ represents any one substituent described in Table L12 to Table L14 (hereinafter referred to as "Compound group SX2216").

The Compound (L-4), wherein $R^{45}$ represents an ethoxymethyl group, $R^{4b}$ represents $CF_3$, $R^{4c}$ represents $CF_2H$, and $R^{3b}$ represents any one substituent described in Table L12 to Table L14 (hereinafter referred to as "Compound group SX2217").

The Compound (L-4), wherein $R^{45}$ represents an ethoxymethyl group, $R^{4b}$ represents $OCF_3$, $R^{4c}$ represents $OCF_2H$, and $R^{3b}$ represents any one substituent described in Table L12 to Table L14 (hereinafter referred to as "Compound group SX2218").

The Compound (L-4), wherein $R^{45}$ represents an ethoxymethyl group, $R^{4b}$ represents $OCF_3$, $R^{4c}$ represents $CF_2H$, and $R^{3b}$ represents any one substituent described in Table L12 to Table L14 (hereinafter referred to as "Compound group SX2219").

The Compound (L-4), wherein $R^{45}$ represents an ethoxymethyl group, $R^{4b}$ represents a bromine atom, $R^{4c}$ represents $OCF_2H$, and $R^{3b}$ represents any one substituent described in Table L12 to Table L14 (hereinafter referred to as "Compound group SX2220").

The Compound (L-4), wherein $R^{45}$ represents an ethoxymethyl group, $R^{4b}$ represents a bromine atom, $R^{4c}$ represents $CF_2H$, and $R^{3b}$ represents any one substituent described in Table L12 to Table L14 (hereinafter referred to as "Compound group SX2221").

The Compound (L-4), wherein $R^{45}$ represents an ethoxymethyl group, $R^{4b}$ represents $OCF_2H$, $R^{4c}$ represents $OCF_2H$, and $R^{3b}$ represents any one substituent described in Table L12 to Table L14 (hereinafter referred to as "Compound group SX2222").

The Compound (L-4), wherein $R^{45}$ represents an ethoxymethyl group, $R^{4b}$ represents $OCF_2H$, $R^{4c}$ represents $CF_2H$, and $R^{3b}$ represents any one substituent described in Table L12 to Table L14 (hereinafter referred to as "Compound group SX2223").

The Compound (L-4), wherein $R^{45}$ represents an ethoxymethyl group, $R^{4b}$ represents $CF_2H$, $R^{4c}$ represents $OCF_2H$, and $R^{3b}$ represents any one substituent described in Table L12 to Table L14 (hereinafter referred to as "Compound group SX2224").

The Compound (L-4), wherein $R^{45}$ represents an ethoxymethyl group, $R^{4b}$ represents $CF_2H$, $R^{4c}$ represents $CF_2H$, and $R^{3b}$ represents any one substituent described in Table L12 to Table L14 (hereinafter referred to as "Compound group SX2225").

The Compound (L-4), wherein $R^{45}$ represents an ethoxymethyl group, $R^{4b}$ represents a bromine atom, $R^{4c}$ represents a hydrogen atom, and $R^{3b}$ represents any one substituent described in Table L12 to Table L14 (hereinafter referred to as "Compound group SX2226").

The Compound (L-4), wherein $R^{45}$ represents an ethoxymethyl group, $R^{4b}$ represents a bromine atom, $R^{4c}$ represents a fluorine atom, and $R^{3b}$ represents any one substituent described in Table L12 to Table L14 (hereinafter referred to as "Compound group SX2227").

The Compound (L-4), wherein $R^{45}$ represents an ethoxymethyl group, $R^{4b}$ represents a bromine atom, $R^{4c}$ represents a chlorine atom, and $R^{3b}$ represents any one substituent described in Table L12 to Table L14 (hereinafter referred to as "Compound group SX2228").

The Compound (L-4), wherein $R^{45}$ represents an ethoxymethyl group, $R^{4b}$ represents a bromine atom, $R^{4c}$ represents a bromine atom, and $R^{3b}$ represents any one substituent described in Table L12 to Table L14 (hereinafter referred to as "Compound group SX2229").

The Compound (L-4), wherein $R^{45}$ represents an ethoxymethyl group, $R^{4b}$ represents a bromine atom, $R^{4c}$ represents an iodine atom, and $R^{3b}$ represents any one substituent described in Table L12 to Table L14 (hereinafter referred to as "Compound group SX2230").

The Compound (L-4), wherein $R^{45}$ represents an ethoxymethyl group, $R^{4b}$ represents a bromine atom, $R^{4c}$ represents $CF_3$, and $R^{3b}$ represents any one substituent described in Table L12 to Table L14 (hereinafter referred to as "Compound group SX2231").

The Compound (L-4), wherein $R^{45}$ represents an ethoxymethyl group, $R^{4b}$ represents a bromine atom, $R^{4c}$ represents $OCF_3$, and $R^{3b}$ represents any one substituent described in Table L12 to Table L14 (hereinafter referred to as "Compound group SX2232").

The Compound (L-4), wherein $R^{45}$ represents a cyanomethyl group, $R^{4b}$ represents a hydrogen atom, $R^{4c}$ represents a hydrogen atom, and $R^{3b}$ represents any one substituent described in Table L12 to Table L14 (hereinafter referred to as "Compound group SX2233").

The Compound (L-4), wherein $R^{45}$ represents a cyanomethyl group, $R^{4b}$ represents a hydrogen atom, $R^{4c}$ represents a fluorine atom, and $R^{3b}$ represents any one substituent described in Table L12 to Table L14 (hereinafter referred to as "Compound group SX2234").

The Compound (L-4), wherein $R^{45}$ represents a cyanomethyl group, $R^{4b}$ represents a hydrogen atom, $R^{4c}$ represents a chlorine atom, and $R^{3b}$ represents any one substituent described in Table L12 to Table L14 (hereinafter referred to as "Compound group SX2235").

The Compound (L-4), wherein $R^{45}$ represents a cyanomethyl group, $R^{4b}$ represents a hydrogen atom, $R^{4c}$ represents a bromine atom, and $R^{3b}$ represents any one substituent described in Table L12 to Table L14 (hereinafter referred to as "Compound group SX2236").

The Compound (L-4), wherein $R^{45}$ represents a cyanomethyl group, $R^{4b}$ represents a hydrogen atom, $R^{4c}$ represents an iodine atom, and $R^{3b}$ represents any one substituent described in Table L12 to Table L14 (hereinafter referred to as "Compound group SX2237").

The Compound (L-4), wherein $R^{45}$ represents a cyanomethyl group, $R^{4b}$ represents a hydrogen atom, $R^{4c}$ represents $CF_3$, and $R^{3b}$ represents any one substituent described in Table L12 to Table L14 (hereinafter referred to as "Compound group SX2238").

The Compound (L-4), wherein $R^{45}$ represents a cyanomethyl group, $R^{4b}$ represents a hydrogen atom, $R^{4c}$ represents $OCF_3$, and $R^{3b}$ represents any one substituent described in Table L12 to Table L14 (hereinafter referred to as "Compound group SX2239").

The Compound (L-4), wherein $R^{45}$ represents a cyanomethyl group, $R^{4b}$ represents a fluorine atom, $R^{4c}$ represents a hydrogen atom, and $R^{3b}$ represents any one substituent described in Table L12 to Table L14 (hereinafter referred to as "Compound group SX2240").

The Compound (L-4), wherein $R^{45}$ represents a cyanomethyl group, $R^{4b}$ represents a fluorine atom, $R^{4c}$ represents a fluorine atom, and $R^{3b}$ represents any one substituent described in Table L12 to Table L14 (hereinafter referred to as "Compound group SX2241").

The Compound (L-4), wherein $R^{45}$ represents a cyanomethyl group, $R^{4b}$ represents a fluorine atom, $R^{4c}$ represents a chlorine atom, and $R^{3b}$ represents any one substituent described in Table L12 to Table L14 (hereinafter referred to as "Compound group SX2242").

The Compound (L-4), wherein $R^{45}$ represents a cyanomethyl group, $R^{4b}$ represents a fluorine atom, $R^{4c}$ represents a bromine atom, and $R^{3b}$ represents any one substituent described in Table L12 to Table L14 (hereinafter referred to as "Compound group SX2243").

The Compound (L-4), wherein $R^{45}$ represents a cyanomethyl group, $R^{4b}$ represents a fluorine atom, $R^{4c}$ represents an iodine atom, and $R^{3b}$ represents any one substituent described in Table L12 to Table L14 (hereinafter referred to as "Compound group SX2244").

The Compound (L-4), wherein $R^{45}$ represents a cyanomethyl group, $R^{4b}$ represents a fluorine atom, $R^{4c}$ represents $CF_3$, and $R^{3b}$ represents any one substituent described in Table L12 to Table L14 (hereinafter referred to as "Compound group SX2245").

The Compound (L-4), wherein $R^{45}$ represents a cyanomethyl group, $R^{4b}$ represents a fluorine atom, $R^{4c}$ represents $OCF_3$, and $R^{3b}$ represents any one substituent described in Table L12 to Table L14 (hereinafter referred to as "Compound group SX2246").

The Compound (L-4), wherein $R^{45}$ represents a cyanomethyl group, $R^{4b}$ represents a chlorine atom, $R^{4c}$ represents a hydrogen atom, and $R^{3b}$ represents any one substituent described in Table L12 to Table L14 (hereinafter referred to as "Compound group SX2247").

The Compound (L-4), wherein $R^{45}$ represents a cyanomethyl group, $R^{4b}$ represents a chlorine atom, $R^{4c}$ represents a fluorine atom, and $R^{3b}$ represents any one substituent described in Table L12 to Table L14 (hereinafter referred to as "Compound group SX2248").

The Compound (L-4), wherein $R^{45}$ represents a cyanomethyl group, $R^{4b}$ represents a chlorine atom, $R^{4c}$ represents a chlorine atom, and $R^{3b}$ represents any one substituent described in Table L12 to Table L14 (hereinafter referred to as "Compound group SX2249").

The Compound (L-4), wherein $R^{45}$ represents a cyanomethyl group, $R^{4b}$ represents a chlorine atom, $R^{4c}$ represents a bromine atom, and $R^{3b}$ represents any one substituent described in Table L12 to Table L14 (hereinafter referred to as "Compound group SX2250").

The Compound (L-4), wherein $R^{45}$ represents a cyanomethyl group, $R^{4b}$ represents a chlorine atom, $R^{4c}$ represents an iodine atom, and $R^{3b}$ represents any one substituent described in Table L12 to Table L14 (hereinafter referred to as "Compound group SX2251").

The Compound (L-4), wherein $R^{45}$ represents a cyanomethyl group, $R^{4b}$ represents a chlorine atom, $R^{4c}$ represents $CF_3$, and $R^{3b}$ represents any one substituent described in Table L12 to Table L14 (hereinafter referred to as "Compound group SX2252").

The Compound (L-4), wherein $R^{45}$ represents a cyanomethyl group, $R^{4b}$ represents a chlorine atom, $R^{4c}$ represents $OCF_3$, and $R^{3b}$ represents any one substituent described in Table L12 to Table L14 (hereinafter referred to as "Compound group SX2253").

The Compound (L-4), wherein $R^{45}$ represents a cyanomethyl group, $R^{4b}$ represents an iodine atom, $R^{4c}$ represents a hydrogen atom, and $R^{3b}$ represents any one substituent described in Table L12 to Table L14 (hereinafter referred to as "Compound group SX2254").

The Compound (L-4), wherein $R^{45}$ represents a cyanomethyl group, $R^{4b}$ represents an iodine atom, $R^{4c}$ represents a fluorine atom, and $R^{3b}$ represents any one substituent described in Table L12 to Table L14 (hereinafter referred to as "Compound group SX2255").

The Compound (L-4), wherein $R^{45}$ represents a cyanomethyl group, $R^{4b}$ represents an iodine atom, $R^{4c}$ represents a chlorine atom, and $R^{3b}$ represents any one substituent described in Table L12 to Table L14 (hereinafter referred to as "Compound group SX2256").

The Compound (L-4), wherein $R^{45}$ represents a cyanomethyl group, $R^{4b}$ represents an iodine atom, $R^{4c}$ represents a bromine atom, and $R^{3b}$ represents any one substituent described in Table L12 to Table L14 (hereinafter referred to as "Compound group SX2257").

The Compound (L-4), wherein $R^{45}$ represents a cyanomethyl group, $R^{4b}$ represents an iodine atom, $R^{4c}$ represents an iodine atom, and $R^{3b}$ represents any one substituent described in Table L12 to Table L14 (hereinafter referred to as "Compound group SX2258").

The Compound (L-4), wherein $R^{45}$ represents a cyanomethyl group, $R^{4b}$ represents an iodine atom, $R^{4c}$ represents $CF_3$, and $R^{3b}$ represents any one substituent described in Table L12 to Table L14 (hereinafter referred to as "Compound group SX2259").

The Compound (L-4), wherein $R^{45}$ represents a cyanomethyl group, $R^{4b}$ represents an iodine atom, $R^{4c}$ represents $OCF_3$, and $R^{3b}$ represents any one substituent described in Table L12 to Table L14 (hereinafter referred to as "Compound group SX2260").

The Compound (L-4), wherein $R^{45}$ represents a cyanomethyl group, $R^{4b}$ represents $CF_3$, $R^{4c}$ represents a hydrogen atom, and $R^{3b}$ represents any one substituent described in Table L12 to Table L14 (hereinafter referred to as "Compound group SX2261").

The Compound (L-4), wherein $R^{45}$ represents a cyanomethyl group, $R^{4b}$ represents $CF_3$, $R^{4c}$ represents a fluorine atom, and $R^{3b}$ represents any one substituent described in Table L12 to Table L14 (hereinafter referred to as "Compound group SX2262").

The Compound (L-4), wherein $R^{45}$ represents a cyanomethyl group, $R^{4b}$ represents $CF_3$, $R^{4c}$ represents a chlorine atom, and $R^{3b}$ represents any one substituent described in Table L12 to Table L14 (hereinafter referred to as "Compound group SX2263").

The Compound (L-4), wherein $R^{45}$ represents a cyanomethyl group, $R^{4b}$ represents $CF_3$, $R^{4c}$ represents a bromine atom, and $R^{3b}$ represents any one substituent described in Table L12 to Table L14 (hereinafter referred to as "Compound group SX2264").

The Compound (L-4), wherein $R^{45}$ represents a cyanomethyl group, $R^{4b}$ represents $CF_3$, $R^{4c}$ represents an iodine atom, and $R^{3b}$ represents any one substituent described in Table L12 to Table L14 (hereinafter referred to as "Compound group SX2265").

The Compound (L-4), wherein $R^{45}$ represents a cyanomethyl group, $R^{4b}$ represents $CF_3$, $R^{4c}$ represents $CF_3$, and $R^{3b}$ represents any one substituent described in Table L12 to Table L14 (hereinafter referred to as "Compound group SX2266").

The Compound (L-4), wherein $R^{45}$ represents a cyanomethyl group, $R^{4b}$ represents $CF_3$, $R^{4c}$ represents $OCF_3$, and $R^{3b}$ represents any one substituent described in Table L12 to Table L14 (hereinafter referred to as "Compound group SX2267").

The Compound (L-4), wherein $R^{45}$ represents a cyanomethyl group, $R^{4b}$ represents $OCF_3$, $R^{4c}$ represents a hydrogen atom, and $R^{3b}$ represents any one substituent described in Table L12 to Table L14 (hereinafter referred to as "Compound group SX2268").

The Compound (L-4), wherein $R^{45}$ represents a cyanomethyl group, $R^{4b}$ represents $OCF_3$, $R^{4c}$ represents a fluorine atom, and $R^{3b}$ represents any one substituent described in Table L12 to Table L14 (hereinafter referred to as "Compound group SX2269").

The Compound (L-4), wherein $R^{45}$ represents a cyanomethyl group, $R^{4b}$ represents $OCF_3$, $R^{4c}$ represents a chlorine atom, and $R^{3b}$ represents any one substituent described in Table L12 to Table L14 (hereinafter referred to as "Compound group SX2270").

The Compound (L-4), wherein $R^{45}$ represents a cyanomethyl group, $R^{4b}$ represents $OCF_3$, $R^{4c}$ represents a bromine atom, and $R^{3b}$ represents any one substituent described in Table L12 to Table L14 (hereinafter referred to as "Compound group SX2271").

The Compound (L-4), wherein $R^{45}$ represents a cyanomethyl group, $R^{4b}$ represents $OCF_3$, $R^{4c}$ represents an iodine atom, and $R^{3b}$ represents any one substituent described in Table L12 to Table L14 (hereinafter referred to as "Compound group SX2272").

The Compound (L-4), wherein $R^{45}$ represents a cyanomethyl group, $R^{4b}$ represents $OCF_3$, $R^{4c}$ represents $CF_3$, and $R^{3b}$ represents any one substituent described in Table L12 to Table L14 (hereinafter referred to as "Compound group SX2273").

The Compound (L-4), wherein $R^{45}$ represents a cyanomethyl group, $R^{4b}$ represents $OCF_3$, $R^{4c}$ represents $OCF_3$, and $R^{3b}$ represents any one substituent described in Table L12 to Table L14 (hereinafter referred to as "Compound group SX2274").

The Compound (L-4), wherein $R^{45}$ represents a cyanomethyl group, $R^{4b}$ represents a hydrogen atom, $R^{4c}$ represents $OCF_2H$, and $R^{3b}$ represents any one substituent described in Table L12 to Table L14 (hereinafter referred to as "Compound group SX2275").

The Compound (L-4), wherein $R^{45}$ represents a cyanomethyl group, $R^{4b}$ represents a hydrogen atom, $R^{4c}$ represents $CF_2H$, and $R^{3b}$ represents any one substituent described in Table L12 to Table L14 (hereinafter referred to as "Compound group SX2276").

The Compound (L-4), wherein $R^{45}$ represents a cyanomethyl group, $R^{4b}$ represents a fluorine atom, $R^{4c}$ represents $OCF_2H$, and $R^{3b}$ represents any one substituent described in Table L12 to Table L14 (hereinafter referred to as "Compound group SX2277").

The Compound (L-4), wherein $R^{45}$ represents a cyanomethyl group, $R^{4b}$ represents a fluorine atom, $R^{4c}$ represents $CF_2H$, and $R^{3b}$ represents any one substituent described in Table L12 to Table L14 (hereinafter referred to as "Compound group SX2278").

The Compound (L-4), wherein $R^{45}$ represents a cyanomethyl group, $R^{4b}$ represents a chlorine atom, $R^{4c}$ represents $OCF_2H$, and $R^{3b}$ represents any one substituent described in Table L12 to Table L14 (hereinafter referred to as "Compound group SX2279").

The Compound (L-4), wherein $R^{45}$ represents a cyanomethyl group, $R^{4b}$ represents a chlorine atom, $R^{4c}$ represents $CF_2H$, and $R^{3b}$ represents any one substituent described in Table L12 to Table L14 (hereinafter referred to as "Compound group SX2280").

The Compound (L-4), wherein $R^{45}$ represents a cyanomethyl group, $R^{4b}$ represents an iodine atom, $R^{4c}$ represents $OCF_2H$, and $R^{3b}$ represents any one substituent described in Table L12 to Table L14 (hereinafter referred to as "Compound group SX2281").

The Compound (L-4), wherein $R^{45}$ represents a cyanomethyl group, $R^{4b}$ represents an iodine atom, $R^{4c}$ represents $CF_2H$, and $R^{3b}$ represents any one substituent described in Table L12 to Table L14 (hereinafter referred to as "Compound group SX2282").

The Compound (L-4), wherein $R^{45}$ represents a cyanomethyl group, $R^{4b}$ represents $CF_3$, $R^{4c}$ represents $OCF_2H$, and $R^{3b}$ represents any one substituent described in Table L12 to Table L14 (hereinafter referred to as "Compound group SX2283").

The Compound (L-4), wherein $R^{45}$ represents a cyanomethyl group, $R^{4b}$ represents $CF_3$, $R^{4c}$ represents $CF_2H$, and $R^{3b}$ represents any one substituent described in Table L12 to Table L14 (hereinafter referred to as "Compound group SX2284").

The Compound (L-4), wherein $R^{45}$ represents a cyanomethyl group, $R^{4b}$ represents $OCF_3$, $R^{4c}$ represents $OCF_2H$, and $R^{3b}$ represents any one substituent described in Table L12 to Table L14 (hereinafter referred to as "Compound group SX2285").

The Compound (L-4), wherein $R^{45}$ represents a cyanomethyl group, $R^{4b}$ represents $OCF_3$, $R^{4c}$ represents $CF_2H$, and $R^{3b}$ represents any one substituent described in Table L12 to Table L14 (hereinafter referred to as "Compound group SX2286").

The Compound (L-4), wherein $R^{45}$ represents a cyanomethyl group, $R^{4b}$ represents a bromine atom, $R^{4c}$ represents $OCF_2H$, and $R^{3b}$ represents any one substituent described in Table L12 to Table L14 (hereinafter referred to as "Compound group SX2287").

The Compound (L-4), wherein $R^{45}$ represents a cyanomethyl group, $R^{4b}$ represents a bromine atom, $R^{4c}$ represents $CF_2H$, and $R^{3b}$ represents any one substituent described in Table L12 to Table L14 (hereinafter referred to as "Compound group SX2288").

The Compound (L-4), wherein $R^{45}$ represents a cyanomethyl group, $R^{4b}$ represents $OCF_2H$, $R^{4c}$ represents $OCF_2H$, and $R^{3b}$ represents any one substituent described in Table L12 to Table L14 (hereinafter referred to as "Compound group SX2289").

The Compound (L-4), wherein $R^{45}$ represents a cyanomethyl group, $R^{4b}$ represents $OCF_2H$, $R^{4c}$ represents $CF_2H$, and $R^{3b}$ represents any one substituent described in Table L12 to Table L14 (hereinafter referred to as "Compound group SX2290").

The Compound (L-4), wherein $R^{45}$ represents a cyanomethyl group, $R^{4b}$ represents $CF_2H$, $R^{4c}$ represents $OCF_2H$, and $R^{3b}$ represents any one substituent described in Table L12 to Table L14 (hereinafter referred to as "Compound group SX2291").

The Compound (L-4), wherein $R^{45}$ represents a cyanomethyl group, $R^{4b}$ represents $CF_2H$, $R^{4c}$ represents $CF_2H$, and $R^{3b}$ represents any one substituent described in Table L12 to Table L14 (hereinafter referred to as "Compound group SX2292").

The Compound (L-4), wherein $R^{45}$ represents a cyanomethyl group, $R^{4b}$ represents a bromine atom, $R^{4c}$ represents a hydrogen atom, and $R^{3b}$ represents any one substituent described in Table L12 to Table L14 (hereinafter referred to as "Compound group SX2293").

The Compound (L-4), wherein $R^{45}$ represents a cyanomethyl group, $R^{4b}$ represents a bromine atom, $R^{4c}$ represents a fluorine atom, and $R^{3b}$ represents any one substituent described in Table L12 to Table L14 (hereinafter referred to as "Compound group SX2294").

The Compound (L-4), wherein $R^{45}$ represents a cyanomethyl group, $R^{4b}$ represents a bromine atom, $R^{4c}$ represents a chlorine atom, and $R^{3b}$ represents any one substituent described in Table L12 to Table L14 (hereinafter referred to as "Compound group SX2295").

The Compound (L-4), wherein $R^{45}$ represents a cyanomethyl group, $R^{4b}$ represents a bromine atom, $R^{4c}$ represents a bromine atom, and $R^{3b}$ represents any one substituent described in Table L12 to Table L14 (hereinafter referred to as "Compound group SX2296").

The Compound (L-4), wherein $R^{45}$ represents a cyanomethyl group, $R^{4b}$ represents a bromine atom, $R^{4c}$ represents an iodine atom, and $R^{3b}$ represents any one substituent described in Table L12 to Table L14 (hereinafter referred to as "Compound group SX2297").

The Compound (L-4), wherein $R^{45}$ represents a cyanomethyl group, $R^{4b}$ represents a bromine atom, $R^{4c}$ represents $CF_3$, and $R^{3b}$ represents any one substituent described in Table L12 to Table L14 (hereinafter referred to as "Compound group SX2298").

The Compound (L-4), wherein $R^{45}$ represents a cyanomethyl group, $R^{4b}$ represents a bromine atom, $R^{4c}$ represents $OCF_3$, and $R^{3b}$ represents any one substituent described in Table L12 to Table L14 (hereinafter referred to as "Compound group SX2299").

A Compound Represented by Formula (L-5)

(L-5)

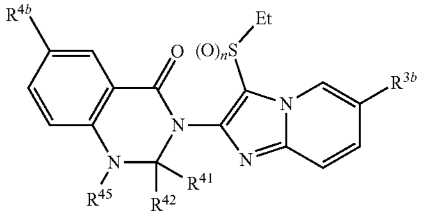

(hereinafter referred to as "Compound (L-5))"), wherein n represents 0, $R^{41}$ represents a hydrogen atom, $R^{42}$ represents a hydrogen atom, $R^{45}$ represents a hydrogen atom, $R^{3b}$ represents a hydrogen atom, and $R^{4b}$ represents any one substituent described in Table L15 to Table L16 (hereinafter referred to as "Compound group SX1480").

TABLE L15

| |
|---|
| F |
| Cl |
| Br |
| I |
| Me |
| $CF_3$ |
| $CHF_2$ |
| $CH_2CF_3$ |
| $CF_2CF_3$ |
| $CF(CF_3)_2$ |
| $C(Me)_2CN$ |
| $CH_2C(Me)_2CN$ |
| $CH_2CH_2C(Me)_2CN$ |
| c-Pr |
| 1-CN-c-Pr |
| $SCF_3$ |
| $S(O)CF_3$ |
| $S(O)_2CF_3$ |
| $OCF_3$ |

TABLE L16

| |
|---|
| OMe |
| OEt |
| OPr |
| Oc-Pr |
| Oi-Pr |
| Ot-Bu |
| $OCHF_2$ |
| $OCH_2CF_3$ |
| $OC_2CF_3$ |
| $OSCF_3$ |
| $OS(O)CF_3$ |
| $OS(O)_2CF_3$ |
| OPh |
| pyrimidin-2-yl |
| pyrimidin-4-yl |
| pyrazin-2-yl |
| 3-(trifluoromethyl)-1H-pyrazol-1-yl |
| 4-(trifluoromethyl)-1H-pyrazol-1-yl |
| 1,2,4-triazol-1-yl |

The Compound (L-5), wherein n represents 0, $R^{41}$ represents a hydrogen atom, $R^{42}$ represents a hydrogen atom, $R^{45}$ represents a hydrogen atom, $R^{3b}$ represents a fluorine atom, and $R^{4b}$ represents any one substituent described in Table L15 to Table L16 (hereinafter referred to as "Compound group SX1481").

The Compound (L-5), wherein n represents 0, $R^{41}$ represents a hydrogen atom, $R^{42}$ represents a hydrogen atom, $R^{45}$ represents a hydrogen atom, $R^{3b}$ represents a chlorine atom, and $R^{4b}$ represents any one substituent described in Table L15 to Table L16 (hereinafter referred to as "Compound group SX1482").

The Compound (L-5), wherein n represents 0, $R^{41}$ represents a hydrogen atom, $R^{42}$ represents a hydrogen atom, $R^{45}$ represents a hydrogen atom, $R^{3b}$ represents a bromine atom, and $R^{4b}$ represents any one substituent described in Table L15 to Table L16 (hereinafter referred to as "Compound group SX1483").

The Compound (L-5), wherein n represents 0, $R^{41}$ represents a hydrogen atom, $R^{42}$ represents a hydrogen atom, $R^{45}$ represents a hydrogen atom, $R^{3b}$ represents $CF_3$, and $R^{4b}$ represents any one substituent described in Table L15 to Table L16 (hereinafter referred to as "Compound group SX1484").

The Compound (L-5), wherein n represents 0, $R^{41}$ represents a hydrogen atom, $R^{42}$ represents a hydrogen atom, $R^{45}$ represents a methyl group, $R^{3b}$ represents a hydrogen atom, and $R^{4b}$ represents any one substituent described in Table L15 to Table L16 (hereinafter referred to as "Compound group SX1485").

The Compound (L-5), wherein n represents 0, $R^{41}$ represents a hydrogen atom, $R^{42}$ represents a hydrogen atom, $R^{45}$ represents a methyl group, $R^{3b}$ represents a fluorine atom, and $R^{4b}$ represents any one substituent described in Table L15 to Table L16 (hereinafter referred to as "Compound group SX1486").

The Compound (L-5), wherein n represents 0, $R^{41}$ represents a hydrogen atom, $R^{42}$ represents a hydrogen atom, $R^{45}$ represents a methyl group, $R^{3b}$ represents a chlorine atom, and $R^{4b}$ represents any one substituent described in Table L15 to Table L16 (hereinafter referred to as "Compound group SX1487").

The Compound (L-5), wherein n represents 0, $R^{41}$ represents a hydrogen atom, $R^{42}$ represents a hydrogen atom, $R^{45}$ represents a methyl group, $R^{3b}$ represents a bromine atom, and $R^{4b}$ represents any one substituent described in Table L15 to Table L16 (hereinafter referred to as "Compound group SX1488").

The Compound (L-5), wherein n represents 0, $R^{41}$ represents a hydrogen atom, $R^{42}$ represents a hydrogen atom, $R^{45}$ represents a methyl group, $R^{3b}$ represents $CF_3$, and $R^{4b}$ represents any one substituent described in Table L15 to Table L16 (hereinafter referred to as "Compound group SX1489").

The Compound (L-5), wherein n represents 0, $R^{41}$ represents a hydrogen atom, $R^{42}$ represents a hydrogen atom, $R^{45}$ represents an ethyl group, $R^{3b}$ represents a hydrogen atom, and $R^{4b}$ represents any one substituent described in Table L15 to Table L16 (hereinafter referred to as "Compound group SX1490").

The Compound (L-5), wherein n represents 0, $R^{41}$ represents a hydrogen atom, $R^{42}$ represents a hydrogen atom, $R^{45}$ represents an ethyl group, $R^{3b}$ represents a fluorine atom, and $R^{4b}$ represents any one substituent described in Table L15 to Table L16 (hereinafter referred to as "Compound group SX1491").

The Compound (L-5), wherein n represents 0, $R^{41}$ represents a hydrogen atom, $R^{42}$ represents a hydrogen atom, $R^{45}$ represents an ethyl group, $R^{3b}$ represents a chlorine atom, and $R^{4b}$ represents any one substituent described in Table L15 to Table L16 (hereinafter referred to as "Compound group SX1492").

The Compound (L-5), wherein n represents 0, $R^{41}$ represents a hydrogen atom, $R^{42}$ represents a hydrogen atom, $R^{45}$ represents an ethyl group, $R^{3b}$ represents a bromine atom, and $R^{4b}$ represents any one substituent described in Table L15 to Table L16 (hereinafter referred to as "Compound group SX1493").

The Compound (L-5), wherein n represents 0, $R^{41}$ represents a hydrogen atom, $R^{42}$ represents a hydrogen atom, $R^{45}$ represents an ethyl group, $R^{3b}$ represents $CF_3$, and $R^{4b}$ represents any one substituent described in Table L15 to Table L16 (hereinafter referred to as "Compound group SX1494").

The Compound (L-5), wherein n represents 0, $R^{41}$ represents a hydrogen atom, $R^{42}$ represents a methyl group, $R^{45}$ represents a hydrogen atom, $R^{3b}$ represents a hydrogen atom, and $R^{4b}$ represents any one substituent described in Table L15 to Table L16 (hereinafter referred to as "Compound group SX1495").

The Compound (L-5), wherein n represents 0, $R^{41}$ represents a hydrogen atom, $R^{42}$ represents a methyl group, $R^{45}$ represents a hydrogen atom, $R^{3b}$ represents a fluorine atom, and $R^{4b}$ represents any one substituent described in Table L15 to Table L16 (hereinafter referred to as "Compound group SX1496").

The Compound (L-5), wherein n represents 0, $R^{41}$ represents a hydrogen atom, $R^{42}$ represents a methyl group, $R^{45}$ represents a hydrogen atom, $R^{3b}$ represents a chlorine atom, and $R^{4b}$ represents any one substituent described in Table L15 to Table L16 (hereinafter referred to as "Compound group SX1497").

The Compound (L-5), wherein n represents 0, $R^{41}$ represents a hydrogen atom, $R^{42}$ represents a methyl group, $R^{45}$ represents a hydrogen atom, $R^{3b}$ represents a bromine atom, and $R^{4b}$ represents any one substituent described in Table L15 to Table L16 (hereinafter referred to as "Compound group SX1498").

The Compound (L-5), wherein n represents 0, $R^{41}$ represents a hydrogen atom, $R^{42}$ represents a methyl group, $R^{45}$ represents a hydrogen atom, $R^{3b}$ represents $CF_3$, and $R^{4b}$ represents any one substituent described in Table L15 to Table L16 (hereinafter referred to as "Compound group SX1499").

The Compound (L-5), wherein n represents 0, $R^{41}$ represents a hydrogen atom, $R^{42}$ represents a methyl group, $R^{45}$ represents a methyl group, $R^{3b}$ represents a hydrogen atom, and $R^{4b}$ represents any one substituent described in Table L15 to Table L16 (hereinafter referred to as "Compound group SX1500").

The Compound (L-5), wherein n represents 0, $R^{41}$ represents a hydrogen atom, $R^{42}$ represents a methyl group, $R^{45}$ represents a methyl group, $R^{3b}$ represents a fluorine atom, and $R^{4b}$ represents any one substituent described in Table L15 to Table L16 (hereinafter referred to as "Compound group SX1501").

The Compound (L-5), wherein n represents 0, $R^{41}$ represents a hydrogen atom, $R^{42}$ represents a methyl group, $R^{45}$ represents a methyl group, $R^{3b}$ represents a chlorine atom, and $R^{4b}$ represents any one substituent described in Table L15 to Table L16 (hereinafter referred to as "Compound group SX1502").

The Compound (L-5), wherein n represents 0, $R^{41}$ represents a hydrogen atom, $R^{42}$ represents a methyl group, $R^{45}$ represents a methyl group, $R^{3b}$ represents a bromine atom, and $R^{4b}$ represents any one substituent described in Table L15 to Table L16 (hereinafter referred to as "Compound group SX1503").

The Compound (L-5), wherein n represents 0, $R^{41}$ represents a hydrogen atom, $R^{42}$ represents a methyl group, $R^{45}$ represents a methyl group, $R^{3b}$ represents $CF_3$, and $R^{4b}$ represents any one substituent described in Table L15 to Table L16 (hereinafter referred to as "Compound group SX1504").

The Compound (L-5), wherein n represents 0, $R^{41}$ represents a hydrogen atom, $R^{42}$ represents a methyl group, $R^{45}$ represents an ethyl group, $R^{3b}$ represents a hydrogen atom, and $R^{4b}$ represents any one substituent described in Table L15 to Table L16 (hereinafter referred to as "Compound group SX1505").

The Compound (L-5), wherein n represents 0, $R^{41}$ represents a hydrogen atom, $R^{42}$ represents a methyl group, $R^{45}$ represents an ethyl group, $R^{3b}$ represents a fluorine atom, and $R^{4b}$ represents any one substituent described in Table L15 to Table L16 (hereinafter referred to as "Compound group SX1506").

The Compound (L-5), wherein n represents 0, $R^{41}$ represents a hydrogen atom, $R^{42}$ represents a methyl group, $R^{45}$ represents an ethyl group, $R^{3b}$ represents a chlorine atom, and $R^{4b}$ represents any one substituent described in Table L15 to Table L16 (hereinafter referred to as "Compound group SX1507").

The Compound (L-5), wherein n represents 0, $R^{41}$ represents a hydrogen atom, $R^{42}$ represents a methyl group, $R^{45}$ represents an ethyl group, $R^{3b}$ represents a bromine atom, and $R^{4b}$ represents any one substituent described in Table L15 to Table L16 (hereinafter referred to as "Compound group SX1508").

The Compound (L-5), wherein n represents 0, $R^{41}$ represents a hydrogen atom, $R^{42}$ represents a methyl group, $R^{45}$ represents an ethyl group, $R^{3b}$ represents $CF_3$, and $R^{4b}$ represents any one substituent described in Table L15 to Table L16 (hereinafter referred to as "Compound group SX1509").

The Compound (L-5), wherein n represents 0, $R^{41}$ represents a methyl group, $R^{42}$ represents a hydrogen atom, $R^{45}$ represents a hydrogen atom, $R^{3b}$ represents a hydrogen atom, and $R^{4b}$ represents any one substituent described in Table L15 to Table L16 (hereinafter referred to as "Compound group SX1510").

The Compound (L-5), wherein n represents 0, $R^{41}$ represents a methyl group, $R^{42}$ represents a hydrogen atom, $R^{45}$ represents a hydrogen atom, $R^{3b}$ represents a fluorine atom, and $R^{4b}$ represents any one substituent described in Table L15 to Table L16 (hereinafter referred to as "Compound group SX1511").

The Compound (L-5), wherein n represents 0, $R^{41}$ represents a methyl group, $R^{42}$ represents a hydrogen atom, $R^{45}$ represents a hydrogen atom, $R^{3b}$ represents a chlorine atom, and $R^{4b}$ represents any one substituent described in Table L15 to Table L16 (hereinafter referred to as "Compound group SX1512").

The Compound (L-5), wherein n represents 0, $R^{41}$ represents a methyl group, $R^{42}$ represents a hydrogen atom, $R^{45}$ represents a hydrogen atom, $R^{3b}$ represents a bromine atom, and $R^{4b}$ represents any one substituent described in Table L15 to Table L16 (hereinafter referred to as "Compound group SX1513").

The Compound (L-5), wherein n represents 0, $R^{41}$ represents a methyl group, $R^{42}$ represents a hydrogen atom, $R^{45}$ represents a hydrogen atom, $R^{3b}$ represents $CF_3$, and $R^{4b}$ represents any one substituent described in Table L15 to Table L16 (hereinafter referred to as "Compound group SX1514").

The Compound (L-5), wherein n represents 0, $R^{41}$ represents a methyl group, $R^{42}$ represents a hydrogen atom, $R^{45}$ represents a methyl group, $R^{3b}$ represents a hydrogen atom, and $R^{4b}$ represents any one substituent described in Table L15 to Table L16 (hereinafter referred to as "Compound group SX1515").

The Compound (L-5), wherein n represents 0, $R^{41}$ represents a methyl group, $R^{42}$ represents a hydrogen atom, $R^{45}$ represents a methyl group, $R^{3b}$ represents a fluorine atom, and $R^{4b}$ represents any one substituent described in Table L15 to Table L16 (hereinafter referred to as "Compound group SX1516").

The Compound (L-5), wherein n represents 0, $R^{41}$ represents a methyl group, $R^{42}$ represents a hydrogen atom, $R^{45}$ represents a methyl group, $R^{3b}$ represents a chlorine atom, and $R^{4b}$ represents any one substituent described in Table L15 to Table L16 (hereinafter referred to as "Compound group SX1517").

The Compound (L-5), wherein n represents 0, $R^{41}$ represents a methyl group, $R^{42}$ represents a hydrogen atom, $R^{45}$ represents a methyl group, $R^{3b}$ represents a bromine atom, and $R^{4b}$ represents any one substituent described in Table L15 to Table L16 (hereinafter referred to as "Compound group SX1518").

The Compound (L-5), wherein n represents 0, $R^{41}$ represents a methyl group, $R^{42}$ represents a hydrogen atom, $R^{45}$ represents a methyl group, $R^{3b}$ represents $CF_3$, and $R^{4b}$ represents any one substituent described in Table L15 to Table L16 (hereinafter referred to as "Compound group SX1519").

The Compound (L-5), wherein n represents 0, $R^{41}$ represents a methyl group, $R^{42}$ represents a hydrogen atom, $R^{45}$ represents an ethyl group, $R^{3b}$ represents a hydrogen atom, and $R^{4b}$ represents any one substituent described in Table L15 to Table L16 (hereinafter referred to as "Compound group SX1520").

The Compound (L-5), wherein n represents 0, $R^{41}$ represents a methyl group, $R^{42}$ represents a hydrogen atom, $R^{45}$ represents an ethyl group, $R^{3b}$ represents a fluorine atom, and $R^{4b}$ represents any one substituent described in Table L15 to Table L16 (hereinafter referred to as "Compound group SX1521").

The Compound (L-5), wherein n represents 0, $R^{41}$ represents a methyl group, $R^{42}$ represents a hydrogen atom, $R^{45}$ represents an ethyl group, $R^{3b}$ represents a chlorine atom, and $R^{4b}$ represents any one substituent described in Table L15 to Table L16 (hereinafter referred to as "Compound group SX1522").

The Compound (L-5), wherein n represents 0, $R^{41}$ represents a methyl group, $R^{42}$ represents a hydrogen atom, $R^{45}$ represents an ethyl group, $R^{3b}$ represents a bromine atom, and $R^{4b}$ represents any one substituent described in Table L15 to Table L16 (hereinafter referred to as "Compound group SX1523").

The Compound (L-5), wherein n represents 0, $R^{41}$ represents a methyl group, $R^{42}$ represents a hydrogen atom, $R^{45}$ represents an ethyl group, $R^{3b}$ represents $CF_3$, and $R^{4b}$ represents any one substituent described in Table L15 to Table L16 (hereinafter referred to as "Compound group SX1524").

The Compound (L-5), wherein n represents 0, $R^{41}$ represents a methyl group, $R^{42}$ represents a methyl group, $R^{45}$ represents a hydrogen atom, $R^{3b}$ represents a hydrogen atom, and $R^{4b}$ represents any one substituent described in Table L15 to Table L16 (hereinafter referred to as "Compound group SX1525").

The Compound (L-5), wherein n represents 0, $R^{41}$ represents a methyl group, $R^{42}$ represents a methyl group, $R^{45}$ represents a hydrogen atom, $R^{3b}$ represents a fluorine atom, and $R^{4b}$ represents any one substituent described in Table L15 to Table L16 (hereinafter referred to as "Compound group SX1526").

The Compound (L-5), wherein n represents 0, $R^{41}$ represents a methyl group, $R^{42}$ represents a methyl group, $R^{45}$ represents a hydrogen atom, $R^{3b}$ represents a chlorine atom, and $R^{4b}$ represents any one substituent described in Table L15 to Table L16 (hereinafter referred to as "Compound group SX1527").

The Compound (L-5), wherein n represents 0, $R^{41}$ represents a methyl group, $R^{42}$ represents a methyl group, $R^{45}$ represents a hydrogen atom, $R^{3b}$ represents a bromine atom, and $R^{4b}$ represents any one substituent described in Table L15 to Table L16 (hereinafter referred to as "Compound group SX1528").

The Compound (L-5), wherein n represents 0, $R^{41}$ represents a methyl group, $R^{42}$ represents a methyl group, $R^{45}$ represents a hydrogen atom, $R^{3b}$ represents $CF_3$, and $R^{4b}$ represents any one substituent described in Table L15 to Table L16 (hereinafter referred to as "Compound group SX1529").

The Compound (L-5), wherein n represents 0, $R^{41}$ represents a methyl group, $R^{42}$ represents a methyl group, $R^{45}$ represents a methyl group, $R^{3b}$ represents a hydrogen atom, and $R^{4b}$ represents any one substituent described in Table L15 to Table L16 (hereinafter referred to as "Compound group SX1530").

The Compound (L-5), wherein n represents 0, $R^{41}$ represents a methyl group, $R^{42}$ represents a methyl group, $R^{45}$ represents a methyl group, $R^{3b}$ represents a fluorine atom, and $R^{4b}$ represents any one substituent described in Table L15 to Table L16 (hereinafter referred to as "Compound group SX1531").

The Compound (L-5), wherein n represents 0, $R^{41}$ represents a methyl group, $R^{42}$ represents a methyl group, $R^{45}$ represents a methyl group, $R^{3b}$ represents a chlorine atom, and $R^{4b}$ represents any one substituent described in Table L15 to Table L16 (hereinafter referred to as "Compound group SX1532").

The Compound (L-5), wherein n represents 0, $R^{41}$ represents a methyl group, $R^{42}$ represents a methyl group, $R^{45}$ represents a methyl group, $R^{3b}$ represents a bromine atom, and $R^{4b}$ represents any one substituent described in Table L15 to Table L16 (hereinafter referred to as "Compound group SX1533").

The Compound (L-5), wherein n represents 0, $R^{41}$ represents a methyl group, $R^{42}$ represents a methyl group, $R^{45}$ represents a methyl group, $R^{3b}$ represents $CF_3$, and $R^{4b}$ represents any one substituent described in Table L15 to Table L16 (hereinafter referred to as "Compound group SX1534").

The Compound (L-5), wherein n represents 0, $R^{41}$ represents a methyl group, $R^{42}$ represents a methyl group, $R^{45}$ represents an ethyl group, $R^{3b}$ represents a hydrogen atom, and $R^{4b}$ represents any one substituent described in Table L15 to Table L16 (hereinafter referred to as "Compound group SX1535").

The Compound (L-5), wherein n represents 0, $R^{41}$ represents a methyl group, $R^{42}$ represents a methyl group, $R^{45}$ represents an ethyl group, $R^{3b}$ represents a fluorine atom, and $R^{4b}$ represents any one substituent described in Table L15 to Table L16 (hereinafter referred to as "Compound group SX1536").

The Compound (L-5), wherein n represents 0, $R^{41}$ represents a methyl group, $R^{42}$ represents a methyl group, $R^{45}$ represents an ethyl group, $R^{3b}$ represents a chlorine atom, and $R^{4b}$ represents any one substituent described in Table L15 to Table L16 (hereinafter referred to as "Compound group SX1537").

The Compound (L-5), wherein n represents 0, $R^{41}$ represents a methyl group, $R^{42}$ represents a methyl group, $R^{45}$ represents an ethyl group, $R^{3b}$ represents a bromine atom, and $R^{4b}$ represents any one substituent described in Table L15 to Table L16 (hereinafter referred to as "Compound group SX1538").

The Compound (L-5), wherein n represents 0, $R^{41}$ represents a methyl group, $R^{42}$ represents a methyl group, $R^{45}$ represents an ethyl group, $R^{3b}$ represents $CF_3$, and $R^{4b}$ represents any one substituent described in Table L15 to Table L16 (hereinafter referred to as "Compound group SX1539").

The Compound (L-5), wherein n represents 1, $R^{41}$ represents a hydrogen atom, $R^{42}$ represents a hydrogen atom, $R^{45}$ represents a hydrogen atom, $R^{3b}$ represents a hydrogen atom, and $R^{4b}$ represents any one substituent described in Table L15 to Table L16 (hereinafter referred to as "Compound group SX1540").

The Compound (L-5), wherein n represents 1, $R^{41}$ represents a hydrogen atom, $R^{42}$ represents a hydrogen atom, $R^{45}$ represents a hydrogen atom, $R^{3b}$ represents a fluorine atom, and $R^{4b}$ represents any one substituent described in Table L15 to Table L16 (hereinafter referred to as "Compound group SX1541").

The Compound (L-5), wherein n represents 1, $R^{41}$ represents a hydrogen atom, $R^{42}$ represents a hydrogen atom, $R^{45}$ represents a hydrogen atom, $R^{3b}$ represents a chlorine atom, and $R^{4b}$ represents any one substituent described in Table L15 to Table L16 (hereinafter referred to as "Compound group SX1542").

The Compound (L-5), wherein n represents 1, $R^{41}$ represents a hydrogen atom, $R^{42}$ represents a hydrogen atom, $R^{45}$ represents a hydrogen atom, $R^{3b}$ represents a bromine atom, and $R^{4b}$ represents any one substituent described in Table L15 to Table L16 (hereinafter referred to as "Compound group SX1543").

The Compound (L-5), wherein n represents 1, $R^{41}$ represents a hydrogen atom, $R^{42}$ represents a hydrogen atom, $R^{45}$ represents a hydrogen atom, $R^{3b}$ represents $CF_3$, and $R^{4b}$ represents any one substituent described in Table L15 to Table L16 (hereinafter referred to as "Compound group SX1544").

The Compound (L-5), wherein n represents 1, $R^{41}$ represents a hydrogen atom, $R^{42}$ represents a hydrogen atom, $R^{45}$ represents a methyl group, $R^{3b}$ represents a hydrogen atom, and $R^{4b}$ represents any one substituent described in Table L15 to Table L16 (hereinafter referred to as "Compound group SX1545").

The Compound (L-5), wherein n represents 1, $R^{41}$ represents a hydrogen atom, $R^{42}$ represents a hydrogen atom, $R^{45}$ represents a methyl group, $R^{3b}$ represents a fluorine atom, and $R^{4b}$ represents any one substituent described in Table L15 to Table L16 (hereinafter referred to as "Compound group SX1546").

The Compound (L-5), wherein n represents 1, $R^{41}$ represents a hydrogen atom, $R^{42}$ represents a hydrogen atom, $R^{45}$ represents a methyl group, $R^{3b}$ represents a chlorine atom, and $R^{4b}$ represents any one substituent described in Table L15 to Table L16 (hereinafter referred to as "Compound group SX1547").

The Compound (L-5), wherein n represents 1, $R^{41}$ represents a hydrogen atom, $R^{42}$ represents a hydrogen atom, $R^{45}$ represents a methyl group, $R^{3b}$ represents a bromine atom, and $R^{4b}$ represents any one substituent described in Table L15 to Table L16 (hereinafter referred to as "Compound group SX1548").

The Compound (L-5), wherein n represents 1, $R^{41}$ represents a hydrogen atom, $R^{42}$ represents a hydrogen atom, $R^{45}$ represents a methyl group, $R^{3b}$ represents $CF_3$, and $R^{4b}$ represents any one substituent described in Table L15 to Table L16 (hereinafter referred to as "Compound group SX1549").

The Compound (L-5), wherein n represents 1, $R^{41}$ represents a hydrogen atom, $R^{42}$ represents a hydrogen atom, $R^{45}$ represents an ethyl group, $R^{3b}$ represents a hydrogen atom, and $R^{4b}$ represents any one substituent described in Table L15 to Table L16 (hereinafter referred to as "Compound group SX1550").

The Compound (L-5), wherein n represents 1, $R^{41}$ represents a hydrogen atom, $R^{42}$ represents a hydrogen atom, $R^{45}$ represents an ethyl group, $R^{3b}$ represents a fluorine atom, and $R^{4b}$ represents any one substituent described in Table L15 to Table L16 (hereinafter referred to as "Compound group SX1551").

The Compound (L-5), wherein n represents 1, $R^{41}$ represents a hydrogen atom, $R^{42}$ represents a hydrogen atom, $R^{45}$ represents an ethyl group, $R^{3b}$ represents a chlorine atom, and $R^{4b}$ represents any one substituent described in Table L15 to Table L16 (hereinafter referred to as "Compound group SX1552").

The Compound (L-5), wherein n represents 1, $R^{41}$ represents a hydrogen atom, $R^{42}$ represents a hydrogen atom, $R^{45}$ represents an ethyl group, $R^{3b}$ represents a bromine atom, and $R^{4b}$ represents any one substituent described in Table L15 to Table L16 (hereinafter referred to as "Compound group SX1553").

The Compound (L-5), wherein n represents 1, $R^{41}$ represents a hydrogen atom, $R^{42}$ represents a hydrogen atom, $R^{45}$ represents an ethyl group, $R^{3b}$ represents $CF_3$, and $R^{4b}$ represents any one substituent described in Table L15 to Table L16 (hereinafter referred to as "Compound group SX1554").

The Compound (L-5), wherein n represents 1, $R^{41}$ represents a hydrogen atom, $R^{42}$ represents a methyl group, $R^{45}$ represents a hydrogen atom, $R^{3b}$ represents a hydrogen atom, and $R^{4b}$ represents any one substituent described in Table L15 to Table L16 (hereinafter referred to as "Compound group SX1555").

The Compound (L-5), wherein n represents 1, $R^{41}$ represents a hydrogen atom, $R^{42}$ represents a methyl group, $R^{45}$ represents a hydrogen atom, $R^{3b}$ represents a fluorine atom, and $R^{4b}$ represents any one substituent described in Table L15 to Table L16 (hereinafter referred to as "Compound group SX1556").

The Compound (L-5), wherein n represents 1, $R^{41}$ represents a hydrogen atom, $R^{42}$ represents a methyl group, $R^{45}$ represents a hydrogen atom, $R^{3b}$ represents a chlorine atom, and $R^{4b}$ represents any one substituent described in Table L15 to Table L16 (hereinafter referred to as "Compound group SX1557").

The Compound (L-5), wherein n represents 1, $R^{41}$ represents a hydrogen atom, $R^{42}$ represents a methyl group, $R^{45}$ represents a hydrogen atom, $R^{3b}$ represents a bromine atom, and $R^{4b}$ represents any one substituent described in Table L15 to Table L16 (hereinafter referred to as "Compound group SX1558").

The Compound (L-5), wherein n represents 1, $R^{41}$ represents a hydrogen atom, $R^{42}$ represents a methyl group, $R^{45}$ represents a hydrogen atom, $R^{3b}$ represents $CF_3$, and $R^{4b}$ represents any one substituent described in Table L15 to Table L16 (hereinafter referred to as "Compound group SX1559").

The Compound (L-5), wherein n represents 1, $R^{41}$ represents a hydrogen atom, $R^{42}$ represents a methyl group, $R^{45}$ represents a methyl group, $R^{3b}$ represents a hydrogen atom, and $R^{4b}$ represents any one substituent described in Table L15 to Table L16 (hereinafter referred to as "Compound group SX1560").

The Compound (L-5), wherein n represents 1, $R^{41}$ represents a hydrogen atom, $R^{42}$ represents a methyl group, $R^{45}$ represents a methyl group, $R^{3b}$ represents a fluorine atom, and $R^{4b}$ represents any one substituent described in Table L15 to Table L16 (hereinafter referred to as "Compound group SX1561").

The Compound (L-5), wherein n represents 1, $R^{41}$ represents a hydrogen atom, $R^{42}$ represents a methyl group, $R^{45}$ represents a methyl group, $R^{3b}$ represents a chlorine atom, and $R^{4b}$ represents any one substituent described in Table L15 to Table L16 (hereinafter referred to as "Compound group SX1562").

The Compound (L-5), wherein n represents 1, $R^{41}$ represents a hydrogen atom, $R^{42}$ represents a methyl group, $R^{45}$ represents a methyl group, $R^{3b}$ represents a bromine atom, and $R^{4b}$ represents any one substituent described in Table L15 to Table L16 (hereinafter referred to as "Compound group SX1563").

The Compound (L-5), wherein n represents 1, $R^{41}$ represents a hydrogen atom, $R^{42}$ represents a methyl group, $R^{45}$ represents a methyl group, $R^{3b}$ represents $CF_3$, and $R^{4b}$ represents any one substituent described in Table L15 to Table L16 (hereinafter referred to as "Compound group SX1564").

The Compound (L-5), wherein n represents 1, $R^{41}$ represents a hydrogen atom, $R^{42}$ represents a methyl group, $R^{45}$ represents an ethyl group, $R^{3b}$ represents a hydrogen atom, and $R^{4b}$ represents any one substituent described in Table L15 to Table L16 (hereinafter referred to as "Compound group SX1565").

The Compound (L-5), wherein n represents 1, $R^{41}$ represents a hydrogen atom, $R^{42}$ represents a methyl group, $R^{45}$ represents an ethyl group, $R^{3b}$ represents a fluorine atom, and $R^{4b}$ represents any one substituent described in Table L15 to Table L16 (hereinafter referred to as "Compound group SX1566").

The Compound (L-5), wherein n represents 1, $R^{41}$ represents a hydrogen atom, $R^{42}$ represents a methyl group, $R^{45}$ represents an ethyl group, $R^{3b}$ represents a chlorine atom, and $R^{4b}$ represents any one substituent described in Table L15 to Table L16 (hereinafter referred to as "Compound group SX1567").

The Compound (L-5), wherein n represents 1, $R^{41}$ represents a hydrogen atom, $R^{42}$ represents a methyl group, $R^{45}$ represents an ethyl group, $R^{3b}$ represents a bromine atom, and $R^{4b}$ represents any one substituent described in Table L15 to Table L16 (hereinafter referred to as "Compound group SX1568").

The Compound (L-5), wherein n represents 1, $R^{41}$ represents a hydrogen atom, $R^{42}$ represents a methyl group, $R^{45}$ represents an ethyl group, $R^{3b}$ represents $CF_3$, and $R^{4b}$ represents any one substituent described in Table L15 to Table L16 (hereinafter referred to as "Compound group SX1569").

The Compound (L-5), wherein n represents 1, $R^{41}$ represents a methyl group, $R^{42}$ represents a hydrogen atom, $R^{45}$ represents a hydrogen atom, $R^{3b}$ represents a hydrogen atom, and $R^{4b}$ represents any one substituent described in Table L15 to Table L16 (hereinafter referred to as "Compound group SX1570").

The Compound (L-5), wherein n represents 1, $R^{41}$ represents a methyl group, $R^{42}$ represents a hydrogen atom, $R^{45}$ represents a hydrogen atom, $R^{3b}$ represents a fluorine atom, and $R^{4b}$ represents any one substituent described in Table L15 to Table L16 (hereinafter referred to as "Compound group SX1571").

The Compound (L-5), wherein n represents 1, $R^{41}$ represents a methyl group, $R^{42}$ represents a hydrogen atom, $R^{45}$ represents a hydrogen atom, $R^{3b}$ represents a chlorine atom, and $R^{4b}$ represents any one substituent described in Table L15 to Table L16 (hereinafter referred to as "Compound group SX1572").

The Compound (L-5), wherein n represents 1, $R^{41}$ represents a methyl group, $R^{42}$ represents a hydrogen atom, $R^{45}$ represents a hydrogen atom, $R^{3b}$ represents a bromine atom, and $R^{4b}$ represents any one substituent described in Table L15 to Table L16 (hereinafter referred to as "Compound group SX1573").

The Compound (L-5), wherein n represents 1, $R^{41}$ represents a methyl group, $R^{42}$ represents a hydrogen atom, $R^{45}$ represents a hydrogen atom, $R^{3b}$ represents $CF_3$, and $R^{4b}$ represents any one substituent described in Table L15 to Table L16 (hereinafter referred to as "Compound group SX1574").

The Compound (L-5), wherein n represents 1, $R^{41}$ represents a methyl group, $R^{42}$ represents a hydrogen atom, $R^{45}$ represents a methyl group, $R^{3b}$ represents a hydrogen atom, and $R^{4b}$ represents any one substituent described in Table L15 to Table L16 (hereinafter referred to as "Compound group SX1575").

The Compound (L-5), wherein n represents 1, $R^{41}$ represents a methyl group, $R^{42}$ represents a hydrogen atom, $R^{45}$ represents a methyl group, $R^{3b}$ represents a fluorine atom, and $R^{4b}$ represents any one substituent described in Table L15 to Table L16 (hereinafter referred to as "Compound group SX1576").

The Compound (L-5), wherein n represents 1, $R^{41}$ represents a methyl group, $R^{42}$ represents a hydrogen atom, $R^{45}$ represents a methyl group, $R^{3b}$ represents a chlorine atom, and $R^{4b}$ represents any one substituent described in Table L15 to Table L16 (hereinafter referred to as "Compound group SX1577").

The Compound (L-5), wherein n represents 1, $R^{41}$ represents a methyl group, $R^{42}$ represents a hydrogen atom, $R^{45}$ represents a methyl group, $R^{3b}$ represents a bromine atom, and $R^{4b}$ represents any one substituent described in Table L15 to Table L16 (hereinafter referred to as "Compound group SX1578").

The Compound (L-5), wherein n represents 1, $R^{41}$ represents a methyl group, $R^{42}$ represents a hydrogen atom, $R^{45}$ represents a methyl group, $R^{3b}$ represents $CF_3$, and $R^{4b}$ represents any one substituent described in Table L15 to Table L16 (hereinafter referred to as "Compound group SX1579").

The Compound (L-5), wherein n represents 1, $R^{41}$ represents a methyl group, $R^{42}$ represents a hydrogen atom, $R^{45}$ represents an ethyl group, $R^{3b}$ represents a hydrogen atom, and $R^{4b}$ represents any one substituent described in Table L15 to Table L16 (hereinafter referred to as "Compound group SX1580").

The Compound (L-5), wherein n represents 1, $R^{41}$ represents a methyl group, $R^{42}$ represents a hydrogen atom, $R^{45}$ represents an ethyl group, $R^{3b}$ represents a fluorine atom, and $R^{4b}$ represents any one substituent described in Table L15 to Table L16 (hereinafter referred to as "Compound group SX1581").

The Compound (L-5), wherein n represents 1, $R^{41}$ represents a methyl group, $R^{42}$ represents a hydrogen atom, $R^{45}$ represents an ethyl group, $R^{3b}$ represents a chlorine atom, and $R^{4b}$ represents any one substituent described in Table L15 to Table L16 (hereinafter referred to as "Compound group SX1582").

The Compound (L-5), wherein n represents 1, $R^{41}$ represents a methyl group, $R^{42}$ represents a hydrogen atom, $R^{45}$ represents an ethyl group, $R^{3b}$ represents a bromine atom, and $R^{4b}$ represents any one substituent described in Table L15 to Table L16 (hereinafter referred to as "Compound group SX1583").

The Compound (L-5), wherein n represents 1, $R^{41}$ represents a methyl group, $R^{42}$ represents a hydrogen atom, $R^{45}$ represents an ethyl group, $R^{3b}$ represents $CF_3$, and $R^{4b}$ represents any one substituent described in Table L15 to Table L16 (hereinafter referred to as "Compound group SX1584").

The Compound (L-5), wherein n represents 1, $R^{41}$ represents a methyl group, $R^{42}$ represents a methyl group, $R^{45}$ represents a hydrogen atom, $R^{3b}$ represents a hydrogen atom, and $R^{4b}$ represents any one substituent described in Table L15 to Table L16 (hereinafter referred to as "Compound group SX1585").

The Compound (L-5), wherein n represents 1, $R^{41}$ represents a methyl group, $R^{42}$ represents a methyl group, $R^{45}$ represents a hydrogen atom, $R^{3b}$ represents a fluorine atom, and $R^{4b}$ represents any one substituent described in Table L15 to Table L16 (hereinafter referred to as "Compound group SX1586").

The Compound (L-5), wherein n represents 1, $R^{41}$ represents a methyl group, $R^{42}$ represents a methyl group, $R^{45}$ represents a hydrogen atom, $R^{3b}$ represents a chlorine atom, and $R^{4b}$ represents any one substituent described in Table L15 to Table L16 (hereinafter referred to as "Compound group SX1587").

The Compound (L-5), wherein n represents 1, $R^{41}$ represents a methyl group, $R^{42}$ represents a methyl group, $R^{45}$ represents a hydrogen atom, $R^{3b}$ represents a bromine atom, and $R^{4b}$ represents any one substituent described in Table L15 to Table L16 (hereinafter referred to as "Compound group SX1588").

The Compound (L-5), wherein n represents 1, $R^{41}$ represents a methyl group, $R^{42}$ represents a methyl group, $R^{45}$ represents a hydrogen atom, $R^{3b}$ represents $CF_3$, and $R^{4b}$ represents any one substituent described in Table L15 to Table L16 (hereinafter referred to as "Compound group SX1589").

The Compound (L-5), wherein n represents 1, $R^{41}$ represents a methyl group, $R^{42}$ represents a methyl group, $R^{45}$ represents a methyl group, $R^{3b}$ represents a hydrogen atom, and $R^{4b}$ represents any one substituent described in Table L15 to Table L16 (hereinafter referred to as "Compound group SX1590").

The Compound (L-5), wherein n represents 1, $R^{41}$ represents a methyl group, $R^{42}$ represents a methyl group, $R^{45}$ represents a methyl group, $R^{3b}$ represents a fluorine atom, and $R^{4b}$ represents any one substituent described in Table L15 to Table L16 (hereinafter referred to as "Compound group SX1591").

The Compound (L-5), wherein n represents 1, $R^{41}$ represents a methyl group, $R^{42}$ represents a methyl group, $R^{45}$ represents a methyl group, $R^{3b}$ represents a chlorine atom, and $R^{4b}$ represents any one substituent described in Table L15 to Table L16 (hereinafter referred to as "Compound group SX1592").

The Compound (L-5), wherein n represents 1, $R^{41}$ represents a methyl group, $R^{42}$ represents a methyl group, $R^{45}$ represents a methyl group, $R^{3b}$ represents a bromine atom, and $R^{4b}$ represents any one substituent described in Table L15 to Table L16 (hereinafter referred to as "Compound group SX1593").

The Compound (L-5), wherein n represents 1, $R^{41}$ represents a methyl group, $R^{42}$ represents a methyl group, $R^{45}$ represents a methyl group, $R^{3b}$ represents $CF_3$, and $R^{4b}$ represents any one substituent described in Table L15 to Table L16 (hereinafter referred to as "Compound group SX1594").

The Compound (L-5), wherein n represents 1, $R^{41}$ represents a methyl group, $R^{42}$ represents a methyl group, $R^{45}$ represents an ethyl group, $R^{3b}$ represents a hydrogen atom, and $R^{4b}$ represents any one substituent described in Table L15 to Table L16 (hereinafter referred to as "Compound group SX1595").

The Compound (L-5), wherein n represents 1, $R^{41}$ represents a methyl group, $R^{42}$ represents a methyl group, $R^{45}$ represents an ethyl group, $R^{3b}$ represents a fluorine atom, and $R^{4b}$ represents any one substituent described in Table L15 to Table L16 (hereinafter referred to as "Compound group SX1596").

The Compound (L-5), wherein n represents 1, $R^{41}$ represents a methyl group, $R^{42}$ represents a methyl group, $R^{45}$ represents an ethyl group, $R^{3b}$ represents a chlorine atom, and $R^{4b}$ represents any one substituent described in Table L15 to Table L16 (hereinafter referred to as "Compound group SX1597").

The Compound (L-5), wherein n represents 1, $R^{41}$ represents a methyl group, $R^{42}$ represents a methyl group, $R^{45}$ represents an ethyl group, $R^{3b}$ represents a bromine atom, and $R^{4b}$ represents any one substituent described in Table L15 to Table L16 (hereinafter referred to as "Compound group SX1598").

The Compound (L-5), wherein n represents 1, $R^{41}$ represents a methyl group, $R^{42}$ represents a methyl group, $R^{45}$ represents an ethyl group, $R^{3b}$ represents $CF_3$, and $R^{4b}$ represents any one substituent described in Table L15 to Table L16 (hereinafter referred to as "Compound group SX1599").

The Compound (L-5), wherein n represents 2, $R^{41}$ represents a hydrogen atom, $R^{42}$ represents a hydrogen atom, $R^{45}$ represents a hydrogen atom, $R^{3b}$ represents a hydrogen atom, and $R^{4b}$ represents any one substituent described in Table L15 to Table L16 (hereinafter referred to as "Compound group SX1600").

The Compound (L-5), wherein n represents 2, $R^{41}$ represents a hydrogen atom, $R^{42}$ represents a hydrogen atom, $R^{45}$ represents a hydrogen atom, $R^{3b}$ represents a fluorine atom, and $R^{4b}$ represents any one substituent described in Table L15 to Table L16 (hereinafter referred to as "Compound group SX1601").

The Compound (L-5), wherein n represents 2, $R^{41}$ represents a hydrogen atom, $R^{42}$ represents a hydrogen atom, $R^{45}$ represents a hydrogen atom, $R^{3b}$ represents a chlorine atom, and $R^{4b}$ represents any one substituent described in Table L15 to Table L16 (hereinafter referred to as "Compound group SX1602").

The Compound (L-5), wherein n represents 2, $R^{41}$ represents a hydrogen atom, $R^{42}$ represents a hydrogen atom, $R^{45}$ represents a hydrogen atom, $R^{3b}$ represents a bromine atom, and $R^{4b}$ represents any one substituent described in Table L15 to Table L16 (hereinafter referred to as "Compound group SX1603").

The Compound (L-5), wherein n represents 2, $R^{41}$ represents a hydrogen atom, $R^{42}$ represents a hydrogen atom, $R^{45}$ represents a hydrogen atom, $R^{3b}$ represents $CF_3$, and $R^{4b}$ represents any one substituent described in Table L15 to Table L16 (hereinafter referred to as "Compound group SX1604").

The Compound (L-5), wherein n represents 2, $R^{41}$ represents a hydrogen atom, $R^{42}$ represents a hydrogen atom, $R^{45}$ represents a methyl group, $R^{3b}$ represents a hydrogen atom, and $R^{4b}$ represents any one substituent described in Table L15 to Table L16 (hereinafter referred to as "Compound group SX1605").

The Compound (L-5), wherein n represents 2, $R^{41}$ represents a hydrogen atom, $R^{42}$ represents a hydrogen atom, $R^{45}$ represents a methyl group, $R^{3b}$ represents a fluorine atom, and $R^{4b}$ represents any one substituent described in Table L15 to Table L16 (hereinafter referred to as "Compound group SX1606").

The Compound (L-5), wherein n represents 2, $R^{41}$ represents a hydrogen atom, $R^{42}$ represents a hydrogen atom, $R^{45}$ represents a methyl group, $R^{3b}$ represents a chlorine atom, and $R^{4b}$ represents any one substituent described in Table L15 to Table L16 (hereinafter referred to as "Compound group SX1607").

The Compound (L-5), wherein n represents 2, $R^{41}$ represents a hydrogen atom, $R^{42}$ represents a hydrogen atom, $R^{45}$ represents a methyl group, $R^{3b}$ represents a bromine atom, and $R^{4b}$ represents any one substituent described in Table L15 to Table L16 (hereinafter referred to as "Compound group SX1608").

The Compound (L-5), wherein n represents 2, $R^{41}$ represents a hydrogen atom, $R^{42}$ represents a hydrogen atom, $R^{45}$ represents a methyl group, $R^{3b}$ represents $CF_3$, and $R^{4b}$ represents any one substituent described in Table L15 to Table L16 (hereinafter referred to as "Compound group SX1609").

The Compound (L-5), wherein n represents 2, $R^{41}$ represents a hydrogen atom, $R^{42}$ represents a hydrogen atom, $R^{45}$ represents an ethyl group, $R^{3b}$ represents a hydrogen atom, and $R^{4b}$ represents any one substituent described in Table L15 to Table L16 (hereinafter referred to as "Compound group SX1610").

The Compound (L-5), wherein n represents 2, $R^{41}$ represents a hydrogen atom, $R^{42}$ represents a hydrogen atom, $R^{45}$ represents an ethyl group, $R^{3b}$ represents a fluorine atom, and $R^{4b}$ represents any one substituent described in Table L15 to Table L16 (hereinafter referred to as "Compound group SX1611").

The Compound (L-5), wherein n represents 2, $R^{41}$ represents a hydrogen atom, $R^{42}$ represents a hydrogen atom, $R^{45}$ represents an ethyl group, $R^{3b}$ represents a chlorine atom, and $R^{4b}$ represents any one substituent described in Table L15 to Table L16 (hereinafter referred to as "Compound group SX1612").

The Compound (L-5), wherein n represents 2, $R^{41}$ represents a hydrogen atom, $R^{42}$ represents a hydrogen atom, $R^{45}$ represents an ethyl group, $R^{3b}$ represents a bromine atom, and $R^{4b}$ represents any one substituent described in Table L15 to Table L16 (hereinafter referred to as "Compound group SX1613").

The Compound (L-5), wherein n represents 2, $R^{41}$ represents a hydrogen atom, $R^{42}$ represents a hydrogen atom, $R^{45}$ represents an ethyl group, $R^{3b}$ represents $CF_3$, and $R^{4b}$ represents any one substituent described in Table L15 to Table L16 (hereinafter referred to as "Compound group SX1614").

The Compound (L-5), wherein n represents 2, $R^{41}$ represents a hydrogen atom, $R^{42}$ represents a methyl group, $R^{45}$ represents a hydrogen atom, $R^{3b}$ represents a hydrogen atom, and $R^{4b}$ represents any one substituent described in Table L15 to Table L16 (hereinafter referred to as "Compound group SX1615").

The Compound (L-5), wherein n represents 2, $R^{41}$ represents a hydrogen atom, $R^{42}$ represents a methyl group, $R^{45}$ represents a hydrogen atom, $R^{3b}$ represents a fluorine atom, and $R^{4b}$ represents any one substituent described in Table L15 to Table L16 (hereinafter referred to as "Compound group SX1616").

The Compound (L-5), wherein n represents 2, $R^{41}$ represents a hydrogen atom, $R^{42}$ represents a methyl group, $R^{45}$ represents a hydrogen atom, $R^{3b}$ represents a chlorine atom, and $R^{4b}$ represents any one substituent described in Table L15 to Table L16 (hereinafter referred to as "Compound group SX1617").

The Compound (L-5), wherein n represents 2, $R^{41}$ represents a hydrogen atom, $R^{42}$ represents a methyl group, $R^{45}$ represents a hydrogen atom, $R^{3b}$ represents a bromine atom, and $R^{4b}$ represents any one substituent described in Table L15 to Table L16 (hereinafter referred to as "Compound group SX1618").

The Compound (L-5), wherein n represents 2, $R^{41}$ represents a hydrogen atom, $R^{42}$ represents a methyl group, $R^{45}$ represents a hydrogen atom, $R^{3b}$ represents $CF_3$, and $R^{4b}$ represents any one substituent described in Table L15 to Table L16 (hereinafter referred to as "Compound group SX1619").

The Compound (L-5), wherein n represents 2, $R^{41}$ represents a hydrogen atom, $R^{42}$ represents a methyl group, $R^{45}$ represents a methyl group, $R^{3b}$ represents a hydrogen atom, and $R^{4b}$ represents any one substituent described in Table L15 to Table L16 (hereinafter referred to as "Compound group SX1620").

The Compound (L-5), wherein n represents 2, $R^{41}$ represents a hydrogen atom, $R^{42}$ represents a methyl group, $R^{45}$ represents a methyl group, $R^{3b}$ represents a fluorine atom, and $R^{4b}$ represents any one substituent described in Table L15 to Table L16 (hereinafter referred to as "Compound group SX1621").

The Compound (L-5), wherein n represents 2, $R^{41}$ represents a hydrogen atom, $R^{42}$ represents a methyl group, $R^{45}$ represents a methyl group, $R^{3b}$ represents a chlorine atom, and $R^{4b}$ represents any one substituent described in Table L15 to Table L16 (hereinafter referred to as "Compound group SX1622").

The Compound (L-5), wherein n represents 2, $R^{41}$ represents a hydrogen atom, $R^{42}$ represents a methyl group, $R^{45}$ represents a methyl group, $R^{3b}$ represents a bromine atom, and $R^{4b}$ represents any one substituent described in Table L15 to Table L16 (hereinafter referred to as "Compound group SX1623").

The Compound (L-5), wherein n represents 2, $R^{41}$ represents a hydrogen atom, $R^{42}$ represents a methyl group, $R^{45}$ represents a methyl group, $R^{3b}$ represents $CF_3$, and $R^{4b}$ represents any one substituent described in Table L15 to Table L16 (hereinafter referred to as "Compound group SX1624").

The Compound (L-5), wherein n represents 2, $R^{41}$ represents a hydrogen atom, $R^{42}$ represents a methyl group, $R^{45}$ represents an ethyl group, $R^{3b}$ represents a hydrogen atom, and $R^{4b}$ represents any one substituent described in Table L15 to Table L16 (hereinafter referred to as "Compound group SX1625").

The Compound (L-5), wherein n represents 2, $R^{41}$ represents a hydrogen atom, $R^{42}$ represents a methyl group, $R^{45}$ represents an ethyl group, $R^{3b}$ represents a fluorine atom, and $R^{4b}$ represents any one substituent described in Table L15 to Table L16 (hereinafter referred to as "Compound group SX1626").

The Compound (L-5), wherein n represents 2, $R^{41}$ represents a hydrogen atom, $R^{42}$ represents a methyl group, $R^{45}$ represents an ethyl group, $R^{3b}$ represents a chlorine atom, and $R^{4b}$ represents any one substituent described in Table L15 to Table L16 (hereinafter referred to as "Compound group SX1627").

The Compound (L-5), wherein n represents 2, $R^{41}$ represents a hydrogen atom, $R^{42}$ represents a methyl group, $R^{45}$ represents an ethyl group, $R^{3b}$ represents a bromine atom, and $R^{4b}$ represents any one substituent described in Table L15 to Table L16 (hereinafter referred to as "Compound group SX1628").

The Compound (L-5), wherein n represents 2, $R^{41}$ represents a hydrogen atom, $R^{42}$ represents a methyl group, $R^{45}$ represents an ethyl group, $R^{3b}$ represents $CF_3$, and $R^{4b}$ represents any one substituent described in Table L15 to Table L16 (hereinafter referred to as "Compound group SX1629").

The Compound (L-5), wherein n represents 2, $R^{41}$ represents a methyl group, $R^{42}$ represents a hydrogen atom, $R^{45}$ represents a hydrogen atom, $R^{3b}$ represents a hydrogen atom, and $R^{4b}$ represents any one substituent described in Table L15 to Table L16 (hereinafter referred to as "Compound group SX1630").

The Compound (L-5), wherein n represents 2, $R^{41}$ represents a methyl group, $R^{42}$ represents a hydrogen atom, $R^{45}$ represents a hydrogen atom, $R^{3b}$ represents a fluorine atom, and $R^{4b}$ represents any one substituent described in Table L15 to Table L16 (hereinafter referred to as "Compound group SX1631").

The Compound (L-5), wherein n represents 2, $R^{41}$ represents a methyl group, $R^{42}$ represents a hydrogen atom, $R^{45}$ represents a hydrogen atom, $R^{3b}$ represents a chlorine atom, and $R^{4b}$ represents any one substituent described in Table L15 to Table L16 (hereinafter referred to as "Compound group SX1632").

The Compound (L-5), wherein n represents 2, $R^{41}$ represents a methyl group, $R^{42}$ represents a hydrogen atom, $R^{45}$ represents a hydrogen atom, $R^{3b}$ represents a bromine atom, and $R^{4b}$ represents any one substituent described in Table L15 to Table L16 (hereinafter referred to as "Compound group SX1633").

The Compound (L-5), wherein n represents 2, $R^{41}$ represents a methyl group, $R^{42}$ represents a hydrogen atom, $R^{45}$ represents a hydrogen atom, $R^{3b}$ represents $CF_3$, and $R^{4b}$ represents any one substituent described in Table L15 to Table L16 (hereinafter referred to as "Compound group SX1634").

The Compound (L-5), wherein n represents 2, $R^{41}$ represents a methyl group, $R^{42}$ represents a hydrogen atom, $R^{45}$ represents a methyl group, $R^{3b}$ represents a hydrogen atom, and $R^{4b}$ represents any one substituent described in Table L15 to Table L16 (hereinafter referred to as "Compound group SX1635").

The Compound (L-5), wherein n represents 2, $R^{41}$ represents a methyl group, $R^{42}$ represents a hydrogen atom, $R^{45}$ represents a methyl group, $R^{3b}$ represents a fluorine atom, and $R^{4b}$ represents any one substituent described in Table L15 to Table L16 (hereinafter referred to as "Compound group SX1636").

The Compound (L-5), wherein n represents 2, $R^{41}$ represents a methyl group, $R^{42}$ represents a hydrogen atom, $R^{45}$ represents a methyl group, $R^{3b}$ represents a chlorine atom, and $R^{4b}$ represents any one substituent described in Table L15 to Table L16 (hereinafter referred to as "Compound group SX1637").

The Compound (L-5), wherein n represents 2, $R^{41}$ represents a methyl group, $R^{42}$ represents a hydrogen atom, $R^{45}$ represents a methyl group, $R^{3b}$ represents a bromine atom, and $R^{4b}$ represents any one substituent described in Table L15 to Table L16 (hereinafter referred to as "Compound group SX1638").

The Compound (L-5), wherein n represents 2, $R^{41}$ represents a methyl group, $R^{42}$ represents a hydrogen atom, $R^{45}$ represents a methyl group, $R^{3b}$ represents $CF_3$, and $R^{4b}$ represents any one substituent described in Table L15 to Table L16 (hereinafter referred to as "Compound group SX1639").

The Compound (L-5), wherein n represents 2, $R^{41}$ represents a methyl group, $R^{42}$ represents a hydrogen atom, $R^{45}$ represents an ethyl group, $R^{3b}$ represents a hydrogen atom, and $R^{4b}$ represents any one substituent described in Table L15 to Table L16 (hereinafter referred to as "Compound group SX1640").

The Compound (L-5), wherein n represents 2, $R^{41}$ represents a methyl group, $R^{42}$ represents a hydrogen atom, $R^{45}$ represents an ethyl group, $R^{3b}$ represents a fluorine atom, and $R^{4b}$ represents any one substituent described in Table L15 to Table L16 (hereinafter referred to as "Compound group SX1641").

The Compound (L-5), wherein n represents 2, $R^{41}$ represents a methyl group, $R^{42}$ represents a hydrogen atom, $R^{45}$ represents an ethyl group, $R^{3b}$ represents a chlorine atom, and $R^{4b}$ represents any one substituent described in Table L15 to Table L16 (hereinafter referred to as "Compound group SX1642").

The Compound (L-5), wherein n represents 2, $R^{41}$ represents a methyl group, $R^{42}$ represents a hydrogen atom, $R^{45}$ represents an ethyl group, $R^{3b}$ represents a bromine atom, and $R^{4b}$ represents any one substituent described in Table L15 to Table L16 (hereinafter referred to as "Compound group SX1643").

The Compound (L-5), wherein n represents 2, $R^{41}$ represents a methyl group, $R^{42}$ represents a hydrogen atom, $R^{45}$ represents an ethyl group, $R^{3b}$ represents $CF_3$, and $R^{4b}$ represents any one substituent described in Table L15 to Table L16 (hereinafter referred to as "Compound group SX1644").

The Compound (L-5), wherein n represents 2, $R^{41}$ represents a methyl group, $R^{42}$ represents a methyl group, $R^{45}$ represents a hydrogen atom, $R^{3b}$ represents a hydrogen atom, and $R^{4b}$ represents any one substituent described in Table L15 to Table L16 (hereinafter referred to as "Compound group SX1645").

The Compound (L-5), wherein n represents 2, $R^{41}$ represents a methyl group, $R^{42}$ represents a methyl group, $R^{45}$ represents a hydrogen atom, $R^{3b}$ represents a fluorine atom, and $R^{4b}$ represents any one substituent described in Table L15 to Table L16 (hereinafter referred to as "Compound group SX1646").

The Compound (L-5), wherein n represents 2, $R^{41}$ represents a methyl group, $R^{42}$ represents a methyl group, $R^{45}$ represents a hydrogen atom, $R^{3b}$ represents a chlorine atom, and $R^{4b}$ represents any one substituent described in Table L15 to Table L16 (hereinafter referred to as "Compound group SX1647").

The Compound (L-5), wherein n represents 2, $R^{41}$ represents a methyl group, $R^{42}$ represents a methyl group, $R^{45}$ represents a hydrogen atom, $R^{3b}$ represents a bromine atom, and $R^{4b}$ represents any one substituent described in Table L15 to Table L16 (hereinafter referred to as "Compound group SX1648").

The Compound (L-5), wherein n represents 2, $R^{41}$ represents a methyl group, $R^{42}$ represents a methyl group, $R^{45}$ represents a hydrogen atom, $R^{3b}$ represents $CF_3$, and $R^{4b}$ represents any one substituent described in Table L15 to Table L16 (hereinafter referred to as "Compound group SX1649").

The Compound (L-5), wherein n represents 2, $R^{41}$ represents a methyl group, $R^{42}$ represents a methyl group, $R^{45}$ represents a methyl group, $R^{3b}$ represents a hydrogen atom, and $R^{4b}$ represents any one substituent described in Table L15 to Table L16 (hereinafter referred to as "Compound group SX1650").

The Compound (L-5), wherein n represents 2, $R^{41}$ represents a methyl group, $R^{42}$ represents a methyl group, $R^{45}$ represents a methyl group, $R^{3b}$ represents a fluorine atom, and $R^{4b}$ represents any one substituent described in Table L15 to Table L16 (hereinafter referred to as "Compound group SX1651").

The Compound (L-5), wherein n represents 2, $R^{41}$ represents a methyl group, $R^{42}$ represents a methyl group, $R^{45}$ represents a methyl group, $R^{3b}$ represents a chlorine atom, and $R^{4b}$ represents any one substituent described in Table L15 to Table L16 (hereinafter referred to as "Compound group SX1652").

The Compound (L-5), wherein n represents 2, $R^{41}$ represents a methyl group, $R^{42}$ represents a methyl group, $R^{45}$ represents a methyl group, $R^{3b}$ represents a bromine atom, and $R^{4b}$ represents any one substituent described in Table L15 to Table L16 (hereinafter referred to as "Compound group SX1653").

The Compound (L-5), wherein n represents 2, $R^{41}$ represents a methyl group, $R^{42}$ represents a methyl group, $R^{45}$ represents a methyl group, $R^{3b}$ represents $CF_3$, and $R^{4b}$ represents any one substituent described in Table L15 to Table L16 (hereinafter referred to as "Compound group SX1654").

The Compound (L-5), wherein n represents 2, $R^{41}$ represents a methyl group, $R^{42}$ represents a methyl group, $R^{45}$ represents an ethyl group, $R^{3b}$ represents a hydrogen atom, and $R^{4b}$ represents any one substituent described in Table L15 to Table L16 (hereinafter referred to as "Compound group SX1655").

The Compound (L-5), wherein n represents 2, $R^{41}$ represents a methyl group, $R^{42}$ represents a methyl group, $R^{45}$ represents an ethyl group, $R^{3b}$ represents a fluorine atom, and $R^{4b}$ represents any one substituent described in Table L15 to Table L16 (hereinafter referred to as "Compound group SX1656").

The Compound (L-5), wherein n represents 2, $R^{41}$ represents a methyl group, $R^{42}$ represents a methyl group, $R^{45}$ represents an ethyl group, $R^{3b}$ represents a chlorine atom, and $R^{4b}$ represents any one substituent described in Table L15 to Table L16 (hereinafter referred to as "Compound group SX1657").

The Compound (L-5), wherein n represents 2, $R^{41}$ represents a methyl group, $R^{42}$ represents a methyl group, $R^{45}$ represents an ethyl group, $R^{3b}$ represents a bromine atom, and $R^{4b}$ represents any one substituent described in Table L15 to Table L16 (hereinafter referred to as "Compound group SX1658").

The Compound (L-5), wherein n represents 2, $R^{41}$ represents a methyl group, $R^{42}$ represents a methyl group, $R^{45}$ represents an ethyl group, $R^{3b}$ represents $CF_3$, and $R^{4b}$ represents any one substituent described in Table L15 to Table L16 (hereinafter referred to as "Compound group SX1659").

A compound represented by formula (L-6)

(L-6)

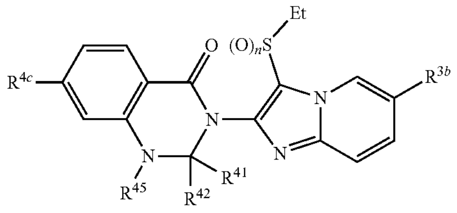

(hereinafter referred to as "Compound (L-6)", wherein n represents 0, $R^{41}$ represents a hydrogen atom, $R^{42}$ represents a hydrogen atom, $R^{45}$ represents a hydrogen atom, $R^{3b}$ represents a hydrogen atom, and $R^{4c}$ represents any one substituent described in Table L15 to Table L16 (hereinafter referred to as "Compound group SX1660").

The Compound (L-6), wherein n represents 0, $R^{41}$ represents a hydrogen atom, $R^{42}$ represents a hydrogen atom, $R^{43}$ represents a hydrogen atom, $R^{3b}$ represents a fluorine atom, and $R^{4c}$ represents any one substituent described in Table L15 to Table L16 (hereinafter referred to as "Compound group SX1661").

The Compound (L-6), wherein n represents 0, $R^{41}$ represents a hydrogen atom, $R^{42}$ represents a hydrogen atom, $R^{45}$ represents a hydrogen atom, $R^{3b}$ represents a chlorine atom, and $R^{4c}$ represents any one substituent described in Table L15 to Table L16 (hereinafter referred to as "Compound group SX1662").

The Compound (L-6), wherein n represents 0, $R^{41}$ represents a hydrogen atom, $R^{42}$ represents a hydrogen atom, $R^{45}$ represents a hydrogen atom, $R^{3b}$ represents a bromine atom, and $R^{4c}$ represents any one substituent described in Table L15 to Table L16 (hereinafter referred to as "Compound group SX1663").

The Compound (L-6), wherein n represents 0, $R^{41}$ represents a hydrogen atom, $R^{42}$ represents a hydrogen atom, $R^{45}$ represents a hydrogen atom, $R^{3b}$ represents $CF_3$, and $R^{4c}$ represents any one substituent described in Table L15 to Table L16 (hereinafter referred to as "Compound group SX1664").

The Compound (L-6), wherein n represents 0, $R^{41}$ represents a hydrogen atom, $R^{42}$ represents a hydrogen atom, $R^{45}$ represents a methyl group, $R^{3b}$ represents a hydrogen atom, and $R^{4c}$ represents any one substituent described in Table L15 to Table L16 (hereinafter referred to as "Compound group SX1665").

The Compound (L-6), wherein n represents 0, $R^{41}$ represents a hydrogen atom, $R^{42}$ represents a hydrogen atom, $R^{45}$ represents a methyl group, $R^{3b}$ represents a fluorine atom, and $R^{4c}$ represents any one substituent described in Table L15 to Table L16 (hereinafter referred to as "Compound group SX1666").

The Compound (L-6), wherein n represents 0, $R^{41}$ represents a hydrogen atom, $R^{42}$ represents a hydrogen atom, $R^{45}$ represents a methyl group, $R^{3b}$ represents a chlorine atom, and $R^{4c}$ represents any one substituent described in Table L15 to Table L16 (hereinafter referred to as "Compound group SX1667").

The Compound (L-6), wherein n represents 0, $R^{41}$ represents a hydrogen atom, $R^{42}$ represents a hydrogen atom, $R^{45}$ represents a methyl group, $R^{3b}$ represents a bromine atom, and $R^{4c}$ represents any one substituent described in Table L15 to Table L16 (hereinafter referred to as "Compound group SX1668").

The Compound (L-6), wherein n represents 0, $R^{41}$ represents a hydrogen atom, $R^{42}$ represents a hydrogen atom, $R^{45}$ represents a methyl group, $R^{3b}$ represents $CF_3$, and $R^{4c}$ represents any one substituent described in Table L15 to Table L16 (hereinafter referred to as "Compound group SX1669").

The Compound (L-6), wherein n represents 0, $R^{41}$ represents a hydrogen atom, $R^{42}$ represents a hydrogen atom, $R^{45}$ represents an ethyl group, $R^{3b}$ represents a hydrogen atom, and $R^{4c}$ represents any one substituent described in Table L15 to Table L16 (hereinafter referred to as "Compound group SX1670").

The Compound (L-6), wherein n represents 0, $R^{41}$ represents a hydrogen atom, $R^{42}$ represents a hydrogen atom, $R^{45}$ represents an ethyl group, $R^{3b}$ represents a fluorine atom, and $R^{4c}$ represents any one substituent described in Table L15 to Table L16 (hereinafter referred to as "Compound group SX1671").

The Compound (L-6), wherein n represents 0, $R^{41}$ represents a hydrogen atom, $R^{42}$ represents a hydrogen atom, $R^{45}$ represents an ethyl group, $R^{3b}$ represents a chlorine atom, and $R^{4c}$ represents any one substituent described in Table L15 to Table L16 (hereinafter referred to as "Compound group SX1672").

The Compound (L-6), wherein n represents 0, $R^{41}$ represents a hydrogen atom, $R^{42}$ represents a hydrogen atom, $R^{45}$ represents an ethyl group, $R^{3b}$ represents a bromine atom, and $R^{4c}$ represents any one substituent described in Table L15 to Table L16 (hereinafter referred to as "Compound group SX1673").

The Compound (L-6), wherein n represents 0, $R^{41}$ represents a hydrogen atom, $R^{42}$ represents a hydrogen atom, $R^{45}$ represents an ethyl group, $R^{3b}$ represents $CF_3$, and $R^{4c}$ represents any one substituent described in Table L15 to Table L16 (hereinafter referred to as "Compound group SX1674").

The Compound (L-6), wherein n represents 0, $R^{41}$ represents a hydrogen atom, $R^{42}$ represents a methyl group, $R^{45}$ represents a hydrogen atom, $R^{3b}$ represents a hydrogen atom, and $R^{4c}$ represents any one substituent described in Table L15 to Table L16 (hereinafter referred to as "Compound group SX1675").

The Compound (L-6), wherein n represents 0, $R^{41}$ represents a hydrogen atom, $R^{42}$ represents a methyl group, $R^{45}$ represents a hydrogen atom, $R^{3b}$ represents a fluorine atom, and $R^{4c}$ represents any one substituent described in Table L15 to Table L16 (hereinafter referred to as "Compound group SX1676").

The Compound (L-6), wherein n represents 0, $R^{41}$ represents a hydrogen atom, $R^{42}$ represents a methyl group, $R^{45}$ represents a hydrogen atom, $R^{3b}$ represents a chlorine atom, and $R^{4c}$ represents any one substituent described in Table L15 to Table L16 (hereinafter referred to as "Compound group SX1677").

The Compound (L-6), wherein n represents 0, $R^{41}$ represents a hydrogen atom, $R^{42}$ represents a methyl group, $R^{45}$ represents a hydrogen atom, $R^{3b}$ represents a bromine atom, and $R^{4c}$ represents any one substituent described in Table L15 to Table L16 (hereinafter referred to as "Compound group SX1678").

The Compound (L-6), wherein n represents 0, $R^{41}$ represents a hydrogen atom, $R^{42}$ represents a methyl group, $R^{45}$ represents a hydrogen atom, $R^{3b}$ represents $CF_3$, and $R^{4c}$ represents any one substituent described in Table L15 to Table L16 (hereinafter referred to as "Compound group SX1679").

The Compound (L-6), wherein n represents 0, $R^{41}$ represents a hydrogen atom, $R^{42}$ represents a methyl group, $R^{45}$ represents a methyl group, $R^{3b}$ represents a hydrogen atom, and $R^{4c}$ represents any one substituent described in Table L15 to Table L16 (hereinafter referred to as "Compound group SX1680").

The Compound (L-6), wherein n represents 0, $R^{41}$ represents a hydrogen atom, $R^{42}$ represents a methyl group, $R^{45}$ represents a methyl group, $R^{3b}$ represents a fluorine atom, and $R^{4c}$ represents any one substituent described in Table L15 to Table L16 (hereinafter referred to as "Compound group SX1681").

The Compound (L-6), wherein n represents 0, $R^{41}$ represents a hydrogen atom, $R^{42}$ represents a methyl group, $R^{45}$ represents a methyl group, $R^{3b}$ represents a chlorine atom, and $R^{4c}$ represents any one substituent described in Table L15 to Table L16 (hereinafter referred to as "Compound group SX1682").

The Compound (L-6), wherein n represents 0, $R^{41}$ represents a hydrogen atom, $R^{42}$ represents a methyl group, $R^{45}$ represents a methyl group, $R^{3b}$ represents a bromine atom, and $R^{4c}$ represents any one substituent described in Table L15 to Table L16 (hereinafter referred to as "Compound group SX1683").

The Compound (L-6), wherein n represents 0, $R^{41}$ represents a hydrogen atom, $R^{42}$ represents a methyl group, $R^{45}$ represents a methyl group, $R^{3b}$ represents $CF_3$, and $R^{4c}$ represents any one substituent described in Table L15 to Table L16 (hereinafter referred to as "Compound group SX1684").

The Compound (L-6), wherein n represents 0, $R^{41}$ represents a hydrogen atom, $R^{42}$ represents a methyl group, $R^{45}$ represents an ethyl group, $R^{3b}$ represents a hydrogen atom, and $R^{4c}$ represents any one substituent described in Table L15 to Table L16 (hereinafter referred to as "Compound group SX1685").

The Compound (L-6), wherein n represents 0, $R^{41}$ represents a hydrogen atom, $R^{42}$ represents a methyl group, $R^{45}$ represents an ethyl group, $R^{3b}$ represents a fluorine atom, and $R^{4c}$ represents any one substituent described in Table L15 to Table L16 (hereinafter referred to as "Compound group SX1686").

The Compound (L-6), wherein n represents 0, $R^{41}$ represents a hydrogen atom, $R^{42}$ represents a methyl group, $R^{45}$ represents an ethyl group, $R^{3b}$ represents a chlorine atom, and $R^{4c}$ represents any one substituent described in Table L15 to Table L16 (hereinafter referred to as "Compound group SX1687").

The Compound (L-6), wherein n represents 0, $R^{41}$ represents a hydrogen atom, $R^{42}$ represents a methyl group, $R^{45}$ represents an ethyl group, $R^{3b}$ represents a bromine atom, and $R^{4c}$ represents any one substituent described in Table L15 to Table L16 (hereinafter referred to as "Compound group SX1688").

The Compound (L-6), wherein n represents 0, $R^{41}$ represents a hydrogen atom, $R^{42}$ represents a methyl group, $R^{45}$ represents an ethyl group, $R^{3b}$ represents $CF_3$, and $R^{4c}$ represents any one substituent described in Table L15 to Table L16 (hereinafter referred to as "Compound group SX1689").

The Compound (L-6), wherein n represents 0, $R^{41}$ represents a methyl group, $R^{42}$ represents a hydrogen atom, $R^{45}$ represents a hydrogen atom, $R^{3b}$ represents a hydrogen atom, and $R^{4c}$ represents any one substituent described in Table L15 to Table L16 (hereinafter referred to as "Compound group SX1690").

The Compound (L-6), wherein n represents 0, $R^{41}$ represents a methyl group, $R^{42}$ represents a hydrogen atom, $R^{45}$ represents a hydrogen atom, $R^{3b}$ represents a fluorine atom, and $R^{4c}$ represents any one substituent described in Table L15 to Table L16 (hereinafter referred to as "Compound group SX1691").

The Compound (L-6), wherein n represents 0, $R^{41}$ represents a methyl group, $R^{42}$ represents a hydrogen atom, $R^{45}$ represents a hydrogen atom, $R^{3b}$ represents a chlorine atom, and $R^{4c}$ represents any one substituent described in Table L15 to Table L16 (hereinafter referred to as "Compound group SX1692").

The Compound (L-6), wherein n represents 0, $R^{41}$ represents a methyl group, $R^{42}$ represents a hydrogen atom, $R^{45}$ represents a hydrogen atom, $R^{3b}$ represents a bromine atom, and $R^{4c}$ represents any one substituent described in Table L15 to Table L16 (hereinafter referred to as "Compound group SX1693").

The Compound (L-6), wherein n represents 0, $R^{41}$ represents a methyl group, $R^{42}$ represents a hydrogen atom, $R^{45}$ represents a hydrogen atom, $R^{3b}$ represents $CF_3$, and $R^{4c}$ represents any one substituent described in Table L15 to Table L16 (hereinafter referred to as "Compound group SX1694").

The Compound (L-6), wherein n represents 0, $R^{41}$ represents a methyl group, $R^{42}$ represents a hydrogen atom, $R^{45}$ represents a methyl group, $R^{3b}$ represents a hydrogen atom, and $R^{4c}$ represents any one substituent described in Table L15 to Table L16 (hereinafter referred to as "Compound group SX1695").

The Compound (L-6), wherein n represents 0, $R^{41}$ represents a methyl group, $R^{42}$ represents a hydrogen atom, $R^{45}$ represents a methyl group, $R^{3b}$ represents a fluorine atom, and $R^{4c}$ represents any one substituent described in Table L15 to Table L16 (hereinafter referred to as "Compound group SX1696").

The Compound (L-6), wherein n represents 0, $R^{41}$ represents a methyl group, $R^{42}$ represents a hydrogen atom, $R^{45}$ represents a methyl group, $R^{3b}$ represents a chlorine atom, and $R^{4c}$ represents any one substituent described in Table L15 to Table L16 (hereinafter referred to as "Compound group SX1697").

The Compound (L-6), wherein n represents 0, $R^{41}$ represents a methyl group, $R^{42}$ represents a hydrogen atom, $R^{45}$ represents a methyl group, $R^{3b}$ represents a bromine atom, and $R^{4c}$ represents any one substituent described in Table L15 to Table L16 (hereinafter referred to as "Compound group SX1698").

The Compound (L-6), wherein n represents 0, $R^{41}$ represents a methyl group, $R^{42}$ represents a hydrogen atom, $R^{45}$ represents a methyl group, $R^{3b}$ represents $CF_3$, and $R^{4c}$ represents any one substituent described in Table L15 to Table L16 (hereinafter referred to as "Compound group SX1699").

The Compound (L-6), wherein n represents 0, $R^{41}$ represents a methyl group, $R^{42}$ represents a hydrogen atom, $R^{45}$ represents an ethyl group, $R^{3b}$ represents a hydrogen atom, and $R^{4c}$ represents any one substituent described in Table L15 to Table L16 (hereinafter referred to as "Compound group SX1700").

The Compound (L-6), wherein n represents 0, $R^{41}$ represents a methyl group, $R^{42}$ represents a hydrogen atom, $R^{45}$ represents an ethyl group, $R^{3b}$ represents a fluorine atom, and $R^{4c}$ represents any one substituent described in Table L15 to Table L16 (hereinafter referred to as "Compound group SX1701").

The Compound (L-6), wherein n represents 0, $R^{41}$ represents a methyl group, $R^{42}$ represents a hydrogen atom, $R^{45}$ represents an ethyl group, $R^{3b}$ represents a chlorine atom, and $R^{4c}$ represents any one substituent described in Table L15 to Table L16 (hereinafter referred to as "Compound group SX1702").

The Compound (L-6), wherein n represents 0, $R^{41}$ represents a methyl group, $R^{42}$ represents a hydrogen atom, $R^{45}$ represents an ethyl group, $R^{3b}$ represents a bromine atom, and $R^{4c}$ represents any one substituent described in Table L15 to Table L16 (hereinafter referred to as "Compound group SX1703").

The Compound (L-6), wherein n represents 0, $R^{41}$ represents a methyl group, $R^{42}$ represents a hydrogen atom, $R^{45}$ represents an ethyl group, $R^{3b}$ represents $CF_3$, and $R^{4c}$ represents any one substituent described in Table L15 to Table L16 (hereinafter referred to as "Compound group SX1704").

The Compound (L-6), wherein n represents 0, $R^{41}$ represents a methyl group, $R^{42}$ represents a methyl group, $R^{45}$ represents a hydrogen atom, $R^{3b}$ represents a hydrogen atom, and $R^{4c}$ represents any one substituent described in Table L15 to Table L16 (hereinafter referred to as "Compound group SX1705").

The Compound (L-6), wherein n represents 0, $R^{41}$ represents a methyl group, $R^{42}$ represents a methyl group, $R^{45}$ represents a hydrogen atom, $R^{3b}$ represents a fluorine atom, and $R^{4c}$ represents any one substituent described in Table L15 to Table L16 (hereinafter referred to as "Compound group SX1706").

The Compound (L-6), wherein n represents 0, $R^{41}$ represents a methyl group, $R^{42}$ represents a methyl group, $R^{45}$ represents a hydrogen atom, $R^{3b}$ represents a chlorine Table L15 to Table L16 (hereinafter referred to as "Compound group SX1707").

The Compound (L-6), wherein n represents 0, $R^{41}$ represents a methyl group, $R^{42}$ represents a methyl group, $R^{45}$ represents a hydrogen atom, $R^{3b}$ represents a bromine atom, and $R^{4c}$ represents any one substituent described in Table L15 to Table L16 (hereinafter referred to as "Compound group SX1708").

The Compound (L-6), wherein n represents 0, $R^{41}$ represents a methyl group, $R^{42}$ represents a methyl group, $R^{45}$ represents a hydrogen atom, $R^{3b}$ represents $CF_3$, and $R^{4c}$ represents any one substituent described in Table L15 to Table L16 (hereinafter referred to as "Compound group SX1709").

The Compound (L-6), wherein n represents 0, $R^{41}$ represents a methyl group, $R^{42}$ represents a methyl group, $R^{45}$ represents a methyl group, $R^{3b}$ represents a hydrogen atom, and $R^{4c}$ represents any one substituent described in Table L15 to Table L16 (hereinafter referred to as "Compound group SX1710").

The Compound (L-6), wherein n represents 0, $R^{41}$ represents a methyl group, $R^{42}$ represents a methyl group, $R^{45}$ represents a methyl group, $R^{3b}$ represents a fluorine atom, and $R^{4c}$ represents any one substituent described in Table L15 to Table L16 (hereinafter referred to as "Compound group SX1711").

The Compound (L-6), wherein n represents 0, $R^{41}$ represents a methyl group, $R^{42}$ represents a methyl group, $R^{45}$ represents a methyl group, $R^{3b}$ represents a chlorine atom, and $R^{4c}$ represents any one substituent described in Table L15 to Table L16 (hereinafter referred to as "Compound group SX1712").

The Compound (L-6), wherein n represents 0, $R^{41}$ represents a methyl group, $R^{42}$ represents a methyl group, $R^{45}$ represents a methyl group, $R^{3b}$ represents a bromine atom, and $R^{4c}$ represents any one substituent described in Table L15 to Table L16 (hereinafter referred to as "Compound group SX1713").

The Compound (L-6), wherein n represents 0, $R^{41}$ represents a methyl group, $R^{42}$ represents a methyl group, $R^{45}$ represents a methyl group, $R^{3b}$ represents $CF_3$, and $R^{4c}$ represents any one substituent described in Table L15 to Table L16 (hereinafter referred to as "Compound group SX1714").

The Compound (L-6), wherein n represents 0, $R^{41}$ represents a methyl group, $R^{42}$ represents a methyl group, $R^{45}$ represents an ethyl group, $R^{3b}$ represents a hydrogen atom, and $R^{4c}$ represents any one substituent described in Table L15 to Table L16 (hereinafter referred to as "Compound group SX1715").

The Compound (L-6), wherein n represents 0, $R^{41}$ represents a methyl group, $R^{42}$ represents a methyl group, $R^{45}$ represents an ethyl group, $R^{3b}$ represents a fluorine atom, and $R^{4c}$ represents any one substituent described in Table L15 to Table L16 (hereinafter referred to as "Compound group SX1716").

The Compound (L-6), wherein n represents 0, $R^{41}$ represents a methyl group, $R^{42}$ represents a methyl group, $R^{45}$ represents an ethyl group, $R^{3b}$ represents a chlorine atom, and $R^{4c}$ represents any one substituent described in Table L15 to Table L16 (hereinafter referred to as "Compound group SX1717").

The Compound (L-6), wherein n represents 0, $R^{41}$ represents a methyl group, $R^{42}$ represents a methyl group, $R^{45}$ represents an ethyl group, $R^{3b}$ represents a bromine atom, and $R^{4c}$ represents any one substituent described in Table L15 to Table L16 (hereinafter referred to as "Compound group SX1718").

The Compound (L-6), wherein n represents 0, $R^{41}$ represents a methyl group, $R^{42}$ represents a methyl group, $R^{45}$ represents an ethyl group, $R^{3b}$ represents $CF_3$, and $R^{4c}$ represents any one substituent described in Table L15 to Table L16 (hereinafter referred to as "Compound group SX1719").

The Compound (L-6), wherein n represents 1, $R^{41}$ represents a hydrogen atom, $R^{42}$ represents a hydrogen atom, $R^{45}$ represents a hydrogen atom, $R^{3b}$ represents a hydrogen atom, and $R^{4c}$ represents any one substituent described in Table L15 to Table L16 (hereinafter referred to as "Compound group SX1720").

The Compound (L-6), wherein n represents 1, $R^{41}$ represents a hydrogen atom, $R^{42}$ represents a hydrogen atom, $R^{45}$ represents a hydrogen atom, $R^{3b}$ represents a fluorine atom, and $R^{4c}$ represents any one substituent described in Table L15 to Table L16 (hereinafter referred to as "Compound group SX1721").

The Compound (L-6), wherein n represents 1, $R^{41}$ represents a hydrogen atom, $R^{42}$ represents a hydrogen atom, $R^{45}$ represents a hydrogen atom, $R^{3b}$ represents a chlorine atom, and $R^{4c}$ represents any one substituent described in Table L15 to Table L16 (hereinafter referred to as "Compound group SX1722").

The Compound (L-6), wherein n represents 1, $R^{41}$ represents a hydrogen atom, $R^{42}$ represents a hydrogen atom, $R^{45}$ represents a hydrogen atom, $R^{3b}$ represents a bromine atom, and $R^{4c}$ represents any one substituent described in Table L15 to Table L16 (hereinafter referred to as "Compound group SX1723").

The Compound (L-6), wherein n represents 1, $R^{41}$ represents a hydrogen atom, $R^{42}$ represents a hydrogen atom, $R^{45}$ represents a hydrogen atom, $R^{3b}$ represents $CF_3$, and $R^{4c}$ represents any one substituent described in Table L15 to Table L16 (hereinafter referred to as "Compound group SX1724").

The Compound (L-6), wherein n represents 1, $R^{41}$ represents a hydrogen atom, $R^{42}$ represents a hydrogen atom, $R^{45}$ represents a methyl group, $R^{3b}$ represents a hydrogen atom, and $R^{4c}$ represents any one substituent described in Table L15 to Table L16 (hereinafter referred to as "Compound group SX1725").

The Compound (L-6), wherein n represents 1, $R^{41}$ represents a hydrogen atom, $R^{42}$ represents a hydrogen atom, $R^{45}$ represents a methyl group, $R^{3b}$ represents a fluorine atom, and $R^{4c}$ represents any one substituent described in Table L15 to Table L16 (hereinafter referred to as "Compound group SX1726").

The Compound (L-6), wherein n represents 1, $R^{41}$ represents a hydrogen atom, $R^{42}$ represents a hydrogen atom, $R^{45}$ represents a methyl group, $R^{3b}$ represents a chlorine atom, and $R^{4c}$ represents any one substituent described in Table L15 to Table L16 (hereinafter referred to as "Compound group SX1727").

The Compound (L-6), wherein n represents 1, $R^{41}$ represents a hydrogen atom, $R^{42}$ represents a hydrogen atom, $R^{45}$ represents a methyl group, $R^{3b}$ represents a bromine atom, and $R^{4c}$ represents any one substituent described in Table L15 to Table L16 (hereinafter referred to as "Compound group SX1728").

The Compound (L-6), wherein n represents 1, $R^{41}$ represents a hydrogen atom, $R^{42}$ represents a hydrogen atom, $R^{45}$ represents a methyl group, $R^{3b}$ represents $CF_3$, and $R^{4c}$ represents any one substituent described in Table L15 to Table L16 (hereinafter referred to as "Compound group SX1729").

The Compound (L-6), wherein n represents 1, $R^{41}$ represents a hydrogen atom, $R^{42}$ represents a hydrogen atom, $R^{45}$ represents an ethyl group, $R^{3b}$ represents a hydrogen atom, and $R^{4c}$ represents any one substituent described in Table L15 to Table L16 (hereinafter referred to as "Compound group SX1730").

The Compound (L-6), wherein n represents 1, $R^{41}$ represents a hydrogen atom, $R^{42}$ represents a hydrogen atom, $R^{45}$ represents an ethyl group, $R^{3b}$ represents a fluorine atom, and $R^{4c}$ represents any one substituent described in Table L15 to Table L16 (hereinafter referred to as "Compound group SX1731").

The Compound (L-6), wherein n represents 1, $R^{41}$ represents a hydrogen atom, $R^{42}$ represents a hydrogen atom, $R^{45}$ represents an ethyl group, $R^{3b}$ represents a chlorine Table L15 to Table L16 (hereinafter referred to as "Compound group SX1732").

The Compound (L-6), wherein n represents 1, $R^{41}$ represents a hydrogen atom, $R^{42}$ represents a hydrogen atom, $R^{45}$ represents an ethyl group, $R^{3b}$ represents a bromine atom, and $R^{4c}$ represents any one substituent described in Table L15 to Table L16 (hereinafter referred to as "Compound group SX1733").

The Compound (L-6), wherein n represents 1, $R^{41}$ represents a hydrogen atom, $R^{42}$ represents a hydrogen atom, $R^{45}$ represents an ethyl group, $R^{3b}$ represents $CF_3$, and $R^{4c}$ represents any one substituent described in Table L15 to Table L16 (hereinafter referred to as "Compound group SX1734").

The Compound (L-6), wherein n represents 1, $R^{41}$ represents a hydrogen atom, $R^{42}$ represents a methyl group, $R^{45}$ represents a hydrogen atom, $R^{3b}$ represents a hydrogen atom, and $R^{4c}$ represents any one substituent described in Table L15 to Table L16 (hereinafter referred to as "Compound group SX1735").

The Compound (L-6), wherein n represents 1, $R^{41}$ represents a hydrogen atom, $R^{42}$ represents a methyl group, $R^{45}$ represents a hydrogen atom, $R^{3b}$ represents a fluorine atom, and $R^{4c}$ represents any one substituent described in Table L15 to Table L16 (hereinafter referred to as "Compound group SX1736").

The Compound (L-6), wherein n represents 1, $R^{41}$ represents a hydrogen atom, $R^{42}$ represents a methyl group, $R^{45}$ represents a hydrogen atom, $R^{3b}$ represents a chlorine atom, and $R^{4c}$ represents any one substituent described in Table L15 to Table L16 (hereinafter referred to as "Compound group SX1737").

The Compound (L-6), wherein n represents 1, $R^{41}$ represents a hydrogen atom, $R^{42}$ represents a methyl group, $R^{45}$ represents a hydrogen atom, $R^{3b}$ represents a bromine atom, and $R^{4c}$ represents any one substituent described in Table L15 to Table L16 (hereinafter referred to as "Compound group SX1738").

The Compound (L-6), wherein n represents 1, $R^{41}$ represents a hydrogen atom, $R^{42}$ represents a methyl group, $R^{45}$ represents a hydrogen atom, $R^{3b}$ represents $CF_3$, and $R^{4c}$ represents any one substituent described in Table L15 to Table L16 (hereinafter referred to as "Compound group SX1739").

The Compound (L-6), wherein n represents 1, $R^{41}$ represents a hydrogen atom, $R^{42}$ represents a methyl group, $R^{45}$ represents a methyl group, $R^{3b}$ represents a hydrogen atom, and $R^{4c}$ represents any one substituent described in Table L15 to Table L16 (hereinafter referred to as "Compound group SX1740").

The Compound (L-6), wherein n represents 1, $R^{41}$ represents a hydrogen atom, $R^{42}$ represents a methyl group, $R^{45}$ represents a methyl group, $R^{3b}$ represents a fluorine atom, and $R^{4c}$ represents any one substituent described in Table L15 to Table L16 (hereinafter referred to as "Compound group SX1741").

The Compound (L-6), wherein n represents 1, $R^{41}$ represents a hydrogen atom, $R^{42}$ represents a methyl group, $R^{45}$ represents a methyl group, $R^{3b}$ represents a chlorine atom, and $R^{4c}$ represents any one substituent described in Table L15 to Table L16 (hereinafter referred to as "Compound group SX1742").

The Compound (L-6), wherein n represents 1, $R^{41}$ represents a hydrogen atom, $R^{42}$ represents a methyl group, $R^{45}$ represents a methyl group, $R^{3b}$ represents a bromine atom, and $R^{4c}$ represents any one substituent described in Table L15 to Table L16 (hereinafter referred to as "Compound group SX1743").

The Compound (L-6), wherein n represents 1, $R^{41}$ represents a hydrogen atom, $R^{42}$ represents a methyl group, $R^{45}$ represents a methyl group, $R^{3b}$ represents $CF_3$, and $R^{4c}$ represents any one substituent described in Table L15 to Table L16 (hereinafter referred to as "Compound group SX1744").

The Compound (L-6), wherein n represents 1, $R^{41}$ represents a hydrogen atom, $R^{42}$ represents a methyl group, $R^{45}$ represents an ethyl group, $R^{3b}$ represents a hydrogen atom, and $R^{4c}$ represents any one substituent described in Table L15 to Table L16 (hereinafter referred to as "Compound group SX1745").

The Compound (L-6), wherein n represents 1, $R^{41}$ represents a hydrogen atom, $R^{42}$ represents a methyl group, $R^{45}$ represents an ethyl group, $R^{3b}$ represents a fluorine atom, and $R^{4c}$ represents any one substituent described in Table L15 to Table L16 (hereinafter referred to as "Compound group SX1746").

The Compound (L-6), wherein n represents 1, $R^{41}$ represents a hydrogen atom, $R^{42}$ represents a methyl group, $R^{45}$ represents an ethyl group, $R^{3b}$ represents a chlorine atom, and $R^{4c}$ represents any one substituent described in Table L15 to Table L16 (hereinafter referred to as "Compound group SX1747").

The Compound (L-6), wherein n represents 1, $R^{41}$ represents a hydrogen atom, $R^{42}$ represents a methyl group, $R^{45}$ represents an ethyl group, $R^{3b}$ represents a bromine atom, and $R^{4c}$ represents any one substituent described in Table L15 to Table L16 (hereinafter referred to as "Compound group SX1748").

The Compound (L-6), wherein n represents 1, $R^{41}$ represents a hydrogen atom, $R^{42}$ represents a methyl group, $R^{45}$ represents an ethyl group, $R^{3b}$ represents $CF_3$, and $R^{4c}$ represents any one substituent described in Table L15 to Table L16 (hereinafter referred to as "Compound group SX1749").

The Compound (L-6), wherein n represents 1, $R^{41}$ represents a methyl group, $R^{42}$ represents a hydrogen atom, $R^{45}$ represents a hydrogen atom, $R^{3b}$ represents a hydrogen atom, and $R^{4c}$ represents any one substituent described in Table L15 to Table L16 (hereinafter referred to as "Compound group SX1750").

The Compound (L-6), wherein n represents 1, $R^{41}$ represents a methyl group, $R^{42}$ represents a hydrogen atom, $R^{45}$ represents a hydrogen atom, $R^{3b}$ represents a fluorine atom, and $R^{4c}$ represents any one substituent described in Table L15 to Table L16 (hereinafter referred to as "Compound group SX1751").

The Compound (L-6), wherein n represents 1, $R^{41}$ represents a methyl group, $R^{42}$ represents a hydrogen atom, $R^{45}$ represents a hydrogen atom, $R^{3b}$ represents a chlorine atom, and $R^{4c}$ represents any one substituent described in Table L15 to Table L16 (hereinafter referred to as "Compound group SX1752").

The Compound (L-6), wherein n represents 1, $R^{41}$ represents a methyl group, $R^{42}$ represents a hydrogen atom, $R^{45}$ represents a hydrogen atom, $R^{3b}$ represents a bromine atom, and $R^{4c}$ represents any one substituent described in Table L15 to Table L16 (hereinafter referred to as "Compound group SX1753").

The Compound (L-6), wherein n represents 1, $R^{41}$ represents a methyl group, $R^{42}$ represents a hydrogen atom, $R^{45}$ represents a hydrogen atom, $R^{3b}$ represents $CF_3$, and $R^{4c}$ represents any one substituent described in Table L15 to Table L16 (hereinafter referred to as "Compound group SX1754").

The Compound (L-6), wherein n represents 1, $R^{41}$ represents a methyl group, $R^{42}$ represents a hydrogen atom, $R^{45}$ represents a methyl group, $R^{3b}$ represents a hydrogen atom, and $R^{4c}$ represents any one substituent described in Table L15 to Table L16 (hereinafter referred to as "Compound group SX1755").

The Compound (L-6), wherein n represents 1, $R^{41}$ represents a methyl group, $R^{42}$ represents a hydrogen atom, $R^{45}$ represents a methyl group, $R^{3b}$ represents a fluorine atom, and $R^{4c}$ represents any one substituent described in Table L15 to Table L16 (hereinafter referred to as "Compound group SX1756").

The Compound (L-6), wherein n represents 1, $R^{41}$ represents a methyl group, $R^{42}$ represents a hydrogen atom, $R^{45}$ represents a methyl group, $R^{3b}$ represents a chlorine Table L15 to Table L16 (hereinafter referred to as "Compound group SX1757").

The Compound (L-6), wherein n represents 1, $R^{41}$ represents a methyl group, $R^{42}$ represents a hydrogen atom, $R^{45}$ represents a methyl group, $R^{3b}$ represents a bromine atom, and $R^{4c}$ represents any one substituent described in Table L15 to Table L16 (hereinafter referred to as "Compound group SX1758").

The Compound (L-6), wherein n represents 1, $R^{41}$ represents a methyl group, $R^{42}$ represents a hydrogen atom, $R^{45}$ represents a methyl group, $R^{3b}$ represents $CF_3$, and $R^{4c}$ represents any one substituent described in Table L15 to Table L16 (hereinafter referred to as "Compound group SX1759").

The Compound (L-6), wherein n represents 1, $R^{41}$ represents a methyl group, $R^{42}$ represents a hydrogen atom, $R^{45}$ represents an ethyl group, $R^{3b}$ represents a hydrogen atom, and $R^{4c}$ represents any one substituent described in Table L15 to Table L16 (hereinafter referred to as "Compound group SX1760").

The Compound (L-6), wherein n represents 1, $R^{41}$ represents a methyl group, $R^{42}$ represents a hydrogen atom, $R^{45}$ represents an ethyl group, $R^{3b}$ represents a fluorine atom, and $R^{4c}$ represents any one substituent described in Table L15 to Table L16 (hereinafter referred to as "Compound group SX1761").

The Compound (L-6), wherein n represents 1, $R^{41}$ represents a methyl group, $R^{42}$ represents a hydrogen atom, $R^{45}$ represents an ethyl group, $R^{3b}$ represents a chlorine atom, and $R^{4c}$ represents any one substituent described in Table L15 to Table L16 (hereinafter referred to as "Compound group SX1762").

The Compound (L-6), wherein n represents 1, $R^{41}$ represents a methyl group, $R^{42}$ represents a hydrogen atom, $R^{45}$ represents an ethyl group, $R^{3b}$ represents a bromine atom, and $R^{4c}$ represents any one substituent described in Table L15 to Table L16 (hereinafter referred to as "Compound group SX1763").

The Compound (L-6), wherein n represents 1, $R^{41}$ represents a methyl group, $R^{42}$ represents a hydrogen atom, $R^{45}$ represents an ethyl group, $R^{3b}$ represents $CF_3$, and $R^{4c}$ represents any one substituent described in Table L15 to Table L16 (hereinafter referred to as "Compound group SX1764").

The Compound (L-6), wherein n represents 1, $R^{41}$ represents a methyl group, $R^{42}$ represents a methyl group, $R^{45}$ represents a hydrogen atom, $R^{3b}$ represents a hydrogen atom, and $R^{4c}$ represents any one substituent described in Table L15 to Table L16 (hereinafter referred to as "Compound group SX1765").

The Compound (L-6), wherein n represents 1, $R^{41}$ represents a methyl group, $R^{42}$ represents a methyl group, $R^{45}$ represents a hydrogen atom, $R^{3b}$ represents a fluorine atom, and $R^{4c}$ represents any one substituent described in Table L15 to Table L16 (hereinafter referred to as "Compound group SX1766").

The Compound (L-6), wherein n represents 1, $R^{41}$ represents a methyl group, $R^{42}$ represents a methyl group, $R^{45}$ represents a hydrogen atom, $R^{3b}$ represents a chlorine atom, and $R^{4c}$ represents any one substituent described in Table L15 to Table L16 (hereinafter referred to as "Compound group SX1767").

The Compound (L-6), wherein n represents 1, $R^{41}$ represents a methyl group, $R^{42}$ represents a methyl group, $R^{45}$ represents a hydrogen atom, $R^{3b}$ represents a bromine atom, and $R^{4c}$ represents any one substituent described in Table L15 to Table L16 (hereinafter referred to as "Compound group SX1768").

The Compound (L-6), wherein n represents 1, $R^{41}$ represents a methyl group, $R^{42}$ represents a methyl group, $R^{45}$ represents a hydrogen atom, $R^{3b}$ represents $CF_3$, and $R^{4c}$ represents any one substituent described in Table L15 to Table L16 (hereinafter referred to as "Compound group SX1769").

The Compound (L-6), wherein n represents 1, $R^{41}$ represents a methyl group, $R^{42}$ represents a methyl group, $R^{45}$ represents a methyl group, $R^{3b}$ represents a hydrogen atom, and $R^{4c}$ represents any one substituent described in Table L15 to Table L16 (hereinafter referred to as "Compound group SX1770").

The Compound (L-6), wherein n represents 1, $R^{41}$ represents a methyl group, $R^{42}$ represents a methyl group, $R^{45}$ represents a methyl group, $R^{3b}$ represents a fluorine atom, and $R^{4c}$ represents any one substituent described in Table L15 to Table L16 (hereinafter referred to as "Compound group SX1771").

The Compound (L-6), wherein n represents 1, $R^{41}$ represents a methyl group, $R^{42}$ represents a methyl group, $R^{45}$ represents a methyl group, $R^{3b}$ represents a chlorine atom, and $R^{4c}$ represents any one substituent described in Table L15 to Table L16 (hereinafter referred to as "Compound group SX1772").

The Compound (L-6), wherein n represents 1, $R^{41}$ represents a methyl group, $R^{42}$ represents a methyl group, $R^{45}$ represents a methyl group, $R^{3b}$ represents a bromine atom, and $R^{4c}$ represents any one substituent described in Table L15 to Table L16 (hereinafter referred to as "Compound group SX1773").

The Compound (L-6), wherein n represents 1, $R^{41}$ represents a methyl group, $R^{42}$ represents a methyl group, $R^{45}$ represents a methyl group, $R^{3b}$ represents $CF_3$, and $R^{4c}$ represents any one substituent described in Table L15 to Table L16 (hereinafter referred to as "Compound group SX1774").

The Compound (L-6), wherein n represents 1, $R^{41}$ represents a methyl group, $R^{42}$ represents a methyl group, $R^{45}$ represents an ethyl group, $R^{3b}$ represents a hydrogen atom, and $R^{4c}$ represents any one substituent described in Table L15 to Table L16 (hereinafter referred to as "Compound group SX1775").

The Compound (L-6), wherein n represents 1, $R^{41}$ represents a methyl group, $R^{42}$ represents a methyl group, $R^{45}$ represents an ethyl group, $R^{3b}$ represents a fluorine atom, and $R^{4c}$ represents any one substituent described in Table L15 to Table L16 (hereinafter referred to as "Compound group SX1776").

The Compound (L-6), wherein n represents 1, $R^{41}$ represents a methyl group, $R^{42}$ represents a methyl group, $R^{45}$ represents an ethyl group, $R^{3b}$ represents a chlorine atom, and $R^{4c}$ represents any one substituent described in Table L15 to Table L16 (hereinafter referred to as "Compound group SX1777").

The Compound (L-6), wherein n represents 1, $R^{41}$ represents a methyl group, $R^{42}$ represents a methyl group, $R^{45}$ represents an ethyl group, $R^{3b}$ represents a bromine atom, and $R^{4c}$ represents any one substituent described in Table L15 to Table L16 (hereinafter referred to as "Compound group SX1778").

The Compound (L-6), wherein n represents 1, $R^{41}$ represents a methyl group, $R^{42}$ represents a methyl group, $R^{45}$ represents an ethyl group, $R^{3b}$ represents $CF_3$, and $R^{4c}$ represents any one substituent described in Table L15 to Table L16 (hereinafter referred to as "Compound group SX1779").

The Compound (L-6), wherein n represents 2, $R^{41}$ represents a hydrogen atom, $R^{42}$ represents a hydrogen atom, $R^{45}$ represents a hydrogen atom, $R^{3b}$ represents a hydrogen atom, and $R^{4c}$ represents any one substituent described in Table L15 to Table L16 (hereinafter referred to as "Compound group SX1780").

The Compound (L-6), wherein n represents 2, $R^{41}$ represents a hydrogen atom, $R^{42}$ represents a hydrogen atom, $R^{45}$ represents a hydrogen atom, $R^{3b}$ represents a fluorine atom, and $R^{4c}$ represents any one substituent described in Table L15 to Table L16 (hereinafter referred to as "Compound group SX1781").

The Compound (L-6), wherein n represents 2, $R^{41}$ represents a hydrogen atom, $R^{42}$ represents a hydrogen atom, $R^{45}$ represents a hydrogen atom, $R^{3b}$ represents a chlorine Table L15 to Table L16 (hereinafter referred to as "Compound group SX1782").

The Compound (L-6), wherein n represents 2, $R^{41}$ represents a hydrogen atom, $R^{42}$ represents a hydrogen atom, $R^{45}$ represents a hydrogen atom, $R^{3b}$ represents a bromine atom, and $R^{4c}$ represents any one substituent described in Table L15 to Table L16 (hereinafter referred to as "Compound group SX1783").

The Compound (L-6), wherein n represents 2, $R^{41}$ represents a hydrogen atom, $R^{42}$ represents a hydrogen atom, $R^{45}$ represents a hydrogen atom, $R^{3b}$ represents $CF_3$, and $R^{4c}$ represents any one substituent described in Table L15 to Table L16 (hereinafter referred to as "Compound group SX1784").

The Compound (L-6), wherein n represents 2, $R^{41}$ represents a hydrogen atom, $R^{42}$ represents a hydrogen atom, $R^{45}$ represents a methyl group, $R^{3b}$ represents a hydrogen atom, and $R^{4c}$ represents any one substituent described in Table L15 to Table L16 (hereinafter referred to as "Compound group SX1785").

The Compound (L-6), wherein n represents 2, $R^{41}$ represents a hydrogen atom, $R^{42}$ represents a hydrogen atom, $R^{45}$ represents a methyl group, $R^{3b}$ represents a fluorine atom, and $R^{4c}$ represents any one substituent described in Table L15 to Table L16 (hereinafter referred to as "Compound group SX1786").

The Compound (L-6), wherein n represents 2, $R^{41}$ represents a hydrogen atom, $R^{42}$ represents a hydrogen atom, $R^{45}$ represents a methyl group, $R^{3b}$ represents a chlorine atom, and $R^{4c}$ represents any one substituent described in Table L15 to Table L16 (hereinafter referred to as "Compound group SX1787").

The Compound (L-6), wherein n represents 2, $R^{41}$ represents a hydrogen atom, $R^{42}$ represents a hydrogen atom, $R^{45}$ represents a methyl group, $R^{3b}$ represents a bromine atom, and $R^{4c}$ represents any one substituent described in Table L15 to Table L16 (hereinafter referred to as "Compound group SX1788").

The Compound (L-6), wherein n represents 2, $R^{41}$ represents a hydrogen atom, $R^{42}$ represents a hydrogen atom, $R^{45}$ represents a methyl group, $R^{3b}$ represents $CF_3$, and $R^{4c}$ represents any one substituent described in Table L15 to Table L16 (hereinafter referred to as "Compound group SX1789").

The Compound (L-6), wherein n represents 2, $R^{41}$ represents a hydrogen atom, $R^{42}$ represents a hydrogen atom, $R^{45}$ represents an ethyl group, $R^{3b}$ represents a hydrogen atom, and $R^{4c}$ represents any one substituent described in Table L15 to Table L16 (hereinafter referred to as "Compound group SX1790").

The Compound (L-6), wherein n represents 2, $R^{41}$ represents a hydrogen atom, $R^{42}$ represents a hydrogen atom, $R^{45}$ represents an ethyl group, $R^{3b}$ represents a fluorine atom, and $R^{4c}$ represents any one substituent described in Table L15 to Table L16 (hereinafter referred to as "Compound group SX1791").

The Compound (L-6), wherein n represents 2, $R^{41}$ represents a hydrogen atom, $R^{42}$ represents a hydrogen atom, $R^{45}$ represents an ethyl group, $R^{3b}$ represents a chlorine atom, and $R^{4c}$ represents any one substituent described in Table L15 to Table L16 (hereinafter referred to as "Compound group SX1792").

The Compound (L-6), wherein n represents 2, $R^{41}$ represents a hydrogen atom, $R^{42}$ represents a hydrogen atom, $R^{45}$ represents an ethyl group, $R^{3b}$ represents a bromine atom, and $R^{4c}$ represents any one substituent described in Table L15 to Table L16 (hereinafter referred to as "Compound group SX1793").

The Compound (L-6), wherein n represents 2, $R^{41}$ represents a hydrogen atom, $R^{42}$ represents a hydrogen atom, $R^{45}$ represents an ethyl group, $R^{3b}$ represents $CF_3$, and $R^{4c}$ represents any one substituent described in Table L15 to Table L16 (hereinafter referred to as "Compound group SX1794").

The Compound (L-6), wherein n represents 2, $R^{41}$ represents a hydrogen atom, $R^{42}$ represents a methyl group, $R^{45}$ represents a hydrogen atom, $R^{3b}$ represents a hydrogen atom, and $R^{4c}$ represents any one substituent described in Table L15 to Table L16 (hereinafter referred to as "Compound group SX1795").

The Compound (L-6), wherein n represents 2, $R^{41}$ represents a hydrogen atom, $R^{42}$ represents a methyl group, $R^{45}$ represents a hydrogen atom, $R^{3b}$ represents a fluorine atom, and $R^{4c}$ represents any one substituent described in Table L15 to Table L16 (hereinafter referred to as "Compound group SX1796").

The Compound (L-6), wherein n represents 2, $R^{41}$ represents a hydrogen atom, $R^{42}$ represents a methyl group, $R^{45}$ represents a hydrogen atom, $R^{3b}$ represents a chlorine atom, and $R^{4c}$ represents any one substituent described in Table L15 to Table L16 (hereinafter referred to as "Compound group SX1797").

The Compound (L-6), wherein n represents 2, $R^{41}$ represents a hydrogen atom, $R^{42}$ represents a methyl group, $R^{45}$ represents a hydrogen atom, $R^{3b}$ represents a bromine atom, and $R^{4c}$ represents any one substituent described in Table L15 to Table L16 (hereinafter referred to as "Compound group SX1798").

The Compound (L-6), wherein n represents 2, $R^{41}$ represents a hydrogen atom, $R^{42}$ represents a methyl group, $R^{45}$ represents a hydrogen atom, $R^{3b}$ represents $CF_3$, and $R^{4c}$ represents any one substituent described in Table L15 to Table L16 (hereinafter referred to as "Compound group SX1799").

The Compound (L-6), wherein n represents 2, $R^{41}$ represents a hydrogen atom, $R^{42}$ represents a methyl group, $R^{45}$ represents a methyl group, $R^{3b}$ represents a hydrogen atom, and $R^{4c}$ represents any one substituent described in Table L15 to Table L16 (hereinafter referred to as "Compound group SX1800").

The Compound (L-6), wherein n represents 2, $R^{41}$ represents a hydrogen atom, $R^{42}$ represents a methyl group, $R^{45}$ represents a methyl group, $R^{3b}$ represents a fluorine atom, and $R^{4c}$ represents any one substituent described in Table L15 to Table L16 (hereinafter referred to as "Compound group SX1801").

The Compound (L-6), wherein n represents 2, $R^{41}$ represents a hydrogen atom, $R^{42}$ represents a methyl group, $R^{45}$ represents a methyl group, $R^{3b}$ represents a chlorine atom, and $R^{4c}$ represents any one substituent described in Table L15 to Table L16 (hereinafter referred to as "Compound group SX1802").

The Compound (L-6), wherein n represents 2, $R^{41}$ represents a hydrogen atom, $R^{42}$ represents a methyl group, $R^{45}$ represents a methyl group, $R^{3b}$ represents a bromine atom, and $R^{4c}$ represents any one substituent described in Table L15 to Table L16 (hereinafter referred to as "Compound group SX1803").

The Compound (L-6), wherein n represents 2, $R^{41}$ represents a hydrogen atom, $R^{42}$ represents a methyl group, $R^{45}$ represents a methyl group, $R^{3b}$ represents $CF_3$, and $R^{4c}$ represents any one substituent described in Table L15 to Table L16 (hereinafter referred to as "Compound group SX1804").

The Compound (L-6), wherein n represents 2, $R^{41}$ represents a hydrogen atom, $R^{42}$ represents a methyl group, $R^{45}$ represents an ethyl group, $R^{3b}$ represents a hydrogen atom, and $R^{4c}$ represents any one substituent described in Table L15 to Table L16 (hereinafter referred to as "Compound group SX1805").

The Compound (L-6), wherein n represents 2, $R^{41}$ represents a hydrogen atom, $R^{42}$ represents a methyl group, $R^{45}$ represents an ethyl group, $R^{3b}$ represents a fluorine atom, and $R^{4c}$ represents any one substituent described in Table L15 to Table L16 (hereinafter referred to as "Compound group SX1806").

The Compound (L-6), wherein n represents 2, $R^{41}$ represents a hydrogen atom, $R^{42}$ represents a methyl group, $R^{45}$ represents an ethyl group, $R^{3b}$ represents a chlorine Table L15 to Table L16 (hereinafter referred to as "Compound group SX1807").

The Compound (L-6), wherein n represents 2, $R^{41}$ represents a hydrogen atom, $R^{42}$ represents a methyl group, $R^{45}$ represents an ethyl group, $R^{3b}$ represents a bromine atom, and $R^{4c}$ represents any one substituent described in Table L15 to Table L16 (hereinafter referred to as "Compound group SX1808").

The Compound (L-6), wherein n represents 2, $R^{41}$ represents a hydrogen atom, $R^{42}$ represents a methyl group, $R^{45}$ represents an ethyl group, $R^{3b}$ represents $CF_3$, and $R^{4c}$ represents any one substituent described in Table L15 to Table L16 (hereinafter referred to as "Compound group SX1809").

The Compound (L-6), wherein n represents 2, $R^{41}$ represents a methyl group, $R^{42}$ represents a hydrogen atom, $R^{45}$ represents a hydrogen atom, $R^{3b}$ represents a hydrogen atom, and $R^{4c}$ represents any one substituent described in Table L15 to Table L16 (hereinafter referred to as "Compound group SX1810").

The Compound (L-6), wherein n represents 2, $R^{41}$ represents a methyl group, $R^{42}$ represents a hydrogen atom, $R^{45}$ represents a hydrogen atom, $R^{3b}$ represents a fluorine atom, and $R^{4c}$ represents any one substituent described in Table L15 to Table L16 (hereinafter referred to as "Compound group SX1811").

The Compound (L-6), wherein n represents 2, $R^{41}$ represents a methyl group, $R^{42}$ represents a hydrogen atom, $R^{45}$ represents a hydrogen atom, $R^{3b}$ represents a chlorine atom, and $R^{4c}$ represents any one substituent described in Table L15 to Table L16 (hereinafter referred to as "Compound group SX1812").

The Compound (L-6), wherein n represents 2, $R^{41}$ represents a methyl group, $R^{42}$ represents a hydrogen atom, $R^{45}$ represents a hydrogen atom, $R^{3b}$ represents a bromine atom, and $R^{4c}$ represents any one substituent described in Table L15 to Table L16 (hereinafter referred to as "Compound group SX1813").

The Compound (L-6), wherein n represents 2, $R^{41}$ represents a methyl group, $R^{42}$ represents a hydrogen atom, $R^{45}$ represents a hydrogen atom, $R^{3b}$ represents $CF_3$, and $R^{4c}$ represents any one substituent described in Table L15 to Table L16 (hereinafter referred to as "Compound group SX1814").

The Compound (L-6), wherein n represents 2, $R^{41}$ represents a methyl group, $R^{42}$ represents a hydrogen atom, $R^{45}$ represents a methyl group, $R^{3b}$ represents a hydrogen atom, and $R^{4c}$ represents any one substituent described in Table L15 to Table L16 (hereinafter referred to as "Compound group SX1815").

The Compound (L-6), wherein n represents 2, $R^{41}$ represents a methyl group, $R^{42}$ represents a hydrogen atom, $R^{45}$ represents a methyl group, $R^{3b}$ represents a fluorine atom, and $R^{4c}$ represents any one substituent described in Table L15 to Table L16 (hereinafter referred to as "Compound group SX1816").

The Compound (L-6), wherein n represents 2, $R^{41}$ represents a methyl group, $R^{42}$ represents a hydrogen atom, $R^{45}$ represents a methyl group, $R^{3b}$ represents a chlorine atom, and $R^{4c}$ represents any one substituent described in Table L15 to Table L16 (hereinafter referred to as "Compound group SX1817").

The Compound (L-6), wherein n represents 2, $R^{41}$ represents a methyl group, $R^{42}$ represents a hydrogen atom, $R^{45}$ represents a methyl group, $R^{3b}$ represents a bromine atom, and $R^{4c}$ represents any one substituent described in Table L15 to Table L16 (hereinafter referred to as "Compound group SX1818").

The Compound (L-6), wherein n represents 2, $R^{41}$ represents a methyl group, $R^{42}$ represents a hydrogen atom, $R^{45}$ represents a methyl group, $R^{3b}$ represents $CF_3$, and $R^{4c}$ represents any one substituent described in Table L15 to Table L16 (hereinafter referred to as "Compound group SX1819").

The Compound (L-6), wherein n represents 2, $R^{41}$ represents a methyl group, $R^{42}$ represents a hydrogen atom, $R^{45}$ represents an ethyl group, $R^{3b}$ represents a hydrogen atom, and $R^{4c}$ represents any one substituent described in Table L15 to Table L16 (hereinafter referred to as "Compound group SX1820").

The Compound (L-6), wherein n represents 2, $R^{41}$ represents a methyl group, $R^{42}$ represents a hydrogen atom, $R^{45}$ represents an ethyl group, $R^{3b}$ represents a fluorine atom, and $R^{4c}$ represents any one substituent described in Table L15 to Table L16 (hereinafter referred to as "Compound group SX1821").

The Compound (L-6), wherein n represents 2, $R^{41}$ represents a methyl group, $R^{42}$ represents a hydrogen atom, $R^{45}$ represents an ethyl group, $R^{3b}$ represents a chlorine atom, and $R^{4c}$ represents any one substituent described in Table L15 to Table L16 (hereinafter referred to as "Compound group SX1822").

The Compound (L-6), wherein n represents 2, $R^{41}$ represents a methyl group, $R^{42}$ represents a hydrogen atom, $R^{45}$ represents an ethyl group, $R^{3b}$ represents a bromine atom, and $R^{4c}$ represents any one substituent described in Table L15 to Table L16 (hereinafter referred to as "Compound group SX1823").

The Compound (L-6), wherein n represents 2, $R^{41}$ represents a methyl group, $R^{42}$ represents a hydrogen atom, $R^{45}$ represents an ethyl group, $R^{3b}$ represents $CF_3$, and $R^{4c}$ represents any one substituent described in Table L15 to Table L16 (hereinafter referred to as "Compound group SX1824").

The Compound (L-6), wherein n represents 2, $R^{41}$ represents a methyl group, $R^{42}$ represents a methyl group, $R^{45}$ represents a hydrogen atom, $R^{3b}$ represents a hydrogen atom, and $R^{4c}$ represents any one substituent described in Table L15 to Table L16 (hereinafter referred to as "Compound group SX1825").

The Compound (L-6), wherein n represents 2, $R^{41}$ represents a methyl group, $R^{42}$ represents a methyl group, $R^{45}$ represents a hydrogen atom, $R^{3b}$ represents a fluorine atom, and $R^{4c}$ represents any one substituent described in Table L15 to Table L16 (hereinafter referred to as "Compound group SX1826").

The Compound (L-6), wherein n represents 2, $R^{41}$ represents a methyl group, $R^{42}$ represents a methyl group, $R^{45}$ represents a hydrogen atom, $R^{3b}$ represents a chlorine atom, and $R^{4c}$ represents any one substituent described in Table L15 to Table L16 (hereinafter referred to as "Compound group SX1827").

The Compound (L-6), wherein n represents 2, $R^{41}$ represents a methyl group, $R^{42}$ represents a methyl group, $R^{45}$ represents a hydrogen atom, $R^{3b}$ represents a bromine atom, and $R^{4c}$ represents any one substituent described in Table L15 to Table L16 (hereinafter referred to as "Compound group SX1828").

The Compound (L-6), wherein n represents 2, $R^{41}$ represents a methyl group, $R^{42}$ represents a methyl group, $R^{45}$ represents a hydrogen atom, $R^{3b}$ represents $CF_3$, and $R^{4c}$ represents any one substituent described in Table L15 to Table L16 (hereinafter referred to as "Compound group SX1829").

The Compound (L-6), wherein n represents 2, $R^{41}$ represents a methyl group, $R^{42}$ represents a methyl group, $R^{45}$ represents a methyl group, $R^{3b}$ represents a hydrogen atom, and $R^{4c}$ represents any one substituent described in Table L15 to Table L16 (hereinafter referred to as "Compound group SX1830").

The Compound (L-6), wherein n represents 2, $R^{41}$ represents a methyl group, $R^{42}$ represents a methyl group, $R^{45}$ represents a methyl group, $R^{3b}$ represents a fluorine atom, and $R^{4c}$ represents any one substituent described in Table L15 to Table L16 (hereinafter referred to as "Compound group SX1831").

The Compound (L-6), wherein n represents 2, $R^{41}$ represents a methyl group, $R^{42}$ represents a methyl group, $R^{45}$ represents a methyl group, $R^{3b}$ represents a chlorine Table L15 to Table L16 (hereinafter referred to as "Compound group SX1832").

The Compound (L-6), wherein n represents 2, $R^{41}$ represents a methyl group, $R^{42}$ represents a methyl group, $R^{45}$ represents a methyl group, $R^{3b}$ represents a bromine atom, and $R^{4c}$ represents any one substituent described in Table L15 to Table L16 (hereinafter referred to as "Compound group SX1833").

The Compound (L-6), wherein n represents 2, $R^{41}$ represents a methyl group, $R^{42}$ represents a methyl group, $R^{45}$ represents a methyl group, $R^{3b}$ represents $CF_3$, and $R^{4c}$ represents any one substituent described in Table L15 to Table L16 (hereinafter referred to as "Compound group SX1834").

The Compound (L-6), wherein n represents 2, $R^{41}$ represents a methyl group, $R^{42}$ represents a methyl group, $R^{45}$ represents an ethyl group, $R^{3b}$ represents a hydrogen atom, and $R^{4c}$ represents any one substituent described in Table L15 to Table L16 (hereinafter referred to as "Compound group SX1835").

The Compound (L-6), wherein n represents 2, $R^{41}$ represents a methyl group, $R^{42}$ represents a methyl group, $R^{45}$ represents an ethyl group, $R^{3b}$ represents a fluorine atom, and $R^{4c}$ represents any one substituent described in Table L15 to Table L16 (hereinafter referred to as "Compound group SX1836").

The Compound (L-6), wherein n represents 2, $R^{41}$ represents a methyl group, $R^{42}$ represents a methyl group, $R^{45}$ represents an ethyl group, $R^{3b}$ represents a chlorine atom, and $R^{4c}$ represents any one substituent described in Table L15 to Table L16 (hereinafter referred to as "Compound group SX1837").

The Compound (L-6), wherein n represents 2, $R^{41}$ represents a methyl group, $R^{42}$ represents a methyl group, $R^{45}$ represents an ethyl group, $R^{3b}$ represents a bromine atom, and $R^{4c}$ represents any one substituent described in Table L15 to Table L16 (hereinafter referred to as "Compound group SX1838").

The Compound (L-6), wherein n represents 2, $R^{41}$ represents a methyl group, $R^{42}$ represents a methyl group, $R^{45}$ represents an ethyl group, $R^{3b}$ represents $CF_3$, and $R^{4c}$ represents any one substituent described in Table L15 to Table L16 (hereinafter referred to as "Compound group SX1839").

Next, Formulation Examples of the Present compound X are shown below. The "part(s)" represents "part(s) by weight". Also, the expression of "Present compound S" represents the compounds described in the Compound groups SX1 to SX2299.

Formulation Example 1

A mixture of polyoxyethylene alkyl ether sulfate ammonium salt and silica (weight ratio of 1:1) (35 parts), any one of the Present compound S (10 parts), and water (55 parts)

are mixed, and the resulting mixture is subjected to fine grinding according to a wet grinding method to obtain each formulation.

Formulation Example 2

Any one of the Present compound S (50 parts), calcium lignin sulfonate (3 parts), sodium lauryl sulfate (2 parts), and silica (45 parts) are ground and mixed to obtain each formulation.

Formulation Example 3

Any one of the Present compound S (5 parts), polyoxyethylene styryl phenyl ether (9 parts), polyoxyethylene decyl ether (number of added ethylene-oxide: 5) (5 parts), calcium dodecylbenzene sulfonate (6 parts), and xylene (75 parts) are mixed to obtain each formulation.

Formulation Example 4

Any one of the Present compound S (2 parts), silica (1 part), calcium lignin sulfonate (2 parts), bentonite (30 parts), and kaolin clay (65 parts) are ground and mixed, an appropriate amount of water is added thereto, the resulting mixture is kneaded, subjected to granulation with a granulator, and then dried to obtain each formulation.

Formulation Example 5

Any one of the Present compound S (10 parts), and a mixture of benzyl alcohol (18 parts) and DMSO (9 parts) are mixed, GERONOL (registered trademark) TE250 (6.3 parts), Ethylan (registered trademark) NS-500LQ (2.7 parts), and solvent naphtha (54 parts) are added thereto, and the resulting mixture is mixed to obtain each formulation.

Formulation Example 6

Any one of the Present compound S (0.1 part) is mixed with kerosene (39.9 parts) and dissolved therein, the resulting solution is placed into an aerosol container, and the container is filled with liquefied petroleum gas (a mixture of propane, butane, and isobutane; saturated vapor pressure: 0.47 MPa (25° C.)) (60 parts) to obtain each formulation.

Formulation Example 7

Any one of the Present compound S (0.2 part), lees powder extracted from pyrethrum (50 parts), Tabu powder (30 parts), and wood powder (19.8 parts) are mixed, an appropriate amount of water is added thereto, the resulting mixture is kneaded, then subjected to an extruder to obtain a plate sheet, and the plate sheet is subjected to a punching machine to be converted into a spiral shape to obtain each formulation.

Next, Test Examples are used to show effects of the Present compounds X on harmful arthropods. In the following Test Examples, the tests were carried out at 25° C.

Test Method 1

Each test compound is made to a formulation according to a similar method to that described in the Formulation Example 1, and thereto is added water containing 0.03 v/v % of Shindain (registered trademark) to prepare a diluted solution containing a prescribed concentration of the test compound.

Cucumber (*Cucumis sativus*) seedling (on the developmental stage of the second true leaf) is planted in a container and approximately 30 cotton aphids (*Aphis gossypii*) (all developmental stages of life) are released onto the leaves of the cucumber. After 1 day, the diluted solutions are sprayed to the seedling at a ratio of 10 mL/seedling. Further, after 5 days, the number of the surviving insects is examined and the controlling value is calculated by the following equation.

$$\text{Controlling value } (\%)=\{1-(Cb\times Tai)/(Cai\times Tb)\}\times 100$$

wherein the symbols in the formula represent the following descriptions.

Cb: Number of the test insects in untreated group;

Cai: Number of the surviving insects at the time of the investigation in untreated group;

Tb: Number of the test insects in treated group;

Tai: Number of the surviving insects at the time of the investigation in treated group;

Here the “untreated group” represents a group where the similar treatment procedure to that of the treated group except not using the test compound is done.

Test Example 1-1

The test was conducted by making the prescribed concentration 500 ppm and using each of the below-mentioned Present compounds as a test compound according to the Test Method 1. As a result of the test, the below-mentioned Present compounds showed 90% or greater as the controlling value.

Present compounds: 1, 2, 3, 4, 5, 6, 7, 8, 9, 10, 20, 21, 22, 23, 24, 25, 29, 30, 31, 32, 33, 34, 36, 39, 50, 53, 54, 55, 59, 60, 61, 63, 64, 65, 66, 67, 68, 69, 70, 71, 72, 73, 74, 75, 76, 78, 80, 81, 82, 83, 84, 85, 86, 87, 88, 89, 90, 91, 92, 93, 114, 119, 120, 121, 122, 123, 125, 129, 130, 131, 132, 134, 135, 136, 137, 139, 141, 142, and 143

Test Method 2

Each test compound is made to a formulation according to a similar method to that described in the Formulation Example 5, and thereto is added water to prepare a diluted solution containing a prescribed concentration of the test compound.

Cucumber (cucumber *sativus*) seedling (on the developmental stage of the second true leaf) is planted in a cup, and the diluted solutions are drenched to the bottom of the seedling at a ratio of 5 mL/seedling. After 7 days, approximately 30 cotton aphids (*Aphis gossypii*) (all developmental stages of life) are released onto the leaf of the seedling. After 6 days, the number of the surviving insects is examined and the controlling value is calculated by the following equation.

$$\text{Controlling value } (\%)=\{1-(Cb\times Tai)/(Cai\times Tb)\}\times 100$$

wherein the symbols in the formula represent the following descriptions.

Cb: Number of the test insects in untreated group;

Cai: Number of the surviving insects at the time of the investigation in untreated group;

Tb: Number of the test insects in treated group;

Tai: Number of the surviving insects at the time of the investigation in treated group;

Here the “untreated group” represents a group where the similar treatment procedure to that of the treated group except not using the test compound is done.

Test Example 2-1

The test was conducted by making the prescribed concentration 1000 ppm and using each of the below-mentioned Present compounds as a test compound according to the Test Method 2. As a result of the test, the below-mentioned Present compounds showed 90% or greater as the controlling value.

Present compounds: 38 and 44

Test Example 2-2

The test was conducted by making the prescribed concentration 200 ppm and using each of the below-mentioned Present compounds as a test compound according to the Test Method 2. As a result of the test, the below-mentioned Present compounds showed 90% or greater as the controlling value.

Present compounds: 38, 44, 48, 69, 71, 73, 74, and 98

Test Method 3

Each test compound is made to a formulation according to a similar method to that described in the Formulation Example 1, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a container, and the diluted solutions are sprayed to the seedling at a ratio of 20 mL/seedling. Thereafter, the aerial part of the seedling is cut out and then is installed into a container in which a filter paper is placed at the bottom of the container. Five of second-instar larvae of cotton worm (*Spodoptera litura*) are released into the container. After 5 days, the number of the surviving insects is counted, and the mortality of insects is calculated by the following equation.

$$\text{Mortality (\%)}=(1-\text{Number of surviving insects}/5)\times 100$$

Test Example 3-1

The test was conducted by making the prescribed concentration 500 ppm and using each of the below-mentioned Present compounds as a test compound according to the Test Method 3. As a result of the test, the below-mentioned Present compounds showed 90% or greater as the mortality.

Present compounds: 10, 20, 29, 31, 39, 44, 50, 59, 60, 61, 70, 78, 80, 86, 88, 90, 94, 123, 129, and 139

Test Method 4

Each test compound is made to a formulation according to a similar method to that described in the Formulation Example 1, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a container, and the diluted solutions are sprayed to the seedling at a ratio of 20 mL/seedling. Thereafter, the aerial part of the seedling is cut out and then is installed into a container in which a filter paper is placed at the bottom of the container. Five of second-instar larvae of diamondback moth (*Plutella xylostella*) are released into the container. After 5 days, the number of the surviving insects is counted, and the mortality of insects is calculated by the following equation.

$$\text{Mortality (\%)}=(1-\text{Number of surviving insects}/5)\times 100$$

Test Example 4-1

The test was conducted by making the prescribed concentration 500 ppm and using each of the below-mentioned Present compounds as a test compound according to the Test Method 4. As a result of the test, the below-mentioned Present compounds showed 80% or greater as the mortality.

Present compounds: 2, 3, 4, 5, 7, 8, 9, 10, 20, 21, 22, 24, 29, 30, 31, 32, 33, 34, 36, 39, 44, 50, 53, 54, 59, 61, 62, 63, 64, 65, 66, 69, 70, 71, 72, 73, 74, 75, 76, 78, 80, 81, 82, 84, 86, 87, 88, 90, 91, 92, 94, 98, 114, 118, 120, 121, 122, 123, 124, 125, 129, 130, 131, 132, 134, 135, 136, 137, 139, 140, 141, 142, and 143

Test Method 5

Each 1 mg of the test compounds is dissolved in 50 μL of a mixed solution consisting of 5% of polyoxyethylene sorbitan mono-cocoate and 95% of acetone by volume ratio. Thereto is added water containing 0.03% by volume of Shindain (registered trademark) to prepare a diluted solution containing a prescribed concentration of the test compound.

A young seedling of corn (*Zea mays*) is immersed into the diluted solution for 30 seconds. Thereafter, two seedlings are installed in a plastic petri dish (90 mm radius), and 10 of second-instar larvae of Western corn rootworm (*Diabrotica virgifera virgifera*) are released into the dish. After 5 days, the number of the dead insects is counted, and the mortality of insects is calculated by the following equation.

$$\text{Mortality (\%)}=(\text{Number of dead insects}/10)\times 100$$

Test Example 5-1

The test was conducted by making the prescribed concentration 200 ppm and using each of the below-mentioned Present compounds as a test compound according to the Test Method 5. As a result of the test, the below-mentioned Present compounds showed 90% or greater as the mortality.

Present compounds: 60 and 63

Test Example 5-2

The test is conducted by making the prescribed concentration 50 ppm and using each of the Present compounds as a test compound according to the Test Method 5, and the effect of the test compound is confirmed.

Test Method 6

An acetone solution which is adjusted to 800 ppm of each test compound is poured into a 50 mL glass vial, and the test compound is coated uniformly on inner face of the vial so as to 40 $mg/m^2$ of the test compound treated, and the vial is then dried.

5 German cockroach (*Blattella germanica*) male adults are released into the treated vial, and the vial is then covered with lid. After the prescribed time, the state of the German cockroach is examined, and the mortality is calculated by the following equation.

$$\text{Mortality (\%)}=(\text{Number of dead insects}/\text{Number of tested insects})\times 100$$

Test Example 6-1

The test was conducted by making the prescribed time 3 days and using each of the below-mentioned Present compounds as a test compound according to the Test Method 6. As a result of the test, the below-mentioned Present compounds showed 80% or greater as the mortality.

Present compounds: 59 and 90

Test Method 7

An acetone solution which is adjusted to 2000 ppm of each test compound is poured into a 20 mL glass vial, and the test compound is coated uniformly on inner face of the vial so as to 100 mg/$m^2$ of the test compound treated, and the vial is then dried.

5 *Haemaphysalis longicornis* nymphs are released into the treated vial, and the vial is then covered with lid. After the prescribed time, the state of the *Haemaphysalis longicornis* is examined, and the mortality is calculated by the following equation.

Mortality (%)=(Number of dead insects/Number of tested insects)×100

Test Example 7-1

The test was conducted by making the prescribed time 2 days and using each of the below-mentioned Present compounds as a test compound according to the Test Method 7. As a result of the test, the below-mentioned Present compounds showed 80% or greater as the mortality.

Present compounds: 34 and 90

Test Method 8

An acetone solution which is adjusted to 800 ppm of each test compound is poured into a 20 mL glass vial, and the test compound is coated uniformly on inner face of the vial so as to 40 mg/$m^2$ of the test compound treated, and the vial is then dried.

5 housefly (*Musca domestica*) female adults are released into the treated vial, and the vial is then covered with lid. After the prescribed time, the state of the housefly is examined, and the mortality is calculated by the following equation.

Mortality (%)=(Number of dead insects/Number of tested insects)×100

Test Example 8-1

The test was conducted by making the prescribed time 1 day and using each of the below-mentioned Present compounds as a test compound according to the Test Method 8. As a result of the test, the below-mentioned Present compounds showed 80% or greater as the mortality.

Present compounds: 7, 8, 9, 20, 22, 29, 34, 38, 50, 59, 61, 64, 90, 92, 94, and 98

Test Method 9

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the third to fourth true leaf) is planted in a cup, and the diluted solutions are sprayed to the seedling at a ratio of 20 mL/seedling. Thereafter, 10 of third-instar larvae of cotton worm (*Spodoptera litura*) are released. After 6 days, the number of the surviving insects is counted, and the mortality of insects is calculated by the following equation.

Mortality (%)=(1-Number of surviving insects/10)×100

Test Example 9-1

The test was conducted by making the prescribed concentration 200 ppm and using each of the below-mentioned Present compounds as a test compound according to the Test Method 9. As a result of the test, the below-mentioned Present compounds showed 80% or greater as the mortality.

Present compounds: 3, 31, 38, 39, 44, 62, 65, 86, 88, 90, 94, 123, and 139

Test Example 9-2

The test is conducted by making the prescribed concentration 50 ppm and using each of the Present compounds as a test compound according to the Test Method 9 to confirm their insecticidal effects on cotton worm (*Spodoptera litura*).

Test Method 10

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the third to fourth true leaf) is planted in a container, and the diluted solutions are sprayed to the seedling at a ratio of 20 mL/seedling. Thereafter, the aerial part of the seedling is cut out and then is installed into a container in which a filter paper is placed at the bottom of the container. Ten of third-instar larvae of diamondback moth (*Plutella xylostella*) are released to the container. After 6 days, the number of the surviving insects is counted, and the mortality of insects is calculated by the following equation.

Mortality (%)=(1−Number of surviving insects/10)×100

Test Example 10-1

The test was conducted by making the prescribed concentration 200 ppm and using each of the below-mentioned Present compounds as a test compound according to the Test Method 10. As a result of the test, the below-mentioned Present compounds showed 80% or greater as the mortality.

Present compounds: 1, 2, 3, 7, 8, 9, 11, 17, 20, 21, 26, 29, 30, 31, 32, 33, 34, 35, 38, 39, 44, 47, 50, 53, 59, 60, 61, 62, 63, 64, 65, 66, 69, 70, 71, 72, 73, 74, 75, 76, 81, 82, 84, 86, 87, 88, 90, 91, 92, 94, 98, 114, 118, 120, 121, 123, 124, 126, 127, 128, 129, 130, 131, 132, 134, 135, 136, 139, and 141

Test Example 10-2

The test was conducted by making the prescribed concentration 50 ppm and using each of the below-mentioned Present compounds as a test compound according to the Test Method 10. As a result of the test, the below-mentioned Present compounds showed 80% or greater as the mortality.

Present compounds: 1, 7, 9, 11, 26, 31, 32, 33, 34, 35, 38, 39, 44, 47, 64, 72, 73, 90, 91, 118, 123, 134, and 139

Test Method 11

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Cucumber (*Cucumis sativus*) seedling (on the developmental stage of the second true leaf) is planted in a container and approximately 30 cotton aphids (*Aphis gossypii*) (all developmental stages of life) are released onto the leaves of the cucumber. After 1 day, the diluted solutions are sprayed to the seedling at a ratio of 10 mL/seedling. Further, after 5 days, the number of the surviving insects is examined and the controlling value is calculated by the following equation.

$$\text{Controlling value }(\%)=\{1-(Cb\times Tai)/(Cai\times Tb)\}\times 100$$

wherein the symbols in the formula represent the following descriptions.

Cb: Number of the test insects in untreated group;

Cai: Number of the surviving insects at the time of the investigation in untreated group;

Tb: Number of the test insects in treated group;

Tai: Number of the surviving insects at the time of the investigation in treated group;

Here the "untreated group" represents a group where the similar treatment procedure to that of the treated group except not using the test compound is done.

Test Example 11-1

The test was conducted by making the prescribed concentration 200 ppm and using each of the below-mentioned Present compounds as a test compound according to the Test Method 11. As a result of the test, the below-mentioned Present compounds showed 90% or greater as the controlling value.

Present compounds: 1, 2, 3, 7, 8, 9, 11, 12, 16, 17, 18, 19, 20, 21, 26, 27, 28, 31, 32, 33, 34, 35, 38, 39, 44, 47, 48, 50, 61, 64, 65, 66, 67, 68, 69, 71, 72, 73, 74, 75, 78, 79, 81, 82, 83, 84, 85, 86, 87, 88, 91, 92, 93, 115, 116, 117, 118, 119, 120, 123, 127, 129, 130, 131, 132, 134, 135, 136, 139, 140, 141, 142, and 143

Test Example 11-2

The test was conducted by making the prescribed concentration 50 ppm and using each of the below-mentioned Present compounds as a test compound according to the Test Method 11. As a result of the test, the below-mentioned Present compounds showed 90% or greater as the controlling value.

Present compounds: 1, 2, 3, 7, 8, 9, 11, 16, 17, 21, 26, 27, 28, 31, 32, 33, 34, 35, 38, 39, 44, 47, 48, 61, 67, 69, 71, 72, 73, 74, 75, 81, 82, 84, 91, 92, 93, 116, 123, 132, and 139

Test Method 12

Each test compound is formulated to a test formulation according to a similar method to that described in the Formulation Example 1, and water is added in preparing for a diluted solution containing a prescribed concentration of the test compound.

Into the diluted solution, 30 last instar larvae of common house mosquito (*Culex pipiens pallens*) are released, and after 1 day, the state of the house mosquito larvae is examined, and the mortality is calculated by the following equation.

$$\text{Mortality }(\%)=(\text{Number of dead insects}/\text{Number of tested insects})\times 100$$

Test Example 12-1

The test was conducted by making the prescribed concentration 3.5 ppm and using each of the below-mentioned Present compounds as a test compound according to the Test Method 12. As a result of the test, the below-mentioned Present compounds showed greater than 90% as the mortality.

Present compounds: 2, 3, 4, 5, 6, 7, 8, 9, 10, 15, 20, 21, 22, 24, 25, 29, 30, 31, 32, 33, 34, 36, 38, 39, 44, 45, 50, 53, 54, 55, 59, 61, 64, 65, 66, 67, 68, 69, 71, 72, 73, 74, 77, 81, 84, 85, 90, 91, 92, 94, 98, 100, 114, 118, 119, 120, 123, 125, 129, 130, 132, 133, 134, 135, 136, 139, 140, 141, and 143

Test Method 13

Each test compound is made to a formulation according to a similar method to that described in the Formulation Example 1, and thereto is added water containing 0.03 v/v % of Shindain (registered trademark) to prepare a diluted solution containing a prescribed concentration of the test compound.

Rice (*Oryza sativa*) seedling (on the developmental stage of the second true leaf) is planted in a container, and the diluted solutions are sprayed into the seedling in a ratio of 10 mL/seedling. Thereafter, 20 3rd instar larvae of brown planthoppers (*Nilaparvata lugens*) are released onto the rice leaves. After 6 days, the number of the surviving insects is examined, and the mortality is calculated by the following equation.

$$\text{Mortality }(\%)=\{1-\text{the number of the surviving insects}/20\}\times 100$$

Test Example 13-1

The test is conducted by making the prescribed concentration 500 ppm and using each of the Present compounds as a test compound according to the Test Method 13, and the effect of the test compound is confirmed.

Test Method 14

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Rice (*Oryza sativa*) seedling (on the developmental stage of the second true leaf) is planted in a container, and the diluted solutions are sprayed into the seedling in a ratio of 10 mL/seedling. Thereafter, 20 3rd instar larvae of brown planthoppers (*Nilaparvata lugens*) are released onto the rice leaves. After 6 days, the number of the surviving insects is examined, and the mortality is calculated by the following equation.

$$\text{Mortality }(\%)=\{1-\text{the number of the surviving insects}/20\}\times 100$$

Test Example 14-1

The test is conducted by making the prescribed concentration 200 ppm and using each of the Present compounds as a test compound according to the Test Method 14, and the effect of the test compound is confirmed.

Test Example 14-2

The test is conducted by making the prescribed concentration 50 ppm and using each of the Present compounds as a test compound according to the Test Method 14, and the effect of the test compound is confirmed.

Test Method 15

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Silverleaf whiteflies (*Bemisia tabaci*) are released on tomato (*Lycopersicon esculentum*) seedling that is planted in a container, and then spawn for about 24 hours. The seedling is stored for 8 days, and the larvae of silverleaf whiteflies are hatched from the laid eggs. The diluted solutions are sprayed into the seedling in a ratio of 10 mL/seedling. After 7 days, the number of the surviving insects is examined, and the controlling value is calculated by the following equation.

$$\text{Controlling value (\%)}=\{1-(Cb\times Tai)/(Cai\times Tb)\}\times 100$$

wherein the symbols in the formula represent the following descriptions.

Cb: Number of the insects shortly before the treatment in untreated group;

Cai: Number of the surviving insects at the time of the investigation in untreated group;

Tb: Number of the insects shortly before the treatment in treated group;

Tai: Number of the surviving insects at the time of the investigation in treated group;

Here the "untreated group" represents a group where the similar treatment procedure to that of the treated group except not using the test compound is done.

Test Example 15-1

The test is conducted by making the prescribed concentration 200 ppm and using each of the Present compounds as a test compound according to the Test Method 15, and the effect of the test compound is confirmed.

Test Example 15-2

The test is conducted by making the prescribed concentration 50 ppm and using each of the Present compounds as a test compound according to the Test Method 15, and the effect of the test compound is confirmed.

Test Method 16

Each test compound is made to a formulation according to a similar method to that described in the Formulation Example 5, and thereto is added water containing 0.03 v/v % of Shindain (registered trademark) to prepare a diluted solution containing a prescribed concentration of the test compound.

Cucumber (cucumber *sativus*) seedling (on the developmental stage of the second leaf) is planted in a cup, and the diluted solutions are sprayed into the seedling at a ratio of 10 mL/seedling. Thereafter, the first true leaf thereof is cut out and then is installed into a cup, and about twenty (20) instar larvae of Western flower *thrips* (*Frankliniella occidentalis*) are released. After 7 days, the number of the surviving insects is examined, and the mortality is calculated by the following equation.

$$\text{Mortality (\%)}=\{1-\text{the number of the surviving insects}/20\}\times 100$$

Test Example 16-1

The test is conducted by making the prescribed concentration 200 ppm and using each of the Present compounds as a test compound according to the Test Method 16, and the effect of the test compound is confirmed.

Test Example 16-2

The test is conducted by making the prescribed concentration 50 ppm and using each of the Present compounds as a test compound according to the Test Method 16, and the effect of the test compound is confirmed.

Test Method 17

Each 1 mg of the Present compounds is dissolved in 10 μL of a mixed solution consisting of four ninths of xylene, four ninths of dimethylformamide, and one ninth of surfactant by volume ratio. Thereto is added water containing 0.02% by volume of a spreader to prepare diluted solution A containing a prescribed concentration of the Present compound.

Each 1 mg of the Present ingredients is dissolved in 10 μL of a mixed solution consisting of four ninths of xylene, four ninths of dimethylformamide, and one ninth of surfactant by volume ratio. Thereto is added water containing 0.02% by volume of a spreader to prepare diluted solution B containing a prescribed concentration of the Present ingredient.

The diluted solution A is mixed with the diluted solution B to prepare diluted solution C.

A leaf disc of cotyledon of cucumber (*Cucumis sativus*) (1.5 cm in length) is cut out and installed in each well of a 24-well microplate, and 2 apterous adults and 8 nymphs of cotton aphid (*Aphis gossypii*) are release onto the leaf disc in each well. The diluted solution C is sprayed to each leaf disc at the ratio of 20 μL/leaf disc. The procedure mentioned above represents the treated group.

Whereas, the untreated group represents a group where the similar treatment procedure to that of the treated group is done except 20 μL of water containing 0.02% by volume of a spreader is used instead of using the diluted solution C.

After the sprayed diluted solution C is dried, the microplate is covered with a film sheet. After 5 days, the number of the surviving insects in each well is examined and the controlling value is calculated by the following equation.

$$\text{Controlling value (\%)}=\{1-(Tai)/(Cai)\}\times 100$$

wherein the symbols in the formula represent the following descriptions.

Cai: Number of the surviving insects at the time of the investigation in untreated group;

Tai: Number of the surviving insects at the time of the investigation in treated group.

Specific diluted solutions C, which can confirm their effects according to the Test Method 17, are described in the following 1) to 5).

1) The diluted solution C comprises the combination recited in List A wherein a concentration of the Present compound X is 200 ppm and a concentration of the Present ingredient is 2000 ppm. In List A, Comp X represents any one compound selected from the Compound groups SX1 to SX2299 described in Examples.

List A:

Comp X+Clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+Mycorrhizal Fungi; Comp X+*Bradyrhizobium japonicum* TA-11; Comp X+*Bacillus firmus*; Comp X+*Bacillus firmus* I-1582; Comp X+*Bacillus amyloliquefaciens*; Comp X+*Bacillus amyloliquefaciens* FZB42; Comp X+Pasteuria nishizawae; Comp X+Pasteuria nishizawae Pn1; Comp X+Pasteuria *penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Comp X+benzovindiflupyr; Comp X+boscalid; Comp X+carboxin; Comp X+penthiopyrad; Comp X+flutolanil; Comp X+captan; Comp X+thiram; Comp X+tolclofos-methyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.

2) The diluted solution C comprises the combination recited in List A wherein a concentration of the Present compound X is 200 ppm and a concentration of the Present ingredient is 200 ppm.

3) The diluted solution C comprises the combination recited in List A wherein a concentration of the Present compound X is 500 ppm and a concentration of the Present ingredient is 50 ppm.

4) The diluted solution C comprises the combination recited in List A wherein a concentration of the Present compound X is 500 ppm and a concentration of the Present ingredient is 5 ppm.

5) The diluted solution C comprises the combination recited in List A wherein a concentration of the Present compound X is 500 ppm and a concentration of the Present ingredient is 0.5 ppm.

INDUSTRIAL APPLICABILITY

The Present compounds X have excellent control effects on harmful arthropods.

The invention claimed is:

1. A compound represented by formula (I)

(I)

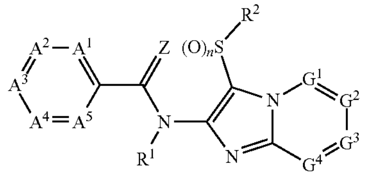

wherein:

Z represents an oxygen atom or a sulfur atom;

$R^1$ represents a C1-C6 chain hydrocarbon group optionally substituted with one or more substituent(s) selected from Group W, a C3-C7 cycloalkyl group optionally substituted with one or more substituent(s) selected from Group U, a phenyl group optionally substituted with one or more substituent(s) selected from Group V, a 5 or 6 membered aromatic heterocyclic group optionally substituted with one or more substituent(s) selected from Group V, $C(O)R^{51}C(O)OR^{51}$, or $C(O)NR^{51}R^{52}$, $R^{51}$ and $R^{52}$ are identical to or different from each other, and each represent a C1-C6 chain hydrocarbon group optionally substituted with one or more halogen atom(s), a phenyl group optionally substituted with one or more substituent(s) selected from Group V, a 5 or 6 membered heterocyclic group optionally substituted with one or more substituent(s) selected from Group V, or a hydrogen atom;

$R^2$ represents a C1-C6 alkyl group optionally substituted with one or more halogen atom(s), a cyclopropyl group, or a cyclopropylmethyl group;

n represents 0, 1, or 2;

$G^1$ represents a nitrogen atom or $CR^{3a}$:

$G^2$ represents a nitrogen atom or $CR^{3b}$;

$G^3$ represents a nitrogen atom or $CR^{3e}$;

$G^4$ represents a nitrogen atom or $CR^{3d}$;

$R^{3a}$, $R^{3b}$, $R^{3c}$, and $R^{3d}$ are identical to or different from each other, and each represent a C1-C6 chain hydrocarbon group optionally substituted with one or more substituent(s) selected from Group B, a C3-C7 cycloalkyl group optionally substituted with one or more substituent(s) selected from Group E, a phenyl group optionally substituted with one or more substituent(s) selected from Group H, a 5 or 6 membered aromatic heterocyclic group optionally substituted with one or more substituent(s) selected from Group H, $OR^{12}$, $NR^{11}R^{12}$, $NR^{11a}R^{12a}$ $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N{=}CHNR^{31}R^{32}$, $N{=}S(O)_pR^{15}R^{16}$, $C(O)R^{13}$, $C(O)OR^{17}$, $C(O)NR^{31}R^{32}$, $C(O)NR^{11}S(O)_2R^{23}$, $CR^{30}{=}NOR^{17}$ $NR^{11}CR^{24}{=}NOR^{17}$, $S(O)_mR^{23}$, a cyano group, a nitro group, a hydrogen atom, or a halogen atom;

p represents 0 or 1;

m represents 0, 1, or 2;

$R^{30}$ represents a C1-C6 chain hydrocarbon group optionally substituted with one or more halogen atom(s), a halogen atom, $OR^{35}$, $NR^{36}R^{37}$, or a hydrogen atom;

$R^{35}$ represents a C1-C6 chain hydrocarbon group optionally substituted with one or more halogen atom(s);

$R^{17}$ represents a C1-C6 chain hydrocarbon group optionally substituted with one or more halogen atom(s), a phenyl group optionally substituted with one or more substituent(s) selected from Group D, or a hydrogen atom;

$R^{11}$, $R^{24}$, $R^{36}$, and $R^{37}$ are identical to or different from each other, and each represent a C1-C6 chain hydrocarbon group optionally substituted with one or more halogen atom(s), or a hydrogen atom;

$R^{12}$ represents a C1-C6 chain hydrocarbon group optionally substituted with one or more substituent(s) selected from Group F, a C3-C7 cycloalkyl group optionally substituted with one or more substituent(s) selected from Group J, a C3-C7 cycloalkenyl group optionally substituted with one or more substituent(s) selected from Group J, a phenyl group optionally substituted with one or more substituent(s) selected from Group D, a 6 membered aromatic heterocyclic group optionally substituted with one or more substituent(s) selected from Group D, a hydrogen atom, or $S(O)_2R^{23}$;

$R^{23}$ represents a C1-C6 chain hydrocarbon group optionally substituted with one or more halogen atom(s) or a phenyl group optionally substituted with one or more substituent(s) selected from Group D;

$RH^{11a}$ and $R^{12a}$ are combined with the nitrogen atom to which they are attached to form a 3-7 membered nonaromatic heterocyclic group optionally substituted with one or more substituent(s) selected from Group E;

$R^{13}$ represents a C1-C6 chain hydrocarbon group optionally substituted with one or more halogen atom(s), a C3-C7 cycloalkyl group optionally substituted with one or more halogen atom(s), a ($C_3$-$C_6$ cycloalkyl) C1-C3 alkyl group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, or a hydrogen atom;

$R^{14}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), or a phenyl C1-C3 alkyl wherein, the phenyl moiety in said phenyl C1-C3 alkyl group optionally being substituted with one or more substituent(s) selected from Group D;

$R^{15}$ and $R^{16}$ are identical to or different from each other, and each represent a C1-C6 alkyl group optionally substituted with one or more halogen atom(s);

$R^{31}$ represents a C1-C6 alkyl group optionally substituted with one or more halogen atom(s), or a hydrogen atom;

$R^{32}$ represents a C1-C6 chain hydrocarbon group optionally substituted with one or more substituent(s) selected from Group F, a C3-C7 cycloalkyl group optionally substituted with one or more substituent(s) selected from Group J, $S(O)_2R^{23}$, or a hydrogen atom;

$A^1$ represents a nitrogen atom or $CR^{4a}$;

$A^2$ represents a nitrogen atom or $CR^{4b}$;

$A^3$ represents a nitrogen atom or $CR^{4c}$;

$A^4$ represents a nitrogen atom or $CR^{4d}$;

$A^5$ represents a nitrogen atom or $CR^{4e}$:

provided that not all of $A^2$, $A^3$, and $A^4$ represent nitrogen atoms;

$R^{4a}$ and $R^{4e}$ are identical to or different from each other, and each represent a C1-C6 chain hydrocarbon group optionally substituted with one or more substituent(s) selected from Group X, a C3-C6 cycloalkyl group optionally substituted with one or more substituent(s) selected from Group Y, a phenyl group optionally substituted with one or more substituent(s) selected from Group Z, a 5 or 6 membered heterocyclic group optionally substituted with one or more substituent(s) selected from Group Z, $OR^{44}$, S(O), $R^{41}$, $S(O)_2$ $NR^{41}R^{42}$, $NR^{41}R^{43}$ $NR^{41}C(O)R^{42}$, $NR^{41}C(O)OR^{42}$, $NR^{41}S(O)_2R^{43}$, $C(O)R^{41}$, $C(O)OR^{41}$, $C(O)NR^{41}R^{42}$, $CR^{42}$=$NOR^{41}$, a hydroxy group, a cyano group, a nitro group, a halogen atom, or a hydrogen atom;

when $A^5$ represents $CR^{4c}$, $R^{4e}$ and $R^1$ are optionally combined with each other to form-$NR^{45}$—$CR^{41}R^{42}$ representing the binding position to the nitrogen atom to which $R^1$ is bound;

$R^{4b}$, $R^{4c}$, and $R^{4d}$ are identical to or different from each other, and each represent a C1-C6 chain hydrocarbon group optionally substituted with one or more substituent(s) selected from Group X, a $C_3$-$C_6$ cycloalkyl group optionally substituted with one or more substituent(s) selected from Group Y, a phenyl group optionally substituted with one or more substituent(s) selected from Group Z, a 5 or 6 membered heterocyclic group optionally substituted with one or more substituent(s) selected from Group Z, $OR^{44}$, S(O), $R^{41}$, $S(O)_2$ $NR^{41}R^{42}$, $NR^{41}R^{42}$ $NR^{41}C(O)R^{42}$, $NR^{41}C(O)OR^{42}$, $NR^{41}S(O)_2R^{43}$, $C(O)R^{41}$, $C(O)OR^{41}$, $C(O)NR^{41}R^{42}$, $CR^{42}$=$NOR^{41}$, a hydroxy group, a cyano group, a nitro group, a halogen atom, or a hydrogen atom;

provided that not all of present $R^{4a}$, $R^{4b}$, $R^{4c}$, $R^{4d}$, and $R^{4e}$ represent hydrogen atoms;

k represents 0, 1, or 2;

q represents 0, 1, or 2;

$R^{41}$ and $R^{42}$ are identical to or different from each other, and each represent a C1-C6 chain hydrocarbon group optionally substituted with one or more halogen atom(s), a phenyl group optionally substituted with one or more substituent(s) selected from Group Z, a 5 or 6 membered heterocyclic group optionally substituted with one or more substituent(s) selected from Group Z, or a hydrogen atom;

$R^{43}$ represents a C1-C6 chain hydrocarbon group optionally substituted with one or more halogen atom(s), a phenyl group optionally substituted with one or more substituent(s) selected from Group Z, or a 5 or 6 membered heterocyclic group optionally substituted with one or more substituent(s) selected from Group Z;

$R^{44}$ represents a C1-C6 chain hydrocarbon group optionally substituted with one or more halogen atom(s);

$R^{45}$ represents a C1-C6 chain hydrocarbon group optionally substituted with one or more substituent(s) selected from Group $W^2$, a C3-C7 cycloalkyl group optionally substituted with one or more substituent(s) selected from Group Y, a phenyl group optionally substituted with one or more substituent(s) selected from Group Z, a 5 or 6 membered aromatic heterocyclic group optionally substituted with one or more substituent(s) selected from Group Z, $C(O)R^{46}$, $C(O)OR^{46}$, $C(O)NR^{46}R^{47}$, or a hydrogen atom; and $R^{46}$ and $R^{47}$ are identical to or different from each other, and each represent a C1-C6 chain hydrocarbon group optionally substituted with one or more halogen atom(s), a phenyl group optionally substituted with one or more substituent(s) selected from Group Z, a 5 or 6 membered heterocyclic group optionally substituted with one or more substituent(s) selected from Group Z, or a hydrogen atom;

Group B: a group consisting of a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a cyano group, a hydroxy group, and a halogen atom;

Group C: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), and a halogen atom;

Group D: a group consisting of a C1-C6 chain hydrocarbon group optionally substituted with one or more halogen atom(s), a hydroxy group, a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a sulfanyl group, a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), an amino group, $NHR^{21}$, $NR^{21}R^{22}$, $C(O)R^{21}$, $OC(O)R^{21}$, $C(O)OR^{21}$, a cyano group, a nitro group, and a halogen atom;

$R^{21}$ and $R^{22}$ are identical to or different from each other, and each represent a C1-C6 alkyl group optionally substituted with one or more halogen atom(s);

Group E: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a halogen atom, an oxo group, a hydroxy group, a cyano group, and a nitro group;

Group F: a group consisting of a C1-C6 alkoxy group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, a C3-C7 cycloalkyl group optionally substituted with one or more halogen atom(s), a 3-7 membered nonaromatic heterocyclic group optionally substituted with one or more substituent(s) selected from Group C, an amino group, $NHR^{21}$, $NR^{21}R^{22}$, a halogen atom, and a cyano group;

Group H: a group consisting of a C1-C6 alkyl group optionally substituted with one or more halogen atom(s), a 5 or 6 membered aromatic heterocyclic group optionally substituted with one or more substituent(s) selected from Group D, $OR^{10}$, $NR^9R^{10}$, $C(O)R^{10}$, $C(O)NR^{10}R^{10}$ $OC(O)R^9$, $OC(O)OR^9$, $NR^{10}C(O)R^9$, $NR^{10}C(O)OR^9$, $C(O)OR^{10}$, a halogen atom, a nitro group, a cyano group, and an amino group;

$R^9$ represents a C1-C6 alkyl group optionally substituted with one or more halogen atom(s) or a C3-C6 cycloalkyl group optionally substituted with one or more halogen atom(s);

$R^{10}$ represents a C1-C6 alkyl group optionally substituted with one or more halogen atom(s), a C3-C6 cycloalkyl group optionally substituted with one or more halogen atom(s), or a hydrogen atom;

Group J: a group consisting of a C1-C6 alkyl group optionally substituted with one or more halogen atom(s), a halogen atom, and a cyano group;

Group U: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), and a halogen atom;

Group V: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C1-C6 alkylamino group optionally substituted with one or more halogen atom(s), a di(C1-C6 alkyl optionally substituted with one or more halogen atom(s)amino group, a C2-C6 alkylcarbonyl group optionally substituted with one or more halogen atom(s), a C2-C6 alkoxycarbonyl group optionally substituted with one or more halogen atom(s), a hydroxy group, a sulfanyl group, an amino group, a cyano group, a nitro group, and a halogen atom;

Group W: a group consisting of a C3-C6 cycloalkyl group optionally substituted with one or more substituent(s) selected from the group consisting of a halogen atom and a C1-C3 alkyl group, a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a phenyl group optionally substituted with one or more substituent(s) selected from Group Z, a 5 or 6 membered aromatic heterocyclic group optionally substituted with one or more substituent(s) selected from Group Z, a hydroxy group, a cyano group, and a halogen atom;

Group X: a group consisting of a C3-C6 cycloalkyl group optionally substituted with one or more substituent(s) selected from the group consisting of a halogen atom and a C1-C3 alkyl group, a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a hydroxy group, a sulfanyl group, a cyano group, and a halogen atom;

Group Y: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), and a halogen atom;

Group Z: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C1-C6 alkylamino group optionally substituted with one or more halogen atom(s), a di(C1-C6 alkyl optionally substituted with one or more halogen atom(s))amino group, a C2-C6 alkylcarbonyl group optionally substituted with one or more halogen atom(s), a C2-C6 alkoxycarbonyl group optionally substituted with one or more halogen atom(s), a hydroxy group, a sulfanyl group, an amino group, a cyano group, a nitro group, and a halogen atom;

Group $W^2$: a group consisting of a $C_3$-$C_6$ cycloalkyl group optionally substituted with one or more substituent(s) selected from the group consisting of a halogen atom and a C1-C3 alkyl group, a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a phenyl group optionally substituted with one or more substituent(s) selected from Group Z, a 5 or 6 membered aromatic heterocyclic group optionally substituted with one or more substituent(s) selected from Group Z, a hydroxy group, a sulfanyl group, a cyano group, and a halogen atom, or an N-oxide thereof.

2. The compound or an N-oxide thereof according to claim 1, wherein $R^{45}$ represents a C1-C6 chain hydrocarbon group optionally substituted with one or more substituent(s) selected from Group X, a C3-C7 cycloalkyl group optionally substituted with one or more substituent(s) selected from Group Y, a phenyl group optionally substituted with one or more substituent(s) selected from Group Z, a 5 or 6 membered aromatic heterocyclic group optionally substituted with one or more substituent(s) selected from Group Z, $C(O)R^{46}$, $C(O)OR^{46}$, $C(O)NR^{46}R^{47}$, or a hydrogen atom.

3. The compound or an N-oxide thereof according to claim 1, wherein $G^1$ represents $CR^{3a}$, $G^2$ represents $CR^{3b}$, $G^3$ represents $CR^{3c}$, and $G^4$ represents a nitrogen atom or $CR^{34}$.

4. The compound or an N-oxide thereof according to claim 1, wherein $A^1$ represents $CR^{4a}$, $A^2$ represents $CR^{4b}$, $A^3$ represents a nitrogen atom or $CR^{4c}$, $A^4$ represents a nitrogen atom or $CR^{4d}$, and $A^5$ represents a nitrogen atom or $CR^{4e}$.

5. The compound or an N-oxide thereof according to claim 1, wherein the combination of $A^1$, $A^2$, $A^3$, $A^4$, and $A^5$ represents:

a combination wherein $A^1$ represents $CR^{4a}$, $A^2$ represents $CR^{4b}$, $A^3$ represents $CR^{4c}$, $A^4$ represents $CR^{44}$, and $A^5$ represents $CR^{4e}$;

a combination wherein $A^1$ represents $CR^{4a}$, $A^2$ represents $CR^{4b}$, $A^3$ represents a nitrogen atom, $A^4$ represents $CR^{44}$, and $A^5$ represents $CR^{4e}$;

a combination wherein $A^1$ represents $CR^{42}$, $A^2$ represents $CR^{4b}$, $A^3$ represents $CR^{4c}$, $A^4$ represents a nitrogen atom, and $A^5$ represents $CR^{4e}$; or a combination wherein $A^1$ represents $CR^{4a}$, $A^2$ represents $CR^{4b}$, $A^3$ represents $CR^{4c}$, $A^4$ represents $CR^{44}$, and $A^5$ represents a nitrogen atom.

6. The compound or an N-oxide thereof according to claim 1, wherein $A^1$ represents $CR^{4a}$, $A^2$ represents $CR^{4b}$, $A^3$ represents $CR^{4c}$, $A^4$ represents $CR^{44}$, and $A^5$ represents $CR^{4e}$.

7. The compound or an N-oxide thereof according to claim 1, wherein $G^1$ represents $CR^{3a}$, $G^2$ represents $CR^{3b}$, $G^3$ represents $CR^{3c}$, and $G^4$ represents $CR^{3d}$; and $A^1$ represents $CR^{4a}$, $A^2$ represents $CR^{4b}$, $A^3$ represents $CR^{4c}$, $A^4$ represents $CR^{44}$, and $A^5$ represents $CR^{4c}$.

8. The compound or an N-oxide thereof according to claim 1, wherein $R^2$ represents an ethyl group.

9. The compound or an N-oxide thereof according to claim 1, wherein Z represents an oxygen atom.

10. A composition for controlling a harmful arthropod comprising the compound or an N-oxide thereof according to claim 1.

11. A composition comprising one or more ingredient(s) selected from the group consisting of Group (a), Group (b), Group (c), and Group (d), and the compound or an N-oxide thereof according to claim 1:

Group (a): a group consisting of insecticidal active ingredients, miticidal active ingredients, and nematicidal active ingredients;

Group (b): fungicidal active ingredients;

Group (c): plant growth regulatory ingredients;

Group (d): repellent ingredients.

12. A seed or a vegetative reproductive organ holding an effective amount of the composition according to claim 11.

13. A method for controlling a harmful arthropod which comprises applying an effective amount of the composition according to claim 11 to a harmful arthropod or a habitat where a harmful arthropod lives.

14. A seed or a vegetative reproductive organ, comprising: an effective amount of the compound or an N-oxide thereof according to claim 1.

15. A method for controlling a harmful arthropod which comprises applying an effective amount of the compound or an N-oxide thereof according to claim 1 to a harmful arthropod or a habitat where a harmful arthropod lives.

16. A compound represented by formula (II)

(II)

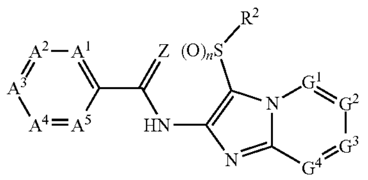

wherein:

Z represents an oxygen atom or a sulfur atom;

$R^2$ represents a C1-C6 alkyl group optionally substituted with one or more halogen atom(s), a cyclopropyl group, or a cyclopropylmethyl group;

n represents 0, 1, or 2;

$G^1$ represents a nitrogen atom or $CR^{3a}$;

$G^2$ represents a nitrogen atom or $CR^{3b}$;

$G^3$ represents a nitrogen atom or $CR^{3c}$;

$G^4$ represents a nitrogen atom or $CR^{3d}$;

$R^{3a}$, $R^{35}$, $R^{3c}$, and $R^{3d}$ are identical to or different from each other, and each represent a C1-C6 chain hydrocarbon group optionally substituted with one or more substituent(s) selected from Group B, a C3-C7 cycloalkyl group optionally substituted with one or more substituent(s) selected from Group E, a phenyl group optionally substituted with one or more substituent(s) selected from Group H, a 5 or 6 membered aromatic heterocyclic group optionally substituted with one or more substituent(s) selected from Group H, $OR^{12}$, $NR^{11}R^{12}$, $NR^{11a}R^{12a}$ $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N{=}CHNR^{31}R^{32}$, $N{=}S(O)_p R^{15}R^{16}$, $C(O)R^{13}$, $C(O)OR^{17}$, $C(O)NR^{31}R^{32}$, $C(O)NR^{11}S(O)_2R^{23}$, $CR^{30}{=}NOR^{17}$, $NR^{11}CR^{24}{=}NOR^{17}$, $S(O)_mR^{23}$, a cyano group, a nitro group, a hydrogen atom, or a halogen atom;

p represents 0 or 1;

m represents 0, 1, or 2;

$R^{30}$ represents a C1-C6 chain hydrocarbon group optionally substituted with one or more halogen atom(s), a halogen atom, $OR^{35}$, $NR^{36}R^{37}$, or a hydrogen atom;

$R^{35}$ represents a C1-C6 chain hydrocarbon group optionally substituted with one or more halogen atom(s);

$R^{17}$ represents a C1-C6 chain hydrocarbon group optionally substituted with one or more halogen atom(s), a phenyl group optionally substituted with one or more substituent(s) selected from Group D, or a hydrogen atom;

$R^{11}$, $R^{24}$, $R^{36}$, and $R^{37}$ are identical to or different from each other, and each represent a C1-C6 chain hydrocarbon group optionally substituted with one or more halogen atom(s), or a hydrogen atom, $R^{12}$ represents a C1-C6 chain hydrocarbon group optionally substituted with one or more substituent(s) selected from Group F, a C3-C7 cycloalkyl group optionally substituted with one or more substituent(s) selected from Group J, a C3-C7 cycloalkenyl group optionally substituted with one or more substituent(s) selected from Group J, a phenyl group optionally substituted with one or more substituent(s) selected from Group D, a 6 membered aromatic heterocyclic group optionally substituted with one or more substituent(s) selected from Group D, a hydrogen atom, or $S(O)_2R^{23}$, $R^{23}$ represents a C1-C6 chain hydrocarbon group optionally substituted with one or more halogen atom(s) or a phenyl group optionally substituted with one or more substituent(s) selected from Group D;

$R^{11a}$ and $R^{12a}$ are combined with the nitrogen atom to which they are attached to form a 3-7 membered nonaromatic heterocyclic group optionally substituted with one or more substituent(s) selected from Group E;

$R^{13}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, or a hydrogen atom;

$R^{14}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), or a phenyl C1-C3 alkyl group, the phenyl moiety in said phenyl C1-C3 alkyl group optionally being substituted with one or more substituent(s) selected from Group D;

$R^{15}$ and $R^{16}$ are identical to or different from each other, and each represent a C1-C6 alkyl group optionally substituted with one or more halogen atom(s);

$R^{31}$ represents a C1-C6 alkyl group optionally substituted with one or more halogen atom(s), or a hydrogen atom;

$R^{32}$ represents a C1-C6 chain hydrocarbon group optionally substituted with one or more substituent(s) selected from Group F, a C3-C7 cycloalkyl group optionally substituted with one or more substituent(s) selected from Group J, $S(O)_2R^{23}$, or a hydrogen atom;

$A^1$ represents a nitrogen atom or $CR^{4a}$;

$A^2$ represents a nitrogen atom or $CR^{4b}$;

$A^3$ represents a nitrogen atom or $CR^{4c}$;

$A^4$ represents a nitrogen atom or $CR^{4d}$;

$A^5$ represents a nitrogen atom or $CR^{4e}$:

provided that not all of $A^2$, $A^3$, and $A^4$ represent nitrogen atoms;

$R^{4a}$ and $R^{4e}$ are identical to or different from each other, and each represent a C1-C6 chain hydrocarbon group optionally substituted with one or more substituent(s) selected from Group X, a $C_3$-$C_6$ cycloalkyl group optionally substituted with one or more substituent(s) selected from Group Y, a phenyl group optionally substituted with one or more substituent(s) selected from Group Z, a 5 or 6 membered heterocyclic group optionally substituted with one or more substituent(s) selected from Group Z, $OR^{44}$, S(O); $R^{41}$, $S(O)_2NR^{41}R^{42}$, $NR^{41}R^{43}$ $NR^{41}C(O)R^{42}$, $NR^{41}C(O)OR^{42}$, $NR^{41}S(O)_2R^{43}$, $C(O)R^{41}$, $C(O)OR^{41}$, $C(O)NR^{41}R^{42}$ $CR^{42}{=}NOR^{41}$, a hydroxy group, a cyano group, a nitro group, a halogen atom, or a hydrogen atom;

$R^{4b}$, $R^{4c}$, and $R^{4d}$ are identical to or different from each other, and each represent a C1-C6 chain hydrocarbon group optionally substituted with one or more substituent(s) selected from Group X, a $C_3$-$C_6$ cycloalkyl group optionally substituted with one or more substituent(s) selected from Group Y, a phenyl group optionally substituted with one or more substituent(s) selected from Group Z, a 5 or 6 membered heterocyclic group optionally substituted with one or more substituent(s) selected from Group Z, $OR^{44}$, S(O), $R^{41}$, $S(O)_2NR^{41}R^{42}$, $NR^{41}R^{42}$ $NR^{41}C(O)R^{42}$, $NR^{41}C(O)OR^{42}$, $NR^{41}S(O)R^{43}$, $C(O)R^{41}$, $C(O)OR^{41}$, $C(O)NR^{41}R^{42}$, $CR^{42}{=}NOR^{41}$, a hydroxy group, a cyano group, a nitro group, a halogen atom, or a hydrogen atom;

provided that not all of present $R^{4a}$, $R^{4b}$, $R^{4c}$, $R^{4d}$, and $R^{4e}$ represent hydrogen atoms;

k represents 0, 1, or 2;

q represents 0, 1, or 2;

$R^{41}$ and $R^{42}$ are identical to or different from each other, and each represent a C1-C6 chain hydrocarbon group optionally substituted with one or more halogen atom(s), a phenyl group optionally substituted with one or more substituent(s) selected from Group Z, a 5 or 6 membered heterocyclic group optionally substituted with one or more substituent(s) selected from Group Z, or a hydrogen atom;

$R^{43}$ represents a C1-C6 chain hydrocarbon group optionally substituted with one or more halogen atom(s), a phenyl group optionally substituted with one or more substituent(s) selected from Group Z, or a 5 or 6 membered heterocyclic group optionally substituted with one or more substituent(s) selected from Group Z; and $R^{44}$ represents a C1-C6 chain hydrocarbon group optionally substituted with one or more halogen atom(s);

Group B: a group consisting of a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a cyano group, a hydroxy group, and a halogen atom;

Group C: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), and a halogen atom;

Group D: a group consisting of a C1-C6 chain hydrocarbon group optionally substituted with one or more halogen atom(s), a hydroxy group, a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a sulfanyl group, a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), an amino group, $NHR^{21}$, $NR^{21}R^{22}$, $C(O)R^{21}$, $OC(O)R^{21}$, $C(O)OR^{21}$, a cyano group, a nitro group, and a halogen atom;

$R^{21}$ and $R^{22}$ are identical to or different from each other, and each represent a C1-C6 alkyl group optionally substituted with one or more halogen atom(s);

Group E: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a $C_3$-$C_6$ alkynyloxy group optionally substituted with one or more halogen atom(s), a halogen atom, an oxo group, a hydroxy group, a cyano group, and a nitro group;

Group F: a group consisting of a C1-C6 alkoxy group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, a C3-C7 cycloalkyl group optionally substituted with one or more halogen atom(s), a 3-7 membered nonaromatic heterocyclic group optionally substituted with one or more substituent(s) selected from Group C, an amino group, $NHR^{21}$, $NR^{21}R^{22}$, a halogen atom, and a cyano group;

Group H: a group consisting of a C1-C6 alkyl group optionally substituted with one or more halogen atom(s), a 5 or 6 membered aromatic heterocyclic group optionally substituted with one or more substituent(s) selected from Group D, $OR^{10}$, $NR^9R^{10}C$, $C(O)R^{10}$, $C(O)NR^9R^{10}$, $OC(O)R^9$, $OC(O)OR^9$, $NR^{10}C(O)R^{10}$, $NR^{10}C(O)\ OR^9$, $C(O)OR^{10}$, a halogen atom, a nitro group, a cyano group, and an amino group;

$R^9$ represents a C1-C6 alkyl group optionally substituted with one or more halogen atom(s) or a C3-C6 cycloalkyl group optionally substituted with one or more halogen atom(s);

$R^{10}$ represents a C1-C6 alkyl group optionally substituted with one or more halogen atom(s), a C3-C6 cycloalkyl group optionally substituted with one or more halogen atom(s), or a hydrogen atom;

Group J: a group consisting of a C1-C6 alkyl group optionally substituted with one or more halogen atom(s), a halogen atom, and a cyano group;

Group X: a group consisting of a C3-C6 cycloalkyl group optionally substituted with one or more substituent(s) selected from the group consisting of a halogen atom and a C1-C3 alkyl group, a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a hydroxy group, a sulfanyl group, a cyano group, and a halogen atom;

Group Y: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), and a halogen atom;

Group Z: a group consisting of a C1-C6 alkyl group optionally substituted with one or more halogen atom(s), a C1-C6 alkoxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C1-C6 alkylamino group optionally substituted with one or more halogen atom(s), a di(C1-C6 alkyl optionally substituted with one or more halogen atom(s))amino group, a C2-C6 alkylcarbonyl group optionally substituted with one or more halogen atom(s), a C2-C6 alkoxycarbonyl group optionally substituted with one or more halogen atom(s), a hydroxy group, a sulfanyl group, an amino group, a cyano group, a nitro group, and a halogen atom, or a salt thereof.

* * * * *